(12) United States Patent
Van Niel et al.

(10) Patent No.: US 9,315,503 B2
(45) Date of Patent: Apr. 19, 2016

(54) KINASE INHIBITORS

(71) Applicant: CHIESI FARMACEUTICI S.p.A., Parma (IT)

(72) Inventors: Monique Bodil Van Niel, Harlow (GB); Nicholas Charles Ray, Harlow (GB); Lilian Alcaraz, Harlow (GB); Terry Aaron Panchal, Harlow (GB); Andrew Stephen Robert Jennings, Harlow (GB); Elisabetta Armani, Parma (IT); Andrew Peter Cridland, Harlow (GB); Christopher Hurley, Harlow (GB)

(73) Assignee: CHIESI FARMACEUTICI S.p.A., Parma (IT)

( * ) Notice: Subject to any disclaimer, the term of this patent is extended or adjusted under 35 U.S.C. 154(b) by 0 days.

(21) Appl. No.: 14/819,722

(22) Filed: Aug. 6, 2015

(65) Prior Publication Data
US 2015/0344475 A1  Dec. 3, 2015

Related U.S. Application Data

(60) Division of application No. 14/330,145, filed on Jul. 14, 2014, now Pat. No. 9,145,413, which is a continuation of application No. 13/708,324, filed on Dec. 7, 2012, now Pat. No. 8,907,094.

(30) Foreign Application Priority Data

Dec. 9, 2011 (EP) .................................... 11192871
Oct. 10, 2012 (EP) .................................... 12187931

(51) Int. Cl.
  *C07D 498/02* (2006.01)
  *A61K 31/553* (2006.01)
  *C07D 471/04* (2006.01)

(52) U.S. Cl.
  CPC .................................. *C07D 471/04* (2013.01)

(58) Field of Classification Search
  None
  See application file for complete search history.

(56) References Cited

U.S. PATENT DOCUMENTS

| | | | |
|---|---|---|---|
| 8,907,094 B2 | 12/2014 | Van Niel et al. |
| 9,029,373 B2 | 5/2015 | Van Niel et al. |
| 9,139,584 B2 | 9/2015 | Van Niel et al. |
| 9,145,413 B2 | 9/2015 | Van Niel et al. |
| 2012/0088763 A1 | 4/2012 | Finch et al. |
| 2013/0143914 A1 | 6/2013 | Woo et al. |
| 2013/0150361 A1 | 6/2013 | Van Niel et al. |
| 2014/0364411 A1 | 12/2014 | Woo et al. |
| 2014/0364412 A1 | 12/2014 | Alcaraz et al. |
| 2015/0057273 A1 | 2/2015 | Finch et al. |

FOREIGN PATENT DOCUMENTS

| | | |
|---|---|---|
| WO | 2007/091152 | 8/2007 |
| WO | 2013/083206 | 6/2013 |
| WO | 2014/194956 | 12/2014 |

OTHER PUBLICATIONS

European Search Report in Application 11192871.9, issued Mar. 14, 2012.

*Primary Examiner* — Heidi Reese
(74) *Attorney, Agent, or Firm* — Oblon, McClelland, Maier & Neustadt, L.L.P.

(57) ABSTRACT

Compounds of formula (I) and pharmaceutically acceptable salts thereof:

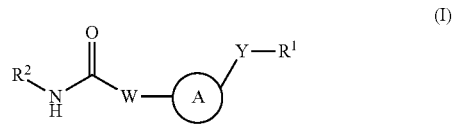

wherein $R^2$, W, A, Y and $R^1$ are as defined in the specification, are p38 MAPK inhibitors, and are useful as anti-inflammatory agents in the treatment of, inter alia, diseases of the respiratory tract.

20 Claims, 2 Drawing Sheets

KINASE INHIBITORS

CROSS REFERENCES TO RELATED APPLICATIONS

This application is a Divisional Application of U.S. patent application Ser. No. 14/330,145, filed on Jul. 14, 2014, now U.S. Pat. No. 9,145,413, which was a Continuation Application of U.S. patent application Ser. No. 13/708,324, filed on Dec. 7, 2012, now U.S. Pat. No. 8,907,094, and claims priority to European Patent Application No. 11192871.9, filed on Dec. 9, 2011, and European Patent Application No. 12187931.6, filed on Oct. 10, 2012, both of which are incorporated herein by reference in their entireties.

BACKGROUND OF THE INVENTION

1. Field of the Invention

The present invention relates to compounds and compositions that are p38 MAPK inhibitors, and which are useful as anti-inflammatory agents in the treatment of, inter alia, diseases of the respiratory tract. The present invention further relates to methods for the treatment and/or prevention of certain diseases and conditions by administering such a compound.

2. Discussion of the Background

Mitogen activated protein kinases (MAPK) constitute a family of proline-directed serine/threonine kinases that activate their substrates by dual phosphorylation. There are four known human isoforms of p38 MAP kinase, p38α, p38β, p38γ, and p38δ. The p38 kinases, which are also known as cytokine suppressive anti-inflammatory drug binding proteins (CSBP), stress activated protein kinases (SAPK) and RK, are responsible for phosphorylating (Stein et al., Ann. Rep. Med Chem., 1996, 31, 289-298, which is incorporated herein by reference in its entirety) and activating transcription factors (such as ATF-2, MAX, CHOP and C/ERPb) as well as other kinases (such as MAPKAP-K2/3 or MK2/3), and are themselves activated by physical and chemical stress (e.g. UV, osmotic stress), pro-inflammatory cytokines and bacterial lipopolysaccharide (LPS) (see Herlaar E. & Brown Z., Molecular Medicine Today, 1999, 5, 439-447, which is incorporated herein by reference in its entirety). The products of p38 phosphorylation have been shown to mediate the production of inflammatory cytokines, including tumor necrosis factor alpha (TNF a) and interleukin-(IL)-1, and cyclooxygenase-2 (COX-2). IL-1 and TNFα are also known to stimulate the production of other proinflammatory cytokines such as IL-6 and IL-8.

IL-1 and TNFα are biological substances produced by a variety of cells, such as monocytes or macrophages. IL-1 has been demonstrated to mediate a variety of biological activities thought to be important in immunoregulation and other physiological conditions such as inflammation (see, e.g. Dinarello et al., Rev. Infect. Disease, 1984, 6, 51, which is incorporated herein by reference in its entirety). Excessive or unregulated TNF production (particularly TNFα) has been implicated in mediating or exacerbating a number of diseases, and it is believed that TNF can cause or contribute to the effects of inflammation in general. IL-8 is a chemotactic factor produced by several cell types including mononuclear cells, fibroblasts, endothelial cells, and keratinocytes. Its production from endothelial cells is induced by IL-1, TNF, or lipopolysaccharide (LPS). IL-8 stimulates a number of functions in vitro. It has been shown to have chemoattractant properties for neutrophils, T-lymphocytes and basophils. Increase in IL-8 production is also responsible for chemotaxis of neutrophils into the inflammatory site in vivo.

Inhibition of signal transduction via p38, which in addition to IL-1, TNF and IL-8 described above is also required for the synthesis and/or action of several additional pro-inflammatory proteins (e.g., IL-6, GM-CSF, COX-2, collagenase and stromelysin), is expected to be a highly effective mechanism for regulating the excessive and destructive activation of the immune system. This expectation is supported by the potent and diverse anti-inflammatory activities described for p38 kinase inhibitors (see Badger et al., J. Pharm. Exp. Thera., 1996, 279, 1453-1461; Griswold et al, Pharmacol. Comm., 1996, 7, 323-229, which are incorporated herein by reference in their entireties). In particular, p38 kinase inhibitors have been described as potential agents for treating rheumatoid arthritis. In addition to the links between p38 activation and chronic inflammation and arthritis, there is also data implicating a role for p38 in the pathogenesis of airway diseases in particular COPD and asthma. Stress stimuli (including tobacco smoke, infections or oxidative products) can cause inflammation within the lung environment. Inhibitors of p38 have been shown to inhibit LPS and ovalbumin induced airway TNF-α IL-1β, IL-6, IL-4, IL-5, and IL-13 (see Haddad et al, Br. J. Pharmacol., 2001, 132 (8), 1715-1724; Underwood et al, Am. J. Physiol. Lung Cell. Mol. 2000, 279, 895-902; Duan et al., 2005 Am. J. Respir. Crit. Care Med., 171, 571-578; Escott et al Br. J. Pharmacol., 2000, 131, 173-176; Underwood et al., J. Pharmacol. Exp. Ther. 2000, 293, 281-288, which are incorporated herein by reference in their entireties). Furthermore, they significantly inhibit neutrophilia and the release of MMP-9 in LPS, ozone or cigarette smoke animal models. There is also a significant body of preclinical data highlighting the potential benefits of inhibition of the p38 kinase that could be relevant in the lung (see Lee et al., Immunopharmacology, 2000, 47, 185-200, which is incorporated herein by reference in its entirety). Thus, therapeutic inhibition of p38 activation may be important in the regulation of airway inflammation.

The implication of the p38MAPK pathway in various diseases has been reviewed by P. Chopra et al. (Expert Opinion on Investigational Drugs, 2008, 17(10), 1411-1425, which is incorporated herein by reference in its entirety).

Known P38 kinase inhibitors have been reviewed by G. J. Hanson (Expert Opinions on Therapeutic Patents, 1997, 7, 729-733) J Hynes et al. (Current Topics in Medicinal Chemistry, 2005, 5, 967-985), C. Dominguez et al (Expert Opinions on Therapeutics Patents, 2005, 15, 801-816) and L. H. Pettus & R. P. Wurtz (Current Topics in Medicinal Chemistry, 2008, 8, 1452-1467), which are incorporated herein by reference in their entireties. P38 kinase inhibitors containing a triazolopyridine motif are known in the art, see for example WO 2007/091152, WO 2004/072072, and WO 2006/018727, which are incorporated herein by reference in their entireties.

International Patent Application WO 2010/094956, which is incorporated herein by reference in its entirety, discloses triazolopyridine derivatives of formula (I) as being p38 MAP Kinase inhibitors:

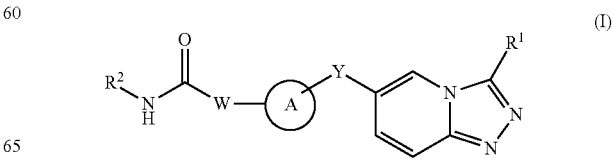

In such compounds, A represents an optionally substituted divalent arylene radical, an heteroarylene radical, a (C₃-C₆) divalent cycloalkylene radical having 5 or 6 ring atoms or a pyperidinylene radical. The compounds are said to be useful in as anti-inflammatory agents in the treatment of diseases of the respiratory tract.

There remains, however, a need for improved p38 MAP Kinase inhibitors.

SUMMARY OF THE INVENTION

Accordingly, it is one object of the present invention to provide novel p38 MAP Kinase inhibitors.

It is another object of the present invention to provide novel and potent p38 mitogen activated protein kinase inhibitors which are useful in the treatment of inflammatory and obstructive diseases of the respiratory tract.

It is another object of the present invention, to provide novel potent p38 mitogen activated protein kinase inhibitors which show an appropriate developability profile on inhalatory administration to effectively treat respiratory obstructive or inflammatory diseases. It is to be understood that such profile may be achieved in a number of different ways by modulation of specific properties; by way of example, it could be achieved by administration of a low effective dose of the drug thus limiting side effects or via a long duration of action in the lungs which may reduce the frequency of administration.

These and other objects, which will become apparent during the following detailed description, have been achieved by the inventors' discovery that compounds formula (I) described below are useful as p38 mitogen activated protein kinase inhibitors.

Thus, the present invention provides compound of formula (I), and pharmaceutically acceptable salted thereof:

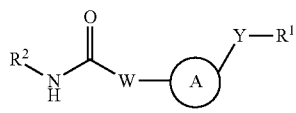

(I)

wherein;

W is a heteroatom selected from N or O, wherein N is substituted with hydrogen, $C_1$-$C_6$ alkyl, or $C_3$-$C_5$ cycloalkyl;

Y is selected from the group consisting of: a group —S(O)$_p$— wherein p is 0, 1 or 2; a group —O(CR³R⁴)$_n$—; a group —(CR⁵R⁶)—; a group —NR⁷—; a group —OC(O)—; a group —OC(O)NH—; and a group —OC(O)O—;

R³, R⁴, R⁵ and R⁶ are each independently hydrogen, fluorine or $C_1$-$C_6$ alkyl, or, respectively, R³ and R⁴, or R⁵ and R⁶ may form, together with the carbon atom to which they are attached, a saturated 3-6 membered carbocyclic monocyclic ring optionally substituted by a group $C_1$-$C_6$ alkyl, hydroxyl or halo;

n is 0, 1, 2 or 3;

R⁷ is hydrogen, $C_1$-$C_6$ alkyl, or $C_3$-$C_7$ cycloalkyl wherein such $C_1$-$C_6$ alkyl or $C_3$-$C_7$ cycloalkyl are optionally substituted by a group $C_1$-$C_3$ alkyl, $C_3$-$C_6$ cycloalkyl, hydroxyl, cyano, or halo;

R¹ is a group selected from (IIa)-(IIc):

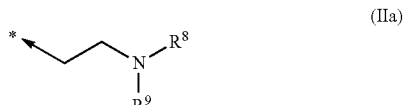

(IIa)

(IIb)

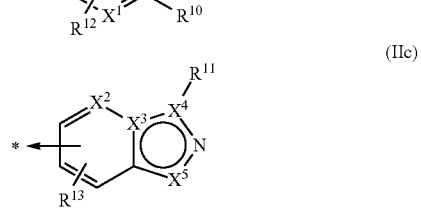

(IIc)

R⁸ and R⁹ are each independently hydrogen or $C_1$-$C_6$ alkyl, or R⁸ and R⁹ may form, together with the nitrogen atom to which they are attached, a 5-11-membered saturated monocyclic or a fused or spiro bicyclic ring system optionally containing a further heteroatom which is oxygen or nitrogen, said nitrogen atom being optionally substituted by $C_1$-$C_6$ alkyl; wherein such $C_1$-$C_6$ alkyl groups may be optionally substituted by a group $C_1$-$C_6$ alkyl, $C_3$-$C_6$ cycloalkyl, hydroxyl, or halo;

X¹, X², X³, X⁴ and X⁵ are each independently a carbon atom, a nitrogen atom, a group —(CH)— or a group —NH—; such that each combination thereof forms an aromatic ring system;

R¹⁰ is selected from a group consisting of: Hydrogen, —CN, —NRᴬRᴮ, —N(Rᶜ)(C₂-C₆alkylene)-NRᴬRᴮ, —N(Rᶜ)(C₃-C₇cycloalkylene)-NRᴬRᴮ, —(C₁-C₆alkylene)-NRᴬRᴮ, —(C₃-C₇cycloalkylene)-NRᴬRᴮ, —O—(C₂-C₆alkylene)-NRᴬRᴮ, —O—(C₃-C₇cycloalkylene)-NRᴬRᴮ, —S—(C₂-C₆alkylene)-NRᴬRᴮ, —S—(C₃-C₇cycloalkylene)-NRᴬRᴮ, —N(Rᶜ)C(O)—(C₁-C₆alkylene)-NRᴬRᴮ, —N(Rᶜ)C(O)—(C₃-C₇cycloalkylene)-NRᴬRᴮ, —C(O)N(Rᶜ)—(C₂-C₆alkylene)-NRᴬRᴮ, —C(O)N(Rᶜ)—(C₃-C₇cycloalkylene)-NRᴬRᴮ, —C(O)N(Rᶜ)—(C₂-C₆alkylene)-ORᴰ, —C(O)N(Rᶜ)—(C₃-C₇cycloalkylene)-ORᴰ, —N(Rᶜ)C(O)NRᴬRᴮ, —C(O)NRᴬRᴮ, —N(Rᶜ)C(O)N(Rᶜ)—(C₂-C₆alkylene)-NRᴬRᴮ, —N(Rᶜ)C(O)N(Rᶜ)—(C₃-C₇cycloalkylene)-NRᴬRᴮ, —(C₂-C₆alkylene)-ORᴰ, —(C₃-C₇cycloalkylene)-ORᴰ, —O—(C₂-C₆alkylene)-ORᴰ, —O—(C₃-C₇cycloalkylene)-ORᴰ, —S—(C₂-C₆alkylene)-ORᴰ, —S—(C₃-C₇cycloalkylene)-ORᴰ, —N(Rᶜ)S(O)₂—(C₁-C₆alkylene)-NRᴬRᴮ, —N(Rᶜ)S(O)₂—(C₃-C₇cycloalkylene)-NRᴬRᴮ, —S(O)₂N(Rᶜ)—(C₂-C₆alkylene)-NRᴬRᴮ, —S(O)₂N(Rᶜ)—(C₃-C₇cycloalkylene)-NRᴬRᴮ, —S(O)₂N(Rᶜ)—(C₂-C₆alkylene)-ORᴰ, —S(O)₂N(Rᶜ)—(C₃-C₇cycloalkylene)-ORᴰ, —N(Rᶜ)S(O)₂—(C₂-C₆alkylene)-ORᴰ, —N(Rᶜ)S(O)₂—(C₃-C₇cycloalkylene)-ORᴰ, —S(O)₂N(RᴬRᴮ), —N(Rᶜ)S(O)₂Rᴰ, —N(Rᶜ)C(O)Rᶜ, —ORᶜ, —SRᶜ, —(C₃-C₇heterocycloalkyl), (C₅-C₇heterocycloalkyl)-(C₁-C₆alkyl), (C₅-C₇heterocycloalkyl)(C₃-C₆cycloalkyl)-, and C₃-C₇ heterocycloalkylcarbonyl; wherein any of such $C_1$-$C_6$alkyl, $C_3$-$C_6$cycloalkyl, —(C₁-C₆alkylene)-, —(C₂-C₆alkylene)-, —(C₃-C₇cycloalkylene)-, —(C₃-C₇heterocycloalkyl), (C₅-C₇heterocycloalkyl)-(C₁-C₆ alkyl), (C₅-C₇ heterocycloalkyl)-(C₃-C₆ cycloalkyl) and (C₃-C₇heterocycloalkyl)

carbonyl portion in the above listed groups may be optionally substituted by a group $C_1$-$C_6$ alkyl, $C_3$-$C_7$ cycloalkyl, hydroxyl or halo;

$R^{11}$ is linked to $X^4$ and is selected from a group consisting of hydrogen; —CN; $C_1$-$C_6$ alkyl which is substituted by a group selected from —CN, —OR$^C$, —SR$^C$, halo; $C_3$-$C_6$cycloalkyl which is substituted by a group selected from $C_1$-$C_4$ alkyl, —CN, —OR$^C$, —SR$^D$, halo; —NR$^A$R$^B$, —N(R$^C$)($C_2$-$C_6$alkylene)-NR$^A$R$^B$, —N(R$^C$)($C_3$-$C_7$cycloalkylene)-NR$^A$R$^B$, —($C_1$-$C_6$alkylene)-NR$^A$R$^B$, —($C_3$-$C_7$cycloalkylene)-NR$^A$R$^B$, —O—($C_2$-$C_6$alkylene)-NR$^A$R$^B$, —O—($C_3$-$C_7$cycloalkylene)-NR$^A$R$^B$, —S—($C_2$-$C_6$alkylene)-NR$^A$R$^B$, —S—($C_3$-$C_7$cycloalkylene)-NR$^A$R$^B$, —N(R$^C$)C(O)—($C_1$-$C_6$alkylene)-NR$^A$R$^B$, —N(R$^C$)C(O)—($C_3$-$C_7$cycloalkylene)-NR$^A$R$^B$, —C(O)N(R$^C$)—($C_2$-$C_6$alkylene)-NR$^A$R$^B$, —C(O)N(R$^C$)—($C_3$-$C_7$cycloalkylene)-NR$^A$R$^B$, —C(O)N(R$^C$)—($C_2$-$C_6$alkylene)-OR$^D$, —C(O)N(R$^C$)—($C_3$-$C_7$cycloalkylene)-OR$^D$, —N(R$^C$)C(O)N(R$^A$R$^B$), —C(O)N(R$^A$R$^B$), —N(R$^C$)C(O)N(R$^C$)—($C_2$-$C_6$alkylene)-NR$^A$R$^B$, —N(R$^C$)C(O)N(R$^C$)—($C_3$-$C_7$cycloalkylene)-NR$^A$R$^B$, —O—($C_2$-$C_6$alkylene)-OR$^D$, —O—($C_3$-$C_7$cycloalkylene)-OR$^D$, —S—($C_2$-$C_6$alkylene)-OR$^D$, —S—($C_3$-$C_7$cycloalkylene)-OR$^D$, —N(R$^C$)S(O)$_2$—($C_1$-$C_6$alkylene)-NR$^A$R$^B$, —N(R$^C$)S(O)$_2$—($C_3$-$C_7$cycloalkylene)-NR$^A$R$^B$, —S(O)$_2$N(R$^C$)—($C_2$-$C_6$alkylene)-NR$^A$R$^B$, —S(O)$_2$N(R$^C$)—($C_3$-$C_7$cycloalkylene)-NR$^A$R$^B$, —S(O)$_2$N(R$^C$)—($C_2$-$C_6$alkylene)-OR$^D$, —S(O)$_2$N(R$^C$)—($C_3$-$C_7$cycloalkylene)-OR$^D$, —N(R$^C$)S(O)$_2$—($C_2$-$C_6$alkylene)-OR$^D$, —N(R$^C$)S(O)$_2$—($C_3$-$C_7$cycloalkylene)-OR$^D$, —S(O)$_2$N(R$^A$R$^B$), —N(R$^C$)S(O)$_2$R$^D$, —N(R$^C$)C(O)R$^C$, OR$^C$, SR$^C$, —($C_3$-$C_7$heterocycloalkyl), ($C_5$-$C_7$heterocycloalkyl)-($C_1$-$C_6$alkyl), ($C_5$-$C_7$heterocycloalkyl)($C_3$-$C_6$cycloalkyl) and ($C_3$-$C_7$ heterocycloalkyl)carbonyl, wherein any of such $C_1$-$C_6$alkyl, $C_3$-$C_6$cycloalkyl, —($C_1$-$C_6$alkylene)-, —($C_2$-$C_6$alkylene)-, —($C_3$-$C_7$cycloalkylene)-, —($C_3$-$C_7$heterocycloalkyl), ($C_5$-$C_7$heterocycloalkyl)-($C_1$-$C_6$ alkyl), ($C_5$-$C_7$ heterocycloalkyl)-($C_3$-$C_6$ cycloalkyl) and ($C_3$-$C_7$heterocycloalkyl)carbonyl portion in the above listed groups may be optionally substituted by one, two or three groups $R^{25}$ which are independently selected from the group consisting of $C_1$-$C_6$ alkyl, ($C_1$-$C_3$) haloalkyl, ($C_1$-$C_4$)hydroxyalkyl, $C_3$-$C_7$ cycloalkyl, hydroxyl and halo; or $R^{11}$ is linked to $X^4$ and is phenyl or 5- or 6-membered monocyclic heteroaryl, wherein such phenyl or 5- or 6-membered monocyclic heteroaryl is substituted by a group selected from the group consisting of: $C_1$-$C_6$ alkyl which is substituted by a group —CN; $C_3$-$C_6$ cycloalkyl which is substituted by a group selected from: —CN, —OR$^C$, —SR$^C$ or halo; —N(R$^C$)($C_2$-$C_6$alkylene)-NR$^A$R$^B$, —N(R$^C$)($C_3$-$C_7$cycloalkylene)-NR$^A$R$^B$, —($C_1$-$C_6$alkylene)-NR$^A$R$^B$, —($C_3$-$C_7$cycloalkylene)-NR$^A$R$^B$, —O—($C_3$-$C_7$cycloalkylene)-NR$^A$R$^B$, —S—($C_2$-$C_6$alkylene)-NR$^A$R$^B$, —S—($C_3$-$C_7$cycloalkylene)-NR$^A$R$^B$, —N(R$^C$)C(O)—($C_1$-$C_6$alkylene)-NR$^A$R$^B$, —N(R$^C$)C(O)—($C_3$-$C_7$cycloalkylene)-NR$^A$R$^B$, —C(O)N(R$^C$)—($C_2$-$C_6$alkylene)-NR$^A$R$^B$, —C(O)N(R$^C$)—($C_3$-$C_7$cycloalkylene)-NR$^A$R$^B$, —C(O)N(R$^C$)—($C_2$-$C_6$alkylene)-OR$^D$, —C(O)N(R$^C$)—($C_3$-$C_7$cycloalkylene)-OR$^D$, —N(R$^C$)C(O)N(R$^C$)—($C_2$-$C_6$alkylene)-NR$^A$R$^B$, —N(R$^C$)C(O)N(R$^C$)—($C_3$-$C_7$cycloalkylene)-NR$^A$R$^B$, —O—($C_3$-$C_7$cycloalkylene)-OR$^D$, —S—($C_3$-$C_7$cycloalkylene)-OR$^D$, —N(R$^C$)S(O)$_2$—($C_1$-$C_6$alkylene)-NR$^A$R$^B$, —N(R$^C$)S(O)$_2$—($C_3$-$C_7$cycloalkylene)-NR$^A$R$^B$, —S(O)$_2$N(R$^C$)—($C_2$-$C_6$alkylene)-NR$^A$R$^B$, —S(O)$_2$N(R$^C$)—($C_3$-$C_7$cycloalkylene)-NR$^A$R$^B$, —S(O)$_2$N(R$^C$)—($C_2$-$C_6$alkylene)-OR$^D$, —S(O)$_2$N(R$^C$)—($C_3$-$C_7$cycloalkylene)-OR$^D$, —N(R$^C$)S(O)$_2$—($C_2$-$C_6$alkylene)-OR$^D$, —N(R$^C$)S(O)$_2$—($C_3$-$C_7$cycloalkylene)-OR$^D$, —N(R$^C$)S(O)$_2$R$^D$, —($C_3$-$C_7$heterocycloalkyl), ($C_5$-$C_7$heterocycloalkyl)-($C_1$-$C_6$alkyl), ($C_5$-$C_7$heterocycloalkyl)($C_3$-$C_6$cycloalkyl) and ($C_3$-$C_7$heterocycloalkyl)carbonyl, wherein any of such $C_1$-$C_6$alkyl, $C_3$-$C_6$cycloalkyl, —($C_1$-$C_6$alkylene)-—($C_2$-$C_6$alkylene)-, —($C_3$-$C_7$cycloalkylene)-, —($C_3$-$C_7$heterocycloalkyl), ($C_5$-$C_7$heterocycloalkyl)-($C_1$-$C_6$ alkyl), ($C_5$-$C_7$ heterocycloalkyl)-($C_3$-$C_6$ cycloalkyl) and ($C_3$-$C_7$heterocycloalkyl)carbonyl portion in the above listed groups may be optionally substituted by one, two or three groups $R^{25}$ which are independently selected from the group consisting of: $C_1$-$C_6$alkyl, ($C_1$-$C_3$) haloalkyl, ($C_1$-$C_4$)hydroxyalkyl, $C_3$-$C_7$cycloalkyl, hydroxyl, and halo;

$R^A$ and $R^B$ are at each occurrence independently hydrogen, $C_1$-$C_6$ alkyl, or $C_3$-$C_7$ cycloalkyl, such $C_1$-$C_6$ alkyl and $C_3$-$C_7$ cycloalkyl being optionally substituted by a group $C_1$-$C_3$ alkyl, $C_3$-$C_7$cycloalkyl, —OR$^D$, —CN, or halo; alternatively, $R^A$ and $R^B$ may form, together with the nitrogen atom to which they are attached, a 5-11-membered saturated heterocyclic monocyclic or bicyclic ring system which is optionally substituted by one or more group —OR$^D$, —CN, halo, $C_1$-$C_6$ alkyl, or $C_3$-$C_7$ cycloalkyl, such $C_1$-$C_6$ alkyl and $C_3$-$C_7$ cycloalkyl being optionally substituted by a group $C_1$-$C_3$ alkyl, $C_3$-$C_7$cycloalkyl, —OR$^D$, —CN, or halo; and which 5-11-membered saturated heterocyclic monocyclic or bicyclic ring optionally contains a further heteroatom which is oxygen or nitrogen, said nitrogen atom optionally substituted by $C_1$-$C_6$ alkyl or $C_3$-$C_6$ cycloalkyl, wherein any of such $C_1$-$C_6$ alkyl or $C_3$-$C_6$ cycloalkyl may be optionally substituted by a group $C_1$-$C_6$ alkyl, $C_3$-$C_7$ cycloalkyl, —OR$^D$, —CN, or halo; and/or $R^A$ and $R^B$ may be linked to one carbon atom of the —($C_1$-$C_6$alkylene)-, —($C_2$-$C_6$alkylene)- or —($C_3$-$C_7$cycloalkylene)-portion of the group linked to the nitrogen to which they are connected to form a saturated cycle of up to 6 ring atoms;

$R^C$ is at each occurrence independently hydrogen, $C_1$-$C_6$ alkyl, or $C_3$-$C_6$ cycloalkyl, such $C_1$-$C_6$ alkyl and $C_3$-$C_6$ cycloalkyl being optionally substituted by a group $C_1$-$C_3$ alkyl, —OR$^D$, —CN, or halo;

$R^D$ is at each occurrence independently hydrogen, —CH$_3$, or —C$_2$H$_5$;

$R^{12}$ and $R^{13}$ are independently hydrogen, $C_1$-$C_6$ alkyl, or halogen;

A is a divalent cycloalkylene radical having 5, 6 or 7 ring atoms; said cycloalkylene ring being attached to W and Y, and fused to a phenyl ring or to a monocyclic heteroaryl ring having 5 or 6 ring atoms, such phenyl or heteroaryl ring being optionally substituted by one or two groups $R^{24}$;

$R^{24}$ is at each occurrence independently selected from the group consisting of $C_1$-$C_6$ alkyl, halogen, and cyano;

$R^2$ is a radical of formula (IIIa), (IIIb), (IIIc), or (IIId):

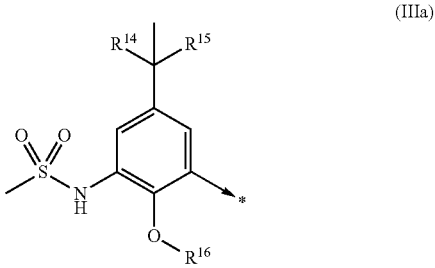

(IIIa)

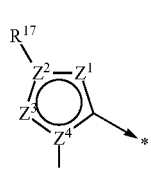

(IIIb)

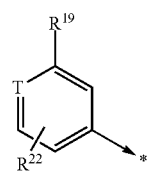

(IIIc)

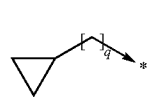

(IIId)

wherein
$R^{14}$ is selected from the group consisting of —F, —CH$_3$, —C$_2$H$_5$, —CH$_2$OH, —CH$_2$OMe, —CF$_2$CF$_3$, —CH$_2$SCH$_3$, —SCH$_3$, and —SC$_2$H$_5$;

$R^{15}$ and $R^{16}$ are independently —CH$_3$ or —C$_2$H$_5$;

$R^{17}$ is selected from the group consisting of lone electron pair, hydrogen, —CF$_3$, —NR$^E$R$^F$, —(C$_3$-C$_7$cycloalkyl), —(C$_3$-C$_7$heterocycloalkyl), aryl, and heteroaryl wherein any of such (C$_3$-C$_7$cycloalkyl), —(C$_3$-C$_7$heterocycloalkyl), aryl or heteroaryl may be optionally substituted by a group C$_1$-C$_6$ alkyl, C$_3$-C$_7$ cycloalkyl, or halo; or $R^{17}$ is a group of general formula (IV):

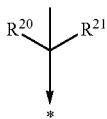

(IV)

wherein
$R^{20}$ is selected from the group consisting of —F, —CH$_3$, —C$_2$H$_5$, —CH$_2$OH, —CH$_2$OMe, —CF$_2$CF$_3$, —CH$_2$SCH$_3$, —SCH$_3$, and —SC$_2$H$_5$;

$R^{21}$ is —CH$_3$ or —C$_2$H$_5$;
or
$R^{20}$ and $R^{21}$ as defined above may form, together with the carbon atom to which they are attached, a saturated 3-7-membered monocyclic ring;

$R^E$ and $R^F$ are each independently C$_1$-C$_6$ alkyl, optionally substituted by a group C$_1$-C$_3$ alkyl, —OR$^G$, —CN or halo; alternatively, $R^E$ and $R^F$ may form, together with the nitrogen atom to which they are attached, a 5-11-membered saturated monocyclic or bicyclic heterocyclic ring system which is optionally substituted by one or more groups —OR$^G$, —CN, halo, C$_1$-C$_6$ alkyl or C$_3$-C$_7$ cycloalkyl, such C$_1$-C$_6$ alkyl and C$_3$-C$_7$ cycloalkyl being optionally substituted by a group C$_1$-C$_3$ alkyl, C$_3$-C$_7$cycloalkyl, —OR$^G$, —CN or halo; and which 5-11-membered saturated monocyclic or bicyclic heterocyclic ring optionally contains a further heteroatom which is oxygen or nitrogen, said nitrogen atom optionally substituted by C$_1$-C$_6$ alkyl or C$_3$-C$_6$ cycloalkyl, wherein any of such C$_1$-C$_6$ alkyl or C$_3$-C$_6$ cycloalkyl may be optionally substituted by a group C$_1$-C$_6$ alkyl or C$_3$-C$_7$ cycloalkyl;

$R^G$ is hydrogen, —CH$_3$, or —C$_2$H$_5$.

$R^{18}$ is selected from the group consisting of lone electron pair, hydrogen, aryl, heteroaryl, —(C$_1$-C$_6$alkyl), —(C$_3$-C$_7$cycloalkyl), —(C$_3$-C$_7$heterocycloalkyl), (C$_5$-C$_7$heterocycloalkyl)-(C$_1$-C$_6$alkyl) and (C$_5$-C$_7$heterocycloalkyl)-(C$_3$-C$_6$ cycloalkyl), wherein any of such aryl, heteroaryl, —(C$_1$-C$_6$alkyl), —(C$_3$-C$_7$cycloalkyl), —(C$_3$-C$_7$heterocycloalkyl), (C$_5$-C$_7$heterocycloalkyl)-(C$_1$-C$_6$alkyl) and (C$_5$-C$_7$heterocycloalkyl)-(C$_3$-C$_6$ cycloalkyl) may be optionally substituted by a group —CN, —OH, halo, —COOR$^M$, C$_1$-C$_6$alkyl, C$_3$-C$_6$cycloalkyl, —O—(C$_1$-C$_6$alkyl), —O—(C$_3$-C$_6$cycloalkyl), —S—(C$_1$-C$_6$alkyl), —S—(C$_3$-C$_6$cycloalkyl), —NR$^H$R$^J$, —N(R$^L$)(C$_2$-C$_6$alkylene)-NR$^H$R$^J$, —N(R$^L$)(C$_3$-C$_7$cycloalkylene)-NR$^H$R$^J$, —(C$_1$-C$_6$alkylene)-NR$^H$R$^J$, —(C$_3$-C$_7$cycloalkylene)-NR$^H$R$^J$, —O—(C$_2$-C$_6$alkylene)-NR$^H$R$^J$, —O—(C$_3$-C$_7$cycloalkylene)-NR$^H$R$^J$, —S—(C$_2$-C$_6$alkylene)-NR$^H$R$^J$, —S—(C$_3$-C$_7$cycloalkylene)-NR$^H$R$^J$, —N(R$^L$)C(O)—(C$_1$-C$_6$alkylene)-NR$^H$R$^J$, —N(R$^L$)C(O)—(C$_3$-C$_7$cycloalkylene)-NR$^H$R$^J$, —C(O)N(R$^L$)—(C$_2$-C$_6$alkylene)-NR$^H$R$^J$, —C(O)N(R$^L$)—(C$_3$-C$_7$cycloalkylene)-NR$^H$R$^J$, —C(O)N(R$^L$)—(C$_2$-C$_6$alkylene)-OR$^M$, —C(O)N(R$^L$)—(C$_3$-C$_7$cycloalkylene)-OR$^M$, —N(R$^L$)C(O)N(R$^H$R$^J$), —C(O)N(R$^H$R$^J$), —N(R$^L$)C(O)N(R$^L$)—(C$_2$-C$_6$alkylene)-NR$^H$R$^J$, —N(R$^L$)C(O)N(R$^L$)—(C$_3$-C$_7$cycloalkylene)-NR$^H$R$^J$, —O—(C$_2$-C$_6$alkylene)-OR$^M$, —O—(C$_3$-C$_7$cycloalkylene)-OR$^M$, —S—(C$_2$-C$_6$alkylene)-OR$^M$, —S—(C$_3$-C$_7$cycloalkylene)-OR$^M$, —N(R$^L$)S(O)$_2$—(C$_1$-C$_6$alkylene)-NR$^H$R$^J$, —N(R$^L$)S(O)$_2$—(C$_3$-C$_7$cycloalkylene)-NR$^H$R$^J$, —S(O)$_2$N(R$^L$)—(C$_2$-C$_6$alkylene)-NR$^H$R$^J$, —S(O)$_2$N(R$^L$)—(C$_3$-C$_7$cycloalkylene)-NR$^H$R$^J$, —S(O)$_2$N(R$^L$)—(C$_2$-C$_6$alkylene)-OR$^M$, —S(O)$_2$N(R$^L$)—(C$_3$-C$_7$cycloalkylene)-OR$^M$, —N(R$^L$)S(O)$_2$—(C$_2$-C$_6$alkylene)-OR$^M$, —N(R$^L$)S(O)$_2$—(C$_3$-C$_7$cycloalkylene)-OR$^M$, —S(O)$_2$N(R$^H$R$^J$), —N(R$^L$)S(O)$_2$R$^L$, —N(R$^L$)C(O)R$^L$, OR$^L$, SR$^L$, —(C$_3$-C$_7$heterocycloalkyl), (C$_5$-C$_7$heterocycloalkyl)-(C$_1$-C$_6$ alkyl), and (C$_5$-C$_7$ heterocycloalkyl)-(C$_3$-C$_6$ cycloalkyl), wherein any of such C$_1$-C$_6$alkyl, C$_3$-C$_6$cycloalkyl, —(C$_1$-C$_6$alkylene)-—(C$_2$-C$_6$alkylene)-, —(C$_3$-C$_7$cycloalkylene)-, —(C$_3$-C$_7$heterocycloalkyl), (C$_5$-C$_7$heterocycloalkyl)-(C$_1$-C$_6$ alkyl), and (C$_5$-C$_7$ heterocycloalkyl)-(C$_3$-C$_6$ cycloalkyl) portion in the above listed groups may be optionally substituted by a group C$_1$-C$_6$ alkyl, C$_3$-C$_7$ cycloalkyl, —OR$^L$, or halo;

$R^H$ and $R^J$, are at each occurrence independently hydrogen, C$_1$-C$_6$ alkyl or C$_3$-C$_6$ cycloalkyl, such C$_1$-C$_6$ alkyl or C$_3$-C$_6$ cycloalkyl being optionally substituted by a group C$_1$-C$_3$ alkyl, —OR$^M$, CN or halo;

alternatively, $R^H$ and $R^J$ may also form, together with the nitrogen atom to which they are attached, a 5-11-membered saturated monocyclic or bicyclic heterocyclic ring system which is optionally substituted by one or more groups —OR$^M$, —CN, halo, C$_1$-C$_6$ alkyl or C$_3$-C$_7$ cycloalkyl, such C$_1$-C$_6$ alkyl and C$_3$-C$_7$ cycloalkyl being optionally substituted by a group C$_1$-C$_3$ alkyl, C$_3$-C$_7$cycloalkyl, —OR$^M$, CN, or halo; and which 5-11-membered saturated monocyclic or bicyclic heterocyclic ring optionally contains a further heteroatom which is oxygen or nitrogen, said nitrogen atom optionally substituted by C$_1$-C$_6$ alkyl or C$_3$-C$_6$ cycloalkyl, wherein any of such C$_1$-C$_6$ alkyl or C$_3$-C$_6$ cycloalkyl may be optionally substituted by a group C$_1$-C$_6$ alkyl, C$_3$-C$_7$ cycloalkyl, —OR$^M$, CN, or halo;

and/or $R^H$ and $R^J$ may be linked to one carbon atom of the —(C$_1$-C$_6$alkylene)-, —(C$_2$-C$_6$alkylene)- or —(C$_3$-C$_7$cycloalkylene)-portion of the group linked to the nitrogen to which they are connected to form a saturated cycle of up to 6 ring atoms;

$R^L$ is at each occurrence independently hydrogen, $C_1$-$C_6$ alkyl, or $C_3$-$C_6$ cycloalkyl, such $C_1$-$C_6$ alkyl or $C_3$-$C_6$ cycloalkyl being optionally substituted by a group $C_1$-$C_3$ alkyl, —$OR^M$, —CN, or halo;

$R^M$ is at each occurrence independently hydrogen, $C_1$-$C_6$ alkyl, or $C_3$-$C_6$ cycloalkyl, such $C_1$-$C_6$ alkyl or $C_3$-$C_6$ cycloalkyl being optionally substituted by a group hydroxyl, —CN or halo;

$z^1$, $z^2$, $z^3$, and $z^4$ are independently selected from the group consisting of C, N, S, O, a group —CH—, and a group —NH—, in such a combination that the resulting ring formed is an aromatic system;

$R^{19}$ is selected from the group consisting of hydrogen, —$CF_3$, —$NR^ER^F$, —($C_3$-$C_7$cycloalkyl), —($C_3$-$C_7$heterocycloalkyl), aryl, and heteroaryl wherein any of such —($C_3$-$C_7$cycloalkyl), —($C_3$-$C_7$heterocycloalkyl), aryl or heteroaryl may be optionally substituted by a group $C_1$-$C_6$ alkyl, $C_3$-$C_7$ cycloalkyl, or halo; or $R^{19}$ is a group of general formula (V):

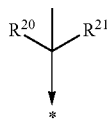

(V)

wherein $R^{20}$, $R^{21}$, $R^E$ and $R^F$ are as above defined;

T is —N= or —$CR^{23}$=;

$R^{23}$ is H, halo, —$CH_3$, or —CN;

$R^{22}$ is H, halo, —$CH_3$, or —CN;

q is 0, 1, 2, or 3;

with the proviso that when Y is a group —$O(CR^3R^4)_n$—, n is 1, and $R^{10}$ is —$NR^AR^B$, —$N(R^C)C(O)$—($C_1$-$C_6$alkylene)-$NR^AR^B$, —$N(R^C)C(O)$—($C_3$-$C_7$cycloalkylene)-$NR^AR^B$, —$N(R^C)C(O)N(R^AR^B)$, —$N(R^C)C(O)N(R^C)$—($C_2$-$C_6$alkylene)-$NR^AR^B$, —$N(R^C)C(O)N(R^C)$—($C_3$-$C_7$cycloalkylene)-$NR^AR^B$, or —$N(R^C)C(O)R^C$, then $X_1$ is nitrogen.

In another embodiment, the present invention provides compounds of formula (IP), and pharmaceutically acceptable salts thereof:

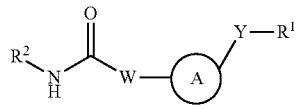

(IP)

wherein:

W is a heteroatom selected from N and O, wherein N is substituted with hydrogen or $C_1$-$C_6$ alkyl, or $C_3$-$C_5$ cycloalkyl;

Y is selected from the group consisting of: a group —$S(O)_p$— wherein p is 0, 1 or 2; a group —$O(CR^3R^4)_n$—; a group —$(CR^5R^6)_n$—; a group —$NR^7$—; a group —OC(O)—; a group —OC(O)NH—; and a group —OC(O)O—;

$R^3$, $R^4$, $R^5$ and $R^6$ are each independently hydrogen, fluorine or $C_1$-$C_6$ alkyl, or, respectively, $R^3$ and $R^4$, or $R^5$ and $R^6$ may form, together with the carbon atom to which they are attached, a saturated 3-6 membered carbocyclic monocyclic ring optionally substituted by a group $C_1$-$C_6$ alkyl, hydroxyl or halo.

n is 0, 1, 2 or 3

$R^7$ is hydrogen, $C_1$-$C_6$ alkyl, or $C_3$-$C_7$ cycloalkyl wherein such $C_1$-$C_6$ alkyl or $C_3$-$C_7$ cycloalkyl are optionally substituted by a group $C_1$-$C_3$ alkyl, $C_3$-$C_6$ cycloalkyl, hydroxyl, cyano, or halo;

$R^1$ is a group selected from (IIa)-(IIc):

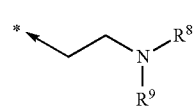

(IIa)

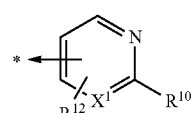

(IIb)

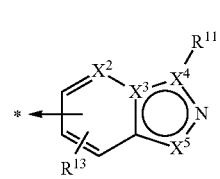

(IIc)

$R^8$ and $R^9$ are each independently hydrogen or $C_1$-$C_6$ alkyl, or $R^8$ and $R^9$ may form, together with the nitrogen atom to which they are attached, a 5-11-membered saturated monocyclic or a fused or Spiro bicyclic ring system optionally containing a further heteroatom which is oxygen or nitrogen, said nitrogen atom being optionally substituted by $C_1$-$C_6$ alkyl; wherein such $C_1$-$C_6$ alkyl groups may be optionally substituted by a group $C_1$-$C_6$ alkyl, $C_3$-$C_6$ cycloalkyl, hydroxyl or halo;

$X^1$, $X^2$, $X^3$, $X^4$ and $X^5$ are each independently a carbon atom, a nitrogen atom, a group —(CH)— or a group —NH—; such that each combination thereof forms an aromatic ring system;

$R^{10}$ is selected from the group consisting of hydrogen, —CN, —$NR^AR^B$, —$N(R^C)(C_2$-$C_6$alkylene)-$NR^AR^B$, —$N(R^C)(C_3$-$C_7$cycloalkylene)-$NR^AR^B$, —($C_1$-$C_6$alkylene)-$NR^AR^B$, —($C_3$-$C_7$cycloalkylene)-$NR^AR^B$, —O—($C_2$-$C_6$alkylene)-$NR^AR^B$, —O—($C_3$-$C_7$cycloalkylene)-$NR^AR^B$, —S—($C_2$-$C_6$alkylene)-$NR^AR^B$, —S—($C_3$-$C_7$cycloalkylene)-$NR^AR^B$, —$N(R^C)C(O)$—($C_1$-$C_6$alkylene)-$NR^AR^B$, —$N(R^C)C(O)$—($C_3$-$C_7$cycloalkylene)-$NR^AR^B$, —$C(O)N(R^C)$—($C_2$-$C_6$alkylene)-$NR^AR^B$, —$C(O)N(R^C)$—($C_3$-$C_7$cycloalkylene)-$NR^AR^B$, —$C(O)N(R^C)$—($C_2$-$C_6$alkylene)-$OR^D$, —$C(O)N(R^C)$—($C_3$-$C_7$cycloalkylene)-$OR^D$, —$N(R^C)C(O)NR^AR^B$, —$C(O)NR^AR^B$, —$N(R^C)C(O)N(R^C)$—($C_2$-$C_6$alkylene)-$NR^AR^B$, —$N(R^C)C(O)N(R^C)$—($C_3$-$C_7$cycloalkylene)-$NR^AR^B$, —($C_2$-$C_6$alkylene)-$OR^D$, —($C_3$-$C_7$cycloalkylene)-$OR^D$, —O—($C_2$-$C_6$alkylene)-$OR^D$, —O—($C_3$-$C_7$cycloalkylene)-$OR^D$, —S—($C_2$-$C_6$alkylene)-$OR^D$, —S—($C_3$-$C_7$cycloalkylene)-$OR^D$, —$N(R^C)S(O)_2$—($C_1$-$C_6$alkylene)-$NR^AR^B$, —$N(R^C)S(O)_2$—($C_3$-$C_7$cycloalkylene)-$NR^AR^B$, —$S(O)_2N(R^C)$—($C_2$-$C_6$alkylene)-$NR^AR^B$, —$S(O)_2N(R^C)$—($C_3$-$C_7$cycloalkylene)-$NR^AR^B$, —$S(O)_2N(R^C)$—($C_2$-$C_6$alkylene)-$OR^D$, —$S(O)_2N(R^C)$—($C_3$-$C_7$cycloalkylene)-$OR^D$, —$N(R^C)S(O)_2$—($C_2$-$C_6$alkylene)-$OR^D$, —$N(R^C)S(O)_2$—($C_3$-$C_7$cycloalkylene)-$OR^D$, —$S(O)_2N(R^AR^B)$, —$N(R^C)S(O)_2R^D$, —$N(R^C)C(O)R^C$, $OR^C$, $SR^C$, —($C_3$-$C_7$heterocycloalkyl), ($C_5$-$C_7$heterocycloalkyl)-($C_1$-$C_6$alkyl), ($C_5$-$C_7$heterocycloalkyl)($C_3$-$C_6$cycloalkyl)-, and $C_3$-$C_7$ heterocycloalkylcarbonyl, wherein any of such alkylene, cycloalkylene, heterocycloalkyl, heterocycloalkyl-($C_1$-$C_6$ alkyl), heterocycloalkyl-($C_3$-$C_6$cycloalkyl) and heterocycloalkylcarbonyl may be optionally substituted by a group $C_1$-$C_6$ alkyl, $C_3$-$C_7$ cycloalkyl, hydroxyl or halo.

$R^{11}$ is linked to $X^4$ and is selected from a group consisting of hydrogen; —CN; $C_1$-$C_6$ alkyl which is substituted by a group selected from —CN, —$OR^C$, —$SR^C$, halo; $C_3$-$C_6$cycloalkyl which is substituted by a group selected from $C_1$-$C_4$ alkyl, —CN, —$OR^C$, —$SR^D$, halo; —$NR^AR^B$, —$N(R^C)$($C_2$-$C_6$alkylene)-$NR^AR^B$, —$N(R^C)$($C_3$-$C_7$cycloalkylene)-$NR^AR^B$, —($C_1$-$C_6$alkylene)-$NR^AR^B$, ($C_3$-$C_7$cycloalkylene)-$NR^AR^B$, —O—($C_2$-$C_6$alkylene)-$NR^AR^B$, —O—($C_3$-$C_7$cycloalkylene)-$NR^AR^B$, —S—($C_2$-$C_6$alkylene)-$NR^AR^B$, —S—($C_3$-$C_7$cycloalkylene)-$NR^AR^B$, —$N(R^C)C(O)$—($C_1$-$C_6$alkylene)-$NR^AR^B$, —$N(R^C)C(O)$—($C_3$-$C_7$cycloalkylene)-$NR^AR^B$, —$C(O)N(R^C)$—($C_2$-$C_6$alkylene)-$NR^AR^B$, —$C(O)N(R^C)$—($C_3$-$C_7$cycloalkylene)-$NR^AR^B$, —$C(O)N(R^C)$—($C_2$-$C_6$alkylene)-$OR^D$, —$C(O)N(R^C)$—($C_3$-$C_7$cycloalkylene)-$OR^D$, —$N(R^C)C(O)N(R^AR^B)$, —$C(O)N(R^AR^B)$, $N(R^C)C(O)N(R^C)$—($C_2$-$C_6$alkylene)-$NR^AR^B$, —$N(R^C)C(O)N(R^C)$—($C_3$-$C_7$cycloalkylene)-$NR^AR^B$, —O—($C_2$-$C_6$alkylene)-$OR^D$, —O—($C_3$-$C_7$cycloalkylene)-$OR^D$, —S—($C_2$-$C_6$alkylene)-$OR^D$, —S—($C_3$-$C_7$cycloalkylene)-$OR^D$, —$N(R^C)S(O)_2$—($C_1$-$C_6$alkylene)-$NR^AR^B$, —$N(R^C)S(O)_2$—($C_3$-$C_7$cycloalkylene)-$NR^AR^B$, —$S(O)_2N(R^C)$—($C_2$-$C_6$alkylene)-$NR^AR^B$, —$S(O)_2N(R^C)$—($C_3$-$C_7$cycloalkylene)-$NR^AR^B$, —$S(O)_2N(R^C)$—($C_2$-$C_6$alkylene)-$OR^D$, —$S(O)_2N(R^C)$—($C_3$-$C_7$cycloalkylene)-$OR^D$, —$N(R^C)S(O)_2$—($C_2$-$C_6$alkylene)-$OR^D$, —$N(R^C)S(O)_2$—($C_3$-$C_7$cycloalkylene)-$OR^D$, —$S(O)_2N(R^AR^B)$, —$N(R^C)S(O)_2R^D$, —$N(R^C)C(O)R^C$, $OR^C$, $SR^C$, —($C_3$-$C_7$heterocycloalkyl), ($C_5$-$C_7$heterocycloalkyl)-($C_1$-$C_6$alkyl), ($C_5$-$C_7$heterocycloalkyl)($C_3$-$C_6$cycloalkyl), $C_3$-$C_7$ heterocycloalkylcarbonyl, wherein any of such alkylene, cycloalkylene, heterocycloalkyl, heterocycloalkyl-($C_1$-$C_6$alkyl), heterocycloalkyl-($C_3$-$C_6$cycloalkyl) and heterocycloalkylcarbonyl may be optionally substituted by a group $C_1$-$C_6$ alkyl, $C_3$-$C_7$ cycloalkyl, hydroxyl or halo; or R11 is linked to $X^4$ and is phenyl or 5- or 6-membered monocyclic heteroaryl, wherein such phenyl or 5- or 6-membered monocyclic heteroaryl is substituted by a group selected from the group consisting of $C_1$-$C_6$ alkyl which is substituted by a group —CN; $C_3$-$C_6$ cycloalkyl which is substituted by a group selected from: —CN, —$OR^C$, —$SR^C$ or halo; —$N(R^C)$($C_2$-$C_6$alkylene)-$NR^AR^B$, —$N(R^C)$($C_3$-$C_7$cycloalkylene)-$NR^AR^B$, —($C_1$-$C_6$alkylene)-$NR^AR^B$, —($C_3$-$C_7$cycloalkylene)-$NR^AR^B$, —O—($C_3$-$C_7$cycloalkylene)-$NR^AR^B$, —S—($C_2$-$C_6$alkylene)-$NR^AR^B$, —S—($C_3$-$C_7$cycloalkylene)-$NR^AR^B$, —$N(R^C)C(O)$—($C_1$-$C_6$alkylene)-$NR^AR^B$, —$N(R^C)C(O)$—($C_3$-$C_7$cycloalkylene)-$NR^AR^B$, —$C(O)N(R^C)$—($C_2$-$C_6$alkylene)-$NR^AR^B$, —$C(O)N(R^C)$—($C_3$-$C_7$cycloalkylene)-$NR^AR^B$, —$C(O)N(R^C)$—($C_2$-$C_6$alkylene)-$OR^D$, —$C(O)N(R^C)$—($C_3$-$C_7$cycloalkylene)-$OR^D$, —$N(R^C)C(O)N(R^C)$—($C_2$-$C_6$alkylene)-$NR^AR^B$, —$N(R^C)C(O)N(R^C)$—($C_3$-$C_7$cycloalkylene)-$NR^AR^B$, —O—($C_3$-$C_7$cycloalkylene)-$OR^D$, —S—($C_3$-$C_7$cycloalkylene)-$OR^D$, —$N(R^C)S(O)_2$—($C_1$-$C_6$alkylene)-$NR^AR^B$, —$N(R^C)S(O)_2$—($C_3$-$C_7$cycloalkylene)-$NR^AR^B$, —$S(O)_2N(R^C)$—($C_2$-$C_6$alkylene)-$NR^AR^B$, —$S(O)_2N(R^C)$—($C_3$-$C_7$cycloalkylene)-$NR^AR^B$, —$S(O)_2N(R^C)$—($C_2$-$C_6$alkylene)-$OR^D$, —$S(O)_2N(R^C)$—($C_3$-$C_7$cycloalkylene)-$OR^D$, —$N(R^C)S(O)_2$—($C_2$-$C_6$alkylene)-$OR^D$, —$N(R^C)S(O)_2$—($C_3$-$C_7$cycloalkylene)-$OR^D$, —$N(R^C)S(O)_2R^D$, —($C_3$-$C_7$heterocycloalkyl), ($C_5$-$C_7$heterocycloalkyl)-($C_1$-$C_6$alkyl), ($C_5$-$C_7$heterocycloalkyl)($C_3$-$C_6$cycloalkyl), $C_3$-$C_7$heterocycloalkylcarbonyl, wherein any of such alkylene, cycloalkylene, heterocycloalkyl, heterocycloalkyl-($C_1$-$C_6$alkyl), heterocycloalkyl-($C_3$-$C_6$cycloalkyl) and heterocycloalkylcarbonyl may be optionally substituted by a group $C_1$-$C_6$alkyl, $C_3$-$C_7$cycloalkyl, hydroxyl or halo;

$R^A$ and $R^B$ are at each occurrence independently hydrogen, $C_1$-$C_6$ alkyl or $C_3$-$C_7$ cycloalkyl, such $C_1$-$C_6$alkyl and $C_3$-$C_7$ cycloalkyl being optionally substituted by a group $C_1$-$C_3$ alkyl, $C_3$-$C_7$cycloalkyl, —$OR^D$, —CN or halo; alternatively, $R^A$ and $R^B$, may form, together with the nitrogen atom to which they are attached, a 5-11-membered saturated monocyclic or bicyclic ring system which is optionally substituted by one or more group $OR^D$, CN, halo, $C_1$-$C_6$ alkyl or $C_3$-$C_7$ cycloalkyl, such $C_1$-$C_6$ alkyl and $C_3$-$C_7$ cycloalkyl being optionally substituted by a group $C_1$-$C_3$ alkyl, $C_3$-$C_7$cycloalkyl, $OR^D$, CN or halo; and which 5-11-membered saturated monocyclic or bicyclic ring optionally contains a further heteroatom which is oxygen or nitrogen, said nitrogen atom optionally substituted by $C_1$-$C_6$ alkyl or $C_3$-$C_6$ cycloalkyl wherein any of such alkyl or cycloalkyl may be optionally substituted by a group $C_1$-$C_6$ alkyl, $C_3$-$C_7$ cycloalkyl, —$OR^D$, —CN, or halo; and/or $R^A$ and $R^B$ may be linked to one carbon atom of the alkylene or cycloalkylene portion of the group linked to the nitrogen to which they are connected to form a saturated cycle of up to 6 ring atoms;

$R^C$ is at each occurrence independently hydrogen, $C_1$-$C_6$ alkyl, or $C_3$-$C_6$ cycloalkyl, such $C_1$-$C_6$ alkyl and $C_3$-$C_6$ cycloalkyl being optionally substituted by a group $C_1$-$C_3$ alkyl, —$OR^D$, —CN, or halo;

$R^D$ is at each occurrence independently hydrogen, —$CH_3$, or —$C_2H_5$;

$R^{12}$ and $R^{13}$ are independently hydrogen, $C_1$-$C_6$ alkyl, or halogen;

A is a divalent cycloalkylene radical having 5, 6 or 7 ring atoms; said cycloalkylene ring being attached to W and Y, and fused to a phenyl ring or to a monocyclic heteroaryl ring having 5 or 6 ring atoms, such phenyl or heteroaryl ring being optionally substituted by one or two groups $R^{24}$;

$R^{24}$ is at each occurrence independently selected from the group consisting of: $C_1$-$C_6$ alkyl, halogen and cyano;

$R^2$ is a radical of formula (IIIa), (IIIb), (IIIc), or (IIId):

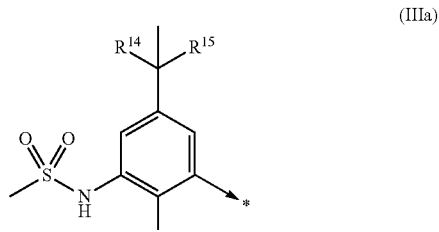

(IIIa)

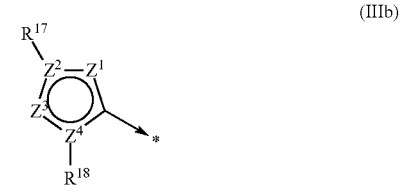

(IIIb)

-continued

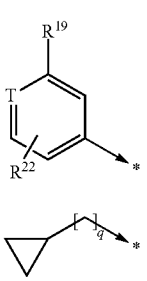

(IIIc)

(IIId)

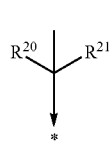

wherein
R$^{14}$ is selected from the group consisting of —F, —CH$_3$, —C$_2$H$_5$, —CH$_2$OH, —CH$_2$OMe, —CF$_2$CF$_3$, —CH$_2$SCH$_3$, —SCH$_3$, and —SC$_2$H$_5$;

R$^{15}$ and R$^{16}$ are independently —CH$_3$ or —C$_2$H$_5$;

R$^{17}$ is selected from the group consisting of lone electron pair, hydrogen, —CF$_3$, —NR$^E$R$^F$, —(C$_3$-C$_7$cycloalkyl), —(C$_3$-C$_7$heterocycloalkyl), aryl, and heteroaryl wherein any of such cycloalkyl, heterocycloalkyl, aryl or heteroaryl may be optionally substituted by a group C$_1$-C$_6$ alkyl, C$_3$-C$_7$ cycloalkyl, or halo; or R$^{17}$ is a group of general formula (IV):

(IV)

wherein
R$^{20}$ is selected in the group consisting of: —F, —CH$_3$, —C$_2$H$_5$, —CH$_2$OH, —CH$_2$OMe, —CF$_2$CF$_3$, —CH$_2$SCH$_3$, —SCH$_3$, and —SC$_2$H$_5$;

R$^{21}$ is —CH$_3$ or —C$_2$H$_5$;
or;

R$^{20}$ and R$^{21}$ as defined above may form, together with the carbon atom to which they are attached, a saturated 3-7-membered monocyclic ring;

R$^E$ and R$^F$ are each independently C$_1$-C$_6$ alkyl, optionally substituted by a group C$_1$-C$_3$ alkyl, —OR$^G$, —CN or halo; alternatively, R$^E$ and R$^F$ may form, together with the nitrogen atom to which they are attached, a 5-11-membered saturated monocyclic or bicyclic ring system which is optionally substituted by one or more groups —OR$^G$, —CN, halo, C$_1$-C$_6$ alkyl or C$_3$-C$_7$ cycloalkyl, such C$_1$-C$_6$ alkyl and C$_3$-C$_7$ cycloalkyl being optionally substituted by a group C$_1$-C$_3$ alkyl, C$_3$-C$_7$cycloalkyl, —OR$^G$, —CN or halo; and which 5-11-membered saturated monocyclic or bicyclic ring optionally contains a further heteroatom which is oxygen or nitrogen, said nitrogen atom optionally substituted by C$_1$-C$_6$ alkyl or C$_3$-C$_6$ cycloalkyl wherein any of such alkyl or cycloalkyl may be optionally substituted by a group C$_1$-C$_6$ alkyl, C$_3$-C$_7$ cycloalkyl;

R$^G$ is hydrogen, —CH$_3$, or —C$_2$H$_5$;

R$^{18}$ is selected from the group consisting of lone electron pair, hydrogen, aryl, heteroaryl, —(C$_1$-C$_6$alkyl), —(C$_3$-C$_7$cycloalkyl), —(C$_3$-C$_7$heterocycloalkyl), (C$_5$-C$_7$heterocycloalkyl)-(C$_1$-C$_6$alkyl) or (C$_5$-C$_7$heterocycloalkyl)-(C$_3$-C$_6$ cycloalkyl), wherein any of such aryl, heteroaryl, alkyl, cycloalkyl, heterocycloalkyl, heterocycloalkyl-(C$_1$-C$_6$ alkyl), or heterocycloalkyl-(C$_3$-C$_6$ cycloalkyl) may be optionally substituted by a group —CN, —OH, halo, —COOR$^M$, C$_3$-C$_6$cycloalkyl, —O—(C$_1$-C$_6$alkyl), —O—(C$_3$-C$_6$cycloalkyl), —S—(C$_1$-C$_6$alkyl), —S—(C$_3$-C$_6$cycloalkyl), —NR$^H$R$^J$, —N(R$^L$)(C$_2$-C$_6$alkylene)-NR$^H$R$^J$, —N(R$^L$)(C$_3$-C$_7$cycloalkylene)-NR$^H$R$^J$, —(C$_1$-C$_6$alkylene)-NR$^H$R$^J$, —(C$_3$-C$_7$cycloalkylene)-NR$^H$R$^J$, —O—(C$_2$-C$_6$alkylene)-NR$^H$R$^J$, —O—(C$_3$-C$_7$cycloalkylene)-NR$^H$R$^J$, —S—(C$_2$-C$_6$alkylene)-NR$^H$R$^J$, —S—(C$_3$-C$_7$cycloalkylene)-NR$^H$R$^J$, —N(R$^L$)C(O)—(C$_1$-C$_6$alkylene)-NR$^H$R$^J$, —N(R$^L$)C(O)—(C$_3$-C$_7$cycloalkylene)-NR$^H$R$^J$, —C(O)N(R$^L$)—(C$_2$-C$_6$alkylene)-NR$^H$R$^J$, —C(O)N(R$^L$)—(C$_3$-C$_7$cycloalkylene)-NR$^H$R$^J$, —C(O)N(R$^L$)—(C$_2$-C$_6$alkylene)-OR$^M$, —C(O)N(R$^L$)—(C$_3$-C$_7$cycloalkylene)-OR$^M$, —N(R$^L$)C(O)N(R$^H$R$^J$), —C(O)N(R$^H$R$^J$), —N(R$^L$)C(O)N(R$^L$)—(C$_2$-C$_6$alkylene)-NR$^H$R$^J$, —N(R$^L$)C(O)N(R$^L$)—(C$_3$-C$_7$cycloalkylene)-NR$^H$R$^J$, —O—(C$_2$-C$_6$alkylene)-OR$^M$, —O—(C$_3$-C$_7$cycloalkylene)-OR$^M$, —S—(C$_2$-C$_6$alkylene)-OR$^M$, —S—(C$_3$-C$_7$cycloalkylene)-OR$^M$, —N(R$^L$)S(O)$_2$—(C$_1$-C$_6$alkylene)-NR$^H$R$^J$, —N(R$^L$)S(O)$_2$—(C$_3$-C$_7$cycloalkylene)-NR$^H$R$^J$, —S(O)$_2$N(R$^L$)—(C$_2$-C$_6$alkylene)-NR$^H$R$^J$, —S(O)$_2$N(R$^L$)—(C$_3$-C$_7$cycloalkylene)-NR$^H$R$^J$, —S(O)$_2$N(R$^L$)—(C$_2$-C$_6$alkylene)-OR$^M$, —S(O)$_2$N(R$^L$)—(C$_3$-C$_7$cycloalkylene)-OR$^M$, —N(R$^L$)S(O)$_2$—(C$_2$-C$_6$alkylene)-OR$^M$, —N(R$^L$)S(O)$_2$—(C$_3$-C$_7$cycloalkylene)-OR$^M$, —S(O)$_2$N(R$^H$R$^J$), —N(R$^L$)S(O)$_2$R$^L$, —N(R$^L$)C(O)R$^L$, OR$^L$, SR$^L$, —(C$_3$-C$_7$heterocycloalkyl), (C$_5$-C$_7$heterocycloalkyl)-(C$_1$-C$_6$ alkyl), and (C$_5$-C$_7$heterocycloalkyl)-(C$_3$-C$_6$ cycloalkyl), wherein any of such alkyl, cycloalkyl, alkylene, cycloalkylene, heterocycloalkyl, heterocycloalkyl-(C$_1$-C$_6$ alkyl), and (heterocycloalkyl)-(C$_3$-C$_6$ cycloalkyl) may be optionally substituted by a group C$_1$-C$_6$ alkyl, C$_3$-C$_7$ cycloalkyl, OR$^L$ or halo;

R$^H$ and R$^J$, are at each occurrence independently hydrogen, C$_1$-C$_6$ alkyl, or C$_3$-C$_6$ cycloalkyl, such C$_1$-C$_6$ alkyl or C$_3$-C$_6$ cycloalkyl being optionally substituted by a group C$_1$-C$_3$ alkyl, OR$^M$, CN or halo; alternatively, R$^H$ and R$^J$ may also form, together with the nitrogen atom to which they are attached, a 5-11-membered saturated monocyclic or bicyclic ring system which is optionally substituted by one or more group OR$^M$, CN, halo, C$_1$-C$_6$ alkyl or C$_3$-C$_7$ cycloalkyl, such C$_1$-C$_6$ alkyl and C$_3$-C$_7$ cycloalkyl being optionally substituted by a group C$_1$-C$_3$ alkyl, C$_3$-C$_7$cycloalkyl, OR$^M$, CN, or halo; and which 5-11-membered saturated monocyclic or bicyclic ring optionally contains a further heteroatom which is oxygen or nitrogen, said nitrogen atom optionally substituted by C$_1$-C$_6$ alkyl or C$_3$-C$_6$ cycloalkyl wherein any of such alkyl or cycloalkyl may be optionally substituted by a group C$_1$-C$_6$ alkyl, C$_3$-C$_7$ cycloalkyl, —OR$^M$, —CN, or halo; and/or R$^H$ and R$^J$ may be linked to one carbon atom of the alkylene or cycloalkylene portion of the group linked to the nitrogen to which they are connected to form a saturated cycle of up to 6 ring atoms;

R$^L$ is at each occurrence independently hydrogen, C$_1$-C$_6$ alkyl, or C$_3$-C$_6$ cycloalkyl, such C$_1$-C$_6$ alkyl or C$_3$-C$_6$ cycloalkyl being optionally substituted by a group C$_1$-C$_3$ alkyl, OR$^M$, CN, or halo;

R$^M$ is at each occurrence independently hydrogen, C$_1$-C$_6$ alkyl, or C$_3$-C$_6$ cycloalkyl, such C$_1$-C$_6$ alkyl or C$_3$-C$_6$ cycloalkyl being optionally substituted by a group hydroxyl, CN, or halo;

z$^1$, z$^2$, z$^3$, and z$^4$ are independently selected from the group consisting of C, N, S, O, a group —CH—, and a group —NH—, in such a combination that the resulting ring formed is an aromatic system;

R$^{19}$ is selected from the group consisting of hydrogen, —CF$_3$, —NR$^E$R$^F$, —(C$_3$-C$_7$cycloalkyl), —(C$_3$-

$C_7$heterocycloalkyl), aryl, and heteroaryl wherein any of such cycloalkyl, heterocycloalkyl, aryl or heteroaryl may be optionally substituted by a group $C_1$-$C_6$ alkyl, $C_3$-$C_7$ cycloalkyl, or halo or;

$R^{19}$ is a group of general formula (V):

wherein $R^{20}$, $R^{21}$, $R^E$ and $R^F$ are as above defined;
T is —N= or —$CR^{23}$=;
$R^{23}$ is H, halo, —$CH_3$, or —CN;
$R^{22}$ is H, halo, —$CH_3$, or —CN;
q is 0, 1, 2 or 3;

with the proviso that when Y is a group —$O(CR^3R^4)_n$—, n is 1 and $R^{10}$ is —$NR^AR^B$, —$N(R^C)C(O)$—$(C_1$-$C_6$alkylene)-$NR^AR^B$, —$N(R^C)C(O)$—$(C_3$-$C_7$cycloalkylene)-$NR^AR^B$, —$N(R^C)C(O)N(R^AR^B)$, —$N(R^C)C(O)N(R^C)$—$(C_2$-$C_6$alkylene)-$NR^AR^B$, —$N(R^C)C(O)N(R^C)$—$(C_3$-$C_7$cycloalkylene)-$NR^AR^B$, or —$N(R^C)C(O)R^C$, then $X_1$ is nitrogen.

In another aspect, the invention includes pharmaceutical compositions comprising a compound or salt thereof of the present invention, together with one or more pharmaceutically acceptable carriers and/or excipients. Particularly preferred are compositions adapted for inhalation for pulmonary administration.

The compounds of the present invention are inhibitors of p38 mitogen activated protein kinase ("p38 MAPK," "p38 kinase," or "p38"), including p38α kinase, and are inhibitors of cytokine and chemokine production including TNFα and IL-8 production. They have a number of therapeutic applications, in the treatment of inflammatory diseases, particularly allergic and non-allergic airways diseases, more particularly obstructive or inflammatory airways diseases such as chronic obstructive pulmonary disease ("COPD") and asthma. They are therefore particularly suited for pulmonary delivery, by inhalation by nose or mouth.

It is believed that the compounds of the present invention can be used to treat p38 mediated diseases such as: chronic obstructive pulmonary disease (COPD), asthma, chronic or acute bronchoconstriction, bronchitis, acute lung injury and bronchiectasis, pulmonary artery hypertension, tuberculosis, lung cancer, inflammation generally (e.g. inflammatory bowel disease), arthritis, neuroinflammation, pain, fever, fibrotic diseases, pulmonary disorders and diseases (e.g., hyperoxic alveolar injury), cardiovascular diseases, post-ischemic reperfusion injury and congestive heart failure, cardiomyopathy, stroke, ischemia, reperfusion injury, renal reperfusion injury, brain edema, neurotrauma and brain trauma, neurodegenerative disorders, central nervous system disorders, liver disease and nephritis, gastrointestinal conditions, ulcerative diseases, Crohn's disease, ophthalmic diseases, ophthalmological conditions, glaucoma, acute injury to the eye tissue and ocular traumas, diabetes, diabetic nephropathy, skin-related conditions, myalgias due to infection, influenza, endotoxic shock, toxic shock syndrome, autoimmune disease, graft rejection, bone resorption diseases, multiple sclerosis, psoriasis, eczema, disorders of the female reproductive system, pathological (but non-malignant) conditions, such as hemangiomas, angiofibroma of the nasopharynx, and avascular necrosis of bone, benign and malignant tumors/neoplasia including cancer, leukaemia, lymphoma, systemic lupus erythematosus (SLE), angiogenesis including neoplasia, haemorrhage, coagulation, radiation damage, and/or metastasis. Chronic release of active TNF can cause cachexia and anorexia, and TNF can be lethal. TNF has also been implicated in infectious diseases. These include, for example, malaria, mycobacterial infection and meningitis. These also include viral infections, such as HIV, influenza virus, and herpes virus, including herpes simplex virus type-1 (HSV-1), herpes simplex virus type-2 (HSV-2), cytomegalovirus (CMV), varicella-zoster virus (VZV), Epstein-Barr virus, human herpes virus-6 (HHV-6), human herpesvirus-7 (HHV7), human herpesvirus-8 (HHV-8), pseudorabies and rhinotracheitis, among others.

Thus, in another aspect, the present invention provides the use of a compound or salt thereof of the present invention for the treatment of diseases or conditions which benefit from inhibition of p38 MAP kinase activity. The treatment of obstructive or inflammatory airways diseases is a preferred use. All forms of obstructive or inflammatory airways diseases are potentially treatable with the compounds of the present invention, in particular an obstructive or inflammatory airways disease that is a member selected from the group consisting of chronic eosinophilic pneumonia, asthma, COPD, COPD that includes chronic bronchitis, pulmonary emphysema or dyspnea associated or not associated with COPD, COPD that is characterized by irreversible, progressive airways obstruction, adult respiratory distress syndrome (ARDS), exacerbation of airways hyper-reactivity consequent to other drug therapy and airways disease that is associated with pulmonary hypertension, chronic inflammatory diseases including cystic fibrosis, broncietasis and pulmonary fibrosis (Idiopathic). Efficacy is anticipated when p38 kinase inhibitors are administered either locally to the lung (for example by inhalation and intranasal delivery) or via systemic routes (for example, oral, intravenous and subcutaneous delivery).

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
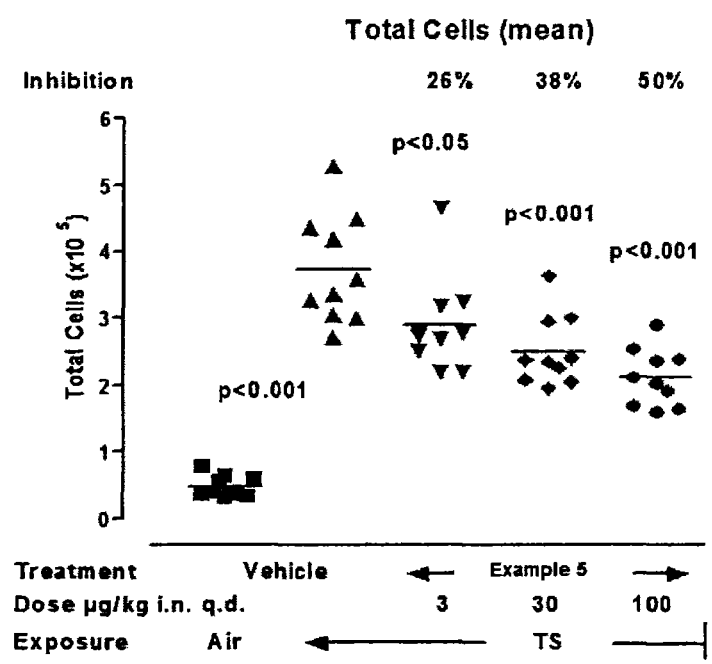
FIG. 1 is a graph that illustrates the effect of intranasal administration to laboratory mice with vehicle (0.2% tween 80 in saline), Example 5 (3 μg/kg), Example 5 (30 μg/kg) or Example 5 (100 μg/kg) on the number of BAL cells induced by tobacco smoke 24 hours post the final exposure.

As used herein, the terms "halogen" or "halo" include fluorine, chlorine, bromine, and iodine atoms.

As used herein, the term "$C_x$-$C_y$alkyl" wherein x and y are integers, refers to a straight or branched chain alkyl radical having from x to y carbon atoms. Thus when x is 1 and y is 6, for example, the term includes methyl, ethyl, n-propyl, isopropyl, n-butyl, isobutyl, sec-butyl, t-butyl, n-pentyl and n-hexyl.

As used herein, the term "$C_x$-$C_y$haloalkyl" refers to the above "$C_x$-$C_y$alkyl" group wherein one or more hydrogen atoms are replaced by one or more halogen atoms.

As used herein, the term "$C_x$-$C_y$hydroxyalkyl" refers to the above "$C_x$-$C_y$alkyl" group wherein one hydrogen atom is replaced by one hydroxyl group.

As used herein, the term "$C_x$-$C_y$alkylene" wherein x and y are integers, refers to a $C_x$-$C_y$alkyl radical having in total two unsatisfied valencies, such as a divalent methylene radical.

As used herein, the term "carbocyclic" refers to a mono-, bi-, or tricyclic radical having up to 16 ring atoms, all of which are carbon, and includes aryl and cycloalkyl.

As used herein, the term "$C_z$-$C_k$cycloalkyl" wherein z and k are integers refers to a monocyclic saturated carbocyclic radical having from z to k carbon atoms and includes, for example, cyclopropyl, cyclobutyl, cyclopentyl, cyclohexyl, cyclohepty, and cyclooctyl. Comprised within the scope of the term "$C_z$-$C_k$cycloalkyl" are those radicals having two unsatisfied valencies on the same carbon atom which will link to any $C_x$-$C_y$alkyl, $C_x$-$C_y$alkylene $C_z$-$C_k$cycloalkyl $C_z$-$C_k$cycloalkylene, $C_z$-$C_k$heterocycloalkyl, $C_z$-$C_k$heterocycloalkyl $C_x$-$C_y$alkyl, $C_z$-$C_k$heterocycloalkyl$C_z$-$C_k$cycloalkyl or ($C_z$-$C_k$)heterocycloalkylcarbonyl group by replacement of two hydrogen atoms placed on the same carbon. In such circumstances, this radical forms a gem-disubstituted or spiro system together with the $C_x$-$C_y$alkyl, $C_x$-$C_y$alkylene $C_z$-$C_k$cycloalkyl $C_z$-$C_k$cycloalkylene, $C_z$-$C_k$heterocycloalkyl, $C_z$-$C_k$heterocycloalkyl$C_x$-$C_y$alkyl, $C_z$-$C_k$heterocycloalkyl$C_z$-$C_k$cycloalkyl or ($C_z$-$C_k$)heterocycloalkylcarbonyl group it is linked to.

The term "$C_z$-$C_k$cycloalkylene radical" refers to a $C_z$-$C_k$cycloalkyl radical having two unsatisfied valencies on different cycle carbon atoms as follows:

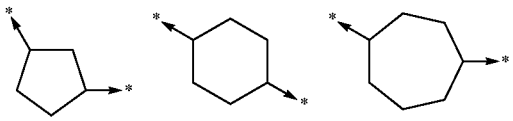

As used herein, the unqualified term "aryl" refers to a mono- or bi-cyclic carbocyclic aromatic radical, and includes radicals having two monocyclic carbocyclic aromatic rings which are directly linked by a covalent bond. Illustrative of such radicals are phenyl, biphenyl and napthyl.

As used herein, the unqualified term "heteroaryl" refers to a mono- or bi-cyclic aromatic radical containing one or more heteroatoms selected from S, N, and O, and includes radicals having two such monocyclic rings, or one such monocyclic ring and one monocyclic aryl ring, which are fused through a common bond. Illustrative examples of 5,6-membered heteroaryl are: are thienyl, furyl, pyrrolyl, imidazolyl, thiazolyl, isothiazolyl, pyrazolyl, oxazolyl, isoxazolyl, isothiazolyl, triazolyl, thiadiazolyl, oxadiazolyl, pyridinyl, pyridazinyl, pyrimidinyl, pyrazinyl, and triazinyl. Illustrative examples of 8,10-membered heteroaryl are: benzothienyl, benzofuryl, benzimidazolyl, benzothiazolyl, benzisothiazolyl, benzoxazolyl, benzisoxazolyl, benzotriazolyl, indolyl and indazolyl.

As used herein, the unqualified term "heterocyclyl" or "heterocyclic" relates to a saturated mono-, bi-, or tri-cyclic non-aromatic radical containing one or more heteroatoms selected from S, N, and O. In the case of bicyclic heterocylic systems, included within the scope of the term are fused, Spiro and bridged bicyclic systems. In particular, the term "$C_z$-$C_k$heterocycloalkyl" refers to monocyclic ($C_z$-$C_k$)cycloalkyl groups, in which at least one ring carbon atom is replaced by a heteroatom (e.g. N, NH, S, or O). Examples of ($C_z$-$C_k$)heterocycloalkyl include pyrrolidinyl, thiazolidinyl, piperazinyl, piperidinyl, morpholinyl, thiomorpholinyl.

By analogy, the term "$C_z$-$C_k$heterocycloalkylene", refers to a divalent $C_z$-$C_k$heterocycloalkyl radical, wherein $C_z$-$C_k$heterocycloalkyl is as above defined.

The term "$C_z$-$C_k$heterocycloalkyl$C_x$-$C_y$alkyl" refers to the above "$C_x$-$C_y$alkyl" group wherein one or more hydrogen atoms are replaced by one or more "$C_z$-$C_k$heterocycloalkyl" groups. Comprised within the scope of the term "$C_z$-$C_k$heterocycloalkyl$C_x$-$C_y$alkyl" are systems where two hydrogen atoms linked to the same carbon atom in "$C_x$-$C_y$alkyl" group are replaced by one "$C_z$-$C_k$heterocycloalkyl" group. Such radical thus form a gem-disubstituted "$C_z$-$C_k$heterocycloalkyl$C_x$-$C_y$alkyl" system, such as a 1,2-dimethyl-pyrrolidin-2-yl radical.

The term "$C_z$-$C_k$heterocycloalkyl$C_z$-$C_k$cycloalkyl" refers to the above "$C_z$-$C_k$cycloalkyl" group wherein one or more hydrogen atoms are replaced by one or more "$C_z$-$C_k$heterocycloalkyl" groups.

The expression "($C_z$-$C_k$)cycloalkylcarbonyl" refers to ($C_z$-$C_k$)cycloalkyl-CO-groups wherein the group "($C_z$-$C_k$)cycloalkyl" has the meaning above defined.

The expression "($C_z$-$C_k$)heterocycloalkylcarbonyl" refers to ($C_z$-$C_k$)heterocycloalkyl-CO— groups wherein the group "($C_z$-$C_k$)heterocycloalkyl" has the meaning above defined.

Compounds of the invention may exist in one or more geometrical, optical, enantiomeric, diastereomeric, and tautomeric forms, including but not limited to cis- and trans-forms, E- and Z-forms, R-, S- and meso-forms, keto-, and enol-forms. Unless otherwise stated a reference to a particular compound includes all such isomeric forms, including racemic and other mixtures thereof. Where appropriate such isomers can be separated from their mixtures by the application or adaptation of known methods (e.g. chromatographic techniques and recrystallisation techniques). Where appropriate such isomers may be prepared by the application of adaptation of known methods (e.g. asymmetric synthesis).

Throughout the specification the use of an asterisk "*" in the definition of a structural formula, indicates the point of attachment for the radical group to the rest of the molecule.

As used herein the term "salt" includes base addition, acid addition and ammonium salts. As briefly mentioned above compounds of the invention which are acidic can form salts, including pharmaceutically acceptable salts, with bases such as alkaline metal hydroxides, e.g. sodium and potassium hydroxides; alkaline earth metal hydroxides e.g. calcium, barium and magnesium hydroxides; with organic bases e.g. N-methyl-D-glucamine, choline tris(hydroxymethyl)aminomethane, L-arginine, L-lysine, N-ethyl piperidine, dibenzylamine and the like. Those compounds of the invention which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, formic, trifluoroacetic, tartaric, succinic, fumaric, maleic, malic, salicylic, citric, methanesulphonic, p-toluenesulphonic, benzoic, benzenesulfonic, glutamic, lactic, and mandelic acids and the like. Those compounds (I) which have a basic nitrogen can also form quaternary ammonium salts with a pharmaceutically acceptable counter-ion such as ammonium, chloride, bromide, acetate, formate, p-toluenesulfonate, succinate, hemi-succinate, naphthalene-bis sulfonate, methanesulfonate, trifluoroacetate, xinafoate, and the like. For a review on salts, see *Handbook of Pharmaceutical Salts: Properties, Selection, and Use* by Stahl and Wermuth (Wiley-VCH, Weinheim, Germany, 2002), which is incorporated herein by reference in its entirety.

It is expected that compounds of the present invention may be prepared in the form of hydrates, and solvates. Any reference herein, including the claims herein, to "compounds with which the invention is concerned" or "compounds of the invention" or "the present compounds", and the like, includes reference to salts hydrates, and solvates of such compounds. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Individual compounds of the present invention may exist in several polymorphic forms and may be obtained in different crystal or co-crystal habits, and they are intended to be included within the meaning of the term "compounds of the invention".

The compounds may also be administered in the form of prodrugs thereof. Thus, certain derivatives of the present compounds which may be active in their own right or may have little or no pharmacological activity themselves can, when administered into or onto the body, be converted into compounds of the invention having the desired activity, for example, by hydrolytic cleavage. Such derivatives are referred to as 'prodrugs'. Further information on the use of prodrugs may be found in *Pro-drugs as Novel Delivery Systems*, Vol. 14, ACS Symposium Series (T. Higuchi and V. J. Stella) and *Bioreversible Carriers in Drug Design*, Pergamon Press, 1987 (ed. E. B. Roche, American Pharmaceutical Association; C. S. Larsen and J. Østergaard, Design and application of prodrugs, In Textbook of Drug Design and Discovery, 3rd Edition, 2002, Taylor and Francis, which are incorporated herein by reference in their entireties).

Prodrugs in accordance with the present invention can, for example, be produced by replacing appropriate functionalities present in the compounds of formula (I) with certain moieties known to those skilled in the art as 'pro-moieties' as described, for example, in *Design of Prodrugs* by H. Bundgaard (Elsevier, 1985), which is incorporated herein by reference in its entirety. Such examples could be a prodrug of a carboxyl group (such as CO—O—CH$_2$—O—CO-tBu as used in the pivampicillin prodrug of ampicillin), an amide (—CO—NH—CH$_2$—NAlk$_2$) or an amidine (C(=N—O—CH$_3$)—NH$_2$). It is to be understood that all preferred groups or embodiments described herebelow for compounds of formula (I) may be combined among each other and apply as well to compounds of formula (Ia), (Ib), (Ic), (IA), (IB), (IC), (ID), (IE) or (IF) as below defined mutatis mutandis.

In one embodiment, compounds of formula (Ia) are provided, which are compounds of formula (I) as above defined wherein the carbon stereogenic center on the cycloalkylene portion of ring A which is linked to group W and identified with number (1) herebelow, possess the absolute configuration herebelow represented:

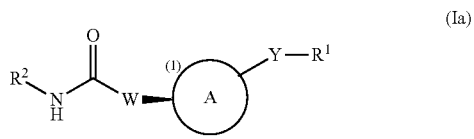

(Ia)

In another embodiment, compounds of formula (Ib) are provided, which are compounds of formula (I) as above defined wherein the carbon stereogenic centers on the cycloalkylene portion of ring A which are linked to group W and Y and identified, respectively, with numbers (1) and (2) herebelow, possess the absolute configuration herebelow represented:

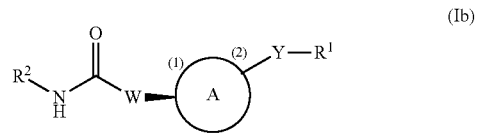

(Ib)

In a further embodiment, compounds of formula (Ic) are provided, which are compounds of formula (I) as above defined wherein the carbon stereogenic centers on the cycloalkylene portion of ring A which are linked to group W and Y and identified, respectively, with numbers (1) and (2) herebelow, possess the absolute configuration herebelow represented:

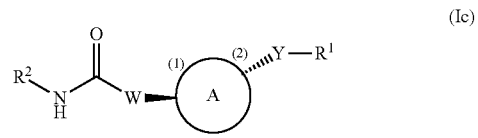

(Ic)

In one embodiment, W is NH or O. In a further embodiment, W is NH.

In one embodiment, Y is a group —S(O)$_p$—, a group —O(CR$^3$R$^4$)$_n$—, a group —(CR$^5$R$^6$)$_n$—, or a group —NR$^7$—; p is zero and n is 0, 1 or 2. In another embodiment, Y is a group —S(O)$_p$ or a group —O(CR$^3$R$^4$)$_n$ or; p is zero and n is 0 or 1.

In a further embodiment, Y is a group —O(CR$^3$R$^4$)$_n$— and n is 0.

In one embodiment, R$^3$, R$^4$, R$^5$ and R$^6$ are each independently hydrogen, fluorine, or C$_1$-C$_6$ alkyl. In another embodiment, R$^3$, R$^4$, R$^5$ and R$^6$ are hydrogen.

In one embodiment, R$^7$ is hydrogen, C$_1$-C$_6$ alkyl, or C$_3$-C$_7$ cycloalkyl.

In one embodiment, R$^7$ is hydrogen.

In one embodiment, A is a divalent cycloalkylene radical having 5 or 6 ring atoms; said cycloalkylene ring being attached to W and Y, and fused to a phenyl ring or to a monocyclic heteroaryl ring having 5 or 6 ring atoms, such phenyl or heteroaryl ring being optionally substituted by one or two groups R$^{24}$.

In a further embodiment, A is group selected in the group consisting of:

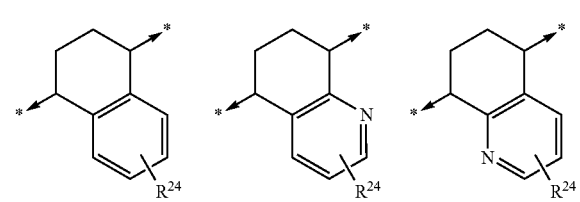

-continued

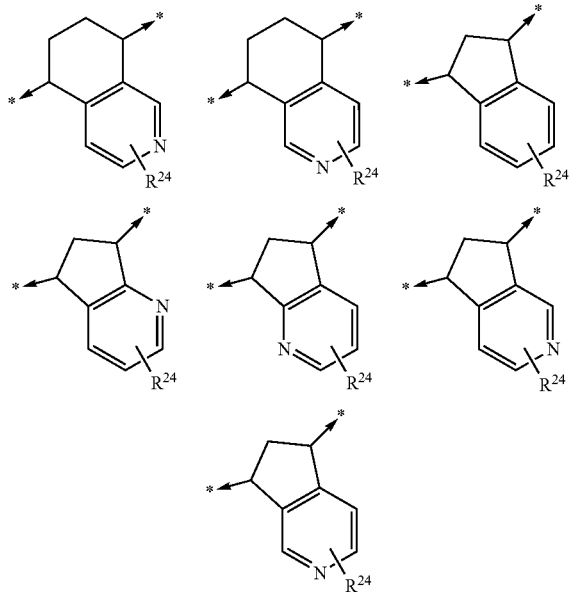

In a still further embodiment, A is group:

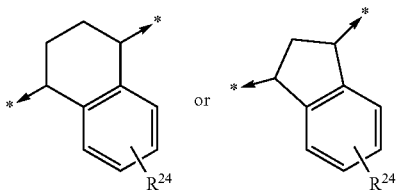

In an additional embodiment, A is group:

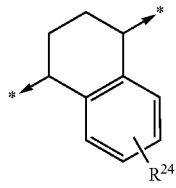

In one embodiment, $R^{24}$ is not present or, if present, is at each occurrence independently selected from the group consisting of: $C_1$-$C_2$ alkyl, —F, —Cl and cyano; in a further embodiment, $R^{24}$ is not present or, if present, is at each occurrence independently Methyl or —F. In a further embodiment, $R^{24}$ is not present.

In one embodiment, $R^1$ is a group of formula (IIa):

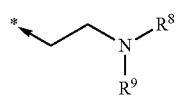

(IIa)

In a further embodiment, $R^1$ is a group of formula (IIa):

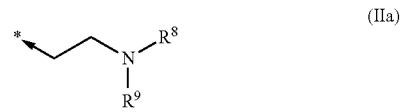

(IIa)

and $R^8$ and $R^9$ form, together with the nitrogen atom to which they are attached, a 5-11-membered saturated monocyclic or a fused or spiro bicyclic ring system optionally containing a further heteroatom which is oxygen or nitrogen, said nitrogen atom being optionally substituted by $C_1$-$C_6$ alkyl; wherein such $C_1$-$C_6$ alkyl groups may be optionally substituted by a group $C_1$-$C_6$ alkyl, $C_3$-$C_6$ cycloalkyl, hydroxyl or halo.

In an additional embodiment, $R^1$ is a group of formula (IIa):

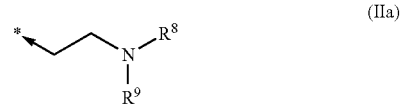

(IIa)

and $R^8$ and $R^9$ form, together with the nitrogen atom to which they are attached, a 5 to 7-membered saturated monocyclic ring system optionally containing a further heteroatom which is oxygen or nitrogen, said nitrogen atom being optionally substituted by $C_1$-$C_6$ alkyl. In a still further embodiment, such saturated monocyclic ring system is a morpholine ring.

In another embodiment, $R^1$ is a group of formula (IIb):

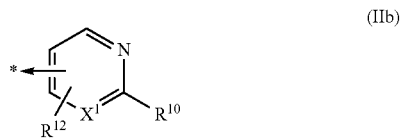

(IIb)

In one embodiment, $X^1$ is a group —(CH)— or a nitrogen atom. In another embodiment, $X^1$ is a group —(CH)—.

In one embodiment, $R^{10}$ is selected from a group consisting of: —CN, —C(O)N($R^A R^B$), and —N($R^C$)C(O)$R^C$.

In one embodiment, $R^{12}$ is hydrogen, $C_1$-$C_6$ alkyl, or halogen.

In a further embodiment, $R^1$ is a group of formula (IIb):

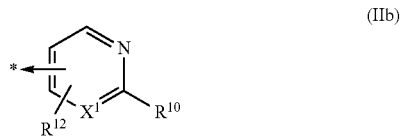

(IIb)

wherein $X^1$ is a group —(CH)—, $R^{10}$ is selected from a group consisting of: —CN, —C(O)N($R^A R^B$), and —N($R^C$)C(O)$R^C$; and $R^{12}$ is hydrogen.

In a further embodiment, $R^1$ is a group of formula (IIc):

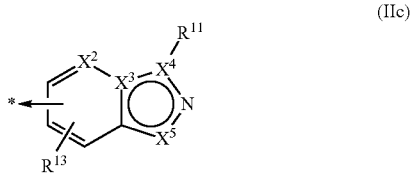
(IIc)

In one embodiment, the group (IIc) is a group of formula (IIca) or (IIcb) which is connected to the group Y through one of the carbons as below indicated:

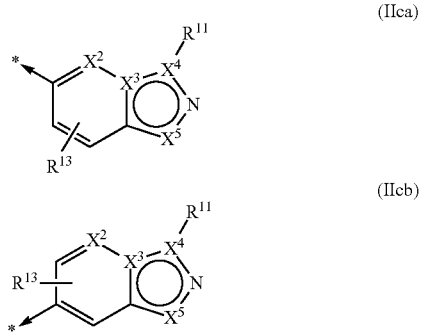
(IIca)

(IIcb)

In another embodiment, the group (IIc) is a group of formula (IIca) as above defined which is connected to the group Y through the carbon adjacent to $X_2$

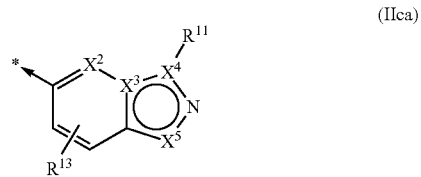
(IIca)

In one embodiment, $X^4$ is a carbon atom.
In one embodiment, $X^5$ is a nitrogen atom.
In another embodiment, $X^4$ is a carbon atom, $X^5$ is a nitrogen atom, $X^3$ is a nitrogen atom, and $X^2$ is nitrogen.
In another embodiment, $X^4$ is a carbon atom, $X^5$ is a nitrogen atom, $X^3$ is a nitrogen atom, and $X^2$ is group —CH—.
In another embodiment, $X^4$ is a nitrogen atom, $X^5$ is a group —CH— atom, $X^3$ is a carbon atom, and $X^2$ is group —CH—.
In one embodiment, $R^{13}$ is hydrogen, $C_1$-$C_6$ alkyl, or halogen.
In a further embodiment, the group (IIc) is a group of formula (IIca) as above defined which is connected to the group Y through the carbon adjacent to $X_2$

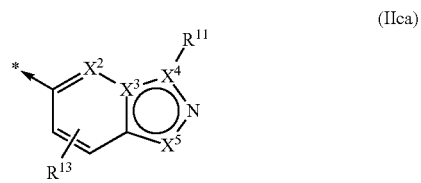
(IIca)

and wherein $X^4$ is a carbon atom, $X^5$ is a nitrogen atom, $X^3$ is a nitrogen atom, and $X^2$ is a group —CH—, and $R^{13}$ is hydrogen.

In one embodiment, $R^{11}$ is selected from a group consisting of: —$NR^AR^B$, ($C_5$-$C_7$heterocycloalkyl)-($C_1$-$C_6$alkyl), —($C_3$-$C_7$heterocycloalkyl), wherein any of such ($C_5$-$C_7$heterocycloalkyl)-($C_1$-$C_6$alkyl) or —($C_3$-$C_7$heterocycloalkyl) may be optionally substituted by a group $C_1$-$C_6$ alkyl, $C_3$-$C_7$ cycloalkyl, hydroxyl or halo.

In another embodiment, $R^{11}$ is selected from a group consisting of: —$NR^AR^B$, —($C_1$-$C_6$alkylene)-$NR^AR^B$, ($C_5$-$C_7$heterocycloalkyl)-($C_1$-$C_6$alkyl), —($C_3$-$C_7$heterocycloalkyl), wherein any of such ($C_5$-$C_7$heterocycloalkyl)-($C_1$-$C_6$alkyl) or —($C_3$-$C_7$heterocycloalkyl) may be optionally substituted by one, two or three groups $R^{25}$ which are independently selected in the list consisting of: $C_1$-$C_6$ alkyl, ($C_1$-$C_3$) haloalkyl, ($C_1$-$C_4$) hydroxyalkyl, $C_3$-$C_7$ cycloalkyl, hydroxyl and halo.

In another embodiment, $R^{11}$ is Phenyl or 5- or 6-membered monocyclic heteroaryl which is substituted by a group selected from: ($C_5$-$C_7$heterocycloalkyl)-($C_1$-$C_6$alkyl), —($C_3$-$C_7$heterocycloalkyl), wherein any of such ($C_5$-$C_7$heterocycloalkyl)-($C_1$-$C_6$alkyl) or —($C_3$-$C_7$heterocycloalkyl) may be optionally substituted by a group $C_1$-$C_6$ alkyl, $C_3$-$C_7$ cycloalkyl, hydroxyl or halo.

In another embodiment, $R^{11}$ is Phenyl or 5- or 6-membered monocyclic heteroaryl which is substituted by ($C_5$-$C_7$heterocycloalkyl)-($C_1$-$C_6$alkyl) or —($C_3$-$C_7$heterocycloalkyl), wherein any ($C_5$-$C_7$heterocycloalkyl)-($C_1$-$C_6$alkyl), —($C_3$-$C_7$heterocycloalkyl), may be optionally substituted by one, two or three groups $R^{25}$ which are independently selected in the list consisting of: $C_1$-$C_6$ alkyl, ($C_1$-$C_3$) haloalkyl, ($C_1$-$C_4$)hydroxyalkyl, $C_3$-$C_7$ cycloalkyl, hydroxyl and halo.

In one embodiment, $R^{25}$ is one, two or three groups independently selected from the group consisting of $C_1$-$C_6$ alkyl, ($C_1$-$C_3$) haloalkyl, ($C_1$-$C_4$)hydroxyalkyl, $C_3$-$C_7$ cycloalkyl, hydroxyl, and halo.

In one embodiment, $R^A$ and $R^B$ are at each occurrence independently hydrogen, $C_1$-$C_6$ alkyl or $C_3$-$C_7$ cycloalkyl, such $C_1$-$C_6$ alkyl and $C_3$-$C_7$ cycloalkyl being optionally substituted by a group $C_1$-$C_3$ alkyl, $C_3$-$C_7$cycloalkyl, $OR^D$, CN or halo.

In another embodiment, $R^A$ and $R^B$ form together with the nitrogen atom to which they are attached a 5-11-membered saturated monocyclic or bicyclic heterocyclic ring system which is optionally substituted by one or more group —$OR^D$, CN, halo, $C_1$-$C_6$ alkyl or $C_3$-$C_7$ cycloalkyl, such $C_1$-$C_6$ alkyl and $C_3$-$C_7$ cycloalkyl being optionally substituted by a group $C_1$-$C_3$ alkyl, $C_3$-$C_7$cycloalkyl, —$OR^D$, —CN, or halo.

In a still further embodiment, $R^A$ and $R^B$ form together with the nitrogen atom to which they are attached a 5-11-membered saturated monocyclic or bicyclic heterocyclic ring system which is optionally substituted by one or more group —$OR^D$, —CN, halo, $C_1$-$C_6$ alkyl or $C_3$-$C_7$ cycloalkyl, such $C_1$-$C_6$ alkyl and $C_3$-$C_7$ cycloalkyl being optionally substituted by a group $C_1$-$C_3$ alkyl, $C_3$-$C_7$cycloalkyl, —$OR^D$, —CN, or halo; and which 5-11-membered saturated monocyclic or bicyclic heterocyclic ring contains a further heteroatom which is oxygen or nitrogen, said nitrogen atom optionally substituted by $C_1$-$C_6$ alkyl or $C_3$-$C_6$ cycloalkyl, wherein any of such $C_1$-$C_6$ alkyl or $C_3$-$C_6$ cycloalkyl may be optionally substituted by a group $C_1$-$C_6$ alkyl, $C_3$-$C_7$ cycloalkyl, $OR^D$, CN, or halo.

In one embodiment, $R^{11}$ is a group:

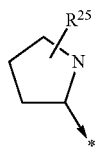

wherein $R^{25}$ is optionally present and represents one, two, or three substituents independently selected from the group consisting of $C_1$-$C_6$ alkyl, ($C_1$-$C_3$) haloalkyl, ($C_1$-$C_4$)hydroxyalkyl, $C_3$-$C_7$ cycloalkyl, hydroxyl and halo; and wherein the asterisk represents the point of attachment for group $R^{11}$ to the rest of the molecule via $X^4$.

In further embodiment, $R^{11}$ is a group:

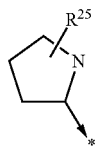

wherein $R^{25}$ represents one or two $C_1$-$C_6$ alkyl substituents; and wherein the asterisk represents the point of attachment for group $R^{11}$ to the rest of the molecule via $X^4$.

In one embodiment, $R^{11}$ is a group:

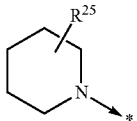

wherein $R^{25}$ is optionally present and represents one, two, or three substituents independently selected from the group consisting of $C_1$-$C_6$ alkyl, ($C_1$-$C_3$) haloalkyl, ($C_1$-$C_4$)hydroxyalkyl, $C_3$-$C_7$ cycloalkyl, hydroxyl, and halo; and wherein the asterisk represents the point of attachment for group $R^{11}$ to the rest of the molecule via $X^4$.

In a further embodiment, $R^{11}$ is a group:

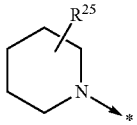

wherein $R^{25}$ represents one, two, or three substituents independently selected from the group consisting of: $C_1$-$C_6$ alkyl, ($C_1$-$C_3$) haloalkyl, ($C_1$-$C_4$)hydroxyalkyl, $C_3$-$C_7$ cycloalkyl, hydroxyl, and halo; and wherein the asterisk represents the point of attachment for group $R^{11}$ to the rest of the molecule via $X^4$.

In a further embodiment, $R^{11}$ is a group:

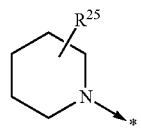

wherein $R^{25}$ represents one or two $C_1$-$C_6$ alkyl substituents; and wherein the asterisk represents the point of attachment for group $R^{11}$ to the rest of the molecule via $X^4$.

In a further embodiment, $R^{11}$ is a group:

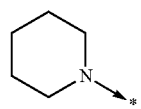

wherein the asterisk represents the point of attachment for group $R^{11}$ to the rest of the molecule via $X^4$.

In a further embodiment, $R^{11}$ is a group:

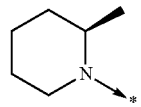

wherein the asterisk represents the point of attachment for group $R^{11}$ to the rest of the molecule via $X^4$.

In a still further embodiment, $R^{11}$ is a group:

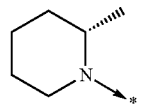

wherein the asterisk represents the point of attachment for group $R^{11}$ to the rest of the molecule via $X^4$.

In one embodiment, $R^2$ is a radical of formula (IIIa):

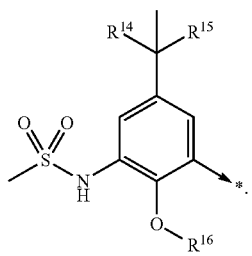

(IIIa)

In one embodiment, $R^{14}$ is selected from the group consisting of —$CH_3$, —$CH_2OH$, or —$CH_2SCH_3$; in another embodiment, $R^{14}$ is —$CH_3$.

In one embodiment, $R^{15}$ and $R^{16}$ are independently —$CH_3$ or —$C_2H_5$; in another embodiment, $R^{15}$ and $R^{16}$ are —$CH_3$.

In another embodiment, $R^2$ is a radical of formula (IIIa):

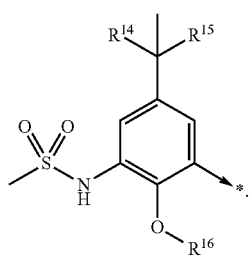

(IIIa)

$R^{14}$ is —$CH_3$, and $R^{15}$ and $R^{16}$ are —$CH_3$.

In another embodiment, $R^2$ is a radical of formula (IIIb):

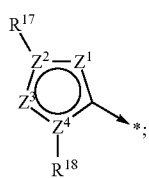

(IIIb)

In one embodiment, $R^{17}$ is selected from the group consisting of lone electron pair, hydrogen, —$CF_3$, —$NR^ER^F$, —($C_3$-$C_6$cycloalkyl), —($C_4$-$C_6$heterocycloalkyl), aryl, and heteroaryl wherein any of such —($C_3$-$C_6$cycloalkyl), —($C_4$-$C_6$heterocycloalkyl), aryl or heteroaryl may be optionally substituted by a group methyl, isopropyl or halo. In another embodiment, $R^{17}$ is selected from the group consisting of lone electron pair, hydrogen, —$CF_3$, morpholine, cyclohexyl, phenyl or pyridyl.

In another embodiment, $R^{17}$ is a group of general formula (IV)

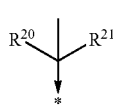

(IV)

In one embodiment, $R^{20}$ is selected from the group consisting of F, —$CH_3$; —$CH_2OH$, —$CH_2OMe$, —$CH_2SCH_3$; in another embodiment, $R^{20}$ is selected from the group consisting of —$CH_3$; —$CH_2OH$, —$CH_2OMe$. In another embodiment, $R^{20}$ is —$CH_3$.

In one embodiment, $R^{21}$ is —$CH_3$.

In another embodiment, $R^{20}$ and $R^{21}$ as defined above may form, together with the carbon atom to which they are attached, a cyclohexane or cyclopropyl ring; in a further embodiment, $R^{20}$ and $R^{21}$ as defined above may form, together with the carbon atom to which they are attached, a cyclopropyl ring.

In one embodiment, $R^{18}$ is phenyl or heteroaryl which is optionally substituted by a group —CN, —OH, halo, —CO-$OR^M$, $C_1$-$C_6$alkyl, $C_3$-$C_6$cycloalkyl, —O—($C_3$-$C_6$cycloalkyl), —S—($C_3$-$C_6$cycloalkyl), —$NR^HR^J$, —N($R^L$)($C_2$-$C_6$alkylene)-$NR^HR^J$, —N($R^1$)($C_3$-$C_7$cycloalkylene)-$NR^HR^J$, —($C_1$-$C_6$alkylene)-$NR^HR^J$, —($C_3$-$C_7$cycloalkylene)-$NR^HR^J$, —O—($C_2$-$C_6$alkylene)-$NR^HR^J$, —O—($C_3$-$C_7$cycloalkylene)-$NR^HR^J$, —S—($C_2$-$C_6$alkylene)-$NR^HR^J$, —S—($C_3$-$C_7$cycloalkylene)-$NR^HR^J$, —N($R^L$)C(O)—($C_1$-$C_6$alkylene)-$NR^HR^J$, —N($R^L$)C(O)—($C_3$-$C_7$cycloalkylene)-$NR^HR^J$, —C(O)N($R^L$)—($C_2$-$C_6$alkylene)-$NR^HR^J$, —C(O)N($R^L$)—($C_3$-$C_7$cycloalkylene)-$NR^HR^J$, —C(O)N($R^L$)—($C_2$-$C_6$alkylene)-$OR^M$, —C(O)N($R^L$)—($C_3$-$C_7$cycloalkylene)-$OR^M$, —N($R^L$)C(O)N($R^HR^J$), —C(O)N($R^HR^J$), —N($R^L$)C(O)N($R^L$)—($C_2$-$C_6$alkylene)-$NR^HR^J$, —N($R^L$)C(O)N($R^L$)—($C_3$-$C_7$cycloalkylene)-$NR^HR^J$, —O—($C_2$-$C_6$alkylene)-$OR^M$, —O—($C_3$-$C_7$cycloalkylene)-$OR^M$, —S—($C_2$-$C_6$alkylene)-$OR^M$, —S—($C_3$-$C_7$cycloalkylene)-$OR^M$, —N($R^L$)S(O)$_2$—($C_1$-$C_6$alkylene)-$NR^HR^J$, —N($R^L$)S(O)$_2$—($C_3$-$C_7$cycloalkylene)-$NR^HR^J$, —S(O)$_2$N($R^L$)—($C_2$-$C_6$alkylene)-$NR^HR^J$, —S(O)$_2$N($R^L$)—($C_3$-$C_7$cycloalkylene)-$NR^HR^J$, —S(O)$_2$N($R^L$)—($C_2$-$C_6$alkylene)-$OR^M$, —S(O)$_2$N($R^L$)—($C_3$-$C_7$cycloalkylene)-$OR^M$, —N($R^L$)S(O)$_2$—($C_2$-$C_6$alkylene)-$OR^M$, —N($R^L$)S(O)$_2$—($C_3$-$C_7$cycloalkylene)-$OR^M$, —S(O)$_2$N($R^HR^J$), —N($R^L$)S(O)$_2$$R^L$, —N($R^L$)C(O)$R^L$, $OR^L$, $SR^L$, —($C_3$-$C_7$heterocycloalkyl), ($C_5$-$C_7$heterocycloalkyl)-($C_1$-$C_6$alkyl), and ($C_5$-$C_7$heterocycloalkyl)-($C_3$-$C_6$cycloalkyl), wherein any of such alkyl, cycloalkyl, alkylene, cycloalkylene, heterocycloalkyl, heterocycloalkyl-($C_1$-$C_6$ alkyl), heterocycloalkyl-($C_3$-$C_6$ cycloalkyl) and heterocycloalkylcarbonyl may be optionally substituted by a group $C_1$-$C_6$ alkyl, $C_3$-$C_7$ cycloalkyl, —$OR^L$ or halo. In a further embodiment, $R^{18}$ is phenyl substituted by —($C_1$-$C_6$alkyl).

In one embodiment, $R^{18}$ is —($C_1$-$C_6$alkyl) or —($C_3$-$C_7$cycloalkyl).

In one embodiment, $z^1$=—CH—, $z^2$=C, $z^3$ and $z^4$ are N; in another embodiment, $z^1$=O, $z^2$=C, $z^3$ and $z^4$ are N; in a further embodiment, $z^1$=—CH—, $z^2$ and $z^3$ are N, and $z^4$ is —CH—; in an additional embodiment, $z^1$=N, $z^2$ is C, $z^3$ is N and $z^4$ is O; in a still further embodiment, $z^1$=N, $z^2$ is C, $z^3$ is O and $z^4$ is N.

In an additional embodiment, $R^2$ is a radical of formula (IIIb):

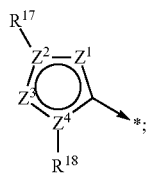

(IIIb)

wherein $z^1$=—CH—, $z^2$=C, $z^3$ is oxygen, $z^4$ is N, $R^{18}$ is a lone pair, and $R^{17}$ is a group of general formula (IV)

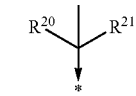

(IV)

wherein $R^{20}$ is —$CH_3$ or —$CH_2OH$, and $R^{21}$ is —$CH_3$.

In a further embodiment, $R^2$ is a radical of formula (IIb):

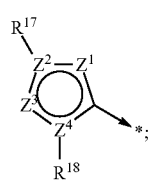

(IIIb)

wherein $z^1$=—CH—, $z^2$=C, $z^3$ and $z^4$ are N and $R^{17}$ is a group of general formula (IV)

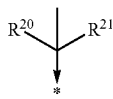

(IV)

wherein $R^{20}$ is —CH$_3$ or —CH$_2$OH, and $R^{21}$ is —CH$_3$.

In another embodiment, $R^2$ is a radical of formula (IIIb):

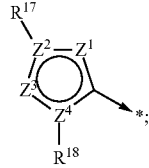

(IIIb)

wherein $z^1$=—CH—, $z^2$=C, $z^3$ and $z^4$ are N and $R^{17}$ is a group of general formula (IV)

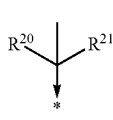

(IV)

wherein $R^{20}$ is —CH$_3$ or —CH$_2$OH, and $R^{21}$ is —CH$_3$ and wherein $R^{18}$ is phenyl, which may be optionally substituted by a group —CN, —OH, —COOR$^M$, C$_1$-C$_6$alkyl, —N(R$^L$)(C$_2$-C$_6$alkylene)-NR$^H$R$^J$, —(C$_1$-C$_6$alkylene)-NR$^H$R$^J$, —O—(C$_2$-C$_6$alkylene)-NR$^H$R$^J$, —O—(C$_2$-C$_6$alkylene)-OR$^M$, —S—(C$_2$-C$_6$alkylene)-OR$^M$, (C$_5$-C$_7$heterocycloalkyl)-(C$_1$-C$_6$ alkyl), and (C$_5$-C$_7$ heterocycloalkyl)-(C$_3$-C$_6$ cycloalkyl), wherein any of such C$_1$-C$_6$alkyl, —(C$_1$-C$_6$alkylene)-, —(C$_2$-C$_6$alkylene)-, (C$_5$-C$_7$heterocycloalkyl)-(C$_1$-C$_6$ alkyl) and (C$_5$-C$_7$ heterocycloalkyl)-(C$_3$-C$_6$ cycloalkyl) may be optionally substituted by a group C$_1$-C$_6$ alkyl, C$_3$-C$_7$ cycloalkyl, OR$^L$ or halo.

In a further embodiment, $R^2$ is a radical of formula (IIIb):

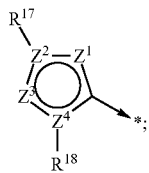

(IIIb)

wherein $z^1$=—CH—, $z^2$=C, $z^3$ and $z^4$ are N and $R^{17}$ is a group of general formula (IV)

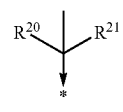

(IV)

wherein $R^{20}$ is —CH$_3$ or —CH$_2$OH, and $R^{21}$ is —CH$_3$ and $R^{18}$ is phenyl, which is substituted in the para position by a group C$_1$-C$_6$alkyl.

In an additional embodiment, $R^2$ is a radical of formula (IIIb):

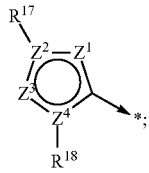

(IIIb)

wherein $z^1$=—CH—, $z^2$=C, $z^3$ and $z^4$ are N and $R^{17}$ is a group of general formula (IV)

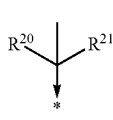

(IV)

wherein $R^{20}$ is —CH$_3$ or —CH$_2$OH, and $R^{21}$ is —CH$_3$ and $R^{18}$ is phenyl, which is substituted in the meta position by a group —O—(C$_2$-C$_6$alkylene)-NR$^H$R$^J$ or —(C$_1$-C$_6$alkylene)-NR$^H$R$^J$.

In another embodiment, $R^2$ is a radical of formula (IIIb):

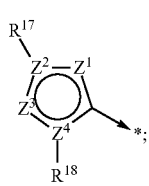

(IIIb)

wherein $z^1$=—CH—, $z^2$=C, $z^3$ and $z^4$ are N and $R^{17}$ is a group of general formula (IV)

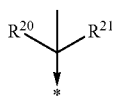

wherein $R^{20}$ is —$CH_3$ or —$CH_2OH$, and $R^{21}$ is —$CH_3$ and $R^{18}$ is a 5 or 6-membered heteroaryl which is optionally substituted by $C_1$-$C_6$alkyl, —$N(R^L)(C_2$-$C_6$alkylene)-$NR^HR^J$, or —($C_1$-$C_6$alkylene)-$NR^HR^J$, wherein any of such $C_1$-$C_6$alkyl, —($C_1$-$C_6$alkylene)-, —($C_2$-$C_6$alkylene)-, ($C_5$-$C_7$heterocycloalkyl)-($C_1$-$C_6$alkyl) and ($C_5$-$C_7$heterocycloalkyl)-($C_3$-$C_6$ cycloalkyl) may be optionally substituted by a group $C_1$-$C_6$ alkyl, $C_3$-$C_7$ cycloalkyl, $OR^L$ or halo. In one embodiment, for such compounds, $R^{18}$ is an imidazole ring which is optionally substituted by $C_1$-$C_6$alkyl, —$N(R^L)(C_2$-$C_6$alkylene)-$NR^HR^J$, or —($C_1$-$C_6$alkylene)-$NR^HR^J$.

In another embodiment, $R^2$ is a radical of formula (IIIb):

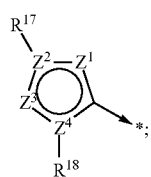

wherein $z^1$=—CH—, $z^2$=C, $z^3$ and $z^4$ are N and $R^{17}$ is a group of general formula (IV)

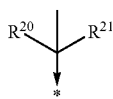

wherein $R^{20}$ is —$CH_3$ or —$CH_2OH$, and $R^{21}$ is —$CH_3$ and $R^{18}$ is a group —($C_1$-$C_6$alkyl), optionally substituted by a group OH or —$NR^HR^J$, or a group ($C_5$-$C_7$heterocycloalkyl)-($C_1$-$C_6$alkyl) which may be optionally substituted by a group $C_1$-$C_6$ alkyl.

In a further embodiment, $R^2$ is a radical of formula (IIIc):

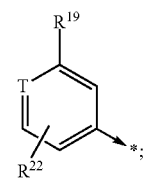

In one embodiment, $R^{19}$ is selected from the group consisting of hydrogen, —$CF_3$, —$NR^ER^F$, —($C_3$-$C_6$cycloalkyl), —($C_3$-$C_6$heterocycloalkyl), aryl, and heteroaryl wherein any of such cycloalkyl, heterocycloalkyl, aryl or heteroaryl may be optionally substituted by a group $C_1$-$C_2$ alkyl, $C_3$-$C_5$ cycloalkyl, or halo. In another embodiment, $R^{19}$ is selected from the group consisting of hydrogen, —$CF_3$, morpholine, cyclohexyl, phenyl or pyridyl wherein any of such morpholine, cyclohexyl, phenyl or pyridyl may be optionally substituted by a group methyl, —F or —Cl.

In another embodiment, $R^{19}$ is a group of general formula (V)

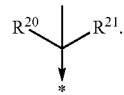

In one embodiment, T is —N=. In another embodiment, T is —$CR^{23}$=.

In one embodiment, $R^{22}$ is H, F, —Cl, —$CH_3$, or —CN; in another embodiment, $R^{22}$ is H or F.

In one embodiment, $R^{23}$ is H, F, —Cl, —$CH_3$, or —CN; in another embodiment, $R^{23}$ is —Cl.

In another embodiment, $R^2$ is a radical of formula (IIIc):

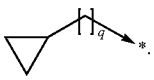

wherein $R^{19}$ is —($C_3$-$C_6$heterocycloalkyl), which is optionally substituted by a group $C_1$-$C_2$ alkyl, $C_3$-$C_5$ cycloalkyl, or halo; wherein T is —$CR^{23}$=, $R^{22}$ is H or F.

In a still further embodiment, $R^2$ is a radical of formula (IIId):

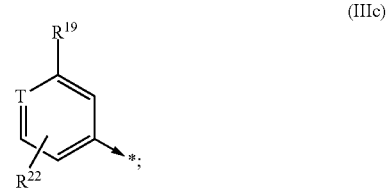

In one embodiment, q is 0, 1 or 2; in another embodiment, q is 0 or 1. In a further embodiment, q is zero.

In one embodiment, compounds of formula (IA) are provided wherein W is NH, Y is a group —$O(CR^3R^4)_n$— and n is 0, A is group:

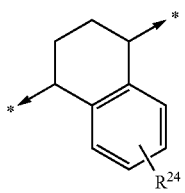 or 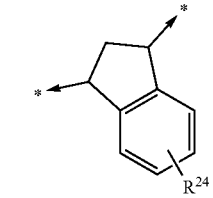

wherein $R^1$ is a group of formula (IIca) as above defined which is connected to the group Y through the carbon adjacent to $X^2$

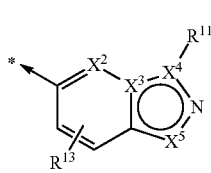

(IIca)

and wherein $X^4$ is a carbon atom, $X^5$ is a nitrogen atom, $X^3$ is a nitrogen atom and $X^2$ is a group —CH—, and $R^{13}$ is hydrogen;

wherein $R^{11}$ is a group:

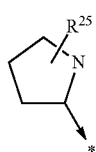

wherein $R^{25}$ is optionally present and represents one, two, or three substituents independently selected from the group consisting of $C_1$-$C_6$ alkyl, ($C_1$-$C_3$) haloalkyl, ($C_1$-$C_4$)hydroxyalkyl, $C_3$-$C_7$ cycloalkyl, hydroxyl, and halo; and wherein the asterisk represents the point of attachment for group $R^{11}$ to the rest of the molecule via $X^4$;

wherein $R^2$ is a radical of formula (IIIb):

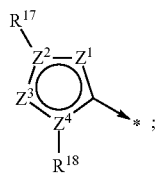

(IIIb)

wherein $z^1$=—CH—, $z^2$=C, $z^3$ and $z^4$ are N and $R^{17}$ is a group of general formula (IV)

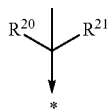

(IV)

wherein $R^{20}$ is —CH$_3$ or —CH$_2$OH, and $R^{21}$ is —CH$_3$ and wherein $R^{18}$ is phenyl, which may be optionally substituted by a group —CN, —OH, —COOR$^M$, $C_1$-$C_6$alkyl, —N(R$^L$)(C$_2$-$C_6$alkylene)-NR$^H$R$^J$, —(C$_1$-C$_6$alkylene)-NR$^H$R$^J$, —O—(C$_2$-C$_6$alkylene)-NR$^H$R$^J$, —O—(C$_2$-C$_6$alkylene)-OR$^M$, —S—(C$_2$-C$_6$alkylene)-OR$^M$, (C$_5$-C$_7$heterocycloalkyl)-(C$_1$-C$_6$ alkyl), and (C$_5$-C$_7$ heterocycloalkyl)-(C$_3$-C$_6$ cycloalkyl), wherein any of such $C_1$-$C_6$alkyl, —(C$_1$-C$_6$alkylene)-, —(C$_2$-C$_6$alkylene)-, (C$_5$-C$_7$heterocycloalkyl)-(C$_1$-C$_6$ alkyl) and (C$_5$-C$_7$ heterocycloalkyl)-(C$_3$-C$_6$ cycloalkyl) may be optionally substituted by a group $C_1$-$C_6$ alkyl, $C_3$-$C_7$ cycloalkyl, OR$^L$ or halo.

In one embodiment, compounds of formula (IB) are provided wherein W is NH, Y is a group —O(CR$^3$R$^4$)$_n$— and n is 0, A is group:

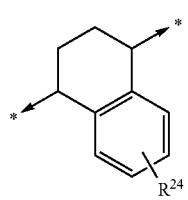 or 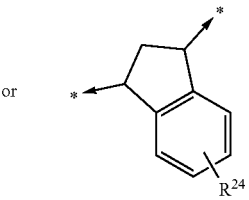

wherein $R^1$ is a group of formula (IIca) as above defined which is connected to the group Y through the carbon adjacent to $X^2$

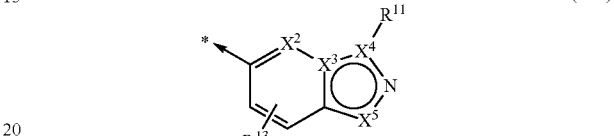

(IIca)

and wherein $X^4$ is a carbon atom, $X^5$ is a nitrogen atom, $X^3$ is a nitrogen atom and $X^2$ is a group —CH—, and $R^{13}$ is hydrogen;

wherein $R^{11}$ is a group:

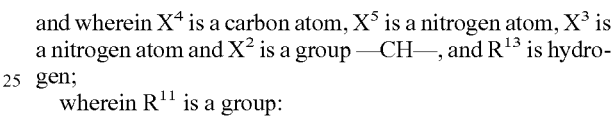

wherein $R^{25}$ is optionally present and represents one, two or three substituents independently selected in the list consisting of: $C_1$-$C_6$ alkyl, ($C_1$-$C_3$) haloalkyl, ($C_1$-$C_4$)hydroxyalkyl, $C_3$-$C_7$ cycloalkyl, hydroxyl and halo; and wherein the asterisk represents the point of attachment for group $R^{11}$ to the rest of the molecule via $X^4$; wherein $R^2$ is a radical of formula (IIIb):

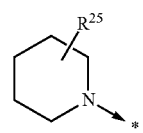

(IIIb)

wherein $z^1$=—CH—, $z^2$=C, $z^3$ and $z^4$ are N and $R^{17}$ is a group of general formula (IV)

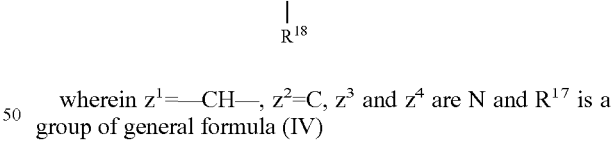

(IV)

wherein $R^{20}$ is —CH$_3$ or —CH$_2$OH, and $R^{21}$ is —CH$_3$ and wherein $R^{18}$ is phenyl, which may be optionally substituted by a group —CN, —OH, —COOR$^M$, $C_1$-$C_6$alkyl, —N(R$^L$)(C$_2$-$C_6$alkylene)-NR$^H$R$^J$, —(C$_1$-C$_6$alkylene)-NR$^H$R$^J$, —O—(C$_2$-C$_6$alkylene)-NR$^H$R$^J$, —O—(C$_2$-C$_6$alkylene)-OR$^M$, —S—(C$_2$-C$_6$alkylene)-OR$^M$, (C$_5$-C$_7$heterocycloalkyl)-(C$_1$-C$_6$ alkyl), and (C$_5$-C$_7$ heterocycloalkyl)-(C$_3$-C$_6$ cycloalkyl), wherein any of such wherein any of such $C_1$-$C_6$alkyl, —(C$_1$-C$_6$alkylene)-, —(C$_2$-

$C_6$alkylene)-, ($C_5$-$C_7$heterocycloalkyl)-($C_1$-$C_6$ alkyl) and ($C_5$-$C_7$ heterocycloalkyl)-($C_3$-$C_6$ cycloalkyl) may be optionally substituted by a group $C_1$-$C_6$ alkyl, $C_3$-$C_7$ cycloalkyl, $OR^L$ or halo.

In one embodiment, compounds of formula (IC) are provided wherein W is NH, Y is a group —$O(CR^3R^4)_n$— and n is 0, A is group:

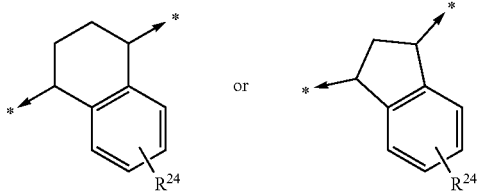

wherein $R^1$ is a group of formula (IIca) as above defined which is connected to the group Y through the carbon adjacent to $X^2$

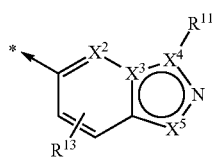
(IIca)

and wherein $X^4$ is a carbon atom, $X^5$ is a nitrogen atom, $X^3$ is a nitrogen atom and $X^2$ is a group —CH—, and $R^{13}$ is hydrogen;

$R^{11}$ is a group:

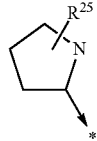

wherein $R^{25}$ is optionally present and represents one, two, or three substituents independently selected from the group consisting of $C_1$-$C_6$ alkyl, ($C_1$-$C_3$) haloalkyl, ($C_1$-$C_4$)hydroxyalkyl, $C_3$-$C_7$ cycloalkyl, hydroxyl, and halo; and wherein the asterisk represents the point of attachment for group $R^{11}$ to the rest of the molecule via $X^4$;

$R^2$ is a radical of formula (IIIb):

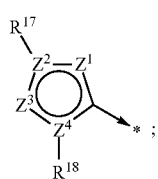
(IIIb)

wherein $z^1$=—CH—, $z^2$=C, $z^3$ and $z^4$ are N and $R^{17}$ is a group of general formula (IV)

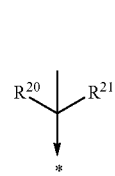
(IV)

wherein $R^{20}$ is —$CH_3$ or —$CH_2OH$, and $R^{21}$ is —$CH_3$ and $R^{18}$ is a 5 or 6-membered heteroaryl, which is optionally substituted by $C_1$-$C_6$alkyl, —$N(R^L)(C_2$-$C_6$alkylene)-$NR^HR^J$, or —($C_1$-$C_6$alkylene)-$NR^HR^J$, wherein any of such $C_1$-$C_6$alkyl, —($C_1$-$C_6$alkylene)-, —($C_2$-$C_6$alkylene)-, ($C_5$-$C_7$heterocyclo alkyl)-($C_1$-$C_6$ alkyl) and ($C_5$-$C_7$ heterocycloalkyl)-($C_3$-$C_6$ cycloalkyl) may be optionally substituted by a group $C_1$-$C_6$ alkyl, $C_3$-$C_7$ cycloalkyl, $OR^L$ or halo.

In one embodiment, compounds of formula (ID) are provided wherein W is NH, Y is a group —$O(CR^3R^4)_n$— and n is 0, A is group:

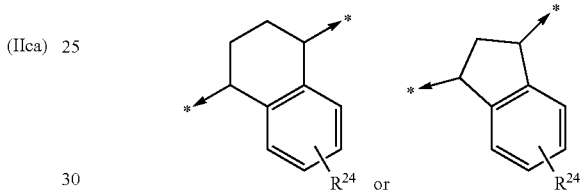

R1 is a group of formula (IIca) as above defined which is connected to the group Y through the carbon adjacent to $X_2$

(IIca)

and wherein $X^4$ is a carbon atom, $X^5$ is a nitrogen atom, $X^3$ is a nitrogen atom and $X^2$ is a group —CH—, and $R^{13}$ is hydrogen;

wherein $R^{11}$ is a group:

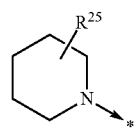

wherein $R^{25}$ is optionally present and represents one, two, or three substituents independently selected in the list consisting of: $C_1$-$C_6$ alkyl, ($C_1$-$C_3$) haloalkyl, ($C_1$-$C_4$)hydroxyalkyl, $C_3$-$C_7$ cycloalkyl, hydroxyl and halo; and wherein the asterisk represents the point of attachment for group $R^{11}$ to the rest of the molecule via $X^4$;

wherein $R^2$ is a radical of formula (IIIb):

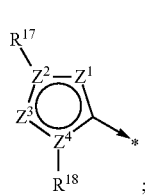
(IIIb)

wherein $z^1$=—CH—, $z^2$=C, $z^3$ and $z^4$ are N and R is a group of general formula (IV)

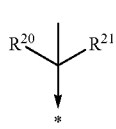
(IV)

wherein $R^{20}$ is —CH$_3$ or —CH$_2$OH, and $R^{21}$ is —CH$_3$ and $R^{18}$ is a 5 or 6-membered heteroaryl, which is optionally substituted by $C_1$-$C_6$alkyl, —N($R^L$)($C_2$-$C_6$alkylene)-NR$^H$R$^J$, or —($C_1$-$C_6$alkylene)-NR$^H$R$^J$, wherein any of such $C_1$-$C_6$alkyl, —($C_1$-$C_6$alkylene)-, —($C_2$-$C_6$alkylene)-, ($C_5$-$C_7$heterocycloalkyl)-($C_1$-$C_6$ alkyl) and ($C_5$-$C_7$ heterocycloalkyl)-($C_3$-$C_6$ cycloalkyl) may be optionally substituted by a group $C_1$-$C_6$ alkyl, $C_3$-$C_7$ cycloalkyl, OR$^L$ or halo.

In one embodiment, compounds of formula (IE) are provided wherein W is NH, Y is a group —O(CR$^3$R$^4$)$_n$— and n is 0, A is group:

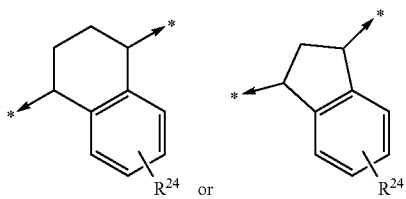

wherein R1 is a group of formula (IIca) as above defined which is connected to the group Y through the carbon adjacent to $X_2$

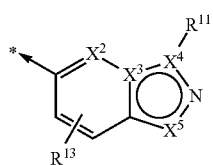
(IIca)

and wherein $X^4$ is a carbon atom, $X^5$ is a nitrogen atom, $X^3$ is a nitrogen atom and $X^2$ is a group —CH—, and $R^{13}$ is hydrogen;

wherein $R^{11}$ is a group:

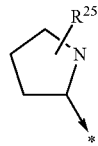

wherein $R^{25}$ is optionally present and represents one, two, or three substituents independently selected in the list consisting of: $C_1$-$C_6$ alkyl, ($C_1$-$C_3$) haloalkyl, ($C_1$-$C_4$)hydroxyalkyl, $C_3$-$C_7$ cycloalkyl, hydroxyl and halo; and wherein the asterisk represents the point of attachment for group $R^{11}$ to the rest of the molecule via $X^4$; wherein $R^2$ is a radical of formula (IIIb):

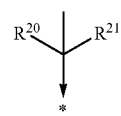
(IIIb)

wherein $z^1$=—CH—, $z^2$=C, $z^3$ and $z^4$ are N and $R^{17}$ is a group of general formula (IV)

(IV)

wherein $R^{20}$ is —CH$_3$ or —CH$_2$OH, and $R^{21}$ is —CH$_3$ and $R^{18}$ is a group —($C_1$-$C_6$alkyl), optionally substituted by a group OH or —NR$^H$R$^J$, or a group ($C_5$-$C_7$heterocycloalkyl)-($C_1$-$C_6$alkyl) which may be optionally substituted by a group $C_1$-$C_6$ alkyl.

In one embodiment, compounds of formula (IF) are provided wherein W is NH, Y is a group —O(CR$^3$R$^4$)$_n$— and n is 0, A is group:

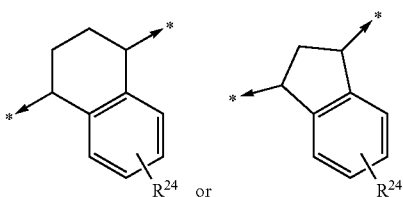

wherein $R^1$ is a group of formula (IIca) as above defined which is connected to the group Y through the carbon adjacent to $X_2$

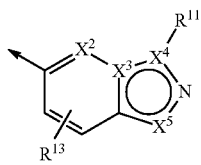

and wherein $X^4$ is a carbon atom, $X^5$ is a nitrogen atom, $X^3$ is a nitrogen atom and $X^2$ is a group —CH—, and $R^{13}$ is hydrogen;

wherein $R^{11}$ is a group:

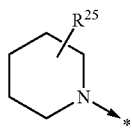

wherein $R^{25}$ is optionally present and represents one, two, or three substituents independently selected in the list consisting of: $C_1$-$C_6$ alkyl, ($C_1$-$C_3$) haloalkyl, ($C_1$-$C_4$)hydroxyalkyl, $C_3$-$C_7$ cycloalkyl, hydroxyl and halo; and wherein the asterisk represents the point of attachment for group $R^{11}$ to the rest of the molecule via $X^4$; wherein $R^2$ is a radical of formula (IIIb):

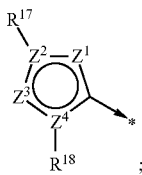

wherein $z^1$=—CH—, $z^2$=C, $z^3$ and $z^4$ are N and $R^{17}$ is a group of general formula (IV)

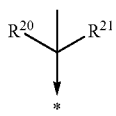

wherein $R^{20}$ is —$CH_3$ or —$CH_2OH$, and $R^{21}$ is —$CH_3$ and $R^{18}$ is a group —($C_1$-$C_6$alkyl), optionally substituted by a group OH or —$NR^HR^J$, or a group ($C_5$-$C_7$heterocycloalkyl)-($C_1$-$C_6$alkyl) which may be optionally substituted by a group $C_1$-$C_6$ alkyl.

In one embodiment, a compound of formula (I) is selected from the group consisting of:

1-(5-tert-Butyl-2-p-tolyl-2H-pyrazol-3-yl)-3-{(1S,4R)-4-[3-(2-pyrrolidin-1-yl-ethyl)-[1,2,4]triazolo[4,3-a]pyridin-6-yloxy]-1,2,3,4-tetrahydro-naphthalen-1-yl}-urea;

1-(5-tert-Butyl-2-p-tolyl-2H-pyrazol-3-yl)-3-((1S,4R)-4-{3-[2-(4-methyl-piperazin-1-yl)-ethyl]-[1,2,4]triazolo[4,3-a]pyridin-6-yloxy}-1,2,3,4-tetrahydro-naphthalen-1-yl)-urea;

1-(5-tert-Butyl-2-p-tolyl-2H-pyrazol-3-yl)-3-[(1S,4R)-4-(3-piperidin-1-yl)-[1,2,4]triazolo[4,3-a]pyridin-6-yloxy)-1,2,3,4-tetrahydro-naphthalen-1-yl]-urea;

1-(5-tert-Butyl-2-p-tolyl-2H-pyrazol-3-yl)-3-[(1S,4R)-4-(3-piperidin-4-yl)-[1,2,4]triazolo[4,3-a]pyridin-6-yloxy)-1,2,3,4-tetrahydro-naphthalen-1-yl]-urea;

1-(5-tert-Butyl-2-p-tolyl-2H-pyrazol-3-yl)-3-[(1S,4R)-4-[3-((S)-1-methyl-pyrrolidin-2-yl)-[1,2,4]triazolo[4,3-a]pyridin-6-yloxy)-1,2,3,4-tetrahydro-naphthalen-1-yl]-urea;

1-(5-tert-Butyl-2-p-tolyl-2H-pyrazol-3-yl)-3-[(1S,4R)-4-((S)-3-pyrrolidin-2-yl-[1,2,4]triazolo[4,3-a]pyridin-6-yloxy)-1,2,3,4-tetrahydro-naphthalen-1-yl]-urea;

1-(5-tert-Butyl-2-p-tolyl-2H-pyrazol-3-yl)-3-[(1S,4R)-4-(3-piperazin-1-ylmethyl-[1,2,4]triazolo[4,3-a]pyridin-6-yloxy)-1,2,3,4-tetrahydro-naphthalen-1-yl]-urea;

1-(5-tert-Butyl-2-p-tolyl-2H-pyrazol-3-yl)-3-[(1S,4R)-4-(3-isopropylamino-[1,2,4]triazolo[4,3-a]pyridin-6-yloxy)-1,2,3,4-tetrahydro-naphthalen-1-yl]-urea;

1-(5-tert-Butyl-2-p-tolyl-2H-pyrazol-3-yl)-3-[(1S,4R)-4-(6-cyano-pyridin-3-yloxy)-1,2,3,4-tetrahydro-naphthalen-1-yl]urea;

N-(4-{(1S,4S)-4-[3-(5-tert-Butyl-2-p-tolyl-2H-pyrazol-3-yl)-ureido]-1,2,3,4-tetrahydro-naphthalen-1-yloxy}-pyridin-2-yl)-2-methoxy-acetamide;

1-(5-tert-Butyl-2-p-tolyl-2H-pyrazol-3-yl)-3-{(1S,4R)-4-[1-(2-hydroxy-ethyl)-1H-indazol-6-yloxy]-1,2,3,4-tetrahydro-naphthalen-1-yl}-urea;

1-(5-tert-Butyl-2-p-tolyl-2H-pyrazol-3-yl)-3-[(1S,4R)-4-((R)-3-pyrrolidin-2-yl-[1,2,4]triazolo[4,3-a]pyridin-6-yloxy)-1,2,3,4-tetrahydro-naphthalen-1-yl]-urea;

N-(4-{(1R,4S)-4-[3-(5-tert-Butyl-2-p-tolyl-2H-pyrazol-3-yl)-ureido]-1,2,3,4-tetrahydro-naphthalen-1-yloxy}-pyridin-2-yl)-2-methoxy-acetamide;

1-(5-tert-Butyl-2-p-tolyl-2H-pyrazol-3-yl)-3-{(1S,4R)-4-[3-(4-methyl-piperazin-1-ylmethyl)-[1,2,4]triazolo[4,3-a]pyridin-6-yloxy]-1,2,3,4-tetrahydro-naphthalen-1-yl}-urea;

1-(5-tert-Butyl-2-p-tolyl-2H-pyrazol-3-yl)-3-[(1S,4R)-4-(3-morpholin-4-ylmethyl-[1,2,4]triazolo[4,3-a]pyridin-6-yloxy)-1,2,3,4-tetrahydro-naphthalen-1-yl]-urea;

1-(5-tert-Butyl-2-p-tolyl-2H-pyrazol-3-yl)-3-[(1S,4R)-4-(3-pyrrolidin-1-ylmethyl-[1,2,4]triazolo[4,3-a]pyridin-6-yloxy)-1,2,3,4-tetrahydro-naphthalen-1-yl]-urea;

1-(5-tert-Butyl-2-p-tolyl-2H-pyrazol-3-yl)-3-{(1S,4R)-4-[6-(morpholine-4-carbonyl)-pyridin-3-yloxy]-1,2,3,4-tetrahydro-naphthalen-1-yl}-urea;

1-(5-tert-Butyl-2-p-tolyl-2H-pyrazol-3-yl)-3-{(1S,4R)-4-[3-(4-morpholin-4-ylmethyl-phenyl)-[1,2,4]triazolo[4,3-a]pyridin-6-yloxy]-1,2,3,4-tetrahydro-naphthalen-1-yl}-urea;

1-(5-tert-Butyl-2-p-tolyl-2H-pyrazol-3-yl)-3-{(1S,4R)-4-[3-(3-morpholin-4-ylmethyl-phenyl)-[1,2,4]triazolo[4,3-a]pyridin-6-yloxy]-1,2,3,4-tetrahydro-naphthalen-1-yl}-urea;

1-(5-tert-Butyl-2-p-tolyl-2H-pyrazol-3-yl)-3-(1S,4R)-4-[3-(2-morpholin-4-ylmethyl-phenyl)-[1,2,4]triazolo[4,3-a]pyridin-6-yloxy]-1,2,3,4-tetrahydro-naphthalen-1-yl}-urea;

1-(5-tert-Butyl-2-p-tolyl-2H-pyrazol-3-yl)-3-[(1S,4R)-4-(6-morpholin-4-ylmethyl-pyridin-3-yloxy)-1,2,3,4-tetrahydro-naphthalen-1-yl]-urea;

1-(5-tert-Butyl-2-p-tolyl-2H-pyrazol-3-yl)-3-{(1S,4R)-4-[3-(1-methyl-piperidin-4-ylmethyl)-[1,2,4]triazolo[4,3-a]pyridin-6-yloxy]-1,2,3,4-tetrahydro-naphthalen-1-yl}-urea;

1-(5-tert-Butyl-2-p-tolyl-2H-pyrazol-3-yl)-3-((1S,4R)-4-{3-[1-(2,2-difluoro-ethyl)-piperidin-4-ylmethyl]-[1,2,4]triazolo[4,3-a]pyridin-6-yloxy}-1,2,3,4-tetrahydro-naphthalen-1-yl)-urea;

1-(5-tert-Butyl-2-p-tolyl-2H-pyrazol-3-yl)-3-[(1S,4R)-4-[3-(4-hydroxypiperidin-1-yl)-[1,2,4]triazolo[4,3-a]pyridine-6-yloxy]-1,2,3,4-tetrahydro-naphthalen-1-yl]-urea;

1-(5-tert-Butyl-2-p-tolyl-2H-pyrazol-3-yl)-3-[(1S,4R)-4-{3-[(2-hydroxy-ethyl)-methyl-amino]-[1,2,4]triazolo[4,3-a]pyridine-6-yloxy]-1,2,3,4-tetrahydro-naphthalen-1-yl]-urea;

1-(5-tert-Butyl-2-p-tolyl-2H-pyrazol-3-yl)-3-{(1S,4R)-4-[3-((S)-3-hydroxy-pyrrolidin-1-yl)-[1,2,4]triazolo[4,3-a]pyridin-6-yloxy]-1,2,3,4-tetrahydro-naphthalen-1-yl}-urea;

1-(5-tert-Butyl-2-p-tolyl-2H-pyrazol-3-yl)-3-{(1S,4R)-4-[3-((S)-3-hydroxy-pyrrolidin-1-yl)-[1,2,4]triazolo[4,3-a]pyridin-6-yloxy]-1,2,3,4-tetrahydro-naphthalen-1-yl}-urea;

1-(5-tert-Butyl-2-p-tolyl-2H-pyrazol-3-yl)-3-{(1S,4R)-4-[3-((R)-2-hydroxymethyl-pyrrolidin-1-yl)-[1,2,4]triazolo[4,3-a]pyridin-6-yloxy]-1,2,3,4-tetrahydro-naphthalen-1-yl}-urea;

1-(5-tert-Butyl-2-p-tolyl-2H-pyrazol-3-yl)-3-{(1S,4R)-4-[3-((S)-2-hydroxymethyl-pyrrolidin-1-yl)-[1,2,4]triazolo[4,3-a]pyridin-6-yloxy]-1,2,3,4-tetrahydro-naphthalen-1-yl}-urea;

1-[5-tert-Butyl-2-(3-hydroxymethyl-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea;

3-[3-tert-Butyl-5-(3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-ureido)-pyrazol-1-yl]-benzoic acid ethyl ester;

1-[5-tert-Butyl-2-(3-hydroxymethyl-phenyl)-2H-pyrazol-3-yl]-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea;

1-(5-tert-Butyl-2-p-tolyl-2H-pyrazol-3-yl)-3-[(1S,4R)-4-(2-morpholin-4-yl-ethoxy)-1,2,3,4-tetrahydro-naphthalen-1-yl]-urea;

1-[5-tert-Butyl-2-(4-hydroxymethyl-phenyl)-2H-pyrazol-3-yl]-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}urea;

1-[5-tert-Butyl-2-(4-hydroxymethyl-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-{5-tert-Butyl-2-[3-(2-hydroxy-ethylsulfanyl)-phenyl]-2H-pyrazol-3-yl}-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea;

1-[5-(2-Hydroxy-1,1-dimethyl-ethyl)-2-p-tolyl-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-[5-tert-Butyl-2-(4-hydroxymethyl-phenyl)-2H-pyrazol-3-yl]-3-{(1S,3S)-3-[3-((S)-1-methyl-pyrrolidin-2-yl)-[1,2,4]triazolo[4,3-a]pyridin-6-yloxy]-indan-1-yl}-urea;

1-(5-tert-Butyl-2-p-tolyl-2H-pyrazol-3-yl)-3-{(1S,4R)-4-[3-((R)-3-hydroxy-pyrrolidin-1-yl)-[1,2,4]triazolo[4,3-a]pyridin-6-yloxy]-1,2,3,4-tetrahydro-naphthalen-1-yl}-urea;

1-{5-tert-Butyl-2-[3-(2-hydroxy-ethoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-{5-tert-Butyl-2-[3-(2-dimethylamino-ethoxy)-phenyl]-2H-pyrazol-3-yl}-3-[(1S,4R)-4-(3-piperidin-1-yl-[1,2,4]triazolo[4,3-c]pyridin-6-yloxy)-1,2,3,4-tetrahydro-naphthalen-1-yl]-urea;

1-{5-tert-Butyl-2-[3-(4-methyl-piperazin-1-ylmethyl)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-{5-tert-Butyl-2-[3-(2-hydroxy-ethoxy)-phenyl]-2H-pyrazol-3-yl}-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea;

1-(5-tert-Butyl-2-p-tolyl-2H-pyrazol-3-yl)-3-((1S,4R)-4-{3-[(2-dimethylamino-ethyl)-methyl-amino]-[1,2,4]triazolo[4,3-a]pyridin-6-yloxy}-1,2,3,4-tetrahydro-naphthalen-1-yl)-urea;

1-[5-tert-Butyl-2-(3-piperidin-1-ylmethyl-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-(5-tert-Butyl-2-p-tolyl-2H-pyrazol-3-yl)-3-((1S,4R)-4-{3-[methyl-(2-morpholin-4-yl-ethyl)-amino]-[1,2,4]triazolo[4,3-a]pyridin-6-yloxy}-1,2,3,4-tetrahydro-naphthalen-1-yl)-urea;

1-(5-tert-Butyl-2-p-tolyl-2H-pyrazol-3-yl)-3-{(1S,4R)-4-[3-((R)-1-morpholin-4-yl-ethyl)-[1,2,4]triazolo[4,3-a]pyridin-6-yloxy]-1,2,3,4-tetrahydro-naphthalen-1-yl}-urea;

1-(5-tert-Butyl-2-p-tolyl-2H-pyrazol-3-yl)-3-{(1S,4R)-4-[3-((S)-1-morpholin-4-yl-ethyl)-[1,2,4]triazolo[4,3-a]pyridin-6-yloxy]-1,2,3,4-tetrahydro-naphthalen-1-yl}-urea;

1-(5-tert-Butyl-2-p-tolyl-2H-pyrazol-3-yl)-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea;

1-{5-tert-Butyl-2-[3-(2-hydroxy-ethoxymethyl)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-(5-tert-Butyl-2-p-tolyl-2H-pyrazol-3-yl)-3-[(1S,4R)-4-(3-[1,4]oxazepan-4-yl-[1,2,4]triazolo[4,3-a]pyridin-6-yloxy)-1,2,3,4-tetrahydro-naphthalen-1-yl]-urea;

1-(5-tert-Butyl-2-{3-[4-(2-hydroxy-ethyl)-piperazin-1-ylmethyl]-phenyl}-2H-pyrazol-3-yl)-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-(2-tert-Butyl-5-p-tolyl-3H-imidazol-4-yl)-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-{5-tert-Butyl-2-[3-(4-hydroxy-piperidin-1-ylmethyl)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-{5-tert-Butyl-2-[3-(2-hydroxy-ethylsulfanyl)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-(5-tert-Butyl-2-p-tolyl-2H-pyrazol-3-yl)-3-{(1S,4R)-4-[3-(4-hydroxymethyl-piperidin-1-yl)-[1,2,4]triazolo[4,3-a]pyridin-6-yloxy]-1,2,3,4-tetrahydro-naphthalen-1-yl}-urea;

1-(5-tert-Butyl-2-p-tolyl-2H-pyrazol-3-yl)-3-[(1S,4S)-4-(3-piperidin-1-yl-[1,2,4]triazolo[4,3-a]pyridin-6-yloxy)-1,2,3,4-tetrahydro-naphthalen-1-yl]-urea;

1-(5-tert-Butyl-2-p-tolyl-2H-pyrazol-3-yl)-3-{(1S,4R)-4-[3-(3-hydroxymethyl-4-methyl-piperazin-1-ylmethyl)-[1,2,4]triazolo[4,3-a]pyridin-6-yloxy]-1,2,3,4-tetrahydro-naphthalen-1-yl}-urea;

1-[5-tert-Butyl-2-(4-hydroxymethyl-phenyl)-2H-pyrazol-3-yl]-3-{(1S,4R)-4-[3-(4-hydroxy-piperidin-1-yl)-[1,2,4]triazolo[4,3-a]pyridin-6-yloxy]-1,2,3,4-tetrahydro-naphthalen-1-yl}-urea;

1-(5-tert-Butyl-2-p-tolyl-2H-pyrazol-3-yl)-3-{(1S,4R)-4-[3-((S)-1-isopropyl-pyrrolidin-2-yl)-[1,2,4]triazolo[4,3-a]pyridin-6-yloxy]-1,2,3,4-tetrahydro-naphthalen-1-yl}-urea;

1-(5-tert-Butyl-2-p-tolyl-2H-pyrazol-3-yl)-3-[(1S,4R)-4-(3-dimethylamino-[1,2,4]triazolo[4,3-a]pyridin-6-yloxy)-1,2,3,4-tetrahydro-naphthalen-1-yl]-urea;

1-(5-tert-Butyl-2-p-tolyl-2H-pyrazol-3-yl)-3-{(1S,4R)-4-[3-((R)-1-methyl-pyrrolidin-2-yl)-[1,2,4]triazolo[4,3-a]pyridin-6-yloxy]-1,2,3,4-tetrahydro-naphthalen-1-yl}-urea;

1-(5-tert-Butyl-2-p-tolyl-2H-pyrazol-3-yl)-3-{(1S,4R)-4-[3-((S)-1-ethyl-pyrrolidin-2-yl)-[1,2,4]triazolo[4,3-a]pyridin-6-yloxy]-1,2,3,4-tetrahydro-naphthalen-1-yl}-urea;

1-(5-tert-Butyl-2-p-tolyl-2H-pyrazol-3-yl)-3-{(1S,4R)-4-[3-((S)-1-methyl-piperidin-2-yl)-[1,2,4]triazolo[4,3-a]pyridin-6-yloxy]-1,2,3,4-tetrahydro-naphthalen-1-yl}-urea;

1-(5-tert-Butyl-2-p-tolyl-2H-pyrazol-3-yl)-3-{(1S,4R)-4-[3-((S)-3-hydroxy-piperidin-1-yl)-[1,2,4]triazolo[4,3-a]pyridin-6-yloxy]-1,2,3,4-tetrahydro-naphthalen-1-yl}-urea;

1-(5-tert-Butyl-2-p-tolyl-2H-pyrazol-3-yl)-3-{(1S,4R)-4-[3-((R)-3-hydroxy-piperidin-1-yl)-[1,2,4]triazolo[4,3-a]pyridin-6-yloxy]-1,2,3,4-tetrahydro-naphthalen-1-yl}-urea;

1-[5-tert-Butyl-2-(4-hydroxymethyl-phenyl)-2H-pyrazol-3-yl]-3-{(1S,4R)-4-[3-((S)-1-methyl-pyrrolidin-2-yl)-[1,2,4]triazolo[4,3-c]pyridin-6-yloxy]-1,2,3,4-tetrahydro-naphthalen-1-yl}-urea;

1-(5-tert-Butyl-2-p-tolyl-2H-pyrazol-3-yl)-3-{(1S,4R)-4-[3-(4-hydroxyethyl-piperidin-1-yl)-[1,2,4]triazolo[4,3-a]pyridin-6-yloxy]-1,2,3,4-tetrahydro-naphthalen-1-yl}-urea;

1-[(1S,4R)-4-(3-Azepan-1-yl-[1,2,4]triazolo[4,3-a]pyridin-6-yloxy)-1,2,3,4-tetrahydro-naphthalen-1-yl]-3-(5-tert-butyl-2-p-tolyl-2H-pyrazol-3-yl)-urea;

1-(5-tert-Butyl-2-p-tolyl-2H-pyrazol-3-yl)-3-{(1S,4R)-4-[3-(4-methyl-piperazine-1-yl)-[1,2,4]triazolo[4,3-a]pyridin-6-yloxy]-1,2,3,4-tetrahydro-naphthalen-1-yl}urea;

1-(5-tert-Butyl-2-p-tolyl-2H-pyrazol-3-yl)-3-{(1S,4R)-4-[3-(4-methyl-[1,4]diazepan-1-yl)-[1,2,4]triazolo[4,3-a]pyridin-6-yloxy]-1,2,3,4-tetrahydro-naphthalen-1-yl}urea;

1-[5-tert-Butyl-2-(4-hydroxy-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-[5-tert-Butyl-2-(4-cyano-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea;

1-(5-tert-Butyl-2-p-tolyl-2H-pyrazol-3-yl)-3-{(1S,4S)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea;

1-[5-tert-Butyl-2-(4-hydroxy-phenyl)-2H-pyrazol-3-yl]-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea;

1-(5-tert-Butyl-2-p-tolyl-2H-pyrazol-3-yl)-3-((1S,4R)-4-{3-[4-(1-hydroxy-1-methyl-ethyl)-piperidin-1-yl]-[1,2,4]triazolo[4,3-a]pyridin-6-yloxy}-1,2,3,4-tetrahydro-naphthalen-1-yl)-urea;

1-(5-tert-Butyl-2-p-tolyl-2H-pyrazol-3-yl)-3-[(1S,4R)-4-(3-pyrrolidin-1-yl-[1,2,4]triazolo[4,3-a]pyridin-6-yloxy)-1,2,3,4-tetrahydro-naphthalen-1-yl]-urea;

1-(5-tert-Butyl-2-p-tolyl-2H-pyrazol-3-yl)-3-{(1S,4R)-4-[3-(1-dimethylamino-1-methyl-ethyl)-[1,2,4]triazolo[4,3-a]pyridin-6-yloxy]-1,2,3,4-tetrahydro-naphthalen-1-yl}-urea;

1-(5-tert-Butyl-2-p-tolyl-2H-pyrazol-3-yl)-3-{(1S,4R)-4-[3-((R)-3-hydroxymethyl-piperidin-1-yl)-[1,2,4]triazolo[4,3-a]pyridin-6-yloxy]-1,2,3,4-tetrahydro-naphthalen-1-yl}-urea;

1-(5-tert-Butyl-2-p-tolyl-2H-pyrazol-3-yl)-3-{(1S,4R)-4-[3-((S)-3-hydroxymethyl-piperidin-1-yl)-[1,2,4]triazolo[4,3-a]pyridin-6-yloxy]-1,2,3,4-tetrahydro-naphthalen-1-yl}-urea;

1-(5-tert-Butyl-2-p-tolyl-2H-pyrazol-3-yl)-3-{(1S,4R)-4-[3-(4-hydroxy-4-methyl-piperidin-1-yl)-[1,2,4]triazolo[4,3-a]pyridin-6-yloxy]-1,2,3,4-tetrahydro-naphthalen-1-yl}-urea;

1-(5-tert-Butyl-2-p-tolyl-2H-pyrazol-3-yl)-3-{(1S,4R)-4-[3-(1-methyl-1-pyrrolidin-1-yl-ethyl)-[1,2,4]triazolo[4,3-a]pyridin-6-yloxy]-1,2,3,4-tetrahydro-naphthalen-1-yl}-urea;

1-(5-tert-Butyl-2-p-tolyl-2H-pyrazol-3-yl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-(5-tert-Butyl-2-p-tolyl-2H-pyrazol-3-yl)-3-{(1S,4R)-4-[3-((R)-2-methyl-piperidin-1-yl)-[1,2,4]triazolo[4,3-a]pyridin-6-yloxy]-1,2,3,4-tetrahydro-naphthalen-1-yl}-urea;

1-(5-tert-Butyl-2-p-tolyl-2H-pyrazol-3-yl)-3-{(1S,4R)-4-[3-((S)-4-methyl-morpholin-3-yl)-[1,2,4]triazolo[4,3-a]pyridin-6-yloxy]-1,2,3,4-tetrahydro-naphthalen-1-yl}-urea;

1-(5-tert-Butyl-2-p-tolyl-2H-pyrazol-3-yl)-3-((1S,4R)-4-{3-[(S)-1-(3-hydroxy-propyl)-pyrrolidin-2-yl]-[1,2,4]triazolo[4,3-a]pyridin-6-yloxy}-1,2,3,4-tetrahydro-naphthalen-1-yl)-urea;

1-(5-tert-Butyl-2-p-tolyl-2H-pyrazol-3-yl)-3-{(1S,4R)-4-[3-((S)-2-hydroxymethyl-1-methyl-pyrrolidin-2-yl)-[1,2,4]triazolo[4,3-a]pyridin-6-yloxy]-1,2,3,4-tetrahydro-naphthalen-1-yl}-urea;

1-(5-tert-Butyl-2-p-tolyl-2H-pyrazol-3-yl)-3-{(1S,4R)-4-[3-(1,4-dimethyl-piperazin-2-yl)-[1,2,4]triazolo[4,3-a]pyridin-6-yloxy]-1,2,3,4-tetrahydro-naphthalen-1-yl}-urea;

1-(5-tert-Butyl-2-p-tolyl-2H-pyrazol-3-yl)-3-{(1S,4R)-4-[3-((S)-1,4,4-trimethyl-pyrrolidin-2-yl)-[1,2,4]triazolo[4,3-a]pyridin-6-yloxy]-1,2,3,4-tetrahydro-naphthalen-1-yl}-urea;

1-(5-tert-Butyl-2-p-tolyl-2H-pyrazol-3-yl)-3-{(1S,4R)-4-[3-((S)-1-methyl-piperidin-3-yl)-[1,2,4]triazolo[4,3-a]pyridin-6-yloxy]-1,2,3,4-tetrahydro-naphthalen-1-yl}-urea;

1-(5-tert-Butyl-2-p-tolyl-2H-pyrazol-3-yl)-3-{(1S,4R)-4-[3-((R)-1-methyl-piperidin-3-yl)-[1,2,4]triazolo[4,3-a]pyridin-6-yloxy]-1,2,3,4-tetrahydro-naphthalen-1-yl}-urea;

1-(5-tert-Butyl-2-p-tolyl-2H-pyrazol-3-yl)-3-{(1S,4R)-4-[3-((R)-1-methyl-pyrrolidin-3-yl)-[1,2,4]triazolo[4,3-a]pyridin-6-yloxy]-1,2,3,4-tetrahydro-naphthalen-1-yl}-urea;

1-(5-tert-Butyl-2-p-tolyl-2H-pyrazol-3-yl)-3-{(1S,4R)-4-[3-((2S,4R)-4-fluoro-1-methyl-pyrrolidin-2-yl)-[1,2,4]triazolo[4,3-a]pyridin-6-yloxy]-1,2,3,4-tetrahydro-naphthalen-1-yl}-urea;

1-(5-tert-Butyl-2-p-tolyl-2H-pyrazol-3-yl)-3-{(1S,4R)-4-[3-((S)-3-hydroxymethyl-pyrrolidin-1-yl)-[1,2,4]triazolo[4,3-a]pyridin-6-yloxy]-1,2,3,4-tetrahydro-naphthalen-1-yl}-urea;

1-(5-tert-Butyl-2-p-tolyl-2H-pyrazol-3-yl)-3-{(1S,4R)-4-[3-((R)-3-hydroxymethyl-pyrrolidin-1-yl)-[1,2,4]triazolo[4,3-a]pyridin-6-yloxy]-1,2,3,4-tetrahydro-naphthalen-1-yl}-urea;

1-(5-tert-Butyl-2-p-tolyl-2H-pyrazol-3-yl)-3-((1S,4R)-4-{3-[4-(2-hydroxy-ethyl)-piperazin-1-yl]-[1,2,4]triazolo[4,3-a]pyridin-6-yloxy}-1,2,3,4-tetrahydro-naphthalen-1-yl)-urea;

1-{5-tert-Butyl-2-[3-(2-dimethylamino-ethoxy)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydronaphthalen-1-yl)-urea;

1-{5-tert-Butyl-2-[3-(2-dimethylamino-ethoxy)-phenyl]-2H-pyrazol-3-yl}-3-{(1S,4R)-4-[3-(cis-2,6-dimethyl-piperidin-1-yl)-[1,2,4]triazolo[4,3-c]pyridin-6-yloxy]-1,2,3,
4-tetrahydro-naphthalen-1-yl}-urea;

1-[5-tert-Butyl-2-(3-morpholin-4-ylmethyl-phenyl)-2H-
pyrazol-3-yl]-3-{(1S,4R)-4-[3-((S)-2-methyl-piperidin-1-
yl)-[1,2,4]triazolo[4,3-a]pyridin-6-yloxy]-1,2,3,4-tet-
rahydro-naphthalen-1-yl}-urea;

1-{5-tert-Butyl-2-[3-(4-methyl-piperazin-1-ylmethyl)-phe-
nyl]-2H-pyrazol-3-yl}-3-{(1S,4R)-4-[3-((S)-2-methyl-pi-
peridin-1-yl)-[1,2,4]triazolo[4,3-a]pyridin-6-yloxy]-1,2,
3,4-tetrahydro-naphthalen-1-yl}-urea;

1-(5-tert-Butyl-2-p-tolyl-2H-pyrazol-3-yl)-3-{(1S,4R)-4-[3-
(1-dimethylamino-cyclopentyl)-[1,2,4]triazolo[4,3-a]py-
ridin-6-yloxy]-1,2,3,4-tetrahydro-naphthalen-1-yl}-urea;

1-(5-tert-Butyl-2-p-tolyl-2H-pyrazol-3-yl)-3-{(1S,4R)-4-[3-
((2S,6R)-2,6-dimethyl-piperidin-1-yl)-[1,2,4]triazolo[4,
3-a]pyridin-6-yloxy]-1,2,3,4-tetrahydro-naphthalen-1-
yl}-urea;

1-[(1S,4R)-4-(3-Amino-[1,2,4]triazolo[4,3-a]pyridin-6-
yloxy)-1,2,3,4-tetrahydro-naphthalen-1-yl]-3-(5-tert-bu-
tyl-2-p-tolyl-2H-pyrazol-3-yl)-urea;

1-[5-tert-Butyl-2-(6-methyl-pyridin-3-yl)-2H-pyrazol-3-yl]-
3-[(1S,4R)-4-(3-piperidin-1-yl-[1,2,4]triazolo[4,3-a]pyri-
din-6-yloxy)-1,2,3,4-tetrahydro-naphthalen-1-yl]-urea;

1-{5-tert-Butyl-2-[3-(2-dimethylamino-ethoxy)-phenyl]-
2H-pyrazol-3-yl}-3-[(1S,4R)-4-(3-diisopropylamino-[1,
2,4]triazolo[4,3-a]pyridin-6-yloxy)-1,2,3,4-tetrahydro-
naphthalen-1-yl]urea;

N-(5-tert-Butyl-2-methoxy-3-{3-[(1S,4R)-4-(3-piperidin-1-
yl-[1,2,4]triazolo[4,3-a]pyridin-6-yloxy)-1,2,3,4-tetrahy-
dro-naphthalen-1-yl]-ureido}-phenyl)-methanesulfona-
mide;

1-(5-tert-Butyl-2-p-tolyl-2H-pyrazol-3-yl)-3-{(1S,4R)-4-[8-
methyl-3-((S)-1-methyl-pyrrolidin-2-yl)-[1,2,4]triazolo
[4,3-a]pyridin-6-yloxy]-1,2,3,4-tetrahydro-naphthalen-1-
yl}-urea;

1-{5-tert-Butyl-2-[4-(4-methyl-piperazin-1-ylmethyl)-phe-
nyl]-2H-pyrazol-3-yl}-3-[(1S,4R)-4-(3-piperidin-1-yl-[1,
2,4]triazolo[4,3-a]pyridin-6-yloxy)-1,2,3,4-tetrahydro-
naphthalen-1-yl]-urea;

1-(3-tert-Butyl-1'-methyl-1'H-[1,4']bipyrazolyl-5-yl)-3-
[(1S,4R)-4-(3-piperidin-1-yl-[1,2,4]triazolo[4,3-a]pyri-
din-6-yloxy)-1,2,3,4-tetrahydro-naphthalen-1-yl]-urea;

1-[3-tert-Butyl-1'-(2-dimethylamino-ethyl)-1'H-[1,4']bi-
pyrazolyl-5-yl]-3-[(1S,4R)-4-(3-piperidin-1-yl-[1,2,4]
triazolo[4,3-a]pyridin-6-yloxy)-1,2,3,4-tetrahydro-naph-
thalen-1-yl]-urea;

N-[5-tert-Butyl-2-methoxy-3-(3-{(1S,4R)-4-[3-((S)-1-me-
thyl-pyrrolidin-2-yl)-[1,2,4]triazolo[4,3-a]pyridin-6-
yloxy]-1,2,3,4-tetrahydro-naphthalen-1-yl}-ureido)-phe-
nyl]-methanesulfonamide;

1-[5-tert-Butyl-2-(2-hydroxy-ethyl)-2H-pyrazol-3-yl]-3-
{(1S,4R)-4-[3-((S)-2-methyl-piperidin-1-yl)-[1,2,4]tria-
zolo[4,3-a]pyridin-6-yloxy]-1,2,3,4-tetrahydro-naphtha-
len-1-yl}-urea;

1-(5-tert-Butyl-isoxazol-3-yl)-3-{(1S,4R)-4-[3-((S)-2-me-
thyl-piperidin-1-yl)-[1,2,4]triazolo[4,3-a]pyridin-6-
yloxy]-1,2,3,4-tetrahydro-naphthalen-1-yl}-urea;

1-[3-tert-Butyl-1'-(2-morpholin-4-yl-ethyl)-1'H-[1,4']bi-
pyrazolyl-5-yl]-3-[(1S,4R)-4-(3-piperidin-1-yl-[1,2,4]
triazolo[4,3-a]pyridin-6-yloxy)-1,2,3,4-tetrahydro-naph-
thalen-1-yl]-urea;

1-[3-tert-Butyl-1'-(3-dimethylamino-propyl)-1'H-[1,4']bi-
pyrazolyl-5-yl]-3-[(1S,4R)-4-(3-piperidin-1-yl-[1,2,4]
triazolo[4,3-a]pyridin-6-yloxy)-1,2,3,4-tetrahydro-naph-
thalen-1-yl]-urea;

1-[3-tert-Butyl-1'-(3-morpholin-4-yl-propyl)-1'H-[1,4']bi-
pyrazolyl-5-yl]-3-[(1S,4R)-4-(3-piperidin-1-yl-[1,2,4]
triazolo[4,3-a]pyridin-6-yloxy]-1,2,3,4-tetrahydro-naph-
thalen-1-yl]-urea;

1-{(1S,4R)-4-[3-((2S,6R)-2,6-Dimethyl-piperidin-1-yl)-[1,
2,4]triazolo[4,3-a]pyridin-6-yloxy]-1,2,3,4-tetrahydro-
naphthalen-1-yl}-3-(3-fluoro-5-morpholin-4-yl-phenyl)-
urea;

1-[5-tert-Butyl-2-(2-morpholin-4-yl-ethyl)-2H-pyrazol-3-
yl]-3-{(1S,4R)-4-[3-((S)-2-methyl-piperidin-1-yl)-[1,2,4]
triazolo[4,3-a]pyridin-6-yloxy]-1,2,3,4-tetrahydro-naph-
thalen-1-yl}-urea;

1-Cyclopropyl-3-{(1S,4R)-4-[3-((2S,6R)-2,6-dimethyl-pip-
eridin-1-yl)-[1,2,4]triazolo[4,3-a]pyridin-6-yloxy]-1,2,3,
4-tetrahydro-naphthalen-1-yl}-urea;

1-[5-tert-Butyl-2-(2-hydroxy-ethyl)-2H-pyrazol-3-yl]-3-
{(1S,4R)-4-[3-((2S,6R)-2,6-dimethyl-piperidin-1-yl)-[1,
2,4]triazolo[4,3-a]pyridin-6-yloxy]-1,2,3,4-tetrahydro-
naphthalen-1-yl}-urea;

1-{5-tert-Butyl-2-[1-(2-dimethylamino-ethyl)-1H-imidazol-
4-yl]-2H-pyrazol-3-yl}-3-[(1S,4R)-4-(3-piperidin-1-yl-
[1,2,4]triazolo[4,3-a]pyridin-6-yloxy)-1,2,3,4-tetrahydro-
naphthalen-1-yl]urea;

1-[5-tert-Butyl-2-(2-hydroxy-ethyl)-2H-pyrazol-3-yl]-3-
{(1S,4R)-4-[3-((S)-1-methyl-piperidin-2-yl)-[1,2,4]tria-
zolo[4,3-a]pyridin-6-yloxy]-1,2,3,4-tetrahydro-naphtha-
len-1-yl}-urea;

1-[5-tert-Butyl-2-(2-morpholin-4-yl-ethyl)-2H-pyrazol-3-
yl]-3-{(1S,4R)-4-[3-((2S,6R)-2,6-dimethyl-piperidin-1-
yl)-[1,2,4]triazolo[4,3-a]pyridin-6-yloxy]-1,2,3,4-tet-
rahydro-naphthalen-1-yl}-urea;

1-{(1S,4R)-4-[3-(8-Aza-bicyclo[3.2.1]oct-8-yl)-[1,2,4]tria-
zolo[4,3-a]pyridin-6-yloxy]-1,2,3,4-tetrahydro-naphtha-
len-1-yl}-3-{5-tert-butyl-2-[3-(2-dimethylamino-
ethoxy)-phenyl]-2H-pyrazol-3-yl}-urea;

1-{5-tert-Butyl-2-[3-(2-dimethylamino-ethoxy)-phenyl]-
2H-pyrazol-3-yl}-3-{(1S,4R)-4-[3-((R)-2-methyl-piperi-
din-1-yl)-[1,2,4]triazolo[4,3-a]pyridin-6-yloxy]-1,2,3,4-
tetrahydro-naphthalen-1-yl}-urea;

1-[3-tert-Butyl-1'-(2-morpholin-4-yl-ethyl)-1'H-[1,4']bi-
pyrazolyl-5-yl]-3-{(1S,4R)-4-[3-((2S,6R)-2,6-dimethyl-
piperidin-1-yl)-[1,2,4]triazolo[4,3-a]pyridin-6-yloxy]-1,
2,3,4-tetrahydro-naphthalen-1-yl}-urea;

1-[3-tert-Butyl-1'-(2-dimethylamino-ethyl)-1'H-[1,4']bi-
pyrazolyl-5-yl]-3-{(1S,4R)-4-[3-((2S,6R)-2,6-dimethyl-
piperidin-1-yl)-[1,2,4]triazolo[4,3-a]pyridin-6-yloxy]-1,
2,3,4-tetrahydro-naphthalen-1-yl}-urea;

1-(5-tert-Butyl-2-methyl-2H-pyrazol-3-yl)-3-{(1S,4R)-4-
[3-((S)-2-methyl-piperidin-1-yl)-[1,2,4]triazolo[4,3-a]py-
ridin-6-yloxy]-1,2,3,4-tetrahydronaphthalen-1-yl}-urea;

1-[5-tert-Butyl-2-(2-dimethylamino-ethyl)-2H-pyrazol-3-
yl]-3-{(1S,4R)-4-[3-((S)-2-methyl-piperidin-1-yl)-[1,2,4]
triazolo[4,3-a]pyridin-6-yloxy]-1,2,3,4-tetrahydro-naph-
thalen-1-yl}-urea;

1-[5-tert-Butyl-2-(2-piperidin-1-yl-ethyl)-2H-pyrazol-3-yl]-
3-{(1S,4R)-4-[3-((S)-2-methyl-piperidin-1-yl)-[1,2,4]
triazolo[4,3-a]pyridin-6-yloxy]-1,2,3,4-tetrahydro-naph-
thalen-1-yl}-urea;

1-{5-tert-Butyl-2-[2-(4-methyl-piperazin-1-yl)-ethyl]-2H-
pyrazol-3-yl}-3-{(1S,4R)-4-[3-((S)-2-methyl-piperidin-
1-yl)-[1,2,4]triazolo[4,3-a]pyridin-6-yloxy]-1,2,3,4-tet-
rahydro-naphthalen-1-yl}-urea;

1-[5-tert-Butyl-2-(3-morpholin-4-ylmethyl-phenyl)-2H-
pyrazol-3-yl]-3-{(1S,4R)-4-[3-((2S,6R)-2,6-dimethyl-pi-
peridin-1-yl)-[1,2,4]triazolo[4,3-a]pyridin-6-yloxy]-1,2,
3,4-tetrahydro-naphthalen-1-yl}-urea;

1-{5-tert-Butyl-2-[3-(2-morpholin-4-yl-ethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-{5-tert-Butyl-2-[3-(2-pyrrolidin-1-yl-ethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-(5-tert-Butyl-2-{3-[2-(ethyl-methyl-amino)-ethyl]-phenyl}-2H-pyrazol-3-yl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-{5-tert-Butyl-2-[3-(2-dimethylamino-ethyl)-phenyl]-2H-pyrazol-3-yl)-3-(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-{5-tert-Butyl-2-[3-(2-piperidin-1-yl-ethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-(5-tert-Butyl-2-{3-[2-(4-methyl-piperazin-1-yl)-ethyl]-phenyl}-2H-pyrazol-3-yl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-{5-tert-Butyl-2-[3-(2-[1,4]oxazepan-4-yl-ethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-(5-tert-Butyl-2-{3-[2-(4-methyl-[1,4]diazepan-1-yl)-ethyl]-phenyl}-2H-pyrazol-3-yl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-[5-tert-Butyl-2-(2-hydroxy-ethyl)-2H-pyrazol-3-yl]-3-{(1S,4R)-4-[3-((S)-3-methyl-morpholin-4-yl)-[1,2,4]triazolo[4,3-a]pyridin-6-yloxy]-1,2,3,4-tetrahydro-naphthalen-1-yl}-urea;

1-(5-tert-Butyl-2-{2-[(2-dimethylamino-ethyl)-methyl-amino]-pyrimidin-4-yl}-2H-pyrazol-3-yl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-{5-tert-Butyl-2-[3-(2-dimethylamino-ethoxy)-phenyl]-2H-pyrazol-3-yl}-3-{(1S,4R)-4-[3-((S)-3-methyl-morpholin-4-yl)-[1,2,4]triazolo[4,3-a]pyridin-6-yloxy]-1,2,3,4-tetrahydro-naphthalen-1-yl}-urea;

1-[5-tert-Butyl-2-(2-morpholin-4-yl-ethyl)-2H-pyrazol-3-yl]-3-{(1S,4R)-4-[3-((S)-3-methyl-morpholin-4-yl)-[1,2,4]triazolo[4,3-a]pyridin-6-yloxy]-1,2,3,4-tetrahydro-naphthalen-1-yl}-urea;

1-{5-tert-Butyl-2-[3-(4-methyl-piperazin-1-ylmethyl)-phenyl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea;

1-[5-tert-Butyl-2-(3-pyrrolidin-1-ylmethyl-phenyl)-2H-pyrazol-3-yl]-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea;

1-{5-tert-Butyl-2-[3-(2-pyrrolidin-1-yl-ethoxy)-phenyl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea;

1-(5-tert-Butyl-2-{3-[2-(4-methyl-piperazin-1-yl)-ethoxy]-phenyl}-2H-pyrazol-3-yl)-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea;

1-(5-tert-Butyl-2-{3-[2-(ethyl-methyl-amino)-ethoxy]-phenyl}-2H-pyrazol-3-yl)-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea;

1-{(1S,4R)-4-[3-(4-Aza-spiro[2.5]oct-4-yl)-[1,2,4]triazolo[4,3-a]pyridin-6-yloxy]-1,2,3,4-tetrahydro-naphthalen-1-yl}-3-{5-tert-butyl-2-[3-(2-dimethylamino-ethoxy)-phenyl]-2H-pyrazol-3-yl}-urea;

1-[5-tert-Butyl-2-(3-morpholin-4-yl-methyl-phenyl)-2H-pyrazol-3-yl]-3-{(1S,4R)-4-[3-((S)-1-methyl-pyrrolidin-2-yl)-[1,2,4]triazolo[4,3-a]pyridin-6-yloxy]-1,2,3,4-tetrahydronaphthalen-1-yl}-urea;

1-(5-tert-Butyl-2-{3-[(2-dimethylamino-ethyl)-methyl-amino]-phenyl}-2H-pyrazol-3-yl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-{5-tert-Butyl-2-[3-((R)-2-dimethylamino-1-methyl-ethoxy)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-{5-tert-Butyl-2-[3-((S)-2-dimethylamino-1-methyl-ethoxy)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-[2-[3-(2-Dimethylamino-ethoxy)-phenyl]-5-(2-hydroxy-1,1-dimethyl-ethyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-{5-tert-Butyl-2-[3-(2-pyrrolidin-1-yl-ethoxy)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-{5-tert-Butyl-2-[3-(2-diethylamino-ethoxy)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-{5-tert-Butyl-2-[3-(2-morpholin-4-yl-ethoxy)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-{5-tert-Butyl-2-[3-(2-piperidin-1-yl-ethoxy)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-(5-tert-Butyl-2-{3-[2-(4-methyl-piperazin-1-yl)-ethoxy]-phenyl}-2H-pyrazol-3-yl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-{5-tert-Butyl-2-{3-[2-(4-fluoropiperidin-1-yl)-ethoxy]-phenyl}-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-(5-tert-Butyl-2-{3-[2-(4-methyl-[1,4]-diazepan-1-yl)-ethoxy]-phenyl}-2H-pyrazol-3-yl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-{5-tert-Butyl-2-[3-(2-[1,4]oxazepan-4-yl-ethoxy)-phenyl]-2H-pyrazol-3-yl}-3-{(1S,4R)-4-[3-((S)-2-methyl-piperidin-1-yl)-[1,2,4]triazolo[4,3-a]pyridin-6-yl oxy]-1,2,3,4-tetrahydro-naphthalen-1-yl}-urea;

1-(2-{3-[2-(8-Aza-bicyclo[3.2.1]oct-8-yl)-ethoxy]-phenyl}-5-tert-butyl-2H-pyrazol-3-yl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-(5-tert-Butyl-2-{3-[2-(ethyl-methyl-amino)-ethoxy]-phenyl}-2H-pyrazol-3-yl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-{5-tert-Butyl-2-(3-{2-[(2-methoxy-ethyl)-methyl-amino]-ethoxy}-phenyl)-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-(5-tert-Butyl-2-{3-[2-(4-methoxy-piperidin-1-yl-ethoxy]-phenyl}-2H-pyrazol-3-yl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-(5-tert-Butyl-2-{3-[2-(3-oxa-8-aza-bicyclo[3.2.1]oct-8-yl)-ethoxy]-phenyl}-2H-pyrazol-3-yl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-{5-tert-Butyl-2-[3-(4-methoxy-piperidin-1-ylmethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-(5-tert-Butyl-2-(3-{[(2-methoxy-ethyl)-methyl-amino]-methyl}-phenyl)-2H-pyrazol-3-yl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-{5-tert-Butyl-2-[3-(4-fluoro-piperidin-1-ylmethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-[5-tert-Butyl-2-(3-dimethylaminomethyl-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-[5-tert-Butyl-2-(3-pyrrolidin-1-ylmethyl-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-{(1S,4R)-4-[3-(4-Aza-spiro[2.5]oct-4-yl)-[1,2,4]triazolo[4,3-a]pyridin-6-yloxy]-1,2,3,4-tetrahydro-naphthalen-1-yl}-3-{5-tert-butyl-2-[3-(2-morpholin-4-yl-ethoxy)-phenyl]-2H-pyrazol-3-yl}-urea;

1-[5-tert-Butyl-2-(3-piperidin-1-ylmethyl-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-{5-tert-Butyl-2-[3-(4-methyl-[1,4]diazepan-1-ylmethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-{5-tert-Butyl-2-[3-((1S,4S)-5-methyl-2,5-diaza-bicyclo[2.2.1]hept-2-ylmethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-aphthalen-1-yl}-urea;

1-[5-tert-Butyl-2-(4-morpholin-4-ylmethyl-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-[5-tert-Butyl-2-(4-dimethylaminomethyl-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-{5-tert-Butyl-2-[4-(4-methyl-piperazin-1-ylmethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-{5-tert-Butyl-2-[4-(4-methyl-[1,4]diazepan-1-ylmethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-{5-tert-Butyl-2-[4-(4-methoxy-piperidin-1-ylmethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-[5-tert-Butyl-2-(4-pyrrolidin-1-ylmethyl-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-[5-tert-Butyl-2-(4-piperidin-1-ylmethyl-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-{5-tert-Butyl-2-[4-(4-fluoro-piperidin-1-ylmethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-(5-tert-Butyl-2-{4-[(ethyl-methyl-amino)-methyl]-phenyl}-2H-pyrazol-3-yl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-[5-tert-Butyl-2-(4-{[(2-methoxy-ethyl)-methyl-amino]-methyl}-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea;

1-{(5-tert-Butyl-2-[3-(2-dimethylamino-ethoxy)-phenyl]-2H-pyrazol-3-yl-3-{(1S,4S)-4-[3-((S)-2-methyl-piperidin-1-yl)-[1,2,4]triazolo[4,3-a]pyridin-6-yloxy]-1,2,3,4-tetrahydronaphthalen-1-yl]-urea;

and pharmaceutically acceptable salts thereof.

According to another aspect of the present invention there is provided a compound of formula (J), or a pharmaceutically acceptable salt thereof:

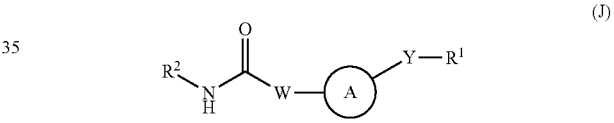

(J)

wherein $R^2$, W, A and Y have the same meaning as provided above for compounds of formula (I); and wherein $R^1$ is a group (IIc) wherein $R^{13}$, $X^2$, $X^3$, $X^4$ and $X^5$ have the same meaning as provided above for compounds of formula (I);

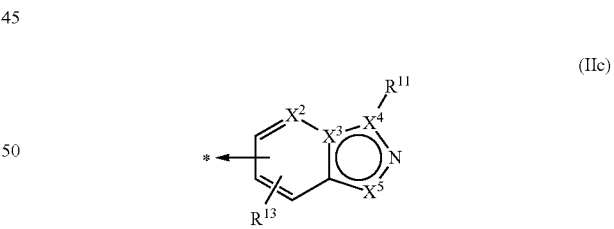

(IIc)

and wherein $R^{11}$ is phenyl or 5- or 6-membered monocyclic heteroaryl, wherein such phenyl or 5- or 6-membered monocyclic heteroaryl is substituted by a group —O—($C_2$-$C_6$alkylene)-$NR^R R^S$, wherein such $C_2$-$C_6$alkylene may be optionally substituted by a group $C_1$-$C_6$alkyl, $C_3$-$C_7$cycloalkyl, hydroxyl or halo;

$R^R$ and $R^S$ are at each occurrence independently $C_1$-$C_6$ alkyl or $C_3$-$C_7$ cycloalkyl, such $C_1$-$C_6$ alkyl and $C_3$-$C_7$ cycloalkyl being substituted by one or more group $OR^T$, CN, or halo; alternatively, $R^R$ and $R^S$, may form, together with the nitrogen atom to which they are attached, a 5-11-membered saturated monocyclic or bicyclic ring system which is substituted by one or more group $OR^T$, CN, halo, $C_1$-$C_6$ alkyl, or $C_3$-$C_7$ cycloalkyl, such $C_1$-$C_6$ alkyl and $C_3$-$C_7$ cycloalkyl being optionally substituted by a group $C_1$-$C_3$ alkyl, $C_3$-$C_7$cycloalkyl, $OR^D$, CN, or halo; and which 5-11-membered saturated monocyclic or bicyclic ring optionally contains a further heteroatom which is oxygen or nitrogen, said nitrogen atom optionally substituted by $C_1$-$C_6$ alkyl or $C_3$-$C_6$ cycloalkyl wherein any of such alkyl or cycloalkyl may be optionally substituted by a group $C_1$-$C_6$ alkyl, $C_3$-$C_7$ cycloalkyl, $OR^D$, CN, or halo; and $R^T$ is at each occurrence independently hydrogen, —$CH_3$, or —$C_2H_5$.

Where applicable, all preferred groups or embodiments described herebelow for compounds of formula (I), (Ia), (Ib), and (Ic) may be combined among each other and apply as well to compounds of formula (J) as above defined mutatis mutandis.

Utility.

As mentioned above the compounds of the invention are p38MAPK inhibitors, and thus may have utility for the treatment of diseases or conditions which benefit from inhibition of the p38 enzyme. Such diseases and conditions are known from the literature and several have been mentioned above. However, the compounds are generally of use as anti-inflammatory agents, particularly for use in the treatment of respiratory disease. In particular, the compounds may be used in the treatment of chronic obstructive pulmonary disease (COPD), chronic bronchitis, lung fibrosis, pneumonia, acute respiratory distress syndrome (ARDS), pulmonary emphysema, or smoking-induced emphysema, intrinsic (non-allergic asthma and extrinsic (allergic) asthma, mild asthma, moderate asthma, severe asthma, steroid resistant asthma, neutrophilic asthma, bronchitic asthma, exercise induced asthma, occupational asthma and asthma induced following bacterial infection, cystic fibrosis, pulmonary fibrosis and bronchiectasis.

The present invention provides the use of the compounds of the invention for the prevention and/or treatment of any disease or condition which benefit from inhibition of the p38 enzyme.

In a further aspect the present invention provides the use of compounds of the invention for the preparation of a medicament for the prevention and/or treatment of any disease or condition which benefit from inhibition of the p38 enzyme.

Moreover the present invention provides a method for prevention and/or treatment of any disease which benefit from inhibition of the p38 enzyme, said method comprises administering to a patient in need of such treatment a therapeutically effective amount of a compound of the invention.

Compositions.

As mentioned above, the compounds with which the present invention is concerned are p38 kinase inhibitors, and are useful in the treatment of several diseases for example inflammatory diseases of the respiratory tract. Examples of such diseases are referred to above, and include asthma, rhinitis, allergic airway syndrome, bronchitis and chronic obstructive pulmonary disease.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will be determined by clinical trial, as is required in the pharmaceutical art. In general, the daily dose range for oral administration will lie within the range of from about 0.001 mg to about 100 mg per kg body weight of a human, often 0.01 mg to about 50 mg per kg, for example 0.1 to 10 mg per kg, in single or divided doses. In general, the daily dose range for inhaled administration will lie within the range of from about 0.1 μg to about 1 mg per kg body weight of a human, preferably 0.1 μg to 50 μg per kg, in single or divided doses. On the other hand, it may be necessary to use dosages outside these limits in some cases. For the purpose of the invention, inhaled administration is preferred.

The compounds with which the present invention is concerned may be prepared for administration by any route consistent with their pharmacokinetic properties. Orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulfate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

However, for treatment of an inflammatory disease of the respiratory tract, compounds of the invention may also be formulated for inhalation, for example as a nasal spray, or dry powder or aerosol inhalers. For delivery by inhalation, the active compound is preferably in the form of microparticles. They may be prepared by a variety of techniques, including spray-drying, freeze-drying and micronisation. Aerosol generation can be carried out using, for example, pressure-driven jet atomizers or ultrasonic atomizers, preferably using propellant-driven metered aerosols or propellant-free administration of micronized active compounds from, for example, inhalation capsules or other "dry powder" delivery systems.

By way of example, a composition of the invention may be prepared as a suspension for delivery from a nebuliser or as an aerosol in a liquid propellant, for example for use in a pressurised metered dose inhaler (PMDI). Propellants suitable for use in a PMDI are known to the skilled person, and include CFC-12, HFA-134a, HFA-227, HCFC-22 ($CCl_2F_2$) and HFA-152 ($CH_4F_2$ and isobutane)

In a preferred embodiment of the invention, a composition of the invention is in dry powder form, for delivery using a dry powder inhaler (DPI). Many types of DPI are known.

Microparticles for delivery by administration may be formulated with excipients that aid delivery and release. For example, in a dry powder formulation, microparticles may be formulated with large carrier particles that aid flow from the DPI into the lung. Suitable carrier particles are known, and include lactose particles; they may have a mass median aerodynamic diameter of greater than 90 μm.

In the case of an aerosol-based formulation, an example is:

| | |
|---|---|
| Compound of the invention | 24 mg/canister |
| Lecithin, NF Liq. Conc. | 1.2 mg/canister |
| Trichlorofluoromethane, NF | 4.025 g/canister |
| Dichlorodifluoromethane, NF | 12.15 g/canister. |

The active compounds may be dosed as described depending on the inhaler system used. In addition to the active compounds, the administration forms may additionally contain excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of systems are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhalers for example as described EP-A-0505321). Additionally, compounds of the invention may be delivered in multi-chamber devices thus allowing for delivery of combination agents.

Combinations.

Other compounds may be combined with compounds with which the invention is concerned for the prevention and treatment of inflammatory diseases, in particular respiratory diseases. Thus the present invention is also concerned with pharmaceutical compositions comprising a therapeutically effective amount of a compound of the invention and one or more other therapeutic agents. Suitable therapeutic agents for a combination therapy with compounds of the invention include, but are not limited to: (1) corticosteroids, such as fluticasone propionate, fluticasone furoate, mometasone furoate, beclometasone dipropionate, ciclesonide, budesonide, GSK 685698, GSK 870086, QAE 397, QMF 149, and TPI-1020; (2) β2-adrenoreceptor agonists such as salbutamol, albuterol, terbutaline, fenoterol, and long acting β2-adrenoreceptor agonists such as salmeterol, indacaterol, formoterol (including formoterol fumarate), arformoterol, carmoterol, GSK 642444, GSK 159797, GSK 159802, GSK 597501, GSK 678007, and AZD3199; (3) corticosteroid/long acting β2 agonist combination products such as salmeterol/fluticasone propionate (Advair/Seretide), formoterol/budesonide (Symbicort), formoterol/fluticasone propionate (Flutiform), formoterol/ciclesonide, formoterol/mometasone furoate, formoterol/beclometasone dipropionate, indacaterol/mometasone furoate, Indacaterol/QAE 397, GSK 159797/GSK 685698, GSK 159802/GSK 685698, GSK 642444/GSK 685698, GSK 159797/GSK 870086, GSK 159802/GSK 870086, GSK 642444/GSK 870086, and arformoterol/ciclesonide; (4) anticholinergic agents, for example muscarinic-3 (M3) receptor antagonists such as ipratropium bromide, tiotropium bromide, Aclidinium (LAS-34273), NVA-237, GSK 233705, Darotropium, GSK 573719, GSK 961081, QAT 370, QAX 028, and EP-101; (5) dual pharmacology M3-anticholinergic/p2-adrenoreceptor agonists such as GSK961081, AZD2115, and LAS190792; (6) leukotriene modulators, for example leukotriene antagonists such as montelukast, zafirulast or pranlukast or leukotriene biosynthesis inhibitors such as Zileuton or BAY-1005, or LTB4 antagonists such as Amelubant, or FLAP inhibitors such as GSK 2190914 or AM-103; (7) phosphodiesterase-IV (PDE-IV) inhibitors (oral or inhaled), such as roflumilast, cilomilast, Oglemilast, ONO-6126, Tetomilast, Tofimilast, UK 500, 001, and GSK 256066; (8) antihistamines, for example selective histamine-1 (H1) receptor antagonists, such as fexofenadine, citirizine, loratidine or astemizole or dual H1/H3 receptor antagonists such as GSK 835726, GSK 1004723, or selective histamine-4 (H4) receptor antagonists, such as ZPL3893787; (9) antitussive agents, such as codeine or dextramorphan; (10) a mucolytic, for example N acetyl cysteine or fudostein; (11) a expectorant/mucokinetic modulator, for example ambroxol, hypertonic solutions (e.g. saline or mannitol) or surfactant; (12) a peptide mucolytic, for example recombinant human deoxyribonoclease I (dornase-alfa and rhDNase) or helicidin; (13) antibiotics, for example azithromycin, tobramycin, and aztreonam; (14) non-selective COX-1/COX-2 inhibitors, such as ibuprofen or ketoprofen; (15) COX-2 inhibitors, such as celecoxib and rofecoxib; (16) VLA-4 antagonists, such as those described in WO 1997/03094 and WO 1997/02289, which are incorporated herein by reference in their entireties; (17) TACE inhibitors and TNF-α inhibitors, for example anti-TNF monoclonal antibodies, such as Remicade and CDP-870 and TNF receptor immunoglobulin molecules, such as Enbrel; (18) inhibitors of matrix metalloprotease, for example MMP-12; (19) human neutrophil elastase inhibitors, such as ONO-6818 or those described in WO 2005/026124, WO 2003/053930 and WO 2006/082412, which are incorporated herein by reference in their entireties; (20) A2b antagonists such as those described in WO 2002/42298, which is incorporated herein by reference in its entirety; (21) modulators of chemokine receptor function, for example antagonists of CCR3 and CCR8; (22) compounds which modulate the action of other prostanoid receptors, for example a thromboxane $A_2$ antagonist; DP1 antagonists such as MK-0524, CRTH2 antagonists such as ODC9101 and 00000459 and AZD1981 and mixed DP1/CRTH2 antagonists such as AMG 009 and AMG853; (23) PPAR agonists including PPAR alpha agonists (such as fenofibrate), PPAR delta agonists, PPAR gamma agonists such as Pioglitazone, Rosiglitazone and Balaglitazone; (24) methylxanthines such as theophylline or aminophylline and methylxanthine/corticosteroid combinations such as theophylline/budesonide, theophylline/fluticasone propionate, theophylline/ciclesonide, theophylline/mometasone furoate and theophylline/beclometasone dipropionate; (25) Ata agonists such as those described in EP 1 052 264 and EP 1 241 176, which are incorporated herein by reference in their entireties; (26) CXCR2 or IL-8 antagonists such as SCH 527123 or GSK 656933; (27) IL-R signalling modulators such as kineret and ACZ 885; (28) MCP-1 antagonists such as ABN-912.

The present invention is also directed to a kit comprising the pharmaceutical compositions of compounds of the present invention alone or in combination with or in admixture with one or more pharmaceutically acceptable carriers and/or excipients and a device which may be a single- or multi-dose dry powder inhaler, a metered dose inhaler or a nebulizer.

Methods of Synthesis.

In one aspect of the present invention, a process for the preparation of compounds of the invention is provided, according to general synthetic routes described in this section. In the following reaction schemes, unless otherwise indicated, the groups mentioned assume the same meaning as those reported for compounds of formula (I).

The skilled person may introduce, where appropriate, suitable variations to the conditions specifically described in the examples in order to adapt the synthetic routes to the provision of further compounds of the invention. Such variations may include, but are not limited to, use of appropriate starting materials to generate different compounds, changes in the solvent and temperature of reactions, replacements of reactives with analogous chemical role, introduction or removal of protection/deprotection stages of functional groups sensitive to reaction conditions and reagents, as well as introduction or removal of specific synthetic steps oriented to further functionalisation of the chemical scaffold.

Processes which can be used and are described and reported in Examples and Schemes, should not be viewed as limiting the scope of the synthetic methods available for the preparation of the compounds of the invention.

The process described is particularly advantageous as it is susceptible of being properly modulated, through any proper variant known to the skilled person, so as to obtained any of the desired compounds of the invention. Such variants are comprised within the scope of the present invention.

From all of the above, it should be clear to the skilled person that any of the described groups may be present as such or in any properly protected form.

In particular, functional groups present in the intermediate and compounds and which could generate unwanted side reaction and by-products, need to be properly protected before the alkylation, acylation, coupling or sulfonylation takes place. Likewise, subsequent deprotection of those same protected groups may follow upon completion of the said reactions.

In the present invention, unless otherwise indicated, the term "protecting group" designates a protective group adapted to preserve the function of the group it is bound to. Typically, protective groups are used to preserve amino, hydroxyl, or carboxyl functions. Appropriate protecting groups may thus include, for example, benzyl, benzyloxycarbonyl, t-butoxycarbonyl, alkyl or benzyl esters or the like, which are well known to those skilled in the art (see, for a general reference, T. W. Green; Protective Groups in Organic Synthesis (Wiley, N.Y. 1981), which is incorporated herein by reference in its entirety).

Likewise, selective protection and deprotection of any of the said groups, for instance including carbonyl, hydroxyl or amino groups, may be accomplished according to very well known methods commonly employed in organic synthetic chemistry.

Optional salification of the compounds of formula (I) or N-oxides on the pyridine ring thereof may be carried out by properly converting any of the free acidic or amino groups into the corresponding pharmaceutically acceptable salts. In this case too, the operative conditions being employed for the optional salification of the compounds of the invention are all within the ordinary knowledge of the skilled person.

From all of the above, it should be clear that the above process, comprehensive of any variant thereof for the preparation of suitable compounds of the invention, may be conveniently modified so that to adapt the reaction conditions to the specific needs, for instance by choosing appropriate condensing agents, solvents and protective groups, as the case may be.

For example compounds of the invention of formula (I) may be prepared according to the route illustrated in Scheme 1.

Scheme 1

Compounds of general formula (I) may be prepared from compounds of general formula (1a) by reaction with a compound of general formula (1b1) or (1b2) wherein $R^2$ is as defined in general formula (I), in a suitable solvent such as dimethyl sulfoxide, 1,4-dioxane, N,N-dimethylformamide or acetonitrile, in the presence of a base such as diisopropylethylamine at a range of temperatures, preferably between room temperature and 100° C.

Compounds of general formula (1b1) and (1 b2) are either known in the literature or may be prepared from amines of general formula (1c) according to known literature procedures (e.g. see for reference WO 2006/009741 and EP 1 609 789, which are incorporated herein by reference in their entireties).

Compounds of general formula (1c) are either known in the literature or may be synthesised by one skilled in the art by adapting appropriate literature methods (e.g. WO 2010/077836, WO 2006/009741, WO 2008/125014, J. Med Chem., 2007, 50, 4016, Bulletin des Societes Chimiques Beiges, 1987, 96, 675-709, and Organic & Biomolecular Chemistry, 2006, 4, 4158-4164, which are incorporated herein by reference in their entireties).

Compounds of general formula (1 ca), i.e. compounds of formula (1c) wherein $R^2$ is a group of formula (IIIb) and $R^{17}$, $R^{18}$, $z^1$, $z^2$, $z^3$ and $z^4$ are as defined above can be prepared from compounds of formula (1e):

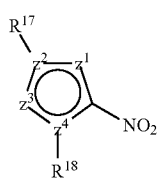

(1e)

using a suitable reducing agent such as tin (II) chloride, iron, or hydrogen gas with a suitable catalyst such as palladium on carbon, in a suitable solvent such as methanol, ethanol or acetic acid, at a range of temperatures, preferably between room temperature and 100° C.

Compounds of general formula (1e) are known in the literature or may be prepared by those skilled in the art using literature methods (e.g. WO 2008/034008, WO 2011/0189167, WO 2010/068258, which are incorporated herein by reference in their entireties).

Alternatively, compounds of general formula (1 ca) as above defined can be prepared from compounds of formula (1f, wherein $R^{17}$, $R^{18}$, $z^1$, $z^2$, $z^3$ and $z^4$ are as defined above and wherein PG is a suitable compatible protecting group known to those skilled in the art, such as benzyl, benzyl carbamate or tert-butyl carbamate,

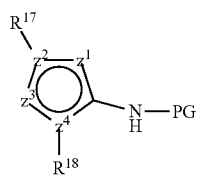

(1f)

using suitable deprotection conditions such as hydrochloric acid, trifluoroacetic acid, or hydrogen catalysed by for example palladium on carbon, in a suitable solvent such as dichloromethane, methanol, ethanol or acetic acid, at a range of temperatures, preferably between 0° C. and 100° C.

Compounds of general formula (1f) can be prepared by reaction of compounds of formula (1g), wherein $R^{17}$, $R^{18}$, $z^1$, $z^2$, $z^3$ and $z^4$ are as defined above

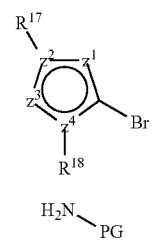

(1g)

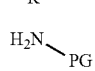

(1h)

with compounds of formula (1h) as above reported wherein PG is a suitable protecting group known to those skilled in the art, such as benzyl, benzyl carbamate or tert-butyl carbamate, using suitable conditions such as in the presence of a base such as potassium carbonate or diisopropylethyl amine or under Buchwald conditions (with a catalyst such as Pd(OAc)$_2$, a ligand such as 2,2'-bis(diphenylphosphino)-1,1'-binaphthyl and base such as sodium tert-butoxide), in a suitable solvent such as toluene or tetrahydrofuran, at a range of temperatures, preferably between room temperature and 150° C.

Compounds of general formula (1g) and (1h) are known in the literature or may be prepared by those skilled in the art by adapting appropriate literature methods (e.g. WO 2011/042389, and Chemistry-A European Journal, 2011, 17, 6606-6609, S6606/1-S6606/38, which are incorporated herein by reference in their entireties).

Compounds of general formula (1a) may be prepared according to the route illustrated in Scheme 2.

Scheme 2

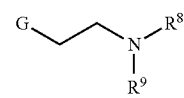

(2b)

or

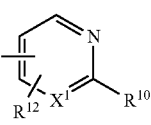

(2a)

(2c)

or

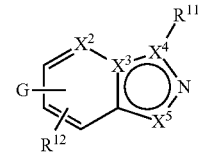

(2d)

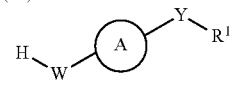

(1a)

Compounds of general formula (1a) may be prepared from compounds of general formula (2a) by reaction with a compound of general formula (2b), (2c) or (2d), wherein G is a suitable chemical group known to those skilled in the art selected such that it can facilitate a suitable coupling reaction such as nucleophilic displacement or metal catalysed cross coupling. For example in cases such that when Y is —O—, —S— or —NR$^7$—, examples of G may include halogen or a suitable leaving group such as mesylate or triflate either directly linked or attached via a group —(CR$^3$R$^4$)$_n$—. Examples of the coupling conditions used may include using a base such as sodium hydride or potassium tert-butoxide and 1,3-dimethyl-3,4,5,6-tetrahydro-2(1H)-pyrimidinone in a suitable solvent such as N,N-dimethylformamide, toluene, 1,4-dioxane or acetonitrile at a range of temperatures, preferably between room temperature and 150° C. For example in cases such that when Y is —O— and G is —OH or —SH a method to perform this coupling may involve Mitsunobu conditions (diethylazodicarboxylate/triphenylphosphine) in a suitable solvent such as tetrahydrofuran or 1,4-dioxane at a range of temperatures preferably between −10° C. and 100° C. For example in cases such as when Y is —O—, —S— or —NR$^7$— and G is a group such as halogen, triflate or boronic acid/ester a method to perform this coupling may be under metal (for example palladium or copper) catalysed coupling conditions in the presence of a suitable ligand such as Xantphos or 1,10-phenanthroline in the presence of a base such as caesium carbonate in a suitable solvent such as tetrahydrofuran, 1,4-dioxane or N,N-dimethylformamide at a range of temperatures preferably between −10° C. and 150° C. For example in cases such as when Y is —O— and G is a group such as —COOMe, —COOH, isocyanate, —OCOCl or NHCOOCH$_2$CCl$_3$ examples of conditions to perform this coupling may involve the use of a base such as sodium hydride or triethylamine or a coupling reagent such as HATU in a suitable solvent such as dichloromethane, tetrahydrofuran, 1,4-dioxane or N,N-dimethylformamide at a range of temperatures preferably between −10° C. and 150° C.

Compounds of formula (2b) are commercial available, are known in the literature or may be synthesised from compounds of formula (2e), wherein $R^8$ and $R^9$ are as defined for compounds of formula (I), by adapting appropriate literature methods (e.g. WO 2006/133006, which is incorporated herein by reference in its entirety) or using methods known to those skilled in the art such as by reacting (2e) with a suitable alkylating agent such as dibromoethane or bromoethanol in the presence of a suitable base such as sodium hydride or potassium carbonate in a suitable solvent such as tetrahydrofuran, 1,4-dioxane or N,N-dimethylformamide at a range of temperatures preferably between −10° C. and 150° C., or by reacting (2e) with a suitable aldehyde in the presence of a reducing agent such as sodium triacetoxyborohydride in a suitable solvent such as dichloroethane or tetrahydrofuran at a range of temperatures preferably between −10° C. and 100° C.

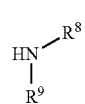

(2e)

Compounds of formula (2e) are commercially available, are known in the literature or may be synthesised by those skilled in the art using literature methods. Compounds of formula (2c) may be synthesised from compounds of formula (2f).

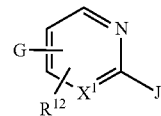

(2f)

wherein $X_1$ and $R^{12}$ are defined as for compounds of formula (I), G is a group such as halogen, —O-PG or —S-PG wherein PG represents a protecting group such as triisopropylsilyl or tert-butyldimethylsilyl (methods for whose introduction and removal are well known by those skilled in the art) and J may represent groups such as halogen, —NH$_2$, —OH, —SH, —COOH, —SO$_2$Cl which can be modified using literature methods to introduce an appropriate group $R^{10}$ by those skilled in the art. For example in cases such as when J is halogen, a method such as nucleophilic substitution with a suitable alcohol, amine or thiol may be used in the presence of a suitable base such as sodium hydride, triethylamine or potassium carbonate in a suitable solvent such as tetrahydrofuran, 1,4-dioxane or N,N-dimethylformamide at a range of temperatures preferably between −10° C. and 150° C. For example in cases such as when J is —NH$_2$, —OH or SH, a method such as alkylation may be used with a suitable alkylating agent such as an alkylhalide in the presence of a suitable base such as sodium hydride or potassium carbonate in a suitable solvent such as tetrahydrofuran, 1,4-dioxane or N,N-dimethylformamide at a range of temperatures preferably between −10° C. and 150° C. For example in cases such as where J is —COOH or —SO$_2$Cl a method such as reaction with a suitable amine in the presence of a suitable base such as triethylamine or a coupling reagent such as HATU in a suitable solvent such as tetrahydrofuran, 1,4-dioxane or N,N-dimethylformamide at a range of temperatures preferably between −10° C. and 150° C.

Compounds of formula (2da), i.e. compounds of formula (2a) wherein $X^4$=C may be prepared according to the routes described in Scheme 3 herebelow:

Scheme 3

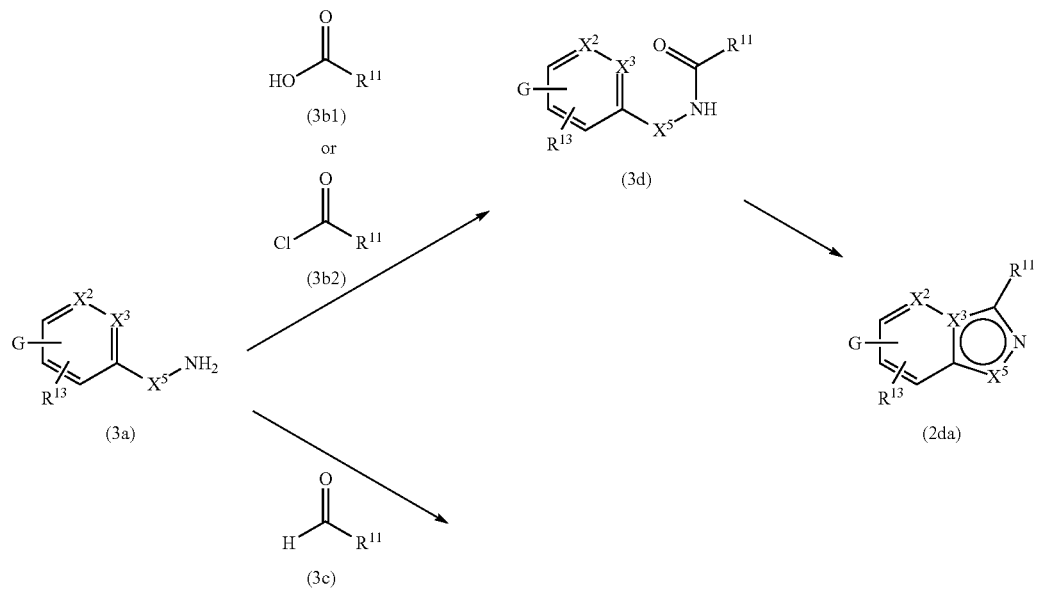

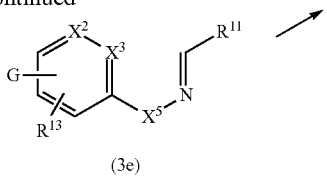

(3e)

Compounds of general formula (2da) as above defined may be prepared from compounds of general formula (3e) using a suitable oxidant such as chloramine T, lead tetracetate or phenyliodine(III) diacetate, in a suitable solvent such as dichloromethane or ethanol at a range of temperatures, preferably between room temperature and 100° C.

Compounds of general formula (3e) may be prepared from compounds of general formula (3a) by reaction with an aldehyde of general formula (3c) above reported. in a suitable solvent such as ethanol or tetrahydrofuran at a range of temperatures, preferably between room temperature and 80° C.

Compounds of formula (3c) are commercially available, known in the literature or may be prepared using literature methods by those skilled in the art.

Alternatively, compounds of formula (2da) may be prepared from compounds of formula (3d) using a suitable dehydrating agent such as Burgess' reagent, triphenyl phosphine and hexachloroethane, phosphorus oxychloride, acetic acid or Mitsunobu conditions (diethylazodicarboxylate/triphenylphosphine/trimethylsilylazide), in the absence or presence of a suitable solvent such as tetrahydrofuran, toluene, or NMP, at a range of temperatures, preferably between room temperature and 150° C.

Compounds of formula (3d) may be prepared from compounds of formula (3a) by reaction with a compound of general formula (3b1) using a suitable acylating/dehydrating agent such as triphenylphosphine/trichloroacetonitrile in the presence of a base such as diisopropylethylamine, in a suitable solvent such as dichloromethane or acetonitrile, at a range of temperatures, preferably between room temperature and 150° C. or by reaction with a compound of general formula (3b2) in the presence of a base such as diisopropylethylamine, in a suitable solvent such as dichloromethane or THF at a range of temperatures preferably between −10° C. and the boiling point of the solvent.

Compounds of formulae (3b1) and (3b2) are commercially available, known in the literature or may be prepared by literature methods by those skilled in the art.

Alternatively, compounds of formula (2da) as above defined may be prepared according to the route in Scheme 4:

Scheme 4

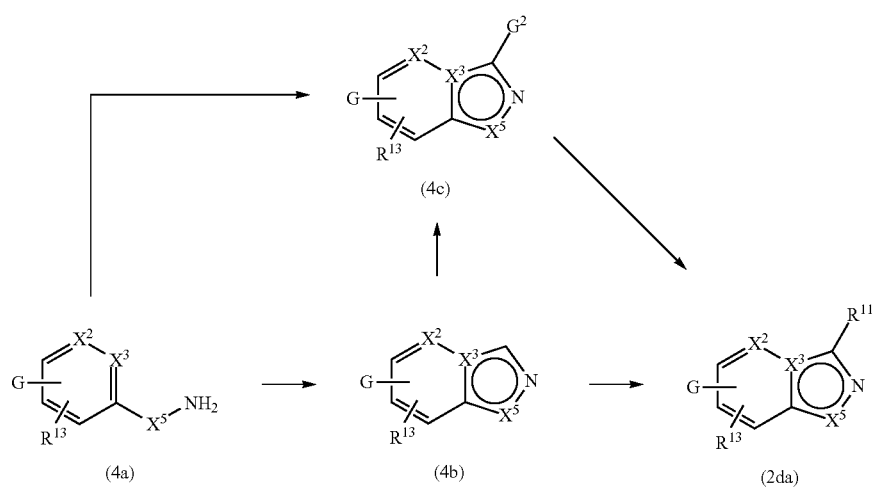

Compounds of general formula (2da) may be prepared from compounds of general formula (4c), wherein $G^2$ may represent groups such as halogen, —CHO, —COOH, —COOEt and $SO_2Cl$. For example, compounds of general formula (2da) may be prepared from compounds of general formula (4c), wherein $G^2$ represents halogen, using methods such as a metal (for example palladium) catalysed coupling with a suitable $R^{11}G^5$ derivative wherein $G^5$ is a group such as boronate acid/ester or stannane in a suitable solvent such as tetrahydrofuran or 1,4-dioxane at a range of temperatures preferably between ambient temperature and 150° C. An alternative method may involve displacement of said halogen with a suitable group $R^{11}H$ (such as that containing an —NH, —OH or —SH group) in the presence of a base such as sodium hydride, potassium tert-butoxide or N,N-diethylisopropylamine in a suitable solvent such as N,N-dimethylformamide, toluene, 1,4-dioxane, or acetonitrile at a range of temperatures, preferably between room temperature and 150° C.

The group $G^2$ may be also transformed from groups such as halogen to groups such as CHO, —COOH, —COOEt and $SO_2Cl$ by means of metal insertion methods known to those skilled in the art such as palladium catalysis, Grignard formation or lithium halogen exchange.

Compounds of general formula (2da) wherein $R^{11}$ is a group such as —$CH_2$—$NR^AR^B$, —C(O)N($R^C$)—($C_2$-$C_6$alkylene)-$NR^AR^B$, —C(O)N($R^C$)—($C_3$-$C_7$cycloalkylene)-$NR^AR^B$, —C(O)N($R^C$)—($C_2$-$C_6$alkylene)-$OR^D$, —C(O)N($R^C$)—($C_3$-$C_7$cycloalkylene)-$OR^D$, —C(O)N($R^AR^B$), —S(O)$_2$N($R^C$)—($C_2$-$C_6$alkylene)-$NR^AR^B$, —S(O)$_2$N($R^C$)—($C_3$-$C_7$cycloalkylene)-$NR^AR^B$, —S(O)$_2$N($R^C$)—($C_2$-$C_6$alkylene)-$OR^D$ or —S(O)$_2$N($R^C$)—($C_3$-$C_7$cycloalkylene)-$OR^D$ may be prepared from compounds of general formula (4c), wherein $G^2$ represents —CHO, —COOH, —COOEt and —$SO_2$Cl, by reaction with a suitable amine such as $HNR^AR^B$ etc using methods such as reductive amination (using a reagent such as sodium triacetoxyborohydride) or amide/sulphonamide formation in the presence of suitable reagents such as HATU with a base such as N,N-diethylisopropylamine or trimethylaluminium in a suitable solvent such as dichloromethane, N,N-dimethylformamide, toluene, 1,4-dioxane, or acetonitrile at a range of temperatures, preferably between room temperature and 150° C.

Compounds of general formula (4c) wherein $G^2$ is a group such as —COOEt, may be synthesised from compounds of general formula (4a) by reaction with a compound such as diethyloxalate in the presence of an acid such as acetic acid at a range of temperatures, preferably between room temperature and 120° C.

Compounds of general formula (4c) wherein $G^2$ is a group such as bromine or chlorine, may be synthesised from compounds of general formula (4b) by reaction with a compound such as N-chlorosuccinimide or N-bromosuccinimide in a solvent such as chloroform at a range of temperatures, preferably between –10° C. and room temperature.

Compounds of general formula (4b) may be synthesised from compounds of general formula (4a) by reaction with a compound such as diethoxymethylacetate at a range of temperatures, preferably between room temperature and 100° C.

Compounds of general formula (2db), i.e. compounds of formula (2d) wherein $X_4$ is nitrogen, may be prepared from compounds of general formula (4b) wherein $X^4$=NH, by reaction with a suitable alkylating agent $R^{11}$ in the presence of a base such as caesium carbonate in a suitable solvent such as N,N-dimethylformamide at a range of temperatures, preferably between room temperature and 150° C.

Alternatively, compounds of general formula (1aa), i.e compounds of formula (1a) wherein $X^4$ is CH may be prepared according to the route illustrated in Scheme 5.

Compounds of general formula (1aa) may be prepared from compounds of general formula (5e) wherein PG is a suitable protecting group known in the art such as Boc by using the appropriate deprotection conditions such as trifluoroacetic acid in a solvent such as dichloromethane at a range of temperatures, preferably between –10° C. and room temperature.

Compounds of general formula (5e) may be prepared from compounds of general formula (5d) using a suitable dehydrating agent such as Burgess' reagent, triphenyl phosphine and hexachloroethane, phosphorus oxychloride, acetic acid or Mitsunobu conditions (diethylazodicarboxylate/triphenylphosphine/trimethylsilylazide), in the absence or presence of a suitable solvent such as tetrahydrofuran, toluene, or NMP, at a range of temperatures, preferably between room temperature and 120° C.

Compounds of general formula (5d) may be prepared from compounds of general formula (5c) by reaction with a compound of general formula (3b1) as above defined using a suitable acylating/dehydrating agent such as triphenylphosphine/trichloroacetonitrile in the presence of a base such as diisopropylethylamine, in a suitable solvent such as dichloromethane or acetonitrile, at a range of temperatures, preferably between room temperature and 150° C., or by reaction with a compound of general formula (3b2) as above defined in the presence of a base such as diisopropylethylamine, in a suitable solvent such as dichloromethane or THF at a range of temperatures preferably between –10° C. and the boiling point of the solvent.

Compounds of general formula (5c) may be prepared from compounds of general formula (5b) wherein $G^3$ is a suitable leaving group such as halogen, by reaction with a reagent such as hydrazine monohydrate in a suitable solvent such as ethanol at a range of temperatures preferably between room temperature and 100° C.

Compounds of general formula (5b) may be prepared from compounds of general formula (5a) by reaction with a suitable protecting group reagent known in the art such as Boc anhydride in the presence of a base such as triethylamine in a suitable solvent such as dichloromethane or tetrahydrofuran at a range of temperatures preferably between room temperature and 100° C.

Compounds of general formula (5a) can be synthesised by the methods described above for the synthesis of (1a).

Compounds of general formula (2aa), i.e. compounds of formula (2a) wherein Y=O, W=NH and PG is a suitable

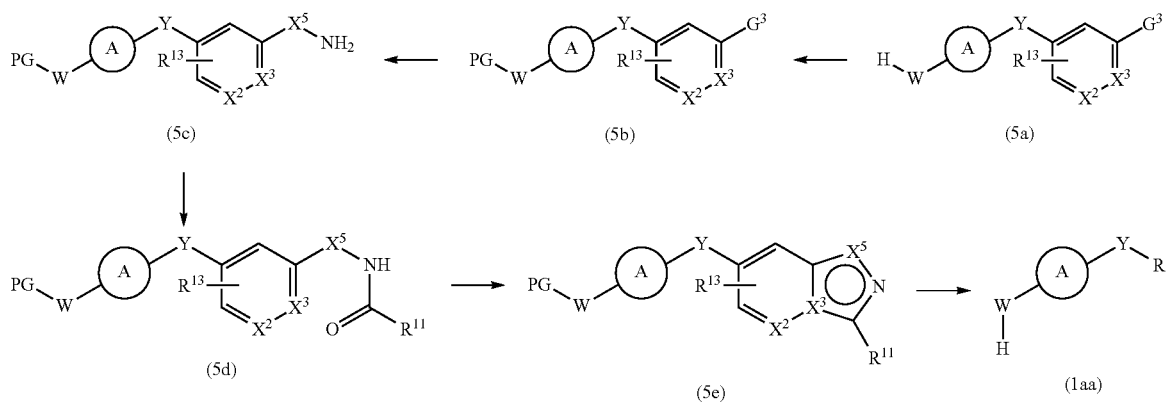

Scheme 5 protective group such as trifuloroacetate may be prepared according to the route illustrated in scheme 6:

Scheme 6

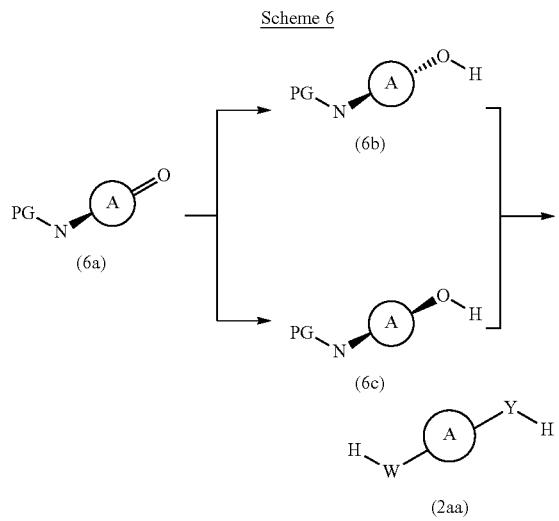

Compounds of general formula (2aa) may be prepared from compounds of general formula (6b) and (6c) by removal of the protecting group PG using methods known in the art such as aqueous sodium hydroxide in a solvent such as methanol at a range of temperatures preferably between room temperature and 100° C.

Compounds of general formula (6b), wherein PG is a protecting group, preferably trifluoroacetamide, and the group —OH is placed on the cycloalkylene portion of ring A may be prepared from compounds of general formula (6a) by using a chiral reductive method such as using formic acid and RuCl [S,S-Tsdpen(p-cymene)] in the presence of a base such as triethylamine in a solvent such as N,N-dimethylformamide at a range of temperatures preferably between room temperature and 150° C. It will be recognised that compounds of formula (6a) may be homochiral as illustrated or be the opposite enantiomer or racemic.

It will be realised by those skilled in the art that any combination of stereocentres in (2aa) can be prepared using both enantiomers of (6a) and using RuCl[R,R-Tsdpen(p-cymene)] or RuCl[S,S-Tsdpen(p-cymene)]. Compound (2a) is drawn with no defined stereocentres but any combination can be obtained as illustrated in Scheme 2.

Compounds of formula (6a) can be prepared from compounds of formula (6d)

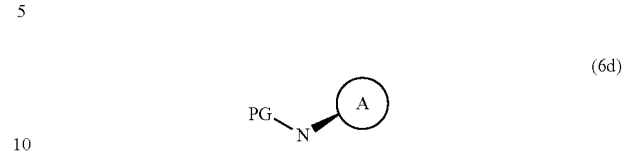

using a suitable oxidant such as potassium permanganate and magnesium sulfate in a suitable solvent methanol/water at a range of temperatures preferably between room temperature and the boiling point of the solvent. It will be recognised that compounds of formula (6d) may be homochiral as illustrated or be the opposite enantiomer or racemic.

Compounds of formula (6d) can be prepared from compounds of formula (6e) where PG is a suitable protecting group such as trifluoroacetate or tert-butyl carbonate:

using ethyl trifluoroacetate or di-tert-butyl dicarbonate in the presence of base such as triethylamine or diisopropylethylamine in a solvent such as methanol or dichloromethane at a range of temperatures preferably between 0° C. and the boiling point of the solvent. It will be recognised that compounds of formula (6e) may be homochiral as illustrated or be the opposite enantiomer or racemic.

Compounds of formula (6e) are known in the literature and may be prepared by those skilled in the art by adapting literature methods (e.g. for S-(+)-1-amino-1,2,3,4-tetrahydronaphthalene, see Journal of the Chemical Society, Perkin Transactions 1: 1985, 2039-44; for (S)-(+)-8-amino-5,6,7,8-tetrahydroquinoline, see Journal of Organic Chemistry, 2007, 72, 669-671; and for 1-aminoindan, see Tetrahedron Letters, 2011, 52, 1310-1312, which are incorporated herein by reference in their entireties).

Compounds of general formula (2ab), i.e. compounds of formula (2a) wherein Y=NR$^7$ and W=NH, may be prepared according to the route illustrated in scheme 7:

Scheme 7

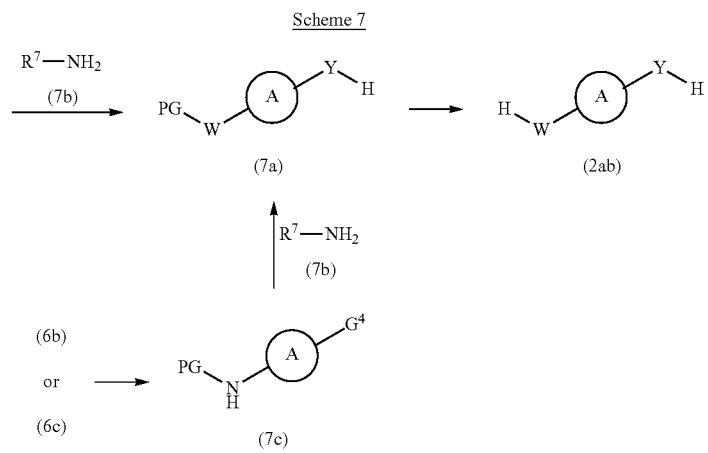

Compounds of general formula (2ab) may be prepared from compounds of general formula (7a) by removal of the protecting group PG using methods known in the art such as aqueous sodium hydroxide in a solvent such as methanol or trifluoroacetic acid in dichloromethane at a range of temperatures preferably between room temperature and 100° C.

Compounds of formula (7a) may be prepared from compounds of general formula (6a) and amines (7b) by reaction under reductive amination conditions, using a reducing agent such as sodium triacetoxyborohydride and a solvent such as 1,2-dichloroethane at a range of temperatures preferably between room temperature and 100° C.

Compounds for formula (7b) are known in the literature and may be prepared by those skilled in the art using literature procedures. Compounds of formula (6a) can be prepared as described above.

Alternatively, compounds of formula (7a) may be prepared from compounds of general formula (7c) wherein $G^4$ is a suitable chemical group known to those skilled in the art selected such that it can facilitate a reaction such as a nucleophilic substitution. For example G is a suitable leaving group such as halogen or mesylate which can react with a suitable amine (7b) in the presence of a suitable base such as sodium hydride or potassium tert-butoxide and 1,3-dimethyl-3,4,5,6-tetrahydro-2(1H)-pyrimidinone in a suitable solvent such as N,N-dimethylformamide, toluene, 1,4-dioxane or acetonitrile at a range of temperatures, preferably between room temperature and 150° C.

Compounds of formula (7c) can be prepared from compounds of formulae (6b) or (6c) using halogenating conditions such as carbon tetrabromide and triphenylphosphine in dichloromethane or activation conditions such as methane sulfonyl chloride in dichloromethane in the presence of base such as diisopropylamine.

Alternatively, compounds of general formula (Id), i.e. compounds of formula (I) wherein Y=S and W=NH may be prepared according to the route illustrated in scheme 8:

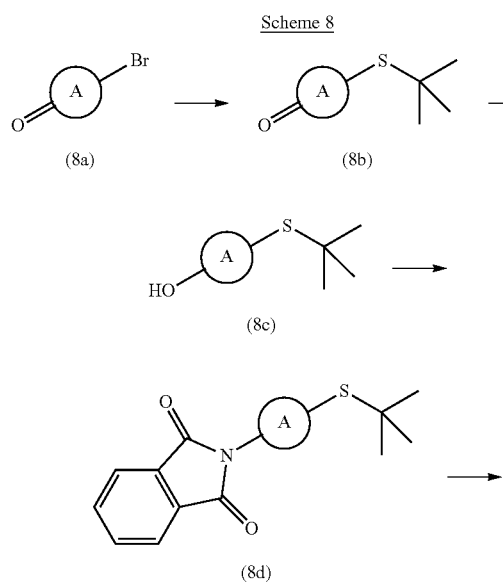

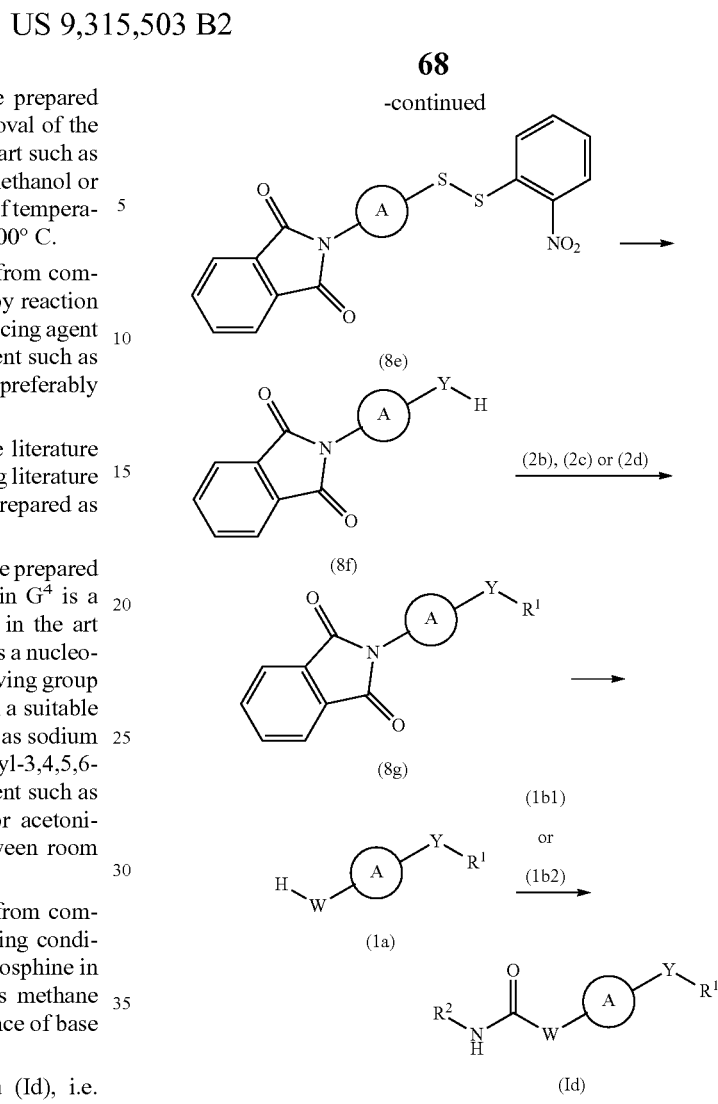

Compounds of general formula (Id) may be prepared from compounds of general formula (1 ab), i.e. compounds of formula (1a) wherein Y=S and W=NH: using compounds of formula (1b1) or (1 b2) in a suitable solvent such as dimethyl sulfoxide, 1,4-dioxane, N,N-dimethylformamide, or acetonitrile, in the presence of a base such as diisopropylethylamine at a range of temperatures, preferably between room temperature and 100° C.

Compounds of formula (1ab) as above defined may be prepared from compounds of formula (8g) using deprotection conditions such as hydrazine in methanol at a range of temperatures preferably between room temperature and the boiling point of the solvent.

Compounds of formula (8g) wherein Y=S, can be prepared from compounds of formula (8f) by reaction with compounds of formulae (2b), (2c) or (2d). Examples of the coupling conditions used may include using a base such as sodium hydride or potassium tert-butoxide and 1,3-dimethyl-3,4,5,6-tetrahydro-2(1H)-pyrimidinone in a suitable solvent such as N,N-dimethylformamide, toluene, 1,4-dioxane, or acetonitrile at a range of temperatures, preferably between room temperature and 150° C. Alternative methods to perform this coupling may involve Mitsunobu conditions (diethylazodicarboxylate/triphenylphosphine) or metal (for example palladium) catalysed coupling conditions in a suitable solvent such as tetrahydrofuran or 1,4-dioxane at a range of temperatures preferably between −10° C. and 150° C. and starting from the appropriate derivative of formula (2b), (2c), or (2d).

Compounds of formula (8D can be prepared from compounds of formula (8e) using dithiothreitol, monopotassium phosphate, potassium carbonate in a solvent such as methanol in the presence of acetic acid at a range of temperatures preferably between room temperature and the boiling point of the solvent.

Compounds of formula (8e) can be prepared from compounds of formula (8d) using 2-nitrobenzenesulfenyl chloride in acetic acid at a range of temperatures preferably between room temperature and 100° C.

Compounds of formula (8d) can be prepared from compounds of formula (8c) using phthalimide, triphenylphosphine and diisopropyl azodicarboxylate in a solvent such as tetrahydrofuran at a range of temperature preferably between 0° C. and the boiling point of the solvent.

Compounds of formula (8c) can be prepared from compounds of formula (8b) using a reducing agent such as sodium borohydride in a solvent such as methanol at a range of temperatures preferably between 0° C. and the boiling point of the solvent.

Compounds of formula (8b) can be prepared from compounds of formula (8a) using tert-butanethiol in the presence of a base such as diisopropylethylamine in a solvent such as tetrahydrofuran at a range of temperatures preferably between 0° C. and the boiling point of the solvent.

Compounds of formula (8a) are known in the literature and can be prepared by those skilled in the art using literature methods (e.g. 3-bromo-indan-1-one see WO 2010/108058, which is incorporated herein by reference in its entirety).

Alternatively, compounds of general formula (1ab), i.e. compounds of formula (1a) wherein Y=CH$_2$, W=NH and PG is a suitable protective group such as trifuloroacetate may be prepared according to the route illustrated in scheme 9:

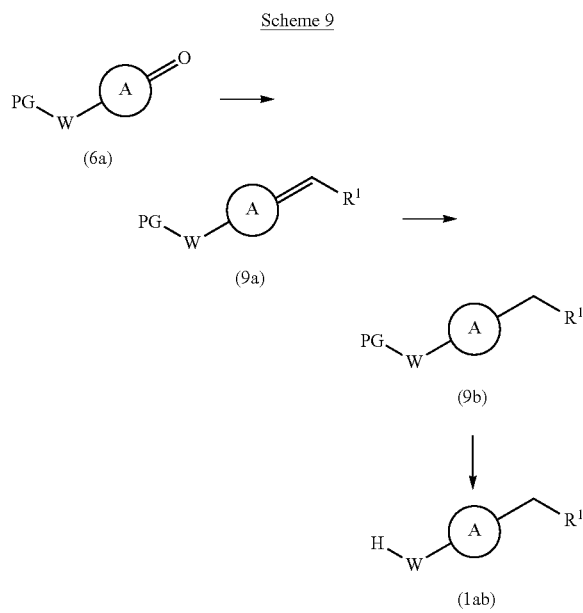

Compounds of general formula (1ab) may be prepared from compounds of general formula (9b) by removal of the protecting group PG using methods known in the art such as aqueous sodium hydroxide in a solvent such as methanol at a range of temperatures preferably between room temperature and 100° C.

Compounds of formula (9b) may be prepared from compounds of general formula (9a) by reaction with a suitable reduction agent for example hydrogen gas in the presence of a suitable catalyst such as palladium on activated charcoal in a suitable solvent such as ethanol at a range of temperatures between room temperature and 70° C. and pressures between atmospheric and 4 Barr.

Compounds of formula (9a) may be prepared from compounds of general formula (6a) by means of a reaction such as a Wittig (or one of the closely related variants such as the Horner-Wadsworth-Emmons) with a suitable substrate such as $R^1$—$CH_2$—$P(O)(OMe)_2$ in the presence of a suitable base such as sodium hydride in a suitable solvent such as tetrahydrofuran at a range of temperatures preferably between −10° C. and 100° C.

Compounds such as $R^1$—$CH_2$—$P(O)(OMe)_2$ may be synthesised from compounds of the general formula $R^1$—$CH_2$—Hal wherein Hal represents a halogen such as —Br or —Cl by reaction with a compound such as trimethylphosphite at a range of temperatures preferably between 0° C. and 100° C.

Compounds such as $R^1$—$CH_2$—Hal may be synthesised from compounds of formula $R^1$—$CH_3$ by means of a reaction such as a radial halogenation using a reagent such as N-bromosuccinimide in the presence of a catalyst such as AIBN in a suitable solvent such as carbon tetrachloride at a range of temperatures preferably between 0° C. and 80° C. Compounds such as $R^1$—$CH_2$—Hal may also be synthesised from compounds formula $R^1$—$CH_2$—OH by means of using halogenating conditions such as carbon tetrabromide and triphenylphosphine in dichloromethane or activation conditions such as methane sulfonyl chloride in dichloromethane in the presence of base such as diisopropylamine.

Compounds such as $R^1$—$CH_3$ and $R^1$—$CH_2$—OH may be prepared by methods outlined above for compounds (2b), (2c) and (2d).

Compounds of the invention of formula (1ac), i.e. compounds of formula (1a) where Y=$(CR^5R^6)_n$ and W=NH, may be prepared according to the route illustrated in Scheme 10.

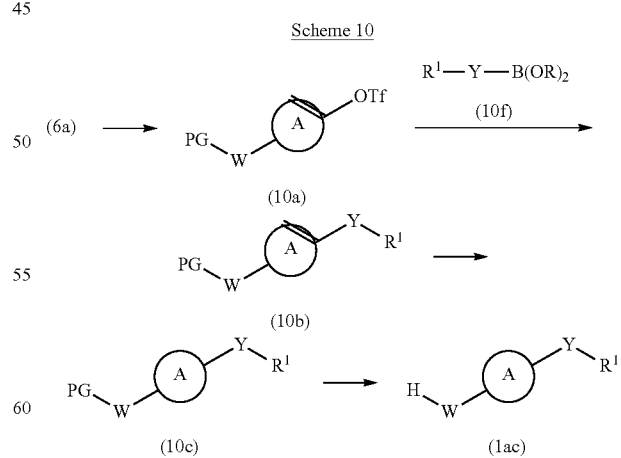

Compounds of formula (1ac) may be prepared from compounds of formula (10c) wherein PG is a suitable protecting group known to those skilled in the art, such as trifluoroacetamide, tert-butyl carbamate and benzyl carbamate by using suitable deprotection conditions such as, sodium hydroxide in methanol, trifluoroacetic acid in dichloromethane or hydrogen gas catalysed by for example palladium on carbon in ethanol, at a range of temperatures, preferably between 0° C. and 100° C.

Compounds of formula (10c) may be prepared from compounds of formula (10b) wherein PG is a suitable protecting group known to those skilled in the art, such as trifluoroacetamide, tert-butyl carbamate, and benzyl carbamate by using hydrogen gas in the presence of a catalyst such as palladium on carbon, in a suitable solvent such as methanol or ethanol, in the presence or absence of an acid such as HCl, at a range of temperatures, preferably between 0° C. and 100° C.

Compounds of formula (10b) may be prepared from compounds of formula (10a) and (10f) by a reaction such as a cross-coupling using a suitable catalyst such as tetrakis(triphenylphosphine)palladium (0) or palladium acetate, and a base such as diisopropylethylamine, sodium tert-butoxide, or caesium carbonate in a suitable solvent such as NMP, toluene, or DMF, at a range of temperatures, preferably between 0° C. and 100° C. Alternatively (10b) may be prepared by adapting literature procedures (e.g. those reported in WO 2009/022633, which is incorporated herein by reference in its entirety).

Compounds of formula (10f) are known in the literature or may be prepared by those skilled in the art by adapting literature procedures (e.g. WO 2008/063287, which is incorporated herein by reference in its entirety).

Compounds of formula (10a) may be prepared from compounds of formula (6a) using a triflating agent such as triflic anhydride, in the presence of a suitable base such as pyridine or 2,6-bis(tert-butyl)-4-methylpyridine, in a solvent such as dichloromethane or chloroform at a range of temperatures, preferably between 0° C. and boiling point of the solvent. Alternatively (10a) may be prepared by adapting literature procedures (e.g. those described in WO 2009/022633, which is incorporated herein by reference in its entirety).

Other features of the invention will become apparent in the course of the following descriptions of exemplary embodiments which are given for illustration of the invention and are not intended to be limiting thereof.

EXAMPLES

General Experimental Details

Abbreviations used in the experimental section:
AcOH=acetic acid;
aq.=aqueous;
DCM=dichloromethane;
DIAD=Diisopropyl azodicarboxylate;
DIPEA=diisopropylethylamine;
DMAP=N,N-dimethylaminopyridine;
DMF=N,N-dimethylformamide;
DMSO=dimethyl sulfoxide;
EDC=1-ethyl-3-(3'-dimethylaminopropyl)carbodiimide Hydrochloride;
EtOAc=ethyl acetate;
EtOH=ethanol;
$Et_2O$=diethyl ether;
$Et_3N$=triethylamine;
$EtNiPr_2$=diisopropylethylamine;
FCC=flash column chromatography;
h=hour;
HATU=2-(7-aza-1H-benzotriazole-1-yl)-1,1,3,3-tetramethyluronium hexafluorophosphate;
HOBt=1-hydroxy-benzotriazole;
HPLC=high performance liquid chromatography;
IMS=Industrial Methylated Spirits;
LCMS=liquid chromatography mass spectrometry;
NaOH=sodium hydroxide;
MeCN=acetonitrile;
MeOH=MeOH;
min=minutes;
$NH_3$=ammonia;
NMR=nuclear magnetic resonance;
RT=room temperature;
Rt=retention time;
sat.=saturated;
SCX-2=strong cation exchange chromatography;
TFA=trifluoroacetic acid;
THF=Tetrahydrofuran;
$H_2O$=water;
IMS=industrial methylated spirit;
Xantphos=4,5-Bis(diphenylphosphino)-9,9-dimethylxanthene;
X-Select=Waters X-select HPLC column;
IPA=propan-2-ol;
LDA=lithium diisopropylamide;
MDAP=mass-directed auto-purification;
MeOH=methanol;
$Ph_3P$=triphenylphosphine;
TBAF=tetrabutylammonium fluoride.

In the procedures that follow, after each starting material, reference to a Intermediate/Example number is usually provided. This is provided merely for assistance to the skilled chemist. The starting material may not necessarily have been prepared from the batch referred to.

When reference is made to the use of a "similar" or "analogous" procedure, as will be appreciated by those skilled in the art, such a procedure may involve minor variations, for example reaction temperature, reagent/solvent amount, reaction time, work-up conditions or chromatographic purification conditions.

The nomenclature of structures was assigned using Autonom 2000 Name software from MDL Inc. When the nomenclature of structures could not be assigned using Autonom, ACD/Name software utility part of the ACD/Labs Release 12.00 Product Version 12.5 (Build 45133, 16 Dec. 2010) was used. Stereochemical assignments of compounds are based on comparisons with data reported in WO 2008/043019, which is incorporated herein by reference in its entirety, for key intermediates. All reactions were carried out under anhydrous conditions and an atmosphere of nitrogen or argon unless specified otherwise. Unless otherwise stated all transformations were carried at ambient temperature (room temperature).

NMR spectra were obtained on a Varian Unity Inova 400 spectrometer with a 5 mm inverse detection triple resonance probe operating at 400 MHz or on a Bruker Avance DRX 400 spectrometer with a 5 mm inverse detection triple resonance TXI probe operating at 400 MHz or on a Bruker Avance DPX 300 spectrometer with a standard 5 mm dual frequency probe operating at 300 MHz. Shifts are given in ppm relative to tetramethylsilane ($\delta$=0 ppm). J values are given in Hz through-out. NMR spectra were assigned using DataChord Spectrum Analyst Version 4.0.b21 or SpinWorks version 3.

Where products were purified by flash column chromatography, 'flash silica' refers to silica gel for chromatography, 0.035 to 0.070 mm (220 to 440 mesh) (e.g. Fluka silica gel 60), and an applied pressure of nitrogen up to 10 p.s.i accelerated column elution or use of the CombiFlash® Companion purification system or use of the Biotage SP1 purification system. All solvents and commercial reagents were used as received.

Compounds purified by preparative HPLC were purified using a C18-reverse-phase column (100×22.5 mm i.d Genesis column with 7 µm particle size), or a Phenyl-Hexyl column (250×21.2 mm i.d. Gemini column with 5 µm particle size), UV detection between 220-254 nm, flow 5-20 mL/min), eluting with gradients from 100-0 to 0-100% water/acetonitrile (containing 0.1% TFA or 0.1% formic acid) or water/MeOH (containing 0.1% TFA or 0.1% formic acid), or a C18-reverse-phase column (19×250 mm, XBridge OBD, with 5 µm particle size), eluting with gradients from 100-0 to 0-100% water/acetonitrile (containing 0.1% NH$_4$OH); or a ChiralPak IC column (10×250 mm i.d., with 5 µm particle size), unless otherwise indicated. Fractions containing the required product (identified by LCMS analysis) were pooled, the organic solvent removed by evaporation, and the remaining aqueous residue lyophilised, to give the final product. Products purified by preparative HPLC were isolated as free base, formate or TFA salts, unless otherwise stated.

The Liquid Chromatography Mass Spectroscopy (LCMS) and HPLC systems used are:

Method 1.

Waters Platform LC Quadrupole mass spectrometer with a C18-reverse-phase column (30×4.6 mm Phenomenex Luna 3 µm particle size), elution with A: water+0.1% formic acid; B: acetonitrile+0.1% formic acid. Gradient:

| Gradient - Time | flow mL/min | % A | % B |
|---|---|---|---|
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection—MS, ELS, UV (200 µL split to MS with in-line HP1100 DAD detector). MS ionization method—Electrospray (positive and negative ion).

Method 2.

Waters ZMD quadrupole mass spectrometer with a C, 18-reverse-phase column (30×4.6 mm Phenomenex Luna 3 µm particle size), elution with A: water+0.1% formic acid; B: acetonitrile+0.1% formic acid. Gradient:

| Gradient - Time | flow mL/min | % A | % B |
|---|---|---|---|
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection—MS, ELS, UV (200 µL split to MS with in-line Waters 996 DAD detector). MS ionization method—Electrospray (positive and negative ion).

Method 3.

Waters ZMD quadrupole mass spectrometer with a C18-reverse-phase column (30×4.6 mm Phenomenex Luna 3 µm particle size), elution with A: water+0.1% formic acid; B: acetonitrile+0.1% formic acid. Gradient:

| Gradient - Time | flow mL/min | % A | % B |
|---|---|---|---|
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection—MS, ELS, UV (200 µL split to MS with in-line HP1100 DAD detector). MS ionization method—Electrospray (positive and negative ion).

Method 4.

VG Platform II quadrupole spectrometer with a C18-reverse-phase column (30×4.6 mm Phenomenex Luna 3 µm particle size, elution with A: water+0.1% formic acid; B: acetonitrile+0.1% formic acid. Gradient:

| Gradient - Time | flow mL/min | % A | % B |
|---|---|---|---|
| 0.00 | 2.0 | 95 | 5 |
| 0.30 | 2.0 | 95 | 5 |
| 4.30 | 2.0 | 5 | 95 |
| 5.30 | 2.0 | 5 | 95 |
| 5.80 | 2.0 | 95 | 5 |
| 6.00 | 2.0 | 95 | 5 |

Detection—MS, ELS, UV (200 µl/min split to the ESI source with inline HP1050 DAD detector). MS ionization method—Electrospray (positive and negative ion).

Method 5.

Waters micromass ZQ2000 quadrupole mass spectrometer with an Acquity BEH C18 1.7 um 100×2.1 mm, Acquity BEH Shield RP18 1.7 um 100×2.1 mm or Acquity HSST3 1.8 um 100×2.1 mm, maintained at 40° C. Elution with A: water+0.1% formic acid; B: acetonitrile+0.1% formic acid. Gradient:

| Gradient - Time | flow mL/min | % A | % B |
|---|---|---|---|
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection—MS, UV PDA. MS ionization method—Electrospray (positive and negative ion).

Method 6.

Phenomenex Gemini C18-reverse-phase column (250×21.20 mm 5 µm particle size), elution with A: water+0.1% formic acid; B: CH$_3$CN+0.1% formic acid. Gradient—90% A/10% B to 2% A/98% B over 20 min—flow rate 18 mL/min. Detection—In-line UV detector set at 254 nM wavelength.

Method 7.

Agilent 1260 infinity purification system. Column: XSELECT CSH Prep C18 OBD, particle size 5 µm, 30×150 mm, RT. Elution with A: water+0.1% formic acid; B: CH$_3$CN+0.1% formic acid. Gradient—90% A/10% B to 2% A/95% B over 22 min—flow rate 60 mL/min. Detection—In-line Agilent 6100 series single Quadrupole LC/MS.

Method 8.

Agilent 1260 infinity purification system. Column: XBridge Prep C, 18 OBD, particle size 5 µm, 30×150 mm, RT. Elution with A: water+0.1% ammonia; B: CH$_3$CN+0.1% ammonia. Gradient—90% A/10% B to 2% A/95% B over 22 min—flow rate 60 mL/min. Detection—In-line Agilent 6100 series single Quadrupole LC/MS.

Differential Scanning Calorimetry (DSC).

It should be recognized that the endotherm peak as measured is dependent on a number of factors including the machine used, the rate of heating, the calibration standard, humidity and the purity of the sample used. Melting points reported in the experimentals are estimated on the basis of the onset of endotherm peaks registered during DSC analysis.

It is to be understood by the skilled person that, where the expression "partial formate salt" is used, it is to be intended as identifying derivatives where only part of the basic compound has been converted into formate salt and thus containing less than one equivalent of formate counterion. Exact salt/free base ratio is provided by associated NMS analysis.

Intermediate A (1R,4S)-4-Amino-1,2,3,4-tetrahydro-naphthalen-1-ol

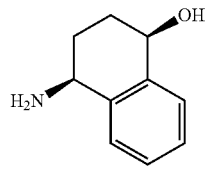

a. 2,2,2-Trifluoro-N-(S)-1,2,3,4-tetrahydro-naphthalen-1-yl-acetamide (Intermediate Aa).

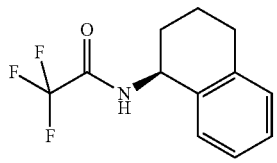 [SMILES: O=C(N[C@H]1CCCc2ccccc21)C(F)(F)F]

Ethyl trifluoroacetate (24.2 mL, 204 mmol) was added dropwise to a solution of (S)-(1,2,3,4-tetrahydro-naphthalen-1-yl)amine (Alfa Aesar; 25.0 g, 170 mmol) and triethylamine (35.5 mL, 255 mmol) in MeOH (250 mL) at RT and stirred for 18 h. The mixture was concentrated to approximately ⅓ of its volume and then partitioned between DCM (200 mL) and water (200 mL). The aqueous layer was extracted into DCM (3×) and the combined organic layers were washed with brine, dried (MgSO₄) and concentrated in vacuo to yield the title compound (41.1 g, 169 mmol, 99%). ¹H NMR (400 MHz, CDCl₃): 1.80-1.95 (3H, m), 2.05-2.15 (1H, m), 2.75-2.90 (2H, m), 5.18-5.25 (1H, q, J 5.0 Hz), 6.38-6.48 (1H, br s), 7.12-7.16 (1H, m), 7.20-7.26 (3H, m).

b. 2,2,2-Trifluoro-N-((S)-4-oxo-1,2,3,4-tetrahydro-naphthalen-1-yl)-acetamide (Intermediate Ab).

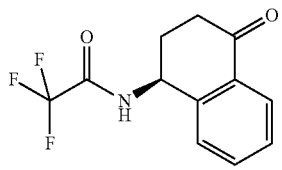 [SMILES: O=C1CC[C@H](NC(=O)C(F)(F)F)c2ccccc21]

Magnesium sulfate monohydrate (46.6 g, 338 mmol) in water (500 mL) was added to an ice cold solution of Intermediate Aa (41.1 g, 169 mmol) in acetone (1.0 L). Potassium permanganate (80.1 g, 507 mmol) was added portionwise (10.0 g portions) over a period of 45 min. The mixture was then stirred for 18 h. Sodium thiosulfate pentahydrate (126 g, 510 mmol) in water (400 mL) was added and the reaction stirred for 30 min. The mixture was concentrated to ~300 mL, then water (1.0 L), Celite (60 g) and EtOAc (1.0 L) were sequentially added. The mixture was thoroughly stirred, and then filtered through a pad of Celite. The aqueous layer was extracted into EtOAc (3×) and the combined organic layers washed with brine, dried (MgSO₄) and concentrated in vacuo to yield the title compound (36.6 g, 142 mmol, 84%). ¹H NMR (400 MHz, CDCl₃): 2.20-2.30 (1H, dddd, J 13.3, 10.0, 8.8, 4.5 Hz), 2.43-2.52 (1H, dddd, J 13.3, 7.2, 4.6, 4.6 Hz), 2.67-2.77 (1H, ddd, J 17.4, 10.1, 4.6 Hz), 2.78-2.88 (1H, ddd, J 17.4, 7.1, 4.6 Hz), 5.39-5.47 (1H, td, 8.5, 4.5 Hz), 7.32-7.37 (1H, d, J 7.7 Hz), 7.44-7.49 (1H, t, J 7.6 Hz), 7.59-7.64 (1H, td, J 7.6, 1.4 Hz), 8.03-8.07 (1H, dd, J 7.7, 1.4 Hz).

c. 2,2,2-Trifluoro-N-((1S,4R)-4-hydroxy-1,2,3,4-tetrahydro-naphthalen-1-yl)-acetamide (Intermediate Ac).

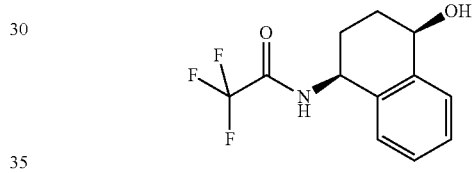

Degassed DMF (argon sparged, 100 mL) was added to Intermediate Ab (8.00 g, 31.3 mmol) and [N-[(1R,2R)-2-(amino-κN)-1,2-diphenylethyl]-4-methylbenzenesulfonamidato-κN]chloro[(1,2,3,4,5,6-η)-1-methyl-4-(1-methylethyl)benzene]-ruthenium (Strem Chemicals Inc.; 594 mg, 0.93 mmol). Triethylamine (8.66 mL, 62.6 mmol) was added slowly to ice cold formic acid (2.34 mL, 62.6 mmol) and stirred for 20 min, this was then added to the DMF solution. The reaction was heated to 60° C. for 18 h. After cooling, the mixture was partitioned between DCM (200 mL) and water (600 mL). The aqueous layer was extracted DCM (3×) and the combined organic layers washed with brine, dried (MgSO₄) and concentrated in vacuo. Purification by FCC, using 0-100% EtOAc in cyclohexane, afforded the title compound (7.10 g, 27.4 mmol, 88%). ¹H NMR (400 MHz, CDCl₃): 1.88-1.92 (1H, d, J 4.8 Hz), 1.98-2.18 (4H, m), 4.80-4.88 (1H, m), 5.165-5.24 (1H, m), 6.70-6.80 (1H, br s), 7.25-7.30 (1H, m), 7.30-7.40 (2H, m), 7.45-7.50 (1H, m).

d. (1R,4S)-4-Amino-1,2,3,4-tetrahydro-naphthalen-1-ol (Intermediate A).

Sodium hydroxide (2.10 g, 53.0 mmol) was added to an ice cold solution of Intermediate Ac (3.43 g, 13.2 mmol) in MeOH/water (2:1, 50 mL) and stirred for 3.5 h. The mixture was loaded on to a SCX-2 cartridge, eluting with MeOH then 2M NH₃ in MeOH, to yield the title compound (2.30 g, 13.2 mmol, 99%). ¹H NMR (400 MHz, d₆-DMSO): 1.66-1.90

(4H, m), 3.71-3.77 (1H, t, J 5.4 Hz), 4.46-4.54 (1H, t, J 5.4 Hz), 7.14-7.22 (2H, m), 7.32-7.38 (1H, m), 7.40-7.46 (1H, m).

Intermediate B (1S,4S)-4-Amino-1,2,3,4-tetrahydro-naphthalen-1-ol

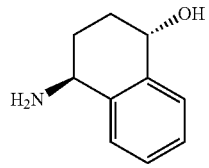

a. 2,2,2-Trifluoro-N-((1S,4S)-4-hydroxy-1,2,3,4-tetrahydro-naphthalen-1-yl)-acetamide (Intermediate Ba).

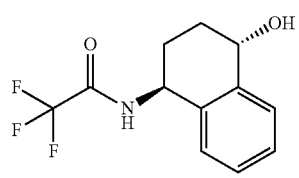 [SMILES: O=C(N[C@H]1CC[C@H](O)c2ccccc21)C(F)(F)F]

Argon was bubbled through a solution of Intermediate Ab (8.00 g, 31.1 mmol) and [N-[(1S,2S)-2-(amino-κN)-1,2-diphenylethyl]-4-methylbenzenesulfonamidato-κN]chloro[(1,2,3,4,5,6-η)-1-methyl-4-(1-methylethyl)benzene]-ruthenium (Strem Chemicals Inc.; 0.06 g, 0.93 mmol) in dry DMF (100 mL) for 10 min. A premixed combination of formic acid (2.4 mL, 62.2 mmol) and Et₃N (8.60 mL, 62.2 mmol) was added and the mixture stirred at 50° C. for 24 h. After cooling, the mixture was concentrated to ~25 mL. Water (70 mL) was added and the resulting precipitate filtered, and washed with DCM (3×30 mL) and diethyl ether (30 mL) to leave a solid (4.75 g). The filtrate was decanted to leave a dark solid. Subsequent purification by FCC, using 0-30% EtOAc in cyclohexane, gave a solid. This was combined with the first obtained solid to give the title compound as a beige solid (5.93 g, 74%). ¹H NMR (400 MHz, d₆-DMSO): 1.60-1.83 (2H, m), 2.06-2.17 (2H, m), 4.60 (1H, m), 5.08 (1H, m), 5.28 (1H, d), 7.07 (1H, m), 7.25 (1H, ddd), 7.28 (1H, ddd), 7.50 (1H, dd), 9.78 (1H, d).

b. (1S,4S)-4-Amino-1,2,3,4-tetrahydro-naphthalen-1-ol (Intermediate B).

To a grey solution of Intermediate Ba (5.55 g, 21.4 mmol) in MeOH (50 mL), NaOH (1.28 g, 32.1 mmol) in water (15 mL) was added and the mixture stirred at RT for 3 days. NaOH (1.28 g, 32.1 mmol) was added and the brown solution was stirred for 5 h. The solution was loaded on to a SCX-2 cartridge, eluting with MeOH then 2M NH₃ in MeOH, to leave a grey solid. The solid was suspended in DCM (50 mL), sonicated, filtered and dried under vacuum to leave the title compound as a pale grey solid (2.93 g, 84%). ¹H NMR (400 MHz, d₆-DMSO): 1.41-1.64 (2H, m), 2.02-2.13 (2H, m), 3.82 (1H, dd), 4.55 (1H, dd), 5.08 (1H, br s), 7.13-7.22 (2H, m), 7.35-7.49 (2H, m).

Example 1

1-(5-tert-Butyl-2-p-tolyl-2H-pyrazol-3-yl)-3-{(1S,4R)-4-[3-(2-pyrrolidin-1-yl-ethyl)-[1,2,4]triazolo[4,3-a]pyridin-6-yloxy]-1,2,3,4-tetrahydro-naphthalen-1-yl}-urea

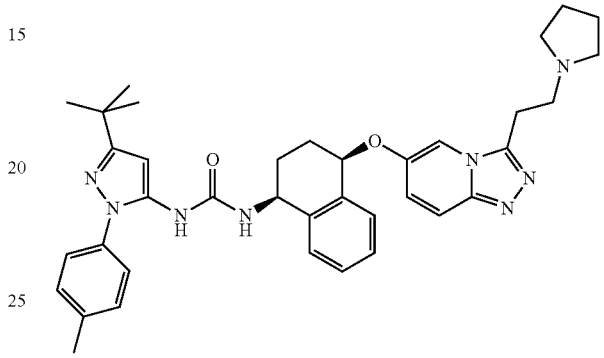

a. 3-Pyrrolidin-1-yl-propionic acid N-(5-fluoro-pyridin-2-yl)-hydrazide (Intermediate 1a).

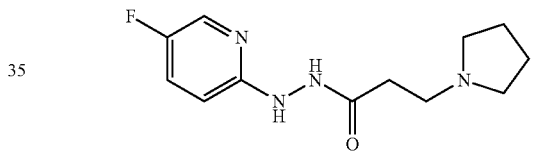

5-fluoro-2-hydrazinopyridine (285 mg, 2.24 mmol) and 3-(pyrrolidin-1-yl)propanoic acid hydrochloride (400 mg, 2.24 mmol) were dissolved in DMF (15 mL). EDC (516 mg, 2.69 mmol), HOBt (30.0 mg, 0.22 mmol) and triethylamine (374 µL, 2.69 mmol) were added and the reaction stirred for 18 h. The mixture was loaded onto an SCX-2 cartridge, which was washed with MeOH then with 2M NH₃ in MeOH. The basic fractions were evaporated in vacuo then purified by FCC using 0-10% [2M NH₃ in MeOH] in DCM to give the title compound contaminated with several impurities (400 mg). The product was used in the next step without further purification.

b. 6-Fluoro-3-(2-pyrrolidin-1-yl-ethyl)-[1,2,4]triazolo[4,3-a]pyridine (Intermediate 1b).

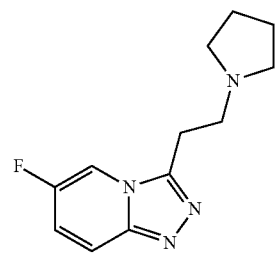 [SMILES: Fc1ccc2nnc(CCN3CCCC3)n2c1]

Intermediate 1a (400 mg) was dissolved in THF (20 mL) and cooled in an ice/water bath. Triphenylphosphine (643 mg, 2.45 mmol) was added followed by triethylamine (682 µL, 4.90 mmol) and hexachloroethane (581 mg, 2.45 mmol). The reaction mixture was stirred for 18 h and then loaded onto an SCX-2 cartridge, which was washed with MeOH then eluted with 2M $NH_3$ in MeOH. The resulting residue was purified by FCC using 0-10% [2M $NH_3$ in MeOH] in DCM to give the title compound (292 mg, 1.16 mmol, 52%). $^1$H NMR (400 MHz, $CDCl_3$): 1.80-1.87 (4H, m), 2.60-2.68 (4H, m), 3.00-3.10 (2H, t, J 7.3), 3.24-3.34 (2H, t, J 7.3), 7.13-7.21 (1H, ddd, J 9.9, 7.6, 2.3), 7.70-7.77 (1H, dd, J 9.8, 4.5), 8.00-8.04 (1H, m).

c. (1S,4R)-4-[3-(2-Pyrrolidin-1-yl-ethyl)-[1,2,4]triazolo[4,3-a]pyridin-6-yloxy]-1,2,3,4-tetrahydro-naphthalen-1-ylamine (Intermediate 1c).

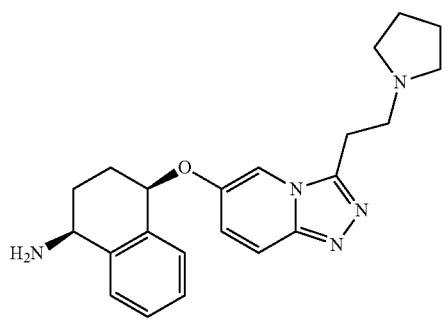 [SMILES: N[C@H]1CC[C@@H](Oc2ccc3nnc(CCN4CCCC4)n3c2)c2ccccc21]

Intermediate A (189 mg, 1.16 mmol) was added to a suspension of sodium hydride (60% in mineral oil, 139 mg, 3.48 mmol) in DMF (5 mL). The reaction was stirred for 20 mins, then Intermediate 1b (292 mg, 1.16 mmol) was added in DMF (5 mL) and the reaction heated to 60° C. for 2 h. The mixture was cooled and quenched by dropwise addition of MeOH. The solution was loaded onto an SCX-2 cartridge, which was washed with MeOH and product eluted with 2M $NH_3$ in MeOH. The residue was purified by FCC using 0-10% [2M $NH_3$ in MeOH] in DCM to give the title compound (270 mg, 0.74 mmol, 64%). $^1$H NMR (400 MHz, $d_4$-MeOD): 1.80-1.86 (4H, m), 1.92-2.02 (1H, m), 2.05-2.18 (2H, m), 2.30-2.40 (1H, m), 2.62-2.70 (4H, m), 2.99-3.05 (2H, t, J 7.8), 3.28-3.36 (2H, t, J 7.8), 3.98-4.04 (1H, dd, J 8.6, 5.2), 5.46-5.50 (1H, t, J 4.3), 7.22-7.40 (4H, m), 7.54-7.58 (1H, d, J 7.8), 7.63-7.68 (1H, dd, J 9.8, 0.7), 7.97 (1H, s), 8.09-8.11 (1H, d, J 1.6).

d. 1-(5-tert-Butyl-2-p-tolyl-2H-pyrazol-3-yl)-3-{(1S,4R)-4-[3-(2-pyrrolidin-1-yl-ethyl)-[1,2,4]triazolo[4,3-a]pyridin-6-yloxy]-1,2,3,4-tetrahydro-naphthalen-1-yl}-urea (Example 1).

Intermediate 1c (270 mg, 0.74 mmol) was dissolved in 1,4-dioxane (6 mL) and (5-tert-butyl-2-p-tolyl-2H-pyrazol-3-yl)-carbamic acid 2,2,2-trichloro-ethyl ester (Synthetic Communications, 2009, 39, 3999-4009, which is incorporated herein by reference in its entirety; 329 mg, 0.81 mmol) and DIPEA (257 µL, 1.48 mmol) were added. The reaction was heated to 60° C. for 18 h. After cooling, the mixture was partitioned between EtOAc (50 mL) and water (50 mL), and then extracted into EtOAc (3×). The combined organic extracts were washed with brine, dried ($MgSO_4$) and evaporated in vacuo. The residue was purified by FCC, using 0-10% [2M $NH_3$ in MeOH] in DCM, then further purified by HPLC (C18 X-select column, 10-98% MeCN in $H_2O$, 0.1% formic acid) to give the title compound (78.0 mg, 0.12 mmol, 17%). LCMS (Method 5): Rt 3.67 mins, m/z 633 [MH$^+$]. $^1$H NMR (400 MHz, $d_4$-MeOD): 1.30 (9H, s), 1.90-2.06 (6H, m), 2.07-2.18 (1H, m), 2.22-2.30 (1H, m), 2.39 (3H, s), 3.08-3.16 (4H, m), 3.42-3.50 (4H, m), 4.87-4.92 (1H, dd, J 9.0, 5.6), 5.43-5.47 (1H, t, J 4.2), 6.33 (1H, s), 7.20-7.36 (10H, m), 7.62-7.66 (1H, d, J 9.7), 8.07-8.09 (1H, d, J 1.6), 8.45 (0.6H, s).

Example 2

1-(5-tert-Butyl-2-p-tolyl-2H-pyrazol-3-yl)-3-((1S,4R)-4-{3-[2-(4-methyl-piperazin-1-yl)-ethyl]-[1,2,4]triazolo[4,3-a]pyridin-6-yloxy}-1,2,3,4-tetrahydro-naphthalen-1-yl)-urea formate salt

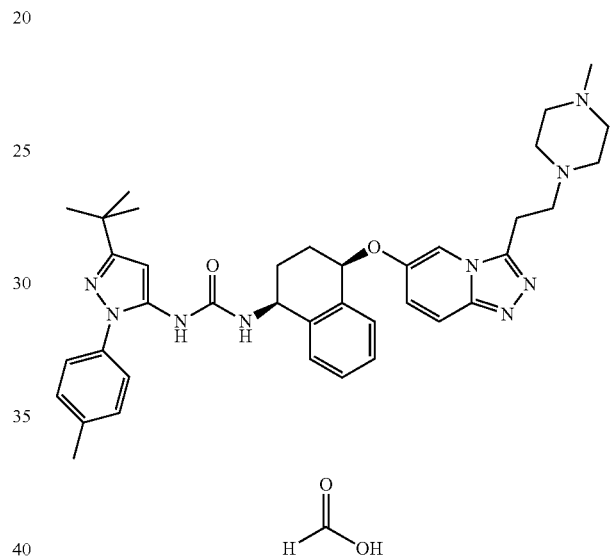

a. 3-(4-Methyl-piperazin-1-yl)-propionic acid N'45-fluoro-pyridin-2-yl)-hydrazide (Intermediate 2a).

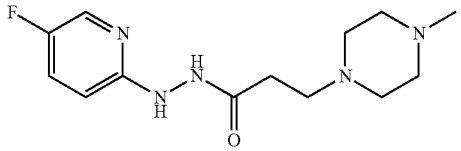 [SMILES: CN1CCN(CCC(=O)NNc2ccc(F)cn2)CC1]

5-fluoro-2-hydrazinopyridine (295 mg, 2.32 mmol) and 3-(4-methyl-1-piperazinyl)propionic acid (400 mg, 2.32 mmol) were dissolved in DCM (15 mL). EDC (536 mg, 2.79 mmol) and HOBt (31.0 mg, 0.23 mmol) were added and the reaction stirred for 18 h. The mixture was loaded onto an SCX-2 cartridge, which was washed with MeOH product eluted with 2M $NH_3$ in MeOH. Further purification by FCC, using 0-10% [2M $NH_3$ in MeOH] in DCM, afforded the title compound (458 mg, 1.63 mmol, 73%). $^1$H NMR (400 MHz, $CDCl_3$): 2.32 (3H, s), 2.48-2.54 (2H, t, J 6.0), 2.54-2.70 (8H, br s), 2.69-2.75 (2H, t, J 6.0), 6.60-6.65 (1H, dd, J 8.9, 3.3), 6.75-6.78 (1H, d, J 4.4), 7.25-7.34 (1H, m), 8.02-8.05 (1H, d, J 3.0), 10.50 (1H, s).

b. 6-Fluoro-3-[2(4-methyl-piperazin-1-yl)-ethyl]-[1,2,4]triazolo[4,3-a]pyridine (Intermediate 2b).

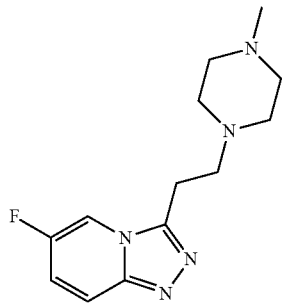 [SMILES: CN1CCN(CCc2nnc3ccc(F)cn23)CC1]

Intermediate 2a (458 mg, 1.63 mmol) was dissolved in THF (15 mL) and cooled in an ice/water bath. Triphenylphosphine (854 mg, 3.26 mmol) was added followed by triethylamine (907 μL, 6.52 mmol) and hexachloroethane (773 mg, 3.26 mmol). The reaction was stirred for 18 h and then loaded onto an SCX-2 cartridge, which was washed with MeOH and product eluted with 2M NH$_3$ in MeOH. Further purification by FCC, using 0-10% [2M NH$_3$ in MeOH] in DCM, afforded the title compound (310 mg, 1.18 mmol, 72%). LCMS (Method 4): Rt 0.28 min, m/z 264 [MH$^+$].

c. (1S,4R)-4-{3-[2-(4-Methyl-piperazin-1-yl)-ethyl]-[1,2,4]triazolo[4,3-a]pyridin-6-yloxy}-1,2,3,4-tetrahydro-naphthalen-1-ylamine (Intermediate 2c).

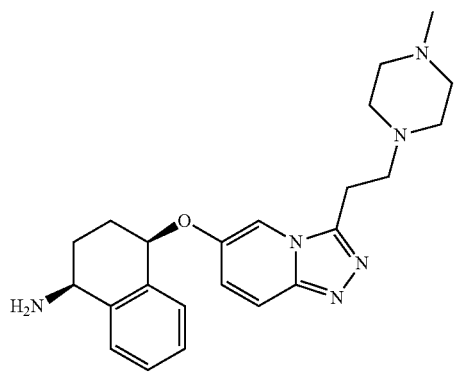 [SMILES: CN1CCN(CCc2nnc3ccc(O[C@@H]4CC[C@H](N)c5ccccc54)cn23)CC1]

Intermediate A (180 mg, 1.11 mmol) was added to a suspension of sodium hydride (60% in mineral oil, 133 mg, 3.33 mmol) in DMF (5 mL). The reaction was stirred for 20 min, then Intermediate 2b (310 mg, 1.11 mmol) was added in DMF (5 mL) and the resulting mixture heated to 60° C. for 3 h. After cooling, the reaction was quenched by dropwise addition of MeOH. The solution was loaded onto an SCX-2 cartridge, which was washed with MeOH and product eluted with 2M NH$_3$ in MeOH. The residue was purified by FCC, using 2-20% [2M NH$_3$ in MeOH] in DCM, to give the title compound (200 mg, 0.47 mmol, 43%). LCMS (Method 4): Rt 0.28 min, m/z 407 [MH$^+$].

d. 1-(5-tert-Butyl-2-p-tolyl-2H-pyrazol-3-yl)-3-((1S,4R)-4-{3-[2-(4-methyl-piperazin-1-yl)-ethyl]-[1,2,4]triazolo[4,3-a]pyridin-6-yloxy}-1,2,3,4-tetrahydro-naphthalen-1-yl)-urea formate salt (Example 2).

Intermediate 2c (85.0 mg, 0.21 mmol) was dissolved in 1,4-dioxane (2 mL) and (5-tert-butyl-2-p-tolyl-2H-pyrazol-3-yl)-carbamic acid 2,2,2-trichloro-ethyl ester (Synthetic Communications, 2009, 39, 3999-4009, which is incorporated herein by reference in its entirety; 96.0 mg, 0.24 mmol) and DIPEA (75.0 μl, 0.43 mmol) were added. The reaction was heated to 60° C. for 18 h. After cooling, the mixture was partitioned between EtOAc (50 mL) and water (50 mL), and extracted into EtOAc (3×). The combined organic layers were washed with brine, dried (MgSO$_4$) and evaporated in vacuo. The residue was purified by FCC, using 0-10% [2M NH$_3$ in MeOH] in DCM, then further purified by HPLC (C, 18 X-select column, 10-40% MeCN in H$_2$O, 0.1% formic acid) to give the title compound mainly as formic acid salt (43.0 mg, 0.065 mmol, 31%). LCMS (Method 5) Rt 3.54 mins, m/z 662 [MH$^+$]. $^1$H NMR (400 MHz, d$_4$-MeOD): 1.30 (9H, s), 1.90-2.05 (2H, m), 2.06-2.15 (1H, m), 2.20-2.30 (1H, m), 2.38 (3H, s), 2.40 (3H, s), 2.55-2.75 (8H, br s), 2.90-2.95 (2H, t, J 7.4), 3.29-3.32 (2H, t, J 7.4), 4.86-4.92 (1H, dd, J 8.8, 5.6), 5.43-5.47 (1H, t, J 4.2), 6.33 (1H, s), 7.21-7.35 (11H, m), 7.60-7.64 (1H, d, J 9.9), 8.07-8.09 (1H, d, J 1.9), 8.40-8.50 (0.4H, br s, formate).

Example 3

1-(5-tert-Butyl-2-p-tolyl-2H-pyrazol-3-yl)-3-[(1S,4R)-4-(3-piperidin-1-yl)-[1,2,4]triazolo[4,3-a]pyridin-6-yloxy)-1,2,3,4-tetrahydro-naphthalen-1-yl]-urea

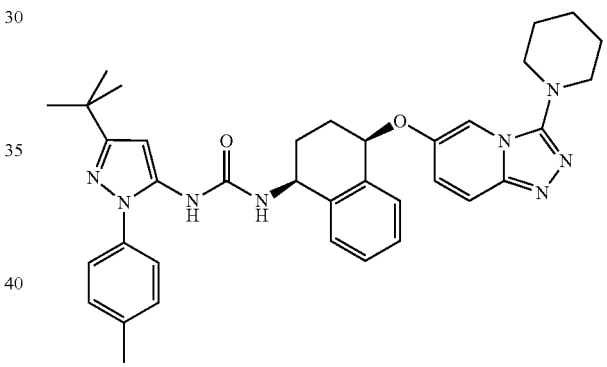

a. Piperidine-1-carboxylic acid N'-(5-fluoro-pyridin-2-yl)-hydrazide (Intermediate 3a).

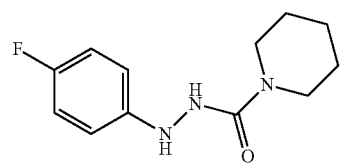 [SMILES: O=C(NNc1ccc(F)cc1)N1CCCCC1]

1-Piperidine carbonyl chloride (348 mg, 0.30 mL, 2.36 mmol) was added dropwise to a solution of 5-fluoro-2-hydrazinyl-pyridine (see for reference WO 2010/022076, which is incorporated herein by reference in its entirety; 0.30 g, 2.36 mmol) and DIPEA (1.2 mL, 7.08 mmol) in DCM (10 mL) at RT under nitrogen and the mixture stirred for 2 h. The solution was washed with water (2×15 mL) and dried (Na$_2$SO$_4$). The solvent was evaporated and the residue triturated (diethyl ether) and filtered to afford the title compound as an off-white solid (475 mg, 84%). LCMS (Method 1): Rt 1.82 min, m/z 239 [MH$^+$].

b. 6-Fluoro-3-piperidin-1-yl-[1,2,4]triazolo[4,3-a]pyridine (Intermediate 3b).

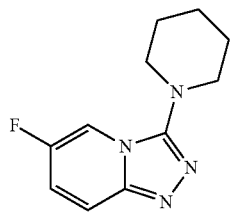 [SMILES: Fc1ccc2nnc(N3CCCCC3)n2c1]

Hexachloroethane (826 mg, 3.92 mmol) was added portionwise to a solution of Intermediate 3a (466 mg, 1.95 mmol), triphenylphosphine (1.03 g, 3.92 mmol) and triethylamine (1.1 mL, 7.83 mmol) in dry THF (30 mL) at RT, and the mixture stirred for 2 h. The resulting precipitate was filtered off and the filtrate evaporated. The residue was purified by SCX-2, eluting with MeOH followed by 2M $NH_3$ in MeOH, to give the title compound as pale orange coloured gum (206 mg, 48%). LCMS (Method 1): Rt 2.44 min, m/z 221 [$MH^+$].

c. (1S,4R)-4-(3-Piperidin1-yl-[1,2,4]triazolo[4,3-a]pyridin-6-yloxy)-cis-1,2,3,4-tetrahydro-naphthalen-1-ylamine (Intermediate 3c).

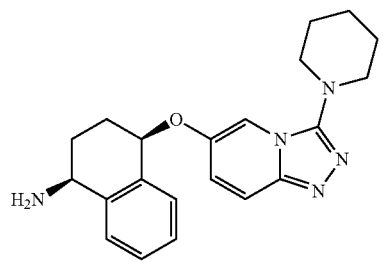 [SMILES: N[C@H]1CC[C@@H](Oc2ccc3nnc(N4CCCCC4)n3c2)c2ccccc21]

Intermediate A (100 mg, 0.61 mmol) was added portionwise to a suspension of sodium hydride (60% in mineral oil, 73 mg, 1.84 mmol) in dry DMF (2 mL) at RT, and the mixture stirred for 15 min. Intermediate 3b (135 mg, 0.61 mmol) was then added in one portion and the mixture heated at 60° C. for 3 h. After cooling, saturated $NH_4Cl$ (ca. 0.2 mL) added. The mixture was then partitioned between water (15 mL) and ethyl acetate (3×15 mL) and the combined organic extracts washed with brine (2×15 mL) and dried ($Na_2SO_4$). The solvent was evaporated and the residue purified by SCX-2, eluting with MeOH followed by $NH_3$ in MeOH, to give the title compound as brown coloured gum (133 mg, 60%). LCMS (Method 1): Rt 1.95 min, m/z 364 [$MH^+$].

d. 1-(5-tert-Butyl-2-p-tolyl-2H-pyrazol-3-yl)-3-[(1S,4R)-4-(3-piperidin-1-3-yl)-[1,2,4]triazolo[4,3-a]pyridin-6-yloxy)-1,2,3,4-tetrahydro-naphthalen-1-yl]-urea (Example 3).

The title compound was prepared starting from Intermediate 3c and [5-tert-butyl-2-p-tolyl-2H-pyrazol-3-yl]-carbamic acid 2,2,2-trichloro-ethyl ester (Synthetic Communications, 2009, 39, 3999-4009, which is incorporated herein by reference in its entirety) by using an analogous procedure to that described in Example 1 step d. LCMS (Method 5): Rt 4.79 min, m/z 916 [$MH^+$]. $^1H$ NMR (400 MHz, $CDCl_3$): 1.32 (9H, s), 1.60-1.77 (6H, m), 1.86-1.95 (1H, m), 2.01-2.11 (2H, m), 2.20-2.27 (1H, m), 2.36 (3H, t), 3.15 (4H, m), 5.08 (1H, m), 5.18 (1H, m), 5.41 (1H, d, J 9.20), 6.28 (1H, s), 6.48 (1H br s), 6.96 (1H, dd, J 2.12, 9.75), 7.21 (2H, d, J 8.13), 7.24-7.33 (6H, m), 7.38-7.41 (2H, m), 7.45-7.48 (1H, d, J 9.65).

e. 1-(5-tert-Butyl-2-p-tolyl-2H-pyrazol-3-yl)-3-[(1S,4R)-4-(3-piperidin-1-3-yl)-[1,2,4]triazolo[4,3-a]pyridin-6-yloxy)-1,2,3,4-tetrahydro-naphthalen-1-yl]-urea Crystallization of Example 3

1-(5-tert-Butyl-2-p-tolyl-2H-pyrazol-3-yl)-3-[(1S,4R)-4-(3-piperidin-1-yl)-[1,2,4]triazolo[4,3-a]pyridin-6-yloxy)-1,2,3,4-tetrahydro-naphthalen-1-yl]-urea (3.974 g, Example 3) was dissolved in hot tert-butyl alcohol (~130 ml) and then dried by lyophilisation overnight. The solid material was then slurried in iso-propyl acetate (120 ml) in a maturation chamber which cycled between ambient and 50° C. with four hours spent under each condition. After 3 days the reaction was cooled to RT and then stirred at RT for four days. The resulting off-white solid was isolated by filtration and dried at 40° C./0.5 mbar. Yield=3.67 g (92%). Mpt=253° C.

Example 4

1-(5-tert-Butyl-2-p-tolyl-2H-pyrazol-3-yl)-3-[(1S,4R)-4-(3-piperidin-4-yl)-[1,2,4]triazolo[4,3-a]pyridin-6-yloxy)-1,2,3,4-tetrahydro-naphthalen-1-yl]-urea

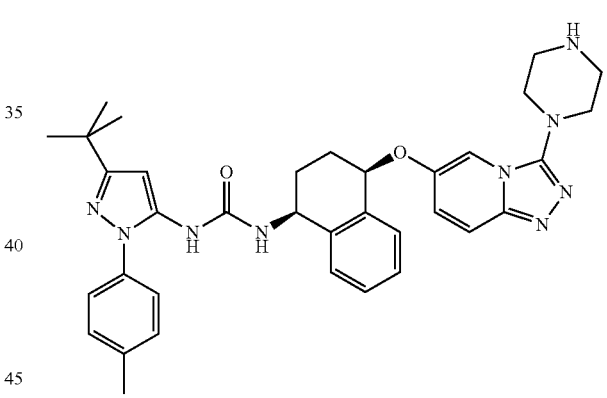

a. 4-[N'-(5-fluoro-pyridin-2-yl)-hydrazinocarbonyl]-piperidine-1-carboxylic acid tert-butyl ester (Intermediate 4a).

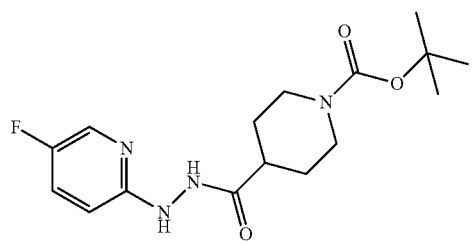 [SMILES: CC(C)(C)OC(=O)N1CCC(C(=O)NNc2ccc(F)cn2)CC1]

EDC (543 mg, 2.83 mmol) was added portionwise to a stirred solution of 5-fluoro-2-hydrazinyl-pyridine (for reference procedure see WO 2010/022076, which is incorporated herein by reference in its entirety; 0.30 g, 2.36 mmol), piperidine-1,4-dicarboxylic acid mono-tert-butyl ester (Aldrich, 649 mg, 2.83 mmol) and HOBt (32 mg, 0.24 mmol) in dry DCM (20 mL). The mixture was stirred at RT for 18 h. The solution was washed with water (2×20 mL), dried (Na₂SO₄) and evaporated. The residue was triturated (diethyl ether) to give the title compound as an off-white solid (713 mg, 82%). LCMS (Method 1): Rt 2.76 min, m/z 339 [MH⁺].

b. 4-(6-Fluoro-[1,2,4]triazolo[4,3-a]pyridin-3-yl)-piperidine-1-carboxylic acid tert-butyl ester (Intermediate 4b).

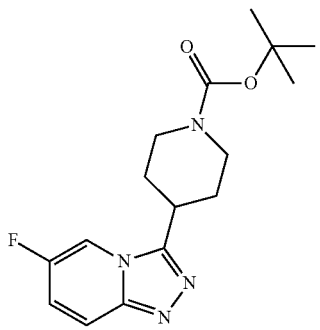 [SMILES: CC(C)(C)OC(=O)N1CCC(c2nnc3ccc(F)cn23)CC1]

Hexachloroethane (990 mg, 4.18 mmol) was added portionwise to a solution of Intermediate 4a (707 mg, 2.09 mmol), triphenylphosphine (1.103 g, 4.18 mmol) and triethylamine (1.2 mL, 8.36 mmol) in dry THF (30 mL) at RT. The mixture was stirred for 2 h. The resulting precipitate was filtered off and the filtrate evaporated. The residue was purified by SCX-2, eluting with MeOH followed by 2M NH₃ in MeOH, to give a pale orange coloured solid. This was triturated (diethyl ether) to give the title compound as a buff-coloured solid (540 mg, 80%). LCMS (Method 1): Rt 2.79 min, m/z 321 and 221(-Boc) [MH⁺].

c. 4-[6-((1S,4R)-4-Amino-1,2,3,4-tetrahydro-naphthalen-1-yloxy-[1,2,4]triazolo[4,3-a]pyridin-3-yl]-piperidine-1-carboxylic acid tert-butyl ester (Intermediate 4c).

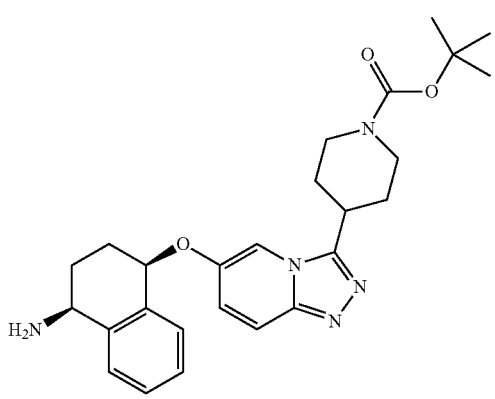 [SMILES: CC(C)(C)OC(=O)N1CCC(c2nnc3ccc(O[C@@H]4CC[C@H](N)c5ccccc54)cn23)CC1]

Intermediate A (100 mg, 0.61 mmol) was added portionwise to a suspension of sodium hydride (60% in mineral oil, 73 mg, 1.84 mmol) in dry DMF (2 mL) at RT. The mixture was then stirred for 15 min. Intermediate 4b (193 mg, 0.61 mmol) was added in one portion and the mixture heated at 60° C. for 3 h. After cooling, saturated NH₄Cl (ca. 0.2 mL) added. The mixture was partitioned between water (15 mL) and ethyl acetate (3×15 mL) and the combined organic extracts washed with brine (2×15 mL), dried (Na₂SO₄) and evaporated. The residue was purified by SCX-2, eluting with MeOH followed by 2M NH₃ in MeOH, to give the title compound as brown coloured foam (261 mg, 92%). LCMS (Method 1): Rt 2.19 min, m/z 464 [MH⁺].

d. 4-(6-[{(1S,4R)-4-[3-(5-tert-Butyl-2-p-tolyl-2H-pyrazol-3-yl)-ureido]-1,2,3,4-tetrahydro-naphthalen-1-yloxy}-[1,2,4]triazolo[4,3-a]pyridin-3-yl)-piperidine-1-carboxylic acid tert-butyl ester (Intermediate 4d).

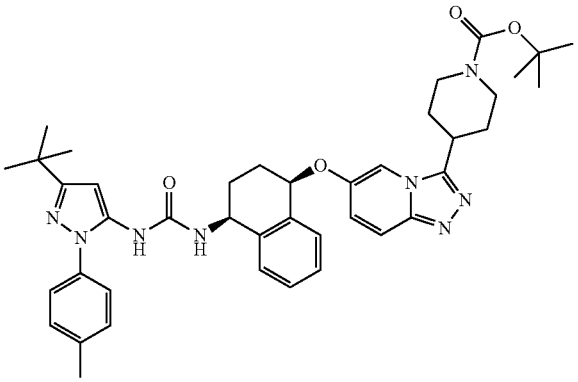 [SMILES: Cc1ccc(-n2nc(C(C)(C)C)cc2NC(=O)N[C@H]2CC[C@@H](Oc3ccc4nnc(C5CCN(C(=O)OC(C)(C)C)CC5)n4c3)c3ccccc32)cc1]

The title compound was prepared starting from Intermediate 4c and [5-tert-butyl-2-p-tolyl-2H-pyrazol-3-yl]-carbamic acid 2,2,2-trichloro-ethyl ester (Synthetic Communications, 2009, 39, 3999-4009, which is incorporated herein by reference in its entirety) by using an analogous procedure to that described in Example 1 step d. LCMS (Method 1): Rt 3.89 min, m/z 719 [MH⁺].

e. 1-(5-tert-Butyl-2-p-tolyl-2H-pyrazol-3-yl)-3-[(1S,4R)-4-(3-piperidin-4-yl)-[1,2,4]triazolo[4,3-a]pyridin-6-yloxy)-1,2,3,4-tetrahydro-naphthalen-1-yl]-urea (Example 4).

HCl (4M in dioxane, 1 mL) was added dropwise to a solution of Intermediate 4d (272 mg, 0.37 mmol) in MeOH (1 mL) and the mixture stirred at RT for 5 h. The reaction mixture was passed down a SCX-2 cartridge, eluting with MeOH followed by 2M NH₃ in MeOH, to afford a brown foam. Further purification by HPLC (50-95% MeCN in H₂O) gave the title compound as a off-white powder (37 mg). LCMS (Method 5): Rt 3.65 min, m/z 519 [MH⁺]. ¹H NMR (400 MHz, CDCl₃): 1.33 (9H, s), 1.87-1.97 (5H, m), 2.05-2.13 (2H, m), 2.22-2.29 (1H, m), 2.37 (3H, s), 2.71-2.81 (1H, m), 3.10 (1H, m), 3.19 (2H, m), 5.08 (1H, m), 5.22 (1H, m), 5.44 (1H, m), 6.29 (1H, s), 7.06 (1H, dd, J 2.13, 9.80), 7.23-7.32 (7H, m), 7.39-7.45 (3H, m), 7.63 (1H, d, J 9.75).

Example 5

1-(5-tert-Butyl-2-p-tolyl-2H-pyrazol-3-yl)-3-[(1S,4R)-4-[3-((S)-1-methyl-pyrrolidin-2-yl)-[1,2,4]triazolo[4,3-a]pyridin-6-yloxy)-1,2,3,4-tetrahydro-naphthalen-1-yl]-urea

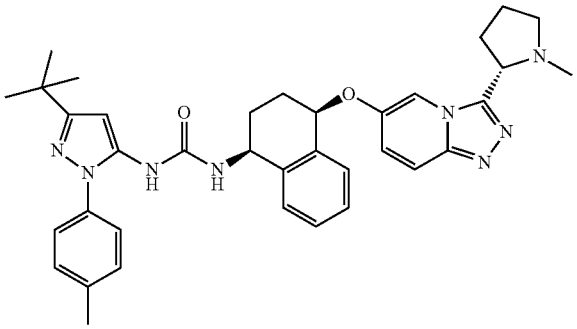 [SMILES: Cc1ccc(-n2nc(C(C)(C)C)cc2NC(=O)N[C@H]2CC[C@@H](Oc3ccc4nnc([C@@H]5CCCN5C)n4c3)c3ccccc32)cc1]

a. (S)-1-Methyl-pyrrolidine-2-carboxylic acid [N'-(5-fluoro-pyridin-2-yl)-hydrazide (Intermediate 5a).

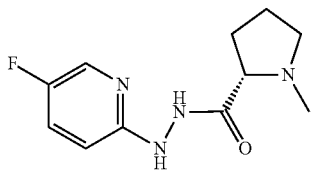 [SMILES: CN1CCC[C@H]1C(=O)NNc1ccc(F)cn1]

EDC (271 mg, 1.41 mmol) was added portionwise to a solution of 5-fluoro-2-hydrazinyl-pyridine (for reference procedure see WO 2010/022076, which is incorporated herein by reference in its entirety; 0.15 g, 1.18 mmol), N-methyl-L-proline monohydrate (0.20 g, 1.36 mmol) and HOBt (16 mg, 0.12 mmol) in dry DCM (5 mL) at RT and stirred for 16 h. The solution was diluted with DCM (15 mL), washed with water (150 mL), dried (Na$_2$SO$_4$) and evaporated to give the title compound as a pale yellow gum (189 mg, 67%). LCMS (Method 1): Rt 0.31 min, m/z 239 [MH$^+$].

b. 6-Fluoro-3-((S)-1-methyl-pyrrolidin-2-yl)-[1,2,4]triazolo[4,3-a]pyridine (Intermediate 5b).

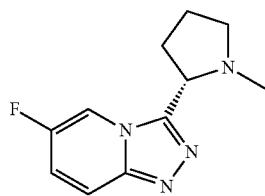 [SMILES: CN1CCC[C@H]1c1nnc2ccc(F)cn12]

Hexachloroethane (375 mg, 1.59 mmol) was added portionwise to a solution of Intermediate 5a (189 mg, 0.79 mmol), triphenylphosphine (416 mg, 1.59 mmol) and triethylamine (0.44 mL, 3.17 mmol) in dry THF (10 mL) at RT and stirred for 4 h. The resulting precipitate was filtered off and the filtrate evaporated. The residue was purified by SCX-2, eluting with MeOH followed by 2M NH$_3$ in MeOH gave the title compound as a brown foam (136 mg, 78%). LCMS (Method 1): Rt 0.45 min, m/z 221 [MH$^+$].

c. (1S,4R)-4-[3-((S)-1-Methyl-pyrrolidin-2-yl)-[1,2,4]triazolo[4,3-a]pyridin-6-yloxy]-1,2,3,4-tetrahydro-naphthalen-1-ylamine (Intermediate 5c).

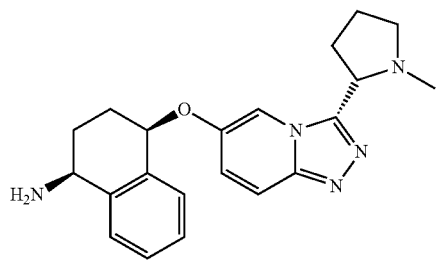

Intermediate A (128 mg, 0.77 mmol) was added portionwise to a suspension of sodium hydride (60% in mineral oil, 92 mg, 2.30 mmol) in dry DMF (3 mL) at RT and stirred for 15 mins. Intermediate 5b (169 mg, 0.77 mmol) was then added in one portion and the mixture heated at 60° C. for 4 h. After cooling, saturated NH$_4$Cl (ca 0.2 mL) was added. The mixture was partitioned between water (10 mL) and ethyl acetate (3×10 mL). The aqueous phase was concentrated in vacuo and the residue purified by SCX-2, eluting with MeOH followed by 2M NH$_3$ in MeOH, to give the title compound as brown coloured foam (103 mg, 36%). LCMS (Method 1): Rt 1.34 min, m/z 364 [MH$^+$].

d. 1-(5-tert-Butyl-2-p-tolyl-2H-pyrazol-3-yl)-3-[(1S,4R)-4-[3-((S)-1-methyl-pyrrolidin-2-yl)-[1,2,4]triazolo[4,3-a]pyridin-6-yloxy)-1,2,3,4-tetrahydro-naphthalen-1-yl]-urea (Example 5).

The title compound was prepared with Intermediate 5c and [5-tert-butyl-2-p-tolyl-2H-pyrazol-3-yl]-carbamic acid 2,2,2-trichloro-ethyl ester (Synthetic Communications, 2009, 39, 3999-4009, which is incorporated herein by reference in its entirety) using an analogous procedure to that described in Example 1 step d. LCMS (Method 5): Rt 3.76 min, m/z 319 [MH$^+$]. $^1$H NMR (400 MHz, CDCl$_3$): 1.33 (9H, s), 1.88-2.12 (6H, m), 2.21 (3H, s), 2.21-2.30 (2H, m), 2.33-2.39 (1H, m), 2.37 (3H, s), 3.19-3.24 (1H, m), 3.98-4.02 (1H, m), 5.05-5.12 (1H, m), 5.17 (1H, t, J 4.0), 5.25 (1H, d, J 8.7), 6.25-6.27 (2H, m), 7.03 (1H, dd, J 2.0, 9.8), 7.22-7.34 (6H, m), 7.40 (2H, d, J 8.5), 7.61 (1H, d, J 9.8), 8.27 (1H, m).

Example 6

1-(5-tert-Butyl-2-p-tolyl-2H-pyrazol-3-yl)-3-[(1S,4R)-4-((S)-3-pyrrolidin-2-yl-[1,2,4]triazolo[4,3-a]pyridin-6-yloxy)-1,2,3,4-tetrahydro-naphthalen-1-yl]-urea

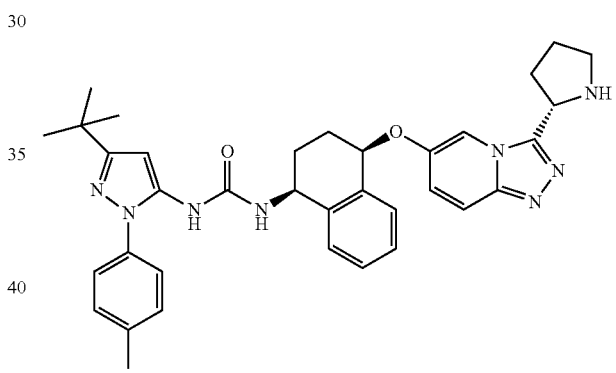

a. (S)-2-[N'-(5-fluoro-pyridin-2-yl)-hydrazinocarbonyl]-pyrrolidine-1-carboxylic acid tert-butyl ester (Intermediate 6a).

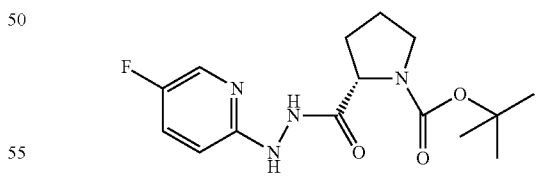

EDC (543 mg, 2.83 mmol) was added portionwise to a stirred solution of 5-fluoro-2-hydrazinyl-pyridine (for reference procedure see WO 2010/022076, which is incorporated herein by reference in its entirety; 0.30 g, 2.36 mmol), N-tert-butylcarbonyl-L-proline (609 mg, 2.83 mmol) and HOBt (32 mg, 0.24 mmol) in dry DCM (15 mL) at RT and stirred for 18 h. The solution was washed with water (2×20 mL) and dried (Na$_2$SO$_4$) and evaporated to give the title compound as a pale yellow foam (767 mg, 100%). LCMS (Method 1): Rt 2.69 min, m/z 325 [MH$^+$].

b. (S)-2-(6-Fluoro-[1,2,4]triazolo[4,3-a]pyridin-3-yl)-pyrrolidine-1-carboxylic acid tert-butyl ester (Intermediate 6b).

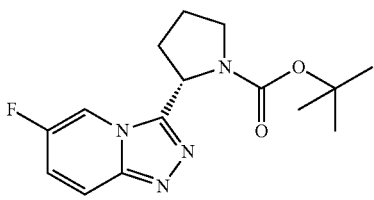 [SMILES: CC(C)(C)OC(=O)N1CCC[C@H]1c1nnc2ccc(F)cn12]

Hexachloroethane (1.34 g, 5.65 mmol) was added portionwise to a solution of Intermediate 6a (917 mg, 2.83 mmol), triphenylphosphine (1.48 g, 5.65 mmol) and triethylamine (1.6 mL, 11.3 mmol) in dry THF (15 mL) at RT and stirred for 4 h. The resulting precipitate was filtered off and the filtrate evaporated. The residue was purified by SCX-2, eluting with MeOH followed by 2M NH₃ in MeOH, to give the title compound as a buff-coloured foam (669 mg, 77%). LCMS (Method 4): Rt 2.48 min, m/z 307 [MH⁺].

c. (S)-2-[6-((1S,4R)-4-Amino-1,2,3,4-tetrahydro-naphthalen-1-yloxy-[1,2,4]triazolo[4,3-a]pyridin-3-yl]-pyrrolidine-1-carboxylic acid tert-butyl ester (Intermediate 6c).

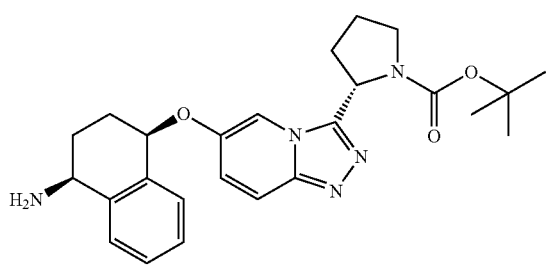 [SMILES: CC(C)(C)OC(=O)N1CCC[C@H]1c1nnc2ccc(O[C@@H]3CC[C@H](N)c4ccccc43)cn12]

Intermediate A (150 mg, 0.92 mmol) was added portionwise to a suspension of sodium hydride (60% in mineral oil, 110 mg, 2.76 mmol) in dry DMF (2 mL) at RT and stirred for 15 mins. Intermediate 6b (281 mg, 0.92 mmol) was then added in one portion and the mixture heated at 60° C. for 3 h. After cooling, saturated NH₄Cl (ca. 0.2 mL) was added. The mixture was partitioned between water (15 mL) and ethyl acetate (3×15 mL). The combined organic extracts were washed with brine (20 mL), dried (Na₂SO₄) and evaporated to give the title compound as brown coloured gum (74 mg, 18%). LCMS (Method 1): Rt 2.08 min, m/z 450 [MH⁺].

d. (S)-2-(6-[{(1S,4R)-4-[3-(5-tert-Butyl-2-p-tolyl-2H-pyrazol-3-yl)-ureido]-1,2,3,4-tetrahydro-naphthalen-1-yloxy}-[1,2,4]triazolo[4,3-a]pyridin-3-yl)-pyrrolidine-1-carboxylic acid tert-butyl ester (Intermediate 6d).

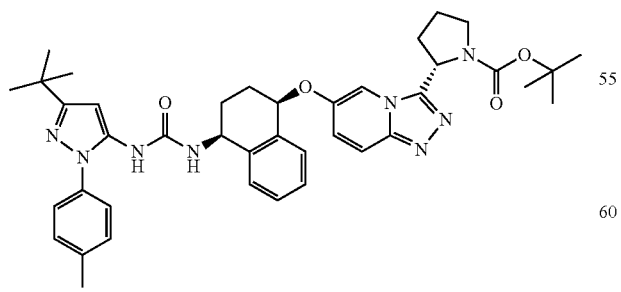

The title compound was prepared starting from Intermediate 6c and [5-tert-butyl-2-p-tolyl-2H-pyrazol-3-yl]-carbamic acid 2,2,2-trichloro-ethyl ester (Synthetic Communications, 2009, 39, 3999-4009, which is incorporated herein by reference in its entirety) by using an analogous procedure to that described in Example 1 step d. LCMS (Method 1): Rt 3.88 min, m/z 705 [MH⁺].

e. 1-(5-tert-Butyl-2-p-tolyl-2H-pyrazol-3-yl)-3-[(1S,4R)-4-((S)-3-pyrrolidin-2-yl-[1,2,4]triazolo[4,3-a]pyridin-6-yloxy)-1,2,3,4-tetrahydro-naphthalen-1-yl]-urea (Example 6).

HCl (4M in dioxane; 1 mL) was added to a solution of Intermediate 6d (225 mg, 0.32 mmol) in MeOH (0.5 mL) at RT and stirred for 8 h. The solution was loaded on to a SCX-2 (10 g) cartridge, eluting with MeOH followed by 2M NH₃ in MeOH, to give a brown foam. Further purification by HPLC (50-85% MeCN in H₂O (0.1% NH₃)) gave the title compound as an off-white powder after freeze drying (7 mg, 4%). LCMS (Method 5): Rt 3.73 min, m/z 605 [MH⁺]. ¹H NMR (400 MHz, CDCl₃): 1.29 (9H, s), 1.84-2.07 (5H, m), 2.18-2.31 (3H, m), 2.35 (3H, s), 2.96-3.07 (2H, m), 4.64 (1H, t, J 7.5), 5.01-5.08 (1H, m), 5.19 (1H, t, J 4.0), 5.27 (1H, d, J 8.8), 6.24 (2H, s), 7.02 (1H, dd, J 2.2, 10.0), 7.19-7.28 (6H, m), 7.37 (2H, d, J 8.4), 7.58 (1H, d, J 10.0), 7.98 (1H, m).

Example 7

1-(5-tert-Butyl-2-p-tolyl-2H-pyrazol-3-yl)-3-[(1S,4R)-4-(3-piperazin-1-ylmethyl-[1,2,4]triazolo[4,3-a]pyridin-6-yloxy)-1,2,3,4-tetrahydro-naphthalen-1-yl]-urea

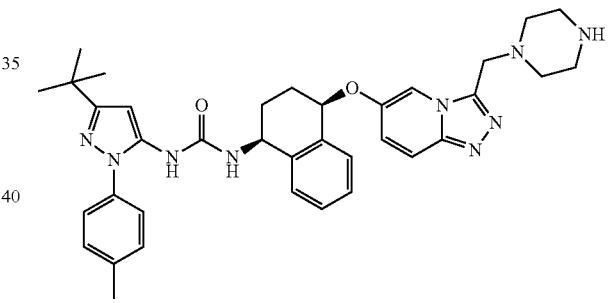

a. 4-[N'-(5-fluoro-pyridin-2-yl)-hydrazinocarbonylmethyl]-piperazine-1-carboxylic acid tert-butyl ester (Intermediate 7a).

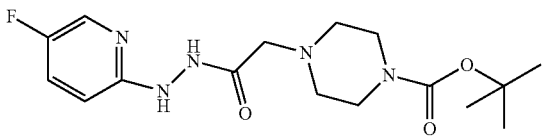 [SMILES: CC(C)(C)OC(=O)N1CCN(CC(=O)NNc2ccc(F)cn2)CC1]

EDC (543 mg, 2.83 mmol) was added portionwise to a solution of 2-(4-Boc-1-piperazinyl)acetic acid (576 mg, 2.36 mmol), 5-fluoro-2-hydrazinyl-pyridine (for reference procedure see WO 2010/022076, which is incorporated herein by reference in its entirety; 0.30 g, 2.36 mmol) and HOBt (32 mg, 0.24 mmol) in dry DCM (15 mL) at RT and stirred for 16 h. The solution was diluted with DCM (20 mL), washed with water (2×20 mL) and dried (Na₂SO₄). The solvent was evaporated to give the title compound as an off-white solid (667 mg, 80%). LCMS (Method 1): Rt 1.99 min, m/z 354 [MH⁺].

b. 4-(6-Fluoro-[1,2,4]triazolo[4,3-a]pyridin-3-ylmethyl)-piperazine-1-carboxylic acid tert-butyl ester (Intermediate 7b).

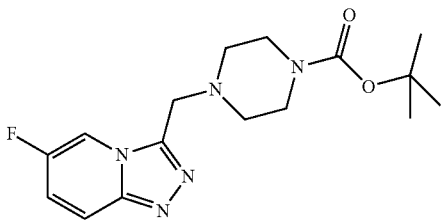 [SMILES: CC(C)(C)OC(=O)N1CCN(Cc2nnc3ccc(F)cn23)CC1]

Hexachloroethane (893 mg, 3.77 mmol) was added portionwise to a solution of Intermediate 7a (667 mg, 1.89 mmol), triphenylphosphine (990 mg, 3.77 mmol) and triethylamine (1.05 mL, 7.55 mmol) in dry THF (20 mL) at RT and stirred for 4 h. The resulting precipitate was filtered off and the filtrate evaporated. The residue was purified by SCX-2, eluting with MeOH followed by 2M $NH_3$ in MeOH, to give an off-white solid. This was triturated (diethyl ether) to give the title compound as a colourless solid LCMS (Method 1): Rt 2.33 min, in/z 336 [MH+].

c. 4-[6-((1S,4R)-4-Amino-1,2,3,4-tetrahydro-naphthalen-1-yloxy-[1,2,4]triazolo[4,3-a]pyridin-3-ylmethyl]-piperazine-1-carboxylic acid tert-butyl ester (Intermediate 7c).

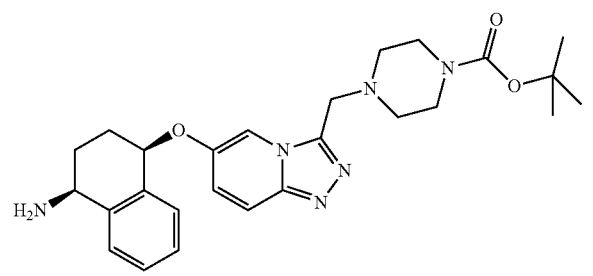 [SMILES: CC(C)(C)OC(=O)N1CCN(Cc2nnc3ccc(O[C@@H]4CC[C@H](N)c5ccccc54)cn23)CC1]

The title compound was prepared with Intermediate 7b and Intermediate A using an analogous procedure to that described in Example 6 step c. LCMS (Method 1): Rt 1.98 min, in/z 479 [MH+].

d. 4-(6-{(1S,4R)-4-[3-(5-tert-Butyl-2-p-tolyl-2H-pyrazol-3-yl)-ureido]-1,2,3,4-tetrahydro-naphthalen-1-yloxy}-[1,2,4]triazolo[4,3-a]pyridin-3-ylmethyl)-piperazine-1-carboxylic acid tert-butyl ester (Intermediate 7d).

The title compound was prepared starting from Intermediate 7c and [5-tert-butyl-2-p-tolyl-2H-pyrazol-3-yl]-carbamic acid 2,2,2-trichloro-ethyl ester (Synthetic Communications, 2009, 39, 3999-4009, which is incorporated herein by reference in its entirety) by using an analogous procedure to that described in Example 1 step d. LCMS (Method 1): Rt 3.59 min, m/z 734 [MH+].

e. 1-(5-tert-Butyl-2-p-tolyl-2H-pyrazol-3-yl)-3-[(1S,4R)-4-(3-piperazin-1-ylmethyl-[1,2,4]triazolo[4,3-a]pyridin-6-yloxy)-1,2,3,4-tetrahydro-naphthalen-1-yl]-urea (Example 7).

HCl (4M in dioxane; 1 mL) was added to a solution of Intermediate 7d (92 mg, 0.12 mmol) in MeOH (1 mL) at Rt and stirred for 4.5 h. The solution was loaded on to a SCX-2 cartridge, eluting with MeOH followed by 2M $NH_3$ in MeOH, to give a pale yellow foam. Further purification by HPLC (40-80% MeCN in $H_2O$ (0.1% NH3)) gave the title compound as an off-white powder after freeze drying (28 mg, 35%). LCMS (Method 5): Rt 3.59 min, m/z 634 [MH+]. $^1$H NMR (400 MHz, $CDCl_3$): 1.33 (9H, s), 1.89-1.98 (1H, m), 2.06-2.14 (2H, m), 2.25-2.32 (1H, m), 2.38 (3H, s), 2.38-2.48 (4H, m), 2.80-2.83 (4H, m), 4.03 (2H, s), 5.06-5.12 (1H, m), 5.20-5.24 (2H, m), 6.28 (1H, s), 6.34 (1H, br s), 7.08 (1H, dd, J 9.8, 2.0), 7.23-7.36 (6H, m), 7.40 (2H, d, J 7.7), 7.63 (1H, d, J 9.5), 8.14 (1H, m).

Example 8

1-(5-tert-Butyl-2-p-tolyl-2H-pyrazol-3-yl)-3-[(1S,4R)-4-(3-isopropylamino-[1,2,4]triazolo[4,3-a]pyridin-6-yloxy)-1,2,3,4-tetrahydro-naphthalen-1-yl]-urea

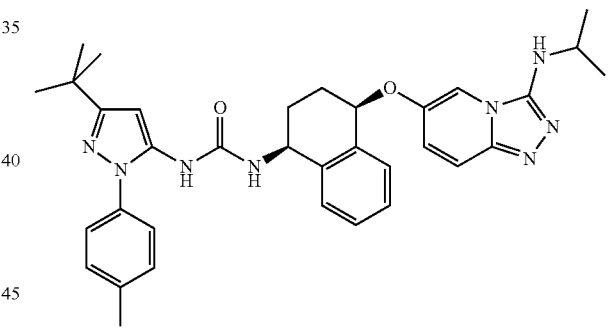

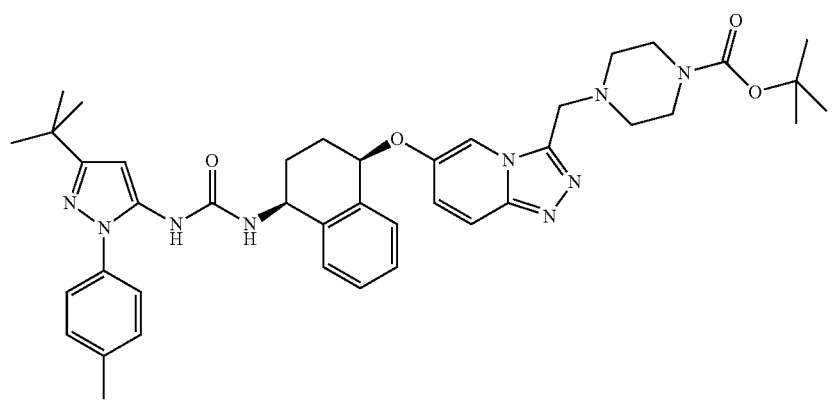 [SMILES: Cc1ccc(-n2nc(C(C)(C)C)cc2NC(=O)N[C@H]2CC[C@@H](Oc3ccc4nnc(CN5CCN(C(=O)OC(C)(C)C)CC5)n4c3)c3ccccc32)cc1]

a. 2-(5-Fluoropyridin-2-yl)-N-(propan-2-yl)hydrazinecarboxamide (Intermediate 8a).

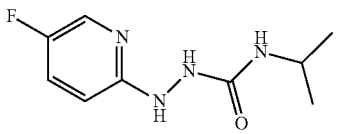

Isopropyl isocyanate (0.25 mL, 2.60 mmol) was added dropwise, over 2 min, to a solution of 5-fluoro-2-hydrazinylpyridine (for reference procedure see WO 2010/022076, which is incorporated herein by reference in its entirety; 0.30 g, 2.36 mmol) in dry DCM (10 mL) at RT and stirred for 3 h. The solvent was evaporated and the residue triturated (diethyl ether) and filtered to give the title compound as a colourless solid (464 mg, 93%). LCMS (Method 1): Rt 1.92 min, m/z 213 [MH$^+$].

b. (6-Fluoro-[1,2,4]triazolo[4,3-a]pyridin-3-yl)-isopropylamine (Intermediate 8b).

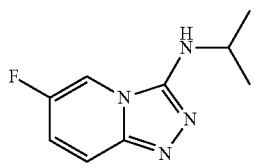

Hexachloroethane (1.77 g, 7.75 mmol) was added portionwise to a solution of Intermediate 8a 822 mg, 3.87 mmol), triphenylphosphine (2.03 g, 7.75 mmol) and triethylamine (2.2 mL, 15.49 mmol) in dry THF (15 mL) at RT and stirred for 16 h. The resulting precipitate was filtered off and the filtrate evaporated. The residue was purified by SCX-2, eluting with MeOH followed by 2M NH$_3$ in MeOH, to give the title compound as a buff-coloured foam (618 mg, 82%). LCMS (Method 1): Rt 1.55 min, m/z 195 [MH$^+$].

c. (6-Fluoro-[1,2,4]triazolo[4,3-a]pyridin-3-yl)-isopropyl-carbamic acid tert-butyl ester (Intermediate 8c).

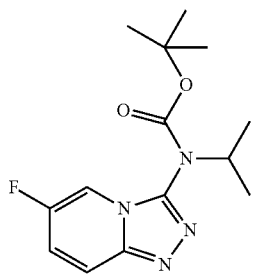 [SMILES: CC(C)N(C(=O)OC(C)(C)C)c1nnc2ccc(F)cn12]

Di-tert-butyl dicarbonate (472 mg, 2.16 mmol) in dry DCM (1 mL) was added to a solution of Intermediate 8b (168 mg, 0.86 mmol) in DCM (2 mL). 4-(1-pyrrolidinyl)pyridine (ca. 5 mg) was then added at RT and stirred for 5 h. The solvent was evaporated and the residue purified by SCX-2, eluting with MeOH then 2M NH$_3$ in MeOH, affording a dark coloured foam. Further purification by FCC, using 0-10% [2M NH$_3$ in MeOH] in DCM, afforded the title compound (112 mg). LCMS (Method 4): Rt 2.90 min, m/z 295 [MH$^+$]/ 589 [2MH$^+$]

d. [6-((1S,4R)-4-Amino-1,2,3,4-tetrahydro-naphthalen-1-yloxy-[1,2,4]triazolo[4,3-a]pyridin-3-yl]-isopropyl-carbamic acid tert-butyl ester (Intermediate 8d).

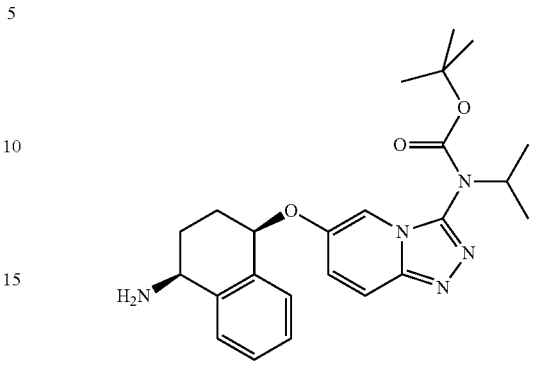

Sodium hydride (60% in mineral oil, 45 mg, 1.14 mmol) was added portionwise to a solution of Intermediate A (62 mg, 0.38 mmol) in dry DMF (1 mL) at RT and stirred for 15 min. Intermediate 8c (112 mg, 0.38 mmol) was added and the mixture heated at 60° C. for 4 h. After cooling, the mixture was partitioned between water (10 mL) and EtOAc (3×10 mL) and the combined organic extracts washed with brine (2×15 mL), dried (Na$_2$SO$_4$) and evaporated. The residue was purified by SCX-2, eluting with MeOH then 2M NH$_3$ in MeOH, affording a dark gum. Further purification by FCC, using 0-10% [2M NH$_3$ in MeOH] in DCM, afforded the title compound (75 mg, 45%). LCMS (Method 1): Rt 2.20 min, m/z 438 [MH$^+$].

e. (6-{(1S,4R)-4-[3-(5-tert-Butyl-2-p-tolyl-2H-pyrazol-3-yl)-ureido]-1,2,3,4-tetrahydro-naphthalen-1-yloxy}-[1,2,4]triazolo[4,3-a]pyridin-3-yl)-isopropyl-carbamic acid tert-butyl ester (Intermediate 8e).

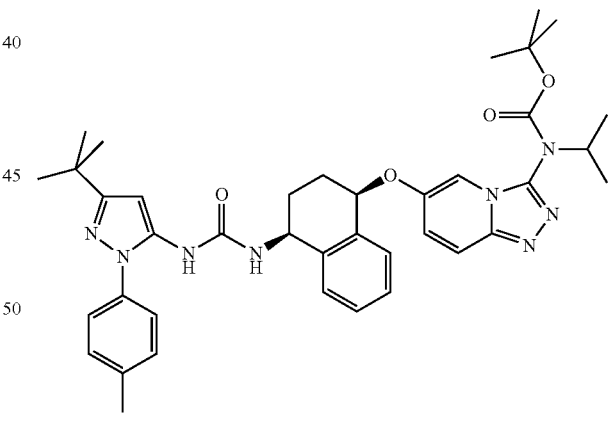

The title compound was prepared starting from Intermediate 8d and [5-tert-butyl-2-p-tolyl-2H-pyrazol-3-yl]-carbamic acid 2,2,2-trichloro-ethyl ester (Synthetic Communications, 2009, 39, 3999-4009, which is incorporated herein by reference in its entirety) by using an analogous procedure to that described in Example 1 step d. LCMS (Method 4): Rt 3.98 min, m/z 693 [MH$^+$].

f. 1-(5-tert-Butyl-2-p-tolyl-2H-pyrazol-3-yl)-3-[(1S,4R)-4-(3-isopropylamino-[1,2,4]triazolo[4,3-a]pyridin-6-yloxy)-1,2,3,4-tetrahydro-naphthalen-1-yl]-urea (Example 8).

HCl (4.0 M in dioxane; 1 mL) was added to a solution of Intermediate 8e (110 mg, 0.16 mmol) in MeOH (1 mL) at RT and stirred for 5 h. The solution was loaded on to a SCX-2 cartridge, eluting with MeOH then 2M $NH_3$ in MeOH, to afford a dark gum. Further purification by HPLC (eluting with 50-90% MeCN in $H_2O$ (0.1% NH3)) gave the title compound as a colourless powder after freeze drying (10 mg, 11%). LCMS (Method 5): Rt 4.15 min, m/z 593 [MH+]. $^1$H NMR (400 MHz, $CDCl_3$): 1.21-1.27 (15H, m), 1.87 (1H, m), 2.00 (2H, m), 2.10 (1H, m), 2.31 (3H, s), 3.85 (1H, br s), 3.94 (1H, m), 5.02 (1H, m), 5.11 (1H, t, J 4.13), 5.59 (1H, d), 6.24 (1H, s), 6.54 (1H, s), 6.84 (1H, dd, J 9.93, 2.05), 7.14 (3H, d, J 8.13), 7.20-7.26 (3H, m), 7.30-7.34 (3H, m).

Example 9

1-(5-tert-Butyl-2-p-tolyl-2H-pyrazol-3-yl)-3-[(1S,4R)-4-(6-cyano-pyridin-3-yloxy)-1,2,3,4-tetrahydro-naphthalen-1-yl]-urea

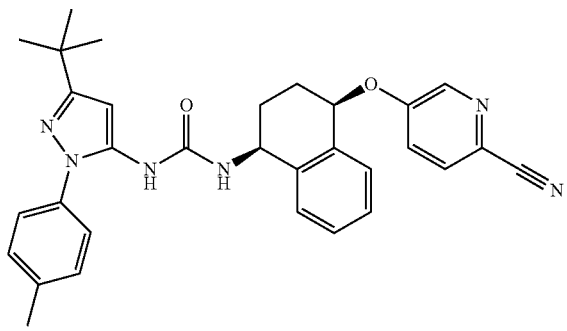 [SMILES: Cc1ccc(-n2nc(C(C)(C)C)cc2NC(=O)N[C@H]2CC[C@@H](Oc3ccc(C#N)nc3)c3ccccc32)cc1]

a. 5-((1R,4S)-4-Amino-1,2,3,4-tetrahydro-naphthalen-1-yloxy)-pyridine-2-carbonitrile (Intermediate 9a).

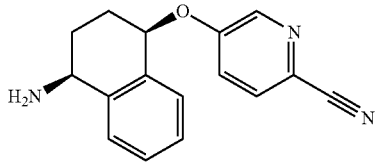 [SMILES: N#Cc1ccc(O[C@@H]2CC[C@H](N)c3ccccc32)cn1]

Intermediate A (300 mg, 1.84 mmol) was added to an ice cold stirred suspension of sodium hydride (60% in mineral oil, 221 mg, 5.52 mmol) in DMF (15 mL) and stirred for 15 min. 2-Cyano-5-fluoropyridine (224 mg, 1.84 mmol) was added and the reaction warmed to RT. After 90 min, the reaction was quenched by dropwise addition of water and the mixture partitioned between EtOAc (75 mL) and water (150 mL). The aqueous layer was then extracted with EtOAc (3×). The combined organic layers were washed with brine, dried ($MgSO_4$), filtered and evaporated in vacuo. The residue was purified by FCC, using 0-5% [2M $NH_3$ in MeOH] in DCM, to give the title compound (255 mg, 0.96 mmol, 52%). LCMS (Method 4): Rt 0.28, 1.73, ink 266.1 [MH+].

b. 1-(5-tert-Butyl-2-p-tolyl-2H-pyrazol-3-yl)-3-[(1S,4R)-4-(6-cyano-pyridin-3-yloxy)-1,2,3,4-tetrahydro-naphthalen-1-yl]-urea (Example 9).

The title compound was prepared starting from Intermediate 9a and [5-tert-butyl-2-p-tolyl-2H-pyrazol-3-yl]-carbamic acid 2,2,2-trichloro-ethyl ester (Synthetic Communications, 2009, 39, 3999-4009, which is incorporated herein by reference in its entirety) using an analogous procedure to that described in Example 1 step d. LCMS (Method 5): Rt 5.25 mins, m/z 521 [MH+]. $^1$H NMR (400 MHz, $CDCl_3$): 1.29 (9H, s), 1.76-1.88 (1H, m), 2.00-2.20 (3H, m), 2.36 (3H, s), 4.94-4.98 (1H, d, J 8.8), 5.00-5.08 (1H, m), 5.38-5.42 (1H, t, J 3.6), 6.03 (1H, s), 6.22 (1H, s), 7.16-7.20 (1H, m), 7.21-7.26 (3H, m), 7.26-7.32 (3H, m), 7.34-7.38 (2H, d, J 8.3), 7.63-7.66 (1H, d, J 8.8), 8.36-8.38 (1H, d, J 2.7).

Example 10

N-(4-{(1S,4S)-4-[3-(5-tert-Butyl-2-p-tolyl-2H-pyrazol-3-yl)-ureido]-1,2,3,4-tetrahydro-naphthalen-1-yloxy}-pyridin-2-yl)-2-methoxy-acetamide

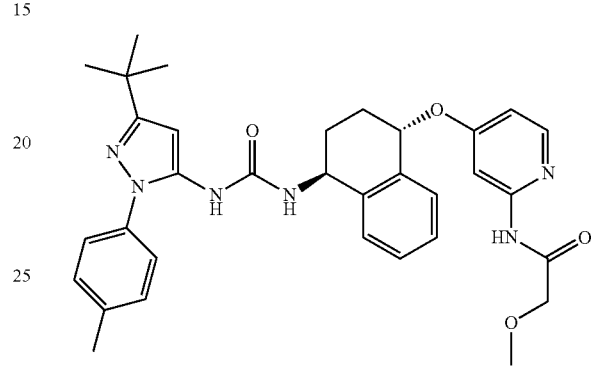

a. ((1S,4S)-4-Hydroxy-1,2,3,4-tetrahydro-naphthalen-1-yl)-carbamic acid tert-butyl ester (Intermediate 10a).

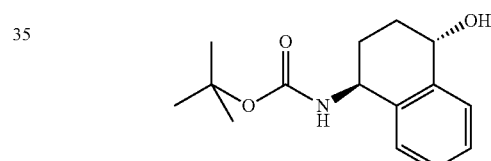

Intermediate B (1.62 g, 9.94 mmol) was suspended in acetonitrile (35 mL) then di-tert-butyl-dicarbonate (2.40 g, 11 mmol) was added. Mixture stirred at RT for 16 h. Some insoluble material was still present, so mixture filtered through Celite, washing with DCM. Filtrate was evaporated to give an off-white solid and then purified by FCC, eluting with 0-80% ethyl acetate in cyclohexane, to give the title compound as a white solid (2.38 g, 91%). $^1$H NMR (300 MHz, $d_6$-DMSO): 1.42 (9H, s), 1.54-1.70 (2H, m), 1.92-2.18 (2H, m), 4.46-4.73 (2H, m), 5.17 (1H, d, J 6.3), 7.10-7.25 (4H, m), 7.39-7.46 (1H, m).

b. [(1S,4S)-4-(2-Chloro-pyridin-4-yloxy)-1,2,3,4-tetrahydro-naphthalen-1-yl]-carbamic acid tert-butyl ester (Intermediate 10b).

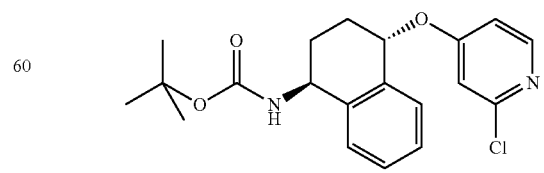

Sodium hydride (60% in mineral oil, 0.32 g, 8.00 mmol) was suspended in dry DMF (15 mL) under argon. To this was added Intermediate 10a (1.05 g, 4.00 mmol) followed by 2-chloro-4-nitropyridine (0.64 g, 4.02 mmol). The dark coloured mixture was stirred at RT under argon for 30 min. The reaction mixture was diluted with water and extracted with DCM (3×30 mL). The combined organic layers were washed with brine, dried (Na$_2$SO$_4$), filtered, concentrated in vacuo. Purification by FCC, eluting with 0-70% ethyl acetate in cyclohexane, gave the title compound as a white foam (1.43 g, 95%). LCMS (Method 3): Rt 4.22 min, m/z 373.1 [MH$^-$].

c. {(1S,4S)-4-[2-(2-Methoxy-acetylamino)-pyridin-4-yloxy]-1,2,3,4-tetrahydro-naphthalen-1-yl}-carbamic acid tert-butyl ester (Intermediate 10c).

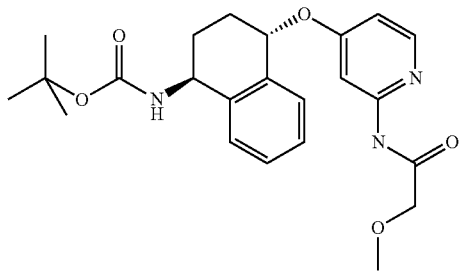 [SMILES: COCC(=O)Nc1cc(O[C@H]2CC[C@H](NC(=O)OC(C)(C)C)c3ccccc32)ccn1]

Intermediate 10b (562 mg, 1.50 mmol), 2-methoxyacetamide (334 mg, 3.75 mmol), Xantphos (173 mg, 0.30 mmol) and potassium carbonate (518 mg, 3.75 mmol) were suspended in 1,4-dioxane (20 mL), warmed, degassed, and placed under argon. To this mixture palladium acetate (34.0 mg, 0.15 mmol) was added. The mixture was degassed and then heated at reflux for 17 h. After cooling, the mixture was filtered through Celite, washing with DCM, and evaporated to a yellow gum. Purification by FCC, eluting with 0-100% ethyl acetate in cyclohexane, gave the title compound as a white foam (281 mg, 44%). LCMS (Method 3): Rt 3.27 min, m/z 450.2 [MNa$^+$].

d. N-[4-((1S,4S)-4-Amino-1,2,3,4-tetrahydro-naphthalen-1-yl oxy)-pyridin-2-yl]-2-methoxy-acetamide (Intermediate 10d).

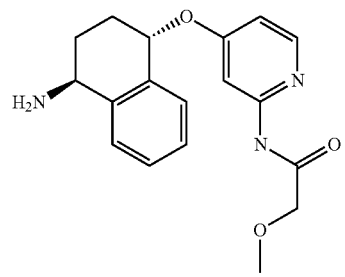

To a solution of Intermediate 10c (272 mg, 0.64 mmol) in DCM (6 mL) was added TFA (2 mL), and the mixture stirred at RT for 30 min. The mixture was concentrated in vacuo. The residue was purified on an Isolute SCX-2 cartridge, eluting with MeOH then 0.4-1M NH$_3$ in MeOH, to give the title compound as a colourless gum (208 mg, 100%). LCMS (Method 3): Rt 0.44 min, in/z 350.2 [MNa$^+$].

e. N-(4-{(1S,4S)-4-[3-(5-tert-Butyl-2-p-tolyl-2H-pyrazol-3-yl)-ureido]-1,2,3,4-tetrahydro-naphthalen-1-yloxy}-pyridin-2-yl)-2-methoxy-acetamide (Example 10).

To a solution of Intermediate 10d (204 mg, 0.62 mmol) and DIPEA (0.127 mL, 0.80 mmol) in 1,4-dioxane (6 mL), (5-tert-butyl-2-p-tolyl-2H-pyrazol-3-yl)-carbamic acid 2,2,2-trichloro-ethyl ester (Synthetic Communications, 2009, 39, 3999-4009, which is incorporated herein by reference in its entirety; 315 mg, 0.78 mmol) was added. The mixture was heated at 80° C. under argon for 17 h, and then evaporated to dryness. The residue was purified by FCC, eluting with 0-100% ethyl acetate in cyclohexane, to give the slightly impure product (0.262 g). Further purification by HPLC (Method 6) gave the title compound as a white solid (102 mg, 28%). LCMS (Method 5): Rt 4.51 min, m/z 583 [MH$^+$]. $^1$H NMR (400 MHz, d$_6$-DMSO): 1.26 (9H, s), 1.69-1.81 (1H, m), 1.90-2.24 (3H, m), 2.36 (3H, s), 3.36 (3H, s), 4.05 (2H, s), 4.86-4.94 (1H, m), 5.62-5.67 (1H, m), 6.32 (1H, s), 6.91 (1H, dd, J 2.5, 5.9), 7.03 (1H, d, J 8.4), 7.26-7.37 (8H, m), 7.60 (1H, br d, J 2.0), 8.01 (1H, s), 8.16 (1H, d, J 5.7), 9.90 (1H, s).

Example 11

1-(5-tert-Butyl-2-p-tolyl-2H-pyrazol-3-yl)-3-{(1S,4R)-4-[1-(2-hydroxy-ethyl)-1H-indazol-6-yloxy]-1,2,3,4-tetrahydro-naphthalen-1-yl}-urea

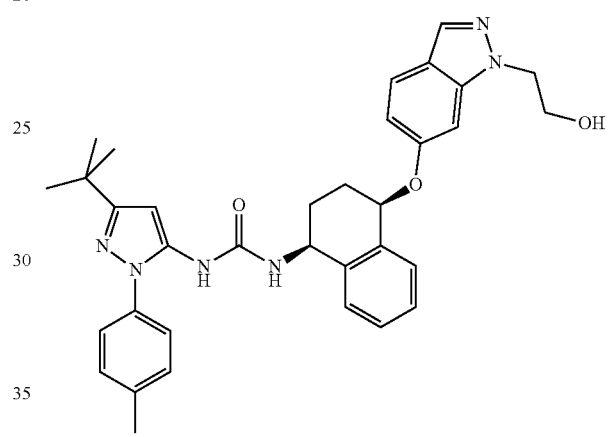

a. 6-Fluoro-1-[2-(tetrahydro-pyran-2-yloxy)-ethyl]-1H-indazole (Intermediate 11a).

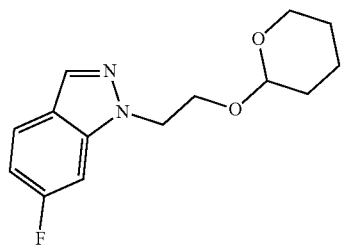 [SMILES: Fc1ccc2cnn(CCOC3CCCCO3)c2c1]

A mixture of 6-fluoro-1H-indazole (2.0 g, 14.7 mmol), and 2-(2-bromo-ethoxy)-tetrahydro-pyran (3.38 g, 16.2 mmol) in DMF (25 mL) was treated with caesium carbonate (6.1 g, 18.7 mmol) and stirred at RT for 18 h. The solvent volume was reduced in vacuo, and the residue partitioned between EtOAc (100 mL) and water (100 mL). The aqueous layer was extracted into EtOAc (3×). The combined organic layers were washed with saturated aqueous sodium chloride solution, dried (MgSO$_4$) and evaporated in vacuo. The residue was purified by FCC, using 0-50% cyclohexane in EtOAc, to afford the title product and a yellow oil. LCMS (Method 1): Rt 3.42 min, m/z 181 [MH$^+$] (M-THP). $^1$H NMR (300 MHz; CDCl$_3$) 1.52-1.56 (6H, m), 3.39-3.49 (1H, m), 3.57-3.68 (1H, m), 3.89-3.91 (1H, m), 4.19-4.21 (1H, m), 4.56-4.57 (3H, m), 6.88 (1H, td, J 9.15 and 2.26), 7.30 (1H, m), 7.62 (1H, m), 8.04 (1H, s).

b. 2-[6-((1R,4S)-4-Amino-1,2,3,4-tetrahydro-naphthalen-1-yloxy)-indazol-1-yl]-ethanol (Intermediate 11b).

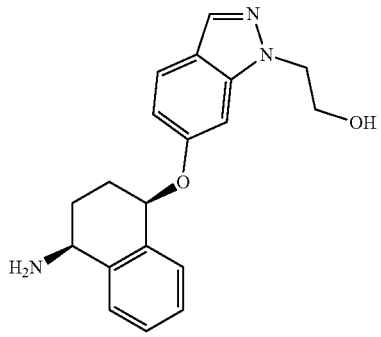 [SMILES: N[C@H]1CC[C@@H](Oc2ccc3cnn(CCO)c3c2)c2ccccc21]

Intermediate A (212 mg, 1.3 mmol) was added portionwise to a suspension of sodium hydride (60% in mineral oil, 120 mg, 3.0 mmol) in DMF (3 mL) at RT and stirred for 20 min. A solution of Intermediate 11a (264.3 mg, 1.0 mmol) in DMF (1 mL) was then added dropwise and the resulting mixture stirred at 60° C. for 2.5 h. After cooling, the mixture was diluted with EtOAc (50 mL) and poured onto ice water. The organic layer was washed with saturated aqueous sodium chloride solution, dried (MgSO$_4$), filtered and concentrated in vacuo. The residue was loaded on to a SCX-2 cartridge, eluting with MeOH then 2M NH$_3$ in MeOH. Further purification by FCC, using 0-10% [2M NH$_3$ in MeOH] in DCM to give the title compound as a brown oil. LCMS (Method 1): Rt 1.80 min, m/z 323 [MH$^+$].

c. 1-(5-tert-Butyl-2-p-tolyl-2H-pyrazol-3-yl)-3-{(1S,4R)-4-[1-(2-hydroxy-ethyl)-1H-indazol-6-yloxy]-1,2,3,4-tetrahydro-naphthalen-1-yl}-urea (Example 11).

The title compound was prepared starting from Intermediate 11b and (5-tert-butyl-2-p-tolyl-2H-pyrazol-3-yl)-carbamic acid 2,2,2-trichloro-ethyl ester (Synthetic Communications, 2009, 39, 3999-4009, which is incorporated herein by reference in its entirety; 315 mg, 0.78 mmol) by using an analogous procedure to that described in Example 1 step d. LCMS (Method 5): Rt 4.99 min, m/z 578 [MH$^+$]. $^1$H NMR (400 MHz, d$_6$-DMSO): 1.22 (9H, s), 1.81-1.92 (2H, m), 2.02-2.06 (2H, m), 2.31 (3H, s), 3.74-3.75 (2H, m), 4.34 (2H, t, J 5.75), 4.78 (2H, m), 5.53 (1H, t, J 4.8), 6.28 (1H, s), 6.74 (1H, dd, J 8.75 and 2.03), 7.08 (1H, d, J 8.53), 7.27-7.28 (9H, m), 7.57 (1H, d, J 8.75), 7.89 (1H, s), 7.96 (1H, s).

Example 12

1-(5-tert-Butyl-2-p-tolyl-2H-pyrazol-3-yl)-3-[(1S,4R)-4-((R)-3-pyrrolidin-2-yl-[1,2,4]triazolo[4,3-a]pyridin-6-yloxy)-1,2,3,4-tetrahydro-naphthalen-1-yl]-urea

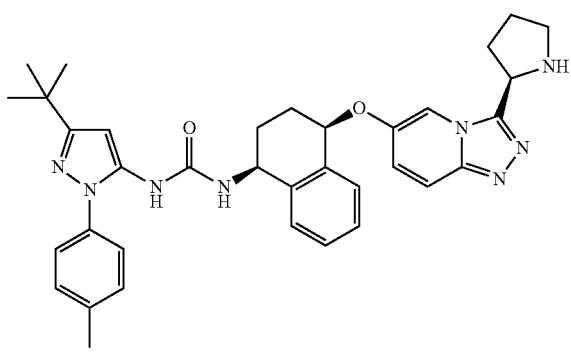 [SMILES: Cc1ccc(-n2nc(C(C)(C)C)cc2NC(=O)N[C@H]2CC[C@@H](Oc3ccc4nnc([C@H]5CCCN5)n4c3)c3ccccc32)cc1]

The title compound was prepared starting from N-tert-butylcarbonyl-D-proline using analogous procedures to those described in Example 6. LCMS (Method 5): Rt 3.69 min, m/z 605 [MH$^+$]; $^1$H NMR (400 MHz, CDCl$_3$): 1.33 (9H, s), 1.86-2.39 (8H, m), 2.36 (3H, s), 2.96-3.08 (2H, m), 4.51 (1H, t, J 7.4 Hz), 5.04-5.10 (1H, m), 5.24 (1H, t, J 4.0 Hz), 5.52 (1H, d, J 8.1 Hz), 6.30 (1H, s), 6.57 (1H, br s), 7.03 (1H, dd, J 2.2, 10.0 Hz), 7.20 (2H, d, J 7.9 Hz), 7.23-7.34 (4H, m), 7.38 (2H, d, J 7.4 Hz), 7.56 (1H, d, J 9.8 Hz), 7.92 (1H, m).

Example 13

N-(4-{(1R,4S)-4-[3-(5-tert-Butyl-2-p-tolyl-2H-pyrazol-3-yl)-ureido]-1,2,3,4-tetrahydro-naphthalen-1-yloxy}-pyridin-2-yl)-2-methoxy-acetamide

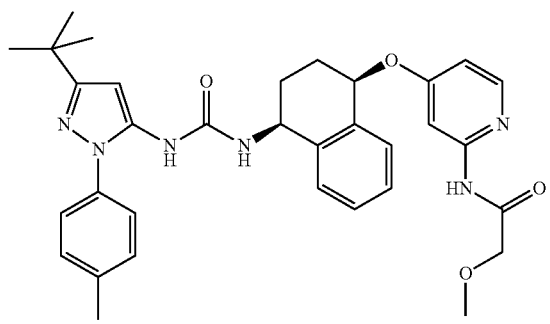 [SMILES: COCC(=O)Nc1cc(O[C@@H]2CC[C@H](NC(=O)Nc3cc(C(C)(C)C)nn3-c3ccc(C)cc3)c3ccccc32)ccn1]

The title compound was prepared starting from Intermediate A by using analogous procedures to those described in Example 10. LCMS (Method 5): Rt 4.54 min, m/z 583 [MH$^+$]; $^1$H NMR (400 MHz, d$_6$-DMSO): 1.21 (9H, s), 1.66-2.11 (4H, m), 2.31 (3H, s), 3.31 (3H, s), 4.0 (2H, s), 4.72-4.81 (1H, m), 5.49-5.58 (1H, m), 6.26 (1H, s), 6.86 (1H, dd, J 5.8, 2.2 Hz), 7.07 (1H, d, J 8.5 Hz), 7.19-7.33 (8H, m), 7.68 (1H, d, J 2.2 Hz), 7.96 (1H, s), 8.12 (1H, d, J 5.8 Hz), 9.86 (1H, br s).

Example 14

1-(5-tert-Butyl-2-p-tolyl-2H-pyrazol-3-yl)-3-{(1S,4R)-4-[3-(4-methyl-piperazin-1-ylmethyl)-[1,2,4]triazolo[4,3-a]pyridin-6-yloxy]-1,2,3,4-tetrahydro-naphthalen-1-yl}-urea formate salt

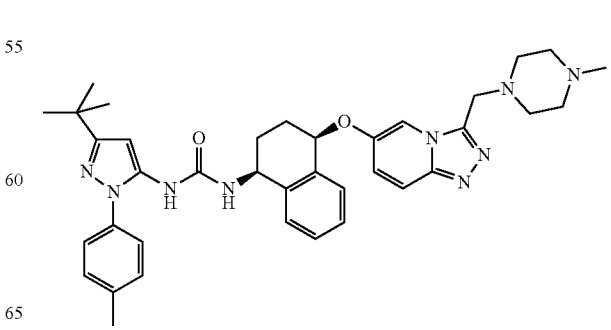

a. (4-Methyl-piperazin-1-yl)-acetic acid N'-(5-fluoro-pyridin-2-yl)-hydrazide (Intermediate 14a).

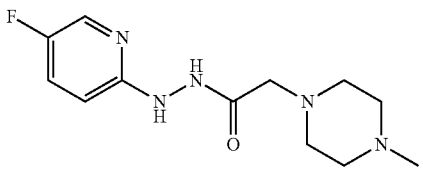 [SMILES: CN1CCN(CC(=O)NNc2ccc(F)cn2)CC1]

5-Fluoro-2-hydrazinyl-pyridine (for reference procedure see WO 2010/022076, which is incorporated herein by reference in its entirety; 500 mg, 3.94 mmol) and 4-methyl-1-piperazin-1-yl acetic acid (684 mg, 4.33 mmol) were dissolved in DMF (10.0 mL). EDC (831 mg, 4.33 mmol) and HOBt (53.0 mg, 0.39 mmol) were added and the reaction stirred for 18 h. The mixture was loaded onto an SCX-2 cartridge, which was washed with MeOH then eluted with 2M $NH_3$ in MeOH. The resulting residue was purified by FCC, using 4-20% [2M $NH_3$ in MeOH] in DCM, to give the title compound (570 mg, 54%). $^1$H NMR (400 MHz, $CDCl_3$): 2.32 (3H, s), 2.47-2.56 (4H, br s), 2.62-2.71 (4H, br s), 3.18 (2H, s), 6.56-6.61 (1H, br s), 6.60-6.66 (1H, dd, J 8.9, 3.4 Hz), 7.26-7.32 (1H, m), 8.02-8.05 (1H, d, J 2.9 Hz), 8.93 (1H, br s).

b. 6-Fluoro-3-(4-methyl-piperazin-1-ylmethyl)-[1,2,4]triazolo[4,3-a]pyridine (Intermediate 14b).

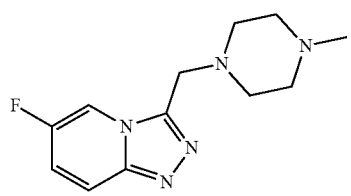 [SMILES: CN1CCN(Cc2nnc3ccc(F)cn23)CC1]

Intermediate 14a (570 mg, 2.13 mmol) was dissolved in THF (20.0 mL) and cooled in an ice/water bath. Triphenylphosphine (1.12 g, 4.27 mmol) was added followed by triethylamine (1.19 mL, 8.54 mmol) and hexachloroethane (1.01 g, 4.27 mmol). The reaction was stirred for 18 h. The mixture was loaded onto an SCX-2 cartridge, washing with MeOH and eluting with 2M $NH_3$ in MeOH. The residue was purified by FCC, using 0-10% [2M $NH_3$ in MeOH] in DCM, to give the title compound (470 mg, 1.89 mmol, 89%). LCMS (Method 1): Rt 0.36 min, m/z 250 [$MH^+$].

c. (1S,4R)-4-[3-(4-Methyl-piperazin-1-ylmethyl)-[1,2,4]triazolo[4,3-a]pyridin-6-yloxy]-1,2,3,4-tetrahydro-naphthalen-1-ylamine (Intermediate 14c).

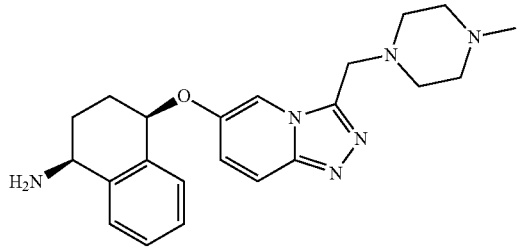 [SMILES: CN1CCN(Cc2nnc3ccc(O[C@@H]4CC[C@H](N)c5ccccc54)cn23)CC1]

Intermediate A (200 mg, 1.22 mmol) was added to a suspension of sodium hydride (60% in mineral oil, 146 mg, 3.66 mmol) in DMF (6.0 mL) and stirred for 20 min. Intermediate 14b (305 mg, 1.22 mmol) was added and the reaction heated to 60° C. for 90 min. The mixture was cooled and quenched by dropwise addition of MeOH. The solution was diluted with MeOH and loaded onto an SCX-2 cartridge, washing with MeOH and eluting with 2M $NH_3$ in MeOH. The residue was purified by FCC, using 0-10% [2M $NH_3$ in MeOH] in DCM to give the title compound (240 mg, 0.61 mmol, 50%). LCMS (Method 4): Rt 0.29 min, m/z 393 [$MH^+$].

d. 1-(5-tert-Butyl-2-p-tolyl-2H-pyrazol-3-yl)-3-{(1S,4R)-4-[3-(4-methyl-piperazin-1-ylmethyl)-[1,2,4]triazolo[4,3-a]pyridin-6-yloxy]-1,2,3,4-tetrahydro-naphthalen-1-yl}-urea formate salt (Example 14).

Intermediate 14c (120 mg, 0.31 mmol) was dissolved in 1,4-dioxane (2.0 mL) and [5-tert-butyl-2-p-tolyl-2H-pyrazol-3-yl]-carbamic acid 2,2,2-trichloro-ethyl ester (Synthetic Communications, 2009, 39, 3999-4009, which is incorporated herein by reference in its entirety; 124 mg, 0.31 mmol) and diisopropylethylamine (106 μL, 0.61 mmol) were added. The reaction was heated to 60° C. for 20 h. After cooling, the mixture was partitioned between EtOAc (50 mL) and water (50 mL), and extracted into EtOAc (3×). The combined organic layers were washed with brine, dried ($MgSO_4$) and evaporated in vacuo. The residue was purified by FCC, using 0-10% [2M $NH_3$ in MeOH] in DCM, then further purified by HPLC (C18 X-select column, 20-70% MeCN in $H_2O$, 0.1% formic acid) to give the title compound as the formic acid salt (103 mg, 0.16 mmol, 52%). LCMS (Method 5): Rt 3.63 min, m/z=648 [$MH^+$]. $^1$H NMR (400 MHz, $d_4$-MeOD): 1.30 (9H, s), 1.90-1.99 (1H, m), 1.99-2.07 (1H, m), 2.10-2.19 (1H, m), 2.21-2.30 (1H, m), 2.37 (3H, s), 2.38 (3H, s), 2.52-2.67 (8H, br s), 4.05-4.09 (1H, d, J 14.3 Hz), 4.11-4.15 (1H, d, J 14.3 Hz), 4.88-4.93 (1H, dd, J 8.9, 5.6 Hz), 5.41-5.44 (1H, t, J 4.3 Hz), 6.33 (1H, s), 7.22-7.36 (11H, m), 7.63-7.67 (1H, d, J 10.0 Hz), 8.21-8.22 (1H, d, J 1.9 Hz), 8.44-8.45 (0.25H, s).

Example 15

1-(5-tert-Butyl-2-p-tolyl-2H-pyrazol-3-yl)-3-[(1S,4R)-4-(3-morpholin-4-ylmethyl-[1,2,4]triazolo[4,3-a]pyridin-6-yloxy)-1,2,3,4-tetrahydro-naphthalen-1-yl]-urea formate salt

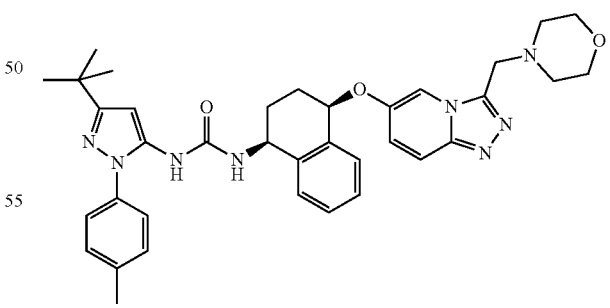

The title compound was prepared starting from 1-morpholinoacetic acid by using analogous procedures to those described for Example 14. LCMS (Method 5): Rt 4.02 min, m/z=635 [$MH^+$]. $^1$H NMR (400 MHz, $d_4$-MeOD): 1.30 (9H, s), 1.90-1.97 (1H, m), 1.97-2.07 (1H, m), 2.10-2.19 (1H, m), 2.23-2.31 (1H, m), 2.38 (3H, s), 2.42-2.53 (4H, m), 3.60-3.64 (4H, m), 4.01-4.05 (1H, d, J 14.3 Hz), 4.08-4.12 (1H, d, J 14.3

Hz), 4.88-4.93 (1H, dd, J 9.0, 5.6 Hz), 5.42-5.45 (1H, t, J 4.3 Hz), 6.33 (1H, s), 7.22-7.36 (11H, m), 7.63-7.66 (1H, d, J 10.0 Hz), 8.24-8.26 (1H, d, J 2.0 Hz), 8.48-8.52 (0.25H, s).

Example 16

1-(5-tert-Butyl-2-p-tolyl-2H-pyrazol-3-yl)-3-[(1S,4R)-4-(3-pyrrolidin-1-ylmethyl-[1,2,4]triazolo[4,3-a]pyridin-6-yloxy)-1,2,3,4-tetrahydro-naphthalen-1-yl]-urea

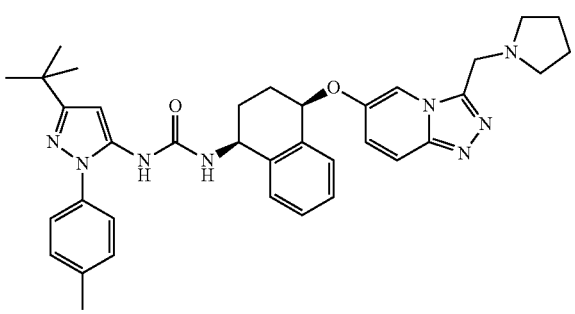 [SMILES: Cc1ccc(-n2nc(C(C)(C)C)cc2NC(=O)N[C@H]2CC[C@@H](Oc3ccc4nnc(CN5CCCC5)n4c3)c3ccccc32)cc1]

The title compound was prepared starting from 1-pyrrolidin-1-yl-acetic acid hydrochloride (for reference procedure see U.S. Pat. No. 5,756,533, which is incorporated herein by reference in its entirety) by using analogous procedures to those described for Example 14. LCMS (Method 5): Rt 3.72 min, m/z=619 [MH⁺]. ¹H NMR (400 MHz, d₄-MeOD): 1.30 (9H, s), 1.80-1.85 (4H, m), 1.90-2.05 (2H, m), 2.07-2.15 (1H, m), 2.21-2.30 (1H, m), 2.38 (3H, s), 2.65-2.70 (4H, m), 4.21-4.26 (1H, d, J 14.3 Hz), 4.26-4.31 (1H, d, J 14.3 Hz), 4.87-4.92 (1H, dd, J 8.9, 5.6 Hz), 5.40-5.43 (1H, t, J 4.3 Hz), 6.33 (1H, s), 7.21-7.36 (11H, m), 7.63-7.67 (1H, d, J 9.9 Hz), 8.23-8.24 (1H, d, J 1.9 Hz), 8.29-8.31 (0.3H, br s).

Example 17

1-(5-tert-Butyl-2-p-tolyl-2H-pyrazol-3-yl)-3-{(1S,4R)-4-[6-(morpholine-4-carbonyl)-pyridin-3-yloxy]-1,2,3,4-tetrahydro-naphthalen-1-yl}-urea

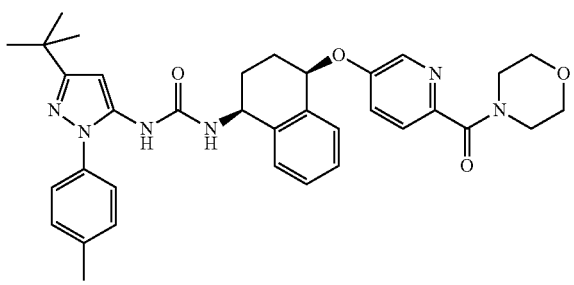 [SMILES: Cc1ccc(-n2nc(C(C)(C)C)cc2NC(=O)N[C@H]2CC[C@@H](Oc3ccc(C(=O)N4CCOCC4)nc3)c3ccccc32)cc1]

a. (5-Fluoro-pyridin-2-yl)-morpholin-4-yl-methanone (Intermediate 17a).

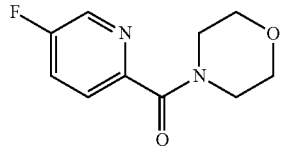 [SMILES: O=C(c1ccc(F)cn1)N1CCOCC1]

2-Cyano-5-fluoropyridine (1.00 g, 8.19 mmol) was dissolved in hydrochloric acid (37% aqueous, 1.0 mL) and heated to 60° C. for 18 h and then evaporated in vacuo. The residue was suspended in DMF (40.0 mL) and EDC (1.89 g, 9.83 mmol), HOBt (111 mg, 0.82 mmol), morpholine (787 µL, 9.00 mmol) and triethylamine (1.25 mL, 9.00 mmol) were added and the reaction stirred for 18 h. The reaction was partitioned between water (200 mL) and EtOAc (100 mL), and extracted into EtOAc (3×). The combined organic layers were washed with brine, dried (MgSO₄) and evaporated in vacuo. The residue was purified by FCC, using 0-8% [2M NH₃ in MeOH] in DCM, to give the title compound (350 mg), contaminated with a single impurity (~10% by NMR integration). The product was used in the next step without further purification. LCMS (Method 1): Rt 1.88 min, m/z 211 [MH⁺].

b. [5-((1R,4S)-4-Amino-1,2,3,4-tetrahydro-naphthalen-1-yloxy)-pyridin-2-yl]-morpholin-4-yl-methanone (Intermediate 17b).

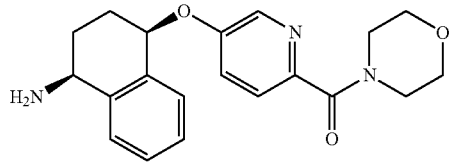 [SMILES: N[C@H]1CC[C@@H](Oc2ccc(C(=O)N3CCOCC3)nc2)c2ccccc21]

Intermediate A (150 mg, 0.92 mmol) was added to a suspension of sodium hydride (60% in mineral oil, 147 mg, 3.66 mmol) in DMF (3.0 mL). The reaction was stirred for 20 min, then Intermediate 17a (280 mg) in DMF (3.0 mL) was added and the reaction heated to 60° C. for 90 min. The mixture was cooled and quenched by dropwise addition of MeOH. The solution was diluted with MeOH and loaded onto an SCX-2 cartridge, which was washed sequentially with MeOH and 2M NH₃ in MeOH. The basic fractions were evaporated in vacuo then purified by FCC, using 0-10% [2M NH₃ in MeOH] in DCM, to give the title compound (234 mg, 0.66 mmol, 72%). LCMS (Method 4): Rt 1.60 min, m/z 354 [MH⁺].

c. 1-(5-tert-Butyl-2-p-tolyl-2H-pyrazol-3-yl)-3-{(1S,4R)-4-[6-(morpholine-4-carbonyl)-pyridin-3-yloxy]-1,2,3,4-tetrahydro-naphthalen-1-yl}-urea (Example 17).

Intermediate 17b (234 mg, 0.66 mmol) was dissolved in 1,4-dioxane (7.0 mL) and [5-tert-butyl-2-p-tolyl-2H-pyrazol-3-yl]-carbamic acid 2,2,2-trichloro-ethyl ester (Synthetic Communications, 2009, 39, 3999-4009, which is incorporated herein by reference in its entirety; 268 mg, 0.66 mmol) and diisopropylethylamine (229 µL, 1.32 mmol) were added. The reaction mixture was heated to 60° C. for 20 h, then cooled, partitioned between EtOAc (50 mL) and water (50 mL), and extracted into EtOAc (3×). The combined organic layers were washed with brine, dried (MgSO₄) and evaporated in vacuo. The residue was purified by FCC, using 0-10% [2M NH₃ in MeOH] in DCM, to give the title compound (120 mg, 0.20 mmol, 30%). LCMS (Method 5): Rt 4.76 min, m/z=609 [MH+]. $^1$H NMR (400 MHz, d$_4$-MeOD): 1.30 (9H, s), 1.85-2.05 (2H, m), 2.05-2.18 (2H, m), 2.38 (3H, s), 3.57-3.76 (8H, br m), 4.86-4.92 (1H, dd, J 8.6, 5.5 Hz), 5.54-5.57 (1H, t, J 4.3 Hz), 6.33 (1H, s), 7.20-7.34 (9H, m), 7.58-7.65 (2H, m), 8.24-8.26 (1H, dd, J 2.4, 0.8 Hz).

Example 18

1-(5-tert-Butyl-2-p-tolyl-2H-pyrazol-3-yl)-3-{(1S,4R)-4-[3-(4-morpholin-4-ylmethyl-phenyl)-[1,2,4]triazolo[4,3-a]pyridin-6-yloxy]-1,2,3,4-tetrahydro-naphthalen-1-yl]-urea

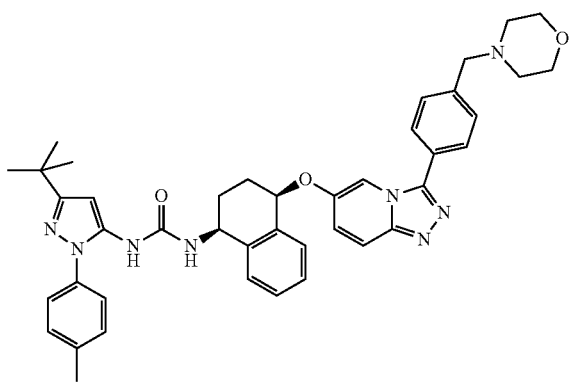 [SMILES: Cc1ccc(-n2nc(C(C)(C)C)cc2NC(=O)N[C@H]2CC[C@@H](Oc3ccc4nnc(-c5ccc(CN6CCOCC6)cc5)n4c3)c3ccccc32)cc1]

a. 4-Morpholin-4-ylmethyl-benzoic acid N'-(5-fluoro-pyridin-2-yl)-hydrazide (Intermediate 18a).

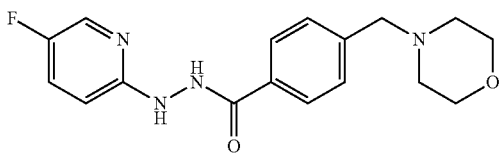 [SMILES: O=C(NNc1ccc(F)cn1)c1ccc(CN2CCOCC2)cc1]

HOBt (53 mg, 0.39 mmol) was added to (5-fluoro-pyridin-2-yl)-hydrazine (for reference procedure see WO 2010/022076, which is incorporated herein by reference in its entirety; 500 mg, 3.94 mmol), 4-morpholin-4-ylmethyl-benzoic acid (1.04 g, 4.72 mmol) and EDC (907 mg, 4.72 mmol) in DCM (5.0 mL) and the reaction stirred for 4 h. The reaction was partitioned between DCM (75 mL) and saturated aqueous NaHCO$_3$ (75 mL) and the aqueous layer extracted with DCM (3×). The combined organic layers were washed with brine, dried (MgSO$_4$), filtered and evaporated in vacuo then purified by FCC using [0.5-7.5% 2M NH$_3$ in MeOH] in DCM to give the title compound (980 mg, 2.97 mmol, 75%). LCMS (Method 4): Rt 0.27, m/z 331 [MH+].

b. 6-Fluoro-3-(4-morpholin-4-ylmethyl-phenyl)-[1,2,4]triazolo[4,3-a]pyridine (Intermediate 18b).

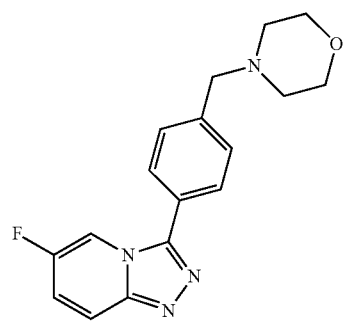 [SMILES: Fc1ccc2nnc(-c3ccc(CN4CCOCC4)cc3)n2c1]

To an ice cold solution of Intermediate 18a (980 mg, 2.97 mmol) in THF (15 mL) was added triphenylphosphine (1.56 g, 5.94 mmol), triethylamine (1.65 mL, 11.9 mmol) and hexachloroethane (1.40 g, 5.94 mmol). The reaction was stirred for 90 min then partitioned between EtOAc (75 mL) and water (75 mL) and the aqueous layer extracted with EtOAc (3×). The combined organic layers were washed with brine, dried (MgSO$_4$), filtered and evaporated in vacuo then purified by SCX-2, washing with MeOH and eluting with 2M NH$_3$ in MeOH to give the title compound (640 mg, 2.05 mmol, 69%). LCMS (Method 2): Rt 0.28, 1.32, m/z 313 [MH+].

c. 1-(5-tert-Butyl-2-p-tolyl-2H-pyrazol-3-yl)-3-{(1S,4R)-4-[3-(4-morpholin-4-ylmethyl-phenyl)-[1,2,4]triazolo[4,3-a]pyridin-6-yloxy]-1,2,3,4-tetrahydro-naphthalen-1-yl]-urea (Example 18).

The title compound was prepared starting from Intermediate 18b using analogous procedures to those described for Example 14. LCMS (Method 5): Rt 3.79 mins, m/z=711 [MH+]. $^1$H NMR (400 MHz, CDCl$_3$): 1.29 (9H, s), 1.80-1.90 (1H, m), 1.96-2.08 (2H, m), 2.16-2.24 (1H, m), 2.33 (3H, s), 2.44-2.49 (4H, t, J 4.2 Hz), 3.56 (2H, s), 3.68-3.71 (4H, t, J 4.6 Hz), 5.00-5.06 (1H, td, J 8.8, 5.2 Hz), 5.11-5.17 (2H, m), 6.22 (2H, s), 7.06-7.10 (1H, dd, J 9.9, 2.1 Hz), 7.17-7.22 (3H, m), 7.24-7.30 (3H, m), 7.33-7.36 (2H, d, J 8.4 Hz), 7.49-7.53 (2H, d, J 8.1 Hz), 8.68-7.71 (2H, d, J 8.2 Hz), 7.71 (1H, s), 7.81-7.82 (1H, d, J 1.6 Hz).

Example 19

1-(5-tert-Butyl-2-p-tolyl-2H-pyrazol-3-yl)-3-{(1S,4R)-4-[3-(3-morpholin-4-ylmethyl-phenyl)-[1,2,4]triazolo[4,3-a]pyridin-6-yloxy]-1,2,3,4-tetrahydro-naphthalen-1-yl}-urea

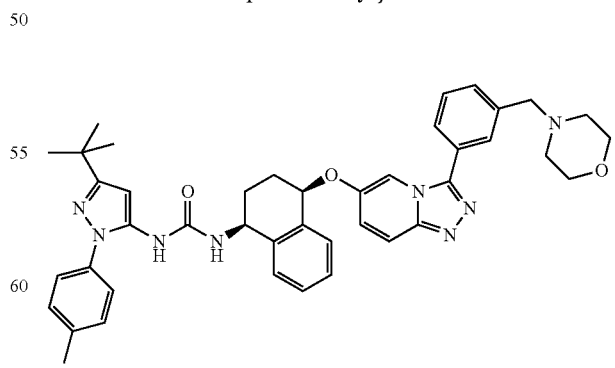

The title compound was prepared starting from 3-morpholin-4-ylmethyl-benzoic acid by using analogous procedures to those described for Example 18. LCMS (Method 5): Rt 3.81 mins, m/z 711.3 [MH⁺]; ¹H NMR (400 MHz, d₄-MeOD): 1.29 (9H, s), 1.89-2.10 (3H, m), 2.20-2.28 (1H, m), 2.37 (3H, s), 2.45-2.50 (4H, t, J 4.3 Hz), 3.61 (2H, s), 3.61-3.65 (4H, t, J 4.6 Hz), 4.84-4.88 (1H, dd, J 8.9, 5.7 Hz), 5.36-5.39 (1H, t, J 4.1 Hz), 6.31 (1H, s), 7.18-7.38 (9H, m), 7.53-7.59 (2H, m), 7.70-7.74 (1H, dt, J 6.4, 2.3 Hz), 7.72-7.75 (1H, d, J 9.9 Hz), 7.80 (1H, s), 8.02-8.04 (1H, d, J 1.7 Hz).

Example 20

1-(5-tert-Butyl-2-p-tolyl-2H-pyrazol-3-yl)-3-{(1S, 4R)-4-[3-(2-morpholin-4-ylmethyl-phenyl)-[1,2,4]triazolo[4,3-a]pyridin-6-yloxy]-1,2,3,4-tetrahydro-naphthalen-1-yl}-urea

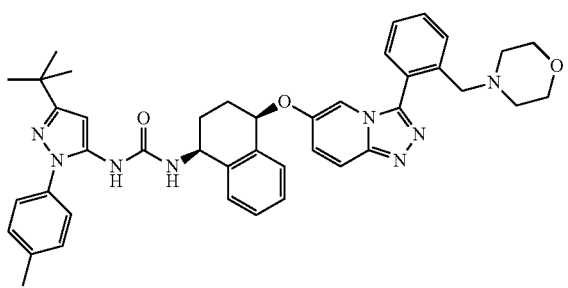 [SMILES: Cc1ccc(-n2nc(C(C)(C)C)cc2NC(=O)N[C@H]2CC[C@@H](Oc3ccc4nnc(-c5ccccc5CN5CCOCC5)n4c3)c3ccccc32)cc1]

The title compound was prepared starting from 2-morpholin-4-ylmethyl-benzoic acid by using analogous procedures to those described for Example 18. LCMS (Method 5): Rt 4.00 mins, ink 711.4 [MH⁺]; ¹H NMR (400 MHz, d₄-MeOD): 1.30 (9H, s), 1.82-2.02 (3H, m), 2.04-2.18 (5H, m), 2.38 (3H, s), 3.08-3.16 (4H, br s), 3.50-3.54 (1H, d, J 13.5 Hz), 3.54-3.58 (1H, d, J 13.5 Hz), 4.81-4.86 (1H, dd, J 8.8, 5.6 Hz), 5.29-5.33 (1H, t, J 4.0 Hz), 6.31 (1H, s), 7.17-7.35 (9H, m), 7.35-7.39 (1H, dd, J 9.9, 2.0 Hz), 7.49-7.59 (6H, m), 7.74-7.78 (1H, d, J 9.9 Hz).

Example 21

1-(5-tert-Butyl-2-p-tolyl-2H-pyrazol-3-yl)-3-[(1S, 4R)-4-(6-morpholin-4-ylmethyl-pyridin-3-yloxy)-1, 2,3,4-tetrahydro-naphthalen-1-yl]-urea

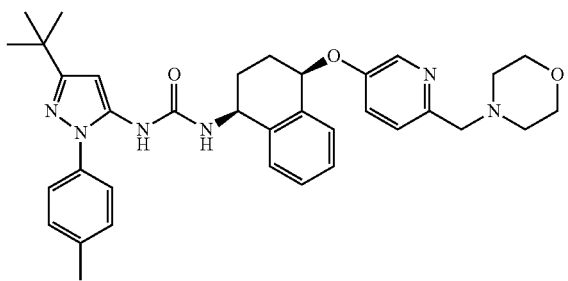 [SMILES: Cc1ccc(-n2nc(C(C)(C)C)cc2NC(=O)N[C@H]2CC[C@@H](Oc3ccc(CN4CCOCC4)nc3)c3ccccc32)cc1]

Borane dimethylsulfide complex (2M in THF, 99 µL, 0.20 mmol) was added to a solution of Example 17 (60.0 mg, 0.099 mmol) in THF (3.00 mL). The reaction stirred for 20 min then heated to 60° C. overnight. The reaction was cooled and further borane dimethylsulfide complex (2M in THF, 99 µL, 0.20 mmol) added. After stirring for 20 min at RT the reaction was heated to 60° C. overnight. The reaction was cooled and further borane dimethylsulfide complex (2M in THF, 99 µL, 0.20 mmol) added. After stirring for 20 min at RT the reaction was heated to 60° C. overnight. The reaction was cooled and quenched by dropwise addition of MeOH, then evaporated in vacuo. The residue was then partitioned between EtOAc and water. The aqueous layer was then extracted with EtOAc (3×). The combined organic layers were washed with brine, dried (MgSO₄), filtered and evaporated in vacuo. The residue was purified by HPLC (C18 X-select column, 10-60% MeCN in H₂O, 0.1% HCO₂H) to give the title compound as a white powder after freeze-drying (11 mg, 19%). LCMS (Method 5): Rt 3.78 min, m/z 595.2 [MH⁺]. ¹H NMR (400 MHz, d₄-MeOD): 1.30 (9H, s), 1.86-2.15 (4H, m), 2.38 (3H, s), 2.46 (4H, t, J 9.3), 3.57 (2H, s), 3.66 (4H, t, J 9.4), 4.89 (1H, dd, J 8.7, 5.7), 5.44 (1H, t, J 8.7), 6.33 (1H, s), 7.19-7.34 (8H, m), 7.44 (1H, d, J 8.5), 7.51 (1H, dd, J 8.7, 2.9), 8.15 (1H, d, J 2.8).

Example 22

1-(5-tert-Butyl-2-p-tolyl-2H-pyrazol-3-yl)-3-{(1S, 4R)-4-[3-(1-methyl-piperidin-4-ylmethyl)-[1,2,4]triazolo[4,3-a]pyridin-6-yloxy]-1,2,3,4-tetrahydro-naphthalen-1-yl}-urea

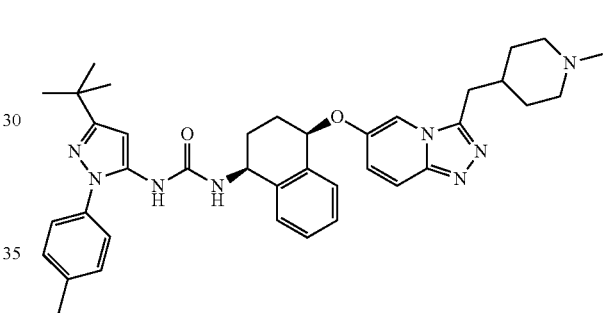

a. 4-(6-Fluoro-[1,2,4]triazolo[4,3-a]pyridin-3-ylmethyl)-piperidine-1-carboxylic acid tert-butyl ester (Intermediate 22a).

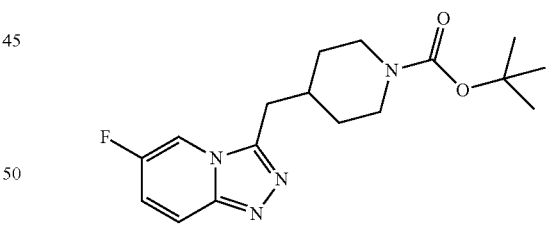

A dark brown solution of (5-fluoro-pyridin-2-yl)-hydrazine (549 mg, 4.32 mmol) and N-Boc-4-piperidine acetaldehyde (Aldrich, 982 mg, 4.32 mmol) in EtOH (10 mL) was stirred at reflux for 30 min, then cooled to 0° C., diluted with DCM (25 mL) and then (diacetoxyiodo)benzene (1.67 g, 5.18 mmol) was added portionwise over 1 min. The purple solution was stirred at RT for 30 min, then aqueous NaOH (1M, 20 mL) was added and the mixture shaken. The aqueous layer was extracted with DCM (2×20 mL), then the combined organics passed through a hydrophobic frit and concentrated in vacuo to leave an orange solid. FCC, using 3% MeOH in DCM, gave the title compound as a pale orange solid (1.53 g, 90%). LCMS (Method 3): Rt 3.15, m/z 235 [M-CO₂C₄H₉+H⁺].

b. 4-[6-((1R,4S)-4-Amino-1,2,3,4-tetrahydro-naphthalen-1-yloxy)-[1,2,4]triazolo[4,3-a]pyridin-3-ylmethyl]-piperidine-1-carboxylic acid tert-butyl ester (Intermediate 22b).

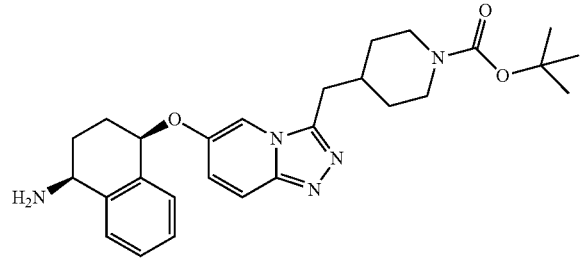 [SMILES: CC(C)(C)OC(=O)N1CCC(Cc2nnc3ccc(O[C@@H]4CC[C@H](N)c5ccccc54)cn23)CC1]

To a solution of Intermediate A (392 mg, 2.40 mmol) in dry DMF (5 mL) was added NaH (60% dispersion in mineral oil, 240 mg, 6.00 mmol) and the resulting brown suspension was stirred at RT for 45 min (CARE: gas evolution). Intermediate 22a (669 mg, 2.00 mmol) was added and the dark brown solution stirred at 60° C. for 2 h. The cooled solution was concentrated in vacuo, redissolved in MeOH (5 mL), applied to an SCX-2 cartridge (20 g) and washed with MeOH (100 mL). The product was eluted with 2M $NH_3$ in MeOH (75 mL); concentration in vacuo left a dark brown residue. FCC, using 4-9% [2M $NH_3$ in MeOH] in DCM, gave the title compound as a brown oil (421 mg, 44%). LCMS (Method 3): Rt 2.45 min, m/z 478 [$MH^+$].

c. 4-(6-{(1R,4S)-4-[3-(5-tert-Butyl-2-p-tolyl-2H-pyrazol-3-yl)-ureido]-1,2,3,4-tetrahydro-naphthalen-1-yloxy}-[1,2,4]triazolo[4,3-a]pyridin-3-ylmethyl)-piperidine-1-carboxylic acid tert-butyl ester (Intermediate 22c).

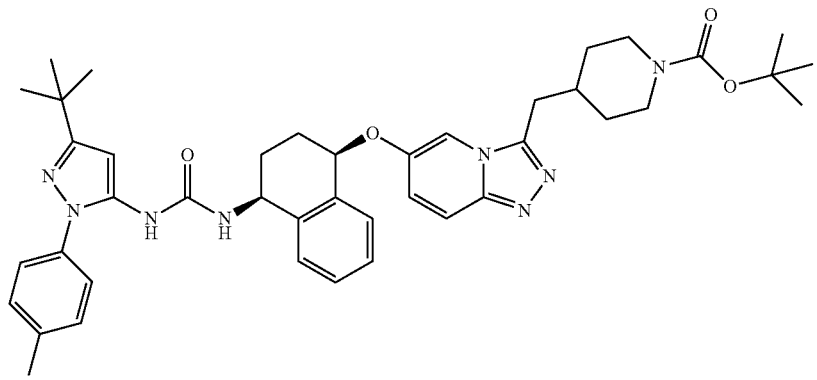 [SMILES: Cc1ccc(-n2nc(C(C)(C)C)cc2NC(=O)N[C@H]2CC[C@@H](Oc3ccc4nnc(CC5CCN(C(=O)OC(C)(C)C)CC5)n4c3)c3ccccc32)cc1]

A dark brown solution of (5-tert-butyl-2-p-tolyl-2H-pyrazol-3-yl)-carbamic acid 2,2,2-trichloro-ethyl ester (Synthetic Communications, 2009, 39, 3999-4009, which is incorporated herein by reference in its entirety; 162 mg, 0.401 mmol), Intermediate 22b (174 mg, 0.364 mmol) and DIPEA (0.079 mL, 0.455 mmol) in DMF (5 mL) was stirred at 100° C. for 3 h. The solution was cooled to RT, concentrated in vacuo, suspended in water (10 mL) and extracted with DCM (2×10 mL). The combined organics were passed through a hydrophobic frit and concentrated in vacuo to leave a brown gum. FCC, using 2-6% MeOH in DCM, gave the title compound as an off-white solid (155 mg, 58%). LCMS (Method 3): Rt 4.16 min, m/z 733 [$MH^+$].

d. 1-(5-tert-Butyl-2-p-tolyl-2H-pyrazol-3-yl)-3-[(1S,4R)-4-(3-piperidin-4-ylmethyl-[1,2,4]triazolo[4,3-a]pyridin-6-yloxy)-1,2,3,4-tetrahydro-naphthalen-1-yl]-urea (Intermediate 22d.

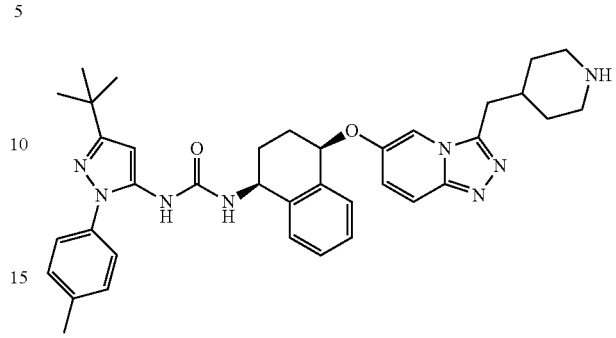

An orange solution of Intermediate 22c (155 mg, 0.211 mmol) and TFA (0.157 mL, 2.11 mmol) in DCM (3 mL) was stirred at RT for 3 h. The solution was concentrated in vacuo, redissolved in MeOH (1 mL), applied to an SCX-2 cartridge (2 g) and washed with MeOH (15 mL). The product was eluted with 2M $NH_3$ in MeOH (15 mL); concentration in vacuo left the title compound as a pale brown solid (116 mg, 87%). LCMS (Method 3): Rt 2.90 min, m/z 633 [$MH^+$].

e. 1-(5-tert-Butyl-2-p-tolyl-2H-pyrazol-3-yl)-3-{(1S,4R)-4-[3-(1-methyl-piperidin-4-ylmethyl)-[1,2,4]triazolo[4,3-a]pyridin-6-yloxy]-1,2,3,4-tetrahydro-naphthalen-1-yl}-urea (Example 22).

To a suspension of Intermediate 22d (58 mg, 0.0917 mmol) and formaldehyde (37% wt in water, 0.074 mL, 0.917 mmol) in DCM-MeOH (4:1, 2.5 mL), were added AcOH (0.0105 mL, 0.183 mmol) and $NaBH(OAc)_3$ (38.8 mg, 0.183 mmol) sequentially, then the solution stirred at RT for 2.5 h. The solution was concentrated in vacuo to 0.5 mL volume, diluted with MeOH (0.5 mL), then applied to an SCX-2 cartridge and washed with MeOH (15 mL). The product was eluted with 2M $NH_3$ in MeOH (15 mL); concentration in vacuo left a pale brown solid. HPLC (XBridge C18, 40-98% MeCN in $H_2O$, 0.1% $NH_4OH$) gave the title compound as a white solid after freeze-drying (15.0 mg, 25%). LCMS (Method 5): Rt 3.66 min, m/z 647 [$MH^+$]. $^1H$ NMR (400 MHz, $d_6$-DMSO): 1.22 (9H, s), 1.26 (2H, m), 1.58 (2H, d, J 12.6), 1.75 (2H, t, J 11.4), 1.78-1.92 (3H, m), 2.03 (2H, m), 2.07 (3H, s), 2.31 (3H, s), 2.68 (2H, d, J 10.7), 2.97 (2H, d, J 7.0), 4.78 (1H, m), 5.48 (1H, t, J 4.5), 6.27 (1H, s), 7.07 (1H, d, J 8.5), 7.11 (1H, dd, J 9.5, 2.0), 7.23-7.35 (8H, m), 7.63 (1H, d, J 9.8), 8.03 (1H, s), 8.17 (1H, s).

Example 23

1-(5-tert-Butyl-2-p-tolyl-2H-pyrazol-3-yl)-3-((1S,4R)-4-{3-[1-(2,2-difluoro-ethyl)-piperidin-4-ylmethyl]-[1,2,4]triazolo[4,3-a]pyridin-6-yloxy}-1,2,3,4-tetrahydro-naphthalen-1-yl)-urea

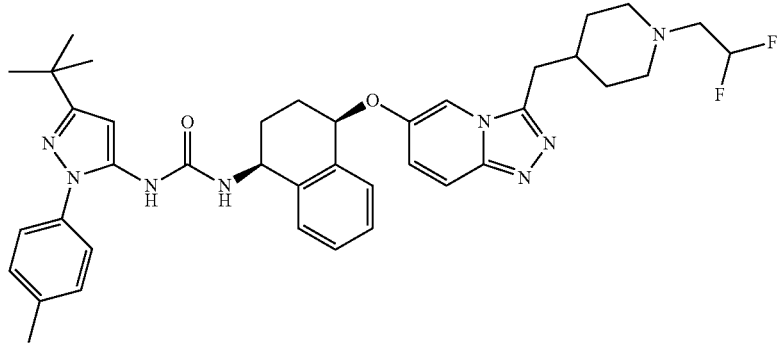 [SMILES: Cc1ccc(-n2nc(C(C)(C)C)cc2NC(=O)N[C@H]2CC[C@@H](Oc3ccc4nnc(CC5CCN(CC(F)F)CC5)n4c3)c3ccccc32)cc1]

To an orange solution of Intermediate 22d (58 mg, 0.0917 mmol) and DIPEA (0.0319 mL, 0.183 mmol) in DCM-MeOH (4:1, 2.5 mL), was added 2,2-difluoroethyl trifluoromethane-sulfonate (Fluorochem, 29.4 mg, 0.138 mmol) and the solution stirred at RT for 2 h. DIPEA (0.0319 mL, 0.183 mmol) and 2,2-difluoroethyl trifluoromethane-sulfonate (29.4 mg, 0.138 mmol) were added sequentially, and the pale green solution stirred at RT for 1 h. Water (2 mL) was added and the mixture extracted with DCM (2×3 mL). The combined organics were passed through a hydrophobic frit and concentrated in vacuo to leave a pale green-brown solid. HPLC (XBridge C18, 50-98% MeCN in H$_2$O, 0.1% NH$_4$OH) gave the title compound as a white solid after freeze-drying (11.5 mg, 18%). LCMS (Method 5): Rt 3.75 min, m/z 697 [MH$^+$]. $^1$H NMR (400 MHz, d$_6$-DMSO): 1.22 (9H, s), 1.24-1.33 (2H, m), 1.59 (2H, d, J 13.0), 1.75-1.92 (3H, m), 2.01-2.10 (4H, m), 2.31 (3H, s), 2.62 (2H, td, J 15.8, 4.8), 2.82 (2H, d, J 11.4), 2.98 (2H, d, J 7.2), 4.78 (1H, m), 5.48 (1H, t, J 4.7), 6.04 (1H, tt, J 55.7, 4.4), 6.27 (1H, s), 7.07 (1H, d, J 8.9), 7.11 (1H, dd, J 10.0, 2.2), 7.21-7.35 (8H, m), 7.63 (1H, d, J 9.8), 8.03 (1H, s), 8.17 (1H, d, J 2.0).

Example 24

1-(5-tert-Butyl-2-p-tolyl-2H-pyrazol-3-yl)-3-[(1S,4R)-4-[3-(4-hydroxypiperidin-1-yl)-[1,2,4]triazolo[4,3-a]pyridine-6-yloxy]-1,2,3,4-tetrahydro-naphthalen-1-yl]-urea

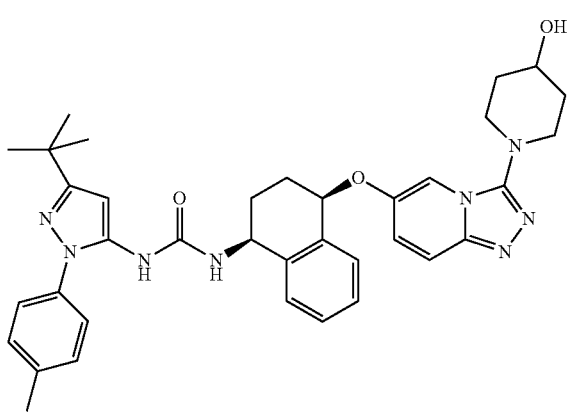 [SMILES: Cc1ccc(-n2nc(C(C)(C)C)cc2NC(=O)N[C@H]2CC[C@@H](Oc3ccc4nnc(N5CCC(O)CC5)n4c3)c3ccccc32)cc1]

a. 6-Fluoro-[1,2,4]triazolo[4,3-a]pyridine (Intermediate 24a).

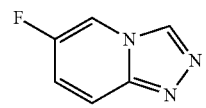

(5-Fluoro-pyridin-2-yl)-hydrazine (500 mg, 3.93 mmol) in diethoxymethyl acetate (5 mL) was stirred at RT for 2 h. The resulting precipitate was diluted with cyclohexane (5 ml) and filtered to give the title compound (379 mg, 70%). $^1$H NMR (400 MHz, CDCl$_3$): 7.25 (1H, m), 7.84 (1H, m), 8.09 (1H, t), 8.84 (1H, s).

b. 3-Chloro-6-fluoro-[1,2,4]triazolo[4,3-a]pyridine (Intermediate 24b).

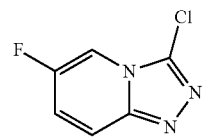 [SMILES: Fc1ccc2nnc(Cl)n2c1]

A solution of Intermediate 24a (789 mg, 5.98 mmol) and N-chlorosuccinimide (878 mg, 6.57 mmol) in chloroform (15 mL) was heated at 65° C. overnight. The cooled mixture was washed with sat. aq. NaHCO$_3$ solution (2×15 mL) and dried (Na$_2$SO$_4$). The solvent was evaporated, then the residue suspended in diethyl ether (10 mL) and filtered to give the title compound (730 mg, 76%). LCMS (Method 1): Rt 1.83 min, m/z 172 [MH$^+$].

c. 1-(6-Fluoro-[1,2,4]triazolo[4,3-a]pyridin-3-yl-piperidin-4-ol (Intermediate 24c).

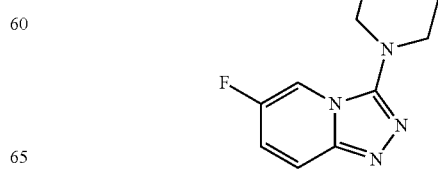

A brown solution of Intermediate 24b (855 mg, 4.98 mmol) and 4-hydroxypiperidine (2.02 g, 19.9 mmol) in DMA (15 mL) was irradiated to 175° C. in the microwave for 3 h. The cooled solution was concentrated in vacuo, then the residue diluted with water (20 mL) and brine (20 mL). The mixture was washed with diethyl ether (2×50 mL), then extracted with EtOAc (2×50 mL). The combined EtOAc layers were washed with brine (50 mL), dried (Na$_2$SO$_4$), filtered and concentrated in vacuo to leave a yellow oil. The aqueous was further extracted with DCM (3×50 mL). The combined DCM layers were passed through a hydrophobic frit and concentrated in vacuo to leave a brown oil. The two oils were combined. FCC, using 4-5% [2M NH$_3$ in MeOH] in DCM, gave the title compound as a yellow crystalline solid (514 mg, 44%). LCMS (Method 3): Rt 1.96 min, m/z 237 [MH$^+$].

d. 6-Fluoro-3-(4-triisopropylsilanyloxy-piperidin-1-yl)-[1,2,4]triazolo[4,3-a]pyridine (Intermediate 24d).

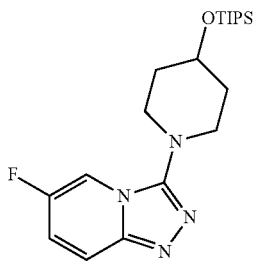

Triisopropylsilyl trifluoromethanesulfonate (395 mg, 1.29 mmol) was added dropwise to a solution of Intermediate 24c (254 mg, 1.07 mmol) and Et$_3$N (0.20 mL, 1.40 mmol) in DMF (3 mL) at RT under N$_2$. The mixture was stirred for 1 h then Et$_3$N (0.10 ml, 0.70 mmol) and triisopropylsilyl trifluoromethanesulfonate (200 mg, 0.65 mmol) were added sequentially, and the mixture stirred for 1 h. The solvent was evaporated, the residue applied to an SCX-2 cartridge and washed with MeOH. The product was eluted with 2M NH$_3$ in MeOH; concentration in vacuo left the title compound (339 mg, 80%). LCMS (Method 1): Rt 4.74 min, m/z 393 [MH$^+$].

e. (1S,4R)-4-[3-(4-Triisopropylsilanyloxy-piperidin-1-yl-[1,2,4]triazolo[4,3a]pyridin-6-yloxy]1,2,3,4-tetrahydro-naphthalen-1-ylamine (Intermediate 24e).

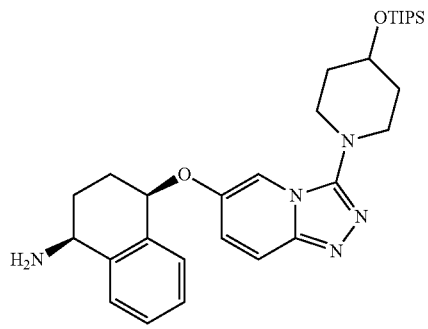

Intermediate A (81 mg, 0.497 mmol) was added dropwise to a suspension of NaH (60% dispersion in oil, 59 mg, 1.49 mmol) in DMF (3 mL) at RT under N$_2$. The mixture was stirred for 15 min then Intermediate 24d (150 mg, 0.382 mmol) was added and the mixture stirred at 60° C. under N$_2$ for 3 h. Sat. aq. NH$_4$Cl solution (0.2 mL) was added to the cooled mixture which was then diluted with water (15 mL) and extracted with EtOAc (3×15 mL). The combined organics were washed with brine (15 mL) and dried (Na$_2$SO$_4$). The solvent was evaporated, the residue applied to an SCX-2 cartridge and washed with MeOH. The product was eluted with 2M NH$_3$ in MeOH; concentration in vacuo left the title compound (180 mg, 90%). LCMS (Method 1): Rt 3.05 min, m/z 536 [MH$^+$].

f. 1-(5-tert-Butyl-2-p-tolyl-2H-pyrazol-3-yl)-3-[(1S,4R)-4-[3-(4-triisopropylsilanyloxy-piperidin-1-yl)-[1,2,4]triazolo[4,3-a]pyridine-6-yloxy]-1,2,3,4-tetrahydro-naphthalen-1-yl]-urea (Intermediate 24f).

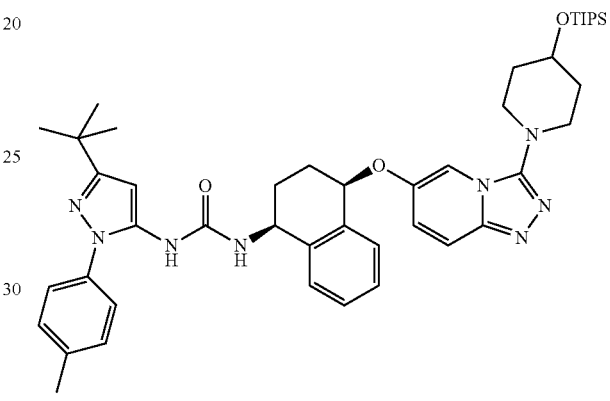

A mixture of (5-tert-butyl-2-p-tolyl-2H-pyrazol-3-yl)carbamic acid 2,2,2-trichloro-ethyl ester (Synthetic Communications, 2009, 39, 3999-4009, which is incorporated herein by reference in its entirety; 140 mg, 0.346 mmol), Intermediate 24e (185 mg, 0.346 mmol) and DIPEA (0.18 mL, 1.03 mmol) in DMF (3 mL) was heated at 60° C. for 4 h under N$_2$. The cooled mixture was applied to an SCX-2 cartridge and washed with MeOH. The product was eluted with 2M NH$_3$ in MeOH; concentration in vacuo left a brown gum. FCC, using 0.6-6% [2M NH$_3$ in MeOH] in DCM, gave the title compound (124 mg, 45%). LCMS (Method 4): Rt 5.15 min, m/z 791 [MH$^+$].

g. 1-(5-tert-Butyl-2-p-tolyl-2H-pyrazol-3-yl)-3-[(1S,4R)-4-[3-(4-hydroxypiperidin-1-yl)-[1,2,4]triazolo[4,3-a]pyridine-6-yloxy]-1,2,3,4-tetrahydro-naphthalen-1-yl]-urea (Example 24).

TBAF (1M in THF, 0.235 mL, 0.235 mmol) was added dropwise to a solution of Intermediate 24f (124 mg, 0.157 mmol) in dry THF (3 mL) at −30° C. for 4 h under N$_2$. The mixture was allowed to warm to RT, then stirred for 5 h. The solution was applied to an SCX-2 cartridge and washed with MeOH. The product was eluted with 2M NH$_3$ in MeOH; concentration in vacuo left a brown foam. HPLC (Gemini C18; 40-90% MeCN in H$_2$O, 0.1% NH$_4$OH) gave the title compound as a white powder (77 mg, 77%). LCMS (Method 5): Rt 4.18 min, m/z 635 [MH$^+$]. $^1$H NMR (400 MHz, CDCl$_3$): 1.33 (9H, s), 1.71-1.80 (2H, m), 1.87-1.96 (1H, m), 2.01-2.12 (4H, m), 2.25 (1H, m), 2.36 (3H, s), 3.04-3.11 (2H, m), 3.37-3.44 (2H, m), 3.93 (1H, m), 5.09 (1H, td, J 8.9, 5.3), 5.19 (1H, t, J 4.0), 5.44 (1H, d, J 8.8), 6.28 (1H, s), 6.46 (1H, br s), 6.99 (1H, dd, J 9.9, 2.1), 7.21 (2H, d, J 8.1), 7.25-7.33 (5H, m), 7.39 (2H, d, J 8.1), 7.49 (1H, d, J 9.9).

Example 25

1-(5-tert-Butyl-2-p-tolyl-2H-pyrazol-3-yl)-3-[(1S, 4R)-4-{3-[(2-hydroxy-ethyl)-methyl-amino]-[1,2,4] triazolo[4,3-a]pyridine-6-yloxy]-1,2,3,4-tetrahydro-naphthalen-1-yl]-urea

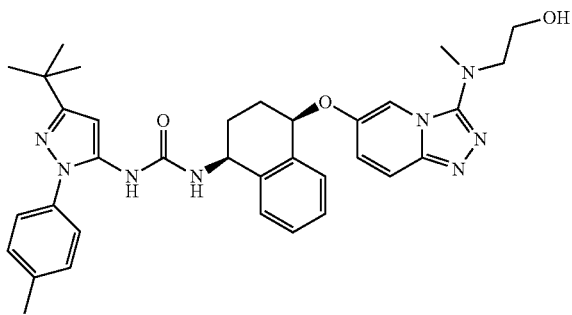 [SMILES: Cc1ccc(-n2nc(C(C)(C)C)cc2NC(=O)N[C@H]2CC[C@@H](Oc3ccc4nnc(N(C)CCO)n4c3)c3ccccc32)cc1]

a. 2-(6-Fluoro-[1,2,4]triazolo[4,3-a]pyridin-3-yl)-methyl-amino]ethanol and 2-[(3-chloro-[1,2,4]triazolo[4,3-a]pyridin-6-yl)-methyl-amino]ethanol (Intermediate 25a).

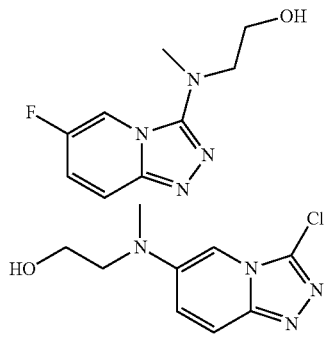

A solution of Intermediate 24b (300 mg, 1.75 mmol) and 2-methylamino ethanol (660 mg, 8.77 mmol) in NMP (2 ml) was heated at 165° C. for 2 h in the microwave. The cooled mixture was applied to an SCX-2 cartridge and washed with MeOH. The product was eluted with 2M NH₃ in MeOH; concentration in vacuo left a brown gum. FCC, using 3-6% [2M NH₃ in MeOH] in DCM, gave a mixture of the title compounds (240 mg, 65%). LCMS (Method 4): Rt 1.05 min, m/z 211 [MH⁺] and Rt 1.76 min, m/z 227 [MH⁺].

b. (6-Fluoro-[1,2,4]triazolo[4,3-a]pyridin-3-yl)-methyl-(2-triisopropylsilanyloxy-ethyl)-amine (Intermediate 25b).

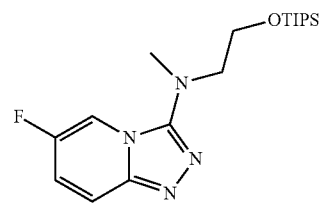

Triisopropylsilyl trifluoromethanesulfonate (454 mg, 1.48 mmol) was added dropwise to a solution of Intermediate 25a (240 mg, 1.14 mmol) and Et₃N (0.24 mL, 1.71 mmol) in DMF (2 mL) at RT under N₂ and the mixture was stirred for 3 h. The solvent was evaporated, the residue applied to an SCX-2 cartridge and washed with MeOH. The product was eluted with 2M NH₃ in MeOH; concentration in vacuo left a brown gum. FCC, using 0-3% [2M NH₃ in MeOH] in DCM, gave the title compound (160 mg, 38%). LCMS (Method 4): Rt 4.25 min, m/z 367 [MH⁺].

c. [6-((1R,4S)-4-Amino-1,2,3,4-tetrahydro-naphthalen-1-yloxy)-[1,2,4]triazolo[4,3-a]pyridin-3-yl]-methyl-(2-triisopropylsilanyloxy-ethyl)-amine (Intermediate 25c).

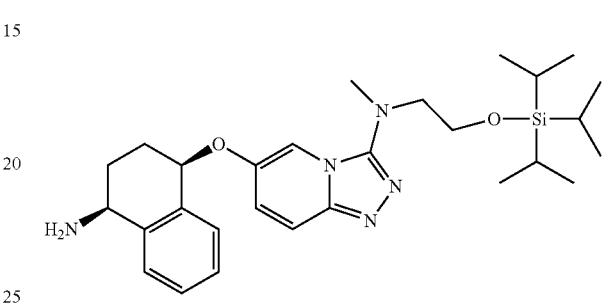

Intermediate A (93 mg, 0.568 mmol) was added dropwise to a suspension of NaH (60% dispersion in oil, 68 mg, 1.71 mmol) in DMF (3 mL) at RT under N₂. The mixture was stirred for 15 min then Intermediate 25b (160 mg, 0.437 mmol) was added and the mixture stirred at 60° C. under N₂ for 3 h. Sat. aq. NH₄Cl solution (0.2 mL) was added to the cooled mixture which was then diluted with water (15 mL) and extracted with EtOAc (3×15 mL). The combined organics were washed with brine (15 mL) and dried (Na₂SO₄). The solvent was evaporated, the residue applied to an SCX-2 cartridge and washed with MeOH. The product was eluted with 2M NH₃ in MeOH; concentration in vacuo left a brown foam. FCC, using 0-6% [2M NH₃ in MeOH] in DCM, gave the title compound (64 mg, 29%). LCMS (Method 1): Rt 2.71 min, m/z 510 [MH⁺].

d. 1-(5-tert-Butyl-2-p-tolyl-2H-pyrazol-3-yl)-3-[(1S,4R)-4-{3-[methyl-(2-triisopropylsilanyloxy-ethyl-amino]-1-[1,2,4]triazolo[4,3-a]pyridine-6-yloxy]-1,2,3,4-tetrahydro-naphthalen-1-yl]-urea (Intermediate 25d).

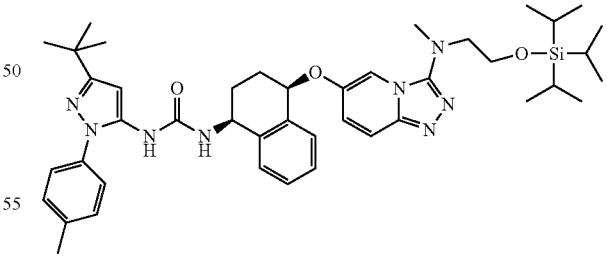

A mixture of (5-tert-butyl-2-p-tolyl-2H-pyrazol-3-yl)carbamic acid 2,2,2-trichloro-ethyl ester (Synthetic Communications, 2009, 39, 3999-4009, which is incorporated herein by reference in its entirety; 71 mg, 0.175 mmol), Intermediate 25c (64 mg, 0.125 mmol) and DIPEA (0.093 mL, 0.524 mmol) in DMF (2 mL) was heated at 60° C. for 4 h under N₂. The cooled mixture was applied to an SCX-2 cartridge and washed with MeOH. The product was eluted with 2M NH₃ in MeOH; concentration in vacuo left a brown gum. FCC, using 3-6% [2M NH₃ in MeOH] in DCM, gave the title compound (65 mg, 68%). LCMS (Method 1): Rt 4.78 min, m/z 765 [MH⁺].

e. 1-(5-tert-Butyl-2-p-tolyl-2H-pyrazol-3-yl)-3-[(1S,4R)-4-{3-[(2-hydroxy-ethyl)-methyl-amino]-[1,2,4]triazolo[4,3-a]pyridine-6-yloxy]-1,2,3,4-tetrahydro-naphthalen-1-yl]-urea (Example 25).

TBAF (1M in THF; 0.127 mL, 0.235 mmol) was added dropwise to a solution of Intermediate 25d (65 mg, 0.085 mmol) in dry THF (0.3 mL) at −30° C. under N₂. The mixture was allowed to warm to RT, then stirred for 1 h. The solution was applied to an SCX-2 cartridge and washed with MeOH. The product was eluted with 2M NH₃ in MeOH; concentration in vacuo left a pale yellow oil. Further purification by HPLC (Gemini C18; 40-100% MeCN in H₂O, 0.1% NH₄OH) gave the title compound as a white powder (32 mg, 62%). LCMS (Method 5): Rt 4.11 min, ink 609 [MH⁺]. ¹H NMR (400 MHz, CDCl₃): 1.32 (9H, s), 1.90-1.99 (1H, m), 2.02-2.12 (2H, m), 2.23-2.30 (1H, m), 2.37 (3H, s), 2.94 (3H, s), 3.11 (1H, ddd, J 14.3, 6.9, 3.5), 3.18 (1H, ddd, J 14.3, 5.6, 3.2), 3.68-3.79 (2H, m), 5.06 (1H, td, J 8.6, 5.5), 5.20 (1H, t, J 4.2), 5.50 (1H, d, J 8.7), 6.31 (1H, s), 6.42 (1H, s), 6.98 (1H, dd, J 9.9, 2.0), 7.18-7.30 (6H, m), 7.39 (2H, d, J 8.2), 7.49 (1H, d, J 9.9), 7.58 (1H, d, J 2.0).

Example 26

1-(5-tert-Butyl-2-p-tolyl-2H-pyrazol-3-yl)-3-{(1S,4R)-4-[3-((S)-3-hydroxy-pyrrolidin-1-yl)-[1,2,4]triazolo[4,3-a]pyridin-6-yloxy]-1,2,3,4-tetrahydro-naphthalen-1-yl}-urea

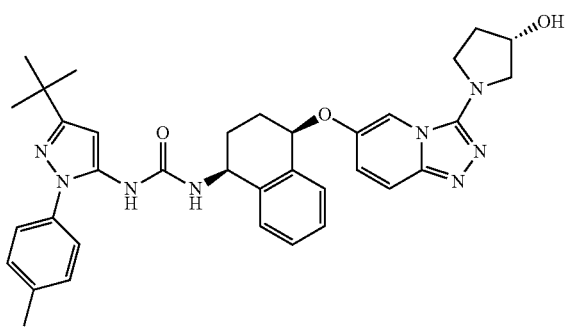 [SMILES: Cc1ccc(-n2nc(C(C)(C)C)cc2NC(=O)N[C@H]2CC[C@@H](Oc3ccc4nnc(N5CC[C@H](O)C5)n4c3)c3ccccc32)cc1]

a. (S)-1-(6-Fluoro-[1,2,4]triazolo[4,3-a]pyridin-3-yl)-pyrrolidin-3-ol (Intermediate 26a.

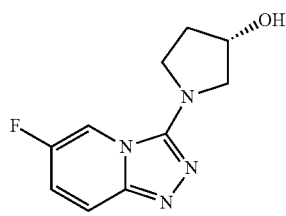 [SMILES: O[C@H]1CCN(c2nnc3ccc(F)cn23)C1]

A mixture of Intermediate 24b (300 mg, 1.74 mmol) and (S)-3-hydroxypyrrolidine (600 mg, 9.96 mmol) in NMP (6 mL) was heated in the microwave at 160° C. for 2 h. The reaction mixture was applied to an SCX-2 cartridge (70 g) and washed with MeOH. The product was eluted with 2M NH₃ in MeOH; concentration in vacuo gave a residue. FCC, using 0-8% [2M NH₃ in MeOH] in DCM, gave the title compound (150 mg, 38%). LCMS (Method 1): Rt 1.45 min, m/z 223 [MH⁺].

b. 6-Fluoro-3-((S)-3-triisopropylsilanyloxy-pyrrolidin-1-yl)-[1,2,4]triazolo[4,3-a]pyridine (Intermediate 26b).

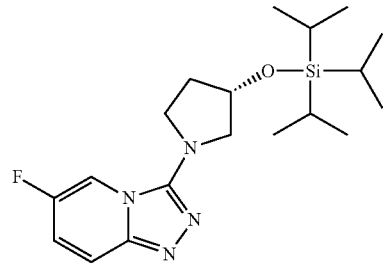 [SMILES: CC(C)[Si](O[C@H]1CCN(c2nnc3ccc(F)cn23)C1)(C(C)C)C(C)C]

Triisopropylsilyl trifluoromethanesulfonate (250 mg, 0.81 mmol) was added to a solution of Intermediate 26a (150 mg, 0.67 mmol) and Et₃N (101 mg, 1.00 mmol) in DMF (2 mL) and the mixture stirred at RT for 1 h. The reaction mixture was applied to an SCX-2 cartridge (5 g) and washed with MeOH. The product was eluted with 2M NH₃ in MeOH; concentration in vacuo gave the title compound (220 mg, 86%). LCMS (Method 4): Rt 4.15 min, m/z 379 [MH⁺].

c. (1S,4R)-4-[3-((S)-3-Triisopropylsilanyloxy-pyrrolidin-1-yl)-[1,2,4]triazolo[4,3-a]pyridin-6-yloxy]-1,2,3,4-tetrahydro-naphthalen-1-ylamine (Intermediate 26c).

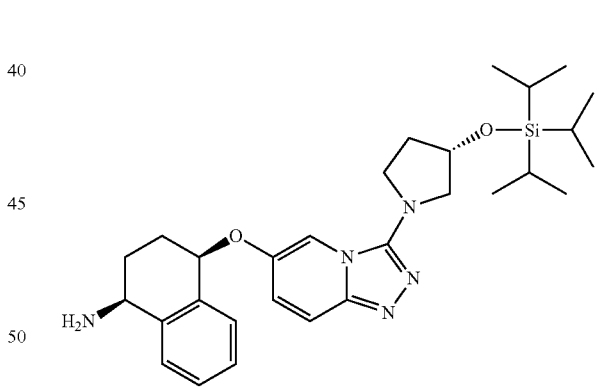

To a solution of Intermediate A (104 mg, 0.640 mmol) in DMF (2 mL) was added NaH (60% in oil, 70 mg, 1.74 mmol) and the mixture stirred at RT for 20 min, before Intermediate 26b (220 mg, 0.582 mmol) was added. This mixture was stirred thermally at 60° C. for 4 h, then at 60° C. in the microwave for 3 h. The cooled reaction mixture was applied to an SCX-2 cartridge (10 g) and washed with MeOH. The product was eluted with 2M NH₃ in MeOH; concentration in vacuo gave a residue. FCC, using 0-10% [2M NH₃ in MeOH] in DCM gave the title compound as a yellow gum (70 mg, 23%). LCMS (Method 1): Rt 2.89, m/z 522 [MH⁺].

d. 1-(5-tert-Butyl-2-p-tolyl-2H-pyrazol-3-yl)-3-{(1S,4R)-4-[3-((S)-3-triisopropylsilanyloxy-pyrrolidin-1-yl)-[1,2,4]triazolo[4,3-a]pyridin-6-yloxy]-1,2,3,4-tetrahydro-naphthalen-1-yl}-urea (Intermediate 26d).

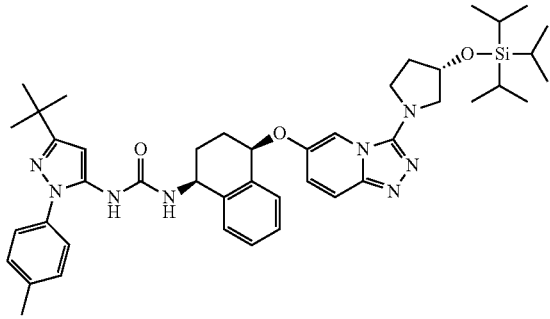 [SMILES: Cc1ccc(-n2nc(C(C)(C)C)cc2NC(=O)N[C@H]2CC[C@@H](Oc3ccc4nnc(N5CC[C@H](O[Si](C(C)C)(C(C)C)C(C)C)C5)n4c3)c3ccccc32)cc1]

A solution of Intermediate 26c (70 mg, 0.134 mmol), (5-tert-butyl-2-p-tolyl-2H-pyrazol-3-yl)-carbamic acid 2,2,2-trichloro-ethyl ester (Synthetic Communications, 2009, 39, 3999-4009, which is incorporated herein by reference in its entirety; 81 mg, 0.201 mmol) and DIPEA (70 mg, 0.54 mmol) in DMF (2 mL) was stirred at 60° C. for 30 min. The reaction mixture was applied to an SCX-2 cartridge (5 g) and washed with MeOH. The product was eluted with 2M NH₃ in MeOH; concentration in vacuo gave a residue. FCC, using 0-10% [2M NH₃ in MeOH] in DCM, gave the title compound as an off-white foam (19 mg, 23%). LCMS (Method 1): Rt 4.70, m/z 777 [MH⁺].

e. 1-(5-tert-Butyl-2-p-tolyl-2H-pyrazol-3-yl)-3-{(1S,4R)-4-[3-((S)-3-hydroxy-pyrrolidin-1-yl)-[1,2,4]triazolo[4,3-a]pyridin-6-yloxy]-1,2,3,4-tetrahydro-naphthalen-1-yl}-urea (Example 26).

To a solution of Intermediate 26d (19 mg, 0.024 mmol) in THF (1 mL) at −30° C. was added TBAF (1M in THF, 36 μL, 0.036 mmol) and the mixture was allowed to warm to RT over 1 h. The reaction mixture was applied to an SCX-2 cartridge (2 g) and washed with MeOH. The product was eluted with 2M NH₃ in MeOH; concentration in vacuo gave a residue. Purification by HPLC (C6-Ph column, 35-75% MeCN in H₂O, 0.1% HCO₂H) gave the title compound as an off-white powder after freeze-drying (10.0 mg, 60%). LCMS (Method 5): Rt 4.00 min, ink 621 [MH⁺]. ¹H NMR (400 MHz, CDCl₃): 1.29 (9H, s), 1.89-2.09 (4H, m), 2.13-2.29 (2H, m), 2.34 (3H, s), 3.35 (1H, td, J 9.2, 4.6), 3.45 (1H, d, J 11.1), 3.50 (1H, dd, J 11.1, 4.3), 3.60 (1H, m), 4.51 (1H, m), 5.04 (1H, td, J 8.5, 5.3), 5.15 (1H, t, J 4.1), 5.57 (1H, d, J 8.6), 6.26 (1H, s), 6.67 (1H, br s), 6.89 (1H, dd, J 9.9, 1.7), 7.15 (2H, d, J 7.1), 7.24-7.29 (4H, m), 7.30-7.38 (4H, m).

Example 27

1-(5-tert-Butyl-2-p-tolyl-2H-pyrazol-3-yl)-3-{(1S,4R)-4-[3-((R)-2-hydroxymethyl-pyrrolidin-1-yl)-[1,2,4]triazolo[4,3-a]pyridin-6-yloxy]-1,2,3,4-tetrahydro-naphthalen-1-yl}-urea

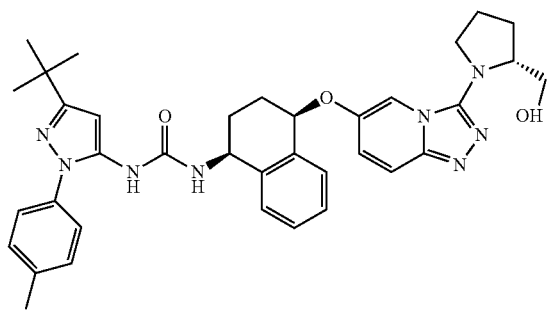 [SMILES: Cc1ccc(-n2nc(C(C)(C)C)cc2NC(=O)N[C@H]2CC[C@@H](Oc3ccc4nnc(N5CCC[C@@H]5CO)n4c3)c3ccccc32)cc1]

a. [(R)-1-(6-Fluoro-[1,2,4]triazolo[4,3-a]pyridin-3-yl)-pyrrolidin-2-yl]-methanol (Intermediate 27a).

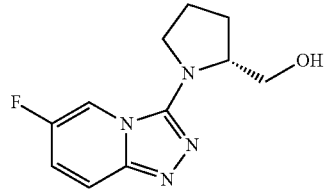 [SMILES: OC[C@H]1CCCN1c1nnc2ccc(F)cn12]

A mixture of Intermediate 24b (300 mg, 1.74 mmol) and (R)-(+2-(hydroxymethyl)-pyrrolidine (704 mg, 9.96 mmol) in NMP (6 mL) was heated in the microwave at 160° C. for 2 h. The reaction mixture was applied to an SCX-2 cartridge (75 g) and washed with MeOH. The product was eluted with 2M NH₃ in MeOH; concentration in vacuo gave a residue. FCC, using 0-10% [2M NH₃ in MeOH] in DCM, gave the title compound (220 mg, 53%). LCMS (Method 4): Rt 1.50, m/z 237 [MH⁺].

b. 6-Fluoro-3-((S)-2-triisopropylsilanyloxy-pyrrolidin-1-yl)-[1,2,4]triazolo[4,3-a]pyridine (Intermediate 27b).

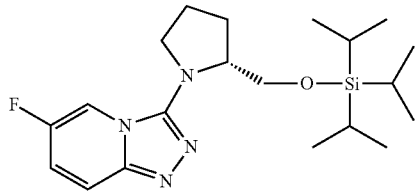 [SMILES: CC(C)[Si](OC[C@H]1CCCN1c1nnc2ccc(F)cn12)(C(C)C)C(C)C]

Triisopropylsilyl trifluoromethanesulfonate (430 mg, 1.40 mmol) was added to a solution of Intermediate 27a (220 mg, 0.93 mmol) and Et₃N (190 mg, 1.86 mmol) in a DMF (2 mL) and the mixture stirred at RT for 1 h. The reaction mixture was applied to an SCX-2 cartridge (10 g) and washed with MeOH. The product was eluted with 2M NH₃ in MeOH; concentration in vacuo gave the title compound (170 mg, 47%). LCMS (Method 1): Rt 4.45, m/z 393 [MH⁺].

c. (1S,4R)-4-[3-((R)-2-Triisopropylsilanyloxymethyl-pyrrolidin-1-yl)-[1,2,4]triazolo[4,3-a]pyridin-6-yloxy]-1,2,3,4-tetrahydro-naphthalen-1-ylamine (Intermediate 27c).

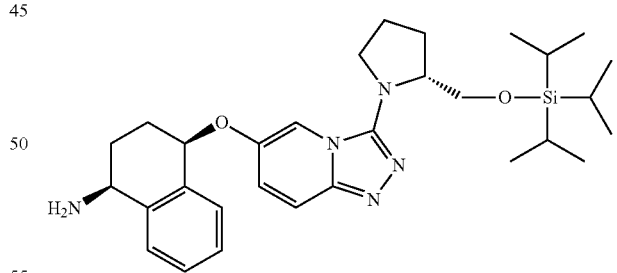

To a solution of Intermediate A (60 mg, 0.364 mmol) in DMF (2 mL) was added NaH (60% in oil, 40 mg, 0.99 mmol) and the mixture stirred at RT for 20 min, before Intermediate 27b (130 mg, 0.331 mmol) was added. This mixture was heated at 60° C. in the microwave for 1.5 h. The reaction mixture was applied to an SCX-2 cartridge (5 g) and washed with MeOH. The product was eluted with 2M NH₃ in MeOH; concentration in vacuo gave a residue. FCC, using 0-7% [2M NH₃ in MeOH] in DCM, gave the title compound as a brown oil (50 mg, 28%). LCMS (Method 4): Rt 2.36, m/z 536 [MH⁺].

d. 1-(5-tert-Butyl-2-p-tolyl-2H-pyrazol-3-yl)-3-{(1S,4R)-4-[3-((R)-2-triisopropylsilanyloxymethyl-pyrrolidin-1-yl)-[1,2,4]triazolo[4,3-a]pyridin-6-yloxy]-1,2,3,4-tetrahydro-naphthalen-1-yl}-urea (Intermediate 27d).

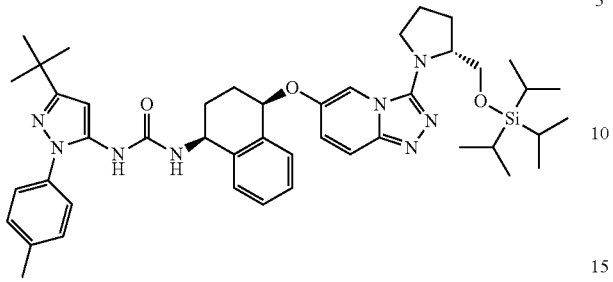

A solution of Intermediate 27c (50 mg, 0.093 mmol), (5-tert-butyl-2-p-tolyl-2H-pyrazol-3-yl)-carbamic acid 2,2,2-trichloro-ethyl ester (Synthetic Communications, 2009, 39, 3999-4009, which is incorporated herein by reference in its entirety; 56 mg, 0.140 mmol) and DIPEA (70 mg, 0.54 mmol) in DMF (2 mL) was stirred at 60° C. for 1 h. The reaction mixture was applied to an SCX-2 cartridge (5 g) and washed with MeOH. The product was eluted with 2M $NH_3$ in MeOH; concentration in vacuo gave a residue. FCC, using 0-10% [2M $NH_3$ in MeOH] in DCM, gave the title compound as an off-white foam (27 mg, 36%). LCMS (Method 4): Rt 4.58, m/z 791 [MH$^+$].

e. 1-(5-tert-Butyl-2-p-tolyl-2H-pyrazol-3-yl)-3-{(1S,4R)-4-[3-((R)-2-hydroxymethyl-pyrrolidin-1-yl)-[1,2,4]triazolo[4,3-a]pyridin-6-yloxy]-1,2,3,4-tetrahydro-naphthalen-1-yl}-urea (Example 27).

To a solution of Intermediate 27d (27 mg, 0.034 mmol) in THF (1 mL) at –30° C. was added TBAF (1M in THF, 36 μL, 0.036 mmol) and the mixture was allowed to warm to RT over 1 h. The reaction mixture was applied to an SCX-2 cartridge (2 g) and washed with MeOH. The product was eluted with 2M $NH_3$ in MeOH; concentration in vacuo gave a residue. Purification by HPLC (C6-Ph column, 10-70% MeCN in $H_2O$, 0.1% $HCO_2H$) gave the title compound as a white powder after freeze-drying (10.0 mg, 45%). LCMS (Method 5): Rt 4.18 min, m/z 635 [MH$^+$]. $^1$H NMR (400 MHz, CDCl$_3$): 1.25 (9H, s), 1.63-1.75 (1H, m), 1.81-1.95 (3H, m), 1.97-2.01 (3H, m), 2.26 (1H, m), 2.31 (3H, s), 3.17-3.26 (1H, m), 3.32-3.47 (2H, m), 3.57 (1H, dd, J 11.6, 3.2), 4.07-4.15 (1H, m), 4.99-5.07 (1H, m), 5.15 (1H, t, J 4.1), 5.57 (1H, d, J 8.9), 6.25 (1H, s), 6.61 (1H, s), 6.91 (1H, d, J 10.2), 7.16 (2H, d, J 8.3), 7.20-7.29 (4H, m), 7.32 (2H, d, J 8.0), 7.35-7.41 (2H, m).

Example 28

1-(5-tert-Butyl-2-p-tolyl-2H-pyrazol-3-yl)-3-{(1S,4R)-4-[3-((S)-2-hydroxymethyl-pyrrolidin-1-yl)-[1,2,4]triazolo[4,3-a]pyridin-6-yloxy]-1,2,3,4-tetrahydro-naphthalen-1-yl}-urea

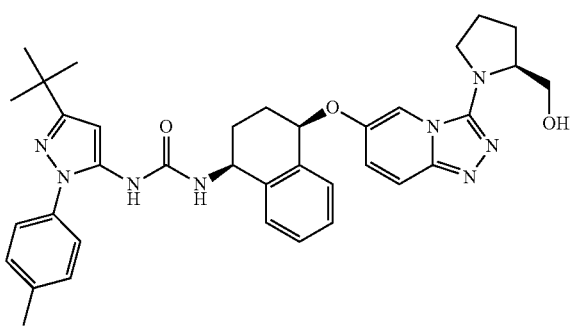 [SMILES: Cc1ccc(-n2nc(C(C)(C)C)cc2NC(=O)N[C@H]2CC[C@@H](Oc3ccc4nnc(N5CCC[C@H]5CO)n4c3)c3ccccc32)cc1]

a. [(S)-1-(6-Fluoro-[1,2,4]triazolo[4,3-a]pyridin-3-yl)-pyrrolidin-2-yl]-methanol (Intermediate 28a).

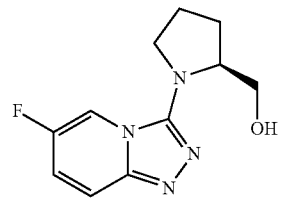 [SMILES: OC[C@@H]1CCCN1c1nnc2ccc(F)cn12]

A mixture of Intermediate 24b (300 mg, 1.74 mmol) and L-prolinol (704 mg, 9.96 mmol) in NMP (4 mL) was heated in the microwave at 160° C. for 2 h. The reaction mixture was applied to an SCX-2 cartridge (70 g) and washed with MeOH. The product was eluted with 2M $NH_3$ in MeOH; concentration in vacuo gave a residue. FCC, using 0-10% [2M $NH_3$ in MeOH] in DCM, gave the title compound (210 mg, 50%). LCMS (Method 4): Rt 1.50 min, m/z 237 [MH$^+$].

b. 6-Fluoro-3-((S)-2-triisopropylsilanyloxymethyl-pyrrolidin-1-yl)-[1,2,4]triazolo[4,3-a]pyridine (Intermediate 28b).

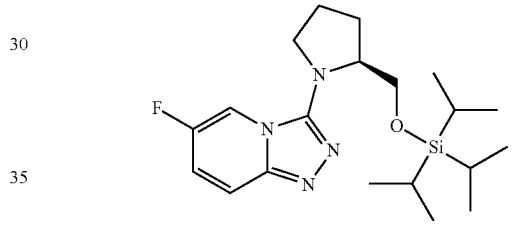

Triisopropylsilyl trifluoromethanesulfonate (327 mg, 1.06 mmol) was added to a solution of Intermediate 28a (210 mg, 0.89 mmol) and Et$_3$N (135 mg, 1.33 mmol) in a DMF (3 mL) and the mixture stirred at RT for 1 h. The reaction mixture was applied to an SCX-2 cartridge (25 g) and washed with MeOH. The product was eluted with 2M $NH_3$ in MeOH; concentration in vacuo gave a residue. FCC, using 0-10% [2M $NH_3$ in MeOH] in DCM, gave the title compound (110 mg, 31%). LCMS (Method 1): Rt 4.45 min, m/z 393 [MH$^+$].

c. (1S,4R)-4-[3-((S)-2-Triisopropylsilanyloxymethyl-pyrrolidin-1-yl)-[1,2,4]triazolo[4,3-a]pyridin-6-yloxy]-1,2,3,4-tetrahydro-naphthalen-1-ylamine (Intermediate 28c).

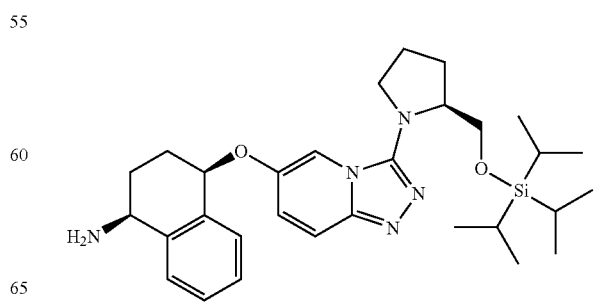

To a solution of Intermediate A (50 mg, 0.309 mmol) in DMF (2 mL) was added NaH (60% in oil, 33 mg, 0.80 mmol) and the mixture stirred at RT for 20 min, before Intermediate 28b (110 mg, 0.280 mmol) was added. This mixture was heated at 60° C. in the microwave for 1.25 h. The reaction mixture was applied to an SCX-2 cartridge (25 g) and washed with MeOH. The product was eluted with 2M NH₃ in MeOH; concentration in vacuo gave a residue. FCC, using 0-7% [2M NH₃ in MeOH] in DCM gave the title compound as a viscous yellow oil (42 mg, 28%). LCMS (Method 4): Rt 2.55 min, m/z 536 [MH⁺].

d. 1-(5-tert-Butyl-2-p-tolyl-2H-pyrazol-3-yl)-3-{(1S,4R)-4-[3-((S)-2-triisopropylsilanyloxymethyl-pyrrolidin-1-yl)-[1,2,4]triazolo[4,3-a]pyridin-6-yloxy]-1,2,3,4-tetrahydro-naphthalen-1-yl}-urea (Intermediate 28d).

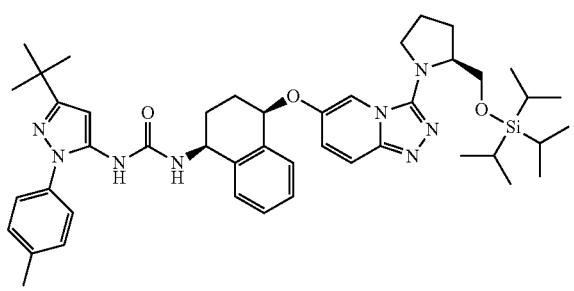 [SMILES: Cc1ccc(-n2nc(C(C)(C)C)cc2NC(=O)N[C@H]2CC[C@@H](Oc3ccc4nnc(N5CCC[C@H]5CO[Si](C(C)C)(C(C)C)C(C)C)n4c3)c3ccccc32)cc1]

A solution of Intermediate 28c (40 mg, 0.074 mmol), (5-tert-butyl-2-p-tolyl-2H-pyrazol-3-yl)-carbamic acid 2,2,2-trichloro-ethyl ester (Synthetic Communications, 2009, 39, 3999-4009, which is incorporated herein by reference in its entirety; 45 mg, 0.112 mmol) and DIPEA (38 mg, 0.296 mmol) in DMF (2 mL) was stirred at 60° C. for 30 min. The reaction mixture was applied to an SCX-2 cartridge (5 g) and washed with MeOH. The product was eluted with 2M NH₃ in MeOH; concentration in vacuo gave a residue. FCC, using 0-7% [2M NH₃ in MeOH] in DCM, gave the title compound as a viscous yellow oil (38 mg, 65%). LCMS (Method 1): Rt 4.72 min, m/z 791 [MH⁺].

e. 1-(5-tert-Butyl-2-p-tolyl-2H-pyrazol-3-yl)-3-{(1S,4R)-4-[3-((S)-2-hydroxymethyl-pyrrolidin-1-yl)-[1,2,4]triazolo[4,3-a]pyridin-6-yloxy]-1,2,3,4-tetrahydro-naphthalen-1-yl}-urea (Example 28).

To a solution of Intermediate 28d (38 mg, 0.048 mmol) in THF (1 mL) at −30° C. was added TBAF (1M in THF, 72 µL, 0.072 mmol) and the mixture was allowed to warm to RT over 1 h. The reaction mixture was applied to an SCX-2 cartridge (5 g) and washed with MeOH. The product was eluted with 2M NH₃ in MeOH; concentration in vacuo gave a residue. Purification by HPLC (C6-Ph column, 10-70% MeCN in H₂O, 0.1% HCO₂H) gave the title compound as a white powder after freeze-drying (12 mg, 39%). LCMS (Method 5): Rt 4.20 min, m/z 635 [MH⁺]. ¹H NMR (400 MHz, d₄-MeOH): 1.29 (9H, s), 1.78-2.28 (8H, m), 2.38 (3H, s), 3.36-3.46 (1H, m), 3.53 (2H, dd, J 5.0, 1.6), 3.64-3.73 (1H, m), 4.04-4.12 (1H, m), 4.85-4.91 (1H, m), 5.36 (1H, t, J 4.1), 6.32 (1H, s), 7.11 (1H, dd, J 10.0, 2.1), 7.20-7.35 (8H, m), 7.44 (1H, d, J 9.9), 7.99-8.01 (1H, m).

Example 29

1-[5-tert-Butyl-2-(3-hydroxymethyl-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea

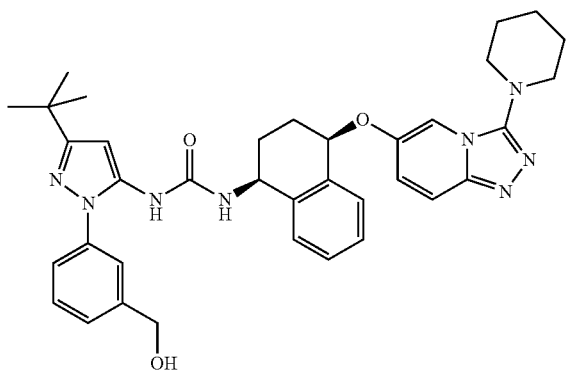 [SMILES: CC(C)(C)c1cc(NC(=O)N[C@H]2CC[C@@H](Oc3ccc4nnc(N5CCCCC5)n4c3)c3ccccc32)n(-c2cccc(CO)c2)n1]

a. 3-(5-Amino-3-tert-butyl-pyrazol-1-yl)-benzoic acid ethyl ester (Intermediate 29a).

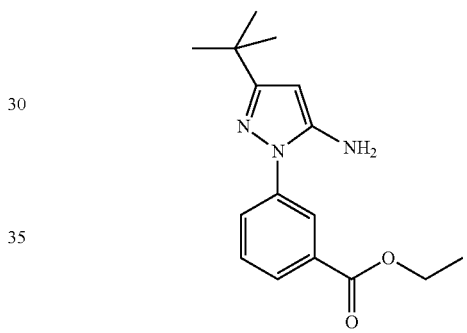

A solution of 3-hydrazino benzoic acid (5.53 g, 36.4 mmol) and 4,4-dimethyl-3-oxo pentanenitrile (5.00 g, 40.0 mmol) and concentrated sulfuric acid (2 mL) in EtOH (72 mL) was stirred at reflux for 19 h. The cooled mixture was concentrated in vacuo, was diluted with 1N NaOH solution (15 mL) and extracted with EtOAc. The combined organics were dried and concentrated in vacuo. The residue was purified by FCC, using 0-40% EtOAc in cyclohexane, to give the title compound as an off-white powder (5.92 g, 56%). LCMS (Method 3): Rt 3.04 min, m/z 288 [MH⁺].

b. [3-(5-Amino-3-tert-butyl-pyrazol-1-yl)-phenyl]-methanol (Intermediate 29b).

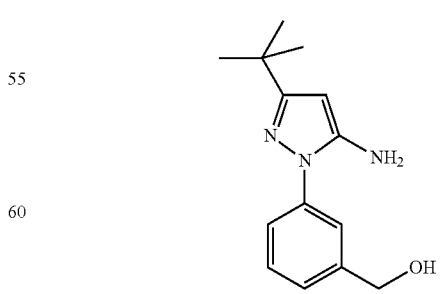

To a solution of Intermediate 29a (1.00 g, 3.48 mmol) and Et₃N (265 µL, 1.91 mmol) in EtOH (35 mL) was added NaBH₄ (198 mg, 5.23 mmol) and the suspension stirred at RT for 1.5 h. NaBH₄ (198 mg, 5.23 mmol) was added and the suspension stirred for a further 19 h. NaBH₄ (1.31 g, 34.8 mmol) was added and the suspension stirred for a further 24 h, then diluted with water and extracted with DCM. The combined organics were dried and concentrated in vacuo. The residue was purified by FCC, using 0-10% [2M NH₃ in MeOH] in DCM, to give the title compound as a white solid (740 mg, 87%). LCMS (Method 3): Rt 2.05 min, m/z 246 [MH⁺].

c. [5-tert-Butyl-2-(3-hydroxymethyl-phenyl)-2H-pyrazol-3-yl]-carbamic acid 2,2,2-trichloro-ethyl ester (Intermediate 29c).

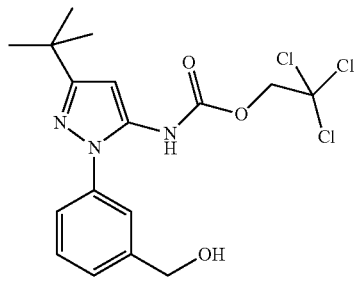 [SMILES: CC(C)(C)c1cc(NC(=O)OCC(Cl)(Cl)Cl)n(-c2cccc(CO)c2)n1]

To a bi-phasic mixture of Intermediate 29b (737 mg, 3.00 mmol) in EtOAc (22.5 mL) and 1N NaOH solution (8.11 mL, 8.11 mmol) at 0° C. was added 2,2,2-trichloroethyl chloroformate (0.45 mL, 3.30 mmol) and the mixture stirred for 1.25 h. The layers were separated and the organic layer was washed with brine, dried and concentrated in vacuo to give the title compound as an off-white solid (1.26 g, 99%). LCMS (Method 3): Rt 4.00 min, m/z 420, 422 [MH⁺].

d. 1-[5-tert-Butyl-2-(3-hydroxymethyl-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea (Example 29).

A solution of Intermediate 29c (509 mg, 1.21 mmol) and Intermediate 3c (400 mg, 1.10 mmol) and DIPEA (0.58 mL, 3.30 mmol) in THF (11 mL) was stirred at reflux for 15 h. The cooled reaction mixture was diluted with water and extracted with DCM. The combined organics were dried and concentrated in vacuo. The residue was purified by FCC, using 0-10% [2M NH₃ in MeOH] in DCM, to give the product. A 50 mg portion of this was further purified by HPLC (XBridge C18 column, 10-98% MeCN in H₂O, 0.1% NH₄OH) to give the title compound as a white powder after freeze-drying (10 mg, 20%). LCMS (Method 5): Rt 4.23 min, m/z 635 [MH⁺]. ¹H NMR (400 MHz, d₄-MeOH): 1.35 (9H, s), 1.57-1.74 (6H, m), 1.89 (1H, t, J 10.7), 2.01-2.08 (2H, m), 2.14-2.22 (1H, m), 3.06 (4H, t, J 5.1), 4.56 (2H, s), 5.09 (1H, m), 5.18 (1H, t, J 4.3), 5.92 (1H, d, J 8.6), 6.40 (1H, s), 6.88 (1H, dd, J 9.2, 2.1), 7.14-7.17 (3H, m), 7.30-7.32 (5H, m), 7.42 (1H, d, J 8.1), 7.50 (1H, s).

Example 30

3-[3-tert-Butyl-5-(3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-ureido)-pyrazol-1-yl]-benzoic acid ethyl ester

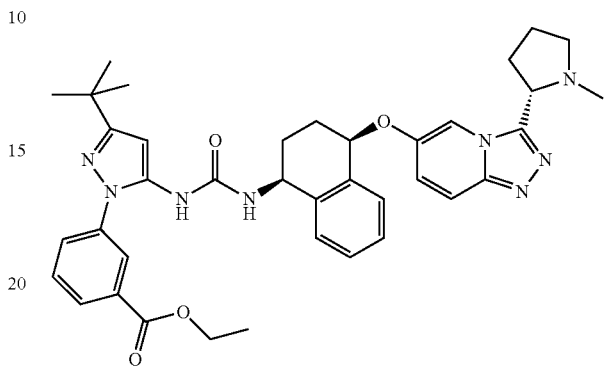

a. 3-[3-tert-Butyl-5-(2,2,2-trichloro-ethoxycarbonylamino)-pyrazol-1-yl]-benzoic acid ethyl ester (Intermediate 30a).

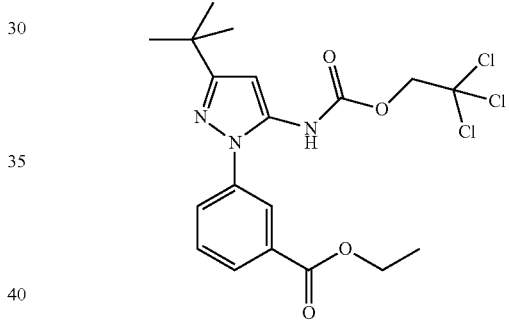

The title compound was prepared from Intermediate 29a using an analogous procedure to that described for Intermediate 29c. LCMS (Method 3): Rt 4.67 min, m/z 462, 464 [MH⁺].

b. 3-[3-tert-Butyl-5-(3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-ureido)-pyrazol-1-yl]-benzoic acid ethyl ester (Example 30).

A mixture of Intermediate 5c (163 mg, 0.45 mmol), Intermediate 30a (208 mg, 0.45 mmol) in 1,4-dioxane (3 mL) and DIPEA (119 µL, 0.68 mmol) was stirred at 90° C. for 3 h. The cooled mixture was concentrated in vacuo. The residue was purified by FCC, using 0-12% MeOH in DCM, to give the product (291 mg, 96%). A 64 mg portion of this was further purified by HPLC (C18 X-select column, 30-98% MeCN in H₂O, 0.1% HCO₂H) to give the title compound as a white powder after freeze-drying powder (38 mg). LCMS (Method 5): Rt 3.85 min, m/z 677.3 [MH⁺]. ¹H NMR (400 MHz, d₆-DMSO): 1.26-1.33 (12H, m), 1.80-2.27 (11H, m), 2.30-2.39 (1H, m), 3.09-3.16 (1H, m), 3.99 (1H, br t, J 8.2), 4.32 (2H, q, J 7.1), 4.74-4.83 (1H, m), 5.36-5.41 (1H, m), 6.33 (1H, s), 7.11 (1H, d, J 8.6), 7.19-7.37 (5H, m), 7.66 (1H, t, J 7.9), 7.75 (1H, d, J 9.9), 7.80-7.84 (1H, m), 7.93-7.98 (1H, m), 8.07-8.09 (1H, m), 8.22-8.28 (2H, m).

Example 31

1-[5-tert-Butyl-2-(3-hydroxymethyl-phenyl)-2H-pyrazol-3-yl]-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea, partial formate salt

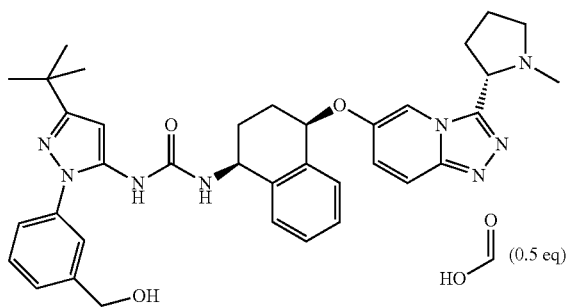

A solution of Example 30 (225 mg, 0.333 mmol) and sodium borohydride (31.5 mg, 0.833 mmol) in ethanol (3 mL) was stirred at RT for 2.5 h. Sodium borohydride (31.5 mg, 0.833 mmol) was added and the solution stirred for 90 min. Sodium borohydride (31.5 mg, 0.833 mmol) was added and the solution stirred for 2.5 h. Sodium borohydride (31.5 mg, 0.833 mmol) was added and the solution stirred for a further 15.5 h. Water was added followed by sat. aq. NH$_4$Cl solution. The mixture was then extracted with DCM (4×20 mL) The combined organic extracts were dried and concentrated in vacuo. The residue was purified by FCC, using 0-14% MeOH in DCM, to give the product (150 mg). This was further purified by HPLC (C18 X-select column, 30-98% MeCN in H$_2$O, 0.1% HCO$_2$H) to give the title compound as a white powder after freeze-drying (97 mg, 46%). LCMS (Method 5): Rt 3.29 min, m/z 635.2 [MH$^+$]. $^1$H NMR (400 MHz, d$_6$-DMSO): 1.28 (9H, s), 1.82-2.26 (11H, m), 2.30-2.39 (1H, m), 3.09-3.16 (1H, m), 3.99 (1H, t, J 8.1), 4.57 (2H, s), 4.78-4.86 (1H, m), 5.39 (1H, t, J 4.3), 6.33 (1H, s), 7.11 (1H, d, J 8.4), 7.24-7.38 (7H, m), 7.42-7.48 (2H, m), 7.75 (1H, d, J 9.9), 8.1 (1H, s), 8.20 (0.5H, s), 8.24 (1H, m).

Example 32

1-(5-tert-Butyl-2-p-tolyl-2H-pyrazol-3-yl)-3-[(1S,4R)-4-(2-morpholin-4-yl-ethoxy)-1,2,3,4-tetrahydro-naphthalen-1-yl]-urea

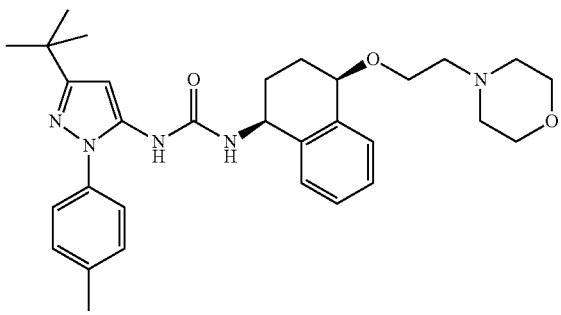 [SMILES: Cc1ccc(-n2nc(C(C)(C)C)cc2NC(=O)N[C@H]2CC[C@@H](OCCN3CCOCC3)c3ccccc32)cc1]

a. 2-((1S,4R)-4-Hydroxy-1,2,3,4-tetrahydro-naphthalen-1-yl)-isoindole-1,3-dione (Intermediate 32a).

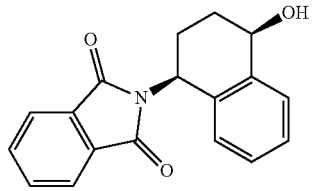 [SMILES: O=C1c2ccccc2C(=O)N1[C@H]1CC[C@@H](O)c2ccccc21]

A solution of Intermediate A (150 mg, 0.92 mmol) and phthalic anhydride (143 mg, 0.97 mmol) in toluene (9 mL) was stirred and heated at reflux for 19.5 h. After cooling, the mixture was concentrated in vacuo. The residue was purified by FCC, using 0-50% EtOAc in cyclohexane, to give the title compound as white powder (215 mg, 79%). LCMS (Method 3): Rt 3.36 min, m/z 316 [MNa$^+$].

b. 2-[(1S,4R)-4-(2-Morpholin-4-yl-2-oxo-ethoxy)-1,2,3,4-tetrahydro-naphthalen-1-yl]-isoindole-1,3-dione (Intermediate 32b).

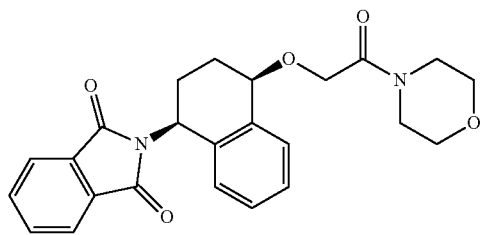 [SMILES: O=C(CO[C@@H]1CC[C@H](N2C(=O)c3ccccc3C2=O)c2ccccc21)N1CCOCC1]

A solution of Intermediate 32a (115 mg, 0.39 mmol) in dry THF (4 mL) was added NaH (60% in mineral oil, 23 mg, 0.59 mmol) at RT and stirred for 15 min. 4-(Chloroacetyl)morpholine (56 µL, 0.43 mmol) was then added and the mixture heated at reflux for 3.5 h. After cooling, the dark brown mixture was diluted with water and extracted with DCM. The combined organics were dried and concentrated in vacuo. The residue was purified by FCC, using 0-5% MeOH in DCM, to give the title compound as light brown foam (103 mg, 62%). LCMS (Method 3): Rt 3.44 min, m/z 443 [MNa$^+$].

c. 2-((1R,4S)-4-Amino-1,2,3,4-tetrahydro-naphthalen-1-yloxy)-1-morpholin-4-yl-ethanone (Intermediate 32c).

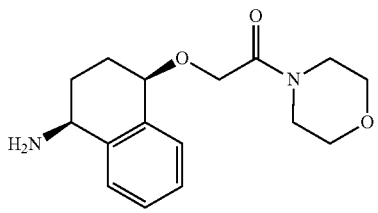 [SMILES: N[C@H]1CC[C@@H](OCC(=O)N2CCOCC2)c2ccccc21]

A solution of Intermediate 32b (100 mg, 0.23 mmol) and hydrazine hydrate (74 µL, 2.4 mmol) in dry MeOH (6 mL) was stirred at RT for 5 h. The reaction mixture was concentrated in vacuo. The residue was purified by FCC, using 0-20% [2M NH$_3$ in MeOH] in DCM, to give the title compound as an off white foam (50 mg, 72%). LCMS (Method 3): Rt 1.70 min, m/z 291 [MH$^+$].

d. 1-(5-tert-Butyl-2-p-tolyl-2H-pyrazol-3-yl)-3-[(1S,4R)-4-(2-morpholin-4-yl-2-oxo-ethoxy)-1,2,3,4-tetrahydro-naphthalen-1-yl]-urea (Intermediate 32d).

Example 33

1-[5-tert-Butyl-2-(4-hydroxymethyl-phenyl)-2H-pyrazol-3-yl]-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}urea

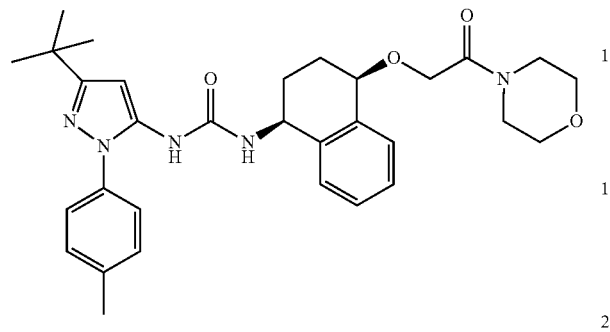

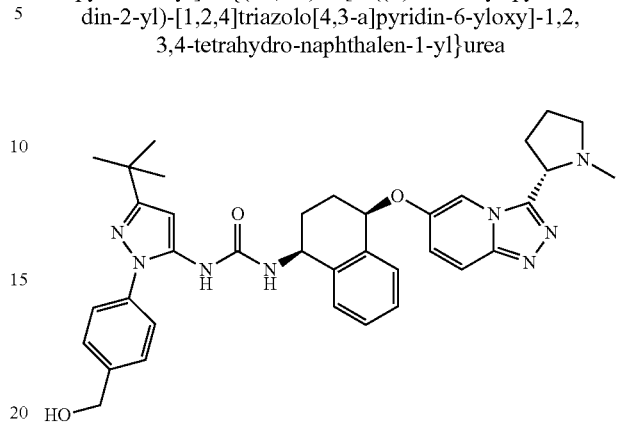

A stirred solution of Intermediate 32c (50 mg, 0.17 mmol) and 5-tert-butyl-2-p-tolyl-2H-pyrazol-3-yl)-carbamic acid 2,2,2-trichloro-ethyl ester (Synthetic Communications, 2009, 39, 3999-4009, which is incorporated herein by reference in its entirety; 84 mg, 0.21 mmol) and DIPEA (90 μL, 0.52 mmol) in THF (1.7 mL) was heated at reflux for 21 h. The cooled reaction mixture was diluted with water and extracted with DCM. The combined organics were dried and concentrated in vacuo. The residue was purified by FCC, using 0-5% [2M NH$_3$ in MeOH] in DCM, to give impure product. This residue purified by HPLC (Gemini C18 column, 30-98% MeCN in H$_2$O, 0.1% HCO$_2$H) to give the title compound as a white powder after freeze-drying (37 mg, 39%). LCMS (Method 5): Rt 4.73 min, m/z 546 [MH$^+$].

e. 1-(5-tert-Butyl-2-p-tolyl-2H-pyrazol-3-yl)-3-[(1S,4R)-4-(2-morpholin-4-yl-ethoxy)-1,2,3,4-tetrahydro-naphthalen-1-yl]-urea (Example 32).

To a solution of Intermediate 32d (50 mg, 62.3 μmol in THF (1.7 mL) was added borane (1M in THF, 0.12 mL, 0.12 mmol) and the mixture stirred at 60° C. After 23 h, further borane (1M in THF, 0.31 mL, 0.31 mmol) was added. After 26 h, further borane (1M in THF, 0.31 mL, 0.31 mmol) was added. After 3 d, the cooled reaction mixture was diluted with water and extracted with DCM. The combined organics were dried and concentrated in vacuo. The residue was purified by HPLC (Gemini C18 column, 20-98% MeCN in H$_2$O, 0.1% HCO$_2$H) to give the title compound as a white powder after freeze-drying (15 mg, 47%). LCMS (Method 5): Rt 3.64 min, m/z 532 [MH$^+$]. $^1$H NMR (400 MHz, CDCl$_3$): 1.32 (9H, s), 1.93-1.96 (3H, m), 2.02-2.07 (1H, m), 2.32 (4H, t, J 4.5), 2.38 (3H, s), 2.47 (1H, dt, J 13.0, 5.3), 2.61 (1H, ddd, J 13.0, 7.3, 5.4), 3.56-3.58 (5H, m), 3.67-3.68 (1H, m), 4.35-4.37 (1H, m), 4.98-5.02 (1H, m), 5.50 (1H, d, J 8.8), 6.27 (2H, s), 7.18-7.28 (5H, m), 7.30-7.32 (1H, m), 7.36 (2H, d, J 8.2).

a. [5-tert-Butyl-2-(4-hydroxymethyl-phenyl)-2H-pyrazol-3-yl]-carbamic acid 2,2,2-trichloro-ethyl ester (Intermediate 33a).

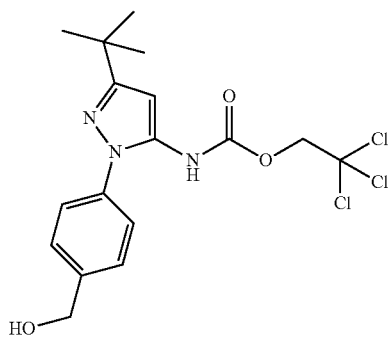 [SMILES: CC(C)(C)c1cc(NC(=O)OCC(Cl)(Cl)Cl)n(-c2ccc(CO)cc2)n1]

To a suspension of [4-(5-amino-3-tert-butyl-pyrazol-1-yl)-phenyl]-methanol (WO 2011/070368, which is incorporated herein by reference in its entirety; 3.05 g, 12.4 mmol) in aq. NaOH solution (1 M, 31 mL, 31 mmol) and EtOAc (30 mL) at RT was added 2,2,2-trichloroethyl chloroformate (1.88 mL, 13.7 mmol) over 3 min (CARE: exotherm to ~35° C.) and the mixture stirred at RT for 1 h. The aqueous layer was extracted with EtOAc (20 mL), then the combined organics washed with brine (25 mL), dried (Na$_2$SO$_4$), filtered and concentrated in vacuo to leave a pale orange solid. Recrystallisation from hot cyclohexane-EtOAc (3:1, 30 mL) and drying in vacuo gave the title compound as a flocculent off-white solid (3.87 g, 74%). LCMS (Method 3): Rt 4.00 min, m/z 420, 422 [MH$^+$].

b. 1-[5-tert-Butyl-2-(4-hydroxymethyl-phenyl)-2H-pyrazol-3-yl]-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}urea (Example 33).

A mixture of Intermediate 5c (109 mg, 0.300 mmol) and Intermediate 33a (126 mg, 0.300 mmol) in 1,4-dioxane (3 mL) and DIPEA (78 μL, 0.45 mmol) was stirred at 80° C. for 3 h, and then at 95° C. for 2 h. The cooled mixture was concentrated in vacuo. The residue was purified by FCC, using 0-14% MeOH in DCM, to give the title compound as an off-white powder after freeze-drying (95 mg, 50%). LCMS (Method 5): Rt 3.26 min, m/z 635.3 [MH$^+$]. $^1$H NMR (400 MHz, d$_6$-DMSO): 1.27 (9H, s), 1.81-2.26 (11H, m), 2.31-2.40 (1H, m) 3.10-3.17 (1H, m), 3.99 (1H, br t, J 8.1), 4.56 (2H, d, J 5.6), 4.78-4.87 (1H, m), 5.29 (1H, t, J 5.7), 5.37-5.42

(1H, m), 6.33 (1H, s), 7.11 (1H, d, J 8.7), 7.24-7.47 (9H, m), 7.75 (1H, d, J 9.7), 8.07 (1H, s), 8.24 (1H, br d).

Example 34

1-[5-tert-Butyl-2-(4-hydroxymethyl-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea

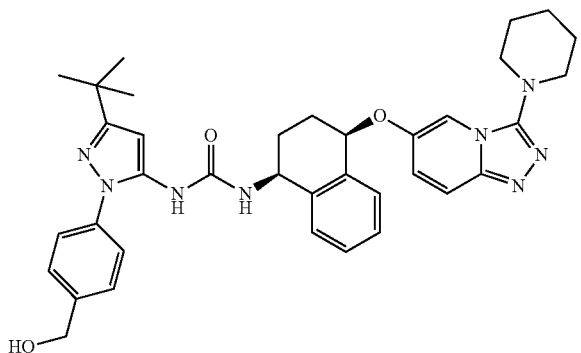 [SMILES: CC(C)(C)c1cc(NC(=O)N[C@H]2CC[C@@H](Oc3ccc4nnc(N5CCCCC5)n4c3)c3ccccc32)n(-c2ccc(CO)cc2)n1]

A mixture of Intermediate 3c (109 mg, 0.300 mmol) and Intermediate 33a (126 mg, 0.300 mmol) in 1,4-dioxane (3 mL) and DIPEA (78 μL, 0.45 mmol) was stirred at 80° C. for 3 h, and then at 95° C. for 2 h. The cooled mixture was concentrated in vacuo. The residue was purified by FCC, using 0-14% MeOH in DCM, to give the title compound as an off-white powder after freeze-drying (95 mg, 50%). LCMS (Method 5): Rt 4.21 min, m/z 635.2 [MH$^+$]. $^1$H NMR (400 MHz, d$_6$-DMSO): 1.28 (9H, s), 1.56-2.17 (10H, m), 3.11-3.17 (4H, m), 4.56 (2H, d, J 5.7), 4.77-4.86 (1H, m), 5.29 (1H, t, J 5.7), 5.52-5.57 (1H, br t), 6.33 (1H, s), 7.09 (1H, d, J 8.4), 7.16 (1H, dd, J 9.7, 2.2), 7.25-7.47 (8H, m), 7.58-7.64 (2H, m), 8.07 (1H, s).

Example 35

1-{5-tert-Butyl-2-[3-(2-hydroxy-ethyl sulfanyl)-phenyl]-2H-pyrazol-3-yl}-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea

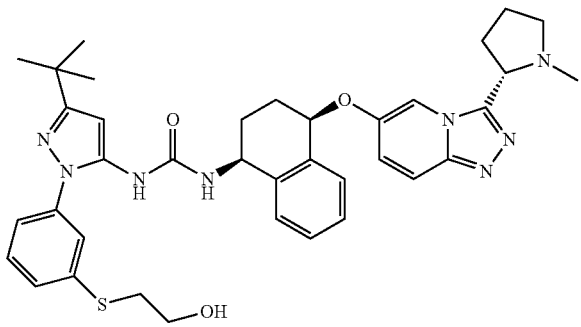 [SMILES: CN1CCC[C@H]1c1nnc2ccc(O[C@@H]3CC[C@H](NC(=O)Nc4cc(C(C)(C)C)nn4-c4cccc(SCCO)c4)c4ccccc43)cn12]

a. Di-tert-butyl 1-{3-[(2-{[tert-butyl(dimethyl)silyl]oxy}ethyl)sulfanyl]phenyl}hydrazine-1,2-dicarboxylate (Intermediate 35a).

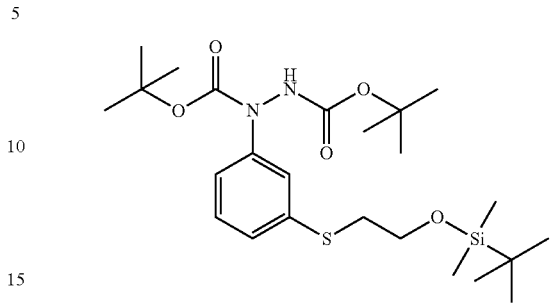

A mixture of 3-bromothiophenol (1.00 g, 5.29 mmol), bromoethoxydimethylsilyl ether (1.36 mL, 6.35 mmol) and K$_2$CO$_3$ (1.46 g, 10.6 mmol) in acetone (15 mL) was stirred at RT overnight. The mixture was filtered, evaporated, and the residue redissolved in dry THF (15 mL) and cooled to −78° C. nBuLi (1.6M in hexanes, 4.5 mL, 7.28 mmol) was added dropwise and the mixture stirred for 10 min. Di-tert-butyl azodicarboxylate (1.54 g, 6.68 mmol) was added in one portion at −78° C. and the mixture stirred for 20 min. The mixture was then allowed to warm to RT over 2 h. The reaction was quenched with sat. aq. NH$_4$Cl solution (15 mL), then extracted with EtOAc (3×15 mL). The combined organic extracts were washed with brine (20 mL), dried (Na$_2$SO$_4$) and concentrated in vacuo. The residue was purified by FCC, using 0-20% EtOAc in pentane, to give the title compound as a pale yellow oil (1.68 g, 64%). $^1$H NMR (400 MHz, CDCl$_3$): 0.04 (6H, s), 0.84 (9H, s), 1.48 (18H, m), 3.04 (2H, t), 3.79 (2H, t), 7.14-7.28 (3H, m), 7.42 (1H, s).

b. 2-[3-(5-Amino-3-tert-butyl-pyrazol-1-yl)phenylsulfanyl]-ethanol (Intermediate 35b).

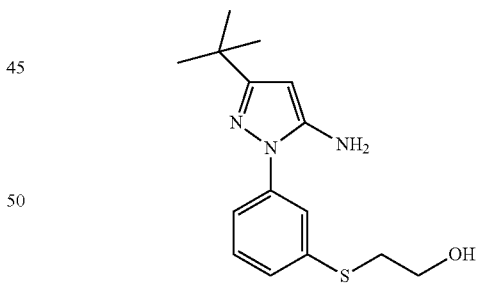

A mixture of Intermediate 35a (1.68 g, 3.37 mmol), pivaloyl acetonitrile (0.42 g, 3.37 mmol) and concentrated HCl solution (1.7 mL) in ethanol (10 mL) was heated under reflux for 3 h. After cooling, the pH was adjusted to 7 (using sat. aq. NaHCO$_3$ solution) and the mixture diluted with water (20 mL) and extracted with EtOAc (3×20 mL). The combined organic extracts were washed with brine (20 mL), dried (Na$_2$SO$_4$) and concentrated in vacuo. The residue was purified by FCC, eluting with 20-80% EtOAc in pentane, to give the title compound as a pale yellow oil (458 mg, 47%). LCMS (Method 1): Rt 2.35 min, m/z 292 [MH$^+$].

c. {5-tert-Butyl-2-[3-(2-hydroxy-ethylsulfanyl)-phenyl]-2H-pyrazol-3-yl}-carbamic acid 2,2,2-trichloro-ethyl ester (Intermediate 35c).

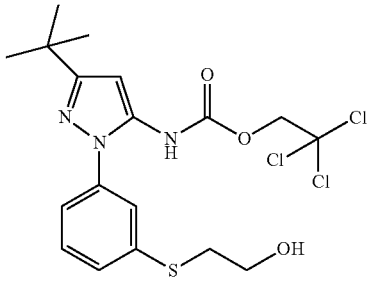 [SMILES: CC(C)(C)c1cc(NC(=O)OCC(Cl)(Cl)Cl)n(-c2cccc(SCCO)c2)n1]

2,2,2-Trichloroethyl chloroformate (0.10 mL, 0.78 mmol) was added to a solution of Intermediate 35b (176 mg, 0.60 mmol) and DIPEA (0.31 mL, 1.81 mmol) in THF (10 mL) and the mixture stirred at RT for 3 h. The mixture was diluted with water (15 mL), extracted with EtOAc (3×20 mL), then the combined organic extracts dried (Na$_2$SO$_4$) and concentrated in vacuo. The residue was suspended in cyclohexane, and filtered to give the title compound as a yellow solid (280 mg, 100%). LCMS (Method 1): Rt 3.93 min, m/z 466, 468 [MH$^+$]

d. 1-{5-tert-Butyl-2-[3-(2-hydroxy-ethylsulfanyl)-phenyl]-2H-pyrazol-3-yl}-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea (Example 35).

A mixture of Intermediate 5c (109 mg, 0.3 mmol) and Intermediate 35c (140 mg, 0.3 mmol) in 1,4-dioxane (3 mL) and DIPEA (78 µL, 0.45 mmol) was stirred at 90° C. for 4 h. The cooled mixture was concentrated in vacuo. The residue was purified by FCC, using 0-14% MeOH in DCM, to give the title compound as an off-white powder after freeze-drying (115 mg, 56%). LCMS (Method 5): Rt 3.47 min, m/z 681 [MH$^+$]. $^1$H NMR (400 MHz, d$_6$-DMSO): 1.28 (9H, s), 1.83-2.26 (11H, m), 2.31-2.39 (1H, m), 3.04 (2H, t, J 6.8), 3.09 (1H, m), 3.59 (2H, q, J 6.0), 3.99 (1H, t, J 8.2), 4.78-4.86 (1H, m), 4.95 (1H, t, J 5.6), 5.36-5.41 (1H, m), 6.33 (1H, s), 7.08 (1H, d, J 8.4), 7.24-7.46 (9H, m), 7.75 (1H, d, J 9.6), 8.12 (1H, s), 8.25 (1H, br d).

Example 36

1-[5-(2-Hydroxy-1,1-dimethyl-ethyl)-2-p-tolyl-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea

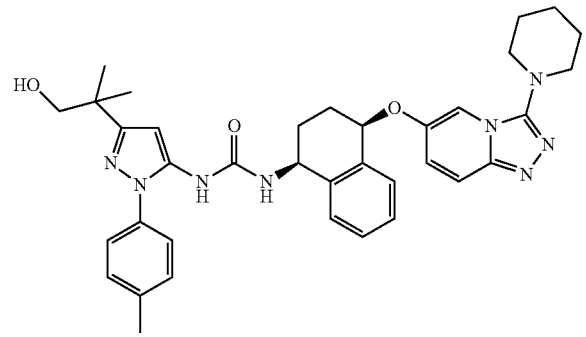 [SMILES: Cc1ccc(-n2nc(C(C)(C)CO)cc2NC(=O)N[C@H]2CC[C@@H](Oc3ccc4nnc(N5CCCCC5)n4c3)c3ccccc32)cc1]

The title compound was prepared as an off-white solid (120 mg, 68%) using Intermediate 3c (100 mg, 0.28 mmol) and [5-(2-hydroxy-1,1-dimethyl-ethyl)-2-p-tolyl-2H-pyrazol-3-yl]-carbamic acid 2,2,2-trichloro-ethyl ester (WO 2009/015000, which is incorporated herein by reference in its entirety; 138 mg, 0.34 mmol) in a similar manner to Example 34. LCMS (Method 5): Rt 4.02 min, m/z 635 [MH$^+$]. $^1$H NMR (400 MHz, d$_6$-DMSO): 1.21 (6H, s), 1.58-1.64 (2H, m), 1.69-1.75 (4H, m), 1.81-1.97 (2H, m), 2.00-2.16 (2H, m), 2.36 (3H, s), 3.14 (4H, t, J 5.4), 3.43 (2H, s), 4.55 (1H, br s), 4.79-4.85 (1H, m), 5.54 (1H, t, J 4.3), 6.32 (1H, s), 7.08 (1H, d, J 8.6), 7.16 (1H, dd, J 4.9, 2.3), 7.26-7.39 (8H, m), 7.59-7.63 (2H, m), 8.07 (1H, s).

Example 37

1-[5-tert-Butyl-2-(4-hydroxymethyl-phenyl)-2H-pyrazol-3-yl]-3-{(1S,3S)-3-[3-((S)-1-methyl-pyrrolidin-2-yl)-[1,2,4]triazolo[4,3-a]pyridin-6-yloxy]-indan-1-yl}-urea

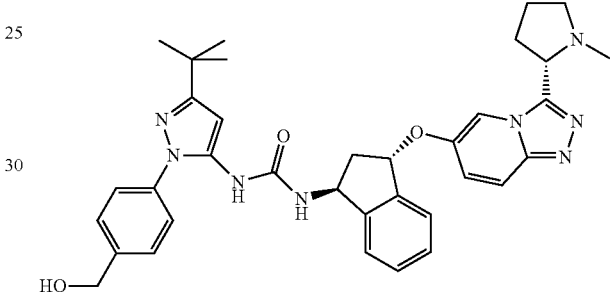

a. (1S,3S)-3-[3-((S)-1-Methyl-pyrrolidin-2-yl)-[1,2,4]triazolo[4,3-a]pyridin-6-yloxy]-indan-1-ylamine (Intermediate 37a).

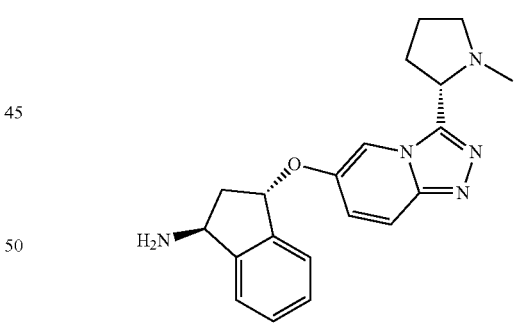

(1S,3S)-3-Amino-indan-1-ol (110 mg, 0.74 mmol) was added to a suspension of NaH (60% in mineral oil, 87 mg, 2.17 mmol) in anhydrous DMF (5 mL) at RT and stirred for 20 min. Intermediate 5b (160 mg, 0.72 mmol) was then added in one portion and the mixture heated at 60° C. for 3 h. After cooling the mixture was diluted with water (20 mL) and extracted with EtOAc (3×50 mL). The combined organics were washed with brine (50 mL), dried (MgSO$_4$) and evaporated in vacuo. The residue was purified by FCC, using 0-10% MeOH in DCM, to give the title compound as a foam (132 mg, 52%). LCMS (Method 1): Rt 0.34 min, m/z 350 [MH$^+$]. $^1$H NMR (300 MHz, CDCl$_3$): 1.95-2.16 (6H, m), 2.24 (3H, s), 2.26-2.45 (2H, m), 2.77 (1H, ddd, J 14.1, 7.0, 2.0), 3.23-3.30 (1H, m), 4.02-4.09 (1H, m), 4.71 (1H, t, J 6.8), 5.68 (1H, dd, J 6.2, 1.9), 7.04 (1H, dd, J 9.9, 2.2), 7.29-7.50 (4H, m), 7.64 (1H, dd, J 9.9, 0.9), 8.35 (1H, d, J 2.2).

b. 1-[5-tert-Butyl-2-(4-hydroxymethyl-phenyl)-2H-pyrazol-3-yl]-3-{(1S,3S)-3-[3-((S)-1-methyl-pyrrolidin-2-yl)-[1,2,4]triazolo[4,3-a]pyridin-6-yloxy]-indan-1-yl}-urea (Example 37).

A solution of Intermediate 33a (190 mg, 0.454 mmol), Intermediate 37a (132 mg, 0.378 mmol) and DIPEA (132 µL, 0.756 mmol) in anhydrous DMF (3 mL) was stirred at 100° C. for 3 h. After cooling, the mixture was partitioned between EtOAc (50 mL) and water (50 mL), and then extracted into EtOAc (3×50 mL). The combined organics were washed with brine (50 mL), dried (MgSO$_4$) and evaporated in vacuo. The residue was purified by FCC, using 0-10% MeOH in DCM, to give the title compound as give an off-white solid after freeze-drying (143 mg, 61%). LCMS (Method 5): Rt 3.23, m/z 621 [MH$^+$]. $^1$H NMR (400 MHz, d$_6$-DMSO): 1.22 (9H, s), 1.95-1.97 (3H, m), 2.07 (3H, s), 2.20-2.23 (3H, m), 2.52-2.53 (1H, m), 3.10 (1H, m), 3.92 (1H, t, J 8.1), 4.51 (2H, d, J 5.6), 5.25-5.27 (2H, m), 5.83 (1H, d, J 5.8), 6.25 (1H, s), 6.99 (1H, d, J 7.9), 7.18 (1H, dd, J 9.9, 2.2), 7.24-7.32 (2H, m), 7.35-7.41 (6H, m), 7.67 (1H, d, J 9.9), 8.10 (1H, s), 8.20 (1H, s).

Example 38

1-(5-tert-Butyl-2-p-tolyl-2H-pyrazol-3-yl)-3-{(1S,4R)-4-[3-((R)-3-hydroxy-pyrrolidin-1-yl)-[1,2,4]triazolo[4,3-a]pyridin-6-yloxy]-1,2,3,4-tetrahydro-naphthalen-1-yl}-urea

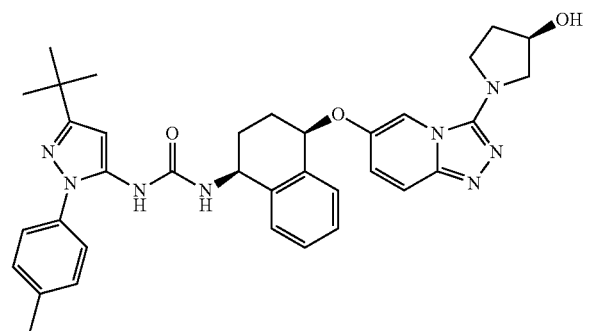 [SMILES: Cc1ccc(-n2nc(C(C)(C)C)cc2NC(=O)N[C@H]2CC[C@@H](Oc3ccc4nnc(N5CC[C@@H](O)C5)n4c3)c3ccccc32)cc1]

a. (R)-1-(6-Fluoro-[1,2,4]triazolo[4,3-a]pyridin-3-yl)-pyrrolidin-3-ol (Intermediate 38a).

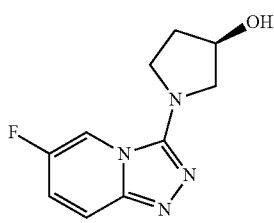 [SMILES: O[C@@H]1CCN(c2nnc3ccc(F)cn23)C1]

A mixture of Intermediate 24b (300 mg, 1.74 mmol) and (R)-3-hydroxypyrrolidine (607 mg, 9.96 mmol) in NMP (4 mL) was heated in the microwave at 160° C. for 2 h. The reaction mixture was applied to an SCX-2 cartridge (70 g) and washed with MeOH. The product was eluted with 2M NH$_3$ in MeOH; concentration in vacuo gave a residue. FCC, using 0-10% [2M NH$_3$ in MeOH] in DCM, gave the title compound (170 mg, 44%). LCMS (Method 1): Rt 0.39 min, m/z 223 [MH$^+$].

b. 6-Fluoro-3-((R)-3-triisopropylsilanyl oxy-pyrrolidin-1-yl)-[1,2,4]triazolo[4,3-a]pyridine (Intermediate 38b).

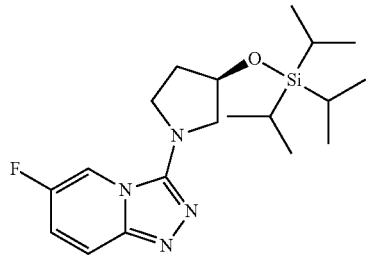 [SMILES: CC(C)[Si](O[C@@H]1CCN(c2nnc3ccc(F)cn23)C1)(C(C)C)C(C)C]

Triisopropylsilyl trifluoromethanesulfonate (280 mg, 0.919 mmol) was added to a solution of Intermediate 38a (170 mg, 0.766 mmol) and Et$_3$N (116 mg, 1.14 mmol) in a DMF (3 mL) and the mixture stirred at RT for 1 h. The reaction mixture was applied to an SCX-2 cartridge (10 g) and washed with MeOH. The product was eluted with 2M NH$_3$ in MeOH; concentration in vacuo gave a residue. FCC, using 0-10% [2M NH$_3$ in MeOH] in DCM, gave the title compound (260 mg, 90%). LCMS (Method 3): Rt 4.26 min, m/z 379 [MH$^+$].

c. (1S,4R)-4-[3-((R)-3-Triisopropylsilanyloxy-pyrrolidin-1-yl)-[1,2,4]triazolo[4,3-a]pyridin-6-yloxy]-1,2,3,4-tetrahydro-naphthalen-1-ylamine (Intermediate 38c).

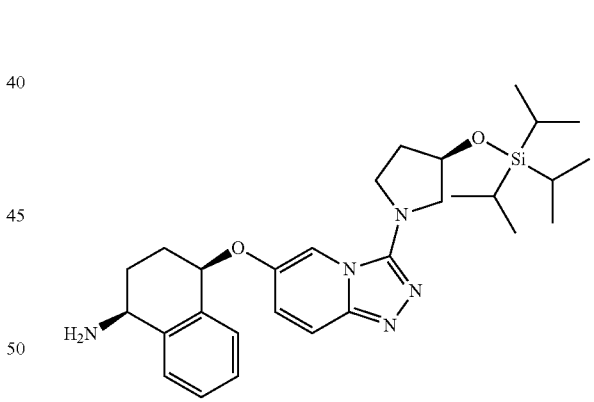

To a solution of Intermediate A (123 mg, 0.755 mmol) in DMF (4 mL) was added NaH (60% in oil, 82 mg, 2.06 mmol) and the mixture stirred at RT for 20 min, before Intermediate 38b (260 mg, 0.687 mmol) was added. This mixture was heated at 60° C. in the microwave for 3 h. The reaction mixture was applied to an SCX-2 cartridge (25 g) and washed with MeOH. The product was eluted with 2M NH$_3$ in MeOH; concentration in vacuo gave a residue. FCC, using 0-7% [2M NH$_3$ in MeOH] in DCM, gave the title compound as a viscous yellow oil (100 mg, 23%). LCMS (Method 1): Rt 2.90 min, m/z 522 [MH$^+$].

d. 1-(5-tert-Butyl-2-p-tolyl-2H-pyrazol-3-yl)-3-{(1S,4R)-4-[3-((R)-3-triisopropylsilanyloxy-pyrrolidin-1-yl)-[1,2,4]triazolo[4,3-a]pyridin-6-yloxy]-1,2,3,4-tetrahydro-naphthalen-1-yl}-urea (Intermediate 38d).

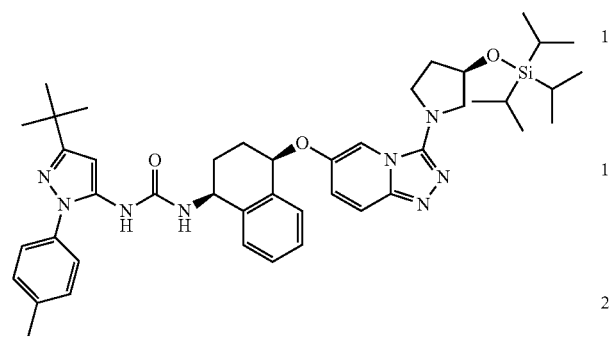

A solution of Intermediate 38c (100 mg, 0.191 mmol), (5-tert-butyl-2-p-tolyl-2H-pyrazol-3-yl)-carbamic acid 2,2,2-trichloro-ethyl ester (Synthetic Communications, 2009, 39, 3999-4009, which is incorporated herein by reference in its entirety; 115 mg, 0.286 mmol) and DIPEA (100 mg, 0.764 mmol) in DMF (2 mL) was stirred at 60° C. for 1 h. The reaction mixture was applied to an SCX-2 cartridge (10 g) and washed with MeOH. The product was eluted with 2M $NH_3$ in MeOH; concentration in vacuo gave a residue. FCC, using 0-10% [2M $NH_3$ in MeOH] in DCM, gave the title compound as a viscous yellow oil (80 mg, 53%). LCMS (Method 4): Rt 4.55 min, m/z 777 [MH+].

e. 1-(5-tert-Butyl-2-p-tolyl-2H-pyrazol-3-yl)-3-{(1S,4R)-4-[3-((R)-3-hydroxy-pyrrolidin-1-yl)-[1,2,4]triazolo[4,3-a]pyridin-6-yloxy]-1,2,3,4-tetrahydro-naphthalen-1-yl}-urea (Example 38).

To a solution of Intermediate 38d (80 mg, 0.10 mmol) in THF (1 mL) at −30° C. was added TBAF (1M in THF, 150 μL, 0.150 mmol) and the mixture was allowed to warm to RT over 1 h. The reaction mixture was applied to an SCX-2 cartridge (5 g) and washed with MeOH. The product was eluted with 2M $NH_3$ in MeOH; concentration in vacuo gave a residue. Purification by HPLC (C6-Ph column, 35-75% MeCN in $H_2O$, 0.1% $HCO_2H$) gave the title compound as a white powder after freeze-drying (22 mg, 35%). LCMS (Method 5): Rt 4.01 min, m/z 621 [MH+]. $^1$H NMR (400 MHz, $d_4$-MeOH): 1.29 (9H, s), 1.86-2.13 (4H, m), 2.14-2.28 (2H, m), 2.38 (3H, s), 3.40-3.45 (1H, m), 3.49-3.56 (1H, m), 3.66-3.71 (1H, m), 3.74-3.81 (1H, m), 4.50-4.55 (1H, m), 4.85-4.91 (1H, m), 5.37 (1H, t J 4.2), 6.33 (1H, s), 7.10 (1H, dd, J 9.8, 2.2), 7.19-7.36 (8H, m), 7.43 (1H, d, J 9.8), 7.76 (1H, d, J 1.6).

Example 39

1-{5-tert-Butyl-2-[3-(2-hydroxy-ethoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea

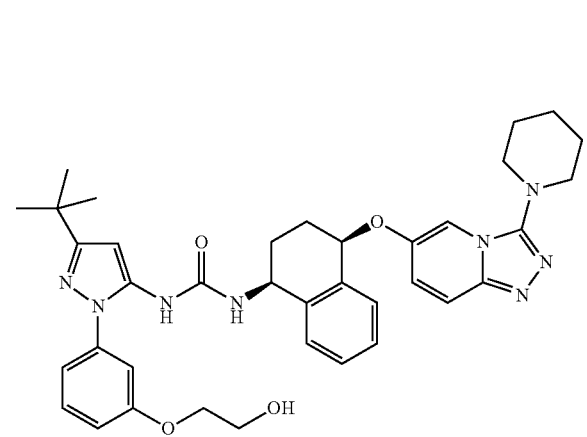 [SMILES: CC(C)(C)c1cc(NC(=O)N[C@H]2CC[C@@H](Oc3ccc4nnc(N5CCCCC5)n4c3)c3ccccc32)n(-c2cccc(OCCO)c2)n1]

a. 5-tert-Butyl-2-{3-[2-(tetrahydro-pyran-2-yloxy)-ethoxy]-phenyl}-2H-pyrazol-3-ylamine (Intermediate 39a).

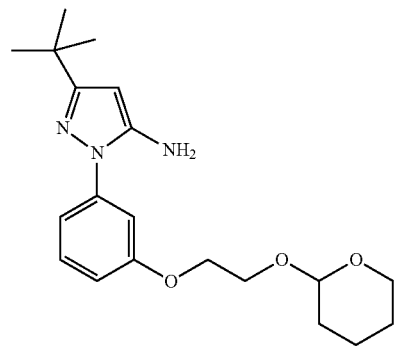 [SMILES: CC(C)(C)c1cc(N)n(-c2cccc(OCCOC3CCCCO3)c2)n1]

DIAD (847 μL, 4.32 mmol) was added slowly to a solution of 3-(5-amino-3-tert-butyl-1H-pyrazol-1-yl)phenol (US 2006/35922, which is incorporated herein by reference in its entirety; 500 mg, 2.16 mmol), 2-(tetrahydro-pyran-2-yloxy)-ethanol (439 μL, 3.25 mmol) and $Ph_3P$ (1.13 g, 4.32 mmol) in THF (10.0 mL) and the mixture stirred for 72 h. The reaction mixture was partitioned between EtOAc (75 mL) and $H_2O$ (75 mL) and the aqueous layer extracted with EtOAc (3×). The combined organic layers were dried ($MgSO_4$), filtered and evaporated in vacuo. Purification by FCC, using 5-60% EtOAc in cyclohexane, gave the title compound (1.26 g). LCMS (Method 4): Rt 2.77, m/z 360 [MH+].

b. (5-tert-Butyl-2-{3-[2-(tetrahydro-pyran-2-yloxy)-ethoxy]-phenyl}-2H-pyrazol-3-yl)-carbamic acid 2,2,2-trichloro-ethyl ester (Intermediate 39b).

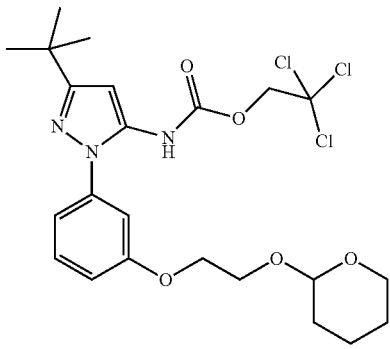 [SMILES: CC(C)(C)c1cc(NC(=O)OCC(Cl)(Cl)Cl)n(-c2cccc(OCCOC3CCCCO3)c2)n1]

The title compound was prepared starting from 2,2,2-trichloroethylchloroformate and Intermediate 39a by using an analogous procedure to that described for Intermediate 35c. LCMS (Method 4): Rt 3.85, m/z 536 [MH+].

c. 1-(5-tert-Butyl-2-{3-[2-(tetrahydro-pyran-2-yloxy)-ethoxy]-phenyl}-2H-pyrazol-3-yl)-3-[(1S,4R)-4-(3-piperidin-1-yl-[1,2,4]triazolo[4,3-a]pyridin-6-yloxy)-1,2,3,4-tetrahydro-naphthalen-1-yl]-urea (Intermediate 39c).

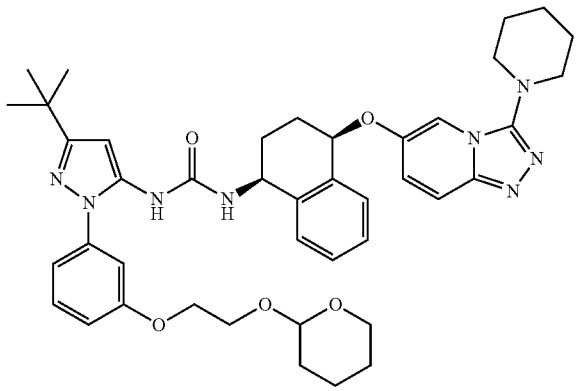 [SMILES: CC(C)(C)c1cc(NC(=O)N[C@H]2CC[C@@H](Oc3ccc4nnc(N5CCCCC5)n4c3)c3ccccc32)n(-c2cccc(OCCOC3CCCCO3)c2)n1]

A solution of Intermediate 39b (287 mg, 0.53 mmol), Intermediate 3c (177 mg, 0.49 mmol) and DIPEA (256 µL, 1.46 mmol) in THF (5 ml) was stirred at 60° C. for 16.5 h. Water was added and the mixture extracted with DCM (3×20 mL). The combined organics were dried and concentrated in vacuo. The residue was purified by FCC, using 0-5% [2M NH$_3$ in MeOH] in DCM, to give the title compound as an off-white powder (361 mg, 99%). LCMS (Method 3): Rt 4.05 min, m/z 749 [MH+].

d. 1-{5-tert-Butyl-2-[3-(2-hydroxy-ethoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea (Example 39).

Pyridinium p-toluenesulfonate (362 mg, 1.44 mmol) was added to a solution of Intermediate 39c (360 mg, 0.48 mmol) in MeOH (5 mL). The solution was stirred at 40° C. for 19 h, then diluted with water and extracted with DCM (3×20 mL). The combined organics were dried and concentrated in vacuo. The residue was purified by FCC, using 0-7.5% [2M NH$_3$ in MeOH] in DCM, to give the title compound as a white powder after freeze-drying (218 mg, 68%). LCMS (Method 5): Rt 4.22 min, m/z 665 [MH+]. $^1$H NMR (400 MHz, d$_6$-DMSO): 1.28 (9H, s), 1.60-1.63 (2H, m), 1.70-1.75 (4H, m), 1.86-1.92 (2H, m), 2.01-2.06 (1H, m), 2.10-2.16 (1H, m), 3.14 (4H, t, J 5.2), 3.71 (2H, q, J 5.1), 4.03 (2H, t, J 5.0), 4.79-4.82 (1H, m), 4.87 (1H, t, J 5.5), 5.54 (1H, t, J 4.3), 6.33 (1H, s), 6.96 (1H, m), 7.11-7.22 (4H, m), 7.34-7.46 (5H, m), 7.61-7.64 (2H, m), 8.11 (1H, s).

Example 40

1-{5-tert-Butyl-2-[3-(2-dimethylamino-ethoxy)-phenyl]-2H-pyrazol-3-yl}-3-[(1S,4R)-4-(3 triazolo[4,3-a]pyridin-6-yloxy)-1,2,3,4-tetrahydro-naphthalen-1-yl]-urea partial formate salt

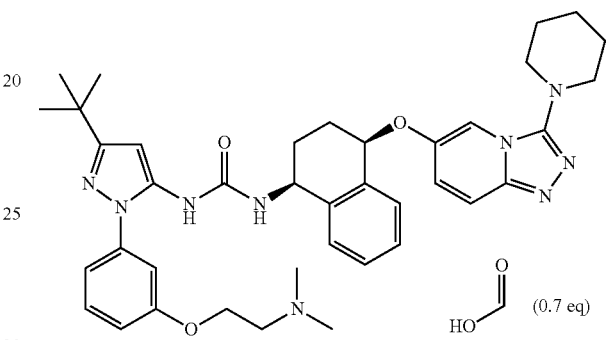

a. Methanesulfonic acid 2-[3-(3-tert-butyl-5-{3-[(1S,4R)-4-(3-piperidin-1-yl-[1,2,4]triazolo[4,3-c]pyridin-6-yloxy)-1,2,3,4-tetrahydro-naphthalen-1-yl]-ureido}-pyrazol-1-yl)-phenoxy]-ethyl ester (Intermediate 40a).

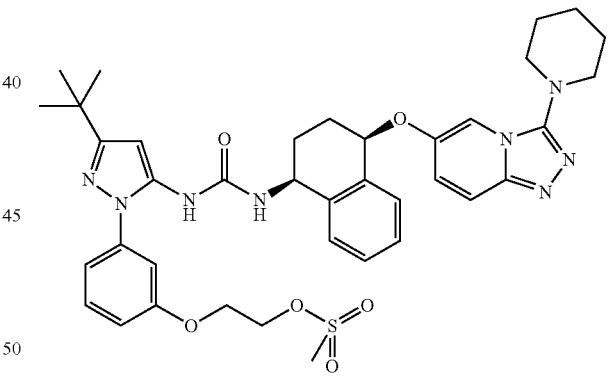

Methane sulfonylchloride (46.0 µL, 0.59 mmol) was added to an ice cold solution of Example 39 (187 mg, 0.28 mmol) and DIPEA (122 µL, 0.70 mmol) in DCM (3.0 mL). After 2.5 h the reaction was partitioned between DCM and water. The aqueous layer was then extracted with DCM (3×). The combined organic layers were washed with brine, dried (MgSO$_4$), filtered and evaporated in vacuo to give the title compound (208 mg, 99%). LCMS (Method 2): Rt 3.38 min, m/z 743 [MH+].

b. 1-{5-tert-Butyl-2-[3-(2-dimethylamino-ethoxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea, partial formate salt (Example 40).

Dimethylamine (2M in MeOH, 1.12 mL, 2.24 mmol) was added to a solution of Intermediate 40a (208 mg, 0.28 mmol)

in THF (3.0 mL). The reaction was heated to 50° C. in a sealed environment overnight. Further dimethylamine (2M in MeOH, 250 μL, 0.50 mmol) was added and heating continued for 8 h then the mixture was cooled and partitioned between EtOAc and water. The aqueous layer was then extracted with EtOAc (3×). The combined organic layers were washed with brine, dried (MgSO₄), filtered and evaporated in vacuo. The residue was purified by FCC, using 0-10% [2M NH₃ in MeOH] in DCM. Further purification by HPLC (C18 X-select column, 20-98% MeCN in H₂O, 0.1% HCO₂H) gave the title compound as a white powder after freeze-drying (110 mg, 57%). LCMS (Method 5): Rt 3.47 min, m/z 692.5 [MH⁺]. ¹H NMR (400 MHz, d₄-MeOD): 1.30 (9H, s), 1.63-1.69 (2H, m), 1.73-1.80 (4H, m), 1.88-2.04 (2H, m), 2.04-2.14 (1H, m), 2.22-2.32 (1H, m), 2.60 (6H, s), 3.08-3.14 (4H, m), 3.17 (2H, t, J 5.4), 4.23 (2H, t, J 5.4), 4.89 (1H, dd, J 8.7, 5.8), 5.41 (1H, t, J 8.2), 6.34 (1H, s), 7.03-7.07 (1H, ddd, J 8.5, 2.4, 0.6), 7.09-7.13 (2H, m), 7.18-7.25 (3H, m), 7.26-7.31 (2H, m), 7.39-7.44 (1H, t, J 7.8), 7.50-7.54 (2H, m), 8.45 (0.7H, br s).

Example 41

1-{5-tert-Butyl-2-[3-(4-methyl-piperazin-1-ylmethyl)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea

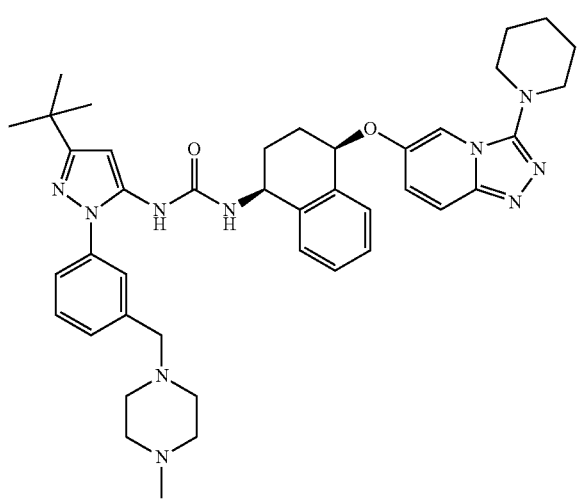 [SMILES: CN1CCN(Cc2cccc(-n3nc(C(C)(C)C)cc3NC(=O)N[C@H]3CC[C@@H](Oc4ccc5nnc(N6CCCCC6)n5c4)c4ccccc43)c2)CC1]

To a solution of Example 29 (100 mg, 0.15 mmol) and Et₃N (65 μL, 0.47 mmol) in THF (7 mL) at 0° C. was added mesyl chloride (19 μL, 0.19 mmol), and the mixture stirred for 30 min. To the solution was added 1-methyl piperazine (52 μL, 0.47 mmol) and the solution heated at reflux for 35 min. Water was added and the mixture extracted with DCM. The combined organics were dried and concentrated in vacuo. The residue was purified by HPLC (Gemini C18 column, 30-98% MeCN in H₂O, 0.1% HCO₂H) to give the title compound as a white powder after freeze-drying (32 mg, 28%). LCMS (Method 5): Rt 3.52 min, m/z 717 [MH⁺]. ¹H NMR (400 MHz, CDCl₃): 1.34 (9H, s), 1.66 (2H, q, J 5.4), 1.72-1.76 (4H, m), 1.90-1.99 (1H, m), 2.04-2.13 (3H, m), 2.23 (3H, s), 2.39-2.55 (10H, m), 3.16 (4H, t, J 5.2), 3.60 (1H, d, J 13.4), 3.62 (1H, d, J 13.4), 5.13 (1H, td, J 8.7, 5.3), 5.21 (1H, t, J 4.4), 6.00 (1H, br s), 6.37 (1H, s), 6.91 (1H, br s), 6.97-6.98 (1H, m), 7.23 (1H, d, J 7.5), 7.29-7.54 (9H, m).

Example 42

1-{5-tert-Butyl-2-[3-(2-hydroxy-ethoxy)-phenyl]-2H-pyrazol-3-yl}-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea

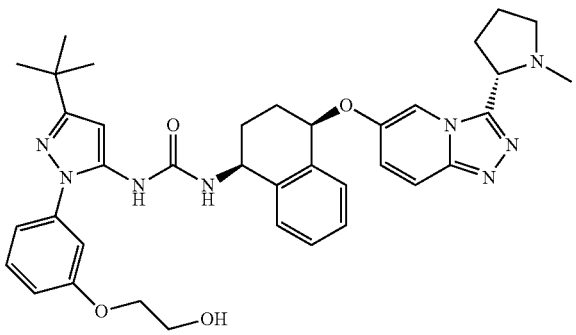 [SMILES: CN1CCC[C@H]1c1nnc2ccc(O[C@@H]3CC[C@H](NC(=O)Nc4cc(C(C)(C)C)nn4-c4cccc(OCCO)c4)c4ccccc43)cn12]

a. 1-(5-tert-Butyl-2-{3-[2-(tetrahydro-pyran-2-yloxy)-ethoxyl-phenyl}-2H-pyrazol-3-yl)-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea (Intermediate 42a).

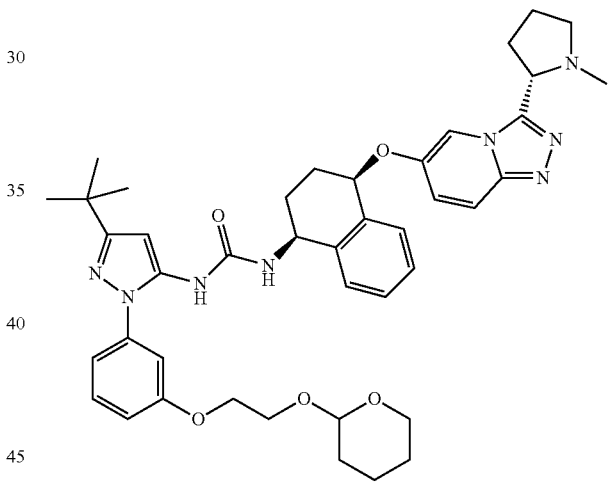

A mixture of Intermediate 5c (150 mg, 0.410 mmol) and Intermediate 39b (230 mg, 0.430 mmol) in 1,4-dioxane (4 mL) and DIPEA (113 μL, 0.65 mmol) was stirred at 90° C. for 4.5 h. The mixture was concentrated in vacuo. The residue was purified by FCC twice, using 0-10% MeOH in DCM, to give the title compound as a pale yellow foam (234 mg, 76%). LCMS (Method 3): Rt 3.03 min, m/z 749.2 [MH⁺].

b. 1-{5-tert-Butyl-2-[3-(2-hydroxy-ethoxy)-phenyl]-2H-pyrazol-3-yl}-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea (Example 42).

A mixture of Intermediate 42a (230 mg, 0.300 mmol) and pyridinium p-toluenesulfonate (226 mg, 0.900 mmol) in MeOH (3 mL) was stirred at RT for 15 h. Pyridinium p-toluenesulfonate (113 mg, 0.450 mmol) was added and the mixture stirred at 50-55° C. for 8 h. The cooled mixture was diluted with sat. aq. NaHCO₃ solution and extracted with DCM (3×15 mL). The combined organics were dried and concentrated in vacuo. The residue was purified by FCC, using 0-14% MeOH in DCM, to give the title compound as a white powder after freeze-drying (163 mg, 82%). LCMS (Method 5): Rt 3.33 min, m/z 665.3 [MH$^+$]. $^1$H NMR (400 MHz, d$_6$-DMSO): 1.28 (9H, s), 1.82-2.27 (11H, m), 2.31-2.39 (1H, m), 3.10-3.17 (1H, m), 3.71 (2H, q, J 5.1), 3.96-4.05 (3H, m), 4.79-4.89 (2H, m), 5.37-5.41 (1H, m), 6.34 (1H, s), 6.95-6.99 (1H, m), 7.05-7.15 (3H, m), 7.24-7.43 (6H, m), 7.75 (1H, d, J 9.9), 8.11 (1H, s), 8.25 (1H, br d).

Example 43

1-(5-tert-Butyl-2-p-tolyl-2H-pyrazol-3-yl)-3-((1S, 4R)-4-{3-[(2-dimethylamino-ethyl)-methyl-amino]-[1,2,4]triazolo[4,3-a]pyridin-6-yloxy}-1,2,3,4-tetrahydro-naphthalen-1-yl)-urea

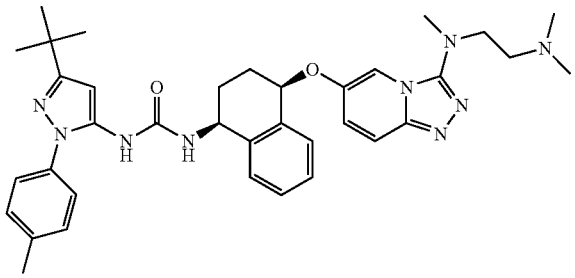 [SMILES: Cc1ccc(-n2nc(C(C)(C)C)cc2NC(=O)N[C@H]2CC[C@@H](Oc3ccc4nnc(N(C)CCN(C)C)n4c3)c3ccccc32)cc1]

a. N-(6-Fluoro-[1,2,4]triazolo[4,3-a]pyridin-3-yl)-N,N',N'-trimethyl-ethane-1,2-diamine (Intermediate 43a).

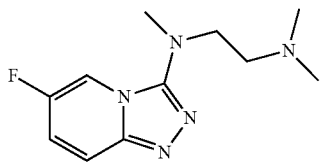 [SMILES: CN(C)CCN(C)c1nnc2ccc(F)cn12]

A mixture of Intermediate 24b (300 mg, 1.74 mmol) and N,N,N-trimethylethane-1,2-diamine (900 mg, 8.77 mmol) in NMP (2 mL) was heated in the microwave at 170° C. for 2 h. The reaction mixture was applied to an SCX-2 cartridge (25 g) and washed with MeOH. The product was eluted with 2M NH$_3$ in MeOH; concentration in vacuo gave a residue. FCC, using 0-10% [2M NH$_3$ in MeOH] in DCM, gave the title compound as a brown oil (190 mg, 46%). LCMS (Method 4): Rt 0.38 min, m/z 238 [MH$^+$].

b. N-[6-((1R,4S)-4-Amino-1,2,3,4-tetrahydro-naphthalen-1-yloxy)-[1,2,4]triazolo[4,3-a]pyridin-3-yl]-N,N',N'-trimethyl-ethane-1,2-diamine (Intermediate 43b).

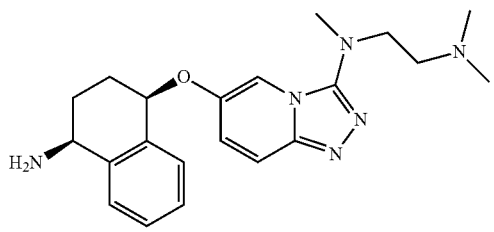 [SMILES: CN(C)CCN(C)c1nnc2ccc(O[C@@H]3CC[C@H](N)c4ccccc43)cn12]

To a solution of Intermediate A (143 mg, 0.88 mmol) in DMF (3 mL) was added
NaH (60% in oil, 96 mg, 2.4 mmol) and the mixture stirred at RT for 20 min, before Intermediate 43a (190 mg, 0.80 mmol) was added. This mixture was heated at 60° C. in the microwave for 1 h. The reaction mixture was applied to an SCX-2 cartridge and washed with MeOH. The product was eluted with 2M NH$_3$ in MeOH; concentration in vacuo gave a residue. FCC, using 0-20% [2M NH$_3$ in MeOH] in DCM, gave the title compound as a pale brown oil (140 mg, 46%). LCMS (Method 1): Rt 1.34 min, m/z 381 [MH$^+$].

c. 1-(5-tert-Butyl-2-p-tolyl-2H-pyrazol-3-yl)-3-((1S,4R)-4-{3-[(2-dimethylamino-ethyl)-methyl-amino]-[1,2,4]triazolo[4,3-a]pyridin-6-yloxy}-1,2,3,4-tetrahydro-naphthalen-1-yl)-urea (Example 43).

A solution of Intermediate 43b (140 mg, 0.36 mmol), (5-tert-butyl-2-p-tolyl-2H-pyrazol-3-yl)-carbamic acid 2,2,2-trichloro-ethyl ester (Synthetic Communications, 2009, 39, 3999-4009, which is incorporated herein by reference in its entirety; 218 mg, 0.54 mmol) and DIPEA (186 mg, 1.44 mmol) in DMF (6 mL) was stirred at 60° C. for 1 h. The reaction mixture was applied to an SCX-2 cartridge (25 g) and washed with MeOH. The product was eluted with 2M NH$_3$ in MeOH; concentration in vacuo gave a residue. FCC, using 0-10% [2M NH$_3$ in MeOH] in DCM, gave a viscous yellow gum. HPLC (C6-Ph column, 10-40% MeCN in H$_2$O, 0.1% HCO$_2$H) gave the title compound as an off-white powder after freeze-drying (80 mg, 35%). LCMS (Method 5): Rt 3.67 min, ink 636.3 [MH$^+$]. $^1$H NMR (400 MHz, d$_4$-MeOH): 1.30 (9H, s), 1.86-2.15 (3H, m), 2.19-2.30 (1H, m), 2.38 (3H, s), 2.57 (6H, s), 2.92 (3H, s), 3.00 (2H, t J 6.2), 3.46-3.60 (2H, m), 4.89 (1H, m), 5.42 (1H, t, J 3.9), 6.33 (1H, s), 7.16-7.36 (9H, m), 7.52 (1H, d, J 10.1), 7.90 (1H, s).

Example 44

1-[5-tert-Butyl-2-(3-piperidin-1-ylmethyl-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea

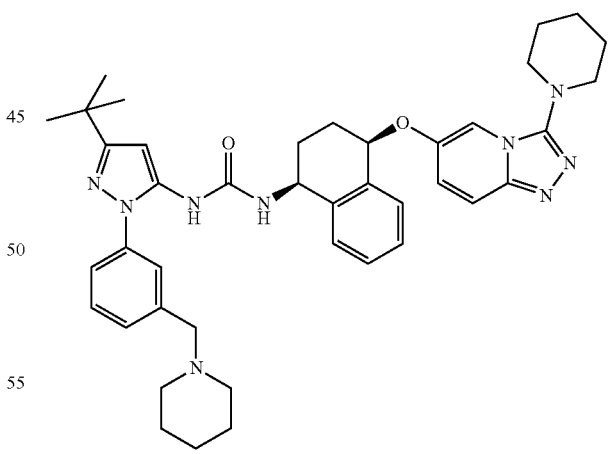

To a solution of Example 29 (100 mg, 0.15 mmol) and Et$_3$N (65 μL, 0.47 mmol) in THF (7 mL) at 0° C. was added mesyl chloride (19 μL, 0.19 mmol), and the mixture stirred for 0.5 h. To the solution was added piperidine (47 μL, 0.47 mmol), and the mixture heated at reflux for 16 h. NaI (24 mg, 0.15 mmol) was added and the solution heated at reflux for 1 h. The cooled reaction mixture was diluted with water and extracted with DCM. The combined organics were dried and concentrated in vacuo. The residue was purified by HPLC (XBridge C18 column, 20-98% MeCN in H₂O, 0.1% HCO₂H) to give the impure product. The residue was re-purified by HPLC (Gemini C18 column, 20-98% MeCN in H₂O, 0.1% HCO₂H), the product containing fractions were partitioned between DCM and saturated NaHCO₃ solution. The combined organics were dried and concentrated in vacuo to give the title compound as a white powder (14 mg, 12%). LCMS (Method 5): Rt 3.60 min, m/z 702 [MH⁺]. ¹H NMR (400 MHz, d₄-MeOH): 1.34 (9H, s), 1.39-1.44 (2H, m), 1.52-1.55 (4H, m), 1.67-1.71 (2H, m), 1.77-1.80 (4H, m), 2.03-2.08 (3H, m), 2.24-2.33 (1H, m), 3.20 (4H, t, J 5.3), 3.55 (2H, s), 4.93 (1H, dd, J 8.6, 5.6), 5.44 (1H, t, J 4.2), 6.38 (1H, s), 7.21-7.33 (5H, m), 7.40-7.56 (6H, m).

Example 45

1-(5-tert-Butyl-2-p-tolyl-2H-pyrazol-3-yl)-3-((1S, 4R)-4-{3-[methyl-(2-morpholin-4-yl-ethyl)-amino]- [1,2,4]triazolo[4,3-a]pyridin-6-yloxy}-1,2,3,4-tetrahydro-naphthalen-1-yl)-urea

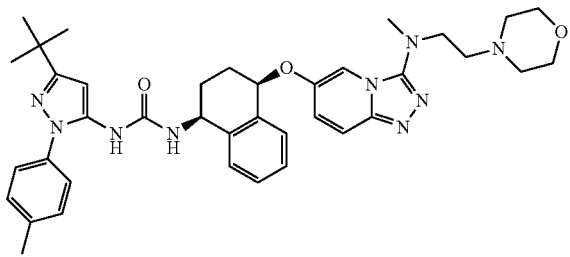 [SMILES: Cc1ccc(-n2nc(C(C)(C)C)cc2NC(=O)N[C@H]2CC[C@@H](Oc3ccc4nnc(N(C)CCN5CCOCC5)n4c3)c3ccccc32)cc1]

a. (2-Morpholin-4-yl-ethyl)-carbamic acid tert-butyl ester (Intermediate 45a).

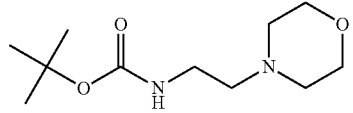 [SMILES: CC(C)(C)OC(=O)NCCN1CCOCC1]

4-(2-Aminoethyl)morpholine (5.00 g, 38.5 mmol) was added to a stirred mixture of di-tert-butyl dicarbonate (8.38 g, 38.5 mmol) and indium(III)chloride (85 mg, 0.39 mmol). This mixture was stirred for 1 min before being diluted with EtOAc (200 mL) and washed with water (×2). The organic layer was dried (MgSO₄) and was evaporated in vacuo to give the title compound as a clear oil (8.14 g, 92%). ¹H NMR (400 MHz, CDCl₃): 1.45 (9H, s), 2.40-2.50 (6H, m), 3.23 (2H, q, J 5.9), 3.70 (4H, t, J 4.7), 4.96 (1H, br s).

b. Methyl-(2-morpholin-4-yl-ethyl)-amine (Intermediate 45b).

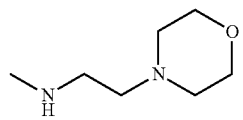

To a solution of Intermediate 45a (6.0 g, 24.6 mmol) in THF (123 mL) was added lithium aluminium hydride (2.33 g, 61.5 mmol) portionwise, then the mixture was stirred at reflux for 4 h. A further portion of lithium aluminium hydride (1.28 g, 33.6 mmol) was added to the cooled solution, then the mixture was stirred at reflux for a further 8 h. Water (3.75 mL) was added dropwise, followed by 4N aqueous NaOH (11.3 mL) and water (3.75 ml). The mixture was filtered, washed with diethyl ether, dried (MgSO₄) and concentrated in vacuo to give the title compound as a yellow oil (3.67 g, 99%). ¹H NMR (400 MHz, CDCl₃): 2.40-2.52 (9H, m), 2.67 (2H, t, J 2.7), 3.70 (4H, t, J 4.5).

c. (6-Fluoro-[1,2,4]triazolo[4,3-a]pyridin-3-yl)-methyl-(2-morpholin-4-yl-ethyl)-amine (Intermediate 45c).

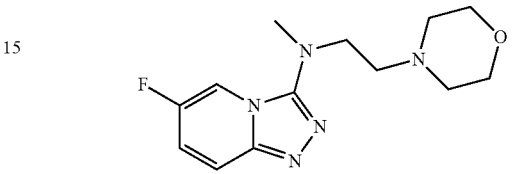

A mixture of Intermediate 24b (300 mg, 1.74 mmol) and Intermediate 45b (1.26 g, 8.77 mmol) in NMP (2 mL) was heated in the microwave at 170° C. for 2 h. The reaction mixture was applied to an SCX-2 cartridge (25 g) and washed with MeOH. The product was eluted with 2M NH₃ in MeOH; concentration in vacuo gave a residue. FCC, using 0-10% [2M NH₃ in MeOH] in DCM, gave the title compound as an orange oil (350 mg, 71%). ¹H NMR (400 MHz, CDCl₃): 2.41-2.52 (4H, m), 2.58 (2H, t, J 5.6), 3.03 (3H, s), 3.27 (2H, t, J 6.0), 3.62 (4H, t, J 5.2), 7.04-7.08 (1H, m), 7.58-7.65 (1H, m), 8.39 (1H, t, J 2.4).

d. [6-((1R,4S)-4-Amino-1,2,3,4-tetrahydro-naphthalen-1-yloxy)-[1,2,4]triazolo[4,3-a]pyridin-3-yl]-methyl-(2-morpholin-4-yl-ethyl)-amine (Intermediate 45d).

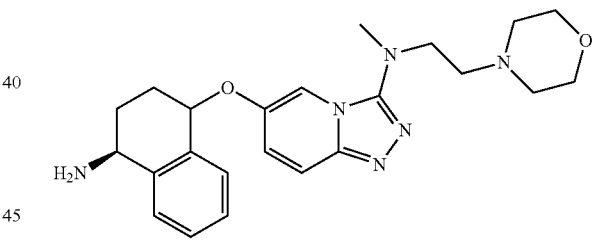

To a solution of Intermediate A (225 mg, 1.38 mmol) in DMF (3 mL) was added NaH (60% in oil, 150 mg, 3.75 mmol) and the mixture stirred at RT for 20 min, before Intermediate 45c (350 mg, 1.25 mmol) was added. This mixture was stirred at 60° C. for 7 h. The reaction mixture was applied to an SCX-2 cartridge (25 g) and washed with MeOH. The product was eluted with 2M NH₃ in MeOH; concentration in vacuo gave a residue. FCC, using 0-20% [2M NH₃ in MeOH] in DCM, gave the title compound as an orange oil (270 mg, 51%). LCMS (Method 4): Rt 0.22 min, m/z 423 [MH⁺].

e. 1-(5-tert-Butyl-2-p-tolyl-2H-pyrazol-3-yl)-3-((1S,4R)-4-{3-[methyl-(2-morpholin-4-yl-ethyl)-amino]-[1,2,4]triazolo[4,3-a]pyridin-6-yloxy}-1,2,3,4-tetrahydro-naphthalen-1-yl)-urea (Example 45).

A solution of Intermediate 45d (270 mg, 0.63 mmol), (5-tert-butyl-2-p-tolyl-2H-pyrazol-3-yl)-carbamic acid 2,2,2-trichloro-ethyl ester (Synthetic Communications, 2009, 39, 3999-4009, which is incorporated herein by reference in its entirety; 380 mg, 0.95 mmol) and DIPEA (325 mg, 2.52 mmol) in DMF (8 mL) was stirred at 60° C. for 1 h. The reaction mixture was applied to an SCX-2 cartridge (25 g) and washed with MeOH. The product was eluted with 2M NH$_3$ in MeOH; concentration in vacuo gave a residue. FCC, using 0-10% [2M NH$_3$ in MeOH] in DCM, gave a stiff yellow gum which was further purified by HPLC (C18 column, 10-45% MeCN in H$_2$O, 0.1% HCO$_2$H). The residue was recrystallized from boiling EtOAc to give the title compound as a white powder (60.0 mg, 14%). LCMS (Method 5): Rt 3.65 min, m/z 678.3 [MH$^+$]. $^1$H NMR (400 MHz, d$_4$-MeOH): 1.30 (9H, s), 1.87-2.15 (3H, m), 2.18-2.27 (1H, m), 2.32 (4H, t, J 4.4), 2.38 (3H, s), 2.55 (2H, t, J 5.6), 2.96 (3H, s), 3.31-3.40 (6H, m), 4.89 (1H, m), 5.40 (1H, t, J 4.2), 6.33 (1H, s), 7.19-7.36 (9H, m), 7.53 (1H, d, J 10.0), 7.92 (1H, d, J 1.6).

Example 46

1-(5-tert-Butyl-2-p-tolyl-2H-pyrazol-3-yl)-3-{(1S, 4R)-4-[3-((R)-1-morpholin-4-yl-ethyl)-[1,2,4]triazolo[4,3-a]pyridin-6-yloxy]-1,2,3,4-tetrahydro-naphthalen-1-yl}-urea and 1-(5-tert-Butyl-2-p-tolyl-2H-pyrazol-3-yl)-3-{(1S,4R)-4-[3-((S)-1-morpholin-4-yl-ethyl)-[1,2,4]triazolo[4,3-a]pyridin-6-yloxy]-1,2,3,4-tetrahydro-naphthalen-1-yl}-urea (1:1 mixture of diastereomers)

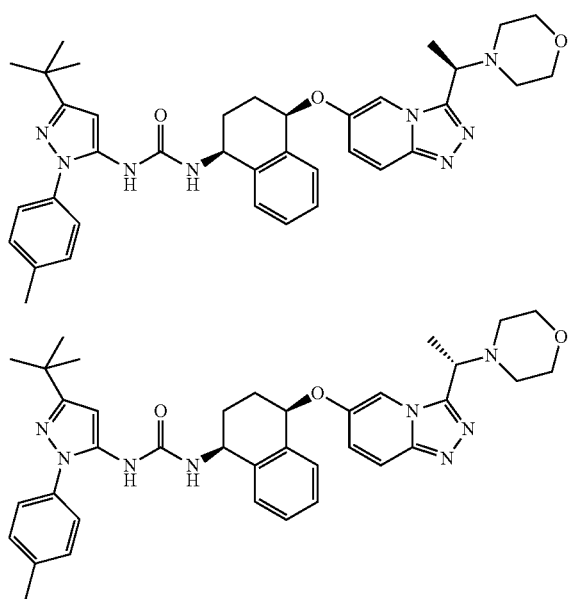

a. 2-Morpholin-4-yl-propionic acid N'-(5-fluoro-pyridin-2-yl)-hydrazide (Intermediate 46a).

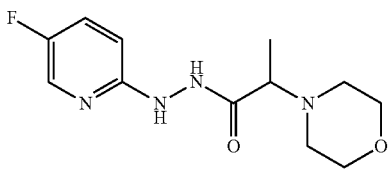 [SMILES: CC(C(=O)NNc1ccc(F)cn1)N1CCOCC1]

To a solution of (5-fluoro-pyridin-2-yl)-hydrazine (1.62 g, 12.8 mmol), 2-(morpholin-4-yl)propanoic acid (Enamine, 2.50 g, 12.8 mmol), HOBt.H$_2$O (196 mg, 1.28 mmol) and Et$_3$N (2.14 mL, 15.3 mmol) in DCM (50 mL) was added EDC (2.94 g, 15.3 mmol) and the brown solution stirred at RT for 16 h. Water (20 mL) and brine (20 mL) were added, and the mixture shaken. The aqueous layer was extracted with DCM (20 mL), then the combined organics were passed through a hydrophobic frit and concentrated in vacuo to give the title compound as a brown foam (3.43 g, >99%). LCMS (Method 3): Rt 0.44 min, m/z 269 [MH$^+$].

b. 6-Fluoro-3-(1-morpholin-4-yl-ethyl)-[1,2,4]triazolo[4,3-a]pyridine (Intermediate 46b).

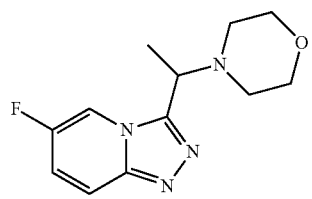 [SMILES: CC(c1nnc2ccc(F)cn12)N1CCOCC1]

To a solution of Intermediate 46a (3.43 g, 12.8 mmol), Ph$_3$P (6.71 g, 25.6 mmol) and Et$_3$N (7.14 mL, 51.2 mmol) in THF (75 mL) at 0° C. was added hexachloroethane (6.06 g, 25.6 mmol) and the solution stirred at RT for 4 h. The brown suspension was filtered and the solid washed with THF (10 mL). The combined organics were applied to an SCX-2 cartridge, which was washed with DCM-MeOH (1:1, 100 mL) and MeOH (100 mL). The product was eluted with 2M NH$_3$ in MeOH; concentration in vacuo gave an off-white solid. FCC, using 1-5% [2M NH$_3$ in MeOH] in DCM, gave the title compound as an off-white solid (1.70 g, 53%). $^1$H NMR (300 MHz, CDCl$_3$): 1.66 (3H, d, J 6.8), 2.45-2.60 (4H, m), 3.63-3.76 (4H, m), 4.28 (1H, q, J 6.8), 7.21 (1H, ddd, J 10.0, 7.5, 2.3), 7.76 (1H, ddd, J 10.0, 4.9, 0.9), 8.50 (1H, ddd, J 3.9, 2.3, 0.9).

c. (1S,4R)-4-[3-((R)-1-Morpholin-4-yl-ethyl)-[1,2,4]triazolo[4,3-a]pyridin-6-yloxy]-1,2,3,4-tetrahydro-naphthalen-1-ylamine and (1S,4R)-4-[3-((S)-1-Morpholin-4-yl-ethyl)-[1,2,4]triazolo[4,3-a]pyridin-6-yloxy]-1,2,3,4-tetrahydro-naphthalen-1-ylam (1:1 mixture diastereomers) (Intermediate 46c).

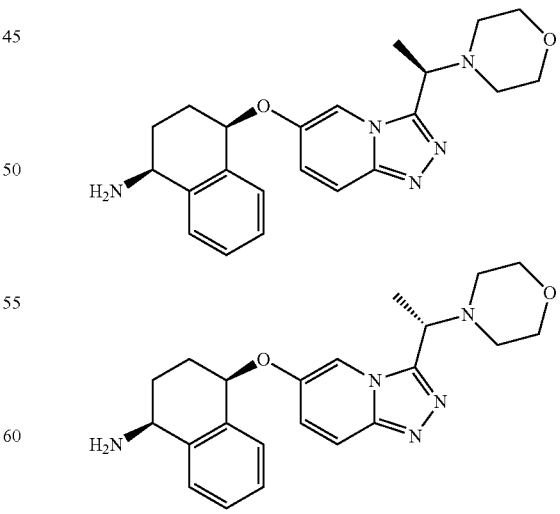

A suspension of Intermediate A (343 mg, 2.10 mmol) and NaH (60% dispersion in oil, 240 mg, 6.00 mmol) in dry DMF (10 mL) at RT under Ar was stirred for 30 min (CARE: gas evolution), then Intermediate 46b (501 mg, 2.00 mmol) was added and the brown mixture stirred at 60° C. under Ar for 1 h. The solution was concentrated in vacuo, redissolved in MeOH (4 mL) and AcOH (0.60 mL, 10.0 mmol), then applied to an SCX-2 cartridge (20 g) and washed with MeOH (100 mL). The product was eluted with 2M NH$_3$ in MeOH (50 mL); concentration in vacuo gave a dark brown foam. FCC, using 2-8% [2M NH$_3$ in MeOH] in DCM, gave the title compounds as a light brown foam (558 mg, 71%). LCMS (Method 3): Rt 0.44 min, m/z 394 [MH$^+$].

d. 1-(5-tert-Butyl-2-p-tolyl-2H-pyrazol-3-yl)-3-{(1S,4R)-4-[3-((R)-1-morpholin-4-yl-ethyl)-[1,2,4]triazolo[4,3-a]pyridin-6-yloxy]-1,2,3,4-tetrahydro-naphthalen-1-yl}-urea and 1-(5-tert-Butyl-2-p-tolyl-2H-pyrazol-3-yl)-3-{(1S,4R)-4-[3-((S)-1-morpholin-4-yl-ethyl)-[1,2,4]triazolo[4,3-a]pyridin-6-yloxy]-1,2,3,4-tetrahydro-naphthalen-1-yl}-urea (1:1 mixture of diastereomers) (Example 46).

A yellow solution of (5-tert-butyl-2-p-tolyl-2H-pyrazol-3-yl)-carbamic acid 2,2,2-trichloro-ethyl ester (Synthetic Communications, 2009, 39, 3999-4009, which is incorporated herein by reference in its entirety; 223 mg, 0.550 mmol), Intermediate 46c (197 mg, 0.500 mmol) and DIPEA (0.109 mL, 0.625 mmol) in dioxane (10 mL) was stirred at 60° C. for 18 h. The cooled solution was concentrated in vacuo, suspended in water (10 ml) and extracted with DCM (2×10 mL). The combined organics were passed through a hydrophobic frit and concentrated in vacuo to leave a yellow-brown gum. FCC, using 2-7% [2M NH$_3$ in MeOH] in DCM, gave the title compounds as a pale yellow solid (192 mg, 59%). LCMS (Method 5): two peaks in 1:1 ratio, Rt 4.13 and 4.15 min, ink 649 [MH$^+$]. $^1$H NMR (400 MHz, d$_6$-DMSO): 1.27 (9H, s), 1.52 (1.5H, d, J 6.8), 1.53 (1.5H, d, J 6.8), 1.83-1.99 (2H, m), 2.10-2.17 (2H, m), 2.36 (3H, s), 2.43 (2H, t, J 4.5), 2.51-2.55 (2H, m), 3.47-3.55 (4H, m), 4.46 (0.5H, q, J 6.8), 4.49 (0.5H, q, J 6.8), 4.83 (1H, m), 5.45 (0.5H, t, J 4.5), 5.52 (0.5H, t, J 4.5), 6.33 (1H, s), 7.10 (1H, d, J 8.5), 7.21-7.44 (9H, m), 7.73 (1H, dd, J 9.9, 2.6), 8.03 (1H, s), 8.32 (0.5H, d, J 2.1), 8.37 (0.5H, d, J 2.1).

Example 47

1-(5-tert-Butyl-2-p-tolyl-2H-pyrazol-3-yl)-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea

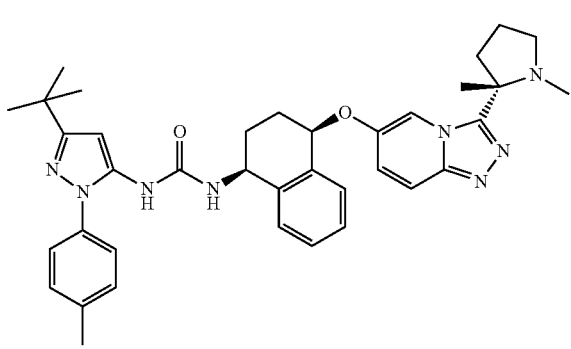 [SMILES: Cc1ccc(-n2nc(C(C)(C)C)cc2NC(=O)N[C@H]2CC[C@@H](Oc3ccc4nnc([C@]5(C)CCCN5C)n4c3)c3ccccc32)cc1]

a. (S)-1,2-Dimethyl-pyrrolidine-2-carboxylic acid N'-(5-fluoro-pyridin-2-yl)-hydrazide (Intermediate 47a)

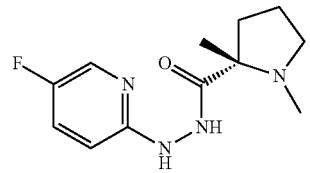 [SMILES: CN1CCC[C@@]1(C)C(=O)NNc1ccc(F)cn1]

To a suspension of (S)-1,2-dimethyl-pyrrolidine-2-carboxylic acid (660 mg, 4.61 mmol), (5-fluoro-pyridin-2-yl)-hydrazine (488 mg, 3.84 mmol) and Et$_3$N (1.1 mL, 7.7 mmol) in DCM (20 mL) were added HOBt.H$_2$O (51 mg, 0.38 mmol) and EDCI.HCl (884 mg, 4.61 mmol) and the mixture stirred at RT overnight. The mixture was partitioned between EtOAc/water and extracted with EtOAc. The combined organics were dried (Na$_2$SO$_4$), filtered and concentrated in vacuo. FCC, using 0-10% MeOH in DCM, gave the title compound as a brown solid (668 mg, 69%). LCMS (Method 4): Rt 0.40, m/z 253 [MH$^+$].

b. 3-((S)-1,2-Dimethyl-pyrrolidin-2-yl)-6-fluoro-[1,2,4]triazolo[4,3-a]pyridine (Intermediate 47b).

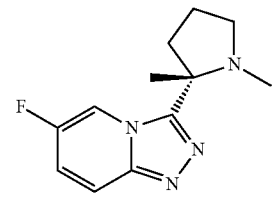 [SMILES: CN1CCC[C@@]1(C)c1nnc2ccc(F)cn12]

To a solution of Intermediate 47a (668 mg, 2.64 mmol), Et$_3$N (1.5 mL, 11 mmol) and Ph$_3$P (1.4 g, 5.3 mmol) in THF (20 mL) at 0° C. was added hexachloroethane (1.25 g, 5.29 mmol). The mixture was stirred at 0° C. for 10 min, then at RT for 1 h. The mixture was partitioned between EtOAc/water and the aqueous extracted with EtOAc. The combined organics were dried (Na$_2$SO$_4$), filtered and concentrated in vacuo. Purification by FCC, using 0-10% MeOH in EtOAc, gave the title compound as a pale brown solid (300 mg, 49%). LCMS (Method 4): Rt 0.39, m/z 235 [MH$^+$].

c. (1S,4R)-4-[3-((S)-1,2-Dimethyl-pyrrolidin-2-yl)-[1,2,4]triazolo[4,3-a]pyridin-6-yloxy]-1,2,3,4-tetrahydro-naphthalen-1-ylamine (Intermediate 47c).

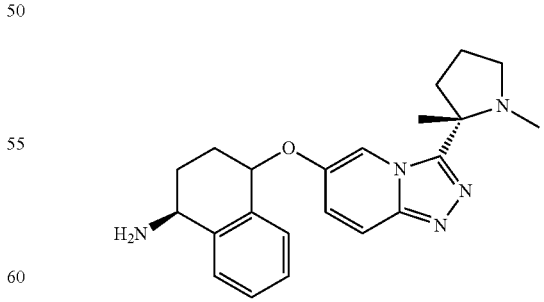

To a solution of Intermediate 47b (150 mg, 0.64 mmol) and Intermediate A (126 mg, 0.64 mmol) in DMF (3 mL) was added NaH (60% in mineral oil, 90 mg, 2.24 mmol) portionwise. The mixture was stirred at 60° C. for 1.5 h then allowed to cool to RT. The mixture was carefully quenched by pouring into MeOH (10 mL), then applied to an SCX-2 cartridge and washed with MeOH. The product was eluted with 2M NH₃ in MeOH; concentration in vacuo gave a residue. FCC, using 0-10% [2M NH₃ in MeOH] in DCM, gave the title compound as a brown solid (180 mg, 75%). LCMS (Method 4): Rt 0.49, m/z 378 [MH⁺].

d. 1-(5-tert-Butyl-2-p-tolyl-2H-pyrazol-3-yl)-3-{(1S,4R)-4-[3-((S)-1,2-dimethyl-pyrrolidin-2-yl)-[1,2,4]triazolo[4,3-a]pyridin-6-yloxy]-1,2,3,4-tetrahydro-naphthalen-1-yl}-urea (Example 47).

The title compound was prepared as an off-white solid (80 mg, 53%) using (5-tert-butyl-2-p-tolyl-2H-pyrazol-3-yl)-carbamic acid 2,2,2-trichloro-ethyl ester (Synthetic Communications, 2009, 39, 3999-4009, which is incorporated herein by reference in its entirety; 80 mg, 0.20 mmol) and Intermediate 47c (90 mg, 0.24 mmol) in a similar manner to Example 1, step d. LCMS (Method 5): Rt 3.83 min, m/z 633 [MH⁺]. ¹H NMR (400 MHz, d₆-DMSO): 1.27 (9H, s), 1.51 (3H, s), 1.78-1.99 (5H, m), 2.02 (3H, s), 2.03-2.22 (3H, m), 2.36 (3H, s), 2.65 (1H, q, J 8.6), 3.11-3.17 (1H, m), 4.79-4.86 (1H, m), 5.32 (1H, t, J 4.2), 6.32 (1H, s), 7.11 (1H, d, J 8.6), 7.25-7.39 (9H, m), 7.75 (1H, d, J 9.8), 8.05 (1H, s), 8.43 (1H, d, J 2.2).

Example 48

1-{5-tert-Butyl-2-[3-(2-hydroxy-ethoxymethyl)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea

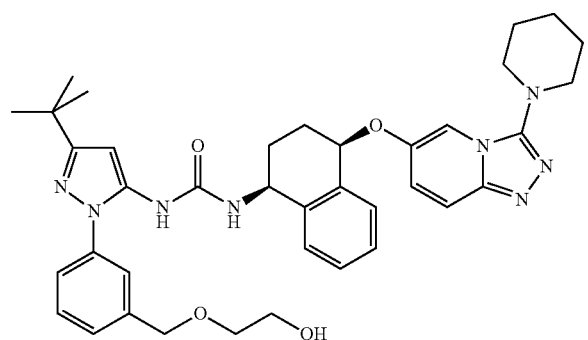 [SMILES: CC(C)(C)c1cc(NC(=O)N[C@H]2CC[C@@H](Oc3ccc4nnc(N5CCCCC5)n4c3)c3ccccc32)n(-c2cccc(COCCO)c2)n1]

To a solution of Example 29 (204 mg, 0.32 mmol) and Et₃N (134 μL, 0.97 mmol) in DCM (3.2 mL) at 0° C. was added mesyl chloride (39 μL, 0.39 mmol), and the mixture stirred for 1 h. The solution was washed with water, dried, and concentrated in vacuo to give methanesulfonic acid 3-(3-tert-butyl-5-{3-[(1S,4R)-4-(3-piperidin-1-yl-[1,2,4]triazolo[4,3-a]pyridin-6-yloxy)-1,2,3,4-tetrahydro-naphthalen-1-yl]-ureido}-pyrazol-1-yl)-benzyl ester. This was immediately dissolved in dioxane (1.5 mL) and ethylene glycol (1.5 mL) and the solution stirred at 85° C. for 1 h. The cooled reaction mixture was suspended in water and filtered to leave a solid. Purification by HPLC (XBridge C18 column, 40-98% MeCN in H₂O, 0.1% NH₄OH) gave the title compound as a white powder after freeze-drying (59 mg, 27%). LCMS (Method 5): Rt 4.27 min, m/z 679 [MH⁺]. ¹H NMR (400 MHz, d₆-DMSO): 1.28 (9H, s), 1.60-1.64 (2H, m), 1.70-1.75 (4H, m), 1.86-1.93 (2H, m), 2.03 (1H, m), 2.11 (1H, m), 3.14 (4H, t, J 5.2), 3.54-3.48 (4H, m), 4.56 (2H, s), 4.64 (1H, s), 4.80 (1H, m), 5.54 (1H, t, J 4.3), 6.34 (1H, s), 7.07 (1H, d, J 8.6), 7.16 (1H, dd, J 9.8, 2.2), 7.37-7.49 (8H, m), 7.60-7.63 (2H, m), 8.11 (1H, s).

Example 49

1-(5-tert-Butyl-2-p-tolyl-2H-pyrazol-3-yl)-3-[(1S,4R)-4-(3-[1,4]oxazepan-4-yl-[1,2,4]triazolo[4,3-a]pyridin-6-yloxy)-1,2,3,4-tetrahydro-naphthalen-1-yl]-urea

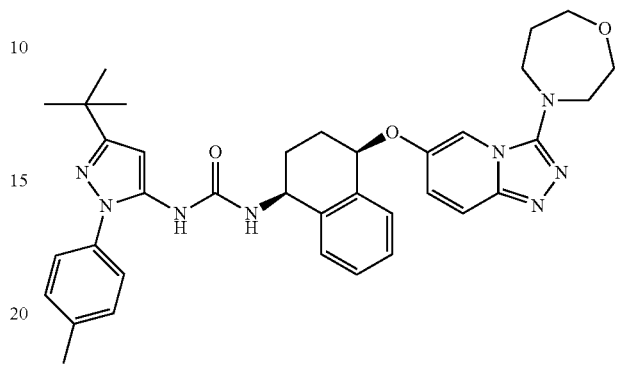

a. 6-Fluoro-3-[1,4]oxazepan-4-yl-[1,2,4]triazolo[4,3-a]pyridine (Intermediate 49a).

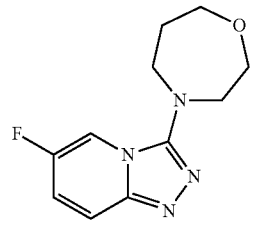 [SMILES: Fc1ccc2nnc(N3CCCOCC3)n2c1]

A solution of Intermediate 24b (429 mg, 2.50 mmol) and homomorpholine (939 mg, 9.30 mmol) in NMP (10 mL) was heated in the microwave at 170° C. for 10 h. The cooled mixture was applied to an SCX-2 cartridge (70 g), washing with methanol then eluting basic components with 0.4-2 M NH₃ in MeOH. Product containing fractions were combined and concentrated in vacuo. The residue was purified by FCC, using 0-12% [2M NH₃ in MeOH] in DCM, to give impure product. Further purified by FCC, using 0-12% MeOH in EtOAc gave the title compound as a pale brown gum (147 mg, 25%). LCMS (Method 3): Rt 2.11 min, m/z 237 [MH⁺].

b. (1S,4R)-4-(3-[1,4]Oxazepan-4-yl-[1,2,4]triazolo[4,3-a]pyridin-6-yloxy)-1,2,3,4-tetrahydro-naphthalen-1-ylamine (Intermediate 49b).

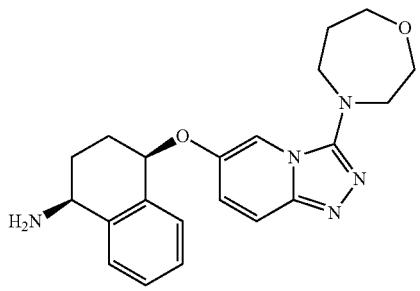 [SMILES: N[C@H]1CC[C@@H](Oc2ccc3nnc(N4CCCOCC4)n3c2)c2ccccc21]

To a solution of Intermediate A (145 mg, 0.614 mmol) in DMF (3 mL) was added NaH (60% dispersion in oil, 74 mg, 1.84 mmol). The mixture was stirred at RT for 15 min, then a solution of Intermediate 49a (100 mg, 0.614 mmol) in DMF (3 mL) was added and the mixture stirred at 60° C. for 2.25 h. The cooled mixture was diluted with water and extracted with DCM (4×25 mL). The combined organics were dried and concentrated in vacuo. The residue was purified by FCC, using 0-12% [2M NH₃ in MeOH] in DCM, to give the title compound as a pale brown gum (93 mg, 40%). LCMS (Method 3): Rt 0.43 min, m/z 380 [MH⁺].

c. 1-(5-tert-Butyl-2-p-tolyl-2H-pyrazol-3-yl)-3-[(1S,4R)-4-(3-[1,4]oxazepan-4-yl-[1,2,4]triazolo[4,3-a]pyridin-6-yloxy)-1,2,3,4-tetrahydro-naphthalen-1-yl]-urea (Example 49).

A solution of Intermediate 49b (90.0 mg, 0.237 mmol) and (5-tert-butyl-2-p-tolyl-2H-pyrazol-3-yl)-carbamic acid 2,2,2-trichloro-ethyl ester (Synthetic Communications, 2009, 39, 3999-4009, which is incorporated herein by reference in its entirety; 97 mg, 0.24 mmol) in 1,4-dioxane (3 mL) and DIPEA (63 µL, 0.36 mmol) was stirred at 90° C. for 4 h, then more DIPEA (63 µL, 0.36 mmol) was added and mixture stirred at 100-110° C. for 3.5 h. The cooled mixture was concentrated in vacuo. The residue was purified by FCC, using 0-12% [2M NH₃ in MeOH] in DCM, to give the product (31 mg, 21%). This was further purified by HPLC (C18 X-select column, 35-98% MeCN in H₂O, 0.1% HCO₂H) to give the title compound as a white powder after freeze-drying (20 mg, 13%). LCMS (Method 5): Rt 4.40 min, m/z 635.2 [MH⁺]. ¹H NMR (400 MHz, d₆-DMSO): 1.27 (9H, s), 1.80-2.18 (6H, m), 2.36 (3H, s), 3.44-3.51 (4H, m), 3.78-3.85 (4H, m), 4.77-4.85 (1H, m), 5.51 (1H, t, J 4.4), 6.32 (1H, s), 7.10-7.16 (2H, m), 7.25-7.40 (8H, m), 7.60 (1H, d, J 9.6), 7.65 (1H, d, J 1.5), 8.10 (1H, s).

Example 50

1-(5-tert-Butyl-2-{3-[4-(2-hydroxy-ethyl)-piperazin-1-ylmethyl]-phenyl}-2H-pyrazol-3-yl)-3-[(1S,4R)-4-(3-piperidin-1-yl-[1,2,4]triazolo[4,3-a]pyridin-6-yloxy)-1,2,3,4-tetrahydro-naphthalen-1-yl]-urea

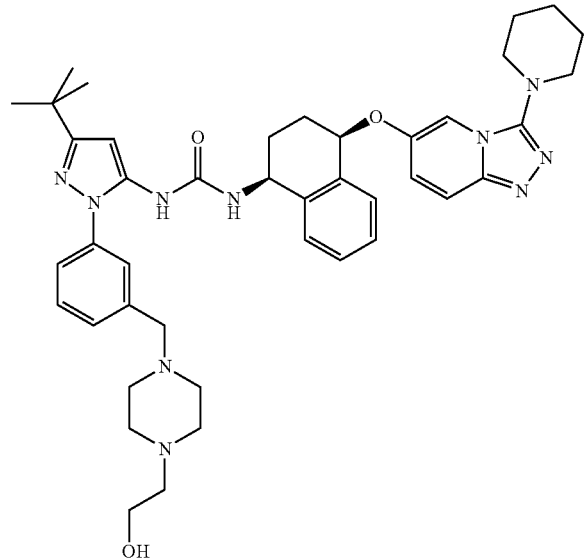 [SMILES: CC(C)(C)c1cc(NC(=O)N[C@H]2CC[C@@H](Oc3ccc4nnc(N5CCCCC5)n4c3)c3ccccc32)n(-c2cccc(CN3CCN(CCO)CC3)c2)n1]

To a solution of Example 29 (150 mg, 0.24 mmol) and Et₃N (98 µL, 0.71 mmol) in DCM (7 mL) at 0° C. was added mesyl chloride (28 µL, 0.28 mmol), and the mixture stirred for 1 h. The solution was washed with water, dried, and concentrated in vacuo to give methanesulfonic acid 3-(3-tert-butyl-5-{3-[(1S,4R)-4-(3-piperidin-1-yl-[1,2,4]triazolo[4,3-a]pyridin-6-yloxy)-1,2,3,4-tetrahydro-naphthalen-1-yl]-ureido}-pyrazol-1-yl)-benzyl ester. This was immediately dissolved in THF (2.5 mL) and DIPEA (83 µL, 0.47 mmol) then 1-(2-hydroxyethyl) piperazine (87 µL, 0.71 mmol) added and the solution stirred at reflux for 1 h. Water was added and the mixture extracted with DCM. The combined organics were dried and concentrated in vacuo. The residue was purified by HPLC (XBridge C18 column, 20-98% MeCN in H₂O, 0.1% NH₄OH) to give the title compound as a white powder after freeze-drying (45 mg, 25%). LCMS (Method 5): Rt 3.42 min, m/z 747 [MH⁺]. ¹H NMR (400 MHz, d₆-DMSO): 1.28 (9H, s), 1.60-1.64 (2H, m), 1.69-1.75 (4H, m), 1.83-1.94 (2H, m), 2.03-2.12 (2H, m), 2.29-2.45 (8H, m), 2.33 (2H, t, J 6.4), 3.14 (4H, t, J 5.2), 3.44 (2H, m), 3.49 (2H, s), 4.31 (1H, s), 4.80 (1H, m), 5.54 (1H, t, J 4.4), 6.33 (1H, s), 7.03 (1H, d, J 8.6), 7.16 (1H, dd, J 9.8, 2.2), 7.34-7.46 (8H, m), 7.60-7.63 (2H, m), 8.10 (1H, s).

Example 51

1-(2-tert-Butyl-5-p-tolyl-3H-imidazol-4-yl)-3-[(1S,4R)-4-(3-piperidin-1-yl-[1,2,4]triazolo[4,3-a]pyridin-6-yloxy)-1,2,3,4-tetrahydro-naphthalen-1-yl]-urea

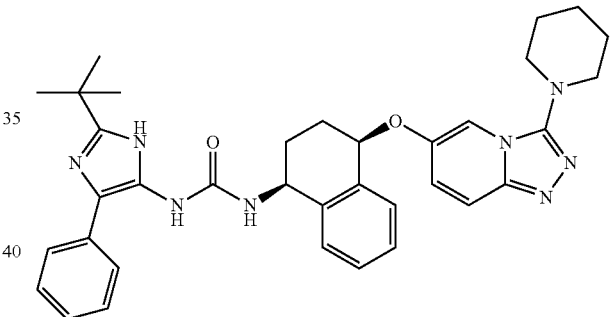

a. 2-tert-Butyl-5-p-tolyl-1H-imidazole (Intermediate 51a).

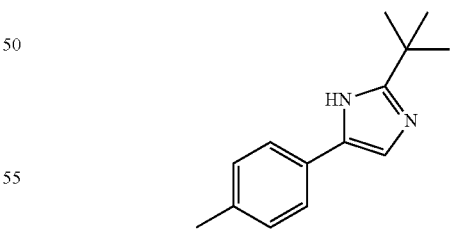

A red suspension of 2,2-dimethylpropionamide hydrochloride (Atlantic, 1.00 g, 7.32 mmol), 2-bromo-4'-methylacetophenone (Aldrich, 1.56 g, 7.32 mmol) and K₂CO₃ (1.52 g, 11.0 mmol) in DMF (20 mL) was stirred at 75° C. for 3 h. The mixture was cooled to RT, concentrated in vacuo, suspended in water (25 mL) and extracted with DCM (2×25 mL). The combined organics were passed through a hydrophobic frit, concentrated in vacuo, redissolved in MeOH (5 mL), applied to an SCX-2 cartridge (20 g) and washed with MeOH (100 mL). The product was eluted with 2M NH₃ in MeOH (60 mL); concentration in vacuo left a yellow foam (1.26 g). FCC, using 1-5% MeOH in DCM, gave the title compound as a pale yellow solid (770 mg, 49%). LCMS (Method 3): Rt 2.26 min, m/z 215 [MH⁺].

b. 2-tert-Butyl-4-nitroso-5-p-tolyl-1H-imidazole (Intermediate 51b).

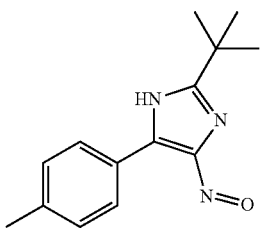 [SMILES: Cc1ccc(-c2[nH]c(C(C)(C)C)nc2N=O)cc1]

A yellow solution of Intermediate 51a (390 mg, 1.82 mmol) and isopentyl nitrite (0.294 mL, 2.18 mmol) in THF (10 mL) was stirred at 50° C. for 8 h, then cooled to RT and concentrated in vacuo to leave a dark green oil. FCC, using 0-25% EtOAc in cyclohexane, gave the title compound as a green solid (154 mg, 35%). LCMS (Method 3): Rt 3.82 min, m/z 244 [MH⁺].

c. 2-tert-Butyl-5-p-tolyl-1H-imidazol-4-ylamine (Intermediate 51c).

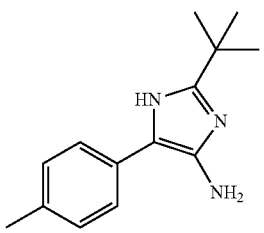 [SMILES: Cc1ccc(-c2[nH]c(C(C)(C)C)nc2N)cc1]

A suspension of Intermediate 51b (150 mg, 0.617 mmol) and Pd/C (10%, 15 mg) in EtOH (10 mL) was stirred at RT under H₂ for 2 h. The flask was evacuated and purged with N₂ thrice, then the mixture filtered through Celite, and the filter-cake washed with EtOH (10 mL). The combined organics were concentrated in vacuo to leave a red-brown gum. FCC, using 1-6% MeOH in DCM, gave the title compound as a yellow-orange gum (96.3 mg, 68%). LCMS (Method 3): Rt 2.26 min, ink 230 [MH⁺].

d. (2-tert-Butyl-5-p-tolyl-1H-imidazol-4-yl)-carbamic acid 2,2,2-trichloro-ethyl ester (Intermediate 51 d).

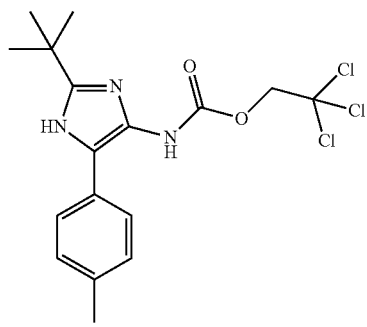 [SMILES: Cc1ccc(-c2[nH]c(C(C)(C)C)nc2NC(=O)OCC(Cl)(Cl)Cl)cc1]

To a solution of Intermediate 51c (45.3 mg, 0.197 mmol) in EtOAc (1 mL) and aqueous NaOH (1 M, 0.49 mL) was added 2,2,2-trichloroethyl chloroformate (0.0326 mL, 0.237 mmol) and the resulting mixture stirred at RT for 45 min. The layers were separated and the aqueous extracted with EtOAc (2 mL). The combined organics were washed with brine (2 mL), dried (Na₂SO₄), filtered and concentrated in vacuo to leave an orange-red gum. FCC, using 0-50% EtOAc in cyclohexane, gave the title compound as a pale orange film (44.1 mg, 55%). LCMS (Method 3): Rt 2.87 min, m/z 404, 406 [MH⁺].

e. 1-(2-tert-Butyl-5-p-tolyl-3H-imidazol-4-yl)-3-[(1S,4R)-4-(3-piperidin-1-yl-[1,2,4]triazolo[4,3-a]pyridin-6-yloxy)-1,2,3,4-tetrahydro-naphthalen-1-yl]-urea (Example 51).

An orange solution of Intermediate 51d (65.4 mg, 0.162 mmol), Intermediate 3c (55.9 mg, 0.153 mmol) and DIPEA (0.042 mL, 0.242 mmol) in dioxane (2 mL) was stirred at 60° C. for 18 h. After cooling, the mixture was concentrated in vacuo, suspended in water (5 ml) and extracted with DCM (2×5 mL). The combined organics were passed through a hydrophobic frit and concentrated in vacuo to leave an orange-brown gum. FCC, using 2-8% MeOH in DCM, gave a pale yellow solid (50.5 mg). Further purification by HPLC (C18 XBridge column, 25-75% MeCN in H₂O, 0.1% NH₄OH) gave the title compound as a white solid after freeze-drying (33.3 mg, 33%). LCMS (Method 5): Rt 3.35 min, m/z 619 [MH⁺]. ¹H NMR (400 MHz, d₆-DMSO): 3:1 ratio of tautomers: 1.30 (6.75H, s), 1.31 (2.25H, s), 1.61 (2H, m), 1.72 (4H, m), 1.83-2.00 (2H, m), 2.05 (1H, m), 2.15 (1H, m), 2.30 (0.75H, s), 2.32 (2.25H, s), 3.13 (4H, q, J 5.2), 4.87 (1H, m), 5.54 (1H, t, J 4.3), 7.14-7.19 (2.5H, m), 7.21 (1.5H, d, J 8.2), 7.25-7.40 (4H, m), 7.54 (1.5H, d, J 8.3), 7.60-7.71 (3.5H, m), 11.56 (0.75H, s), 11.68 (0.25H, s).

Example 52

1-{5-tert-Butyl-2-[3-(4-hydroxy-piperidin-1-ylmethyl)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea

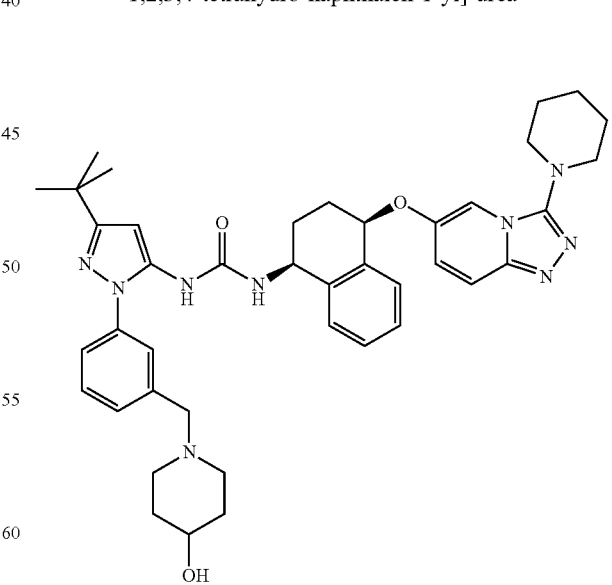

To a solution of Example 29 (150 mg, 0.24 mmol) and Et₃N (98 μL, 0.71 mmol) in DCM (7 mL) at 0° C. was added mesyl chloride (28 μL, 0.28 mmol), and the mixture stirred for 1 h. The solution was washed with water, dried, and concentrated in vacuo to give methanesulfonic acid 3-(3-tert-butyl-5-{3-[(1S,4R)-4-(3-piperidin-1-yl-[1,2,4]triazolo[4,3-a]pyridin-6-yloxy)-1,2,3,4-tetrahydro-naphthalen-1-yl]-ureido}-pyrazol-1-yl)-benzyl ester. This was immediately dissolved in THF (2.5 mL) and DIPEA (83 μL, 0.47 mmol) then 4-hydroxypiperidine (83 μL, 0.71 mmol) added and the solution stirred at reflux for 1 h. Water was added and the mixture extracted with DCM. The combined organics were dried and concentrated in vacuo. The residue was purified by FCC, using 0-10% [2M NH₃ in MeOH] in DCM, to give the product. This was purified further by HPLC (XBridge C18 column, 20-98% MeCN in H₂O, 0.1% NH₄OH) to give the title compound as a white powder after freeze-drying (30 mg, 18%). LCMS (Method 5): Rt 3.41 min, m/z 718 [MH⁺]. ¹H NMR (400 MHz, d₆-DMSO): 1.28 (9H, s), 1.34-1.40 (2H, m), 1.60-1.75 (7H, m), 1.81-1.96 (3H, m), 2.00-2.15 (4H, m), 2.64-2.69 (2H, m), 3.14 (4H, t, J 5.2), 3.40-3.45 (1H, m), 3.47 (2H, s), 4.51 (1H, d, J 3.9), 4.82 (1H, m), 5.54 (1H, t, J 4.4), 6.33 (1H, s), 7.04 (1H, d, J 8.5), 7.16 (1H, dd, J 9.8, 2.2), 7.26-7.33 (4H, m), 7.35-7.46 (4H, m), 7.60-7.63 (2H, m), 8.10 (1H, s).

Example 53

1-{5-tert-Butyl-2-[3-(2-hydroxy-ethylsulfanyl)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea

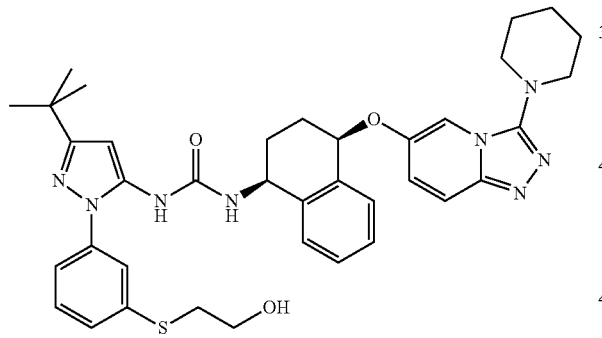

A solution of Intermediate 3c (107 mg, 0.29 mmol) and Intermediate 53c (151 mg, 0.32 mmol) in THF (3 mL) and DIPEA (169 μL, 0.97 mmol) was stirred at reflux for 20.5 h. The cooled reaction mixture was diluted with water and extracted with DCM. The combined organics were dried and concentrated in vacuo. The residue was purified by FCC, using 0-5% [2M NH₃ in MeOH] in DCM, to give the product. This residue purified further by HPLC (XBridge C18 column, 30-98% MeCN in H₂O, 0.1% NH₄OH) to give the title compound as a white powder after freeze-drying (21 mg, 10%). LCMS (Method 5): Rt 4.42 min, m/z 681 [MH⁺]. ¹H NMR (400 MHz, d₆-DMSO): 1.28 (9H, s), 1.60-1.63 (2H, m), 1.69-1.74 (4H, m), 1.86-1.93 (2H, m), 2.03 (1H, m), 2.13 (1H, m), 3.09 (2H, t, J 6.8), 3.14 (4H, t, J 5.2), 3.59 (2H, q, J 6.2), 4.80 (1H, m), 4.95 (1H, t, J 5.6), 5.54 (1H, t, J 4.3), 6.33 (1H, s), 7.07 (1H, d, J 8.6), 7.16 (1H, dd, J 9.8, 2.1), 7.35-7.47 (8H, m), 7.60-7.64 (2H, m), 8.14 (1H, s).

Example 54

1-(5-tert-Butyl-2-p-tolyl-2H-pyrazol-3-yl)-3-{(1S,4R)-4-[3-(4-hydroxymethyl-piperidin-1-yl)-[1,2,4]triazolo[4,3-a]pyridin-6-yloxy]-1,2,3,4-tetrahydro-naphthalen-1-yl}-urea

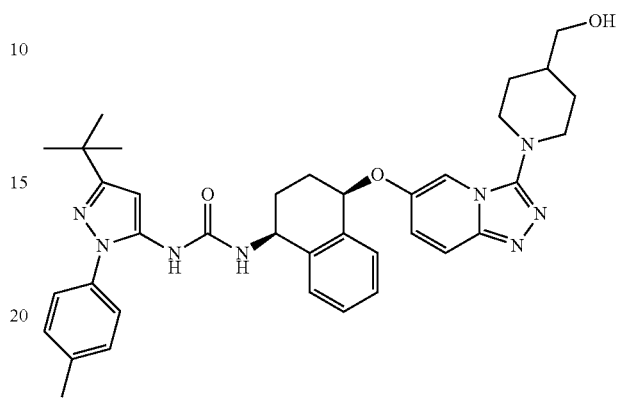

a. [1-(6-Fluoro-[1,2,4]triazolo[4,3-a]pyridin-3-yl)-piperidin-4-yl]-methanol (Intermediate 54a).

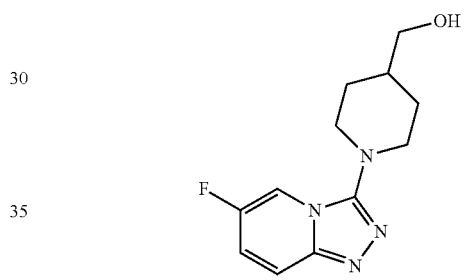

A solution of Intermediate 24b (593 mg, 3.45 mmol) and 4-piperidinemethanol (1.59 g, 13.8 mmol) in NMP (10 mL) was heated in the microwave at 170° C. for 3 h. The cooled mixture was applied to an SCX-2 cartridge (70 g), washing with methanol then eluting basic components with 0.4-2 M NH₃ in MeOH. Product containing fractions were combined and concentrated in vacuo. The residue was purified by FCC, using 0-15% MeOH in EtOAc, to give the title compound as a brown gum (481 mg, 56%). LCMS (Method 3): Rt 2.12 min, m/z 251 [MH⁺].

b. 6-Fluoro-3-(4-triisopropylsilanyloxymethyl-piperidin-1-yl)-[1,2,4]triazolo[4,3-a]pyridin (Intermediate 54b).

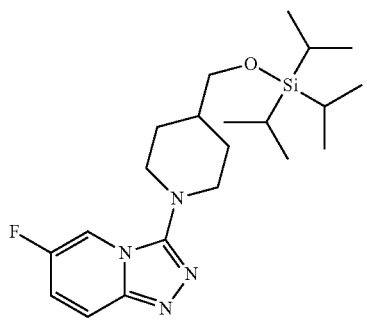 [SMILES: CC(C)[Si](OCC1CCN(c2nnc3ccc(F)cn23)CC1)(C(C)C)C(C)C]

To a solution of Intermediate 54a (470 mg, 1.88 mmol) and Et₃N (390 μL, 2.82 mmol) in DCM (5 mL) was added triisopropylsilyltrifluoromethane sulfonate (607 µL, 2.26 mmol) and the mixture stirred at RT for 0.5 h. The mixture was washed with sat. aq. NaHCO$_3$ solution, dried and concentrated in vacuo. The residue was purified by FCC, using 0-100% EtOAc in cyclohexane, then 10% MeOH in EtOAc, to give the title compound as a pale yellow solid (565 mg, 74%). LCMS (Method 3): Rt 5.21 min, m/z 407 [MH$^+$].

c. (1S,4R)-4-[3-(4-Triisopropylsilanyloxymethyl-piperidin-1-yl)-[1,2,4]triazolo[4,3-a]pyridin-6-yloxy]-1,2,3,4-tetrahydro-naphthalen-1-ylamine (Intermediate 54c).

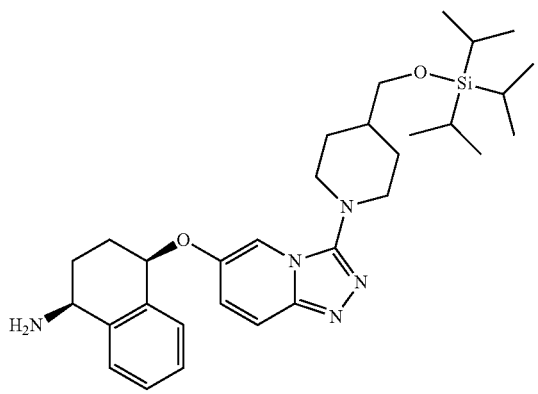 [SMILES: CC(C)[Si](OCC1CCN(c2nnc3ccc(O[C@@H]4CC[C@H](N)c5ccccc54)cn23)CC1)(C(C)C)C(C)C]

To a solution of Intermediate A (223 mg, 1.37 mmol) in DMF (3 mL) was added NaH (60% dispersion in oil, 168 mg, 4.20 mmol) and the mixture stirred at RT for 15 min. A solution of Intermediate 54b (555 mg, 1.37 mmol) in DMF (3 mL) was added and the mixture stirred at 60° C. for 1.75 h. The cooled mixture was diluted with water and extracted with DCM (5×20 mL). The combined organics were dried and concentrated in vacuo. The residue was purified by FCC, using 0-14% [2M NH$_3$ in MeOH] in DCM, to give the title compound as a brown gum (344 mg, 46%). LCMS (Method 3): Rt 3.29 min, m/z 550 [MH$^+$].

d. 1-(5-tert-Butyl-2-p-tolyl-2H-pyrazol-3-yl)-3-{(1S,4R)-4-[3-(4-triisopropyl silanyloxymethyl-piperidin-1-yl)-[1,2,4]triazolo[4,3-a]pyridin-6-yloxy]-1,2,3,4-tetrahydro-naphthalen-1-yl}-urea (Intermediate 54d).

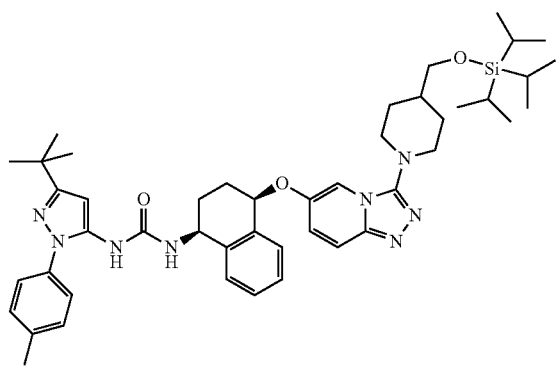 [SMILES: Cc1ccc(-n2nc(C(C)(C)C)cc2NC(=O)N[C@H]2CC[C@@H](Oc3ccc4nnc(N5CCC(CO[Si](C(C)C)(C(C)C)C(C)C)CC5)n4c3)c3ccccc32)cc1]

A solution of Intermediate 54c (171 mg, 0.311 mmol) and (5-tert-butyl-2-p-tolyl-2H-pyrazol-3-yl)-carbamic acid 2,2,2-trichloro-ethyl ester (Synthetic Communications, 2009, 39, 3999-4009, which is incorporated herein by reference in its entirety; 132 mg, 0.327 mmol) in 1,4-dioxane (3 mL) and DIPEA (87 µL, 0.50 mmol) was stirred at 90° C. for 3 h, and then at 100° C. for 2.5 h. The cooled mixture was concentrated in vacuo. The residue was purified by FCC, using 0-8% MeOH in DCM, to give the title compound as a pale brown solid (215 mg, 86%). LCMS (Method 3): Rt 5.70 min, m/z 805.4 [MH$^+$].

e. 1-(5-tert-Butyl-2-p-tolyl-2H-pyrazol-3-yl)-3-{(1S,4R)-4-[3-(4-hydroxymethyl-piperidin-1-yl)-[1,2,4]triazolo[4,3-a]pyridin-6-yloxy]-1,2,3,4-tetrahydro-naphthalen-1-yl}-urea (Example 54).

A solution of Intermediate 54d (210 mg, 0.261 mmol) and TBAF (1M in THF, 0.31 mL, 0.31 mmol) in THF (5 mL) was stirred at RT for 1.25 h. The mixture was diluted with water and extracted with DCM (3×15 mL). The combined organics were dried and concentrated in vacuo. The residue was purified by FCC, using 0-16% MeOH in DCM, to give the title compound as an off-white powder after freeze-drying (134 mg, 79%). LCMS (Method 5): Rt 4.24 min, m/z 649.2 [MH$^+$]. $^1$H NMR (400 MHz, d$_6$-DMSO): 1.27 (9H, s), 1.38-2.16 (9H, m), 2.36 (3H, s), 2.85-2.97 (2H, m), 3.28-3.49 (4H, m), 4.52 (1H, t, J 5.2), 4.78-4.85 (1H, m), 5.55 (1H, t, J 4.3), 6.32 (1H, s), 7.07 (1H, d, J 8.6), 7.15 (1H, dd, J 9.7, 2.1), 7.25-7.41 (8H, m), 7.60 (1H, d, J 9.7), 7.64 (1H, d, J 1.6), 8.04 (1H, s).

Example 55

1-(5-tert-Butyl-2-p-tolyl-2H-pyrazol-3-yl)-3-[(1S,4S)-4-(3-piperidin-1-yl-[1,2,4]triazolo[4,3-a]pyridin-6-yloxy)-1,2,3,4-tetrahydro-naphthalen-1-yl]-urea

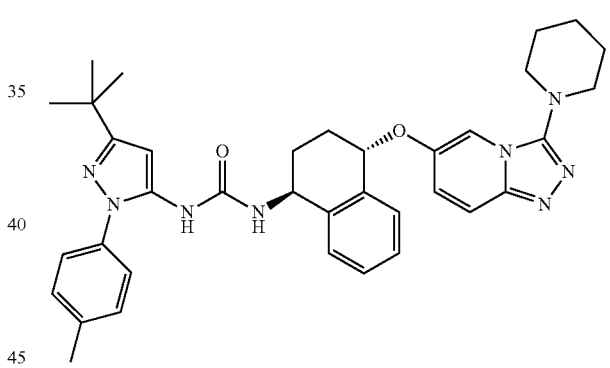

a. (1S,4S)-4-(3-Piperidin-1-yl-[1,2,4]triazolo[4,3-a]pyridin-6-yloxy)-1,2,3,4-tetrahydro-naphthalen-1-ylamine (Intermediate 55a).

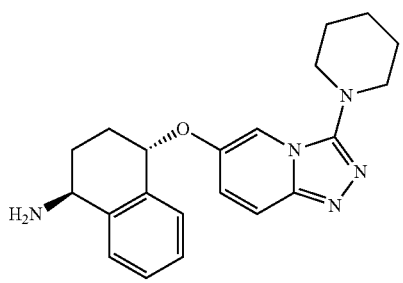 [SMILES: N[C@H]1CC[C@H](Oc2ccc3nnc(N4CCCCC4)n3c2)c2ccccc21]

Intermediate B (74.0 mg, 454 µmol) was added to a mixture of NaH (60% in mineral oil, 27.2 mg, 681 µmol) in DMF (2.5 mL) at RT and stirred for 15 min. Intermediate 3b (100 mg, 454 µmol) was then added and the resulting mixture heated to 60° C. for 1 h. After cooling, the reaction was quenched with sat. aq. NH₄Cl solution. The mixture was diluted with water and extracted with EtOAc. The combined organic extracts were concentrated in vacuo. The resulting residue was purified by FCC, using 0 to 10% [2M NH₃ in MeOH] in DCM, to afford the title compound as an orange residue (122 mg, 74%). LCMS (Method 3): Rt 2.13 min, m/z 364 [MH⁺].

b. 1-(5-tert-Butyl-2-p-tolyl-2H-pyrazol-3-yl)-3-[(1S,4S)-4-(3-piperidin-1-yl-[1,2,4]triazolo[4,3-a]pyridin-6-yloxy)-1,2,3,4-tetrahydro-naphthalen-1-yl]-urea (Example 55).

A mixture of Intermediate 55a (120 mg, 0.33 mmol), (5-tert-butyl-2-p-tolyl-2H-pyrazol-3-yl)-carbamic acid 2,2,2-trichloro-ethyl ester (Synthetic Communications, 2009, 39, 3999-4009, which is incorporated herein by reference in its entirety; 147 mg, 0.36 mmol), DIPEA (86.0 µL, 0.50 mmol) and 1,4-dioxane (2.5 mL) were heated to 60° C. for 18 h. After cooling the solvent was evaporated in vacuo. The residue was purified by FCC, using 0-10% MeOH in DCM, to give a pale yellow foam. This was lyophilised to provide the title compound as an off-white solid (28 mg, 20%). LCMS (Method 5) Rt 4.76 min, m/z 619 [MH⁺]. ¹H NMR (400 MHz, d₆-DMSO): 1.26 (9H, s), 1.61 (2H, m), 1.72 (5H, m), 2.02-2.17 (3H, m), 2.35 (3H, s), 3.13 (4H, m), 4.90 (1H, m), 5.58 (1H, m), 6.31 (1H, s), 6.99 (1H, d, J 7.8), 7.19 (1H, dd, J 9.7, 2.2), 7.26-7.43 (8H, m), 7.58-7.64 (2H, m), 7.98 (1H, s).

Example 56

1-(5-tert-Butyl-2-p-tolyl-2H-pyrazol-3-yl)-3-{(1S,4R)-4-[3-(3-hydroxymethyl-4-methyl-piperazin-1-ylmethyl)-[1,2,4]triazolo[4,3-a]pyridin-6-yloxy]-1,2,3,4-tetrahydro-naphthalen-1-yl}-urea

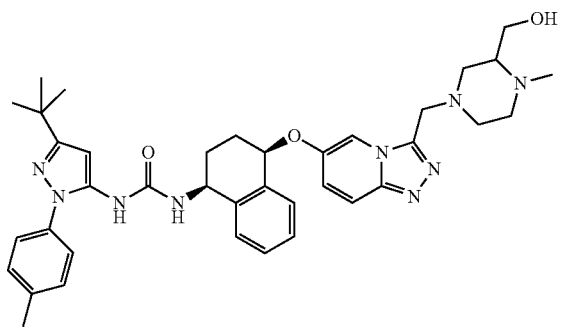 [SMILES: Cc1ccc(-n2nc(C(C)(C)C)cc2NC(=O)N[C@H]2CC[C@@H](Oc3ccc4nnc(CN5CCN(C)C(CO)C5)n4c3)c3ccccc32)cc1]

a. (3-Hydroxymethyl-4-methyl-piperazin-1-yl)-acetic acid ethyl ester (Intermediate 56a).

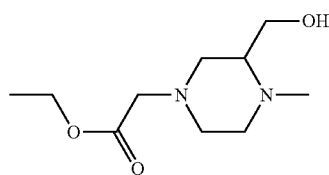

A mixture of (1-methyl-2-piperazinyl)methanol dihydrochloride (500 mg, 2.46 mmol), ethyl bromoacetate (410 mg, 2.46 mmol), K₂CO₃ (1.02 g, 7.38 mmol) and MeCN (15 mL) were heated to reflux for 18 h. After cooling, the mixture was filtered and concentrated in vacuo. The title compound was isolated as a colourless oil (525 mg, 98%) and used without further purification. ¹H NMR (300 MHz, CDCl₃): 1.25 (3H, t, J 7.0), 2.35 (3H, s), 2.35-2.59 (4H, m), 2.76-2.90 (3H, m), 3.19 (2H, m), 3.44 (1H, dd, J 11.3, 2.0), 3.87 (1H, dd, J 11.3, 4.0), 4.15 (2H, q, J 7.1).

b. Sodium (4-methyl-3-triisopropylsilanyloxymethyl-piperazin-1-yl)-acetate (Intermediate 56b).

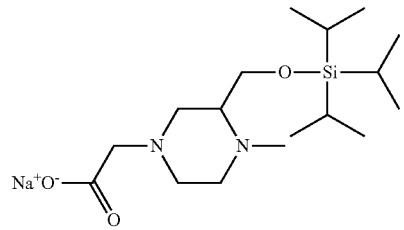

To a mixture of Intermediate 56a (520 mg, 2.40 mmol), Et₃N (485 mg, 4.80 mmol) and DCM (15 mL), triisopropylsilyl trifluoromethanesulfonate (774 µL, 2.88 mmol) was added. The mixture was stirred for 1 h. The mixture was diluted with DCM and washed with water, sat. aq. NaHCO₃ solution and brine, and concentrated in vacuo. The title compound was isolated as a pale yellow oil (882 mg, quant.) and used without further purification. A mixture of crude silyl-protected product (440 mg, 1.18 mmol), NaOH (47.0 mg, 1.18 mmol), water (10 mL) and THF (10 mL) were stirred for 18 h. The mixture was concentrated in vacuo to give the title compound as a pink solid (393 mg, 91%). LCMS (Method 3): Rt 2.81 min, m/z 345 [M-Na+2H⁺].

c. (4-Methyl-3-triisopropylsilanyloxymethyl-piperazin-1-yl)-acetic acid N'-(5-fluoro-pyridin-2-yl)-hydrazide (Intermediate 56c).

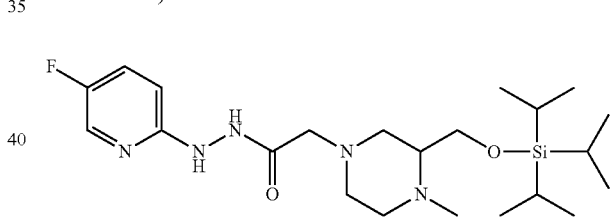

To a mixture of Intermediate 56b (390 mg, 1.06 mmol), (5-fluoro-pyridin-2-yl)-hydrazine (135 mg, 1.06 mmol) and HOBt.H₂O (14.4 mg, 106 mop in DCM (15 mL) was added EDC (245 mg, 1.27 mmol) and stirred for 18 h. The mixture was washed with water, sat. aq. NaHCO₃ and brine, and concentrated in vacuo to leave the title compound as a brown residue (412 mg, 86%). LCMS (Method 3): Rt 3.00 min, m/z 454 [MH⁺].

d. 6-Fluoro-3-(4-methyl-3-triisopropylsilanyloxymethyl-piperazin-1-ylmethyl)-[1,2,4]triazolo[4,3-a]pyridine (Intermediate 56d).

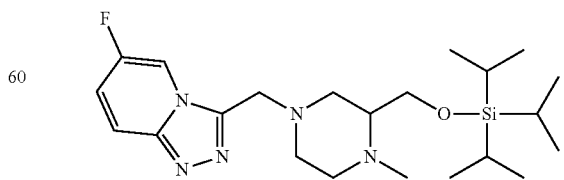

Hexachloroethane (426 mg, 1.80 mmol) was added portion-wise to a stirred mixture of Intermediate 56c (410 mg, 0.90 mmol), Ph₃P (472 mg, 1.80 mmol) and Et₃N (500 μL, 3.60 mmol) in THF (15 mL) at RT. The reaction mixture was stirred for 18 h, then filtered and concentrated in vacuo. The resulting residue was purified by FCC, using 0-25% MeOH in EtOAc, to give the title compound (237 mg, 60%). LCMS (Method 3): Rt 2.95 min, m/z 436 [MH⁺].

e. (1S,4R)-4-[3-(4-Methyl-3-triisopropylsilanyl oxymethyl-piperazin-1-ylmethyl)-[1,2,4]triazolo[4,3-a]pyridin-6-yloxy]-1,2,3,4-tetrahydro-naphthalen-1-ylamine (Intermediate 56e).

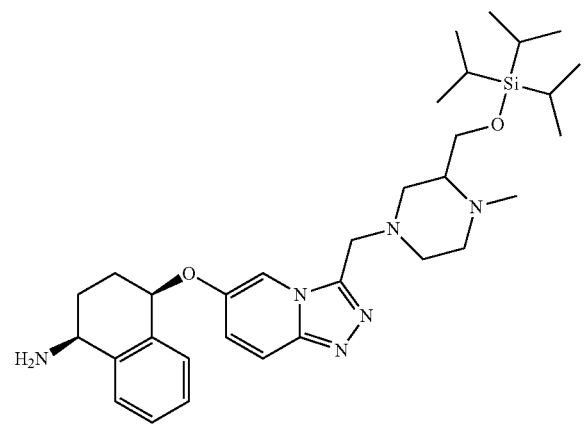 [SMILES: CC(C)[Si](OCC1CN(Cc2nnc3ccc(O[C@@H]4CC[C@H](N)c5ccccc54)cn23)CCN1C)(C(C)C)C(C)C]

Intermediate A (115.4 mg, 0.71 mmol) was added to a mixture of NaH (60% in mineral oil, 87.2 mg, 2.18 mmol) in DMF (4 mL) at RT and stirred for 15 min. Intermediate 56d (237 mg, 0.54 mmol) was then added and the resulting mixture heated to 60° C. for 2 h. After cooling, the reaction was quenched with sat. aq. NH₄Cl solution. The mixture was diluted with water and extracted with EtOAc. The combined organic extracts were washed with sat. aq. NaHCO₃ solution and brine, and concentrated in vacuo. The resulting residue was loaded onto an SCX-2 cartridge, washed with MeOH then eluted with 1M NH₃ in MeOH; concentration in vacuo gave the title compound as a brown residue (91 mg, 29%). LCMS (Method 3): Rt 3.08 min, m/z 579 [MH⁺].

f. 1-(5-tert-Butyl-2-p-tolyl-2H-pyrazol-3-yl)-3-{(1S,4R)-4-[3-(4-methyl-3-triisopropylsilanyloxymethyl-piperazin-1-ylmethyl)-[1,2,4]triazolo[4,3-a]pyridin-6-yloxy]-1,2,3,4-tetrahydro-naphthalen-1-yl}-urea (Intermediate 56f).

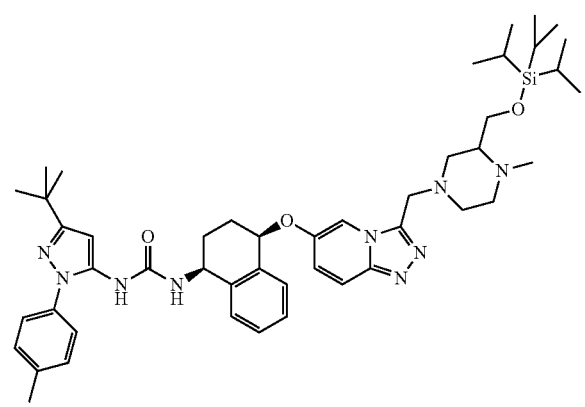 [SMILES: Cc1ccc(-n2nc(C(C)(C)C)cc2NC(=O)N[C@H]2CC[C@@H](Oc3ccc4nnc(CN5CCN(C)C(CO[Si](C(C)C)(C(C)C)C(C)C)C5)n4c3)c3ccccc32)cc1]

A mixture of Intermediate 56e (87.0 mg, 0.15 mmol), (5-tert-butyl-2-p-tolyl-2H-pyrazol-3-yl)-carbamic acid 2,2, 2-trichloro-ethyl ester (Synthetic Communications, 2009, 39, 3999-4009; 66.8 mg, 0.17 mmol), DIPEA (39.2 μL, 0.23 mmol) and 1,4-dioxane (2.5 mL) were heated to 60° C. for 18 h. After cooling the solvent was evaporated in vacuo and the residue purified by FCC, using 0-10% MeOH in DCM, to provide the title compound as a pale yellow foam (64 mg, 51%). LCMS (Method 3): Rt 3.63 min, m/z 834 [M⁺].

g. 1-(5-tert-Butyl-2-p-tolyl-2H-pyrazol-3-yl)-3-{(1S,4R)-4-[3-(3-hydroxymethyl-4-methyl-piperazin-1-ylmethyl)-[1,2,4]triazolo[4,3-a]pyridin-6-yloxy]-1,2,3,4-tetrahydro-naphthalen-1-yl}-urea (Example 56).

A mixture of Intermediate 56f (60.0 mg, 72.0 μmol) and TBAF (1M in THF, 144 μL 144 μmol) in THF (3 mL) was stirred at RT for 1 h. The mixture was diluted with water and extracted with EtOAc (3×). The combined organic extracts were washed with brine, and concentrated in vacuo. The residue was purified by FCC, using 0-20% MeOH in DCM, to afford the title compound as an off-white solid (24.9 mg, 51%). LCMS (Method 5): Rt 3.54 min, m/z 678 [MH⁺]. ¹H NMR (400 MHz, d₆-DMSO): 1.27 (9H, s), 1.82-2.01 (4H, m), 2.01-2.25 (7H, m), 2.53-2.88 (3H, m), 3.21 (1H, m), 3.54 (1H, m), 3.96-4.11 (2H, m), 4.37 (1H, dt, J 12.5, 5.4), 4.84 (1H, m), 5.47 (1H, m), 6.32 (1H, s), 7.10 (1H, d, J 8.4), 7.22-7.44 (9H, m), 7.72 (1H, d, J 10.3), 8.02 (1H, s), 8.30 (1H, m).

Example 57

1-[5-tert-Butyl-2-(4-hydroxymethyl-phenyl)-2H-pyrazol-3-yl]-3-{(1S,4R)-4-[3-(4-hydroxy-piperidin-1-yl)-[1,2,4]triazolo[4,3-a]pyridin-6-yloxy]-1,2,3,4-tetrahydro-naphthalen-1-yl}-urea

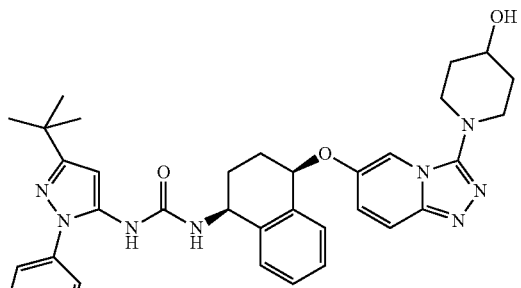

a. 3-(4-Allyloxy-piperidin-1-yl)-6-fluoro-[1,2,4]triazolo[4,3-a]pyridine (Intermediate 57a).

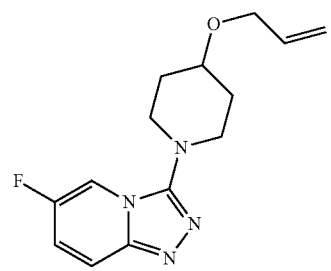 [SMILES: C=CCOC1CCN(c2nnc3ccc(F)cn23)CC1]

To an opaque pale yellow solution of Intermediate 24c (510 mg, 2.16 mmol) in dry THF at 0° C. under Ar was added NaH (60% dispersion in oil, 216 mg, 5.40 mmol) (CARE: gas evolution) and the resulting suspension was stirred at 0° C. for 30 min. Allyl bromide (0.467 mL, 5.40 mmol) was added and the suspension stirred at RT under Ar for 1 h and at 70° C. for 18 h. Water (25 mL) was added to the cooled solution, then the mixture extracted with EtOAc (3×25 mL). The combined organics were washed with brine (25 mL), dried ($Na_2SO_4$), filtered and concentrated in vacuo to leave a dark brown oil. FCC, using 0-8% MeOH in EtOAc, gave the title compound as a brown oil (171 mg, 29%). LCMS (Method 3): Rt 2.81 min, m/z 277 [$MH^+$].

b. (1S,4R)-4-[3-(4-Allyloxy-piperidin-1-yl)-[1,2,4]triazolo[4,3-a]pyridin-6-yloxy]-1,2,3,4-tetrahydro-naphthalen-1-ylamine (Intermediate 57b).

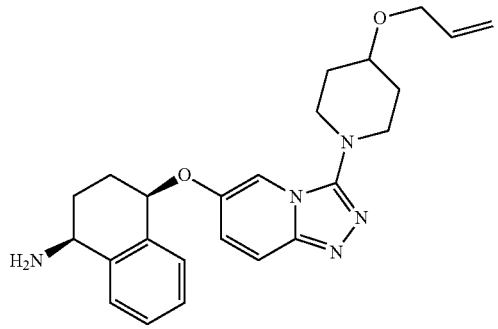 [SMILES: C=CCOC1CCN(c2nnc3ccc(O[C@@H]4CC[C@H](N)c5ccccc54)cn23)CC1]

A suspension of Intermediate A (108 mg, 0.661 mmol) and NaH (60% dispersion in oil, 72.1 mg, 180 mmol) in dry DMF (5 mL) at RT under Ar was stirred for 1 h (CARE: gas evolution). A solution of Intermediate 57a (166 mg, 0.601 mmol) in dry DMF (3 mL) was added and the dark brown solution stirred at 60° C. for 90 min. The solution was concentrated in vacuo, and the residue redissolved in MeOH (5 mL) and AcOH (0.171 mL, 3.00 mmol). The solution was applied to an SCX-2 cartridge (10 g) and was washed with MeOH (100 mL). The product was eluted with 2M $NH_3$ in MeOH (75 mL); concentration in vacuo left a dark brown solid. FCC, using 2-8% [2M $NH_3$ in MeOH] in DCM, gave the title compound as a dark brown oil (204 mg, 81%). LCMS (Method 3): Rt 2.34 min, m/z 420 [$MH^+$].

c. 1-{(1S,4R)-4-[3-(4-Allyloxy-piperidin-1-yl)-[1,2,4]triazolo[4,3-a]pyridin-6-yloxy]-1,2,3,4-tetrahydro-naphthalen-1-yl}-3-[5-tert-butyl-2-(4-hydroxymethyl-phenyl)-2H-pyrazol-3-yl]-urea (Intermediate 57c).

A yellow-brown solution of Intermediate 33a (99.6 mg, 0.237 mmol), Intermediate 57b (90.3 mg, 0.215 mmol) and DIPEA (0.047 mL, 0.269 mmol) in dioxane (3 mL) was stirred at 60° C. for 18 h. The solution was concentrated in vacuo, then the residue suspended in water (5 mL) and extracted with DCM (2×5 mL). The combined organics were passed through a hydrophobic fit and concentrated in vacuo. The residue was purified by FCC, using 2-8% [2M $NH_3$ in MeOH] in DCM, to give the title compound as a pale yellow solid (96.4 mg, 65%). LCMS (Method 3): Rt 3.54 min, m/z 691 [$MH^+$].

d. 1-[5-tert-Butyl-2-(4-hydroxymethyl-phenyl)-2H-pyrazol-3-yl]-3-{(1S,4R)-4-[3-(4-hydroxy-piperidin-1-yl)-[1,2,4]triazolo[4,3-a]pyridin-6-yloxy]-1,2,3,4-tetrahydro-naphthalen-1-yl}-urea (Example 57).

Ar was bubbled through a solution of Intermediate 57c (93.0 mg, 0.135 mmol) and 1,3-dimethyl barbituric acid (63.0 mg, 0.404 mmol) in DCM (5 mL) at RT under Ar for 30 min, then Pd($PPh_3$)$_4$ (15.6 mg, 0.0135 mmol) was added and the orange solution was stirred at RT for 1 h, and then at reflux for 17 h. The suspension was concentrated in vacuo, the residue redissolved in DCE (10 mL) and Ar bubbled through the mixture for 30 min. Pd($PPh_3$)$_4$ (15.6 mg, 0.0135 mmol) was added and the opaque orange-red solution stirred at 75° C. under Ar for 2 h. The cooled solution was concentrated in vacuo to 3 mL volume, then applied to an SCX-2 cartridge (5 g) and washed with MeOH (25 mL). The product was eluted with 2M $NH_3$ in MeOH (20 mL); concentration in vacuo left an orange solid. FCC, using 5-15% MeOH in DCM, gave a pale orange solid (46.0 mg). Further purification by HPLC (XBridge C18 column, 20-80% MeCN in $H_2O$, 0.1% $NH_4OH$) gave the title compound as a white powder after freeze-drying (27.1 mg, 31%). LCMS (Method 5): Rt 3.59 min, m/z 651 [$MH^+$]. $^1H$ NMR (400 MHz, $d_6$-DMSO): 1.23 (9H, s), 1.56-1.67 (2H, m), 1.76-1.92 (4H, m), 1.95-2.11 (2H, m), 2.91-2.97 (2H, m), 3.31-3.35 (2H, m), 3.64-3.71 (1H, m), 4.51 (2H, d, J 4.2), 4.70 (1H, d, J 3.9), 4.77 (1H, m), 5.25 (1H, t, J 5.3), 5.50 (1H, t, J 4.4), 6.29 (1H, s), 7.05 (1H, d, J 8.5), 7.10 (1H, dd, J 9.9, 2.1), 7.21-7.25 (2H, m), 7.28-7.34 (2H, m), 7.39 (2H, d, J 9.1), 7.40 (2H, d, J 9.1), 7.56 (1H, dd, J 9.9, 0.8), 7.61 (1H, dd, J 2.1, 0.9), 8.04 (1H, s).

Example 58

1-(5-tert-Butyl-2-p-tolyl-2H-pyrazol-3-yl)-3-{(1S,4R)-4-[3-((S)-1-isopropyl-pyrrolidin-2-yl)-[1,2,4]triazolo[4,3-a]pyridin-6-yl oxy]-1,2,3,4-tetrahydro-naphthalen-1-yl}-urea, partial formate salt

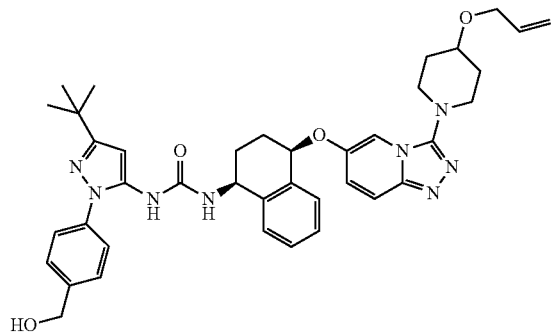 [SMILES: C=CCOC1CCN(c2nnc3ccc(O[C@@H]4CC[C@H](NC(=O)Nc5cc(C(C)(C)C)nn5-c5ccc(CO)cc5)c5ccccc54)cn23)CC1]

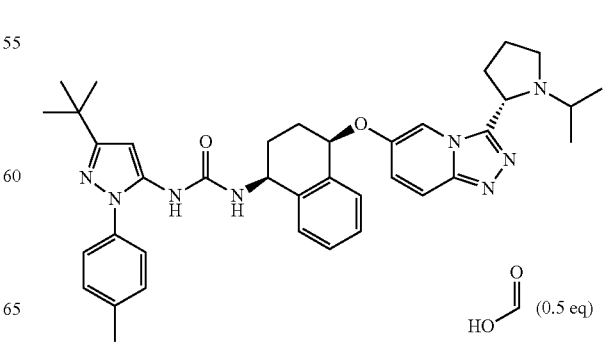

a. (S)-1-Isopropyl-pyrrolidine-2-carboxylic acid N-(5-fluoro-pyridin-2-yl)-hydrazide (Intermediate 58a).

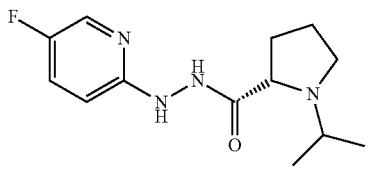

To a solution of (5-fluoro-pyridin-2-yl)-hydrazine (200 mg, 1.57 mmol) in DMF (15.0 mL) was added (S)-1-isopropyl-pyrrolidine-2-carboxylic acid (Chem. Commun. 2006, 14, 1482, which is incorporated herein by reference in its entirety; 247 mg, 1.57 mmol), EDC (332 mg, 1.73 mmol) and HOBt.H$_2$O (20.0 mg, 0.16 mmol). The reaction was stirred overnight then partitioned between EtOAc and water. The aqueous layer was then extracted with EtOAc (3×). The combined organic layers were washed with brine, dried (MgSO$_4$), filtered and evaporated in vacuo. The residue was purified by FCC, using 0-10% MeOH in DCM, to give the title compound (346 mg, 83%). LCMS (Method 1): Rt 0.37 min, m/z 267.1 [MH$^+$].

b. 6-Fluoro-3-((S)-1-isopropyl-pyrrolidin-2-yl)-[1,2,4]triazolo[4,3-a]pyridine (Intermediate 58b).

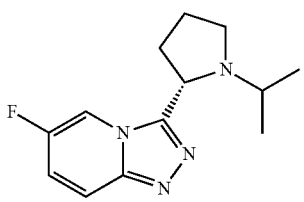 [SMILES: CC(C)N1CCC[C@H]1c1nnc2ccc(F)cn12]

To a solution of Intermediate 58a (346 mg, 1.30 mmol), Ph$_3$P (681 mg, 2.60 mmol) and Et$_3$N (723 µL, 5.20 mmol) in THF (10.0 mL) at 0° C. was added hexachloroethane (616 mg, 2.60 mmol). The reaction was stirred at RT overnight then partitioned between EtOAc and water. The aqueous layer was then extracted with EtOAc (3×). The combined organic layers were washed with brine, dried (MgSO$_4$), filtered and evaporated in vacuo. The residue was dissolved in MeOH and loaded onto an SCX-2 cartridge, which was washed with MeOH. The product was eluted with 2M NH$_3$ in MeOH; concentration in vacuo gave the title compound (220 mg, 68%). LCMS (Method 4): Rt 0.32 min, m/z 249.1 [MH$^+$].

c. (1S,4R)-4-[3-((S)-1-Isopropyl-pyrrolidin-2-yl)-[1,2,4]triazolo[4,3-a]pyridin-6-yloxy]-1,2,3,4-tetrahydro-naphthalen-1-ylamine (Intermediate 58c).

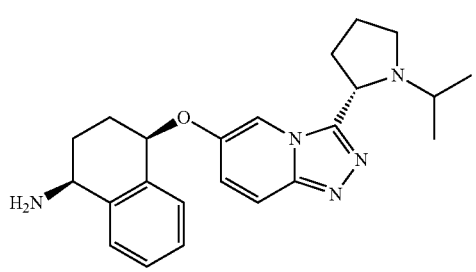 [SMILES: CC(C)N1CCC[C@H]1c1nnc2ccc(O[C@@H]3CC[C@H](N)c4ccccc43)cn12]

To a suspension of NaH (60% in mineral oil, 142 mg, 3.56 mmol) in DMF (2.00 mL) was added (1R,4S)-4-amino-1,2,3,4-tetrahydro-naphthalen-1-ol Intermediate A (145 mg, 0.88 mmol) and the reaction stirred for 20 min. A solution of Intermediate 58b (220 mg, 0.88 mmol) in DMF (2.00 mL) was added and the reaction heated to 60° C. for 1 h. The reaction was cooled and quenched by dropwise addition of methanol, before being diluted with methanol and loaded onto an SCX-2 cartridge, which was washed with MeOH. The product was eluted with 2M NH$_3$ in MeOH; concentration in vacuo gave a residue. FCC, using 2-10% [2M NH$_3$ in MeOH] in DCM, gave the title compound (145 mg, 44%). LCMS (Method 4): Rt 0.29 min, m/z 392.2 [MH$^+$].

d. 1-(5-tert-Butyl-2-p-tolyl-2H-pyrazol-3-yl)-3-{(1S,4R)-4-[3-((S)-1-isopropyl-pyrrolidin-2-yl)-[1,2,4]triazolo[4,3-a]pyridin-6-yloxy]-1,2,3,4-tetrahydro-naphthalen-1-yl}-urea, partial formate salt (Example 58).

To a solution of Intermediate 58c (140 mg, 0.37 mmol) in 1,4-dioxane (3.00 mL) was added DIPEA (130 µL, 0.75 mmol) and (5-tert-butyl-2-p-tolyl-2H-pyrazol-3-yl)-carbamic acid 2,2,2-trichloro-ethyl ester (Synthetic Communications, 2009, 39, 3999-4009, which is incorporated herein by reference in its entirety; 151 mg, 0.37 mmol). The reaction was heated to 60° C. overnight then cooled and partitioned between EtOAc and water. The aqueous layer was then extracted with EtOAc (3×). The combined organic layers were washed with brine, dried (MgSO$_4$), filtered and evaporated in vacuo. The residue was purified by FCC, using 0-5% MeOH in DCM. Further purification by HPLC (C18 X-select column, 10-98% MeCN in H$_2$O, 0.1% HCO$_2$H) gave the title compound as a white powder after freeze-drying (60 mg, 25%). LCMS (Method 5): Rt 3.84 min, m/z 647.3 [MH$^+$]. $^1$H NMR (400 MHz, d$_4$-MeOD): 0.99 (6H, d, J 6.5), 1.29 (9H, s), 1.90-2.06 (5H, m), 2.11 (1H, m), 2.22-2.36 (2H, m), 2.38 (3H, s), 2.73-2.84 (2H, m), 3.25 (1H, m), 4.59 (1H, t, J 7.3), 4.90 (1H, dd, J 9.1, 5.7), 5.29 (1H, t, J 4.1), 6.33 (1H, s), 7.20-7.36 (9H, m), 7.65 (1H, d, J 10.0), 8.25 (0.5H, br s), 8.42 (1H, d, J 1.8).

Example 59

1-(5-tert-Butyl-2-p-tolyl-2H-pyrazol-3-yl)-3-[(1S,4R)-4-(3-dimethylamino-[1,2,4]triazolo[4,3-a]pyridin-6-yloxy)-1,2,3,4-tetrahydro-naphthalen-1-yl]-urea

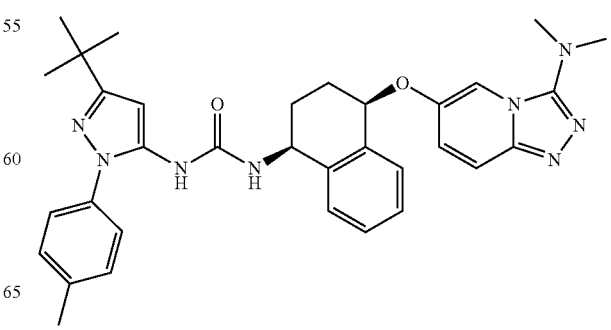

a. 2-(5-Fluoropyridin-2-yl)-N,N-dimethylhydrazine carboxamide (Intermediate 59a).

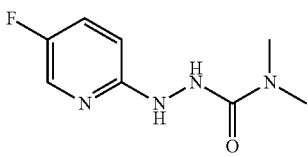

A solution of (5-fluoro-pyridin-2-yl)-hydrazine (500 mg, 3.93 mmol), dimethylcarbamyl chloride (505 mg, 4.72 mmol) and DIPEA (1.01 g, 7.86 mmol) in DCM (20 mL) was stirred at reflux for 16 h. The reaction mixture was applied to an SCX-2 cartridge (25 g) and washed with MeOH. The product was eluted with 2M $NH_3$ in MeOH; concentration in vacuo and then trituration with diethyl ether gave the title compound (600 mg, 77%). $^1$H NMR (400 MHz, $CDCl_3$): 2.99 (6H, s), 6.46 (2H, m), 6.75 (1H, dd, J 9.1, 3.5), 7.22-7.32 (1H, m), 8.03 (1H, d, J 2.7).

b. (6-Fluoro-[1,2,4]triazolo[4,3-a]pyridin-3-yl)-dimethyl-amine (Intermediate 59b).

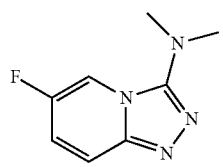

To a solution of Intermediate 59a (590 mg, 2.98 mmol), $Ph_3P$ (1.56 g, 5.96 mmol) and $Et_3N$ (1.20 g, 11.9 mmol) in THF (40 mL) was added hexachloroethane (1.41 g, 5.96 mmol) and the mixture stirred at 60° C. for 9 h. The mixture was diluted with EtOAc (100 mL), washed with water, brine, dried ($MgSO_4$) and then concentrated in vacuo. The residue was purified by FCC, using 0-10% (2M $NH_3$ in MeOH) in DCM, then triturated with diethyl ether to give the title compound (78 mg, 14%). LCMS (Method 1): Rt 2.24 min, m/z 181 [MH$^+$].

c. [6-((1R,4S)-4-Amino-1,2,3,4-tetrahydro-naphthalen-1-yloxy)-[1,2,4]triazolo[4,3-a]pyridin-3-yl]-dimethyl-amine (Intermediate 59c).

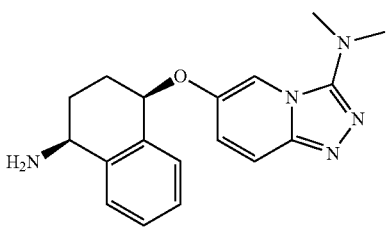 [SMILES: CN(C)c1nnc2ccc(O[C@@H]3CC[C@H](N)c4ccccc43)cn12]

To a solution of Intermediate A (75 mg, 0.458 mmol) in DMF (2 mL) was added NaH (60% in oil, 50 mg, 1.25 mmol) and the mixture stirred at RT for 20 min, before Intermediate 59b (75 mg, 0.416 mmol) was added. This mixture was stirred at 60° C. for 1 h. The reaction mixture was applied to an SCX-2 cartridge (10 g) and washed with MeOH. The product was eluted with 2M $NH_3$ in MeOH; concentration in vacuo gave a residue. FCC, using 0-10% [2M $NH_3$ in MeOH] in DCM gave the title compound as a yellow gum (82 mg, 61%). LCMS (Method 4): Rt 1.49 min, m/z 324 [MH$^+$].

d. 1-(5-tert-Butyl-2-p-tolyl-2H-pyrazol-3-yl)-3-[(1S,4R)-4-(3-dimethylamino-[1,2,4]triazolo[4,3-a]pyridin-6-yloxy)-1,2,3,4-tetrahydro-naphthalen-1-yl]-urea (Example 59).

A solution of Intermediate 59c (80 mg, 0.25 mmol), (5-tert-butyl-2-p-tolyl-2H-pyrazol-3-yl)-carbamic acid 2,2,2-trichloro-ethyl ester (Synthetic Communications, 2009, 39, 3999-4009, which is incorporated herein by reference in its entirety; 150 mg, 0.370 mmol) and DIPEA (129 mg, 1.00 mmol) in DMF (2 mL) was stirred at 60° C. for 30 min. The reaction mixture was applied to an SCX-2 cartridge (10 g) and washed with MeOH. The product was eluted with 2M $NH_3$ in MeOH; concentration in vacuo gave a residue. FCC, using 0-5% [2M $NH_3$ in MeOH] in DCM, gave the title compound as an off-white solid (75 mg, 52%). LCMS (Method 5): Rt 4.39 min, m/z 579.1 [MH$^+$]. $^1$H NMR (400 MHz, $d_4$-MeOH): 1.29 (9H, s), 1.83-2.17 (3H, m), 2.17-3.00 (1H, m), 2.38 (3H, s), 2.92 (6H, s), 4.88 (1H, dd, J 8.5, 5.4), 5.41 (1H, t, J 3.0), 6.33 (1H, s), 7.14-7.36 (9H, m), 7.50 (1H, d, J 9.7), 7.70 (1H, d, J 1.4).

Example 60

1-(5-tert-Butyl-2-p-tolyl-2H-pyrazol-3-yl)-3-{(1S,4R)-4-[3-((R)-1-methyl-pyrrolidin-2-yl)-[1,2,4]triazolo[4,3-a]pyridin-6-yloxy]-1,2,3,4-tetrahydro-naphthalen-1-yl}-urea

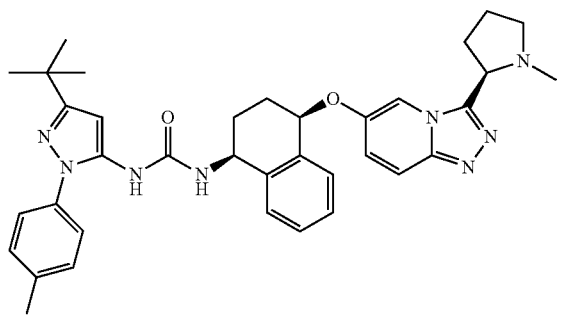 [SMILES: Cc1ccc(-n2nc(C(C)(C)C)cc2NC(=O)N[C@H]2CC[C@@H](Oc3ccc4nnc([C@H]5CCCN5C)n4c3)c3ccccc32)cc1]

a. 6-Fluoro-3-((R)-1-methyl-pyrrolidin-2-yl)-[1,2,4]triazolo[4,3-a]pyridine (Intermediate 60a).

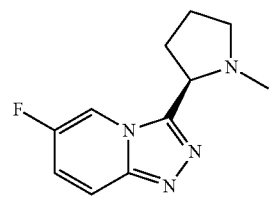 [SMILES: CN1CCC[C@@H]1c1nnc2ccc(F)cn12]

A mixture of (5-fluoro-pyridin-2-yl)-hydrazine (889 mg, 7.00 mmol), N-methyl-D-proline hydrochloride (1.274 g, 7.7 mmol) and HOBt.$H_2O$ (95 mg, 0.70 mmol) in DCM (20 mL) was treated with EDC (1.494 g, 7.8 mmol), and the mixture stirred at RT for 6.5 h. The mixture was then diluted with sat. aq. $NaHCO_3$ solution, NaCl added, and the mixture extracted with DCM (8×20 mL). The combined organics were dried and concentrated in vacuo to give (R)-1-methyl-pyrrolidine-2-carboxylic acid N'-(5-fluoro-pyridin-2-yl)-hydrazide as a pale orange solid (1.09 g). This was dissolved in THF (20 mL) then $Ph_3P$ (2.40 g, 9.16 mmol), $Et_3N$ (2.6 mL, 18.3 mmol), and hexachloroethane (2.17 g, 9.16 mmol) added sequentially. The mixture was stirred at RT for 4 h, then was filtered, the filter-cake washed with diethyl ether, and the combined organics concentrated in vacuo. The residue was purified on a SCX-2 cartridge (50 g), washing with methanol then eluting basic components with 0.2-2 M ammonia in methanol. Product containing fractions were combined and concentrated in vacuo. The residue was further purified by FCC, using 0-100% EtOAc in cyclohexane, then 8-10% MeOH in EtOAc, to give the title compound as a pale red oil (876 mg, 57%). LCMS (Method 3): Rt 0.55 min, m/z 221 [MH⁺].

b. (1S,4R)-4-[3-((R)-1-Methyl-pyrrolidin-2-yl)-[1,2,4]triazolo[4,3-a]pyridin-6-yloxy]-1,2,3,4-tetrahydro-naphthalen-1-ylamine (Intermediate 60b).

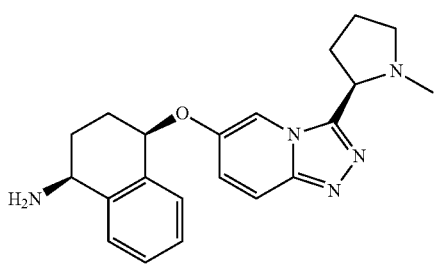 [SMILES: CN1CCC[C@@H]1c1nnc2ccc(O[C@@H]3CC[C@H](N)c4ccccc43)cn12]

To a solution of Intermediate A (245 mg, 1.50 mmol) in DMF (4 mL) was added NaH (60% dispersion in oil, 180 mg, 4.50 mmol) and the mixture stirred at RT for 0.5 h. A solution of Intermediate 60a (330 mg, 1.50 mmol) in DMF (5 mL) was added and the mixture stirred at 60° C. for 2 h. The cooled solution was diluted with water and extracted with DCM (5×20 mL). The combined organics were dried and concentrated in vacuo. The residue was purified by FCC, using 0-15% [2M NH₃ in MeOH] in DCM, to give the title compound as a brown solid after freeze-drying (408 mg, 74%). LCMS (Method 3): Rt 0.44 min, m/z 364 [MH⁺].

c. 1-(5-tert-Butyl-2-p-tolyl-2H-pyrazol-3-yl)-3-{(1S,4R)-4-[3-((R)-1-methyl-pyrrolidin-2-yl)-[1,2,4]triazolo[4,3-a]pyridin-6-yloxy]-1,2,3,4-tetrahydro-naphthalen-1-yl}-urea (Example 60).

A solution of Intermediate 60b (123 mg, 0.339 mmol) and (5-tert-butyl-2-p-tolyl-2H-pyrazol-3-yl)-carbamic acid 2,2,2-trichloro-ethyl ester (Synthetic Communications, 2009, 39, 3999-4009, which is incorporated herein by reference in its entirety; 140 mg, 0.346 mmol) in 1,4-dioxane (4 mL) and DIPEA (91 µL, 0.52 mmol) was stirred at 93° C. for 3.25 h. The cooled mixture was concentrated in vacuo. The residue was purified by FCC, using 0-20% MeOH in DCM, to give the impure product. Further purification by HPLC (C, 18 X-select column, 25-70% MeCN in H₂O, 0.1% formic acid) gave the title compound as a white powder after freeze-drying (118 mg, 56%). LCMS (Method 5): Rt 3.67 min, m/z 619.2 [MH⁺]. ¹H NMR (400 MHz, d₆-DMSO): 1.27 (9H, s), 1.80-2.27 (1H, m), 2.31-2.40 (4H, m), 3.11-3.18 (1H, m), 3.98 (1H, t, J 8.2), 4.78-4.86 (1H, m), 5.42 (1H, t, J 4.3), 6.32 (1H, s), 7.09 (1H, d, J 8.5), 7.26-7.42 (9H, m), 7.75 (1H, dd, J 9.7, 1.0), 8.03 (1H, s), 8.28 (1H, d, J 1.0).

Example 61

1-(5-tert-Butyl-2-p-tolyl-2H-pyrazol-3-yl)-3-{(1S,4R)-4-[3-((S)-1-ethyl-pyrrolidin-2-yl)-[1,2,4]triazolo[4,3-a]pyridin-6-yloxy]-1,2,3,4-tetrahydro-naphthalen-1-yl}-urea

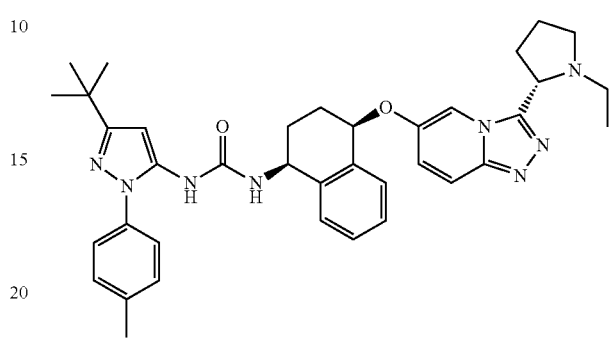

a. (S)-1-Ethyl-pyrrolidine-2-carboxylic acid N'-(5-fluoro-pyridin-2-yl)-hydrazide (Intermediate 61a).

To a solution of (5-fluoro-pyridin-2-yl)-hydrazine (178 mg, 1.39 mmol) in DMF (10.0 mL) was added (S)-1-ethyl-pyrrolidine-2-carboxylic acid (200 mg, 1.39 mmol), EDC (293 mg, 1.53 mmol) and HOBt.H₂O (18.0 mg, 0.14 mmol). The reaction was stirred for 4 h then partitioned between EtOAc and water. The aqueous layer was then extracted with EtOAc (3×). The combined organic layers were washed with brine, dried (MgSO₄), filtered and evaporated in vacuo. The residue was purified by FCC, using 0-10% [2M NH₃ in MeOH] in DCM, to give the title compound (190 mg, 54%). LCMS (Method 4): Rt 0.29 min, m/z 253.1 [MH⁺].

b. 6-Fluoro-3-((S)-1-ethyl-pyrrolidin-2-yl)-[1,2,4]triazolo[4,3-a]pyridine (Intermediate 61 b).

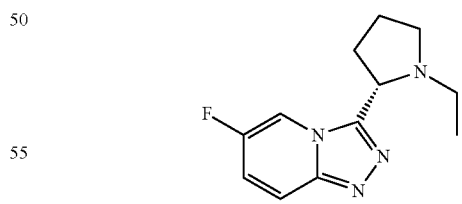

To a solution of Intermediate 61a (190 mg, 0.75 mmol), Ph₃P (395 mg, 1.51 mmol) and Et₃N (419 µL, 3.01 mmol) in THF (6.00 mL) at 0° C. was added hexachloroethane (357 mg, 1.51 mmol). The reaction was stirred at RT overnight then partitioned between EtOAc and water. The aqueous layer was then extracted with EtOAc (3×). The combined organic layers were washed with brine, dried (MgSO₄), filtered and evaporated in vacuo. The residue was dissolved in MeOH and loaded onto an SCX-2 cartridge, which was washed with MeOH. The product was eluted with 2M NH₃ in MeOH; concentration in vacuo gave a residue. FCC, using 0-10% [2M NH₃ in MeOH] in DCM, gave the title compound (157 mg, 89%). LCMS (Method 2): Rt 0.28 min, m/z 235.2 [MH⁺].

c. (1S,4R)-4-[3-((S)-1-Ethyl-pyrrolidin-2-yl)-[1,2,4]triazolo[4,3-c]pyridin-6-yloxy]-1,2,3,4-tetrahydro-naphthalen-1-ylamine (Intermediate 61c).

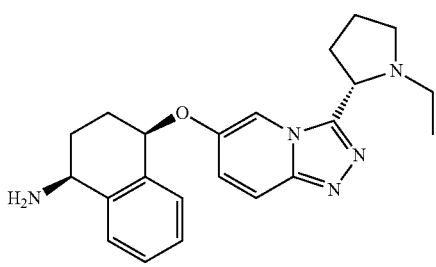 [SMILES: CCN1CCC[C@H]1c1nnc2ccc(O[C@@H]3CC[C@H](N)c4ccccc43)cn12]

To a suspension of NaH (60% in mineral oil, 107 mg, 2.68 mmol) in DMF (2.00 mL) was added Intermediate A (110 mg, 0.67 mmol) and the reaction stirred for 20 min. Intermediate 61b (150 mg, 0.67 mmol) was added in DMF (2.00 mL) and the reaction heated to 60° C. for 1 h. The reaction was cooled and quenched by dropwise addition of methanol, before being diluted with methanol and loaded onto an SCX-2 cartridge, which was washed with MeOH. The product was eluted with 2M NH₃ in MeOH; concentration in vacuo gave a residue. FCC, using 2-10% [2M NH₃ in MeOH] in DCM, gave the title compound (72.0 mg, 28%). LCMS (Method 4): Rt 0.29 min, m/z 378.2 [MH⁺].

d. 1-(5-tert-Butyl-2-p-tolyl-2H-pyrazol-3-yl)-3-{(1S,4R)-4-[3-((S)-1-ethyl-pyrrolidin-2-yl)-[1,2,4]triazolo[4,3-c]pyridin-6-yloxy]-1,2,3,4-tetrahydro-naphthalen-1-yl}-urea (Example 61).

To a solution of Intermediate 61c (72.0 mg, 0.19 mmol) in 1,4-dioxane (2.00 mL) was added DIPEA (66 μL, 0.38 mmol) and (5-tert-butyl-2-p-tolyl-2H-pyrazol-3-yl)-carbamic acid 2,2,2-trichloro-ethyl ester (Synthetic Communications, 2009, 39, 3999-4009, which is incorporated herein by reference in its entirety; 77.0 mg, 0.19 mmol). The reaction was heated to 60° C. overnight then cooled and partitioned between EtOAc and water. The aqueous layer was then extracted with EtOAc (3×). The combined organic layers were washed with brine, dried (MgSO₄), filtered and evaporated in vacuo. The residue was purified by FCC, using 0-7.5% MeOH in DCM. Further purification by HPLC (C18 X-select column, 20-70% MeCN in H₂O, 0.1% HCO₂H) gave the title compound as a white powder after freeze-drying (37 mg, 31%). LCMS (Method 5): Rt 3.73 min, m/z 633.2 [MH⁺]. ¹H NMR (400 MHz, d₄-MeOD): 0.94 (3H, t, J 7.2), 1.30 (9H, s), 1.89-2.16 (6H, m), 2.22-2.31 (2H, m), 2.31-2.38 (2H, m), 2.38 (3H, s), 2.49 (1H, m), 3.32 (1H, m), 4.11 (1H, t, J 8.0), 4.90 (1H, dd, J 9.0, 5.6), 5.28 (1H, t, J 4.1), 6.33 (1H, s), 7.19-7.36 (9H, m), 7.65 (1H, dd, J 10.0, 0.7), 8.37 (1H, d, J 1.9).

Example 62

1-(5-tert-Butyl-2-p-tolyl-2H-pyrazol-3-yl)-3-{(1S,4R)-4-[3-((S)-1-methyl-piperidin-2-yl)-[1,2,4]triazolo[4,3-a]pyridin-6-yloxy]-1,2,3,4-tetrahydro-naphthalen-1-yl}-urea

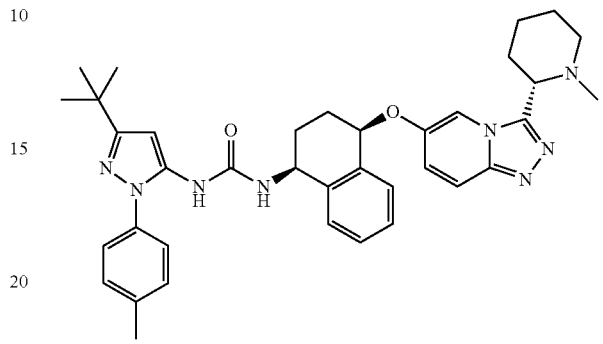

a. (S)-1-Methyl-piperidine-2-carboxylic acid AP-(5-fluoro-pyridin-2-yl)-hydrazide (Intermediate 62a).

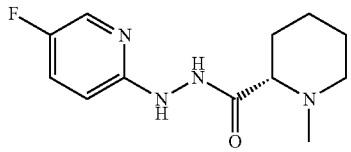 [SMILES: CN1CCCC[C@H]1C(=O)NNc1ccc(F)cn1]

To a solution of (5-fluoro-pyridin-2-yl)-hydrazine (250 mg, 1.96 mmol) in DMF (20.0 mL) was added (S)-1-methyl-piperidine-2-carboxylic acid (281 mg, 1.96 mmol), EDC (416 mg, 2.16 mmol) and HOBt.H₂O (25.0 mg, 0.20 mmol). The reaction was stirred overnight then partitioned between EtOAc and water. The aqueous layer was then extracted with EtOAc (3×). The combined organic layers were washed with brine, dried (MgSO₄), filtered and evaporated in vacuo. The residue was taken up in MeOH and loaded onto an SCX-2 cartridge, which was washed with MeOH. The product was eluted with 2M NH₃ in MeOH; concentration in vacuo gave residue. FCC, using 0-10% [2M NH₃ in MeOH] in DCM, gave the title compound (331 mg, 67%). LCMS (Method 1): Rt 0.35 min, m/z 253.2 [MH⁺].

b. 6-Fluoro-3-((S)-1-methyl-piperidin-2-yl)-[1,2,4]triazolo[4,3-a]pyridine (Intermediate 62b).

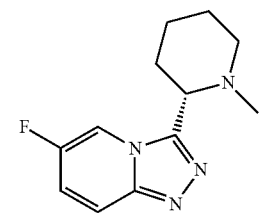 [SMILES: CN1CCCC[C@H]1c1nnc2ccc(F)cn12]

To a solution of Intermediate 62a (331 mg, 1.31 mmol), Ph₃P (688 mg, 2.63 mmol) and Et₃N (731 μL, 5.25 mmol) in THF (13.0 mL) at 0° C. was added hexachloroethane (622 mg, 2.63 mmol). The reaction was stirred at RT overnight then partitioned between EtOAc and water. The aqueous layer was then extracted with EtOAc (3×). The combined organic layers were washed with brine, dried (MgSO$_4$), filtered and evaporated in vacuo. The residue was taken up in MeOH and loaded onto an SCX-2 cartridge, which was washed with MeOH. The product was eluted with 2M NH$_3$ in MeOH; concentration in vacuo gave the title compound (250 mg, 81%). LCMS (Method 4): Rt 0.31 min, m/z 235.1 [MH$^+$].

c. (1S,4R)-4-[3-((S)-1-Methyl-piperidin-2-yl)-[1,2,4]triazolo[4,3-a]pyridin-6-yloxy]-1,2,3,4-tetrahydro-naphthalen-1-ylamine (Intermediate 62c).

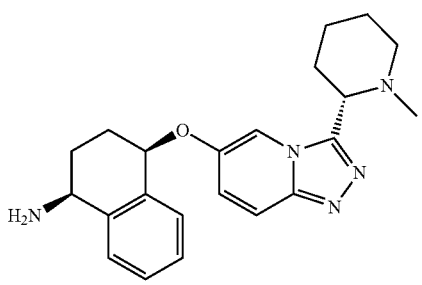 [SMILES: CN1CCCC[C@H]1c1nnc2ccc(O[C@@H]3CC[C@H](N)c4ccccc43)cn12]

To a suspension of NaH (60% in mineral oil, 171 mg, 4.27 mmol) in DMF (4.00 mL) was added Intermediate A (175 mg, 1.07 mmol) and the reaction stirred for 20 min. Intermediate 62b (250 mg, 1.07 mmol) was added in DMF (2.00 mL) and the reaction heated to 60° C. for one hour. The reaction was cooled and quenched by dropwise addition of methanol, before being diluted with methanol and loaded onto an SCX-2 cartridge, which was washed with MeOH and product eluted with 2M NH$_3$ in MeOH. The resulting residue was purified by FCC, using 2-10% [2M NH$_3$ in MeOH] in DCM, to give the title compound (287 mg, 71%). LCMS (Method 1): Rt 1.64, m/z 378.2 [MH$^+$].

d. 1-(5-tert-Butyl-2-p-tolyl-2H-pyrazol-3-yl)-3-{(1S,4R)-4-[3-((S)-1-methyl-piperidin-2-yl)-[1,2,4]triazolo[4,3-a]pyridin-6-yloxy]-1,2,3,4-tetrahydro-naphthalen-1-yl}-urea (Example 62).

To a solution of Intermediate 62c (140 mg, 0.37 mmol) in 1,4-dioxane (4.00 mL) was added DIPEA (129 µL, 0.74 mmol) and (5-tert-butyl-2-p-tolyl-2H-pyrazol-3-yl)-carbamic acid 2,2,2-trichloro-ethyl ester (Synthetic Communications, 2009, 39, 3999-4009, which is incorporated herein by reference in its entirety; 150 mg, 0.37 mmol). The reaction was heated to 60° C. overnight then cooled and partitioned between EtOAc and water. The aqueous layer was then extracted with EtOAc (3×). The combined organic layers were washed with brine, dried (MgSO$_4$), filtered and evaporated in vacuo. The residue was purified by FCC, using 0-7.5% MeOH in DCM. Further purification by HPLC (C18 X-select column, 10-98% MeCN in H$_2$O, 0.1% HCO$_2$H) gave the title compound as a white powder after freeze-drying (73 mg, 31%). LCMS (Method 5): Rt 3.75 min, m/z 633.2 [MH$^+$]. $^1$H NMR (400 MHz, d$_4$-MeOD): 1.30 (9H, s), 1.45 (1H, m), 1.60-1.83 (3H, m), 1.83-1.93 (2H, m), 1.93-2.07 (5H, m), 2.11 (1H, m), 2.20-2.33 (2H, m), 2.38 (3H, s), 3.05 (1H, dt, J 11.8, 2.8), 3.79 (1H, dd, J 10.9, 2.8), 4.91 (1H, dd, J 9.0, 5.7), 5.32 (1H, t, J 4.0), 6.33 (1H, s), 7.19-7.36 (9H, m), 7.64 (1H, d, J 10.0), 8.43 (1H, d, J 1.7).

Example 63

1-(5-tert-Butyl-2-p-tolyl-2H-pyrazol-3-yl)-3-{(1S,4R)-4-[3-((S)-3-hydroxy-piperidin-1-yl)-[1,2,4]triazolo[4,3-a]pyridin-6-yloxy]-1,2,3,4-tetrahydro-naphthalen-1-yl}-urea

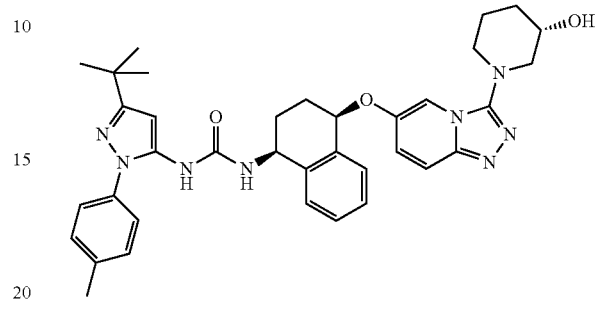

a. (S)-1-(6-Fluoro-[1,2,4]triazolo[4,3-a]pyridin-3-yl)-piperidin-3-ol (Intermediate 63a).

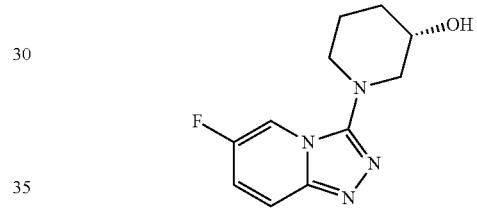

A mixture of Intermediate 24b (394 mg, 2.30 mmol), (S)-3-hydroxypiperidine hydrochloride (1.00 g, 7.27 mmol) and DIPEA (1.27 mL, 7.30 mmol) in DMA (8 mL) was heated in the microwave at 170-180° C. for 9.5 h. The cooled mixture was concentrated in vacuo and applied to an SCX-2 cartridge (70 g), washing with methanol then eluting basic components with 0.4-2 M ammonia in methanol. Product containing fractions were combined and concentrated in vacuo. The residue was purified by FCC, using 0-20% MeOH in DCM, to give the title compound as a pale brown solid (204 mg, 38%). LCMS (Method 3): Rt 2.02 min, m/z 237 [MH$^+$].

b. 6-Fluoro-3-((S)-3-triisopropylsilanyloxy-piperidin-1-yl)-[1,2,4]triazolo[4,3-a]pyridine (Intermediate 63b).

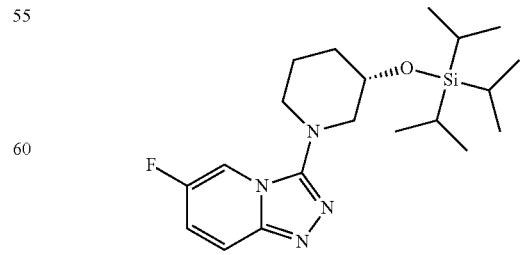

To a solution of Intermediate 63a (204 mg, 0.864 mmol) and Et$_3$N (180 µL, 1.3 mmol) in DCM (5 mL) was added triisopropylsilyltrifluoromethane sulfonate (279 μL, 1.04 mmol) and the mixture stirred at RT for 1 h. The mixture was washed with sat. aq. NaHCO₃ solution, dried and concentrated in vacuo. The residue was purified by FCC, using 0-100% EtOAc in cyclohexane, then 10% MeOH in EtOAc, to give the title compound as a pale brown gum (290 mg, 86%). LCMS (Method 3): Rt 4.99 min, m/z 393 [MH⁺].

c. (1S,4R)-4-[3-((S)-3-Triisopropylsilanyloxy-piperidin-1-yl)-[1,2,4]triazolo[4,3-a]pyridin-6-yloxy]-1,2,3,4-tetrahydro-naphthalen-1-ylamine (Intermediate 63c).

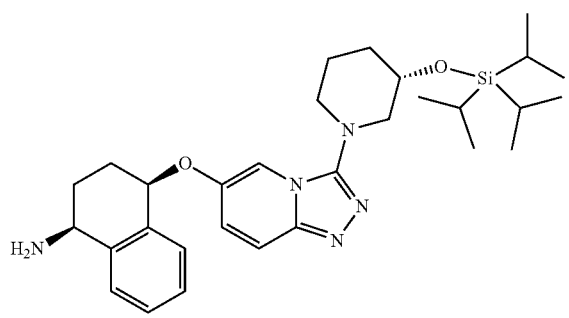 [SMILES: CC(C)[Si](O[C@H]1CCCN(c2nnc3ccc(O[C@@H]4CC[C@H](N)c5ccccc54)cn23)C1)(C(C)C)C(C)C]

To a solution of Intermediate A (116 mg, 0.714 mmol) in DMF (3 mL) was added NaH (60% dispersion in oil, 44 mg, 1.1 mmol) and the mixture stirred at RT for 20 min. A solution of Intermediate 63b (280 mg, 0.714 mmol) in DMF (3 mL) was added and the mixture was stirred at 60° C. for 25 min, and up to 150° C. over 20 min. The cooled mixture was diluted with water and extracted with DCM (4×20 mL). The combined organics were dried and concentrated in vacuo. The residue was purified twice by FCC, using 0-12% [2M NH₃ in MeOH] in DCM, to give the title compound as a dark brown gum (141 mg, 37%). LCMS (Method 3): Rt 3.12 min, ink 536 [MH⁺].

d. 1-(5-tert-Butyl-2-p-tolyl-2H-pyrazol-3-yl)-3-{(1S,4R)-4-[3-((S)-3-triisopropylsilanyloxy-piperidin-1-yl)-[1,2,4]triazolo[4,3-a]pyridin-6-yloxy]-1,2,3,4-tetrahydro-naphthalen-1-yl}-urea (Intermediate 63d).

A solution of Intermediate 63c (140 mg, 0.261 mmol) and (5-tert-butyl-2-p-tolyl-2H-pyrazol-3-yl)-carbamic acid 2,2,2-trichloro-ethyl ester (Synthetic Communications, 2009, 39, 3999-4009, which is incorporated herein by reference in its entirety; 106 mg, 0.261 mmol) in 1,4-dioxane (3 mL) and DIPEA (70 μL, 0.4 mmol) was stirred at 90° C. for 3 h. The cooled mixture was concentrated in vacuo. The residue was purified by FCC, using 0-10% MeOH in DCM, to give the title compound as a pale brown gum (124 mg, 60%). LCMS (Method 3): Rt 5.43 min, m/z 791 [MH⁺].

e. 1-(5-tert-Butyl-2-p-tolyl-2H-pyrazol-3-yl)-3-{(1S,4R)-4-[3-((S)-3-hydroxy-piperidin-1-yl)-[1,2,4]triazolo[4,3-a]pyridin-6-yloxy]-1,2,3,4-tetrahydro-naphthalen-1-yl}-urea (Example 63).

A solution of Intermediate 63d (123 mg, 0.156 mmol) and TBAF (1M in THF, 195 μL, 0.195 mmol) in THF (4 mL) was stirred at RT for 1 h. The mixture was diluted with water and extracted with DCM (4×15 mL). The combined organics were dried and concentrated in vacuo. The residue was purified by FCC, using 0-12% [2M NH₃ in MeOH] in DCM, to give the title compound as a white powder after freeze-drying (82 mg, 83%). LCMS (Method 5): Rt 4.27 min, m/z 635.2 [MH⁺]. ¹H NMR (400 MHz, d₆-DMSO): 1.27 (9H, s), 1.38-1.47 (1H, m), 1.62-1.74 (1H, m), 1.79-1.98 (4H, m), 1.99-2.16 (2H, m), 2.36 (3H, s), 2.78-2.86 (1H, m), 2.89-2.98 (1H, m), 3.20-3.36 (2H, m, under water signal), 3.77-3.86 (1H, m), 4.77-4.86 (1H, m), 4.90 (1H, d, J 5.2), 5.53 (1H, t, J 4.3), 6.32 (1H, s), 7.08 (1H, d, J 8.7), 7.16 (1H, dd, J 10.1, 2.1), 7.26-7.41 (8H, m), 7.61 (1H, d, J 10.0), 7.69 (1H, d, J 1.4), 8.03 (1H, s).

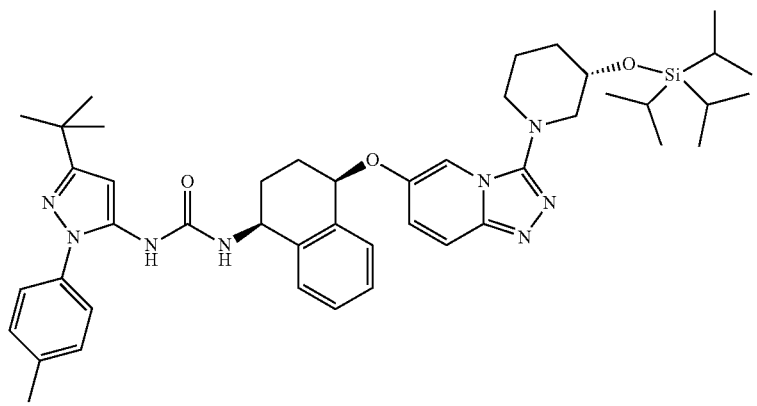 [SMILES: Cc1ccc(-n2nc(C(C)(C)C)cc2NC(=O)N[C@H]2CC[C@@H](Oc3ccc4nnc(N5CCC[C@H](O[Si](C(C)C)(C(C)C)C(C)C)C5)n4c3)c3ccccc32)cc1]

Example 64

1-(5-tert-Butyl-2-p-tolyl-2H-pyrazol-3-yl)-3-{(1S,4R)-4-[3-((R)-3-hydroxy-piperidin-1-yl)-[1,2,4]triazolo[4,3-a]pyridin-6-yloxy]-1,2,3,4-tetrahydro-naphthalen-1-yl}-urea

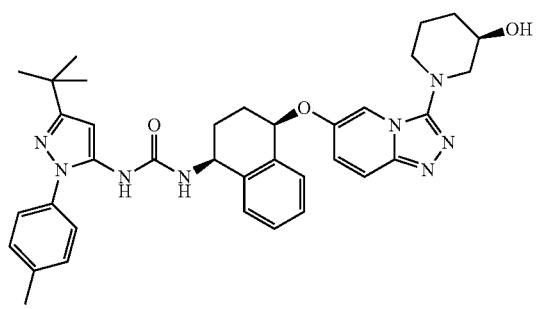 [SMILES: Cc1ccc(-n2nc(C(C)(C)C)cc2NC(=O)N[C@H]2CC[C@@H](Oc3ccc4nnc(N5CCC[C@@H](O)C5)n4c3)c3ccccc32)cc1]

The title compound was prepared starting from (R)-3-hydroxypiperidine hydrochloride using analogous procedures to those described for Example 63. LCMS (Method 5): Rt 4.27 min, m/z 635.2 [MH+]. $^1$H NMR (400 MHz, $d_6$-DMSO): 1.27 (9H, s), 1.36-1.47 (1H, m), 1.65-1.76 (1H, m), 1.77-1.98 (4H, m), 1.99-2.17 (2H, m), 2.36 (3H, s), 2.78-2.85 (1H, m), 2.87-2.95 (1H, m), 3.20-3.37 (2H, m, under water signal), 3.75-3.84 (1H, m), 4.78-4.85 (1H, m), 4.90 (1H, d, J 5.0), 5.51 (1H, t, J 4.3), 6.32 (1H, s), 7.08 (1H, d, J 8.4), 7.17 (1H, dd, J 10.0, 2.2), 7.26-7.41 (8H, m), 7.61 (1H, d, J 10.0), 7.69 (1H, d, J 1.4), 8.03 (1H, s).

Example 65

1-[5-tert-Butyl-2-(4-hydroxymethyl-phenyl)-2H-pyrazol-3-yl]-3-{(1S,4R)-4-[3-((S)-1-methyl-piperidin-2-yl)-[1,2,4]triazolo[4,3-a]pyridin-6-yloxy]-1,2,3,4-tetrahydro-naphthalen-1-yl}-urea, partial formate salt

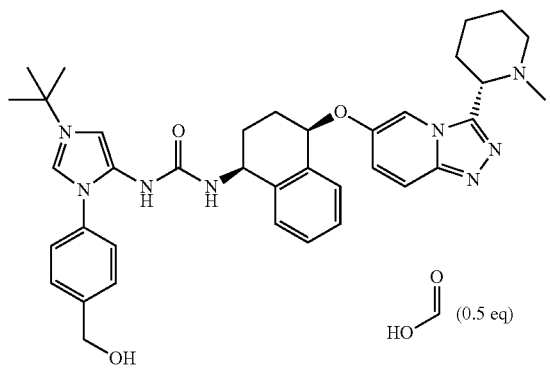

To a solution of Intermediate 62c (117 mg, 0.31 mmol) in 1,4-dioxane (3.00 mL) was added DIPEA (108 µL, 0.62 mmol) and Intermediate 33a (130 mg, 0.31 mmol). The reaction was heated to 60° C. overnight then cooled and partitioned between EtOAc and water. The aqueous layer was then extracted with EtOAc (3×). The combined organic layers were washed with brine, dried (MgSO$_4$), filtered and evaporated in vacuo. The residue was purified by FCC, using 0-10% MeOH in DCM. Further purification by HPLC (C18 X-select column, 10-98% MeCN in H$_2$O, 0.1% HCO$_2$H) gave the title compound as a white powder after freeze-drying (80 mg, 39%). LCMS (Method 5): Rt 3.31 min, m/z 649.3 [MH+]. $^1$H NMR (400 MHz, $d_4$-MeOD): 1.31 (9H, s), 1.49 (1H, m), 1.60-2.05 (7H, m), 2.05 (3H, s), 2.10 (1H, m), 2.25-2.35 (2H, m), 3.09 (1H, m), 3.87 (1H, dd, J 10.9, 2.4), 4.65 (2H, s), 4.91 (1H, m), 5.33 (1H, t, J 4.0), 6.34 (1H, s), 7.19-7.33 (5H, m), 7.42-7.51 (4H, m), 7.65 (1H, d, J 9.6), 8.26 (0.5H, br s), 8.43 (1H, d, J 1.7).

Example 66

1-(5-tert-Butyl-2-p-tolyl-2H-pyrazol-3-yl)-3-{(1S,4R)-4-[3-(4-hydroxyethyl-piperidin-1-yl)-[1,2,4]triazolo[4,3-a]pyridin-6-yloxy]-1,2,3,4-tetrahydro-naphthalen-1-yl}-urea

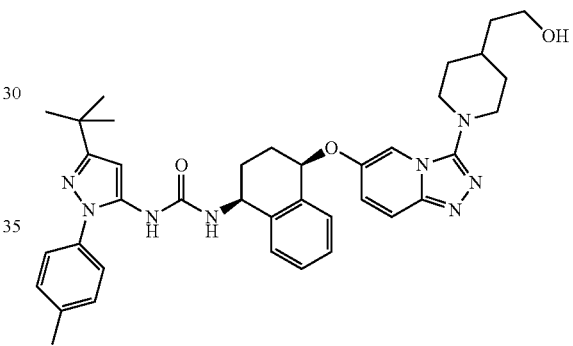

a. [1-(6-Fluoro-[1,2,4]triazolo[4,3-a]pyridin-3-yl)-piperidin-4-yl]-ethanol (Intermediate 66a).

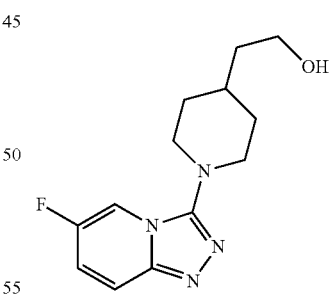

A mixture of Intermediate 24b (542 mg, 3.17 mmol) and 4-piperidine-ethanol (1.54 g, 11.9 mmol) in DMA (10 mL) was heated in the microwave at 170° C. for 3 h. The cooled mixture was applied to an SCX-2 cartridge (50 g), washing with methanol then eluting basic components with 0.4-2 M ammonia in methanol. Product containing fractions were combined and concentrated in vacuo. The residue was purified by FCC, using 0-20% MeOH in DCM, to give the title compound as a pale brown solid (324 mg, 41%). LCMS (Method 3): Rt 2.28 min, m/z 265 [MH+].

b. 6-Fluoro-3-(4-triisopropylsilanyloxyethyl-piperidin-1-yl)-[1,2,4]triazolo[4,3-a]pyridin (Intermediate 66b).

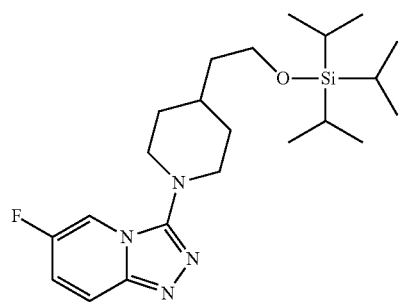 [SMILES: CC(C)[Si](OCCC1CCN(c2nnc3ccc(F)cn23)CC1)(C(C)C)C(C)C]

To a solution of Intermediate 66a (319 mg, 1.21 mmol) and Et₃N (252 μL, 1.82 mmol) in DCM (10 mL) was added triisopropylsilyltrifluoromethane sulfonate (319 μL, 1.45 mmol) and the mixture stirred at RT for 1.5 h. The mixture was washed with sat. aq. NaHCO₃ solution, dried and concentrated in vacuo. The residue was purified by FCC, using 0-10% MeOH in DCM, to give the title compound as an orange solid (465 mg, 92%). LCMS (Method 3): Rt 5.35 min, m/z 421 [MH⁺].

c. (1S,4R)-4-[3-(4-Triisopropylsilanyloxyethyl-piperidin-1-yl)-[1,2,4]triazolo[4,3-a]pyridin-6-yloxy]-1,2,3,4-tetrahydro-naphthalen-1-ylamine (Intermediate 66c).

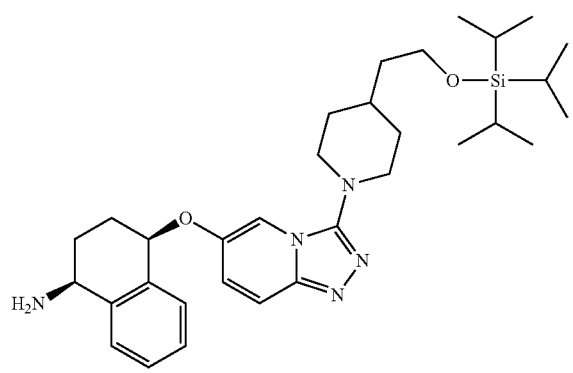 [SMILES: CC(C)[Si](OCCC1CCN(c2nnc3ccc(O[C@@H]4CC[C@H](N)c5ccccc54)cn23)CC1)(C(C)C)C(C)C]

To a solution of Intermediate A (122 mg, 0.75 mmol) in DMF (3 mL) was added NaH (60% dispersion in oil, 60 mg, 1.5 mmol) and the mixture stirred at RT for 25 min. A solution of Intermediate 66b (315 mg, 0.75 mmol) in DMF (2.5 mL) was added and the mixture stirred at 60° C. for 1.5 h. The cooled mixture was diluted with water and extracted with DCM (5×25 mL). The combined organics were dried and concentrated in vacuo. The residue was purified by FCC, using 0-14% [2M NH₃ in MeOH] in DCM, to give the title compound as a dark brown gum (180 mg, 42%). LCMS (Method 3): Rt 3.35 min, m/z 564 [MH⁺].

d. 1-(5-tert-Butyl-2-p-tolyl-2H-pyrazol-3-yl)-3-{(1S,4R)-4-[3-(4-triisopropylsilanyloxyethyl-piperidin-1-yl)-[1,2,4]triazolo[4,3-a]pyridin-6-yloxy]-1,2,3,4-tetrahydro-naphthalen-1-yl}-urea (Intermediate 66d).

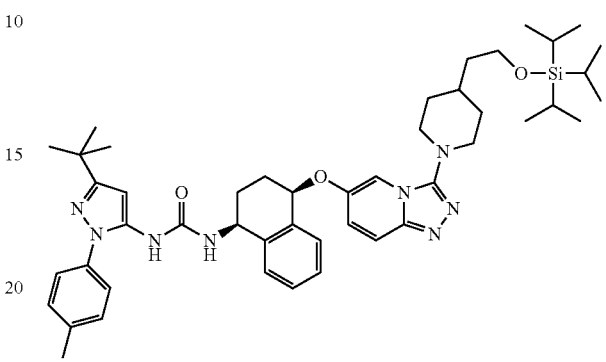

A mixture of Intermediate 66c (178 mg, 0.316 mmol) and (5-tert-butyl-2-p-tolyl-2H-pyrazol-3-yl)-carbamic acid 2,2,2-trichloro-ethyl ester (Synthetic Communications, 2009, 39, 3999-4009, which is incorporated herein by reference in its entirety; 128 mg, 0.316 mmol) in 1,4-dioxane (3 mL) and DIPEA (83 μL, 0.474 mmol) was stirred at 95° C. for 4 h. The cooled mixture was concentrated in vacuo. The residue was purified by FCC, using 0-10% MeOH in DCM, to give the title compound as a brown foam (208 mg, 81%). LCMS (Method 3): Rt 5.96 min, m/z 819 [MH⁺].

e. 1-(5-tert-Butyl-2-p-tolyl-2H-pyrazol-3-yl)-3-{(1S,4R)-4-[3-(4-hydroxyethyl-piperidin-1-yl)-[1,2,4]triazolo[4,3-a]pyridin-6-yloxy]-1,2,3,4-tetrahydro-naphthalen-1-yl}-urea (Example 66).

A solution of Intermediate 66d (207 mg, 0.253 mmol) and TBAF (1M in THF, 0.303 mL, 0.303 mmol) in THF (4 mL) was stirred at RT for 2.25 h. The mixture was diluted with water and extracted with DCM (4×15 mL). The combined organic extracts were dried and concentrated in vacuo. The residue was purified by FCC, using 0-15% MeOH in DCM, to give the product. This was further purified by HPLC (C, 18 X-select column, 30-98% MeCN in H₂O, 0.1% formic acid) to give the title compound as an off-white powder after freeze-drying (114 mg, 68%). LCMS (Method 5): Rt 4.29 min, m/z 663.3 [MH⁺]. ¹H NMR (400 MHz, d₆-DMSO): 1.27 (9H, s), 1.38-1.51 (4H, m), 1.57-1.68 (1H, m), 1.72-1.97 (4H, m), 1.99-2.16 (2H, m), 2.36 (3H, s), 2.85-2.95 (2H, m), 3.30-3.52 (4H, m, under water signal), 4.38 (1H, s), 4.77-4.85 (1H, m), 5.55 (1H, t, J 4.3), 6.32 (1H, s), 7.09 (1H, d, J 8.6), 7.16 (1H, dd, J 9.9, 2.2), 7.26-7.40 (8H, m), 7.61 (1H, d, J 9.9), 7.65 (1H, d, J 1.4), 8.06 (1H, s).

Example 67

1-[(1S,4R)-4-(3-Azepan-1-yl-[1,2,4]triazolo[4,3-a]pyridin-6-yloxy)-1,2,3,4-tetrahydro-naphthalen-1-yl]-3-(5-tert-butyl-2-p-tolyl-2H-pyrazol-3-yl)-urea

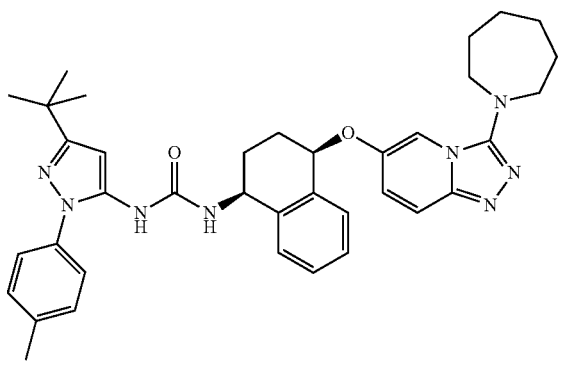 [SMILES: Cc1ccc(-n2nc(C(C)(C)C)cc2NC(=O)N[C@H]2CC[C@@H](Oc3ccc4nnc(N5CCCCCC5)n4c3)c3ccccc32)cc1]

a. 6-Fluoro-3-azepan-1-yl-[1,2,4]triazolo[4,3-a]pyridine (Intermediate 67a).

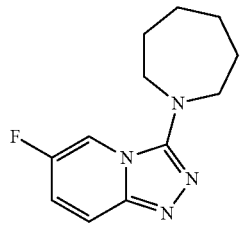 [SMILES: Fc1ccc2nnc(N3CCCCCC3)n2c1]

A solution of Intermediate 24b (451 mg, 2.50 mmol) and azapane (990 mg, 10.0 mmol) in DMA (10 mL) was heated in the microwave at 175-180° C. for 6 h. The mixture was concentrated in vacuo. The residue was purified by FCC, using 0-20% MeOH in DCM, to give impure product. Further purification by FCC, using 0-12% MeOH in DCM, gave impure product. Further purification by FCC, using 0-6% MeOH in EtOAc, gave the title compound as a green gum (260 mg, 44%). LCMS (Method 3): Rt 2.76 min, m/z 235 [MH$^+$].

b. (1S,4R)-4-(3-Azepan-1-yl-[1,2,4]triazolo[4,3-a]pyridin-6-yloxy)-1,2,3,4-tetrahydro-naphthalen-1-ylamine (Intermediate 67b).

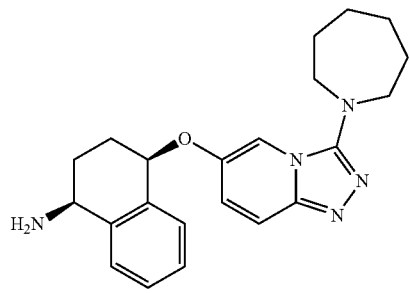 [SMILES: N[C@H]1CC[C@@H](Oc2ccc3nnc(N4CCCCCC4)n3c2)c2ccccc21]

To a solution of Intermediate A (137 mg, 0.84 mmol) in DMF (3 mL) was added NaH (60% dispersion in oil, 68 mg, 1.7 mmol) and the mixture stirred at RT for 25 min. A solution of Intermediate 67a (197 mg, 0.84 mmol) in DMF (3 mL) was added and the mixture stirred at 60° C. for 1.25 h. The cooled mixture was diluted with water and extracted with DCM (5×20 mL). The combined organics were dried and concentrated in vacuo. The residue was purified by FCC, using 0-14% [2M NH$_3$ in MeOH] in DCM, to give the title compound as a dark brown gum (175 mg, 55%). LCMS (Method 3): Rt 2.22 min, m/z 378 [MH$^+$].

c. 1-[(1S,4R)-4-(3-Azepan-1-yl-[1,2,4]triazolo[4,3-a]pyridin-6-yloxy)-1,2,3,4-tetrahydro-naphthalen-1-yl]-3-(5-tert-butyl-2-p-tolyl-2H-pyrazol-3-yl)-urea (Example 67).

A solution of Intermediate 67b (173 mg, 0.458 mmol) and (5-tert-butyl-2-p-tolyl-2H-pyrazol-3-yl)-carbamic acid 2,2,2-trichloro-ethyl ester (Synthetic Communications, 2009, 39, 3999-4009, which is incorporated herein by reference in its entirety; 186 mg, 0.458 mmol) in 1,4-dioxane (3 mL) and DIPEA (122 µL, 0.700 mmol) was stirred at 95° C. for 3.5 h. The cooled mixture was concentrated in vacuo. The residue was purified by FCC, using 0-14% [2M NH$_3$ in MeOH] in DCM. Further purification by FCC, using 0-10% MeOH in DCM, gave impure product. This was further purified by HPLC (C18X-select column, 30-98% MeCN in H$_2$O, 0.1% HCO$_2$H) to give impure product. Further purified by HPLC (XBridge column, 35-98% MeCN in H$_2$O, 0.1% NH$_4$OH) to give an off-white powder after freeze-drying (50 mg). This material was further purified by MDAP (Method 7) to give the title compound as a white solid (28 mg, 10%). LCMS (Method 5): Rt 4.77 min, m/z 633.2 [MH$^+$]. $^1$H NMR (400 MHz, d$_6$-DMSO): 1.27 (9H, s), 1.64-1.71 (4H, m), 1.74-1.97 (6H, m), 1.99-2.18 (2H, m), 2.36 (3H, s), 3.38-3.43 (4H, m, under water signal), 4.77-4.85 (1H, m), 5.47 (1H, t, J 4.3), 6.32 (1H, s), 7.07-7.14 (2H, m), 7.25-7.40 (8H, m), 7.55-7.59 (2H, m), 8.06 (1H, s).

Example 68

1-(5-tert-Butyl-2-p-tolyl-2H-pyrazol-3-yl)-3-{(1S,4R)-4-[3-(4-methyl-piperazin-1-yl)-[1,2,4]triazolo[4,3-a]pyridin-6-yloxy]-1,2,3,4-tetrahydro-naphthalen-1-yl}-urea

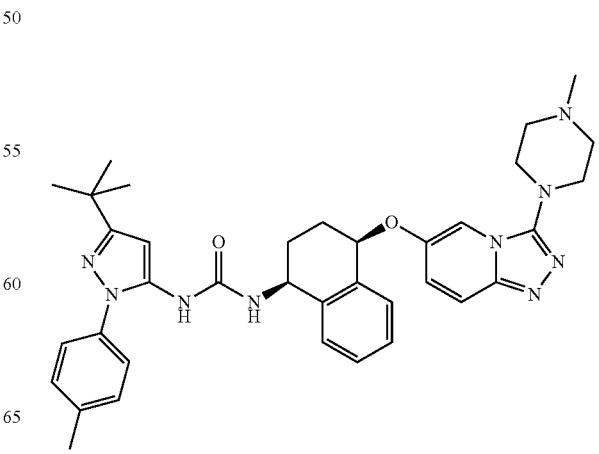

a. 6-Fluoro-3-(4-methyl-piperazin-1-yl)-[1,2,4]triazolo[4,3-a]pyridine (Intermediate 68a).

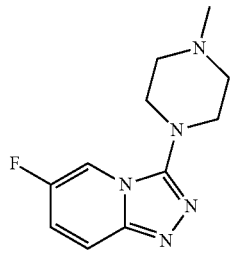 [SMILES: CN1CCN(c2nnc3ccc(F)cn23)CC1]

A solution of Intermediate 24b (451 mg, 2.50 mmol) and N-methyl-piperazine (1.11 mL, 10.0 mmol) in DMA (10 mL) was heated in the microwave at 170° C. for 8 h. The mixture was concentrated in vacuo. The residue was purified by FCC, using 0-20% [2M NH$_3$ in MeOH] in DCM, to give the title compound as an orange gum (190 mg, 32%). LCMS (Method 3): Rt 0.43 min, m/z 236 [MH$^+$].

b. (1S,4R)-4-[3-(4-Methyl-piperazin-1-yl)-[1,2,4]triazolo[4,3-a]pyridin-6-yloxy]-1,2,3,4-tetrahydro-naphthalen-1-ylamine (Intermediate 68b).

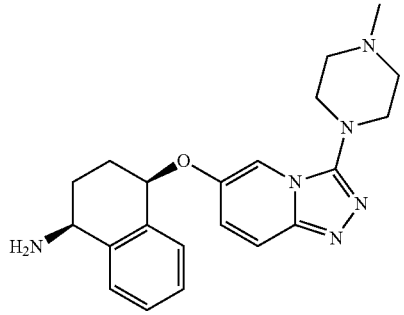 [SMILES: CN1CCN(c2nnc3ccc(O[C@@H]4CC[C@H](N)c5ccccc54)cn23)CC1]

To a solution of Intermediate A (125 mg, 0.766 mmol) in DMF (3 mL) was added NaH (60% dispersion in oil, 62 mg, 1.54 mmol) and the mixture stirred at RT for 0.5 h. A solution of Intermediate 68a (180 mg, 0.766 mmol) in DMF (3 mL) was added and the mixture stirred at 60° C. for 1.75 h. The cooled mixture was diluted with water and extracted with DCM (5×25 mL). The combined organics were dried and concentrated in vacuo. The residue was purified by FCC, using 0-20% [2M NH$_3$ in MeOH] in DCM, to give the title compound as a pale brown gum (225 mg, 78%). LCMS (Method 3): Rt 0.44 min, m/z 379 [MH$^+$].

c. 1-(5-tert-Butyl-2-p-tolyl-2H-pyrazol-3-yl)-3-{(1S,4R)-4-[3-(4-methyl-piperazine-1-yl)-[1,2,4]triazolo[4,3-a]pyridin-6-yloxy]-1,2,3,4-tetrahydro-naphthalen-1-yl}urea (Example 68).

A solution of Intermediate 68b (215 mg, 0.560 mmol) and (5-tert-butyl-2-p-tolyl-2H-pyrazol-3-yl)-carbamic acid 2,2,2-trichloro-ethyl ester (Synthetic Communications, 2009, 39, 3999-4009, which is incorporated herein by reference in its entirety; 226 mg, 0.560 mmol) in 1,4-dioxane (3 mL) and DIPEA (146 µL, 0.840 mmol) was stirred at 65° C. for 18 h. The cooled mixture was concentrated in vacuo. The residue was purified by FCC, using 10% MeOH in DCM, then 0-14% (2M NH$_3$ in MeOH) in DCM, to give impure product. Further purification by HPLC (XBridge C18 column, 35-95% MeCN in H$_2$O, 0.1% NH$_4$OH) gave the title compound as a white powder after freeze-drying (205 mg, 58%). LCMS (Method 5): Rt 3.58 min, m/z 634.2 [MH$^+$]. $^1$H NMR (400 MHz, d$_6$-DMSO): 1.27 (9H, s), 1.79-1.98 (2H, m), 1.99-2.15 (2H, m), 2.26 (3H, s), 2.36 (3H, s), 2.52-2.57 (4H, m), 3.15-3.24 (4H, m), 4.78-4.85 (1H, m), 5.56 (1H, t, J 4.4), 6.33 (1H, s), 7.07 (1H, d, J 8.6), 7.15 (1H, dd, J 9.9, 2.1), 7.26-7.40 (8H, m), 7.62 (1H, d, J 9.9), 7.68 (1H, d, J 1.8), 8.04 (1H, s).

Example 69

1-(5-tert-Butyl-2-p-tolyl-2H-pyrazol-3-yl)-3-{(1S,4R)-4-[3-(4-methyl-[1,4]diazepan-1-yl)-[1,2,4]triazolo[4,3-a]pyridin-6-yloxy]-1,2,3,4-tetrahydro-naphthalen-1-yl}urea

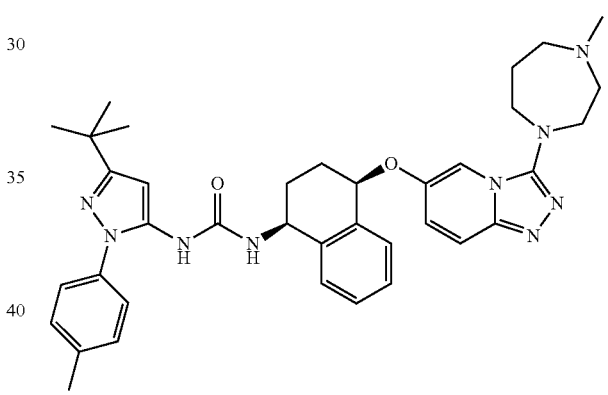

a. 6-Fluoro-3-(4-methyl-[1,4]diazepan-1-yl)-[1,2,4]triazolo[4,3-a]pyridine (Intermediate 69a).

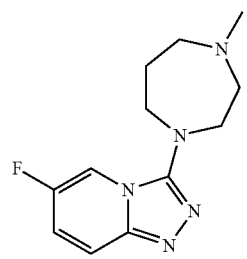 [SMILES: CN1CCCN(c2nnc3ccc(F)cn23)CC1]

A solution of Intermediate 24b (451 mg, 2.50 mmol) and 1-methyl-[1,4]diazepane (1.14 g, 10.0 mmol) in DMA (10 mL) was heated in the microwave at 175° C. for 6 h. The cooled mixture was concentrated in vacuo. The residue was purified by FCC, using 0-20% (2M NH$_3$ in MeOH) in DCM, to give the title compound as a brown oil (480 mg, 77%). LCMS (Method 3): Rt 0.44 min, m/z 250 [MH$^+$].

b. (1S,4R)-4-[3-(4-Methyl-[1,4]diazepan-1-yl)-[1,2,4]triazolo[4,3-a]pyridin-6-yloxy]-1,2,3,4-tetrahydro-naphthalen-1-ylamine (Intermediate 69b).

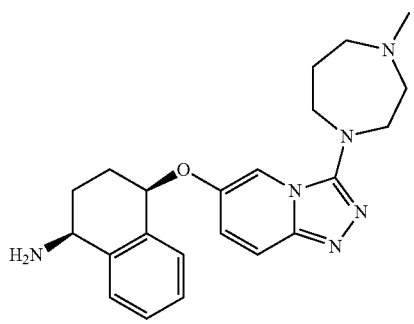 [SMILES: CN1CCCN(c2nnc3ccc(O[C@@H]4CC[C@H](N)c5ccccc54)cn23)CC1]

To a solution of Intermediate A (183 mg, 1.12 mmol) in DMF (3 mL) was added NaH (60% dispersion in oil, 149 mg, 2.24 mmol) and the mixture stirred at RT for 0.5 h. A solution of Intermediate 69a (400 mg, 1.12 mmol) in DMF (3 mL) was added and the mixture stirred at 60° C. for 1.5 h. The cooled mixture was diluted with water and extracted with DCM (3×20 mL) and DCM-MeOH (4:1, 2×25 mL). The combined organics were dried and concentrated in vacuo. The residue was purified by FCC, using 0-25% [2M NH$_3$ in MeOH] in DCM, to give the title compound as a dark brown gum (179 mg, 41%). LCMS (Method 3): Rt 0.44 min, m/z 393 [MH$^+$].

c. 1-(5-tert-Butyl-2-p-tolyl-2H-pyrazol-3-yl)-3-{(1S,4R)-4-[3-(4-methyl-[1,4]diazepan-1-yl)-[1,2,4]triazolo[4,3-a]pyridin-6-yloxy]-1,2,3,4-tetrahydro-naphthalen-1-yl}urea (Example 69).

A solution of Intermediate 69b (170 mg, 0.43 mmol) and (5-tert-butyl-2-p-tolyl-2H-pyrazol-3-yl)-carbamic acid 2,2,2-trichloro-ethyl ester (Synthetic Communications, 2009, 39, 3999-4009, which is incorporated herein by reference in its entirety; 174 mg, 0.43 mmol) in 1,4-dioxane (3 mL) and DIPEA (113 µL, 0.65 mmol) was stirred at 65° C. for 18 h. The cooled mixture was concentrated in vacuo. The residue was purified by FCC, using 10% MeOH in DCM, then 0-15% (2M NH$_3$ in MeOH) in DCM, to give impure product. Further purification by HPLC (XBridge C18 column, 35-95% MeCN in H$_2$O, 0.1% NH$_4$OH) gave the title compound as a white powder after freeze-drying (186 mg, 67%). LCMS (Method 5): Rt 3.57 min, m/z 648.2 [MH$^+$]. $^1$H NMR (400 MHz, d$_6$-DMSO): 1.27 (9H, s), 1.79-1.98 (4H, m), 2.00-2.18 (2H, m), 2.31 (3H, s), 2.36 (3H, s), 2.62-2.67 (2H, m), 2.68-2.73 (2H, m), 3.44-3.52 (4H, m), 4.78-4.85 (1H, m), 5.49 (1H, t, J 4.4), 6.32 (1H, s), 7.08 (1H, d, J 8.5), 7.11 (1H, dd, J 9.7, 2.0), 7.26-7.40 (8H, m), 7.58 (1H, d, J 9.7), 7.63 (1H, d, J 1.9), 8.03 (1H, s).

Example 70

1-[5-tert-Butyl-2-(4-hydroxy-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea

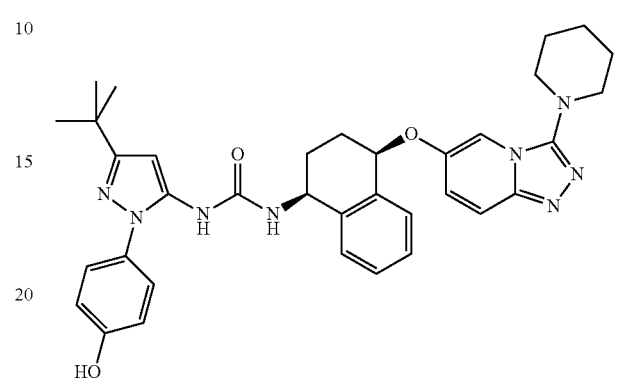

a. 1-{5-tert-Butyl-2-[4-(tert-butyl-dimethyl-silanyl oxy)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea (Intermediate 70a).

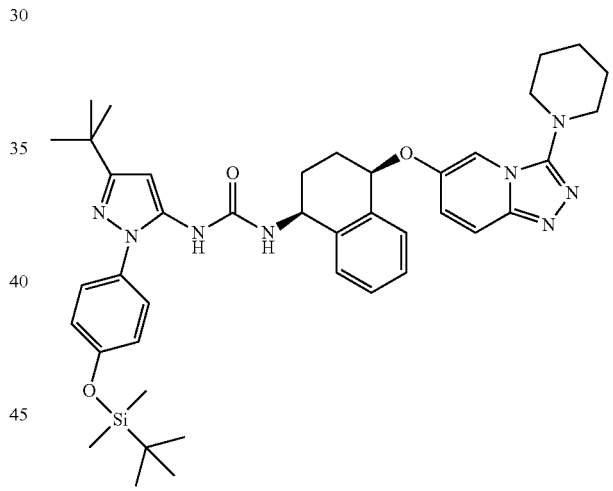

The title compound was synthesised from 5-tert-butyl-2-[4-(tert-butyl-dimethyl-silanyloxy)-phenyl]-2H-pyrazol-3-ylamine (ref: US 2006/035922, which is incorporated herein by reference in its entirety) and Intermediate 3c using analogous procedures to those used in the preparation of Example 30. Beige solid. LCMS (Method 3) Rt 4.78 min, m/z 735 [MH$^+$].

b. 1-[5-tert-Butyl-2-(4-hydroxy-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea (Example 70).

A mixture of Intermediate 70a (124 mg, 169 µmol) and TBAF (1M in THF, 0.34 mL, 0.34 mmol) in THF (5 mL) was stirred for 1 h. The mixture was diluted with water and extracted with EtOAc (3×). The combined organic extracts were washed with brine, and concentrated in vacuo. The residue was purified by FCC, using 0-20% MeOH in DCM, then further purified by HPLC (30-98% MeCN in H$_2$O, 0.1%

HCO₂H) to give the title compound as an off-white solid (18.4 mg, 18%). LCMS (Method 5) Rt 4.22 min, m/z 621 [MH⁺]. ¹H NMR (400 MHz, d₆-DMSO): 1.25 (9H, s), 1.61 (2H, m), 1.72 (4H, m), 1.79-1.98 (2H, m), 1.99-2.15 (2H, m), 3.13 (4H, m), 4.81 (1H, m), 5.54 (1H, t, J 4.5), 6.29 (1H, s), 6.85 (2H, m), 7.09 (1H, d, J 8.7), 7.14 (1H, dd, J 9.7, 2.0), 7.20-7.39 (6H, m), 7.59-7.64 (2H, m), 7.95 (1H, s), 9.77 (1H, br s).

Example 71

1-[5-tert-Butyl-2-(4-cyano-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea

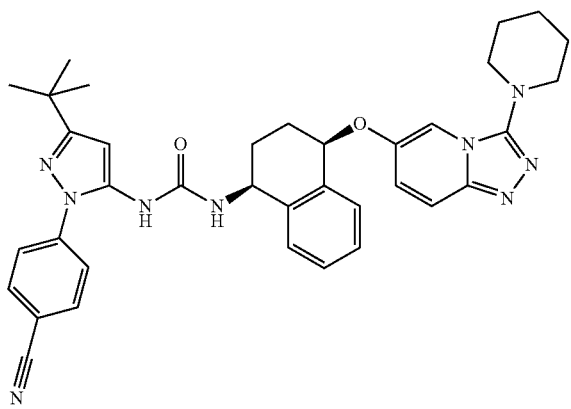 [SMILES: CC(C)(C)c1cc(NC(=O)N[C@H]2CC[C@@H](Oc3ccc4nnc(N5CCCCC5)n4c3)c3ccccc32)n(-c2ccc(C#N)cc2)n1]

a. 4-(5-Amino-3-tert-butyl-pyrazol-1-yl)-benzonitrile (Intermediate 71a).

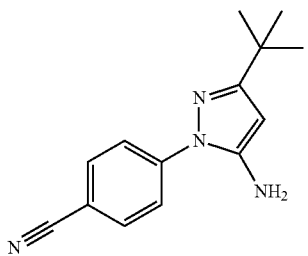 [SMILES: CC(C)(C)c1cc(N)n(-c2ccc(C#N)cc2)n1]

A cream suspension of 4-cyanophenylhydrazine hydrochloride (1.70 g, 10.0 mmol) and 4,4-dimethyl-3-oxopentanenitrile (1.31 g, 10.5 mmol) in EtOH (25 mL) was stirred at reflux for 4 h, then at RT for 64 h, and again at reflux for 24 h. The solution was cooled to RT, concentrated in vacuo, and partitioned between water (50 mL) and EtOAc (75 mL). The organics were washed with brine (50 mL), dried (Na₂SO₄), filtered and concentrated in vacuo to leave an orange solid (2.28 g, 95%). LCMS (Method 3): Rt 3.45 min, m/z 241 [MH⁺].

b. [5-tert-Butyl-2-(4-cyano-phenyl)-2H-pyrazol-3-yl]-carbamic acid 2,2,2-trichloro-ethyl ester (Intermediate 71b).

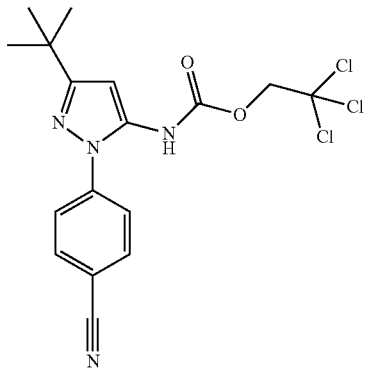 [SMILES: CC(C)(C)c1cc(NC(=O)OCC(Cl)(Cl)Cl)n(-c2ccc(C#N)cc2)n1]

To a suspension of Intermediate 71a (2.28 g, 9.49 mmol) in EtOAc (25 mL) and aqueous NaOH (1M, 23.7 mL, 23.7 mmol) was added 2,2,2-trichloroethyl chloroformate (1.57 mL, 11.4 mmol) dropwise over 2 min. A precipitate formed which redissolved after 15 min, then the orange solution was stirred at RT for 90 min. 2,2,2-Trichloroethyl chloroformate (0.391 mL, 2.85 mmol) was added and the orange mixture stirred at RT for 16 h. The layers were separated and the aqueous extracted with EtOAc (25 mL). The combined organics were washed with brine (25 mL), dried (Na₂SO₄), filtered and concentrated in vacuo to leave an orange-red oil. Recrystallisation from cyclohexane gave an off-white solid (3.12 g, 79%). LCMS (Method 3): Rt 4.46 min, m/z 415, 417 [MH⁺].

c. 1-[5-tert-Butyl-2-(4-cyano-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea (Example 71).

A brown solution of Intermediate 71b (114 mg, 0.275 mmol), Intermediate 3c (91.0 mg, 0.250 mmol) and DIPEA (0.054 mL, 0.313 mmol) in dioxane (3 mL) was stirred at 60° C. for 16 h. The cooled solution was concentrated in vacuo, the residue suspended in water (4 mL) and extracted with DCM (2×4 mL). The combined organics were passed through a hydrophobic frit and concentrated in vacuo. FCC, using 3% [2M NH₃ in MeOH] in DCM, gave a pale yellow solid (99.5 mg, 63%). LCMS (Method 5): Rt 4.63 min, m/z 630 [MH⁺]. ¹H NMR (400 MHz, d₆-DMSO): 1.29 (9H, s), 1.60-1.64 (2H, m), 1.70-1.76 (4H, m), 1.86-1.94 (2H, m), 1.99-2.07 (1H, m), 2.11-2.18 (1H, m), 3.14 (4H, t, J 5.2), 4.79 (1H, m), 5.54 (1H, t, J 4.3), 6.38 (1H, s), 7.12 (1H, d, J 8.6), 7.16 (1H, dd, J 9.8, 2.2), 7.25 (1H, d, J 7.7), 7.27-7.37 (2H, m), 7.39 (1H, d, J 7.6), 7.60-7.63 (2H, m), 7.78 (2H, d, J 8.6), 7.98 (2H, d, J 8.6), 8.30 (1H, s).

Example 72

1-(5-tert-Butyl-2-p-tolyl-2H-pyrazol-3-yl)-3-{(1S,4S)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea

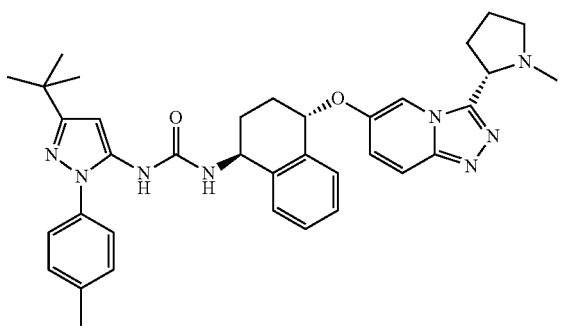 [SMILES: Cc1ccc(-n2nc(C(C)(C)C)cc2NC(=O)N[C@H]2CC[C@H](Oc3ccc4nnc([C@@H]5CCCN5C)n4c3)c3ccccc32)cc1]

a. (1S,4S)-4-[3-((S)-1-Methyl-pyrrolidin-2-yl)-[1,2,4]triazolo[4,3-a]pyridin-6-yloxy]-1,2,3,4-tetrahydro-naphthalen-1-ylamine (Intermediate 72a).

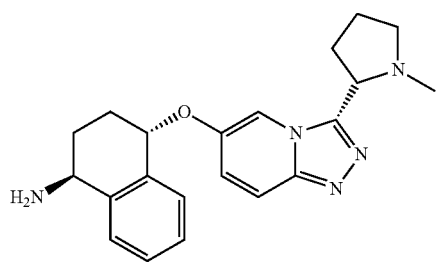

A solution of Intermediate B (179 mg, 1.10 mmol) in dry DMF (2.5 mL) was added NaH (60% in mineral oil, 333 mg, 5.00 mmol) at RT and stirred for 15 min. Intermediate 5b (220 mg, 1.00 mmol) in DMF (2.5 mL) was then added and the mixture heated at 60° C. for 1 h. After cooling, the resulting dark brown mixture was diluted with water and extracted with DCM. The combined organics were dried and concentrated in vacuo. The residue was purified by FCC, using 0-10% MeOH in DCM, to give a residue. FCC, using 0-10% [2M NH$_3$ in MeOH] in DCM, gave the title compound as light brown powder after freeze drying (224 mg, 61%). LCMS (Method 3): Rt 1.34 min, m/z 364 [MH$^+$].

b. 1-(5-tert-Butyl-2-p-tolyl-2H-pyrazol-3-yl)-3-{(1S,4S)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea (Example 72).

A stirred solution of Intermediate 72a (219 mg, 0.60 mmol) and 5-tert-butyl-2-p-tolyl-2H-pyrazol-3-yl)-carbamic acid 2,2,2-trichloro-ethyl ester (Synthetic Communications, 2009, 39, 3999-4009, which is incorporated herein by reference in its entirety; 269 mg, 0.66 mmol) and DIPEA (317 µL, 1.14 mmol) in THF (6 mL) was heated at reflux for 23 h. The cooled reaction mixture was diluted with water and extracted with DCM. The combined organics were dried and concentrated in vacuo. The residue was purified by FCC, using 0-5% [2M NH$_3$ in MeOH] in DCM, to give impure product. This residue was purified further by HPLC (ChiralPak IC column, 50% IPA in heptanes) to give the title compound as a white powder after freeze-drying (225 mg, 60%). LCMS (Method 5): Rt 3.65 min, m/z 619 [MH$^+$]. $^1$H NMR (400 MHz, d$_6$-DMSO): 1.26 (9H, s), 1.74 (1H, m), 1.93-1.99 (3H, m), 2.08 (3H, s), 2.13-2.20 (4H, m), 2.32 (1H, m), 2.36 (3H, s), 3.14 (1H, td, J 8.1, 2.5), 3.95 (1H, t, J 8.1), 4.90 (1H, m), 5.48 (1H, t, J 4.0), 6.32 (1H, s), 7.00 (1H, d, J 8.2), 7.33-7.45 (9H, m), 7.74 (1H, dd, J 9.9, 0.8), 7.98 (1H, s), 8.24 (1H, d, J 2.1).

Example 73

1-[5-tert-Butyl-2-(4-hydroxy-phenyl)-2H-pyrazol-3-yl]-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea

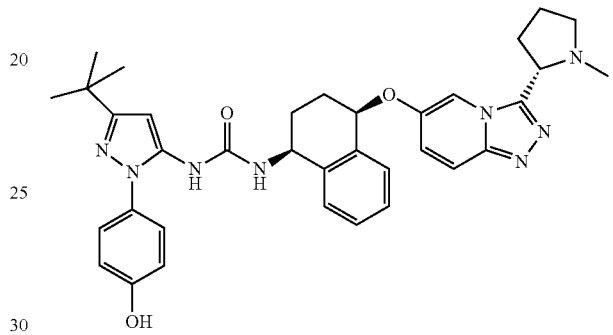

a. 1-{5-tert-Butyl-2-[4-(tert-butyl-dimethyl-silanyloxy)-phenyl]-2H-pyrazol-3-yl}-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea (Intermediate 73a).

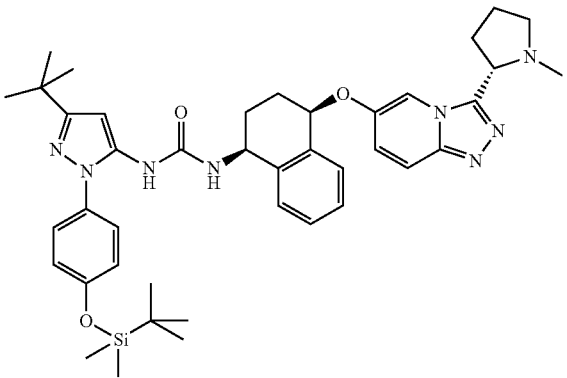 [SMILES: CN1CCC[C@H]1c1nnc2ccc(O[C@@H]3CC[C@H](NC(=O)Nc4cc(C(C)(C)C)nn4-c4ccc(O[Si](C)(C)C(C)(C)C)cc4)c4ccccc43)cn12]

The title compound was synthesised from 5-tert-butyl-2-[4-(tert-butyl-dimethyl-silanyloxy)-phenyl]-2H-pyrazol-3-ylamine (ref: US 2006/035922, which is incorporated herein by reference in its entirety) and Intermediate 5c using analogous procedures to those used in the preparation of Example 30. Yellow powder. LCMS (Method 3): Rt 3.59 min, m/z 735 [MH$^+$].

b. 1-[5-tert-Butyl-2-(4-hydroxy-phenyl)-2H-pyrazol-3-yl]-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea (Example 73).

A solution of Intermediate 73a (160 mg, 0.21 mmol) and TBAF (1M in THF, 0.26 mL, 0.26 mmol) in THF (2 mL) was stirred at RT for 30 min, then diluted with water and extracted with DCM (3×20 mL). The combined organics were dried and concentrated in vacuo. The residue was purified by FCC, using 0-5% [2M NH₃ in MeOH] in DCM, to give the title compound as a white powder after freeze-drying (107 mg, 79%). LCMS (Method 5): Rt 3.24 min, m/z 621 [MH⁺]. ¹H NMR (400 MHz, d₆-DMSO): 1.26 (9H, s), 1.81-2.25 (11H, m), 2.34-2.36 (1H, m), 3.12-3.14 (1H, m), 3.99 (1H, t, J 8.2), 4.81-4.84 (1H, m), 5.39 (1H, t, J 4.3), 6.29 (1H, s), 6.85-6.88 (2H, m), 7.09 (1H, d, J 8.6), 7.28-7.39 (7H, m), 7.75 (1H, dd, J 9.9, 0.8), 7.92 (1H, s), 8.24 (1H, d, J 2.1), 9.72 (1H, s).

Example 74

1-(5-tert-Butyl-2-p-tolyl-2H-pyrazol-3-yl)-3-(1S,4R)-4-{3-[4-(1-hydroxy-1-methyl-ethyl)-piperidin-1-yl]-[1,2,4]triazolo[4,3-a]pyridin-6-yloxy}-1,2,3,4-tetrahydro-naphthalen-1-yl)-urea

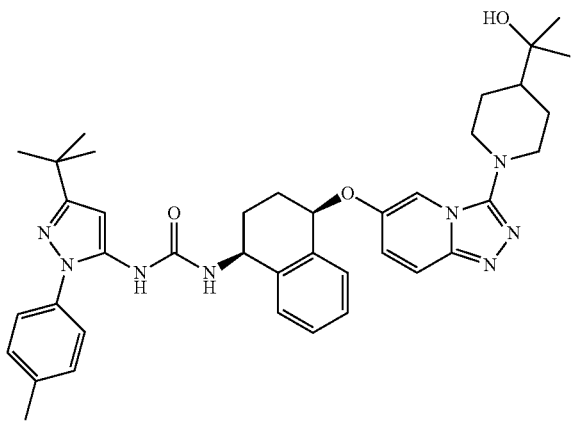 [SMILES: Cc1ccc(-n2nc(C(C)(C)C)cc2NC(=O)N[C@H]2CC[C@@H](Oc3ccc4nnc(N5CCC(C(C)(C)O)CC5)n4c3)c3ccccc32)cc1]

a. 2-[1-(6-Fluoro-[1,2,4]triazolo[4,3-a]pyridin-3-yl)-piperidin-4-yl]-propan-2-ol (Intermediate 74a).

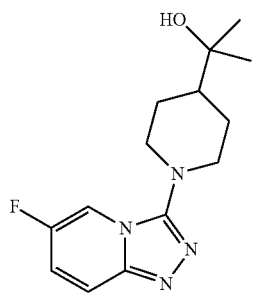 [SMILES: CC(C)(O)C1CCN(c2nnc3ccc(F)cn23)CC1]

A brown solution of Intermediate 24b (666 mg, 3.88 mmol) and 2-piperidinyl propan-2-ol (TCI, 1.39 g, 9.71 mmol) in DMA (10 mL) was irradiated to 175° C. for 3 h in the microwave. The cooled solution was concentrated in vacuo, suspended in water (10 mL) and brine (10 mL), then extracted with DCM (2×20 mL). The combined organics were passed through a hydrophobic fit and concentrated in vacuo to leave a brown oil (1.3 g). FCC, using 5% MeOH in DCM, gave the title compound as a pale yellow solid (484 mg, 45%). LCMS (Method 3): Rt 2.42 min, m/z 279 [MH⁺].

b. 6-Fluoro-3-[4-(1-methyl-1-triisopropylsilanyloxy-ethyl)-piperidin-1-yl]-[1,2,4]triazolo[4,3-a]pyridine (Intermediate 74b).

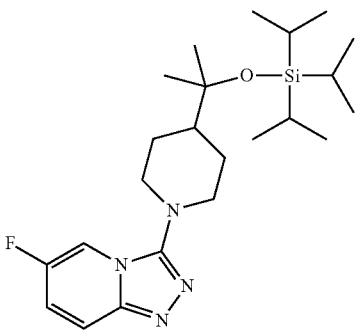 [SMILES: CC(C)[Si](OC(C)(C)C1CCN(c2nnc3ccc(F)cn23)CC1)(C(C)C)C(C)C]

A solution of Intermediate 74a (480 mg, 1.72 mmol), triisopropylsilyl trifluoromethane-sulfonate (0.579 mL, 2.16 mmol) and Et₃N (0.361 mL, 2.59 mmol) in dry DCM (5 mL) under N₂ was stirred at reflux for 2 h. The mixture was cooled to RT, then Et₃N (0.361 mL, 2.59 mmol) and triisopropylsilyl trifluoromethanesulfonate (0.579 mL, 2.16 mmol) were added and the orange solution stirred at reflux for 3 h. To the cooled solution, water (5 mL) was added and the mixture shaken. The aqueous was extracted with DCM (5 mL), then the combined organics passed through a hydrophobic frit and concentrated in vacuo to leave an orange oil. FCC, using 1-3% MeOH in DCM, gave the title compound as a pale yellow solid (592 mg, 79%). LCMS (Method 3): Rt 5.66 min, m/z 435 [MH⁺].

c. (1S,4R)-4-{3-[4-(1-Methyl-1-triisopropylsilanyloxy-ethyl)-piperidin-1-yl]-[1,2,4]triazolo[4,3-a]pyridin-6-yloxy}-1,2,3,4-tetrahydro-naphthalen-1-ylamine (Intermediate 74c).

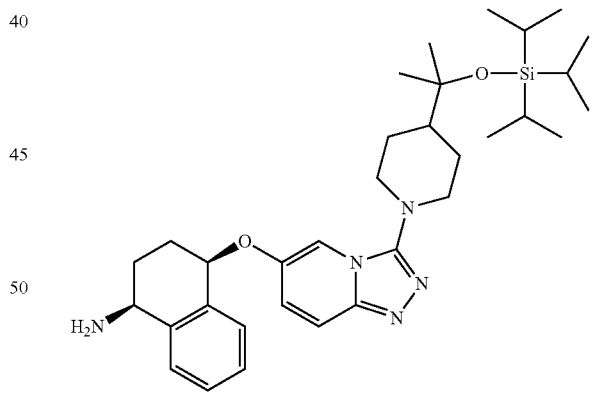

To a solution of Intermediate A (129 mg, 0.788 mmol) in dry DMF (2 mL) at RT under Ar was added NaH (60% dispersion in oil, 45.0 mg, 1.13 mmol) (CARE: gas evolution) and the resulting opaque brown solution stirred at RT for 45 min. A solution of Intermediate 74b (326 mg, 0.750 mmol) in dry DMF (2 mL) was added and the resulting dark brown solution stirred at 60° C. for 2.5 h. The solution was concentrated in vacuo, redissolved in MeOH (2 mL) and AcOH (0.100 mL), applied to an SCX-2 cartridge and washed with MeOH (100 mL). The product was eluted with 2M NH₃ in MeOH (75 mL); concentration in vacuo gave a viscous dark brown oil. FCC, using 1-6% [2M NH₃ in MeOH] in DCM, gave the title compound as a viscous brown oil (131 mg, 30%). LCMS (Method 3): Rt 3.53 min, m/z 578 [MH⁺].

d. 1-(5-tert-Butyl-2-p-tolyl-2H-pyrazol-3-yl)-3-((1S,4R)-4-{3-[4-(1-hydroxy-1-methyl-ethyl)-piperidin-1-yl]-[1,2,4]triazolo[4,3-a]pyridin-6-yloxy}-1,2,3,4-tetrahydro-naphthalen-1-yl)-urea (Example 74).

A brown solution of (5-tert-butyl-2-p-tolyl-2H-pyrazol-3-yl)-carbamic acid 2,2,2-trichloro-ethyl ester (Synthetic Communications, 2009, 39, 3999-4009, which is incorporated herein by reference in its entirety; 89.6 mg, 0.221 mmol), Intermediate 74c (128 mg, 0.221 mmol) and DIPEA (0.048 mL, 0.277 mmol) in dioxane (3 mL) was stirred at 60° C. for 16 h, and at 80° C. for 6 h. The cooled solution was concentrated in vacuo, suspended in water (4 mL) and extracted with DCM (2×4 mL). The combined organics were passed through a hydrophobic frit and concentrated in vacuo to leave a viscous brown oil. FCC, using 1-4% [2M NH₃ in MeOH] in DCM) gave 1-(5-tert-butyl-2-p-tolyl-2H-pyrazol-3-yl)-3-((1S,4R)-4-{3-[4-(1-methyl-1-triisopropylsilanyloxy-ethyl)-piperidin-1-yl]-[1,2,4]triazolo[4,3-a]pyridin-6-yloxy}-1,2,3,4-tetrahydro-naphthalen-1-yl)-urea as a yellow solid (125 mg). The solid was dissolved in THF (3 mL), treated with TBAF (1M in THF, 0.161 mL, 0.161 mmol) and the solution stirred at RT for 2 h, and then at reflux for 1 h. The solution was cooled to 40° C., then TBAF (1M in THF, 0.161 mL, 0.161 mmol) added and the solution stirred at reflux for 16 h. The cooled solution was concentrated in vacuo, suspended in water (10 mL) and extracted with EtOAc-MeOH (19:1, 2×10 mL). The combined organics were washed with brine (10 mL), dried (Na₂SO₄), filtered and concentrated in vacuo to leave a dark green residue. FCC, using 2-7% MeOH in DCM, gave the title compound as a pale yellow solid (60.6 mg, 41%). LCMS (Method 5): Rt 4.42 min, m/z 677 [MH⁺]. ¹H NMR (400 MHz, d₆-DMSO): 1.09 (6H, s), 1.27 (9H, s), 1.37-1.44 (1H, m), 1.49-1.61 (2H, m), 1.80 (2H, d, J 12.6), 1.83-1.96 (2H, m), 2.01-2.10 (2H, m), 2.36 (3H, s), 2.81-2.90 (2H, m), 3.49 (2H, t, J 11.2), 4.16 (1H, s), 4.81 (1H, td, J 8.5, 5.5), 5.56 (1H, t, J 4.4), 6.32 (1H, s), 7.08 (1H, d, J 8.6), 7.14 (1H, dd, J 9.9, 2.1), 7.27-7.40 (8H, m), 7.61 (1H, d, J 9.9), 7.66 (1H, d, J 2.0), 8.04 (1H, s).

Example 75

1-(5-tert-Butyl-2-p-tolyl-2H-pyrazol-3-yl)-3-[(1S,4R)-4-(3-pyrrolidin-1-yl-[1,2,4]triazolo[4,3-a]pyridin-6-yloxy)-1,2,3,4-tetrahydro-naphthalen-1-yl]-urea

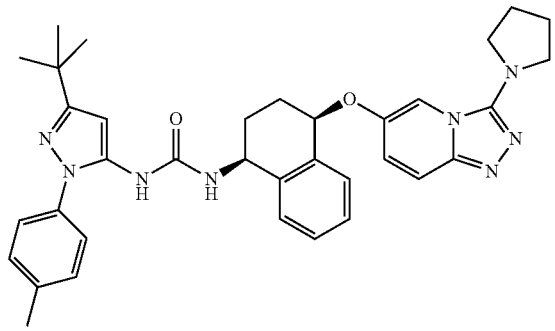 [SMILES: Cc1ccc(-n2nc(C(C)(C)C)cc2NC(=O)N[C@H]2CC[C@@H](Oc3ccc4nnc(N5CCCC5)n4c3)c3ccccc32)cc1]

a. 6-Fluoro-3-pyrrolidin-1-yl-[1,2,4]triazolo[4,3-a]pyridine (Intermediate 75a).

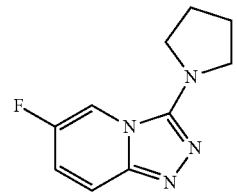 [SMILES: Fc1ccc2nnc(N3CCCC3)n2c1]

A mixture of Intermediate 24b (515 mg, 3.00 mmol), pyrrolidine (0.85 g, 12.0 mmol) and DMA (10 mL) was heated to 175° C. for 4 h using microwave irradiation. After cooling, the solvent was removed in vacuo and the resulting residue purified by FCC, using 0 to 15% MeOH in DCM, to provide the title compound as a brown gum (285 mg, 26%). LCMS (Method 3): Rt 1.95 min, m/z 207 [MH⁺].

b. (1S,4R)-4-(3-Pyrrolidin-1-yl-[1,2,4]triazolo[4,3-a]pyridin-6-yloxy)-1,2,3,4-tetrahydro-naphthalen-1-ylamine (Intermediate 75b).

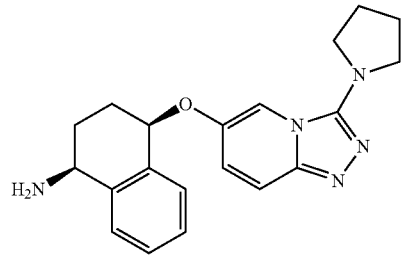 [SMILES: N[C@H]1CC[C@@H](Oc2ccc3nnc(N4CCCC4)n3c2)c2ccccc21]

Intermediate A (222 mg, 1.36 mmol) was added to a mixture of NaH (60% in mineral oil, 163 mg, 4.08 mmol) in DMF (15 mL) at RT and stirred for 30 min. Intermediate 75a (280 mg, 1.36 mmol) was then added and the resulting mixture heated to 60° C. for 1 h. After cooling, the reaction was quenched with sat. aq. NH₄Cl solution. The mixture was diluted with water and extracted with EtOAc. The combined organic extracts were washed with sat. aq. NaHCO₃ solution and brine, and concentrated in vacuo. The resulting residue was purified by FCC, using 0 to 15% [2M NH₃ in MeOH] in DCM, to afford the title compound as a brown solid (65.0 mg, 14%). LCMS (Method 3): Rt 1.89 min, m/z 350 [MH⁺].

c. 1-(5-tert-Butyl-2-p-tolyl-2H-pyrazol-3-yl)-3-[(1S,4R)-4-(3-pyrrolidin-1-yl-[1,2,4]triazolo[4,3-a]pyridin-6-yloxy)-1,2,3,4-tetrahydro-naphthalen-1-yl]-urea (Example 75).

A mixture of Intermediate 75b (62.0 mg, 0.18 mmol), (5-tert-butyl-2-p-tolyl-2H-pyrazol-3-yl)-carbamic acid 2,2,2-trichloro-ethyl ester (Synthetic Communications, 2009, 39, 3999-4009; 78.9 mg, 0.195 mmol), DIPEA (46.3 μL, 0.27 mmol) and 1,4-dioxane (2.5 mL) were heated to 60° C. for 18 h. After cooling the solvent was evaporated in vacuo. The residue was purified by FCC, using 0-10% MeOH in DCM, then further purified by HPLC (30-98% MeCN in H₂O, 0.1% HCO₂H) to give the title compound as an off-white solid (22 mg, 20%). LCMS (Method 5) Rt 4.30 min, m/z 605 [MH⁺]. ¹H NMR (400 MHz, d₆-DMSO): 1.27 (9H, s), 1.79-2.15 (8H, m), 2.36 (3H, s), 3.49 (4H, m), 4.81 (1H, m), 5.51 (1H, t, J 4.5), 6.30 (1H, s), 7.03 (1H, dd, J 10.1, 2.2), 7.09 (1H, d, J 8.5), 7.25-7.40 (8H, m), 7.51 (1H, m), 7.83 (1H, m), 8.07 (1H, s).

Example 76

1-(5-tert-Butyl-2-p-tolyl-2H-pyrazol-3-yl)-3-{(1S,4R)-4-[3-(1-dimethylamino-1-methyl-ethyl)-[1,2,4]triazolo[4,3-a]pyridin-6-yloxy]-1,2,3,4-tetrahydro-naphthalen-1-yl}-urea partial formate salt

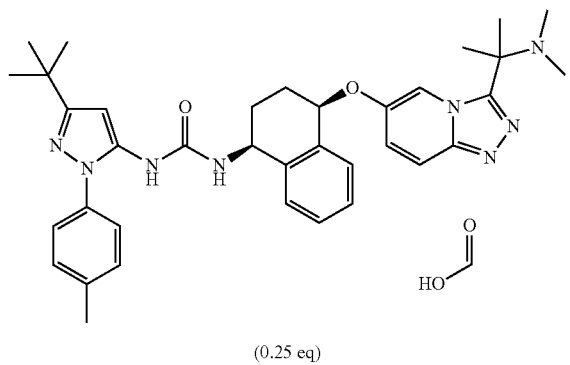 [SMILES: Cc1ccc(-n2nc(C(C)(C)C)cc2NC(=O)N[C@H]2CC[C@@H](Oc3ccc4nnc(C(C)(C)N(C)C)n4c3)c3ccccc32)cc1 ; O=CO]

(0.25 eq)

a. 2-Dimethylamino-2-methyl-propionic acid N'-(5-fluoro-pyridin-2-yl)-hydrazide (Intermediate 76a).

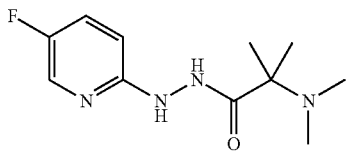 [SMILES: CN(C)C(C)(C)C(=O)NNc1ccc(F)cn1]

To a solution of (5-fluoro-pyridin-2-yl)-hydrazine (200 mg, 1.57 mmol) in DMF (10.0 mL) was added 2-dimethylamino-2-methyl-propionic acid (206 mg, 1.57 mmol), EDC (332 mg, 1.73 mmol) and HOBt.H$_2$O (21.0 mg, 0.16 mmol). The reaction was stirred overnight then partitioned between EtOAc and water. The aqueous layer was then extracted with EtOAc (3×). The combined organic layers were washed with brine, dried (MgSO$_4$), filtered and evaporated in vacuo. The residue was purified by FCC, using 0-10% [2M NH$_3$ in MeOH] in DCM, to give the title compound (195 mg, 51%). $^1$H NMR (300 MHz, CDCl$_3$): 1.25 (6H, s), 2.28 (6H, s), 6.44 (1H, br s), 6.62 (1H, dd, J 9.1, 3.6), 7.27 (1H, ddd, J 9.1, 8.0, 3.1), 8.03 (1H, d, J 2.9), 9.04 (1H, br s).

b. [1-(6-Fluoro-[1,2,4]triazolo[4,3-a]pyridin-3-yl)-1-methyl-ethyl]-dimethyl-amine (Intermediate 76b).

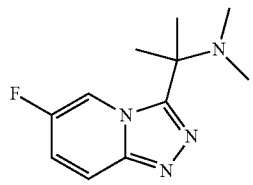 [SMILES: CN(C)C(C)(C)c1nnc2ccc(F)cn12]

To a solution of Intermediate 76a (195 mg, 0.81 mmol), Ph$_3$P (426 mg, 1.62 mmol) and Et$_3$N (452 µL, 3.25 mmol) in THF (9.00 mL) at 0° C. was added hexachloroethane (385 mg, 1.62 mmol). The reaction was stirred at RT overnight then partitioned between EtOAc and water. The aqueous layer was then extracted with EtOAc (3×). The combined organic layers were washed with brine, dried (MgSO$_4$), filtered and evaporated in vacuo. The residue was dissolved in MeOH and loaded onto an SCX-2 cartridge, which was washed with MeOH and eluted with 2M NH$_3$ in MeOH. The reaction showed 50% conversion so was re-submitted to the reaction conditions overnight at 50° C. The workup and purification procedures were repeated to give the title compound (153 mg, 85%). $^1$H NMR (300 MHz, CDCl$_3$): 1.60 (6H, s), 2.20 (6H, s), 7.16 (1H, ddd, J 9.9, 7.4, 2.4), 7.71 (1H, ddd, J 9.9, 5.0, 0.8), 8.89 (1H, ddd, J 4.4, 2.4, 0.8).

c. (1S,4R)-4-[3-(1-Dimethylamino-1-methyl-ethyl)-[1,2,4]triazolo[4,3-a]pyridin-6-yloxy]-1,2,3,4-tetrahydro-naphthalen-1-ylamine (Intermediate 76c).

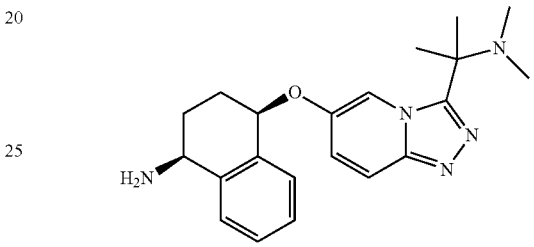

To a suspension of NaH (60% in mineral oil, 112 mg, 2.80 mmol) in DMF (2.50 mL) was added Intermediate A (114 mg, 0.70 mmol) and the reaction stirred for 20 min. Intermediate 76b (153 mg, 0.70 mmol) was added in DMF (2.50 mL) and the reaction heated to 60° C. for 1 h. The reaction was cooled and quenched by dropwise addition of methanol, before being diluted with methanol and loaded onto an SCX-2 cartridge, which was washed with MeOH. The product was eluted with 2M NH$_3$ in MeOH; concentration in vacuo gave a residue. FCC, using 2-10% [2M NH$_3$ in MeOH] in DCM, gave the title compound (120 mg, 47%). LCMS (Method 4): Rt 0.31, m/z 366 [MH$^+$].

d. 1-(5-tert-Butyl-2-p-tolyl-2H-pyrazol-3-yl)-3-{(1S,4R)-4-[3-(1-dimethylamino-1-methyl-ethyl)-[1,2,4]triazolo[4,3-a]pyridin-6-yloxy]-1,2,3,4-tetrahydro-naphthalen-1-yl}-urea, partial formate salt (Example 76).

To a solution of Intermediate 76c (120 mg, 0.33 mmol) in 1,4-dioxane (3.00 mL) was added DIPEA (117 µL, 0.66 mmol) and (5-tert-butyl-2-p-tolyl-2H-pyrazol-3-yl)-carbamic acid 2,2,2-trichloro-ethyl ester (Synthetic Communications, 2009, 39, 3999-4009, which is incorporated herein by reference in its entirety; 133 mg, 0.33 mmol). The reaction was heated to 60° C. overnight then cooled and partitioned between EtOAc and water. The aqueous layer was then extracted with EtOAc (3×). The combined organic layers were washed with brine, dried (MgSO$_4$), filtered and evaporated in vacuo. The residue was purified by FCC, using 0-8% MeOH in DCM. Further purification by HPLC (C18 X-select column, 25-60% MeCN in H$_2$O, 0.1% HCO$_2$H) gave the title compound as a white powder after freeze-drying (21 mg, 10%). LCMS (Method 5): Rt 3.86 min, m/z 621.1 [MH$^+$]. $^1$H NMR (400 MHz, d$_4$-MeOD): 1.30 (9H, s), 1.55 (3H, s), 1.56 (3H, s), 1.88-2.04 (2H, m), 2.10 (1H, m), 2.17 (6H, s), 2.26 (1H, m), 2.38 (3H, s), 4.90 (1H, dd, J 5.7, 8.7), 5.30 (1H, t, J 4.1), 6.33 (1H, s), 7.20-7.36 (9H, m), 7.60-7.64 (1H, d, J 9.9), 8.51 (0.5H, br s), 8.66 (1H, d, J 1.9).

Example 77

1-(5-tert-Butyl-2-p-tolyl-2H-pyrazol-3-yl)-3-{(1S,4R)-4-[3-((R)-3-hydroxymethyl-piperidin-1-yl)-[1,2,4]triazolo[4,3-a]pyridin-6-yloxy]-1,2,3,4-tetrahydro-naphthalen-1-yl}-urea

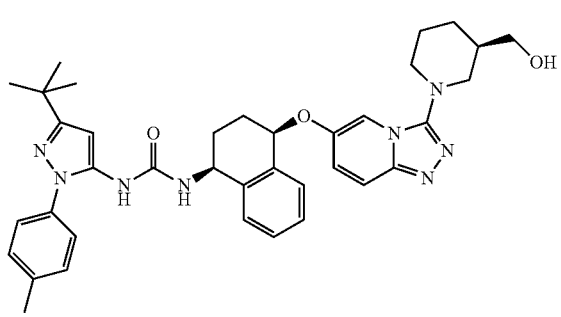 [SMILES: Cc1ccc(-n2nc(C(C)(C)C)cc2NC(=O)N[C@H]2CC[C@@H](Oc3ccc4nnc(N5CCC[C@@H](CO)C5)n4c3)c3ccccc32)cc1]

a. [(R)-1-(6-Fluoro-[1,2,4]triazolo[4,3-a]pyridin-3-yl)-piperidin-3-yl]-methanol (Intermediate 77a).

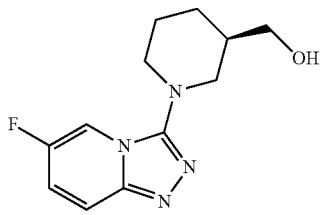 [SMILES: OC[C@@H]1CCCN(c2nnc3ccc(F)cn23)C1]

A brown solution of Intermediate 24b (565 mg, 3.29 mmol) and R-3-hydroxymethyl piperidine (Chess GmbH, 948 mg, 8.23 mmol) in DMA (10 mL) was irradiated at 175° C. for 3 h in the microwave. The cooled solution was concentrated in vacuo, suspended in water (10 mL) and brine (10 mL), and then extracted with DCM (2×20 mL). The combined organics were passed through a hydrophobic frit and concentrated in vacuo to leave a brown oil. FCC, using 4-5% MeOH in DCM, gave the title compound as a viscous yellow oil (237 mg, 29%). LCMS (Method 3): Rt 2.11 min, m/z 251 [MH+].

b. 6-Fluoro-3-((R)-3-triisopropylsilanyloxymethyl-piperidin-1-yl)-[1,2,4]triazolo[4,3-a]pyridine (Intermediate 77b).

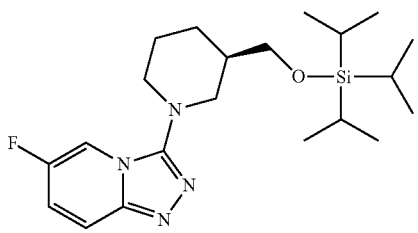 [SMILES: CC(C)[Si](OC[C@@H]1CCCN(c2nnc3ccc(F)cn23)C1)(C(C)C)C(C)C]

To a solution of Intermediate 77a (233 mg, 0.931 mmol) and Et₃N (0.195 mL, 1.40 mmol) in dry DCM (5 mL) at RT under N₂, was added triisopropylsilyl trifluoromethane-sulfonate (0.313 mL, 1.16 mmol) and the yellow solution stirred at RT for 30 min. Water (5 mL) was added and the mixture shaken. The aqueous was extracted with DCM (5 mL), then the combined organics passed through a hydrophobic frit and concentrated in vacuo to leave a yellow oil. FCC, using 1-5% MeOH in DCM, gave the title compound as a yellow oil (333 mg, 88%). LCMS (Method 3): Rt 5.23 min, m/z 407 [MH+].

c. (1S,4R)-4-[3-((R)-3-Triisopropylsilanyloxymethyl-piperidin-1-yl)-[1,2,4]triazolo[4,3-a]pyridin-6-yloxy]-1,2,3,4-tetrahydro-naphthalen-1-ylamine (Intermediate 77c).

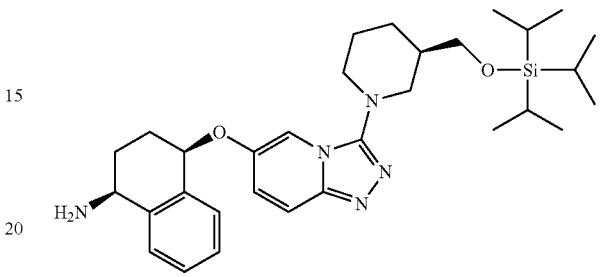

To a solution of Intermediate A (140 mg, 0.860 mmol) in dry DMF (2 mL) at RT under Ar was added NaH (60% dispersion in oil, 49.0 mg, 1.23 mmol) (CARE: gas evolution) and the resulting brown suspension was stirred at RT for 45 min. A solution of Intermediate 77b (333 mg, 0.819 mmol) in dry DMF (2 mL) was added and the resulting dark brown solution stirred at 60° C. under Ar for 2.5 h. The solution was concentrated in vacuo, redissolved in MeOH (2 mL) and AcOH (0.100 mL), then applied to and SCX-2 cartridge, and washed with MeOH (100 ml). The product was eluted with 2M NH₃ in MeOH (75 mL); concentration in vacuo left a viscous dark brown oil. FCC, using 2-7% [2M NH₃ in MeOH] in DCM, gave the title compound as a yellow-brown viscous oil (257 mg, 57%). LCMS (Method 3): Rt 3.27 min, m/z 550 [MH+].

d. 1-(5-tert-Butyl-2-p-tolyl-2H-pyrazol-3-yl)-3-{(1S,4R)-4-[3-((R)-3-triisopropylsilanyloxy-methyl-piperidin-1-yl)-[1,2,4]triazolo[4,3-a]pyridin-6-yloxy]-1,2,3,4-tetrahydro-naphthalen-1-yl}-urea (Intermediate 77d).

An orange-brown solution of (5-tert-butyl-2-p-tolyl-2H-pyrazol-3-yl)-carbamic acid 2,2,2-trichloro-ethyl ester (Synthetic Communications, 2009, 39, 3999-4009, which is incorporated herein by reference in its entirety; 103 mg, 0.255 mmol), Intermediate 77c (140 mg, 0.255 mmol) and DIPEA (0.055 mL, in dioxane (3 mL) was stirred at 60° C. for 16 h and then at 80° C. for 2 h. The cooled solution was concentrated in vacuo, suspended in water (4 mL) and extracted with DCM (2×4 mL). The combined organics were passed through a hydrophobic fit and concentrated in vacuo to 0.5 mL volume. FCC, using 2-3% [2M NH₃ in MeOH] in DCM, gave the title compound as a yellow solid (136 mg, 66%). LCMS (Method 3): Rt 5.65 min, m/z 805 [MH⁺].

e. 1-(5-tert-Butyl-2-p-tolyl-2H-pyrazol-3-yl)-3-{(1S, 4R)-4-[3-((R)-3-hydroxymethyl-piperidin-1-yl)-[1,2, 4]triazolo[4,3-a]pyridin-6-yloxy]-1,2,3,4-tetrahydro-naphthalen-1-yl}-urea (Example 77).

A brown solution of Intermediate 77d (135 mg, 0.168 mmol) and TBAF (1M in THF, 0.184 mL, 0.184 mmol) in THF (3 mL) was stirred at RT for 1 h. The solution was concentrated in vacuo, suspended in water (10 mL) and extracted with EtOAc-MeOH (19:1, 2×10 mL). The combined organics were washed with brine (10 mL), dried (Na₂SO₄), filtered and concentrated in vacuo to leave a brown solid. FCC, using 5-9% MeOH in DCM, gave a pale brown solid. Further purification by HPLC (XBridge C18 column, 25-75% MeCN in H₂O, 0.1% NH₄OH) gave the title compound as a white powder after freeze-drying (63.9 mg, 59%). LCMS (Method 5): Rt 4.33 min, m/z 649 [MH⁺]. ¹H NMR (400 MHz, d₆-DMSO): 1.27 (9H, s), 1.29-1.35 (1H, m), 1.71-1.77 (3H, m), 1.82-1.96 (3H, m), 2.01-2.17 (2H, m), 2.36 (3H, s), 3.02-3.07 (2H, m), 3.20 (1H, dd, J 11.9, 3.3), 3.25-3.28 (1H, m), 3.42 (1H, dt, J 10.5, 5.0), 3.52-3.58 (1H, m), 4.69 (1H, t, J 5.1), 4.81 (1H, td, J 8.6, 5.4), 5.48 (1H, t, J 4.3), 6.32 (1H, s), 7.09 (1H, d, J 8.3), 7.12 (1H, dd, J 9.9, 2.1), 7.27-7.39 (8H, m), 7.60 (1H, d, J 9.9), 7.80 (1H, d, J 2.1), 8.04 (1H, s).

Example 78

1-(5-tert-Butyl-2-p-tolyl-2H-pyrazol-3-yl)-3-{(1S, 4R)-4-[3-((S)-3-hydroxymethyl-piperidin-1-yl)-[1,2, 4]triazolo[4,3-a]pyridin-6-yloxy]-1,2,3,4-tetrahydro-naphthalen-1-yl}-urea

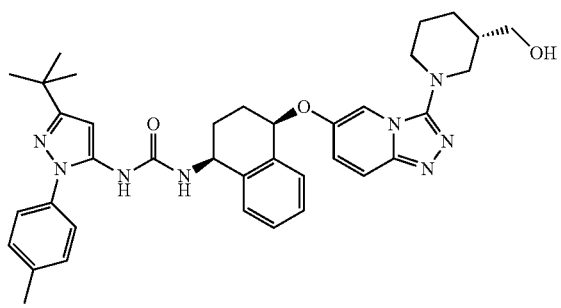 [SMILES: Cc1ccc(-n2nc(C(C)(C)C)cc2NC(=O)N[C@H]2CC[C@@H](Oc3ccc4nnc(N5CCC[C@H](CO)C5)n4c3)c3ccccc32)cc1]

The title compound was prepared starting from (S)-3-hydroxymethyl piperidine (Chess GmbH) using analogous procedures to those described in Example 77. LCMS (Method 5): Rt 4.33 min, m/z 649 [MH⁺]. ¹H NMR (400 MHz, d₆-DMSO): 1.27 (9H, s), 1.27 (1H, m), 1.69-1.79 (3H, m), 1.82-1.96 (3H, m), 2.03-2.14 (2H, m), 2.36 (3H, s), 2.96 (1H, dd, J 11.9, 8.2), 3.02-3.08 (1H, m), 3.24 (1H, dd, J 11.9, 3.3), 3.29 (1H, m), 3.43 (1H, dt, J 10.6, 5.1), 3.47-3.54 (1H, m), 4.65 (1H, t, J 5.2), 4.81 (1H, td, J 8.5, 5.4), 5.50 (1H, t, J 4.4), 6.32 (1H, s), 7.09 (1H, d, J 8.5), 7.13 (1H, dd, J 9.9, 2.1), 7.27-7.40 (8H, m), 7.60 (1H, d, J 9.9), 7.78 (1H, s), 8.05 (1H, s).

Example 79

1-(5-tert-Butyl-2-p-tolyl-2H-pyrazol-3-yl)-3-{(1S, 4R)-4-[3-(4-hydroxy-4-methyl-piperidin-1-yl)-[1,2, 4]triazolo[4,3-a]pyridin-6-yloxy]-1,2,3,4-tetrahydro-naphthalen-1-yl}-urea

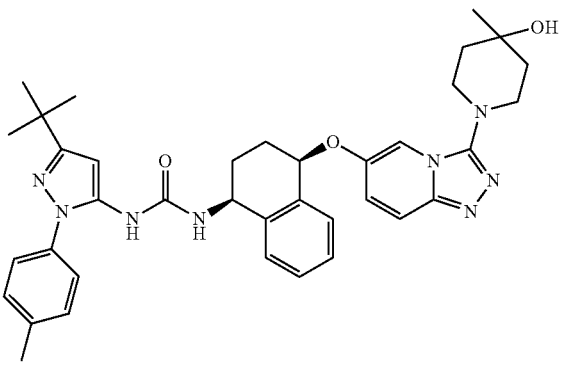 [SMILES: Cc1ccc(-n2nc(C(C)(C)C)cc2NC(=O)N[C@H]2CC[C@@H](Oc3ccc4nnc(N5CCC(C)(O)CC5)n4c3)c3ccccc32)cc1]

a. 4-Hydroxy-4-methyl-piperidine-1-carboxylic acid tert-butyl ester (Intermediate 79a).

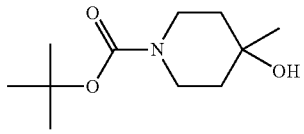

To a solution of 1-Boc-4-piperidone (10.0 g, 50.0 mmol) in diethyl ether (100 mL) at 0° C. was added methylmagnesium bromide (3.0 M in Et₂O, 22.3 mL, 67.0 mmol) maintaining the temperature below +10° C. The reaction mixture was allowed to warm to RT over 1 h. The reaction was quenched by addition of sat. aq. NH₄Cl solution, then the mixture was extracted with diethyl ether (2×). The combined organic layers were washed with brine, dried (MgSO₄), filtered and evaporated in vacuo. The residue was purified by FCC, using 0-100% EtOAc in cyclohexane, to give the title compound (6.76 g, 62%). ¹H NMR (400 MHz, CDCl₃): 1.26 (3H, s), 1.45 (9H, s), 1.48-1.62 (4H, m), 3.15-3.32 (2H, m), 3.70 (2H, d, J 12.5).

b. 4-Methyl-piperidin-4-ol (Intermediate 79b).

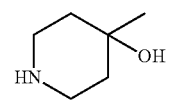

A solution of Intermediate 79a (5.50 g, 25.6 mmol) in TFA (20 mL) and DCM (40 mL) was stirred at RT for 1 h. The reaction mixture was applied to SCX-2 cartridges (2×70 g) and washed with MeOH. The product was eluted with 2M NH₃ in MeOH; concentration in vacuo gave the title compound (3.19 g, 99%). ¹H NMR (400 MHz, CDCl₃): 1.24 (3H, s), 1.51-1.61 (4H, m), 2.75-2.87 (2H, m), 2.89-3.02 (2H, m).

c. 1-(6-Fluoro-[1,2,4]triazolo[4,3-a]pyridin-3-yl)-4-methyl-piperidin-4-ol (Intermediate 79c).

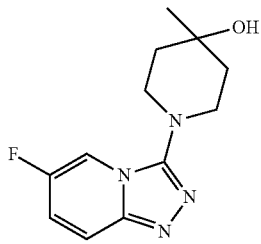 [SMILES: CC1(O)CCN(c2nnc3ccc(F)cn23)CC1]

A mixture of Intermediate 24b (400 mg, 2.32 mmol) and Intermediate 79b (1.33 g, 11.6 mmol) in NMP (5 mL) was heated in the microwave at 170° C. for 3 h. The reaction mixture was applied to an SCX-2 cartridge (25 g) and washed with MeOH. The product was eluted with 2M NH₃ in MeOH; concentration in vacuo gave a residue. FCC, using 0-8% [2M NH₃ in MeOH] in DCM, gave the title compound (190 mg, 32%). LCMS (Method 1): Rt 2.01 min, m/z 251 [MH⁺].

d. 6-Fluoro-3-(4-methyl-4-triisopropylsilanyloxy-piperidin-1-yl)-[1,2,4]triazolo[4,3-a]pyridine (Intermediate 79d).

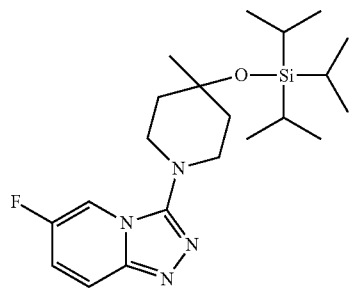 [SMILES: CC(C)[Si](OC1(C)CCN(c2nnc3ccc(F)cn23)CC1)(C(C)C)C(C)C]

Triisopropylsilyl trifluoromethanesulfonate (550 mg, 1.81 mmol) was added to a solution of Intermediate 79c (150 mg, 0.60 mmol) and Et₃N (242 mg, 2.40 mmol) in a DCM (5 mL) and the mixture stirred at reflux for 1 h. The reaction mixture was diluted with DCM (30 mL), washed with water (2×), brine, dried (MgSO₄), and then concentrated in vacuo. The residue was purified by FCC, using 0-10% MeOH in DCM, to give the title compound (235 mg, 96%). ¹H NMR (400 MHz, CDCl₃): 1.00-1.20 (21H, m), 1.40 (3H, s), 1.76-1.93 (4H, m), 3.18-3.29 (2H, m), 3.44-3.58 (2H, m), 7.03-7.12 (1H, m), 7.58-7.69 (2H, m).

e. (1S,4R)-4-[3-(4-Methyl-4-triisopropylsilanyloxy-piperidin-1-yl)-[1,2,4]triazolo[4,3-a]pyridin-6-yloxy]-1,2,3,4-tetrahydro-naphthalen-1-ylamine (Intermediate 79e).

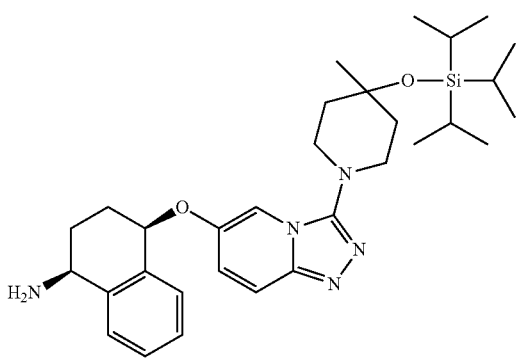 [SMILES: CC(C)[Si](OC1(C)CCN(c2nnc3ccc(O[C@@H]4CC[C@H](N)c5ccccc54)cn23)CC1)(C(C)C)C(C)C]

To a solution of Intermediate A (111 mg, 0.680 mmol) in DMF (2 mL) was added NaH (60% in oil, 68 mg, 1.70 mmol) and the mixture stirred at RT for 20 min, before Intermediate 79d (230 mg, 0.566 mmol) was added. This mixture was stirred at 60° C. for 1 h. The cooled reaction mixture was diluted with EtOAc (100 mL), washed with water (2×), brine, dried (MgSO₄) and concentrated in vacuo. The residue was purified by FCC, using 0-10% [2M NH₃ in MeOH] in DCM, to give the title compound (160 mg, 51%). LCMS (Method 1): Rt 3.06 min, m/z 550 [MH⁺].

f. 1-(5-tert-Butyl-2-p-tolyl-2H-pyrazol-3-yl)-3-{(1S,4R)-4-[3-(4-methyl-4-triisopropylsilanyloxy-piperidin-1-yl)-[1,2,4]triazolo[4,3-a]pyridin-6-yloxy]-1,2,3,4-tetrahydro-naphthalen-1-yl}-urea (Intermediate 79f).

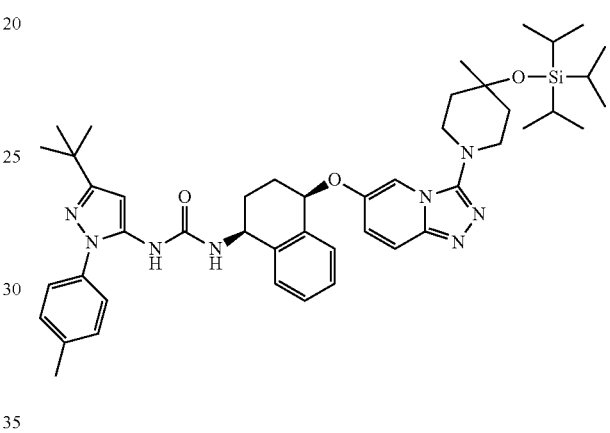

A solution of Intermediate 79e (160 mg, 0.291 mmol), (5-tert-butyl-2-p-tolyl-2H-pyrazol-3-yl)-carbamic acid 2,2,2-trichloro-ethyl ester (Synthetic Communications, 2009, 39, 3999-4009, which is incorporated herein by reference in its entirety; 176 mg, 0.437 mmol) and DIPEA (150 mg, 1.16 mmol) in DMF (4 mL) was stirred at 50° C. for 1 h. The reaction mixture was diluted with EtOAc and washed with water (2×), brine, dried (MgSO₄), filtered and concentrated in vacuo. The residue was purified by FCC, using 0-10% (2M NH₃ in MeOH) in DCM, to give the title compound (210 mg, 93%). LCMS (Method 4): Rt 5.32 min, m/z 805 [MH⁺].

g. 1-(5-tert-Butyl-2-p-tolyl-2H-pyrazol-3-yl)-3-{(1S,4R)-4-[3-(4-hydroxy-4-methyl-piperidin-1-yl)-[1,2,4]triazolo[4,3-a]pyridin-6-yloxy]-1,2,3,4-tetrahydro-naphthalen-1-yl}-urea (Example 79).

To a solution of Intermediate 79f (210 mg, 0.260 mmol) in THF (4 mL) at −30° C. was added TBAF (1M in THF, 390 μL, 0.390 mmol) and the mixture was allowed to warm to RT over 1 h. The reaction mixture was applied to an SCX-2 cartridge (10 g) and washed with MeOH. The product was eluted with 2M NH₃ in MeOH; concentration in vacuo gave a residue. FCC, using 0-10% [2M NH₃ in MeOH] in DCM, and then recrystallisation from boiling EtOAc (~40 mL) gave the title compound as a white powder (67 mg, 40%). LCMS (Method 5): Rt 4.31 min, m/z 649.1 [MH⁺]. ¹H NMR (400 MHz, d₄-MeOH): 1.30 (3H, s), 1.33 (9H, s), 1.71-1.77 (2H, m), 1.84-1.93 (2H, m), 1.95-2.17 (3H, m), 2.25-2.32 (1H, m), 2.41 (3H, s), 3.20-3.28 (2H, m), 3.36-3.45 (2H, m), 4.72-4.92

(1H, m), 5.47 (1H, t, J 4.4), 6.36 (1H, s), 6.88 (1H, d, J 9.3), 7.21-7.40 (8H, m), 7.58 (1H, d, J 9.7), 7.62 (1H, d, J 1.7).

Example 80

1-(5-tert-Butyl-2-p-tolyl-2H-pyrazol-3-yl)-3-{(1S,4R)-4-[3-(1-methyl-1-pyrrolidin-1-yl-ethyl)-[1,2,4]triazolo[4,3-a]pyridin-6-yloxy]-1,2,3,4-tetrahydro-naphthalen-1-yl}-urea

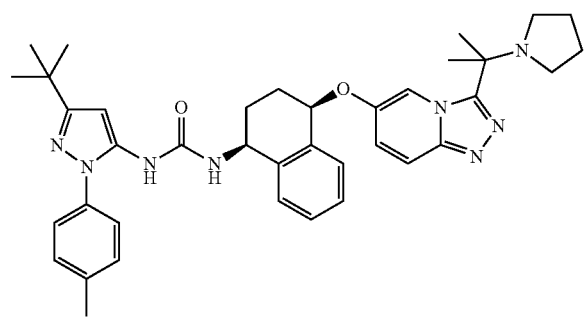 [SMILES: Cc1ccc(-n2nc(C(C)(C)C)cc2NC(=O)N[C@H]2CC[C@@H](Oc3ccc4nnc(C(C)(C)N5CCCC5)n4c3)c3ccccc32)cc1]

a. 2-Methyl-2-pyrrolidin-1-yl-propionic acid N'-(5-fluoro-pyridin-2-yl)-hydrazide (Intermediate 80a).

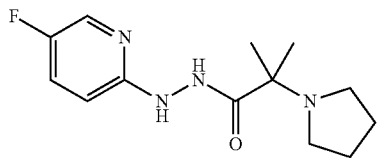 [SMILES: CC(C)(C(=O)NNc1ccc(F)cn1)N1CCCC1]

To a solution of (5-fluoro-pyridin-2-yl)-hydrazine (200 mg, 1.57 mmol) in DMF (10.0 mL) was added 2-methyl-2-pyrrolidin-1-yl-propionic acid (246 mg, 1.57 mmol), EDC (332 mg, 1.73 mmol) and HOBt.H$_2$O (21.0 mg, 0.16 mmol). The reaction was stirred overnight then partitioned between EtOAc and water. The aqueous layer was then extracted with EtOAc (3×). The combined organic layers were washed with brine, dried (MgSO$_4$), filtered and evaporated in vacuo. The residue was purified by FCC, using 0-10% [2M NH$_3$ in MeOH] in DCM, to give the title compound (260 mg, 62%). $^1$H NMR (300 MHz, CDCl$_3$): 1.30 (6H, s), 1.76-1.84 (4H, m), 2.64-2.72 (4H, m), 6.46 (1H, br s), 6.62 (1H, dd, J 9.0, 3.6), 7.28 (1H, ddd, J 9.0, 8.0, 2.9), 8.03 (1H, d, J 2.9), 9.06 (1H, br s).

b. 6-Fluoro-3-(1-methyl-1-pyrrolidin-1-yl-ethyl)-[1,2,4]triazolo[4,3-c]pyridine (Intermediate 80b).

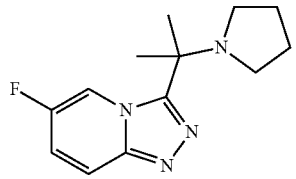 [SMILES: CC(C)(c1nnc2ccc(F)cn12)N1CCCC1]

To a solution of Intermediate 80a (260 mg, 0.98 mmol), Ph$_3$P (511 mg, 1.95 mmol) and Et$_3$N (544 μL, 3.91 mmol) in THF (10.0 mL) at 0° C. was added hexachloroethane (462 mg, 1.95 mmol). The reaction was stirred at RT overnight then partitioned between EtOAc and water. The aqueous layer was then extracted with EtOAc (3×). The combined organic layers were washed with brine, dried (MgSO$_4$), filtered and evaporated in vacuo. The residue was taken up in MeOH and loaded onto an SCX-2 cartridge, which was washed with MeOH and eluted with 2M NH$_3$ in MeOH. The reaction showed 50% conversion so was re-submitted to the reaction conditions overnight at 50° C. The workup and purification procedures were repeated to give the title compound (209 mg, 86%). $^1$H NMR (300 MHz, CDCl$_3$): 1.64 (6H, s), 1.74-1.82 (4H, m), 2.52-2.57 (4H, m), 7.16 (1H, ddd, J 9.8, 7.4, 2.3), 7.69 (1H, m), 8.93 (1H, ddd, J 4.5, 2.3, 0.7).

c. (1S,4R)-4-[3-(1-Methyl-1-pyrrolidin-1-yl-ethyl)-[1,2,4]triazolo[4,3-a]pyridin-6-yloxy]-1,2,3,4-tetrahydro-naphthalen-1-ylamine (Intermediate 80c).

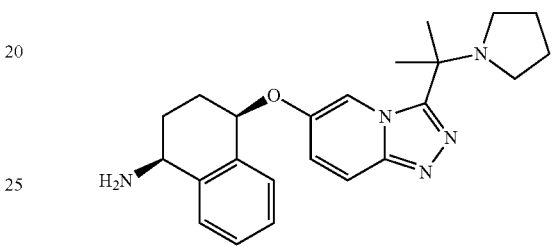

To a suspension of NaH (60% in mineral oil, 135 mg, 3.37 mmol) in DMF (4.50 mL) was added Intermediate A (137 mg, 0.84 mmol) and the reaction stirred for 20 min. Intermediate 80b (209 mg, 0.84 mmol) was added in DMF (1.50 mL) and the reaction heated to 60° C. for 1 h. The reaction was cooled and quenched by dropwise addition of methanol, before being diluted with methanol and loaded onto an SCX-2 cartridge, which was washed with MeOH and product eluted with 2M NH$_3$ in MeOH. The resulting residue was purified by FCC, using 0-10% [2M NH$_3$ in MeOH] in DCM, to give the title compound (180 mg, 55%). LCMS (Method 4): Rt 0.31, m/z 392.2 [MH$^+$].

d. 1-(5-tert-Butyl-2-p-tolyl-2H-pyrazol-3-yl)-3-{(1S,4R)-4-[3-(1-methyl-1-pyrrolidin-1-yl-ethyl)-[1,2,4]triazolo[4,3-a]pyridin-6-yloxy]-1,2,3,4-tetrahydro-naphthalen-1-yl}-urea (Example 80).

To a solution of Intermediate 80c (180 mg, 0.46 mmol) in 1,4-dioxane (5.00 mL) was added DIPEA (160 μL, 0.92 mmol) and (5-tert-butyl-2-p-tolyl-2H-pyrazol-3-yl)-carbamic acid 2,2,2-trichloro-ethyl ester (Synthetic Communications, 2009, 39, 3999-4009, which is incorporated herein by reference in its entirety; 185 mg, 0.46 mmol). The reaction was heated to 60° C. overnight then cooled and partitioned between EtOAc and water. The aqueous layer was then extracted with EtOAc (3×). The combined organic layers were washed with brine, dried (MgSO$_4$), filtered and evaporated in vacuo. The residue was purified by FCC, using 0-8% MeOH in DCM. Further purification by HPLC (C18 X-select column, 10-98% MeCN in H$_2$O, 0.1% HCO$_2$H) gave the title compound as a white powder after freeze-drying (58 mg, 20%). LCMS (Method 5): Rt 3.84 min, m/z 647.2 [MH$^+$]. $^1$H NMR (400 MHz, d$_4$-MeOD): 1.30 (9H, s), 1.60 (6H, s), 1.70-1.76 (4H, m), 1.86-2.06 (2H, m), 2.11 (1H, m), 2.20 (1H, m), 2.38 (3H, s), 2.45-2.52 (2H, m), 2.55-2.62 (2H, m), 4.89

(1H, dd, J 5.6, 8.9), 5.29 (1H, t, J 4.2), 6.33 (1H, s), 7.20-7.36 (9H, m), 7.62 (1H, d, J 9.9), 8.77 (1H, d, J 2.0).

Example 81

1-(5-tert-Butyl-2-p-tolyl-2H-pyrazol-3-yl)-3-{(1S, 4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea

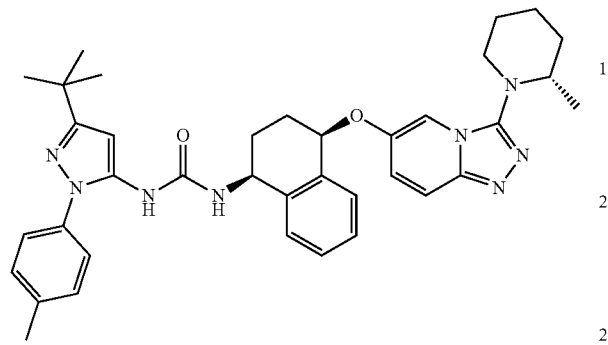

a. (S)-2-Methyl-piperidine-1-carbonyl chloride (Intermediate 81a).

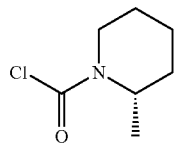

To a pale yellow solution of triphosgene (742 mg, 2.50 mmol) and pyridine (0.404 mL, 5.00 mmol) in dry DCM (10 mL) at 10° C. under N₂ was added (S)-2-methyl piperidine (Aldrich, 0.603 mL, 5.00 mmol) cautiously over 2 min. The vivid orange solution was stirred at RT for 18 h, then pyridine (0.404 mL, 5.00 mmol) and triphosgene (742 mg, 2.50 mmol) were added sequentially (CARE: exotherm on addition of triphosgene) and the orange solution stirred at RT for 4 h. Aqueous HCl solution (1M, 10 mL) was added and the mixture stirred vigorously until gas evolution ceased (30 min). The aqueous layer was extracted with DCM (10 mL), then the combined organics passed through a hydrophobic fit and concentrated in vacuo to leave the title compound as a dark red oil (745 mg, 92%). ¹H NMR (300 MHz, CDCl₃): 1.25 (3H, d, J 7.0), 1.42-1.77 (6H, m), 3.07 (1H, br s), 4.17 (1H, dd, J 13.8, 4.0), 4.62 (1H, apparent quin, J 6.3).

b. (S)-2-Methyl-piperidine-1-carboxylic acid N'-(5-fluoro-pyridin-2-yl)-hydrazide (Intermediate 81 b).

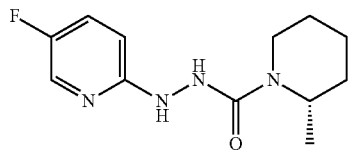 [SMILES: C[C@H]1CCCCN1C(=O)NNc1ccc(F)cn1]

To a solution of (5-fluoro-pyridin-2-yl)-hydrazine (582 mg, 4.58 mmol) and DIPEA (0.997 mL, 5.72 mmol) in dry DCM (20 mL) was added Intermediate 81a (740 mg, 4.58 mmol) and the resulting red solution stirred at RT for 66 h, and at reflux for 4 h. To the cooled solution was added water (20 mL) and the mixture shaken. The aqueous was extracted with DCM (20 mL), then the combined organics passed through a hydrophobic frit and concentrated in vacuo to leave a pale brown solid. FCC, using 0-5% MeOH in DCM, gave the title compound as a pale yellow solid (657 mg, 57%). ¹H NMR (300 MHz, CDCl₃): 1.22 (3H, d, J 6.9), 1.40-1.77 (6H, m), 2.96 (1H, td, J 13.0, 2.9), 3.85 (1H, ddd, J 13.3, 4.5, 2.2), 4.31 (1H, m), 6.50 (1H, s), 6.59 (1H, br s), 6.75 (1H, ddd, J 9.0, 3.6, 0.7), 7.27 (1H, ddd, J 9.1, 8.1, 3.1), 8.02 (1H, d, J 2.9).

c. 6-Fluoro-3-((S)-2-methyl-piperidin-1-yl)-[1,2,4]triazolo[4,3-a]pyridine (Intermediate 81c).

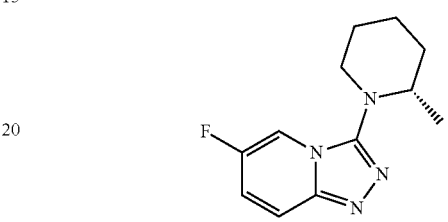

To a solution of Intermediate 81b (657 mg, 2.60 mmol), Ph₃P (1.37 g, 5.21 mmol) and Et₃N (1.45 mL, 10.4 mmol) in THF (20 mL) at 0° C. was added hexachloroethane (1.23 g, 5.21 mmol) and the resulting yellow suspension was stirred at RT for 2 h, and at reflux for 19 h. The cooled solution was filtered and concentrated in vacuo. The brown oil was redissolved in MeOH (3 mL) and applied to an SCX-2 cartridge (20 g), washing with MeOH (100 mL). The product was eluted with 2M NH₃ in MeOH (75 mL); concentration in vacuo gave a brown oil. FCC, using 1-5% [2M NH₃ in MeOH] in DCM, gave the title compound as a brown oil (542 mg, 89%). LCMS (Method 3): Rt 3.00 min, m/z 235 [MH⁺].

d. (1S,4R)-4-[3-((S)-2-Methyl-piperidin-1-yl)-[1,2,4]triazolo[4,3-a]pyridin-6-yloxy]-1,2,3,4-tetrahydro-naphthalen-1-ylamine (Intermediate 81d).

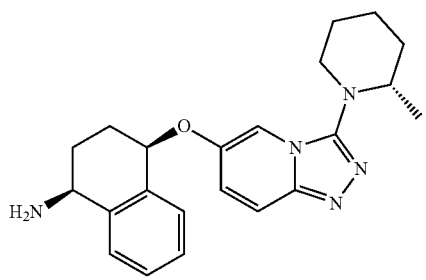 [SMILES: C[C@H]1CCCCN1c1nnc2ccc(O[C@@H]3CC[C@H](N)c4ccccc43)cn12]

To a solution of Intermediate A (374 mg, 2.29 mmol) in dry DMF (3 mL) under N₂ was added NaH (60% dispersion in oil, 183 mg, 4.58 mmol) and the resulting opaque brown solution was stirred at RT for 45 min (CARE: gas evolution). A solution of Intermediate 81c (537 mg, 2.29 mmol) in dry DMF (7 mL) was added and the dark brown solution stirred at 60° C. under N₂ for 90 min. The cooled solution was concentrated in vacuo, redissolved in MeOH (3 mL) and AcOH (0.10 mL) and then applied to an SCX-2 cartridge (20 g), washing with MeOH (50 mL). The product was eluted with 2M NH₃ in MeOH (50 mL); concentration in vacuo gave a dark brown solid. FCC, using 2-7% [2M NH₃ in MeOH] in DCM, gave the title compound as a pale brown foam (505 mg, 58%). LCMS (Method 3): Rt 2.29 min, m/z 378 [MH⁺].

e. 1-(5-tert-Butyl-2-p-tolyl-2H-pyrazol-3-yl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea (Example 81).

An orange-brown solution of (5-tert-butyl-2-p-tolyl-2H-pyrazol-3-yl)-carbamic acid 2,2,2-trichloro-ethyl ester (Synthetic Communications, 2009, 39, 3999-4009, which is incorporated herein by reference in its entirety; 106 mg, 0.263 mmol), Intermediate 81d (94.4 mg, 0.250 mmol) and DIPEA (0.054 mL, 0.313 mmol) in dry dioxane (3 mL) was stirred at 70° C. for 16 h. The cooled solution was concentrated in vacuo, suspended in water (5 mL) and extracted with DCM (2×5 mL). The combined organics were passed through a hydrophobic frit and concentrated in vacuo to leave a brown gum. FCC, using 2-6% MeOH in DCM, gave a pale yellow solid (123 mg). Further purification by HPLC (XBridge C18 column, 40-90% MeCN in H$_2$O, 0.1% NH$_4$OH) gave the title compound as a white powder after freeze-drying (72.4 mg, 46%). LCMS (Method 5): Rt 5.04 min, m/z 633 [MH$^+$]. $^1$H NMR (400 MHz, d$_6$-DMSO): 0.91 (3H, d, J 6.3), 1.27 (9H, s), 1.48-1.55 (2H, m), 1.63-1.71 (2H, m), 1.75-1.97 (4H, m), 2.00-2.16 (2H, m), 2.36 (3H, s), 2.90 (1H, ddd, J 12.1, 9.0, 3.9), 3.16 (1H, dt, J 12.1, 4.3), 3.29 (1H, m), 4.82 (1H, td, J 8.6, 5.5), 5.51 (1H, t, J 4.4), 6.32 (1H, s), 7.08 (1H, d, J 8.6), 7.19 (1H, dd, J 9.9, 2.2), 7.25-7.38 (8H, m), 7.64 (1H, dd, J 9.8, 0.8), 7.69 (1H, d, J 2.1), 8.04 (1H, s).

Example 82

1-(5-tert-Butyl-2-p-tolyl-2H-pyrazol-3-yl)-3-{(1S,4R)-4-[3-((R)-2-methyl-piperidin-1-yl)-[1,2,4]triazolo[4,3-a]pyridin-6-yloxy]-1,2,3,4-tetrahydro-naphthalen-1-yl}-urea

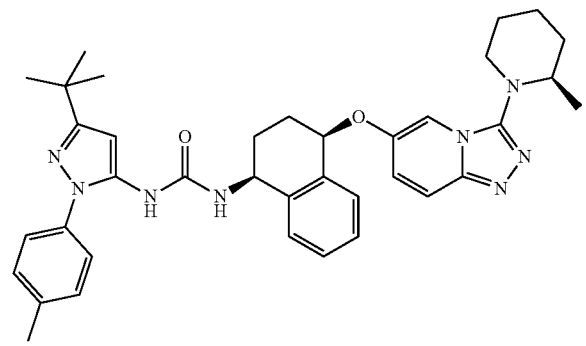 [SMILES: Cc1ccc(-n2nc(C(C)(C)C)cc2NC(=O)N[C@H]2CC[C@@H](Oc3ccc4nnc(N5CCCC[C@H]5C)n4c3)c3ccccc32)cc1]

The title compound was prepared starting from (R)-2-methyl piperidine (ABCR) using analogous procedures to those described in Example 81. LCMS (Method 5): Rt 5.03 min, m/z 633 [MH$^+$]. $^1$H NMR (400 MHz, d$_6$-DMSO): 0.88 (3H, d, J 6.3), 1.27 (9H, s), 1.48-1.55 (2H, m), 1.65-1.71 (2H, m), 1.76-1.98 (4H, m), 2.01-2.14 (2H, m), 2.36 (3H, s), 2.94 (1H, ddd, J 12.2, 8.1, 4.8), 3.17 (1H, dt, J 12.1, 4.3), 3.26-3.30 (1H, m), 4.82 (1H, td, J 8.6, 5.4), 5.54 (1H, t, J 4.4), 6.32 (1H, s), 7.08 (1H, d, J 8.6), 7.18 (1H, dd, J 9.8, 2.2), 7.26-7.38 (8H, m), 7.64 (1H, d, J 9.9), 7.70 (1H, d, J 2.1), 8.04 (1H, s).

Example 83

1-(5-tert-Butyl-2-p-tolyl-2H-pyrazol-3-yl)-3-{(1S,4R)-4-[3-((S)-4-methyl-morpholin-3-yl)-[1,2,4]triazolo[4,3-a]pyridin-6-yloxy]-1,2,3,4-tetrahydro-naphthalen-1-yl}-urea, partial formate salt

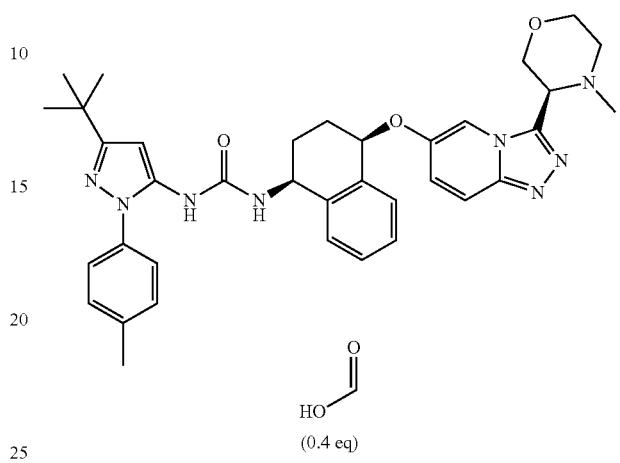

(0.4 eq)

a. (R)-3-[N'-(5-Fluoro-pyridin-2-yl)-hydrazinocarbonyl]-morpholine-4-carboxylic acid tert-butyl ester (Intermediate 83a).

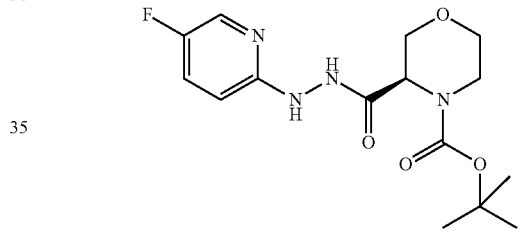

To a solution of (5-fluoro-pyridin-2-yl)-hydrazine (143 mg, 1.13 mmol) in DCM (10.0 mL) was added (R)-morpholine-3,4-dicarboxylic acid 4-tert-butyl ester (260 mg, 1.13 mmol), EDC (238 mg, 1.24 mmol) and HOBt.H$_2$O (15.0 mg, 0.11 mmol). The reaction was stirred overnight then partitioned between EtOAc and water. The aqueous layer was then extracted with EtOAc (3×). The combined organic layers were washed with brine, dried (MgSO$_4$), filtered and evaporated in vacuo. The residue was purified by FCC, using 0-10% [2M NH$_3$ in MeOH] in DCM, to give the title compound (375 mg, 98%). LCMS (Method 1): Rt 2.69, m/z 341.2 [MH$^+$].

b. (S)-3-(6-Fluoro-[1,2,4]triazolo[4,3-c]pyridin-3-yl)-morpholine-4-carboxylic acid tert-butyl ester (Intermediate 83b).

To a solution of Intermediate 83a (375 mg, 1.10 mmol), Ph$_3$P (578 mg, 2.20 mmol) and Et$_3$N (614 µL, 4.41 mmol) in THF (11.0 mL) at 0° C. was added hexachloroethane (523 mg, 2.20 mmol). The reaction was stirred at RT overnight then partitioned between EtOAc and water. The aqueous layer was then extracted with EtOAc (3×). The combined organic layers were washed with brine, dried (MgSO₄), filtered and evaporated in vacuo. The residue was taken up in MeOH and loaded onto an SCX-2 cartridge, which was washed with MeOH and eluted with 2M NH₃ in MeOH; concentration in vacuo gave the title compound (297 mg, 84%). LCMS (Method 1): Rt 2.73, m/z 323.2 [MH⁺].

c. 6-Fluoro-3-((S)-4-methyl-morpholin-3-yl)-[1,2,4]triazolo[4,3-a]pyridine (Intermediate 83c).

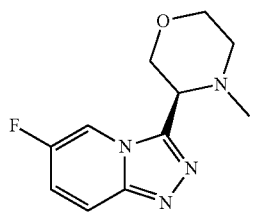 [SMILES: CN1CCOC[C@@H]1c1nnc2ccc(F)cn12]

To a solution of Intermediate 83b (297 mg, 0.92 mmol) in DCM (8.0 mL) at 0° C. was added TFA (400 μL) and the reaction stirred at RT overnight. Further TFA (600 μL) was added and the reaction stirred for 1 h then partitioned between DCM and sat. aq. NaHCO₃ solution. The aqueous layer was then extracted with DCM (3×). The combined organic layers were washed with brine, dried (MgSO₄), filtered and evaporated in vacuo. The residue was taken up in DCM (4.0 ml) and MeOH (3 drops) added. Formaldehyde solution (37 wt % in water, 162 μL, 2.00 mmol) was added followed by sodium triacetoxyborohydride (372 mg, 2.40 mmol). The reaction was stirred overnight then loaded onto an SCX-2 cartridge, which was washed with MeOH and eluted with 2M NH₃ in MeOH; concentration in vacuo gave the title compound (75.0 mg, 34%). ¹H NMR (400 MHz, d₄-MeOD): 2.09 (3H, s), 2.49 (1H, td, J 11.4, 3.8), 2.98 (1H, dt, J 11.9, 2.0), 3.79-3.90 (3H, m), 3.94 (1H, m), 4.01 (1H, dd, J 10.1, 4.0), 7.50 (1H, ddd, J 10.0, 7.7, 2.2), 7.81 (1H, ddd, J 10.1, 4.9, 0.8), 8.98 (1H, ddd, J 4.0, 2.3, 0.8).

d. (1S,4R)-4-[3-((S)-4-Methyl-morpholin-3-yl)-[1,2,4]triazolo[4,3-a]pyridin-6-yloxy]-1,2,3,4-tetrahydro-naphthalen-1-ylamine (Intermediate 83d).

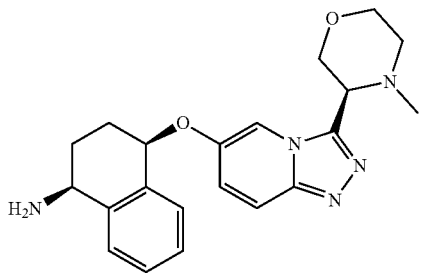 [SMILES: CN1CCOC[C@@H]1c1nnc2ccc(O[C@@H]3CC[C@H](N)c4ccccc43)cn12]

To a suspension of NaH (60% in mineral oil, 51.0 mg, 1.27 mmol) in DMF (1.50 mL) was added Intermediate A (51.0 mg, 0.32 mmol) and the reaction stirred for 20 min. Intermediate 83c (75.0 mg, 0.32 mmol) was added in DMF (1.50 mL) and the reaction heated to 60° C. for 1 h. The reaction was cooled and quenched by dropwise addition of methanol, before being diluted with methanol and loaded onto an SCX-2 cartridge, which was washed with MeOH. The product was eluted with 2M NH₃ in MeOH; concentration in vacuo gave a residue. FCC, using 0-10% [2M NH₃ in MeOH] in DCM, gave the title compound (31 mg, 26%). LCMS (Method 4): Rt 0.32, in/z 380.0 [MH⁺].

e. 1-(5-tert-Butyl-2-p-tolyl-2H-pyrazol-3-yl)-3-{(1S,4R)-4-[3-((S)-4-methyl-morpholin-3-yl)-[1,2,4]triazolo[4,3-a]pyridin-6-yloxy]-1,2,3,4-tetrahydro-naphthalen-1-yl}-urea, partial formate salt (Example 83).

To a solution of Intermediate 83d (31.0 mg, 0.082 mmol) in 1,4-dioxane (2.00 mL) was added DIPEA (28.0 μL, 0.16 mmol) and (5-tert-butyl-2-p-tolyl-2H-pyrazol-3-yl)-carbamic acid 2,2,2-trichloro-ethyl ester (Synthetic Communications, 2009, 39, 3999-4009, which is incorporated herein by reference in its entirety; 33.0 mg, 0.082 mmol). The reaction was heated to 60° C. overnight then cooled and partitioned between EtOAc and water. The aqueous layer was then extracted with EtOAc (3×). The combined organic layers were washed with brine, dried (MgSO₄), filtered and evaporated in vacuo. The residue was purified by FCC, using 0-10% MeOH in DCM. Further purification by HPLC (C18 X-select column, 10-98% MeCN in H₂O, 0.1% HCO₂H) gave the title compound as a white powder after freeze-drying (10 mg, 19%). LCMS (Method 5): Rt 3.90 min, m/z 635.2 [MH⁺]. ¹H NMR (400 MHz, d₄-MeOD): 1.30 (9H, s), 1.86-2.06 (3H, m), 2.11 (1H, m), 2.08 (3H, s), 2.25 (1H, m), 2.38 (3H, s), 2.46 (1H, td, J 11.7, 3.5), 2.92 (1H, dt, J 11.8, 1.7), 3.73-3.91 (3H, m), 3.97 (1H, dd, J 9.9, 4.0), 4.90 (1H, dd, J 8.6, 5.6), 5.39 (1H, t, J 4.1), 6.33 (1H, s), 7.21-7.36 (9H, m), 7.65 (1H, d, J 9.9), 8.24 (0.4H, br s), 8.55 (1H, d, J 1.4).

Example 84

1-(5-tert-Butyl-2-p-tolyl-2H-pyrazol-3-yl)-3-((1S,4R)-4-{3-[(S)-1-(3-hydroxy-propyl)-pyrrolidin-2-yl]-[1,2,4]triazolo[4,3-a]pyridin-6-yloxy}-1,2,3,4-tetrahydro-naphthalen-1-yl)-urea

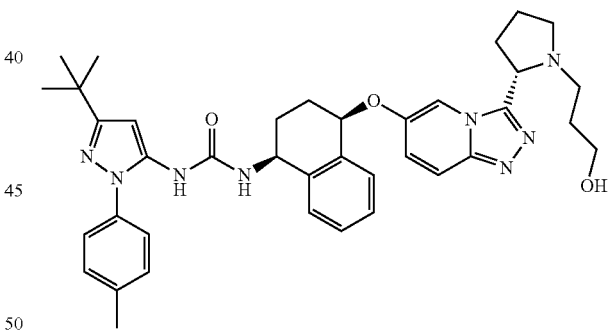

a. (S)-1-(2-tert-Butoxycarbonyl-ethyl)-pyrrolidine-2-carboxylic acid benzyl ester (Intermediate 84a).

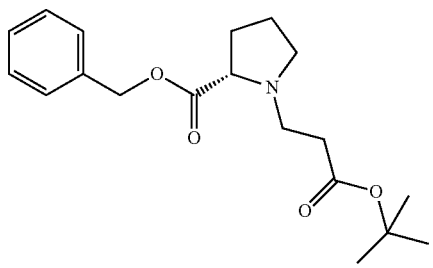 [SMILES: CC(C)(C)OC(=O)CCN1CCC[C@H]1C(=O)OCc1ccccc1]

Tert-butyl acrylate (5.00 mL) was added to a solution of L-proline benzyl ester hydrochloride salt (1.10 g, 4.54 mmol) and Et₃N (632 μL, 4.54 mmol) in tert-butanol (5.00 mL). The reaction was heated to 80° C. for 3 h then and evaporated in vacuo. The residue was purified by FCC, using 0-50% EtOAc in cyclohexane, to give the title compound (1.20 g, 79%). ¹H NMR (300 MHz, CDCl₃): 1.43 (9H, s), 1.72-2.00 (3H, m), 2.08 (1H, m), 2.39-2.48 (3H, m), 2.72 (1H, ddd, J 12.2, 8.4, 6.7), 3.00 (1H, dt, J 12.3, 7.8), 3.13 (1H, m), 3.28 (1H, dd, J 8.6, 5.4), 5.13 (1H, d, J 12.3), 5.18 (1H, d, J 12.3), 7.29-7.39 (5H, m).

b. (S)-1-(2-tert-Butoxycarbonyl-ethyl)-pyrrolidine-2-carboxylic acid (Intermediate 84b).

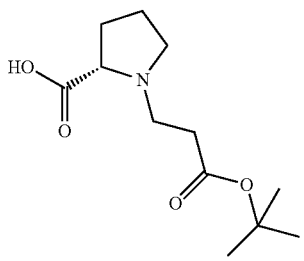 [SMILES: CC(C)(C)OC(=O)CCN1CCC[C@H]1C(=O)O]

A solution of Intermediate 84a (1.10 g, 3.29 mmol) in IMS (25.0 mL) was added to palladium on charcoal (10 wt %, 110 mg) and the reaction stirred under H₂ for 1 h. The mixture was filtered through Celite and evaporated in vacuo to give the title compound (840 mg, 99%). ¹H NMR (300 MHz, d₄-MeOD): 1.48 (9H, s), 1.91 (1H, m), 2.02-2.24 (2H, m), 2.41 (1H, m), 2.74 (2H, t, J 7.1), 3.13 (1H, ddd, J 11.1, 10.2, 7.0), 3.32-3.53 (2H, m), 3.72 (1H, ddd, J 11.0, 7.2, 3.5), 3.89 (1H, dd, J 9.5, 5.3).

c. 3-{(S)-2-[N'-(5-Fluoro-pyridin-2-yl)-hydrazinocarbonyl]-pyrrolidin-1-yl}-propionic acid tert-butyl ester (Intermediate 84c).

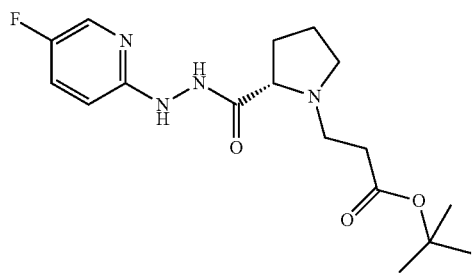 [SMILES: CC(C)(C)OC(=O)CCN1CCC[C@H]1C(=O)NNc1ccc(F)cn1]

HOBt.H₂O (695 mg, 3.62 mmol) was added to a suspension of (5-fluoro-pyridin-2-yl)-hydrazine (418 mg, 3.29 mmol), Intermediate 84b (840 mg, 3.29 mmol), and EDC (44.0 mg, 0.33 mmol) in DMF (25.0 mL). The reaction was stirred overnight then partitioned between EtOAc and water. The aqueous layer was then extracted with EtOAc (3×). The combined organic layers were washed with brine, dried (MgSO₄), filtered and evaporated in vacuo. The residue was purified by FCC, using 0-10% [2M NH₃ in MeOH] in DCM, to give the title compound (1.16 g, 99%). LCMS (Method 1): Rt 2.06 mins, m/z 353.3 [MH⁺].

d. 3-[(S)-2-(6-Fluoro-[1,2,4]triazolo[4,3-a]pyridin-3-yl)-pyrrolidin-1-yl]-propionic acid tert-butyl ester (Intermediate 84d).

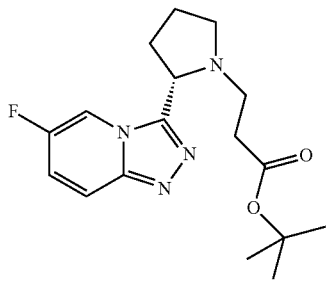 [SMILES: CC(C)(C)OC(=O)CCN1CCC[C@H]1c1nnc2ccc(F)cn12]

Hexachloroethane (1.56 g, 6.58 mmol) was added to a solution of intermediate 84c (1.16 g, 3.29 mmol), Ph₃P (1.72 g, 6.58 mmol) and Et₃N (1.80 mL, 13.1 mmol) in THF (30.0 mL) at 0° C. The reaction was stirred overnight then partitioned between EtOAc and water. The aqueous layer was then extracted with EtOAc (3×). The combined organic layers were washed with brine, dried (MgSO₄), filtered and evaporated in vacuo. The residue was purified by FCC, using EtOAc then 10% [2M NH₃ in MeOH] in DCM, to give the title compound (1.06 g, 99%). LCMS (Method 4): Rt 1.97 min, m/z 335.1 [MH⁺].

e. 3-[(S)-2-(6-Fluoro-[1,2,4]triazolo[4,3-a]pyridin-3-yl)-pyrrolidin-1-yl]-propan-1-ol (Intermediate 84e).

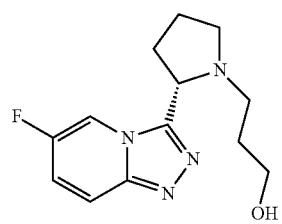 [SMILES: OCCCN1CCC[C@H]1c1nnc2ccc(F)cn12]

Lithium aluminium hydride solution (2M in THF, 1.64 mL, 3.28 mmol) was added to a solution of Intermediate 84d (550 mg, 1.64 mmol) in THF (15.0 mL) at −10° C. The reaction was stirred for 1 h then quenched by dropwise addition of water (125 μL), sodium hydroxide (3M aqueous, 125 μL) and water (375 μL). The reaction was stirred for 10 min then partitioned between EtOAc and water. The aqueous layer was then extracted with EtOAc (3×). The combined organic layers were washed with brine, dried (MgSO₄), filtered and evaporated in vacuo. The residue was purified by FCC, using 2-10% (2M NH₃ in MeOH) in DCM, to give the title compound (145 mg, 33%). LCMS (Method 4): Rt 0.32 mins, m/z 265.2 [MH⁺].

f. 6-Fluoro-3-[(S)-1-(3-triisopropylsilanyloxy-propyl)-pyrrolidin-2-yl]-[1,2,4]triazolo[4,3-a]pyridine (Intermediate 84f).

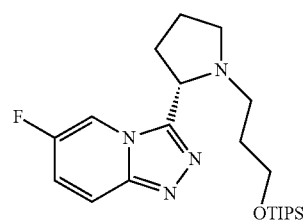

Triisopropylsilyl chloride (266 μL, 1.24 mmol) was added to a solution of Intermediate 84e (218 mg, 0.82 mmol)

and Et₃N (26 μL, 1.24 mmol) in DCM (8.00 mL). The reaction was stirred overnight then 4-(dimethylamino)pyridine (10.0 mg, 0.082 mmol) added. The reaction was stirred for 3 h then partitioned between EtOAc and water. The aqueous layer was then extracted with EtOAc (3×). The combined organic layers were washed with brine, dried (MgSO₄), filtered and evaporated in vacuo. The residue was purified by FCC, using 0-7.5% [2M NH₃ in MeOH] in DCM, to give the title compound (317 mg, 92%). $^1$H NMR (300 MHz, CDCl₃): 0.92 (21H, s), 1.56-1.68 (2H, m), 1.89-2.10 (3H, m), 2.21-2.40 (3H, m), 2.56 (1H, dt, J 12.1, 7.9), 3.40 (1H, m), 3.46-3.64 (2H, m), 4.22 (1H, t, J 8.4), 7.16 (1H, ddd, J 9.9, 7.5, 2.3), 7.71 (1H, ddd, J 10.0, 4.9, 0.6), 8.64 (1H, m).

g. (1S,4R)-4-{3-[(S)-1-(3-Triisopropylsilanyloxy-propyl)-pyrrolidin-2-yl]-[1,2,4]triazolo[4,3-a]pyridin-6-yloxy}-1,2,3,4-tetrahydro-naphthalen-1-yl amine (Intermediate 84g).

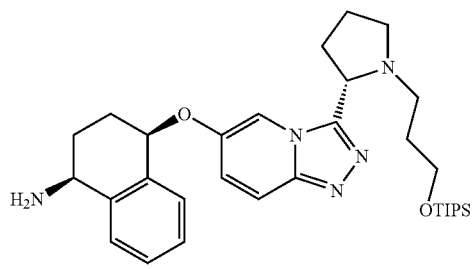

To a suspension of NaH (60% in mineral oil, 121 mg, 3.02 mmol) in DMF (2.00 mL) was added Intermediate A (122 mg, 0.75 mmol) and the reaction stirred for 20 min. Intermediate 84f (317 mg, 0.75 mmol) was added in DMF (2.00 mL) and the reaction heated to 60° C. for 1 h. The cooled reaction was quenched by dropwise addition of methanol, before being diluted with methanol and loaded onto an SCX-2 cartridge, which was washed with MeOH. The product was eluted with 2M NH₃ in MeOH; concentration in vacuo gave a residue. FCC, using 2-10% [2M NH₃ in MeOH] in DCM, gave the title compound (140 mg, 33%). LCMS (Method 4): Rt 2.37, m/z 564.2 [MH⁺].

h. 1-(5-tert-Butyl-2-p-tolyl-2H-pyrazol-3-yl)-3-((1S,4R)-4-{(3-[(S)-1-(3-triisopropylsilanyloxy-propyl)-pyrrolidin-2-yl]-[1,2,4]triazolo[4,3-c]pyridin-6-yloxy}-1,2,3,4-tetrahydro-naphthalen-1-yl)-urea (Intermediate 84h).

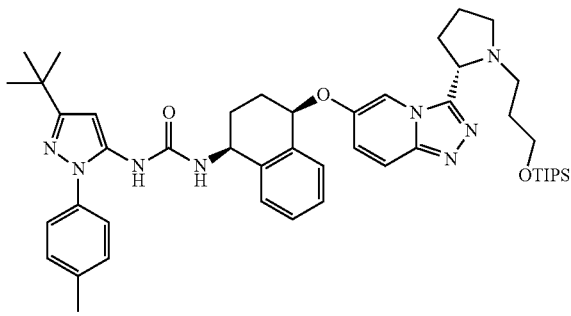

To a solution of Intermediate 84g (140 mg, 0.25 mmol) in 1,4-dioxane (3.00 mL) was added DIPEA (86.0 μL, 0.50 mmol) and (5-tert-butyl-2-p-tolyl-2H-pyrazol-3-yl)-carbamic acid 2,2,2-trichloro-ethyl ester (Synthetic Communications, 2009, 39, 3999-4009, which is incorporated herein by reference in its entirety; 100 mg, 0.25 mmol). The reaction was heated to 60° C. overnight then further (5-tert-butyl-2-p-tolyl-2H-pyrazol-3-yl)-carbamic acid 2,2,2-trichloro-ethyl ester (50.0 mg, 0.12 mmol) was added and heating at 60° C. continued overnight. The reaction was cooled and partitioned between EtOAc and water. The aqueous layer was then extracted with EtOAc (3×). The combined organic layers were washed with brine, dried (MgSO₄), filtered and evaporated in vacuo. The residue was purified by FCC, using 0-10% [2M NH₃ in MeOH] in DCM, to give the title compound (70.0 mg, 34%). LCMS (Method 1): Rt 3.46, m/z 820.4 [MH⁺].

i. 1-(5-tert-Butyl-2-p-tolyl-2H-pyrazol-3-yl)-3-((1S,4R)-4-{3-[(S)-1-(3-hydroxy-propyl)-pyrrolidin-2-yl]-[1,2,4]triazolo[4,3-a]pyridin-6-yloxy}-1,2,3,4-tetrahydro-naphthalen-1-yl)-urea (Example 84).

TBAF (1M in THF, 100 μL, 0.10 mmol) was added to a solution of Intermediate 84h (70.0 mg, 0.085 mmol) in THF (2.00 mL). The reaction was stirred for 2 h then partitioned between EtOAc and water. The aqueous layer was then extracted with EtOAc (3×). The combined organic layers were washed with brine, dried (MgSO₄), filtered and evaporated in vacuo. The residue was purified by FCC, using 0-10% [2M NH₃ in MeOH] in DCM. Further purification by HPLC (C18 X-select column, 10-98% MeCN in H₂O, 0.1% HCO₂H) gave the title compound as a white powder after freeze-drying (29 mg, 52%). LCMS (Method 5): Rt 3.63 min, m/z 663.3 [MH⁺]. $^1$H NMR (400 MHz, d₄-MeOD): 1.30 (9H, s), 1.54-1.62 (2H, quin, J 7.0), 1.88-2.15 (6H, m), 2.20-2.37 (4H, m), 2.38 (3H, s), 2.55 (1H, dt, J 12.0, 8.1), 3.32-3.48 (3H, m), 4.11 (1H, t, J 8.0), 4.90 (1H, dd, J 9.1, 5.7), 5.31 (1H, t, J 4.0), 6.33 (1H, s), 7.20-7.36 (9H, m), 7.65 (1H, d, J 9.9), 8.32 (1H, d, J 1.7).

Example 85

1-(5-tert-Butyl-2-p-tolyl-2H-pyrazol-3-yl)-3-{(1S,4R)-4-[3-((S)-2-hydroxymethyl-1-methyl-pyrrolidin-2-yl)-[1,2,4]triazolo[4,3-a]pyridin-6-yloxy]-1,2,3,4-tetrahydro-naphthalen-1-yl}-urea

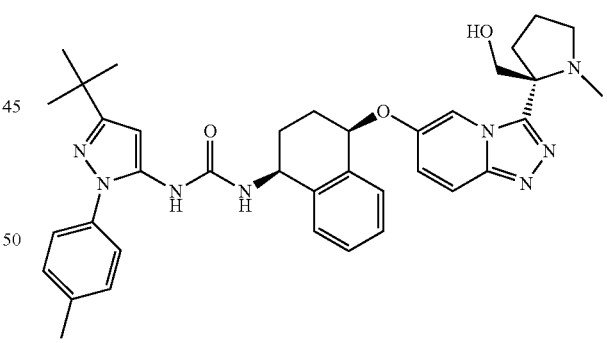

a. (3R,7aS)-3-Trichloromethyl-tetrahydro-pyrrolo[1,2-c]oxazol-1-one (Intermediate 85a).

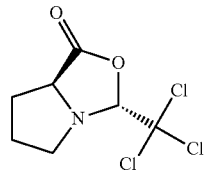 [SMILES: O=C1O[C@H](C(Cl)(Cl)Cl)N2CCC[C@@H]12]

A suspension of L-proline (10.0 g, 87.0 mmol) and chloral hydrate (21.6 g, 130 mmol) in chloroform (100 mL) was heated at reflux for 6 h under a soxlet adapter charged with sodium sulfate. The cooled mixture was washed with water (2×), dried (MgSO$_4$) and concentrated in vacuo. The product was recrystalised from boiling absolute ethanol to give the title compound as white needles (13.3 g, 63%). $^1$H NMR (400 MHz, CDCl$_3$): 1.65-1.83 (1H, m), 1.86-2.01 (1H, m), 2.04-2.31 (2H, m), 3.06-3.18 (1H, m), 3.36-3.49 (1H, m), 4.12 (1H, dd, J 4.6, 4.0), 5.16 (1H, s).

b. (3R,7aR)-7a-Benzyloxymethyl-3-trichloromethyl-tetrahydro-pyrrolo[1,2-c]oxazol-1-one (Intermediate 85b).

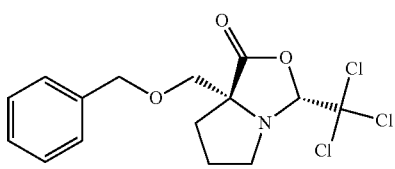 [SMILES: O=C1O[C@H](C(Cl)(Cl)Cl)N2CCC[C@@]12COCc1ccccc1]

To a solution of LDA (531 mL, 0.109M, 58.1 mmol) at −78° C. was added a solution of Intermediate 85a (10.0 g, 41.2 mmol) in THF (200 mL) over 30 min maintaining the temperature below −70° C. The mixture was stirred at −78° C. for 2 h, then a solution of benzyloxymethyl chloride (11.6 g, 74.1 mmol) in THF (50 mL) added, maintaining the temperature below −70° C. The mixture was allowed to warm to −30° C. over 3 h before being quenched with dropwise addition of water (300 mL). The aqueous was extracted with EtOAc (2×). The combined organic layers were dried (MgSO$_4$) and concentrated in vacuo. The residue was purified by FCC, using 0-60% diethyl ether in cyclohexane, to give the title compound as a clear oil (6.39 g, 42%). $^1$H NMR (400 MHz, CDCl$_3$): 1.63-1.77 (1H, m), 1.94-2.04 (1H, m), 2.08-2.17 (1H, m), 2.26-2.36 (1H, m), 3.22-3.29 (1H, m), 3.30-3.38 (1H, m), 3.74, (2H, s), 4.62 (2H, s), 4.99 (1H, s), 7.26-7.37 (5H, m).

c. (R)-2-Benzyloxymethyl-pyrrolidine-2-carboxylic acid methyl ester (Intermediate 85c).

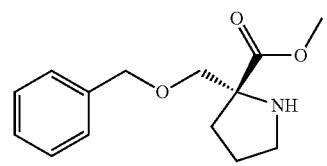 [SMILES: COC(=O)[C@]1(COCc2ccccc2)CCCN1]

A solution of Intermediate 85b (6.39 g, 17.9 mmol) and sodium methoxide (580 mg, 10.8 mmol) in MeOH (100 mL) was stirred at RT for 18 h. The mixture was cooled to 0° C., then acetyl chloride (28.4 g, 359 mmol) added. This mixture was stirred at reflux for 1 h, then cooled and concentrated in vacuo. The residue was divided, applied to SCX-2 cartridges (3×70 g) and washed with MeOH. The product was eluted with 2M NH$_3$ in MeOH; concentration in vacuo gave the title compound as a pale yellow oil (3.92 g, 87%). $^1$H NMR (400 MHz, CDCl$_3$): 1.62-1.86 (3H, m), 1.07-2.13 (1H, m), 2.48 (1H, br s), 2.93-3.11 (2H, m), 3.69-3.78 (4H, m), 4.53 (1H, d, J 12.9), 4.55 (1H, d, J 12.9), 7.21-7.37 (5H, m).

d. (R)-2-Benzyloxymethyl-1-methyl-pyrrolidine-2-carboxylic acid methyl ester (Intermediate 85d).

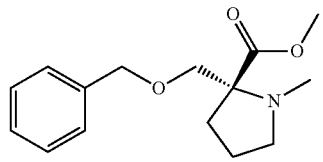 [SMILES: COC(=O)[C@]1(COCc2ccccc2)CCCN1C]

A solution of Intermediate 85c (3.37 g, 13.5 mmol) and formaldehyde (37% aqueous, 4.38 mL, 54.1 mmol) in DCM (140 mL) was stirred at RT for 30 min, then sodium triacetoxyborohydride (5.74 g, 27.1 mmol) was added. This mixture was stirred at RT for 18 h then washed with sat. aq. NaHCO$_3$ solution, dried (MgSO$_4$) and concentrated in vacuo. The residue was purified by FCC, using 0-10% [2M NH$_3$ in MeOH] in DCM, to give the title compound as a clear oil (2.59 g, 72%). LCMS (Method 4): Rt 1.85 min, m/z 263 [MH$^+$].

e. (R)-2-Hydroxymethyl-1-methyl-pyrrolidine-2-carboxylic acid methyl ester (Intermediate 85e).

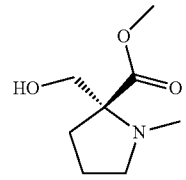

A suspension of Intermediate 85d (2.59 g, 9.84 mmol), palladium hydroxide on charcoal (10%, 250 mg) and glacial acetic acid (1 mL) in IMS (20 mL) under an atmosphere of hydrogen (1 atm) was stirred at RT for 5 d. The mixture was filtered and concentrated in vacuo to give the title compound as a clear oil (1.70 g, 99%), as a mixture of methyl and ethyl esters. Data for major product, methyl ester: $^1$H NMR (400 MHz, CDCl$_3$): 1.75-1.95 (2H, m), 2.01-2.18 (2H, m), 2.36 (3H, s), 2.86-2.99 (2H, m), 3.65 (3H, s), 4.19 (2H, m), 4.91 (1H, br s).

f. (R)-1-Methyl-2-triisopropylsilanyloxymethyl-pyrrolidine-2-carboxylic acid methyl ester (Intermediate 85f).

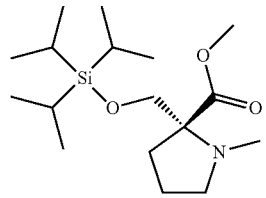 [SMILES: COC(=O)[C@]1(CO[Si](C(C)C)(C(C)C)C(C)C)CCCN1C]

Triisopropylsilyl trifluoromethanesulfonate (11.7 g, 38.1 mmol) was added to a solution of Intermediate 85e (2.20 g, 12.7 mmol) and Et$_3$N (12.8 g, 127 mmol) in DCM (100 mL) at 0° C., then the mixture stirred at RT for 30 min. The mixture was diluted with DCM and washed with 10% aq. K$_2$CO$_3$ solution, water, brine, dried (MgSO$_4$) and concentrated in vacuo. The residue was purified by FCC, using 0-5% [2M NH$_3$ in MeOH] in DCM, to give the title compound as a pale yellow solid (2.51 g, 65%). $^1$H NMR (400 MHz, CDCl$_3$): 0.97-1.15 (21H, m), 1.72-1.96 (2H, m), 2.23-2.35 (2H, m), 2.46 (3H, s), 2.89-2.99 (2H, m), 3.69 (3H, s), 4.12-4.22 (2H, m).

g. (R)-1-Methyl-2-triisopropylsilanyloxymethyl-pyrrolidine-2-carboxylic acid (Intermediate 85g).

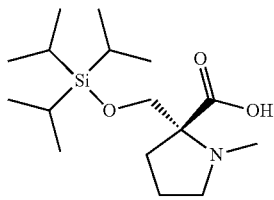 [SMILES: CC(C)[Si](OC[C@@]1(C(=O)O)CCCN1C)(C(C)C)C(C)C]

A solution of Intermediate 85f (2.50 g, 7.93 mmol) and lithium hydroxide monohydrate (3.33 g, 79.3 mmol) in MeOH and water (50 mL) was stirred at reflux for 2 h. The cooled solution was acidified with 1M HCl to pH 5. The MeOH was removed in vacuo and the resulting aqueous layer was extracted with EtOAc (3×). The combined organic layers were dried (MgSO$_4$) and concentrated in vacuo to give the title compound as a white foam (2.21 g, 92%). $^1$H NMR (400 MHz, CDCl$_3$): 1.00-1.21 (21H, m), 1.93-2.04 (2H, m), 2.32-2.42 (1H, m), 2.43-2.56 (1H, m), 2.96-3.09 (4H, m), 3.90-4.00 (1H, m), 4.20 (1H, d, J 10.9), 4.22 (1H, d, J 10.9).

h. (R)-1-Methyl-2-triisopropylsilanyloxymethyl-pyrrolidine-2-carboxylic acid N'-(5-fluoro-pyridin-2-yl)-hydrazide (Intermediate 85h).

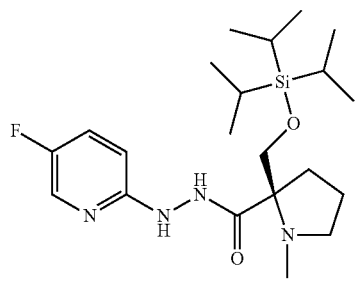 [SMILES: CC(C)[Si](OC[C@@]1(C(=O)NNc2ccc(F)cn2)CCCN1C)(C(C)C)C(C)C]

To a solution of Intermediate 85g (1.08 g, 3.58 mmol), (5-fluoro-pyridin-2-yl)-hydrazine (500 mg, 3.93 mmol) and DIPEA (1.38 g, 10.7 mmol) in DCM (120 mL) was added HATU (2.04 g, 5.37 mmol) and the mixture stirred at RT for 2 h. The solution was washed with 10% aq. K$_2$CO$_3$ solution, brine, dried (MgSO$_4$), and concentrated in vacuo. The residue was purified by FCC, using 0-6% [2M NH$_3$ in MeOH] in DCM, to give the title compound as a pale yellow oil (1.37 g, 90%). LCMS (Method 4): Rt 2.74 min, m/z 425 [MH$^+$].

i. 6-Fluoro-3-((S)-1-methyl-2-triisopropylsilanyloxymethyl-pyrrolidin-2-yl)-[1,2,4]triazolo[4,3-a]pyridine (Intermediate 85i).

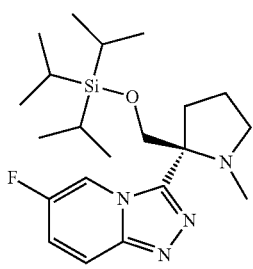 [SMILES: CC(C)[Si](OC[C@@]1(c2nnc3ccc(F)cn23)CCCN1C)(C(C)C)C(C)C]

To a solution of Intermediate 85h (1.37 g, 2.08 mmol), Ph$_3$P (1.09 g, 4.16 mmol) and Et$_3$N (840 mg, 8.32 mmol) in THF (60 mL) was added hexachloroethane (980 mg, 4.16 mmol) and the mixture stirred at RT for 20 h. The mixture was diluted with DCM, washed with 10% aq. K$_2$CO$_3$ solution, brine, dried (MgSO$_4$) and concentrated in vacuo. The residue was purified by FCC, using 0-100% EtOAc in cyclohexane, to give the title compound as a clear oil (350 mg, 41%). LCMS (Method 4): Rt 3.07 min, m/z 407 [MH$^+$].

j. (1S,4R)-4-[3-((S)-1-Methyl-2-triisopropylsilanyloxymethyl-pyrrolidin-2-yl)-[1,2,4]triazolo[4,3-a]pyridin-6-yloxy]-1,2,3,4-tetrahydro-naphthalen-1-yl amine (Intermediate 85j).

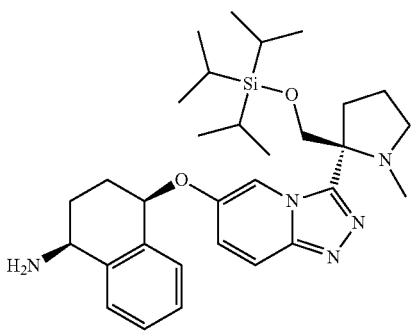 [SMILES: CC(C)[Si](OC[C@@]1(c2nnc3ccc(O[C@@H]4CC[C@H](N)c5ccccc54)cn23)CCCN1C)(C(C)C)C(C)C]

To a solution of Intermediate A (170 mg, 1.03 mmol) in DMF (4 mL) was added NaH (60% in oil, 103 mg, 2.59 mmol) and the mixture stirred at RT for 20 min, before Intermediate 85i (350 mg, 0.862 mmol) was added. This mixture was stirred at 60° C. for 4 h. The cooled mixture was diluted with EtOAc, washed with water (3×), brine, dried (MgSO$_4$) and concentrated in vacuo. The residue was purified by FCC, using 0-10% [2M NH$_3$ in MeOH] in DCM, to give the title compound as a clear viscous oil (230 mg, 48%). LCMS (Method 1): Rt 2.28 min, m/z 550 [MH$^+$].

k. 1-(5-tert-Butyl-2-p-tolyl-2H-pyrazol-3-yl)-3-{(1S,4R)-4-[3-((S)-1-methyl-2-triisopropylsilanyl oxymethyl-pyrrolidin-2-yl)-[1,2,4]triazolo[4,3-a]pyridin-6-yloxy]-1,2,3,4-tetrahydro-naphthalen-1-yl}-urea (Intermediate 85k).

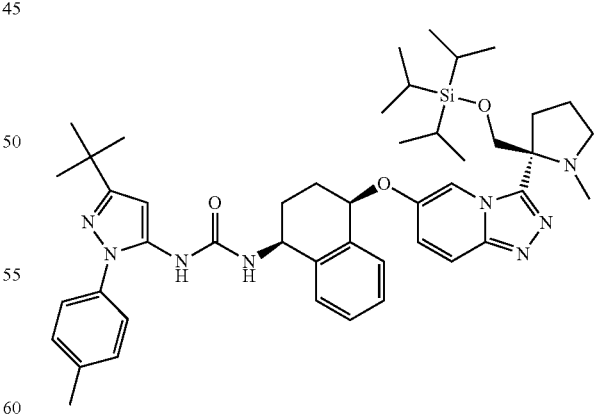

A solution of Intermediate 85j (230 mg, 0.418 mmol), (5-tert-butyl-2-p-tolyl-2H-pyrazol-3-yl)-carbamic acid 2,2,2-trichloro-ethyl ester (Synthetic Communications, 2009, 39, 3999-4009. which is incorporated herein by reference in its entirety; 253 mg, 0.628 mmol) and DIPEA (215 mg, 1.67 mmol) in DMF (4 mL) was stirred at 50° C. for 1 h. The mixture was diluted with EtOAc, washed with water (2×), brine, dried (MgSO₄) and concentrated in vacuo. The residue was purified by FCC, using 0-10% [2M NH₃ in MeOH] in DCM, to give the title compound as a white foam (250 mg, 48%). LCMS (Method 3): Rt 3.70 min, m/z 805 [MH⁺].

l. 1-(5-tert-Butyl-2-p-tolyl-2H-pyrazol-3-yl)-3-{(1S,4R)-4-[3-((S)-2-hydroxymethyl-1-methyl-pyrrolidin-2-yl)-[1,2,4]triazolo[4,3-a]pyridin-6-yloxy]-1,2,3,4-tetrahydro-naphthalen-1-yl}-urea (Example 85).

To a solution of Intermediate 85k (250 mg, 0.310 mmol) in THF (10 mL) at −30° C. was added TBAF (1M in THF, 620 μL, 0.620 mmol) and the mixture was allowed to warm to RT over 2 h. The reaction mixture was applied to an SCX-2 cartridge (10 g) and washed with MeOH. The product was eluted with 2M NH₃ in MeOH; concentration in vacuo gave a residue. FCC, using 0-10% [2M NH₃ in MeOH] in DCM, gave a crude product. Recrystallisation from hot diethyl ether (50 mL), EtOAc (10 mL) and cyclohexane (20 mL) gave the title compound as a white powder (113 mg, 56%). LCMS (Method 5): Rt 3.68 min, m/z 649.1 [MH⁺]. ¹H NMR (400 MHz, d₄-MeOD): 1.29 (9H, s), 1.86-2.34 (11H, m), 2.38 (3H, s), 3.02 (1H, m), 3.09 (1H, dt, J 8.8, 3.5), 4.07 (1H, d, J 11.0), 4.25 (1H, d, J 4.3), 4.52 (1H, br s), 4.90 (1H, m), 5.25 (1H, t, J 4.3), 6.33 (1H, s), 7.18-7.36 (9H, m), 7.62 (1H, d J 7.6), 8.44 (1H, s).

Example 86

1-(5-tert-Butyl-2-p-tolyl-2H-pyrazol-3-yl)-3-{(1S,4R)-4-[3-(1,4-dimethyl-piperazin-2-yl)-[1,2,4]triazolo[4,3-a]pyridin-6-yloxy]-1,2,3,4-tetrahydro-naphthalen-1-yl}-urea formate salt

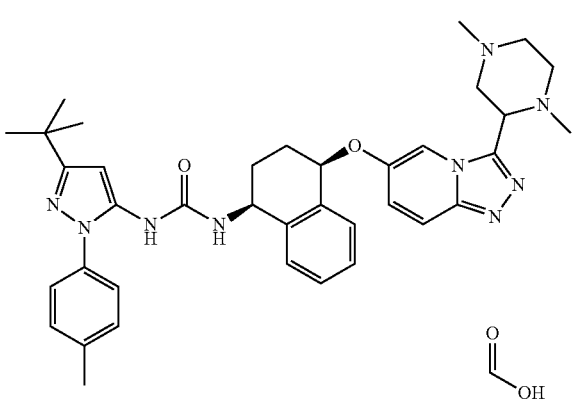 [SMILES: Cc1ccc(-n2nc(C(C)(C)C)cc2NC(=O)N[C@H]2CC[C@@H](Oc3ccc4nnc(C5CN(C)CCN5C)n4c3)c3ccccc32)cc1 ; O=CO]

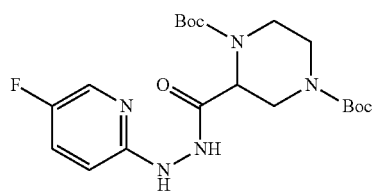 [SMILES: CC(C)(C)OC(=O)N1CCN(C(=O)OC(C)(C)C)C(C(=O)NNc2ccc(F)cn2)C1]

a. 2-[N'-(5-Fluoro-pyridin-2-yl)-hydrazinocarbonyl]-piperazine-1,4-dicarboxylic acid di-tert-butyl ester (Intermediate 86a).

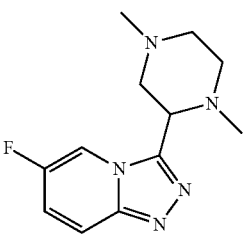

To a solution of piperazine-1,2,4-tricarboxylic acid 1,4-di-tert-butyl ester (780 mg, 2.4 mmol) and (5-fluoro-pyridin-2-yl)-hydrazine (250 mg, 2.0 mmol) and Et₃N (0.83 mL, 6 mmol) in DCM (20 mL) were added HOBt.H₂O (27 mg, 0.2 mmol) and EDC (542 mg, 2.4 mmol) sequentially, and then the mixture stirred at RT overnight. The mixture was partitioned between EtOAc/water and extracted with EtOAc. The combined organics were dried over Na₂SO₄, filtered and concentrated in vacuo. The residue was purified by FCC, using 0-10% MeOH in DCM, to give the title compound as a brown solid (550 mg, 63%). LCMS (Method 4): Rt 3.28, m/z 440 [MH⁺].

b. 6-Fluoro-3-piperazin-2-yl-[1,2,4]triazolo[4,3-a]pyridine (Intermediate 86b).

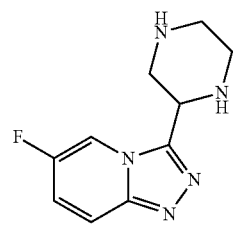 [SMILES: Fc1ccc2nnc(C3CNCCN3)n2c1]

To a solution of Intermediate 86a (550 mg, 1.25 mmol), Et₃N (0.69 mL, 5 mmol) and Ph₃P (657 mg, 2.5 mmol) in THF (20 mL) at 0° C. was added hexachloroethane (590 mg, 2.5 mmol) and the mixture stirred for 10 min. The solution was allowed to warm to RT, stirred for 1 h, then partitioned between EtOAc/water and extracted with EtOAc. The combined organics were dried over Na₂SO₄, filtered and concentrated in vacuo. The residue was purified by FCC, using 0-100% EtOAc in cyclohexane, to give crude 2-(6-fluoro-[1,2,4]triazolo[4,3-a]pyridin-3-yl)-piperazine-1,4-dicarboxylic acid di-tert-butyl ester, contaminated with triphenylphosphine oxide, as a pale brown solid (500 mg). The solid (500 mg) was treated with a 4M HCl solution in dioxane (30 mL) and the mixture stirred at RT for 2 h. The suspension was diluted with MeOH, then applied onto an SCX-2 cartridge and washed with MeOH. The product was eluted with 2M NH₃ in MeOH; concentration in vacuo gave the title compound as a pale yellow solid (100 mg, 23% over 2 steps). LCMS (Method 4): Rt 0.26, m/z 222 [MH⁺].

c. 3-(1,4-Dimethyl-piperazin-2-yl)-6-fluoro-[1,2,4]triazolo[4,3-a]pyridine (Intermediate 86c).

To a suspension of Intermediate 86b (100 mg) in 1,2-dichloroethane (10 mL) were added formaldehyde (30% in water, 104 μL, 1.13 mmol) and NaBH(OAc)₃ (240 mg, 1.13 mmol) sequentially. The mixture was stirred at RT for 2 h, then applied to an SCX-2 cartridge and washed with MeOH. The product was eluted with 2M NH₃ in MeOH; concentration in vacuo gave the title compound as a pale yellow solid (100 mg, 89%). LCMS (Method 4): Rt 0.49, m/z 250 [MH⁺].

d. (1S,4R)-4-[3-(1,4-Dimethyl-piperazin-2-yl)-[1,2,4]triazolo[4,3-a]pyridin-6-yloxy]-1,2,3,4-tetrahydro-naphthalen-1-ylamine (Intermediate 86d).

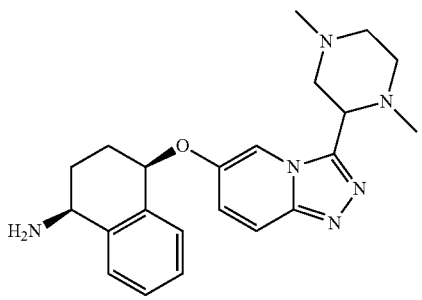 [SMILES: CN1CCN(C)C(c2nnc3ccc(O[C@@H]4CC[C@H](N)c5ccccc54)cn23)C1]

To a solution of Intermediate 86c (100 mg, 0.40 mmol) and Intermediate A (79 mg, 0.40 mmol) in DMF (3 mL) was added NaH (60% in mineral oil, 56 mg, 1.4 mmol) portionwise. The mixture was stirred at 60° C. for 1.5 h then allowed to cool to RT. The mixture was carefully quenched by pouring into MeOH (10 mL) then applied to an SCX-2 cartridge and washed with MeOH. The product was eluted with 2M $NH_3$ in MeOH; concentration in vacuo gave a residue. FCC, using 0-20% [2M $NH_3$ in MeOH] in DCM, gave the title compound as a brown oil (104 mg, 66%). LCMS (Method 4): Rt 0.26, m/z 393 [MH+].

e. 1-(5-tert-Butyl-2-p-tolyl-2H-pyrazol-3-yl)-3-{(1S,4R)-4-[3-(1,4-dimethyl-piperazin-2-yl)-[1,2,4]triazolo[4,3-a]pyridin-6-yloxy]-1,2,3,4-tetrahydro-naphthalen-1-yl}-urea formate salt (Example 86).

The title compound was prepared as an off white solid (70 mg, 42%) using (5-tert-butyl-2-p-tolyl-2H-pyrazol-3-yl)-carbamic acid 2,2,2-trichloro-ethyl ester (Synthetic Communications, 2009, 39, 3999-4009, which is incorporated herein by reference in its entirety; 107 mg, 0.26 mmol) and Intermediate 86d (104 mg, 0.26 mmol) in a similar manner to Example 1, step d. LCMS (Method 5): Rt 3.64 min, m/z 648 [MH+]. $^1$H NMR (400 MHz, $d_6$-DMSO): 1.27 (9H, s), 1.83-1.98 (5H, m), 2.05-2.25 (6H, m), 2.30-2.42 (5H, m), 2.75 (2H, d, J 10.7), 2.89-2.94 (1H, m), 3.92-3.95 (1H, m), 4.80-4.86 (1H, m), 5.38-5.46 (1H, m), 6.32 (1H, s), 7.10 (1H, d, J 8.6), 7.26-7.42 (9H, m), 7.75 (1H, d, J 9.7), 8.04 (1H, s), 8.16 (1H, s), 8.46-8.50 (1H, m).

Example 87

1-(5-tert-Butyl-2-p-tolyl-2H-pyrazol-3-yl)-3-{(1S,4R)-4-[3-((S)-1,4,4-trimethyl-pyrrolidin-2-yl)-[1,2,4]triazolo[4,3a]pyridin-6-yloxy]-1,2,3,4-tetrahydro-naphthalen-1-yl}-urea

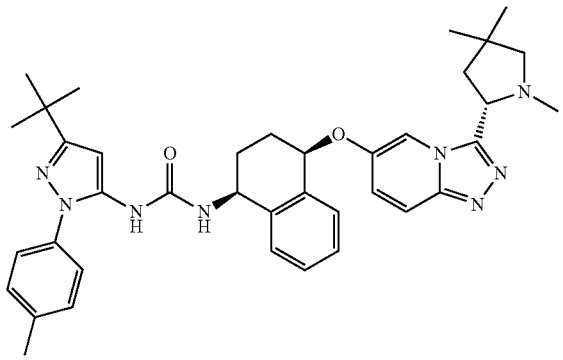 [SMILES: Cc1ccc(-n2nc(C(C)(C)C)cc2NC(=O)N[C@H]2CC[C@@H](Oc3ccc4nnc([C@@H]5CC(C)(C)CN5C)n4c3)c3ccccc32)cc1]

a. (S)-1,4,4-Trimethyl-pyrrolidine-2-carboxylic acid (Intermediate 87a).

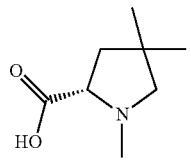

A suspension of 4,4-dimethyl-L-proline hydrochloride (900 mg, 5.00 mmol), formaldehyde (37% aqueous, 450 μL), DIPEA (645 mg, 5.00 mmol) and palladium on carbon (10%, 400 mg) in IMS (50 mL) was stirred under an atmosphere of hydrogen (1 atm) for 4 h. The suspension was filtered and concentrated in vacuo to give the title compound as a viscous pink oil (780 mg, 99%). $^1$H NMR (400 MHz, CDCl$_3$): 1.47 (3H, s), 1.49 (3H, s), 2.04-2.16 (1H, m), 2.23-2.34 (1H, m), 2.93 (3H, s), 3.10 (2H, m), 3.78-3.89 (1H, m), 4.86 (1H, br s).

b. (S)-1,4,4-Trimethyl-pyrrolidine-2-carboxylic acid N'-(5-fluoro-pyridin-2-yl)-hydrazide (Intermediate 87b).

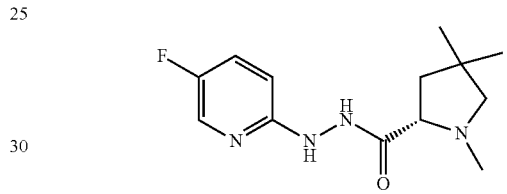

To a solution of Intermediate 87a (1.70 g, 5.00 mmol), (5-fluoro-pyridin-2-yl)-hydrazine (600 mg, 5.00 mmol) and DIPEA (1.29 g, 10.0 mmol) in DCM was added HATU (2.28 g, 6.00 mmol) and the mixture stirred at RT for 1 h. The reaction mixture was applied to an SCX-2 cartridge (70 g) and washed with MeOH. The product was eluted with 2M $NH_3$ in MeOH; concentration in vacuo gave a residue. FCC, using 0-10% [2M $NH_3$ in MeOH] in DCM, gave the title compound as a yellow oil (950 mg, 71%). $^1$H NMR (400 MHz, CDCl$_3$): 1.13 (3H, s), 1.15 (3H, s), 1.74 (1H, dd, J 12.5, 6.2), 2.12 (1H, dd, J 11.6, 10.0), 2.29 (1H, d, J 8.9), 2.46 (3H, s), 2.88 (1H, d, J 8.9), 3.15 (1H, dd, J 9.7, 6.5), 6.56-6.65 (2H, m), 7.28 (1H dt, J 8.6, 2.9), 8.03 (1H, d, J 2.5), 9.09 (1H, br s).

c. 6-Fluoro-3-((S)-1,4,4-trimethyl-pyrrolidin-2-yl)-[1,2,4]triazolo[4,3-a]pyridine (Intermediate 87c).

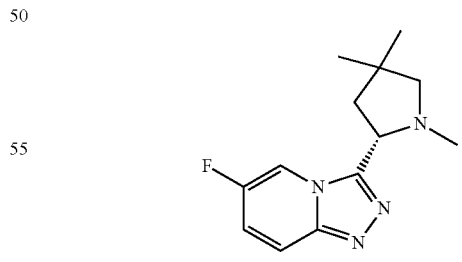

To a solution of Intermediate 87b (950 mg, 3.57 mmol), Ph$_3$P (1.87 g, 7.14 mmol) and Et$_3$N (1.44 g, 14.28 mmol) in THF (40 mL) was added hexachloroethane (1.65 g, 7.14 mmol) and the mixture stirred at RT for 20 h. The reaction mixture was applied to an SCX-2 cartridge (70 g) and washed with MeOH. The product was eluted with 2M $NH_3$ in MeOH; concentration in vacuo gave a residue. FCC, using 0-10%

[2M NH₃ in MeOH] in DCM gave the title compound as a clear oil (750 mg, 84%). ¹H NMR (400 MHz, CDCl₃): 1.22 (3H, s), 1.24 (3H, s), 1.84 (1H, dd, J 12.7, 10.8), 2.04 (1H, dd, J 12.4, 7.4), 2.16 (3H, s), 2.25 (1H, d J, 9.1), 3.04 (1H, d, J 9.3), 4.22 (1H, dd, J 10.0, 7.6), 7.14-7.23 (1H, m), 7.69-7.77 (1H, m), 8.75-8.80 (1H, m).

d. (1S,4R)-4-[3-((S)-1,4,4-Trimethyl-pyrrolidin-2-yl)-[1,2,4]triazolo[4,3-a]pyridin-6-yloxy]-1,2,3,4-tetrahydro-naphthalen-1-ylamine (Intermediate 87d).

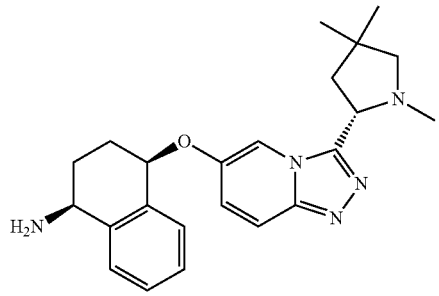 [SMILES: CN1CC(C)(C)C[C@H]1c1nnc2ccc(O[C@@H]3CC[C@H](N)c4ccccc43)cn12]

To a solution of Intermediate A (552 mg, 3.89 mmol) in DMF (25 mL) was added NaH (60% in oil, 338 mg, 8.46 mmol) and the mixture stirred at RT for 20 min, before Intermediate 87c (700 mg, 2.82 mmol) was added. This mixture was stirred at 60° C. for 1 h. The cooled reaction mixture was applied to an SCX-2 cartridge (70 g) and washed with MeOH. The product was eluted with 2M NH₃ in MeOH; concentration in vacuo gave a residue. FCC, using 0-10% (2M NH₃ in MeOH) in DCM gave the title compound (820 mg, 74%). LCMS (Method 4): Rt 1.53 min, m/z 392 [MH⁺].

e. 1-(5-tert-Butyl-2-p-tolyl-2H-pyrazol-3-yl)-3-{(1S,4R)-4-[3-((S)-1,4,4-trimethyl-pyrrolidin-2-yl)-[1,2,4]triazolo[4,3-a]pyridin-6-yloxy]-1,2,3,4-tetrahydro-naphthalen-1-yl}-urea (Example 87).

A solution of Intermediate 87d (150 mg, 0.383 mmol), (5-tert-butyl-2-p-tolyl-2H-pyrazol-3-yl)-carbamic acid 2,2,2-trichloro-ethyl ester (Synthetic Communications, 2009, 39, 3999-4009, which is incorporated herein by reference in its entirety; 232 mg, 0.575 mmol) and DIPEA (198 mg, 1.53 mmol) in DMF (4 mL) was stirred at 50° C. for 1 h. The cooled reaction mixture was applied to an SCX-2 cartridge (10 g) and washed with MeOH. The product was eluted with 2M NH₃ in MeOH; concentration in vacuo gave a residue. FCC, using 0-6% [2M NH₃ in MeOH] in DCM, then trituration with diethyl ether gave the title compound as an off-white powder (170 mg, 68%). LCMS (Method 5): Rt 3.80 min, m/z 647.5 [MH⁺]. ¹H NMR (400 MHz, d₄-MeOH): 1.15 (3H, s), 1.24 (3H, s), 1.30 (9H, s), 1.85-2.05 (4H, m), 2.14 (3H, s), 2.19-2.31 (2H, m), 2.38 (3H, s), 2.97 (1H, d, J 10.3), 3.45 (1H, dd, J 7.5, 6.1), 4.06 (1H, t, J 9.3), 4.90 (1H, m), 5.30 (1H, t, J 4.2), 6.33 (1H, s), 7.20-7.36 (9H, m), 7.65 (1H, d, J 10.8), 8.46 (1H, d, J 1.1).

Example 88

1-(5-tert-Butyl-2-p-tolyl-2H-pyrazol-3-yl)-3-{(1S,4R)-4-[3-((S)-1-methyl-piperidin-3-yl)-[1,2,4]triazolo[4,3-a]pyridin-6-yloxy]-1,2,3,4-tetrahydro-naphthalen-1-yl}-urea

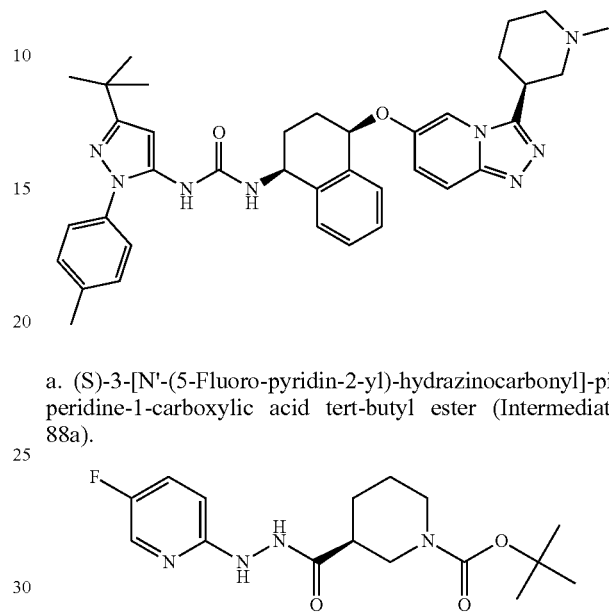

a. (S)-3-[N'-(5-Fluoro-pyridin-2-yl)-hydrazinocarbonyl]-piperidine-1-carboxylic acid tert-butyl ester (Intermediate 88a).

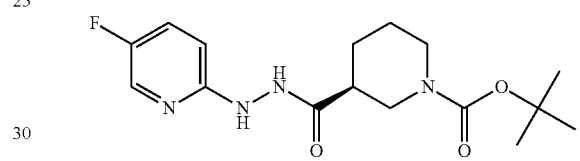

To a solution of (5-fluoro-pyridin-2-yl)-hydrazine (1.27 g, 10.0 mmol), (S)-1-BOC piperidine-3-carboxylic acid (Alfa Aesar, 2.29 g, 10.0 mmol) and HOBt.H₂O (153 mg, 1.00 mmol) in DCM (50 mL) was added EDC (2.30 g, 12.0 mmol) and the resulting orange solution stirred at RT for 16 h. Water (25 mL) was added and the mixture shaken. The aqueous was extracted with DCM (25 mL) then the combined organics were passed through a hydrophobic fit and concentrated in vacuo to leave a pale brown foam. FCC, using 0-5% MeOH in DCM, gave the title compound as a pale orange foam (3.21 g, 95%). LCMS (Method 3): Rt 3.14 min, m/z 361 [MH⁺].

b. (S)-3-(6-Fluoro-[1,2,4]triazolo[4,3-a]pyridin-3-yl)-piperidine-1-carboxylic acid tert-butyl ester (Intermediate 88b).

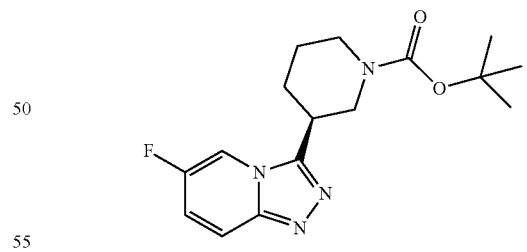

To a solution of Intermediate 88a (3.21 g, 9.49 mmol), Ph₃P (4.98 g, 19.0 mmol) and Et₃N (5.29 mL, 37.9 mmol) in THF (100 mL) at 0° C. was added hexachloroethane (4.49 g, 19.0 mmol) and the resulting opaque orange solution stirred vigorously at RT for 2 h. The suspension was filtered, and the filter-cake washed with THF (20 mL). The combined organics were concentrated in vacuo, redissolved in MeOH (5 mL), applied to an SCX-2 cartridge (70 g) and washed with MeOH (150 mL). The product was eluted with 2M NH₃ in MeOH (150 mL); concentration in vacuo gave a pale orange solid (2.62 g). FCC, using 2-5% MeOH in DCM, gave the title compound as a pale yellow solid (2.01 g, 66%). LCMS (Method 3): Rt 3.09 min, m/z 221 [M-C₅H₉O₂+H⁺].

c. 6-Fluoro-3-(S)-piperidin-3-yl-[1,2,4]triazolo[4,3-a]pyridine (Intermediate 88c).

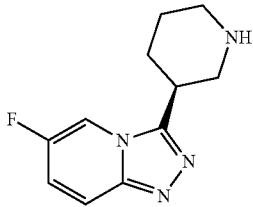

A yellow solution of Intermediate 88b (2.01 g, 6.27 mmol) and TFA (11.0 mL, 148 mmol) in DCM (50 mL) was stirred at reflux for 30 min. The cooled solution was concentrated in vacuo, redissolved in MeOH (3 mL), applied to an SCX-2 cartridge (50 g) and washed with MeOH (150 mL). The product was eluted with 2M NH₃ in MeOH (100 mL); concentration in vacuo left the title compound as a pale orange solid (1.26 g, 91%). LCMS (Method 3): Rt 0.35 min, m/z 221 [MH⁺].

d. 6-Fluoro-3-((S)-1-methyl-piperidin-3-yl)-[1,2,4]triazolo[4,3-a]pyridine (Intermediate 88d).

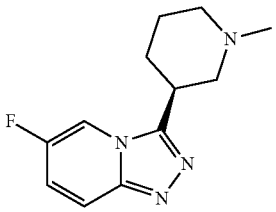 [SMILES: CN1CCC[C@H](c2nnc3ccc(F)cn23)C1]

To a yellow solution of Intermediate 88c (220 mg, 1.00 mmol), formaldehyde (37% in water, 0.811 mL, 10.0 mmol) and AcOH (0.057 mL, 1.00 mmol) in DCM-MeOH (5:1, 12 mL) was added NaBH(OAc)₃ (424 mg, 2.00 mmol) (CARE: gas evolution) and the solution stirred at RT for 2 h. The solution was concentrated in vacuo to ~5 mL volume, then applied to an SCX-2 cartridge (10 g) and washed with MeOH (50 mL). The product was eluted with 2M NH₃ in MeOH (50 mL); concentration in vacuo gave the title compound as a pale yellow gum, that became a white solid on standing (234 mg, quant.). LCMS (Method 3): Rt 0.45 min, m/z 235 [MH⁺].

e. (1S,4R)-4-[3-((S)-1-Methyl-piperidin-3-yl)-[1,2,4]triazolo[4,3-a]pyridin-6-yloxy]-1,2,3,4-tetrahydro-naphthalen-1-ylamine (Intermediate 88e).

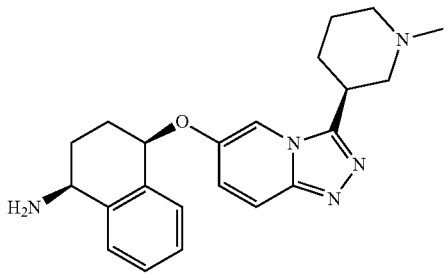 [SMILES: CN1CCC[C@H](c2nnc3ccc(O[C@@H]4CC[C@H](N)c5ccccc54)cn23)C1]

To a solution of Intermediate A (196 mg, 1.20 mmol) in dry DMF (3 mL) at RT under N₂ was added NaH (60% dispersion in oil, 80 mg, 2.00 mmol) and the resulting opaque brown solution stirred for 45 min. A solution of Intermediate 88d (234 mg, 1.00 mmol) in dry DMF (2 mL) was added and the resulting dark brown solution stirred at 60° C. for 90 min. The cooled solution was concentrated in vacuo, redissolved in MeOH (2 mL) and AcOH (0.1 mL), applied to and SCX-2 cartridge and washed with MeOH (75 mL). The product was eluted with 2M NH₃ in MeOH (60 mL); concentration in vacuo left a dark brown solid. FCC, using 3-13% [2M NH₃ in MeOH] in DCM, gave the title compound as a light brown solid after freeze-drying (280 mg, 74%). LCMS (Method 3): Rt 0.44 min, m/z 378 [MH⁺].

f. 1-(5-tert-Butyl-2-p-tolyl-2H-pyrazol-3-yl)-3-{(1S,4R)-4-[3-((S)-1-methyl-piperidin-3-yl)-[1,2,4]triazolo[4,3-a]pyridin-6-yloxy]-1,2,3,4-tetrahydro-naphthalen-1-yl}-urea (Example 88).

An orange-brown solution (5-tert-butyl-2-p-tolyl-2H-pyrazol-3-yl)-carbamic acid 2,2,2-trichloro-ethyl ester (Synthetic Communications, 2009, 39, 3999-4009, which is incorporated herein by reference in its entirety; 243 mg, 0.600 mmol), Intermediate 88e (151 mg, 0.400 mmol) and DIPEA (0.122 mL, 0.700 mmol) in dry dioxane (5 mL) was stirred at 65° C. for 15 h. The cooled solution was concentrated in vacuo, redissolved in MeOH (2 mL), applied to an SCX-2 cartridge (10 g) and washed with MeOH (50 mL). The product was eluted with 2M NH₃ in MeOH (30 mL); concentration in vacuo left a brown solid. FCC, using 2-7% [2M NH₃ in MeOH] in DCM, gave the title compound as a pale yellow solid (188 mg, 74%). LCMS (Method 5): Rt 3.63 min, m/z 633 [MH⁺]. ¹H NMR (400 MHz, d₆-DMSO): 1.27 (9H, s), 1.55 (1H, qd, J 11.9, 5.3), 1.68-1.79 (2H, m), 1.83-2.03 (4H, m), 2.06-2.14 (2H, m), 2.22 (1H, t, J 10.9), 2.22 (3H, s), 2.36 (3H, s), 2.83 (1H, br d, J 10.9), 3.01 (1H, ddd, J 11.1, 3.6, 1.6), 3.54 (1H, tt, J 11.1, 3.7), 4.83 (1H, td, J 8.4, 5.5), 5.57 (1H, t, J 4.5), 6.33 (1H, s), 7.09 (1H, d, J 8.5), 7.15 (1H, dd, J 9.8, 2.0), 7.27-7.42 (8H, m), 7.68 (1H, d, J 9.9), 8.03 (1H, s), 8.32 (1H, d, J 2.0).

Example 89

1-(5-tert-Butyl-2-p-tolyl-2H-pyrazol-3-yl)-3-{(1S,4R)-4-[3-((R)-1-methyl-piperidin-3-yl)-[1,2,4]triazolo[4,3-a]pyridin-6-yloxy]-1,2,3,4-tetrahydro-naphthalen-1-yl}-urea

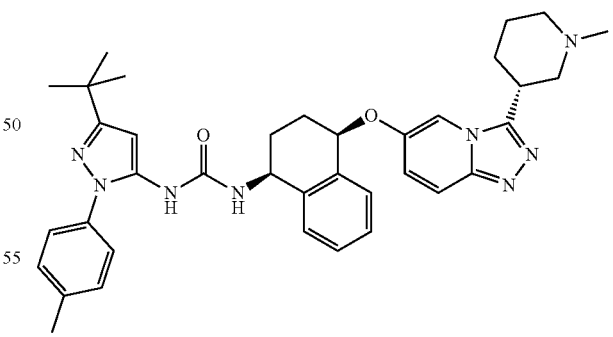

The title compound was prepared starting from (R)-1-BOC-piperidine-3-carboxylic acid (Alfa Aesar) using analogous procedures to those described in Example 88. LCMS (Method 5): Rt 3.62 min, m/z 633 [MH⁺]. ¹H NMR (400 MHz, d₆-DMSO): 1.27 (9H, s), 1.55 (1H, qd, J 12.0, 5.5), 1.67-1.79 (2H, m), 1.82-2.16 (6H, m), 2.22 (3H, s), 2.23 (1H, t, J 11.0), 2.36 (3H, s), 2.83 (1H, br d, J 11.0), 2.99 (1H, br d, J 11.2), 3.53 (1H, tt, J 11.1, 3.7), 4.83 (1H, td, J 8.4, 5.5), 5.57

(1H, t, J 4.5), 6.33 (1H, s), 7.09 (1H, d, J 8.5), 7.16 (1H, dd, J 9.8, 2.1), 7.35-7.33 (8H, m), 7.68 (1H, d, J 9.9), 8.04 (1H, s), 8.29 (1H, d, J 2.0).

Example 90

1-(5-tert-Butyl-2-p-tolyl-2H-pyrazol-3-yl)-3-{(1S, 4R)-4-[3-((R)-1-methyl-pyrrolidin-3-yl)-[1,2,4]triazolo[4,3-a]pyridin-6-yloxy]-1,2,3,4-tetrahydro-naphthalen-1-yl}-urea

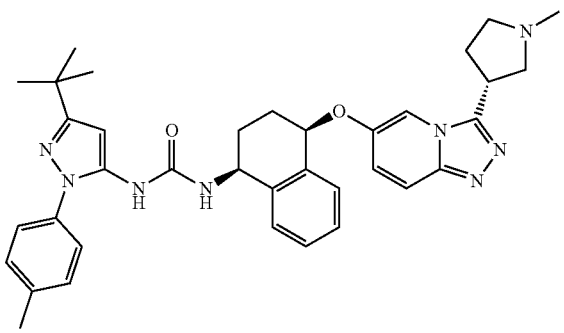 [SMILES: Cc1ccc(-n2nc(C(C)(C)C)cc2NC(=O)N[C@H]2CC[C@@H](Oc3ccc4nnc([C@@H]5CCN(C)C5)n4c3)c3ccccc32)cc1]

a. (R)-3-[N'-(5-Fluoro-pyridin-2-yl)-hydrazinocarbonyl]-pyrrolidine-1-carboxylic acid tert-butyl ester (Intermediate 90a).

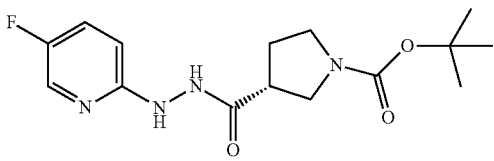 [SMILES: CC(C)(C)OC(=O)N1CC[C@@H](C(=O)NNc2ccc(F)cn2)C1]

To a brown solution of (5-fluoro-pyridin-2-yl)-hydrazine (590 mg, 4.64 mmol), (R)-1-N-BOC-beta proline (Manchester Organics, 1.00 g, 4.64 mmol) and HOBt.H₂O (71.1 mg, 0.464 mmol) in DCM (20 mL) at RT was added EDC (1.07 g, 5.57 mmol) (CARE: exotherm to ~35° C.) and the resulting solution stirred at RT for 4 h. Water (20 mL) was added and the mixture shaken. The aqueous was extracted with DCM (20 mL), then the combined organics were passed through a hydrophobic frit and concentrated in vacuo to 1 mL volume. FCC, using 1-10% MeOH in DCM, gave the title compound as a pale brown foam (1.37 g, 91%). LCMS (Method 3): Rt 2.93 min, m/z 347 [MNa⁺].

b. (R)-3-(6-Fluoro-[1,2,4]triazolo[4,3-a]pyridin-3-yl)-pyrrolidine-1-carboxylic acid tert-butyl ester (Intermediate 90b).

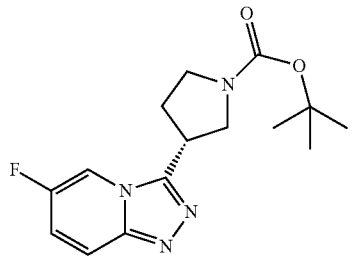 [SMILES: CC(C)(C)OC(=O)N1CC[C@@H](c2nnc3ccc(F)cn23)C1]

To a brown solution Intermediate 90a (1.37 g, 4.22 mmol), Ph₃P (2.22 g, 8.45 mmol) and Et₃N (2.35 mL, 16.9 mmol) in THF (25 mL) at 0° C. was added hexachloroethane (2.00 g, 8.45 mmol) in 3 portions at 1 min intervals. The solution was stirred at 0° C. for 30 min and at RT for 3.5 h. The suspension was filtered and the filter-cake washed with THF (10 mL). The combined organics were applied to an SCX-2 cartridge (50 g), then washed with DCM-MeOH (1:1, 50 mL) and MeOH (50 mL). The product was eluted with 2M NH₃ in MeOH (75 mL); concentration in vacuo gave a brown oil that solidified on standing. The solid was dissolved in DCM (10 mL) then Et₃N (0.580 mL, 4.16 mmol) and BOC anhydride (454 mg, 2.08 mmol) added sequentially. The solution was stirred at RT for 45 min, then water (10 mL) was added and the aqueous extracted with DCM (5 mL). The combined organics were passed through a hydrophobic frit and concentrated in vacuo to leave a brown gum. FCC, using 2.5-3% MeOH in DCM, gave the title compound as a pale brown solid (933 mg, 73%). LCMS (Method 3): Rt 2.94 min, m/z 207 [MH⁺-C₅H₉O₂].

c. 6-Fluoro-3-(R)-pyrrolidin-3-yl-[1,2,4]triazolo[4,3-a]pyridine (Intermediate 90c).

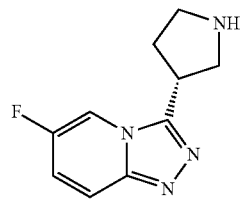 [SMILES: Fc1ccc2nnc([C@@H]3CCNC3)n2c1]

A mixture of Intermediate 90b (335 mg, 1.09 mmol) and TFA (0.812 mL, 10.9 mmol) in DCM (5 mL) was stirred at reflux for 45 min. The cooled solution was concentrated in vacuo, redissloved in MeOH (2 mL), applied to an SCX-2 cartridge (10 g) and washed with MeOH (50 mL). The product was eluted with 2M NH₃ in MeOH; concentration in vacuo left the title compound as a pale yellow solid (225 mg, >99%). LCMS (Method 3): Rt 0.44 min, m/z 207 [MH⁺].

d. 6-Fluoro-3-((R)-1-methyl-pyrrolidin-3-yl)-[1,2,4]triazolo[4,3-a]pyridine (Intermediate 90d).

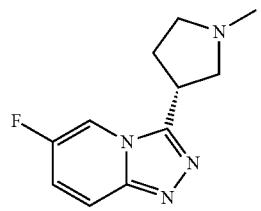 [SMILES: CN1CC[C@@H](c2nnc3ccc(F)cn23)C1]

To a solution of Intermediate 90c (225 mg, 1.09 mmol), formaldehyde (37% in water, 0.885 mL, 10.9 mmol) and AcOH (0.0625 mL, 1.09 mmol) in DCM (20 mL) and MeOH (1 mL) was added NaBH(OAc)₃ (462 mg, 2.18 mmol) (CARE: gas evolution) and the pale yellow solution stirred at RT for 16 h. The solution was concentrated to 2 mL volume, then was applied to an SCX-2 cartridge and was washed with MeOH (25 mL). The product was eluted with 2M NH₃ in MeOH (25 mL); concentration in vacuo left the title compound as a pale brown viscous oil (228 mg, 95%). LCMS (Method 3): Rt 0.44 min, m/z 221 [MH⁺].

e. (1S,4R)-4-[3-((R)-1-Methyl-pyrrolidin-3-yl)-[1,2,4]triazolo[4,3-a]pyridin-6-yloxy]-1,2,3,4-tetrahydro-naphthalen-1-ylamine (Intermediate 90e).

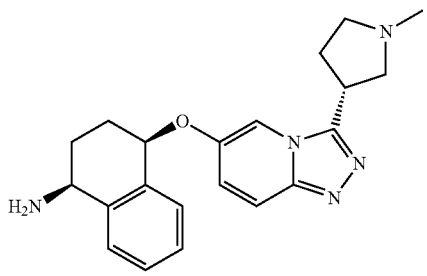 [SMILES: CN1CC[C@@H](c2nnc3ccc(O[C@@H]4CC[C@H](N)c5ccccc54)cn23)C1]

To a solution of Intermediate A (203 mg, 1.24 mmol) in dry DMF (3 mL) under N₂ was added NaH (60% dispersion in oil, 83.0 mg, 2.07 mmol) (CARE: gas evolution) and the resulting opaque brown solution stirred at RT for 45 min. A solution of Intermediate 90d (228 mg, 1.03 mmol) in dry DMF (2 mL) was added and the dark brown solution stirred at 60° C. under N₂ for 90 min. The cooled solution was concentrated in vacuo, redissolved in MeOH (2 mL) and AcOH (0.1 mL), applied to and SCX-2 cartridge (20 g) and washed with MeOH (75 mL). The product was eluted with 2M NH₃ in MeOH (50 mL); concentration in vacuo gave a dark brown solid. FCC, using 5-15% (2M NH₃ in MeOH) in DCM, gave the title compound as a light brown powder after freeze-drying (299 mg, 80%). LCMS (Method 3): Rt 0.44 min, m/z 364 [MH⁺].

f. 1-(5-tert-Butyl-2-p-tolyl-2H-pyrazol-3-yl)-3-{(1S,4R)-4-[3-((R)-1-methyl-pyrrolidin-3-yl)-[1,2,4]triazolo[4,3-a]pyridin-6-yloxy]-1,2,3,4-tetrahydro-naphthalen-1-yl}-urea (Example 90).

A brown solution of (5-tert-butyl-2-p-tolyl-2H-pyrazol-3-yl)-carbamic acid 2,2,2-trichloro-ethyl ester (Synthetic Communications, 2009, 39, 3999-4009, which is incorporated herein by reference in its entirety; 227 mg, 0.560 mmol), Intermediate 90e (145 mg, 0.400 mmol) and DIPEA (0.111 mL, 0.640 mmol) in dry dioxane (5 mL) was stirred at 65° C. for 15 h. The cooled solution was concentrated in vacuo, redissolved in MeOH (2 mL), applied to an SCX-2 cartridge (10 g) and washed with MeOH (50 mL). The product was eluted with 2M NH₃ in MeOH (30 mL); concentration in vacuo gave a brown solid. FCC, using 2-7% [2M NH₃ in MeOH] in DCM, gave a pale brown solid (195 mg). Further purification by MDAP (Method 8) gave the title compound as a white powder after freeze-drying (10.0 mg, 4%). LCMS (Method 5): Rt 3.62 min, m/z 619 [MH⁺]. ¹H NMR (400 MHz, d₆-DMSO): 1.27 (9H, s), 1.83-1.98 (2H, m), 2.08-2.20 (3H, m), 2.32 (3H, s), 2.33-2.40 (1H, m), 2.36 (3H, s), 2.59-2.70 (2H, m), 2.75 (1H, dd, J 9.2, 6.1), 2.96 (1H, t, J 8.7), 3.93-4.01 (1H, m), 4.83 (1H, td, J 8.4, 5.4), 5.46 (1H, t, J 4.6), 6.32 (1H, s), 7.10 (1H, d, J 8.5), 7.18 (1H, dd, J 9.9, 2.1), 7.27-7.40 (8H, m), 7.69 (1H, dd, J 9.9, 0.8), 8.04 (1H, s), 8.44 (1H, d, J 2.0).

Example 91

1-(5-tert-Butyl-2-p-tolyl-2H-pyrazol-3-yl)-3-{(1S,4R)-4-[3-((2S,4R)-4-fluoro-1-methyl-pyrrolidin-2-yl)-[1,2,4]triazolo[4,3-a]pyridin-6-yloxy]-1,2,3,4-tetrahydro-naphthalen-1-yl}-urea

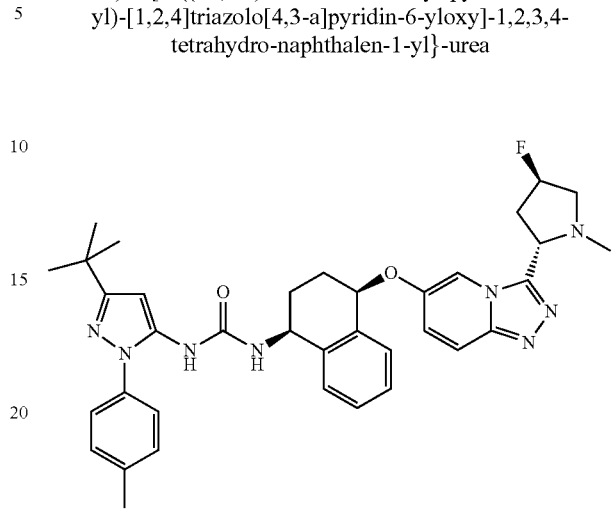

a. (2S,4R)-4-Fluoro-1-methyl-pyrrolidine-2-carboxylic acid (Intermediate 91a).

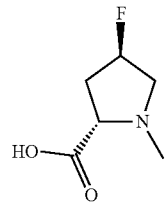

A solution of (2S,4R)-4-fluoropyrrolidine-2-carboxylic acid (1.00 g, 7.52 mmol), formaldehyde (37% wt in water, 1.00 mL, 30.8 mmol), 12N HCl (0.5 mL) in IMS (38 mL) was purged with argon. To the solution was added Pd/C (100 mg), then the flask was evacuated and filled with H₂ the resulting suspension was stirred at RT for 3 d. The reaction mixture was passed through a pad of Celite and the mixture was concentrated in vacuo to give the title compound as a pale yellow gum (600 mg, 54%). ¹H NMR (300 MHz, d₆-DMSO): 2.29-2.37 (1H, m), 2.63-2.67 (1H, m), 2.97 (3H, s), 3.44-3.53 (1H, m), 4.00-4.04 (1H, m), 4.58 (1H, dd, J 11.6, 7.11), 5.41-5.45 (1H, m).

b. (2S,4R)-4-Fluoro-1-methyl-pyrrolidine-2-carboxylic acid N'-(5-fluoro-pyridin-2-yl)-hydrazide (Intermediate 91b).

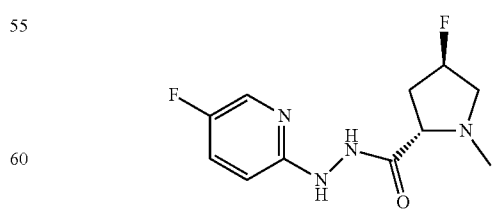

A solution of (5-fluoro-pyridin-2-yl)-hydrazine (378 mg, 2.98 mmol), Intermediate 91a (600 mg, 4.08 mmol) and HOBt.H₂O (44 mg, 0.12 mmol) in DCM (10 mL) and DMF (3 mL) was added EDC (628 mg, 3.28 mmol) portionwise at RT and the mixture stirred at RT for 17 h. The solution was diluted with water and extracted with DCM. The combined organics were dried and concentrated in vacuo. The residue was purified by FCC, using 0-7.5% [2M NH₃ in MeOH] in DCM, to give the title compound as light orange powder (366 mg, 35%). LCMS (Method 3): Rt 0.56 min, m/z 257 [MH⁺].

c. 6-Fluoro-3-((2S,4R)-4-fluoro-1-methyl-pyrrolidin-2-yl)-[1,2,4]triazolo[4,3-a]pyridine (Intermediate 91c).

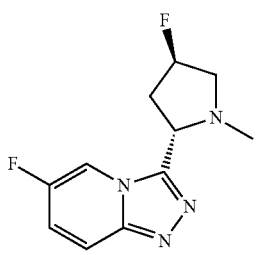 [SMILES: CN1C[C@H](F)C[C@H]1c1nnc2ccc(F)cn12]

A solution of Intermediate 91b (189 mg, 0.79 mmol), Ph₃P (416 mg, 1.59 mmol) and Et₃N (0.44 mL, 3.17 mmol) in THF (10 mL) at RT was added hexachloroethane (375 mg, 1.59 mmol) portion wise and the mixture stirred for 4 h. The solution was diluted with water and extracted with DCM. The combined organics were dried and concentrated in vacuo. The residue was purified by FCC, using 0-10% [2M NH₃ in MeOH] in DCM, to give the title compound as light yellow powder (214 mg, 63%). LCMS (Method 3): Rt 0.42 min, m/z 239 [MH⁺].

d. (1S,4R)-4-[3-((2S,4R)-4-Fluoro-1-methyl-pyrrolidin-2-yl)-[1,2,4]triazolo[4,3-a]pyridin-6-yloxy]-1,2,3,4-tetrahydro-naphthalen-1-ylamine (Intermediate 91d).

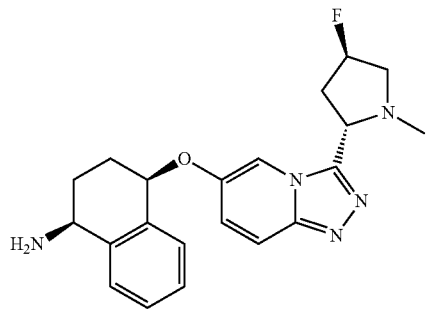 [SMILES: CN1C[C@H](F)C[C@H]1c1nnc2ccc(O[C@@H]3CC[C@H](N)c4ccccc43)cn12]

To a solution of Intermediate A (161 mg, 0.99 mmol) in dry DMF (2.5 mL) at RT was added NaH (60% in mineral oil, 108 mg, 2.70 mmol) and the mixture stirred for 15 min. Intermediate 91c (214 mg, 0.89 mmol) in DMF (2.5 mL) was then added and the mixture heated at 60° C. for 1 h. After cooling, the resulting dark brown mixture was diluted with water and extracted with DCM. The combined organics were dried and concentrated in vacuo. The residue was purified by FCC, using 0-10% MeOH in DCM, to give crude product. FCC, using 0-10% (2M NH₃ in MeOH) in DCM, gave the title compound as light brown foam (175 mg, 51%). LCMS (Method 3): Rt 0.43 min, m/z 382 [MH⁺].

e. 1-(5-tert-Butyl-2-p-tolyl-2H-pyrazol-3-yl)-3-{(1S,4R)-4-[3-((2S,4R)-4-fluoro-1-methyl-pyrrolidin-2-yl)-[1,2,4]triazolo[4,3-a]pyridin-6-yloxy]-1,2,3,4-tetrahydro-naphthalen-1-yl}-urea (Example 91).

A solution of Intermediate 91d (164 mg, 0.43 mmol) and 5-tert-butyl-2-p-tolyl-2H-pyrazol-3-yl)-carbamic acid 2,2,2-trichloro-ethyl ester (Synthetic Communications, 2009, 39, 3999-4009, which is incorporated herein by reference in its entirety; 191 mg, 0.47 mmol) and DIPEA (225 μL, 1.14 mmol) in THF (5 mL) was stirred at reflux for 18.5 h. The cooled reaction mixture was diluted with water and extracted with DCM. The combined organics were dried and concentrated in vacuo. The residue was purified by FCC, using 0-5% [2M NH₃ in MeOH] in DCM, to give impure product. This residue was purified further by HPLC (XBridge C18 column, 30-98% MeCN in H₂O, 0.1% NH₄OH) to give the title compound as a white powder after freeze-drying (63 mg, 23%). LCMS (Method 5): Rt 3.88 min, m/z 637 [MH⁺]. ¹H NMR (400 MHz, d₆-DMSO): 1.27 (9H, s), 1.88-1.93 (2H, m), 2.06-2.10 (2H, m), 2.17 (3H, s), 2.30-2.41 (2H, m), 2.36 (3H, s), 2.61-2.64 (2H, m), 3.49 (1H, ddd, J 25.6, 11.5, 5.5), 4.54 (1H, t, J 7.7), 4.80-4.83 (1H, m), 5.49 (1H, t, J 4.3), 6.32 (1H, s), 7.10 (1H, d, J 8.5), 7.30-7.42 (9H, m), 7.75 (1H, dd, J 9.9, 0.8), 8.05 (1H, s), 8.35 (1H, d, J 2.1).

Example 92

1-(5-tert-Butyl-2-p-tolyl-2H-pyrazol-3-yl)-3-{(1S,4R)-4-[3-((S)-3-hydroxymethyl-pyrrolidin-1-yl)-[1,2,4]triazolo[4,3-a]pyridin-6-yloxy]-1,2,3,4-tetrahydro-naphthalen-1-yl}-urea

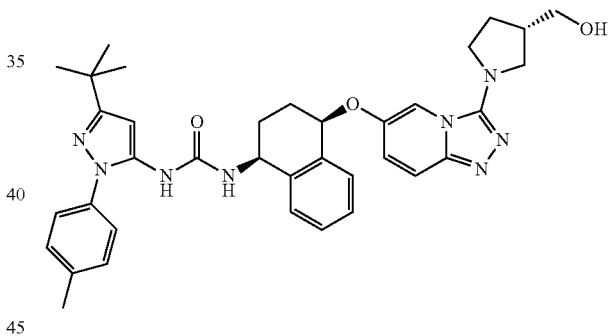

a. [(S)-1-(6-Fluoro-[1,2,4]triazolo[4,3-a]pyridin-3-yl)-pyrrolidin-3-yl]-methanol (Intermediate 92a).

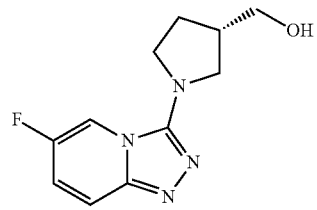 [SMILES: OC[C@H]1CCN(c2nnc3ccc(F)cn23)C1]

A solution of Intermediate 24b (485 mg, 2.83 mmol) and (S)-3-(hydroxymethyl)pyrrolidine (1.00 g, 9.90 mmol) in DMA (10 mL) was heated in the microwave at 175° C. for 2.5 h. The cooled mixture was concentrated in vacuo. The residue was purified by FCC, using 0-20% [2M NH₃ in MeOH] in DCM, to give the title compound as a brown gum (670 mg, quant.). LCMS (Method 3): Rt 0.44 min, in/z 237 [MH⁺].

b. 6-Fluoro-3-((S)-3-triisopropylsilanyloxymethyl-pyrrolidin-1-yl)-[1,2,4]triazolo[4,3-a]pyridine (Intermediate 92b).

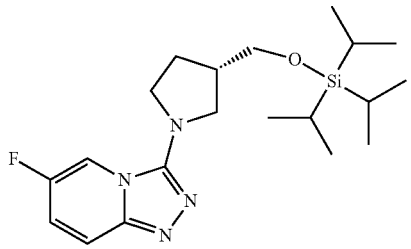 [SMILES: CC(C)[Si](OC[C@H]1CCN(c2nnc3ccc(F)cn23)C1)(C(C)C)C(C)C]

To a solution of Intermediate 92a (667 mg, 2.83 mmol) and Et₃N (630 μL, 4.53 mmol) in DCM (5 mL) was added triisopropylsilyltrifluoromethane sulfonate (950 μL, 3.54 mmol) and the mixture was stirred at RT for 1 h. The mixture was washed with sat. sodium hydrogen carbonate solution then brine, dried and concentrated in vacuo. The residue was purified by FCC, 2-6% MeOH in DCM, to give the title compound as a pale green viscous oil (1.11 g, quant.). LCMS (Method 3): Rt 4.76 min, m/z 393 [MH⁺].

c. (1S,4R)-4-[3-((S)-3-Triisopropylsilanyloxymethyl-pyrrolidin-1-yl)-[1,2,4]triazolo[4,3-a]pyridin-6-yloxy]-1,2,3,4-tetrahydro-naphthalen-1-ylamine (Intermediate 92c).

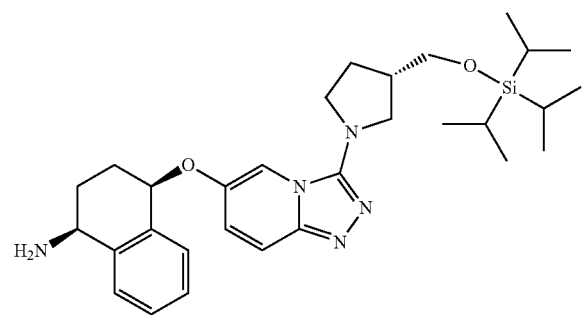 [SMILES: CC(C)[Si](OC[C@H]1CCN(c2nnc3ccc(O[C@@H]4CC[C@H](N)c5ccccc54)cn23)C1)(C(C)C)C(C)C]

To a solution of Intermediate A (179 mg, 1.10 mmol) in DMF (3 mL) was added NaH (60% dispersion in oil, 120 mg, 3.00 mmol) and the mixture stirred at RT for 25 min. A solution of Intermediate 92b (958 mg, 1.10 mmol) in DMF (3 mL) was added and the mixture stirred at 60° C. for 1.5 h. The solution was cooled, water added, and the mixture extracted with DCM (4×25 mL). The combined organics were dried and concentrated in vacuo. The residue was purified by FCC, using 0-16% MeOH in DCM, to give the title compound as a brown gum (216 mg, 37%). LCMS (Method 3): Rt 3.08 min, m/z 536 [MH⁺].

d. 1-(5-tert-Butyl-2-p-tolyl-2H-pyrazol-3-yl)-3-{(1S,4R)-4-[3-((S)-3-triisopropyl silanyloxy-methyl-pyrrolidin-1-yl)-[1,2,4]triazolo[4,3-a]pyridin-6-yloxy]-1,2,3,4-tetrahydro-naphthalen-1-yl}-urea (Intermediate 92d).

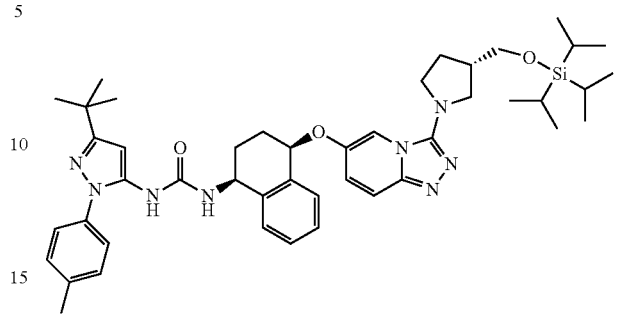

A solution of Intermediate 92c (210 mg, 0.39 mmol) and (5-tert-butyl-2-p-tolyl-2H-pyrazol-3-yl)-carbamic acid 2,2,2-trichloro-ethyl ester (Synthetic Communications, 2009, 39, 3999-4009, which is incorporated herein by reference in its entirety; 159 mg, 0.390 mmol) in 1,4-dioxane (4 mL) and DIPEA (105 μL, 0.600 mmol) was stirred at 65° C. for 15.5 h and at 90° C. for 1.5 h. The cooled mixture was concentrated in vacuo. The residue was purified by FCC, using 0-10% MeOH in DCM, to give the title compound as a pale brown solid (242 mg, 79%). LCMS (Method 3): Rt 5.18 min, m/z 791 [MH⁺].

e. 1-(5-tert-Butyl-2-p-tolyl-2H-pyrazol-3-yl)-3-{(1S,4R)-4-[3-((S)-3-hydroxymethyl-pyrrolidin-1-yl)-[1,2,4]triazolo[4,3-a]pyridin-6-yloxy]-1,2,3,4-tetrahydro-naphthalen-1-yl}-urea (Example 92).

To a solution of Intermediate 92d (240 mg, 0.300 mmol) and TBAF (1M in THF, 0.400 mL, 0.400 mmol) in THF (3 mL) was stirred at RT for 1 h. Water was added and the mixture extracted with DCM (4×20 mL). The combined organics were dried and concentrated in vacuo. The residue was purified by FCC, using 0-14% MeOH in DCM, to give the title compound as an off-white powder after freeze-drying (154 mg, 81%). LCMS (Method 5): Rt 4.01 min, in/z 635.3 [MH⁺]. ¹H NMR (400 MHz, d₆-DMSO): 1.27 (9H, s), 1.68-1.79 (1H, m), 1.79-1.97 (2H, m), 1.98-2.14 (3H, m), 2.36 (3H, s), 2.40-2.48 (1H, m), 3.23-3.30 (1H, m), 3.41-3.64 (5H, m), 4.71 (1H, t, J 5.3), 4.77-4.85 (1H, m), 5.51 (1H, br t, J 4.4), 6.33 (1H, s), 7.03-7.10 (2H, m), 7.25-7.40 (8H, m), 7.53 (1H, d, J 9.9), 7.82 (1H, d, J 1.8), 8.03 (1H, s).

Example 93

1-(5-tert-Butyl-2-p-tolyl-2H-pyrazol-3-yl)-3-{(1S,4R)-4-[3-((R)-3-hydroxymethyl-pyrrolidin-1-yl)-[1,2,4]triazolo[4,3-a]pyridin-6-yloxy]-1,2,3,4-tetrahydro-naphthalen-1-yl}-urea

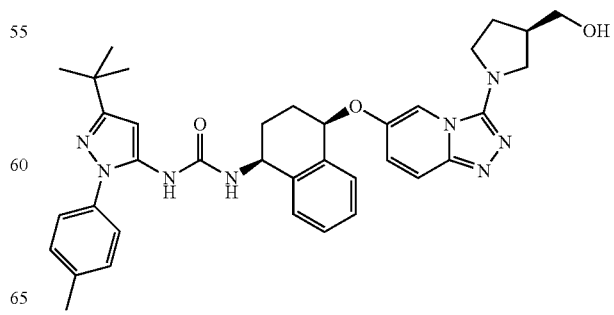

The title compound was prepared starting from (R)-3-(hydroxymethyl)pyrrolidine using analogous procedures to those described in Example 92. LCMS (Method 5): Rt 4.01 min, m/z 635.3 [MH+]. $^1$H NMR (400 MHz, d$_6$-DMSO): 1.27 (9H, s), 1.67-1.77 (1H, m), 1.79-1.97 (2H, m), 1.98-2.15 (3H, m), 2.37 (3H, s), 2.40-2.48 (1H, m), 3.25-3.30 (1H, m), 3.41-3.62 (5H, m), 4.71 (1H, t, J 5.3), 4.77-4.85 (1H, m), 5.51 (1H, br t, J 4.3), 6.33 (1H, s), 7.04-7.10 (2H, m), 7.25-7.40 (8H, m), 7.53 (1H, d, J 9.9), 7.82 (1H, d, J 1.6), 8.04 (1H, s).

Example 94

1-(5-tert-Butyl-2-p-tolyl-2H-pyrazol-3-yl)-3-((1S,4R)-4-{3-[4-(2-hydroxy-ethyl)-piperazin-1-yl]-[1,2,4]triazolo[4,3-a]pyridin-6-yloxy}-1,2,3,4-tetrahydro-naphthalen-1-yl)-urea

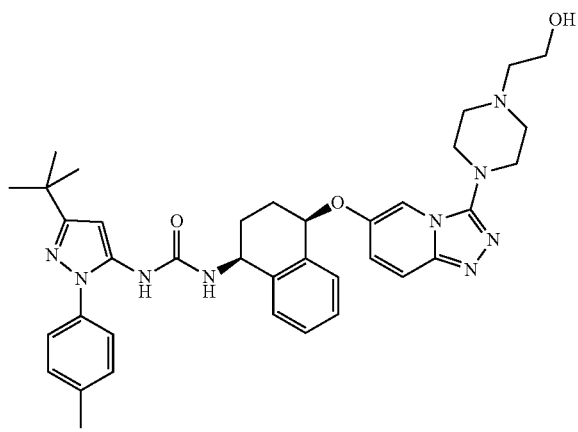 [SMILES: Cc1ccc(-n2nc(C(C)(C)C)cc2NC(=O)N[C@H]2CC[C@@H](Oc3ccc4nnc(N5CCN(CCO)CC5)n4c3)c3ccccc32)cc1]

a. 2-[4-(6-Fluoro-[1,2,4]triazolo[4,3-a]pyridin-3-yl)-piperazin-1-yl]-ethanol (Intermediate 94a).

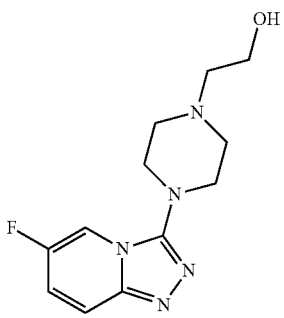 [SMILES: OCCN1CCN(c2nnc3ccc(F)cn23)CC1]

A solution of Intermediate 24b (485 mg, 2.82 mmol) and 1-(2-hydroxyethyl)-piperazine (1.39 mL, 11.3 mmol) in DMA (10 mL) was heated in the microwave at 170° C. for 8 h. The cooled mixture was concentrated in vacuo. The residue was purified by FCC, using 0-20% (2M NH$_3$ in MeOH) in DCM, to give impure product. Further purified by FCC, using 0-7% (2M NH$_3$ in MeOH) in DCM gave the title compound as a pale brown gum (175 mg, 23%). LCMS (Method 3): Rt 0.43 min, m/z 266 [MH+].

b. 6-Fluoro-3-[4-(2-triisopropylsilanyloxy-ethyl)-piperazin-1-yl]-[1,2,4]triazolo[4,3-a]pyridine (Intermediate 94b).

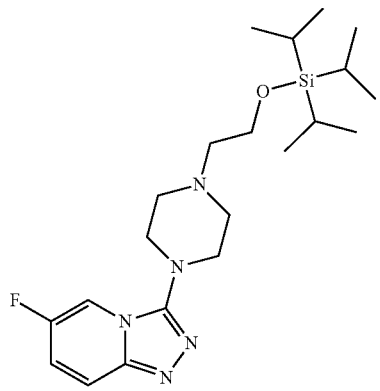 [SMILES: CC(C)[Si](OCCN1CCN(c2nnc3ccc(F)cn23)CC1)(C(C)C)C(C)C]

To a solution of Intermediate 94a (169 mg, 0.64 mmol) and Et$_3$N (265 µL, 1.91 mmol) in DCM (6 mL) was added triisopropylsilyl trifluoromethanesulfonate (189 pt, 0.70 mmol). The solution was stirred for 2.5 h, then diluted with water and extracted with DCM. The combined organics were dried and concentrated in vacuo. The residue was purified by FCC, using 0-5% (2M NH$_3$ in MeOH) in DCM, to give the title compound as a pale brown gum (242 mg, 90%). LCMS (Method 3): Rt 2.93 min, m/z 422 [MH+].

c. (1S,4R)-4-{3-[4-(2-Triisopropylsilanyloxy-ethyl)-piperazin-1-yl]-[1,2,4]triazolo[4,3-a]pyridin-6-yloxy}-1,2,3,4-tetrahydro-naphthalen-1-ylamine (Intermediate 94c).

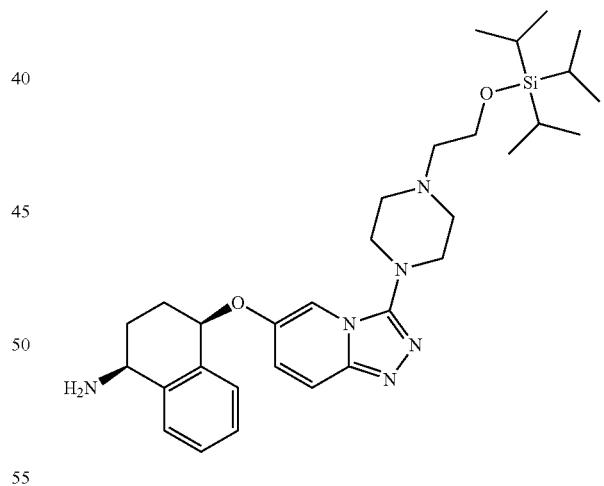

To a solution of Intermediate A (102 mg, 0.63 mmol) in DMF (1.5 mL) was added NaH (60% dispersion in oil, 68 mg, 1.71 mmol). The mixture was stirred at RT for 5 min, then a solution of Intermediate 94b (240 mg, 0.57 mmol) in DMF (1.5 mL) was added and the mixture stirred at 60° C. for 1.25 h. The cooled mixture was diluted with water and extracted with DCM (4×25 mL). The combined organics were dried and concentrated in vacuo. The residue was purified by FCC, using 0-10% (2M NH$_3$ in MeOH) in DCM, to give the title compound as a pale brown gum (219 mg, 68%). LCMS (Method 3): Rt 2.65 min, m/z 565 [MH+].

239 d. 1-(5-tert-Butyl-2-p-tolyl-2H-pyrazol-3-yl)-3-((1S,4R)-4-{3-[4-(2-triisopropylsilanyloxy-ethyl)-piperazin-1-yl]-[1,2,4]triazolo[4,3-a]pyridin-6-yloxy}-1,2,3,4-tetrahydro-naphthalen-1-yl)-urea (Intermediate 94d).

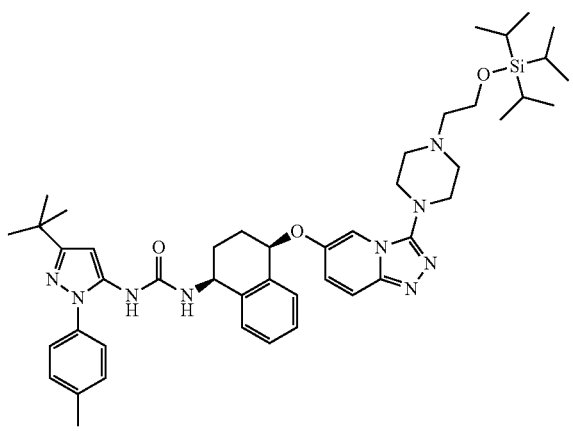 [SMILES: Cc1ccc(-n2nc(C(C)(C)C)cc2NC(=O)N[C@H]2CC[C@@H](Oc3ccc4nnc(N5CCN(CCO[Si](C(C)C)(C(C)C)C(C)C)CC5)n4c3)c3ccccc32)cc1]

A solution of Intermediate 94c (170 mg, 0.42 mmol), 5-tert-butyl-2-p-tolyl-2H-pyrazol-3-yl)-carbamic acid 2,2,2-trichloro-ethyl ester (Synthetic Communications, 2009, 39, 3999-4009, which is incorporated herein by reference in its entirety; 170 mg, 0.42 mmol) and DIPEA (199 μL, 1.14 mmol) in THF (4 mL) was stirred at reflux for 15.5 h. The cooled reaction mixture was diluted with water and extracted with DCM. The combined organics were dried and concentrated in vacuo. The residue was purified by FCC, using 0-7.5% (2M $NH_3$ in MeOH) in DCM, to give the title compound as a yellow powder (293 mg, 93%). LCMS (Method 3): Rt 3.70 min, m/z 820 [MH$^+$].

e. 1-(5-tert-Butyl-2-p-tolyl-2H-pyrazol-3-yl)-3-((1S,4R)-4-{3-[4-(2-hydroxy-ethyl)-piperazin-1-yl]-[1,2,4]triazolo[4,3-a]pyridin-6-yloxy}-1,2,3,4-tetrahydro-naphthalen-1-yl)-urea (Example 94).

A solution of Intermediate 94d (243 mg, 0.29 mmol) and TBAF (1M in THF, 0.53 mL, 0.53 mmol) in THF (3.5 mL) was stirred at RT for 45 min, then diluted with water and extracted with DCM (3×20 mL). The combined organics were dried and concentrated in vacuo. The residue was purified by FCC, using 0-7.5% (2M $NH_3$ in MeOH) in DCM, to give the title compound as a white powder after freeze-drying (135 mg, 58%). LCMS (Method 5): Rt 3.52 min, m/z 664 [MH$^+$]. $^1$H NMR (400 MHz, $d_6$-DMSO): 1.27 (9H, s), 1.86-1.92 (2H, m), 2.04-2.11 (2H, m), 2.36 (3H, s), 2.48 (2H, q, J 5.8), 2.66 (4H, t, J 4.8), 3.19 (4H, t, J 4.5), 3.55 (2H, q, J 5.8), 4.44 (1H, t, J 5.4), 4.79-4.82 (1H, m), 5.57 (1H, t, J 4.4), 6.32 (1H, s), 7.07 (1H, d, J 8.5), 7.15 (1H, dd, J 9.9, 2.1), 7.32-7.44 (8H, m), 7.60-7.63 (1H, m), 7.68 (1H, d, J 2.0), 8.04 (1H, s).

240

Example 95

1-{5-tert-Butyl-2-[3-(2-dimethylamino-ethoxy)-phenyl]-2H-pyrazol-3-yl-3-{(1S,4R)-4-[3-((S)-2-methyl-piperidin-1-yl)-[1,2,4]triazolo[4,3-a]pyridin-6-yloxy]-1,2,3,4-tetrahydronaphthalen-1-yl]urea

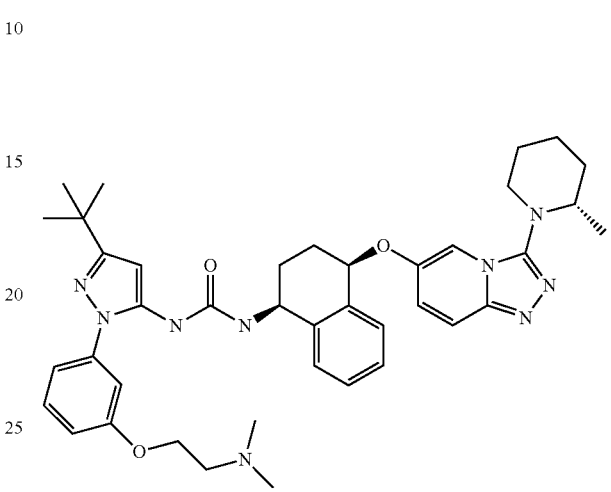

a. 3-(5-Amino-3-tert-butyl-pyrazol-1-yl)-phenol (Intermediate 95a).

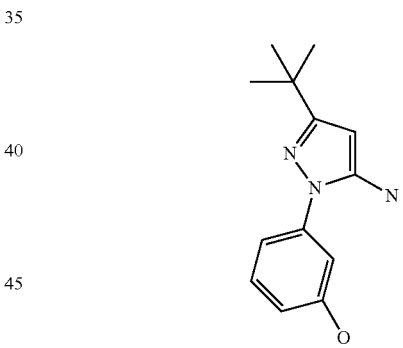

A mixture of 5-tert-butyl-2H-pyrazol-3-ylamine (1 g, 7.18 mmol), 3-iodophenol (1.74 g, 7.90 mmol), copper (I) iodide (68 mg, 0.36 mmol), (1S,2S)—N,N'-dimethyl cyclohexane-1,2-diamine (204 mg, 1.44 mmol) and potassium carbonate (2.08 g, 15.09 mmol) in toluene (8 mL) was de-gassed and flushed with argon (3×). The reaction mixture was then treated with microwave irradiation, at 150° C. for 1 h. The mixture was diluted with EtOAc (20 mL) and washed with water (20 mL). The aqueous layer was extracted with a further 20 mL EtOAc and the combined organic layers were washed with brine (20 mL), dried ($MgSO_4$), filtered and concentrated in vacuo. The residue obtained was purified by FCC, using 0-100% EtOAc in cyclohexane to afford the title compound as a brown gum (1.42 g, 86%). LCMS (Method 3): Rt 2.21 min, m/z 232 [MH$^+$].

b. 5-tert-Butyl-2-{3-[2-(tetrahydro-pyran-2-yloxy)-ethoxy]-phenyl}-2H-pyrazol-3-ylamine (Intermediate 95b).

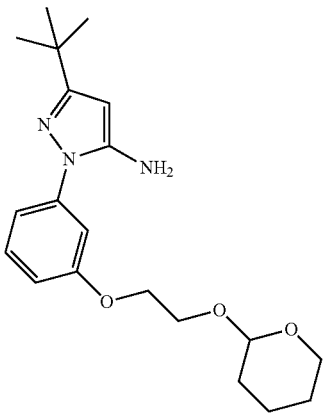 [SMILES: CC(C)(C)c1cc(N)n(-c2cccc(OCCOC3CCCCO3)c2)n1]

A solution of intermediate 95a (1.42 g, 6.15 mmol) and triphenyl phosphine (3.22 g, 12.29 mmol) in THF (50 mL), under an atmosphere of argon was treated with 2-(tetrahydro-pyran-2-yloxy)-ethanol (1.25 mL, 9.22 mmol), followed by the dropwise addition of diethyl azodicarboxylate (1.94 mL, 12.29 mmol). The reaction mixture was then stirred at RT for 1 h. Water (0.5 mL) was added and the mixture was concentrated in vacuo. The residue was taken up in EtOAc (8 mL) and cyclohexane was added until triphenylphosphine oxide had precipitated out of solution. This was filtered and the filtrate was concentrated in vacuo. The residue was purified by FCC, using 0-100% EtOAc in cyclohexane to afford the title compound as an orange/brown oil (2.98 g, >100%). LCMS (Method 3): Rt 3.20 min, m/z 360 [MH$^+$].

c. (5-tert-Butyl-2-{3-[2-(tetrahydro-pyran-2-yloxy)-ethoxy]-phenyl}-2H-pyrazol-3-yl)-carbamic acid 2,2,2-trichloro-ethyl ester (Intermediate 95c).

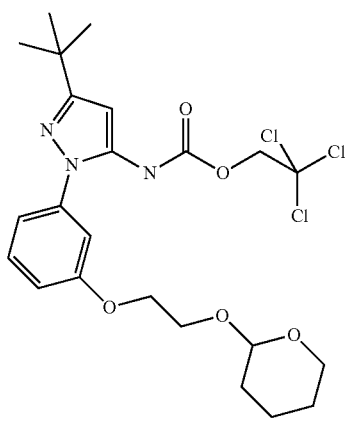 [SMILES: CC(C)(C)c1cc(NC(=O)OCC(Cl)(Cl)Cl)n(-c2cccc(OCCOC3CCCCO3)c2)n1]

A solution of intermediate 95b (2.21 g, 6.16 mmol) in EtOAc (20 mL) was treated with aqueous NaOH (1M, 11.08 mmol), followed by 2,2,2-trichloroethyl chloroformate (1.01 mL, 7.39 mmol) and the reaction mixture was stirred at RT for 1 h. The mixture was partitioned between EtOAc (50 mL) and water (50 mL). The layers were separated and the aqueous layer was extracted with a further 50 mL EtOAc. The combined organic layers were dried (MgSO4), filtered and concentrated in vacuo. The residue was purified by FCC, using 0-100% EtOAc in cyclohexane to afford the title compound as a dark orange oil (2.39 g, 73%). LCMS (Method 3): Rt 4.70 min, m/z 534/536 [MH$^+$].

d. 1-(5-tert-Butyl-2-{3-[2-(tetrahydro-pyran-2-yloxy)-ethoxy]-phenyl}-2-pyrazol-3-yl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea (Intermediate 95d).

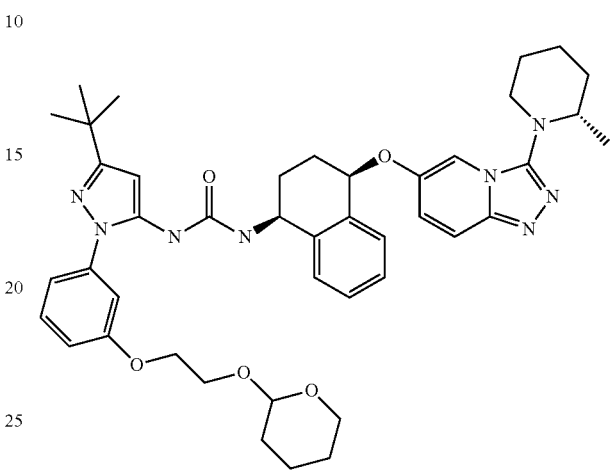

A mixture of intermediate 95c (200 mg, 0.37 mmol), intermediate 81d (141 mg, 0.37 mmol) and DIPEA (98 µL, 0.56 mmol) in dioxane (1.5 mL) was heated at 70° C. for 20 h. The reaction mixture was cooled to RT, diluted with DCM (5 mL) and washed with water (2×5 mL). The organic layer was passed through a hydrophobic frit and concentrated in vacuo. The residue was purified by FCC, using 0-10% (2M NH$_3$ in MeOH) in DCM to afford the title compound as a yellow glass (158 mg, 55%). LCMS (Method 3): Rt 4.25 min, m/z 763 [MH$^+$].

e. 1-{5-tert-Butyl-2-[3-(2-hydroxy-ethoxy)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea (Intermediate 95e).

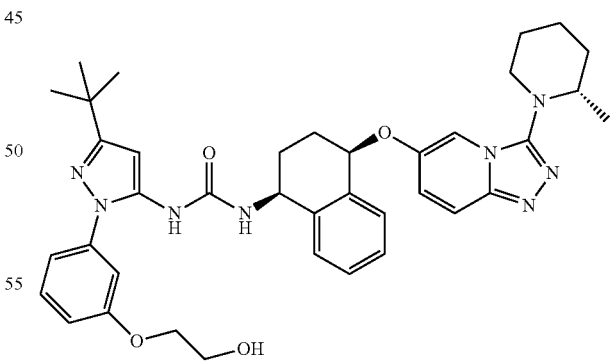

A mixture of intermediate 95d (158 mg, 0.21 mmol) and pyridinium p-toluene sulfonate (156 mg, 0.62 mmol) in methanol was heated at 45° C. for 18 h. The mixture was cooled to RT and was partitioned between DCM (5 mL) and saturated aqueous NaHCO$_3$ (5 mL). The layers were separated and the organic layer was passed through a hydrophobic frit and concentrated in vacuo. The residue was purified by FCC, using 0-10% (2M NH$_3$ in MeOH) in DCM to afford the title compound as a beige solid (105 mg, 74%). LCMS (Method 3): Rt 3.64 min, m/z 679 [MH⁺].

f. 1-{5-tert-Butyl-2-[3-(2-dimethylamino-ethoxy)-phenyl]-2H-pyrazol-3-yl-3-{(1S,4R)-4-[3-((S)-2-methyl-piperidin-1-yl)-[1,2,4]triazolo[4,3-a]pyridin-6-yloxy]-1,2,3,4-tetrahydronaphthalen-1-yl]-urea (Example 95).

To a solution of intermediate 95e (105 mg, 0.15 mmol) and DIPEA (81 μL, 0.46 mmol) in DCM (2 mL) was added methanesulfonyl chloride (16 μL, 0.20 mmol). The reaction mixture was stirred at RT for 30 min. The mixture was diluted with DCM (5 mL) and washed with water (2×5 mL). The organic layer was passed through a hydrophobic frit and concentrated in vacuo. The residue was taken up in THF (2 mL) and dimethylamine solution in THF (2M, 1.55 mL) was added. The reaction mixture was heated at 60° C. in a sealed tube for 20 h. The reaction mixture was cooled to RT and concentrated in vacuo. The residue was triturated with Et₂O (1 mL) and the solid obtained was purified by MDAP to afford the title compound as a glassy solid (44 mg, 40%). LCMS (Method 5): Rt 3.64 min, m/z 706.6 [MH⁺]. ¹H NMR (400 MHz, d₆-DMSO): 0.91 (3H, d, J 6.7 Hz), 1.28 (9H, s), 1.46-1.54 (2H, m), 1.63-1.72 (2H, m), 1.75-1.76 (4H, m), 2.00-2.18 (2H, m), 2.22 (6H, s), 2.66 (2H, t, J 5.8 Hz), 2.85-2.95 (1H, m), 3.12-3.20 (1H, m, obscured by water), 3.27-3.35 (1H, m, obscured by water), 4.10 (2H, t, J 5.4 Hz), 4.78-4.86 (1H, m), 5.52 (1H, t, J 4.0 Hz), 6.33 (1H, s), 6.95-6.99 (1H, m), 7.06-7.14 (3H, m), 7.19 (1H, dd, J 10.0 Hz), 7.25-7.43 (5H, m), 7.64 (1H, d, J 10.6 Hz), 7.69 (1H, d, J 1.8 Hz), 8.12 (1H, s).

Example 96

1-{5-tert-Butyl-2-[3-(2-dimethylamino-ethoxy)-phenyl]-2H-pyrazol-3-yl}-3-{(1S,4R)-4-[3-(cis-2,6-dimethyl-piperidin-1-yl)-[1,2,4]triazolo[4,3-a]pyridin-6-yloxy]-1,2,3,4-tetrahydro-naphthalen-1-yl}-urea formate salt

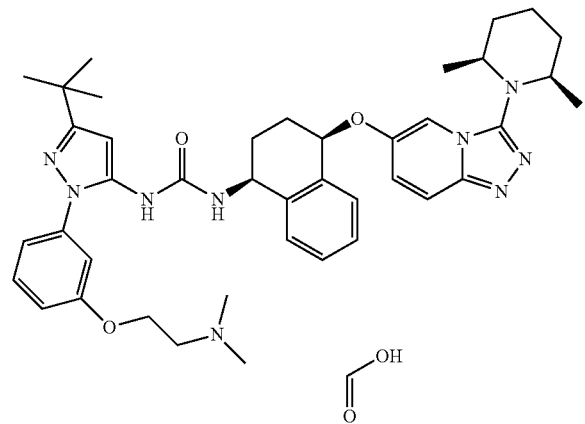 [SMILES: C[C@@H]1CCC[C@H](C)N1c1nnc2ccc(O[C@@H]3CC[C@H](NC(=O)Nc4cc(C(C)(C)C)nn4-c4cccc(OCCN(C)C)c4)c4ccccc43)cn12 ; O=CO]

a. cis-2,6-Dimethyl-piperidine-1-carboxylic acid N'-(5-fluoro-pyridin-2-yl)-hydrazide (Intermediate 96a).

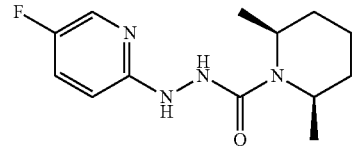 [SMILES: C[C@@H]1CCC[C@H](C)N1C(=O)NNc1ccc(F)cn1]

Pyridine (2.40 mL, 29.7 mmol) was added dropwise to an ice cold suspension of triphosgene (4.42 g, 14.9 mmol) in DCM (30.0 mL). cis-2,6-Dimethylpiperidine (2.00 mL, 14.9 mmol) was added and the reaction stirred for 3 hours, then quenched by dropwise addition of HCl (1M aqueous, 30 mL). The mixture was extracted into DCM (3×). The combined organic layers were washed with brine, dried (MgSO₄), filtered and evaporated in vacuo. The product was used in the next reaction without purification. cis-2,6-Dimethylpiperidine-carbamoylchloride (1.79 g, 10.2 mmol) was dissolved in DCM (90.0 mL) and DIPEA (2.42 mL, 13.9 mmol) was added followed by (5-fluoro-pyridin-2-yl)-hydrazine (WO 2010 022076, which is incorporated herein by reference in its entirety, 1.18 g, 9.30 mmol) and the reaction heated to 45° C. overnight. The reaction was cooled and quenched into water. The mixture was extracted into DCM (3×). The combined organic layers were washed with brine, dried (MgSO₄), filtered and evaporated in vacuo. The residue was purified by FCC using 0-6% [2M NH₃ in MeOH] in DCM to give the title compound (1.38 g, 56%). ¹H NMR (300 MHz, CDCl₃): 1.29 (6H, d, J 7.1 Hz), 1.48-1.90 (6H m), 4.26 (2H, qn, J 6.9 Hz), 6.39 (1H, d, J 2.3 Hz), 6.50 (1H, d, J 2.3 Hz), 6.74 (1H, dd, J 9.0, 3.6 Hz), 7.27 (1H, ddd, J 8.9, 8.0, 2.9 Hz), 8.03 (1H, d, J 2.9 Hz).

b. 3-(cis-2,6-Dimethyl-piperidin-1-yl)-6-fluoro-[1,2,4]triazolo[4,3-a]pyridine (Intermediate 96b).

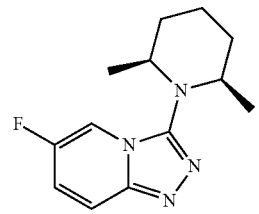 [SMILES: C[C@@H]1CCC[C@H](C)N1c1nnc2ccc(F)cn12]

To an ice cold solution of Intermediate 96a (1.38 g, 5.19 mmol) in THF (50.0 mL) was added sequentially triphenylphosphine (2.72 g, 10.4 mmol), Et₃N (2.89 mL, 20.8 mmol) and hexachloroethane (2.46 g, 10.4 mmol). The cooling bath was removed and the reaction was heated to 55° C. overnight. The reaction was cooled and partitioned between EtOAc and water. The aqueous layer was then extracted with EtOAc (3×). The combined organic layers were washed with brine, dried (MgSO₄), filtered and evaporated in vacuo. The residue was taken up in MeOH and loaded onto an SCX-2 cartridge, which was washed with MeOH and eluted with 2M NH₃ in MeOH. The residue was concentrated in vacuo then resubmitted to the reaction conditions overnight. After analogous workup the residue was concentrated in vacuo to give the title compound (1.03 g, 80%). ¹H NMR (300 MHz, CDCl₃): 0.68 (6H, d, J 6.2 Hz), 1.36-1.68 (3H m), 1.74-1.90 (3H, m), 3.35 (2H, m), 7.14 (1H, ddd, J 9.8, 7.5, 2.3 Hz), 7.65 (1H, ddd, J 9.9, 4.7, 0.8 Hz), 8.02 (1H, ddd, J 3.2, 2.3, 0.8 Hz).

c. (1S,4R)-4-[3-(cis-2,6-Dimethyl-piperidin-1-yl)-[1,2,4]triazolo[4,3-a]pyridin-6-yloxy]-1,2,3,4-tetrahydro-naphthalen-1-ylamine (Intermediate 96c).

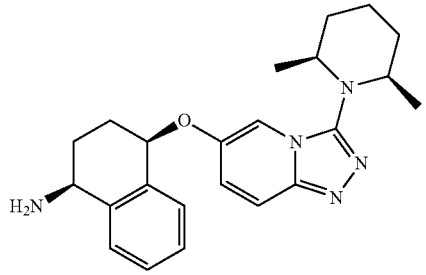 [SMILES: C[C@@H]1CCC[C@H](C)N1c1nnc2ccc(O[C@@H]3CC[C@H](N)c4ccccc43)cn12]

To a suspension of sodium hydride (60% in mineral oil, 323 mg, 8.06 mmol) in DMF (10.0 mL) was added (1R,4S)-4-amino-1,2,3,4-tetrahydro-naphthalen-1-ol (329 mg, 2.02 mmol) and the reaction stirred for 20 min. Intermediate 96b (500 mg, 2.02 mmol) was added in DMF (2.00 mL) and the reaction heated to 60° C. for 1 h. The reaction was cooled and quenched by dropwise addition of methanol, before being diluted with methanol and loaded onto an SCX-2 cartridge, which was washed with MeOH. The product was eluted with 2M NH₃ in MeOH. The residue was purified by FCC, using 0-10% (2M NH₃ in MeOH) in DCM, to give the title compound (453 mg, 57%). LCMS (Method 4): Rt 2.13, m/z 392 [MH⁺].

d. 1-(5-tert-Butyl-2-{3-[2-(tetrahydro-pyran-2-yloxy)-ethoxy]-phenyl}-2H-pyrazol-3-yl)-3-{(1S,4R)-4-[3-(cis-2,6-dimethyl-piperidin-1-yl)-[1,2,4]triazolo[4,3-a]pyridin-6-yloxy]-1,2,3,4-tetrahydro-naphthalen-1-yl}-urea (Intermediate 96d).

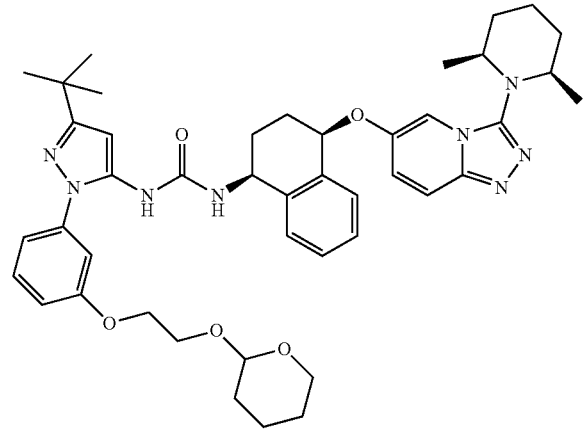 [SMILES: C[C@@H]1CCC[C@H](C)N1c1nnc2ccc(O[C@@H]3CC[C@H](NC(=O)Nc4cc(C(C)(C)C)nn4-c4cccc(OCCOC5CCCCO5)c4)c4ccccc43)cn12]

To a solution of Intermediate 96c (100 mg, 0.25 mmol) in 1,4-dioxane (3.00 mL) was added DIPEA (89.0 μL, 0.51 mmol) and Intermediate 39b (133 mg, 0.25 mmol). The reaction was heated to 70° C. overnight then cooled and partitioned between EtOAc and water. The aqueous layer was then extracted with EtOAc (3×). The combined organic layers were washed with brine, dried (MgSO₄), filtered and evaporated in vacuo. The residue was purified by FCC using 0-8% MeOH in DCM to give the title compound. LCMS (Method 4): Rt 4.09 min, m/z 777 [MH⁺].

e. 1-{5-tert-Butyl-2-[3-(2-hydroxy-ethoxy)-phenyl]-2H-pyrazol-3-yl}-3-{(1S,4R)-4-[3-(cis-2,6-dimethyl-piperidin-1-yl)-[1,2,4]triazolo[4,3-a]pyridin-6-yloxy]-1,2,3,4-tetrahydro-naphthalen-1-yl}-urea (Intermediate 96e).

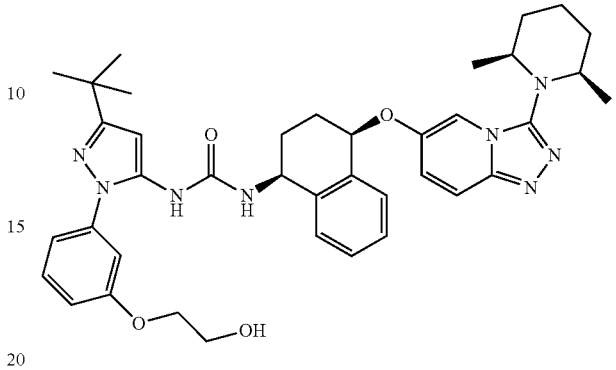

Pyridinium p-toluenesulfonate (65.0 mg, 0.26 mmol) was added to a solution of Intermediate 96d in MeOH (2.0 mL). The reaction was heated to 60° C. for 3.5 h then cooled and solvent volume reduced in vacuo. The residue was partitioned between EtOAc and water. The aqueous layer was then extracted with EtOAc (3×). The combined organic layers were washed with brine, dried (MgSO₄), filtered and evaporated in vacuo to give the title compound (89.0 mg, 99%). LCMS (Method 4): Rt 3.49 min, m/z 693 [MH⁺].

f. Methanesulfonic acid 2-{3-[3-tert-butyl-5-(3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-ureido)-pyrazol-1-yl]-phenoxy}-ethyl ester (Intermediate 96f).

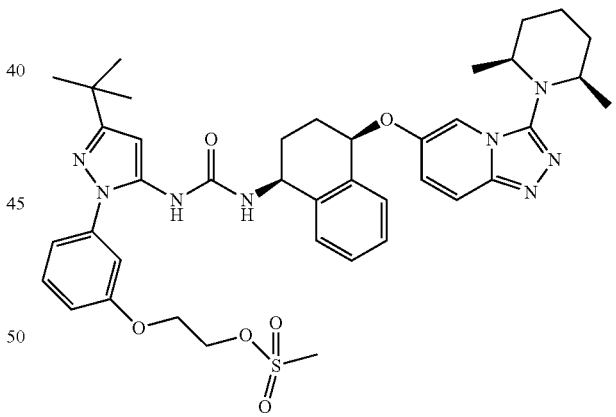

Methane sulfonylchloride (11.0 μL, 0.13 mmol) was added to an ice cold solution of Intermediate 96e (89.0 mg, 0.13 mmol) and DIPEA (27.0 μL, 0.15 mmol) in DCM (1.5 mL). After 1 hour additional DIPEA (27.0 μL, 0.15 mmol) and methane sulfonylchloride (11.0 μL, 0.13 mmol) was added. After a further 1 hour additional DIPEA (27.0 μL, 0.15 mmol) and methane sulfonylchloride (11.0 μL, 0.13 mmol) was added. After 1 hour the reaction was partitioned between DCM and water. The aqueous layer was then extracted with DCM (3×). The combined organic layers were washed with brine, dried (MgSO₄), filtered and evaporated in vacuo to give the title compound (100 mg, 99%). LCMS (Method 1): Rt 3.73 min, m/z 771 [MH⁺].

g. 1-{5-tert-Butyl-2-[3-(2-dimethylamino-ethoxy)-phenyl]-2H-pyrazol-3-yl}-3-{(1S,4R)-4-[3-(cis-2,6-dimethyl-piperidin-1-yl)-[1,2,4]triazolo[4,3-a]pyridin-6-yloxy]-1,2,3,4-tetrahydro-naphthalen-1-yl}-urea formate salt (Example 96).

Dimethylamine (2M in MeOH, 520 µL, 1.04 mmol) was added to a solution of Intermediate 96f (100 mg, 0.13 mmol) in THF (1.5 mL). The reaction was heated to 50° C. in a sealed environment overnight. The mixture was cooled and partitioned between EtOAc and water. The aqueous layer was then extracted with EtOAc (3×). The combined organic layers were washed with brine, dried (MgSO₄), filtered and evaporated in vacuo. The residue was purified by FCC, using 0-10% [2M NH₃ in MeOH] in DCM. Further purification by HPLC (C18 X-select column, 10-98% MeCN in H₂O, 0.1% HCO₂H) gave the title compound as a white powder after freeze-drying (50 mg, 54%). LCMS (Method 5): Rt 3.79 min, m/z 720.5 [MH⁺]. ¹H NMR (400 MHz, d₄-MeOD): 0.65 (3H, d, J 6.0 Hz), 0.68 (3H, d, J 6.0 Hz), 1.31 (9H, s), 1.40-1.50 (2H, m), 1.53-1.65 (1H, m), 1.73-1.87 (3H, m), 1.92-2.05 (2H, m), 2.05-2.15 (1H, m), 2.19-2.26 (1H, m), 2.43 (6H, s), 2.92 (2H, t, J 5.2 Hz), 3.24 (2H, m), 4.18 (2H, t, J 5.3 Hz), 4.90 (1H, dd, J 8.7, 5.8), 5.42 (1H, t, J 8.2), 6.34 (1H, s), 7.02-7.06 (1H, ddd, J 8.5, 2.4, 0.6), 7.08-7.13 (2H, m), 7.17-7.25 (3H, m), 7.26-7.31 (2H, m), 7.38-7.44 (1H, t, J 7.8), 7.56-7.60 (1H, dd, J 9.8, 0.7 Hz), 7.86 (1H, d, J 1.8 Hz), 8.45 (0.3H, br s).

Example 97

1-[5-tert-Butyl-2-(3-morpholin-4-ylmethyl-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

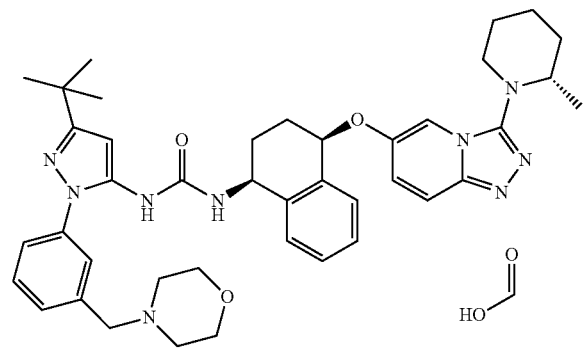 [SMILES: C[C@H]1CCCCN1c1nnc2ccc(O[C@@H]3CC[C@H](NC(=O)Nc4cc(C(C)(C)C)nn4-c4cccc(CN5CCOCC5)c4)c4ccccc43)cn12 ; O=CO]

a. 1-[5-tert-Butyl-2-(3-hydroxymethyl-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea (Intermediate 97a).

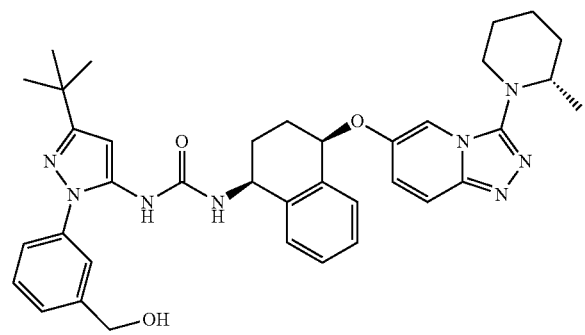 [SMILES: C[C@H]1CCCCN1c1nnc2ccc(O[C@@H]3CC[C@H](NC(=O)Nc4cc(C(C)(C)C)nn4-c4cccc(CO)c4)c4ccccc43)cn12]

A brown solution of Intermediate 29c (177 mg, 0.420 mmol), Intermediate 81d (151 mg, 0.400 mmol) and DIPEA (0.087 mL, 0.50 mmol) in dry dioxane (5 mL) was stirred at 100° C. for 3 h. The cooled solution was concentrated in vacuo, suspended in water (10 mL) and extracted with DCM (2×10 mL). The combined organics were passed through a hydrophobic frit and concentrated under vacuum to leave a dark brown gum. FCC, using 3-8% MeOH in DCM, gave the title compound as an orange solid (188 mg, 72%). LCMS (Method 4): Rt 3.63 min, m/z 649 [MH⁺].

b. Methanesulfonic acid 3-[3-tert-butyl-5-(3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-ureido)-pyrazol-1-yl]benzyl ester and 1-[5-tert-Butyl-2-(3-chloromethyl-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea (1:1 mixture) (Intermediate Mixture 97b).

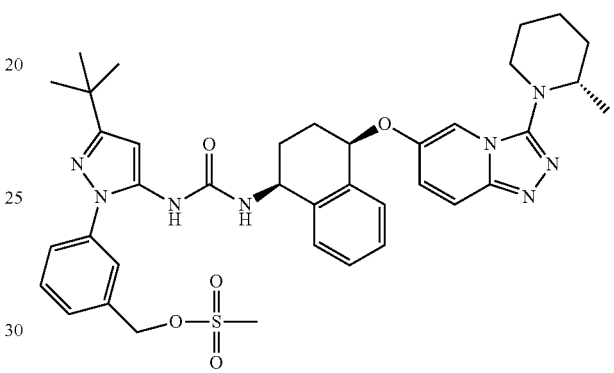

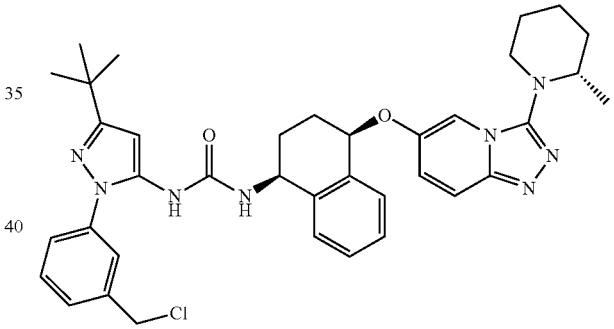

To a solution of Intermediate 97a (187 mg, 0.288 mmol) and DIPEA (0.151 mL, 0.865 mmol) in DCM (5 mL) at 0° C. was added mesyl chloride (0.056 mL, 0.721 mmol) and the resulting orange solution stirred at 0° C. for 1 h. Water (5 mL) was added and the mixture shaken. The aqueous layer was extracted with DCM (5 mL), then the combined organics passed through a hydrophobic fit and concentrated in vacuo to leave the mixture of title compounds as a brown gum. LCMS (Method 4): 1:1 ratio, Rt 3.87 min, m/z 727 [MH⁺] and Rt 4.11, m/z 667 [MH⁺].

c. 1-[5-tert-Butyl-2-(3-morpholin-4-ylmethyl-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt (Example 97).

A brown solution of Intermediate mixture 97b (0.144 mmol) and morpholine (0.063 mL, 0.72 mmol) in dry DMF (3 mL) was stirred at 75° C. for 2 h. The cooled solution was concentrated in vacuo, suspended in water (10 mL) and extracted with DCM (2×10 mL). The combined organics were passed through a hydrophobic fit and concentrated in vacuo to leave a brown gum. FCC, 3-7% MeOH in DCM, gave a pale yellow solid (58.6 mg). MDAP (Method 7) gave the title compound as a pale yellow solid (31 mg, 28%).

LCMS (Method 5): Rt 3.59 min, m/z 718.6 [MH⁺]. ¹H NMR (400 MHz, d₆-DMSO): 0.91 (3H, d, J 6.3), 1.28 (9H, s), 1.48-1.55 (2H, m), 1.63-1.71 (2H, m), 1.75-1.97 (4H, m), 2.00-2.16 (2H, m), 2.37 (4H, t, J 4.2), 2.90 (1H, ddd, J 12.2, 9.0, 4.0), 3.15 (1H, dt, J 12.0, 4.2), 3.51 (2H, s), 3.55 (4H, t, J 4.4), 4.82 (1H, td, J 8.6, 5.6), 5.51 (1H, t, J 4.3), 6.33 (1H, s), 7.04 (1H, d, J 8.6), 7.19 (1H, dd, J 9.9, 2.2), 7.25-7.29 (2H, m), 7.31-7.48 (6H), 7.64 (1H, dd, J 9.8, 0.8), 7.69 (1H, d, J 2.1), 8.10 (1H, s), 8.16 (1H, s). One 1H signal under solvent peak.

Example 98

1-{5-tert-Butyl-2-[3-(4-methyl-piperazin-1-ylmethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

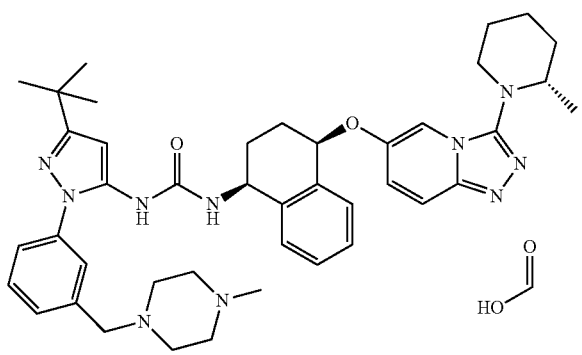 [SMILES: C[C@H]1CCCCN1c1nnc2ccc(O[C@@H]3CC[C@H](NC(=O)Nc4cc(C(C)(C)C)nn4-c4cccc(CN5CCN(C)CC5)c4)c4ccccc43)cn12 ; O=CO]

The title compound was prepared starting from N-methyl piperazine using analogous procedures to those described in Example 97. LCMS (Method 5): Rt 3.61 min, m/z 731.6 [MH⁺]. ¹H NMR (400 MHz, d₆-DMSO): 0.91 (3H, d, J 6.3), 1.28 (9H, s), 1.48-1.56 (2H, m), 1.63-1.71 (2H, m), 1.75-1.96 (4H, m), 2.00-2.16 (2H, m), 2.12 (3H, s), 2.26-2.43 (8H, m), 2.90 (1H, ddd, J 11.8, 9.2, 4.2), 3.16 (1H, dt, J 12.0, 4.2), 3.28-3.34 (1H, m), 3.50 (2H, s), 4.82 (1H, td, J 8.6, 5.5), 5.52 (1H, t, J 4.3), 6.33 (1H, s), 7.04 (1H, d, J 8.6), 7.19 (1H, dd, J 9.9, 2.2), 7.25-7.47 (8H, m), 7.64 (1H, dd, J 9.8, 0.8), 7.69 (1H, d, J 2.1), 8.11 (1H, s), 8.18 (1H, s).

Example 99

1-(5-tert-Butyl-2-p-tolyl-2H-pyrazol-3-yl)-3-{(1S,4R)-4-[3-(1-dimethylamino-cyclopentyl)-[1,2,4]triazolo[4,3-a]pyridin-6-yloxy]-1,2,3,4-tetrahydro-naphthalen-1-yl}-urea

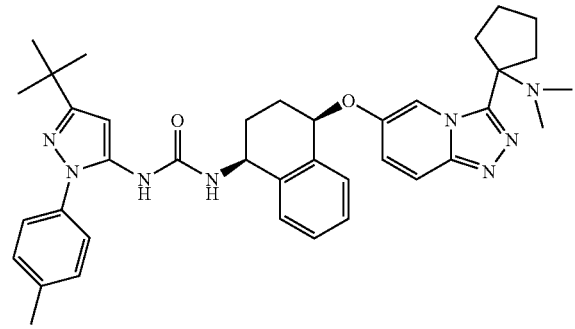 [SMILES: Cc1ccc(-n2nc(C(C)(C)C)cc2NC(=O)N[C@H]2CC[C@@H](Oc3ccc4nnc(C5(N(C)C)CCCC5)n4c3)c3ccccc32)cc1]

a. 1-Dimethylamino-cyclopentanecarboxylic acid (Intermediate 99a).

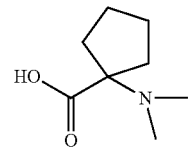

A solution of 1-amino-cyclopentanecarboxylic acid (2.0 g, 15.5 mmol) and formaldehyde (37% aqueous solution, 3 mL) in formic acid (4 mL) was heated at 80° C. for 2.5 h. The volatiles were concentrated in vacuo and the resulting residue was loaded onto an SCX cartridge. The cartridge was washed with MeOH and the product eluted with 2M NH₃ in MeOH to afford the title compound (1.82 g, 75%). ¹H NMR (400 MHz, CD₃OD): 1.71-2.02 (6H, m), 2.16-2.29 (2H, m), 2.77 (6H, s).

b. 1-Dimethylamino-cyclopentanecarboxylic acid N'-(5-fluoro-pyridin-2-yl)-hydrazide (Intermediate 99b).

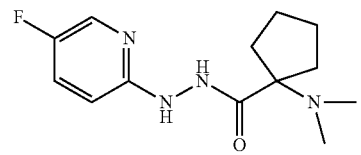 [SMILES: CN(C)C1(C(=O)NNc2ccc(F)cn2)CCCC1]

To a solution of (5-fluoro-pyridin-2-yl)-hydrazine (for reference procedure see WO 2010/022076, which is incorporated herein by reference in its entirety; 200 mg, 1.57 mmol) in DMF (10 mL) were added Intermediate 99a (247 mg, 1.57 mmol), EDC (333 mg, 1.73 mmol) and HOBt (21 mg, 0.16 mmol). The reaction mixture was stirred at RT for 18 h and then partitioned between EtOAc and water. The aqueous phase was further extracted with EtOAc (×3) and the combined organic layers were washed with brine, dried (MgSO₄) and concentrated in vacuo. The resultant residue was purified by FCC on silica, using a gradient of 0-8% (2M NH₃ in MeOH) in DCM, to give the title compound (282 mg, 67%). ¹H NMR (400 MHz, CDCl₃): 1.54-1.73 (4H, m), 1.76-2.04 (4H, m), 2.25 (6H, s), 6.46 (1H, s), 6.64 (1H, dd, J=9.0, 3.5 Hz), 7.23-7.33 (1H, m), 8.04 (1H, d, J=3.0 Hz), 8.94 (1H, s).

c. [1-(6-Fluoro-[1,2,4]triazolo[4,3-a]pyridin-3-yl)-cyclopentyl]-dimethyl-amine (Intermediate 99c).

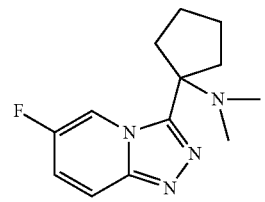 [SMILES: CN(C)C1(c2nnc3ccc(F)cn23)CCCC1]

Hexachloroethane (503 mg, 2.12 mmol) was added portionwise over 5 minutes at RT to a stirred mixture of Intermediate 99b (282 mg, 1.06 mmol), triethylamine (5904, 4.24 mmol) and triphenylphosphine (555 mg, 2.12 mmol) in THF (11 mL). The reaction mixture was stirred at 50° C. for 2.5 h and then partitioned between EtOAc and water. The aqueous phase was extracted with EtOAc (×3) and the combined organic layers were washed with brine, dried (MgSO₄) and concentrated in vacuo. The resultant residue was purified by FCC using SCX-2 cartridge. The cartridge was washed with MeOH and the product was eluted with 2M $NH_3$ in MeOH to give the title compound (207 mg, 79%). $^1$H NMR (400 MHz, $CDCl_3$): 1.67-1.78 (4H, m), 2.10-2.22 (8H, m), 2.24-2.34 (2H, m), 7.15 (1H, ddd, J=10.0, 7.4, 2.3 Hz), 7.69 (1H, dd, J=10.0, 5.0 Hz), 8.65-8.68 (1H, m).

d. (1S,4R)-4-[3-(1-Dimethylamino-cyclopentyl)-[1,2,4]triazolo[4,3-a]pyridin-6-yloxy]-1,2,3,4-tetrahydro-naphthalen-1-ylamine (Intermediate 99d).

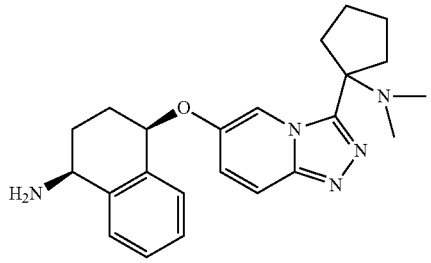 [SMILES: CN(C)C1(c2nnc3ccc(O[C@@H]4CC[C@H](N)c5ccccc54)cn23)CCCC1]

To a suspension of sodium hydride (60% in mineral oil, 133 mg, 3.34 mmol) in DMF (5 mL) was added Intermediate A (136 mg, 0.83 mmol) and the reaction mixture was stirred for 20 min. A solution of Intermediate 99c (207 mg, 0.83 mmol) in DMF (3 mL) was added and the reaction mixture was heated at 60° C. for 90 min. After cooling, the reaction mixture was quenched by careful addition of MeOH and then loaded onto an SCX cartridge. The cartridge was washed with MeOH and the product eluted with 2M $NH_3$ in MeOH. The product containing fractions were concentrated in vacuo and the resultant residue was purified by FCC on silica, using a gradient of 0-10% (2M $NH_3$ in MeOH) in DCM, to give the title compound (211 mg, 65%). LCMS (Method 4): Rt 1.49 min, m/z 392 [MH$^+$].

e. 1-(5-tert-Butyl-2-p-tolyl-2H-pyrazol-3-yl)-3-{(1S,4R)-4-[3-(1-dimethylamino-cyclopentyl)-[1,2,4]triazolo[4,3-a]pyridin-6-yloxy]-1,2,3,4-tetrahydro-naphthalen-1-yl}-urea (Example 99).

A mixture of Intermediate 99d (108 mg, 0.27 mmol), (5-tert-butyl-2-p-tolyl-2H-pyrazol-3-yl)-carbamic acid 2,2,2-trichloro-ethyl ester (for reference procedure see Synthetic Communications, 2009, 39, 3999-4009, which is incorporated herein by reference in its entirety; 105 mg, 0.27 mmol) and DIPEA (93 µL, 0.54 mmol) in dioxane (3 mL) was stirred at 60° C. for 18 h and then at 80° C. for 4 h. The reaction mixture was diluted with EtOAc and then poured into water. The aqueous phase was extracted with EtOAc (×3) and the combined organic layers were washed with brine, dried ($MgSO_4$) and concentrated in vacuo. The resultant residue was purified by MDAP (Method 7) to afford the title compound (23 mg, 13%). LCMS (Method 5): Rt 3.90 min, m/z 647 [MH$^+$]. $^1$H NMR (400 MHz, $CD_3OD$): 1.34 (9H, s), 1.59-1.85 (4H, m), 1.91-2.15 (3H, m), 2.18 (6H, s), 2.21-2.36 (5H, m), 2.42 (3H, s), 4.91-4.96 (1H, m), 5.34 (1H, t, J=4.1 Hz), 6.37 (1H, s), 7.22-7.40 (9H, m), 7.65 (1H, d, J=9.9 Hz), 8.46 (1H, d, J=2.2 Hz).

Example 100

1-(5-tert-Butyl-2-p-tolyl-2H-pyrazol-3-yl)-3-{(1S, 4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea

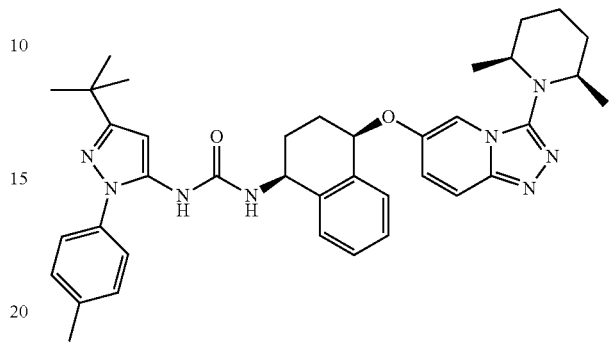

The title compound was prepared starting from Intermediate 96c and (5-tert-butyl-2-p-tolyl-2H-pyrazol-3-yl)-carbamic acid 2,2,2-trichloro-ethyl ester (for reference procedure see Synthetic Communications, 2009, 39, 3999-4009, which is incorporated herein by reference in its entirety) using analogous procedures to those described in Example 3. LCMS (Method 5): Rt 5.33 min, m/z 647 [MH$^+$]. $^1$H NMR (400 MHz, $CD_3OD$): 0.64-0.74 (6H, m), 1.34 (9H, s), 1.41-1.72 (3H, m), 1.75-2.19 (6H, m), 2.21-2.31 (1H, m), 2.42 (3H, s), 3.22-3.35 (2H, m), 4.90-4.98 (1H, m), 5.45 (1H, t, J=4.1 Hz), 6.37 (1H, s), 7.19-7.40 (9H, m), 7.62 (1H, dd, J=9.9, 0.8 Hz), 7.89 (1H, d, J=2.1 Hz).

Example 101

1-[(1S,4R)-4-(3-Amino-[1,2,4]triazolo[4,3-a]pyridin-6-yloxy)-1,2,3,4-tetrahydro-naphthalen-1-yl]-3-(5-tert-butyl-2-p-tolyl-2H-pyrazol-3-yl)-urea

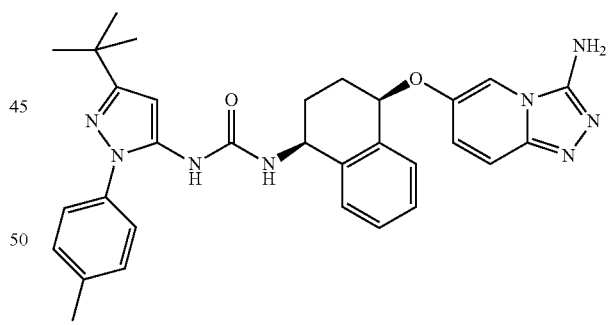

a. 2-(5-Fluoropyridin-2-yl)-N,N-di(prop-2-en-1-yl)hydrazinecarboxamide (Intermediate 101a).

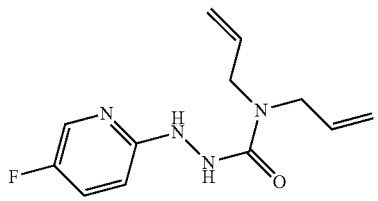 [SMILES: C=CCN(CC=C)C(=O)NNc1ccc(F)cn1]

To a solution of (5-fluoro-pyridin-2-yl)-hydrazine (for reference procedure see WO 2010/022076, which is incorporated herein by reference in its entirety; 2.54 g, 20.0 mmol) in DCM (150 mL) and DIPEA (3.87 g, 30.0 mmol) was added N,N-di-2-propen-1-yl-carbamic chloride (for reference procedure see for example Tetrahedron 1996, 52, 13739-13750, which is incorporated herein by reference in its entirety; 4.13 g, 26.0 mmol) and the reaction mixture was stirred at RT for 18 h. The reaction mixture was diluted with MeOH (50 mL) and loaded onto an SCX cartridge. The cartridge was washed with MeOH and the product eluted with 2M $NH_3$ in MeOH. The compound containing fractions were concentrated in vacuo and the resulting residue was purified by FCC on silica, using a gradient of 0-6% [2M $NH_3$ in MeOH] in DCM, to afford the title compound (2.30 g, 46%) as a yellow solid. LCMS (Method 1): Rt 2.26 min, m/z 251 [MH$^+$].

b. Diallyl-(6-fluoro-[1,2,4]triazolo[4,3-a]pyridin-3-yl)-amine (Intermediate 101b).

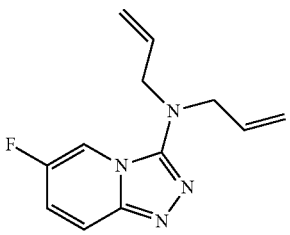 [SMILES: C=CCN(CC=C)c1nnc2ccc(F)cn12]

Hexachloroethane (4.34 g, 18.4 mmol) was added portionwise over 5 min at RT to a stirred mixture of Intermediate 101a (2.30 g, 9.2 mmol), triethylamine (3.71 g, 36.8 mmol) and triphenylphosphine (4.82 g, 18.4 mmol) in THF (90 mL). The reaction mixture was stirred at RT for 1 h, then diluted with MeOH and purified by FCC using SCX-2 cartridge. The cartridge was washed with MeOH and the product was eluted with 2M $NH_3$ in MeOH. The compound containing fractions were combined and concentrated in vacuo. The resultant residue was subjected to the follow purification procedure; FCC on silica (0-6% [2M $NH_3$ in MeOH] in DCM), then SCX-2 cartridge (conditions described above) and finally further FCC on silica (0-2% MeOH in EtOAc), to afford the title compound (1.34 g, 62%). $^1$H NMR (400 MHz, CDCl$_3$): 3.87 (4H, d, J=6.2 Hz), 5.16-5.35 (4H, m), 5.85-6.02 (2H, m), 7.11 (1H, ddd, J=10.0, 7.6, 2.3 Hz), 7.58-7.67 (1H, m), 7.75-7.80 (1H, m).

c. [6-((1R,4S)-4-Amino-1,2,3,4-tetrahydro-naphthalen-1-yloxy)-[1,2,4]triazolo[4,3-a]pyridin-3-yl]-bis-((E)-propenyl)-amine (Intermediate 101c).

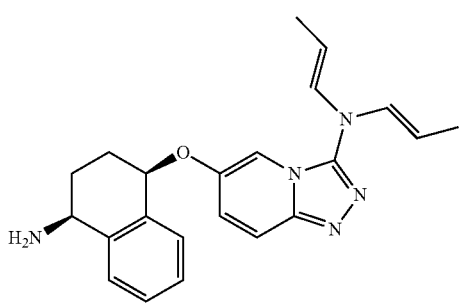 [SMILES: C/C=C/N(/C=C/C)c1nnc2ccc(O[C@@H]3CC[C@H](N)c4ccccc43)cn12]

To a suspension of sodium hydride (40% in mineral oil, 690 mg, 17.31 mmol) in DMF (20 mL) was added Intermediate A (1.12 g, 6.92 mmol) and the reaction mixture was stirred for 20 min at RT. A solution of Intermediate 101b (1.34 g, 5.77 mmol) in DMF (20 mL) was added and the reaction mixture was stirred at RT for 1 h. The reaction mixture was quenched by careful addition of MeOH and then loaded onto an SCX cartridge. The cartridge was washed with MeOH and the product eluted with 2M $NH_3$ in MeOH. The product containing fractions were concentrated in vacuo and the resultant residue was purified by FCC on silica, using a gradient of 0-10% [2M $NH_3$ in MeOH] in DCM, to give the title compound (1.33 g, 61%) as an orange gum. $^1$H NMR (400 MHz, CDCl$_3$): 0.92-1.13 (1H, m), 1.39 (6H, dd, J=7.2, 1.7 Hz), 1.82-2.16 (4H, m), 2.26-2.38 (1H, m), 3.93-3.99 (1H, m), 4.99-5.10 (2H, m), 5.18 (1H, t, J=4.4 Hz), 6.10 (2H, dd, J=8.2, 2.0 Hz), 7.09 (1H, dd, J=9.9, 2.2 Hz), 7.25-7.44 (3H, m), 7.48-7.53 (1H, m), 7.57-7.66 (2H, m).

d. 1-[(1S,4R)-4-(3-Amino-[1,2,4]triazolo[4,3-a]pyridin-6-yloxy)-1,2,3,4-tetrahydro-naphthalen-1-yl]-3-(5-tert-butyl-2-p-tolyl-2H-pyrazol-3-yl)-urea (Example 101).

A mixture of Intermediate 101c (1.33 g, 3.54 mmol), (5-tert-butyl-2-p-tolyl-2H-pyrazol-3-yl)-carbamic acid 2,2,2-trichloro-ethyl ester (for reference procedure see Synthetic Communications, 2009, 39, 3999-4009, which is incorporated herein by reference in its entirety; 2.0 g, 4.96 mmol) and DIPEA (1.82, 14.16 mmol) in DMF (20 mL) was stirred at RT for 20 h. The reaction mixture was diluted with MeOH and loaded onto an SCX cartridge. The cartridge was washed with MeOH and the product eluted with 2M $NH_3$ in MeOH. The product containing fractions were concentrated in vacuo and the resultant residue was purified by FCC on silica, using a gradient of 0-10% [2M $NH_3$ in MeOH] in DCM, followed by recrystallization from 5% MeOH in DCM (few drops of cyclohexane added to start recrystallization), to give the title compound (760 mg, 39%) as an off white dust. LCMS (Method 5): Rt 3.81 min, m/z 551 [MH$^+$]. $^1$H NMR (400 MHz, CD$_3$OD): 1.34 (9H, s), 1.86-2.08 (2H, m), 2.09-2.19 (1H, m), 2.22-2.34 (1H, m), 2.42 (3H, s), 4.89-4.96 (1H, m), 5.32 (1H, t, J=4.4 Hz), 6.37 (1H, s), 7.05 (1H, dd, J=10.0, 2.1 Hz), 7.23-7.44 (9H, m), 7.83 (1H, d, J=2.0 Hz).

Example 102

1-[5-tert-Butyl-2-(6-methyl-pyridin-3-yl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea

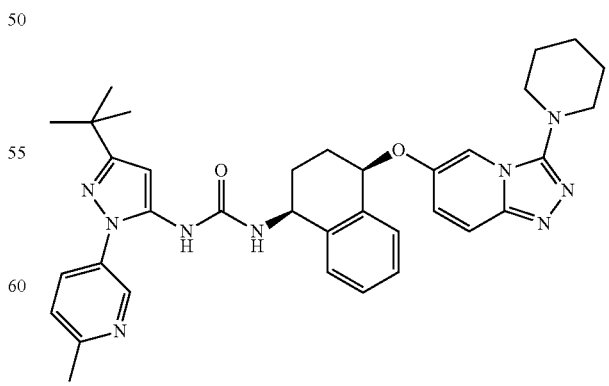

a. [5-tert-Butyl-2-(6-methyl-pyridin-3-yl)-2H-pyrazol-3-yl]-carbamic acid 2,2,2-trichloro-ethyl ester (Intermediate 102a).

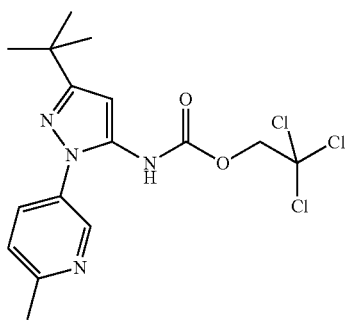 [SMILES: Cc1ccc(-n2nc(C(C)(C)C)cc2NC(=O)OCC(Cl)(Cl)Cl)cn1]

To a mixture of 5-tert-butyl-2-(6-methyl-pyridin-3-yl)-2H-pyrazol-3-ylamine (for reference procedure see for example WO2003072569, which is incorporated herein by reference in its entirety; 833 mg, 3.62 mmol) in NaOH (1M in water, 5.4 mL, 4.4 mmol) and EtOAc (5 mL) was added 2,2,2-trichloroethyl chloroformate (548 μL, 3.98 mmol) and the reaction mixture was stirred at RT for 1 h. Additional NaOH (1M in water, 5.4 mL) and 2,2,2-trichloroethyl chloroformate (548 μL) were added and stirring at RT was continued for 1 h. Additional NaOH (1M in water, 5.4 mL) and 2,2,2-trichloroethyl chloroformate (548 μL) were added and stirring at RT was continued for 2 h. Additional NaOH (1M in water, 10.8 mL) and 2,2,2-trichloroethyl chloroformate (1.10 mL) were added and stirring at RT was continued for 24 h. The aqueous layer was extracted with EtOAc (×3) and the combined organic layers were washed with brine, dried (Na$_2$SO$_4$) and concentrated in vacuo. The resultant residue was purified by FCC on silica, using a gradient of 10-50% EtOAc in cyclohexane, to afford the title compound (550 mg, 37%) as a white foam. LCMS (Method 3): Rt 3.87 min, m/z 405 [MH$^+$].

b. 1-[5-tert-Butyl-2-(6-methyl-pyridin-3-yl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea (Example 102).

A mixture of Intermediate 102a (84 mg, 0.206 mmol), Intermediate 3c (75 mg, 0.206 mmol) and DIPEA (45 μL, 0.258 mmol) in dioxane (3 mL) was stirred at 65° C. for 16 h. After cooling, the volatiles were concentrated in vacuo and the resultant residue was partitioned between water and DCM. The organic layer was dried through a separator phase and concentrated in vacuo. The resultant residue was purified by FCC on silica, using a gradient of 2-7% MeOH in DCM followed by HPLC (XBridge C18 column, 25-75% MeCN in H$_2$O, 0.1% NH$_4$OH), to afford the title compound (41 mg, 32%) as a white solid. LCMS (Method 5): Rt 4.06 min, m/z 620 [MH$^+$]. H NMR (400 MHz, d$_6$-DMSO): 1.27 (9H, s), 1.56-1.66 (2H, m), 1.67-1.77 (4H, m), 1.79-1.96 (2H, m), 1.96-2.20 (2H, m), 2.53 (3H, s), 3.13 (4H, t, J=5.2 Hz), 4.75-4.84 (1H, m), 5.54 (1H, t, J=4.3 Hz), 6.35 (1H, s), 7.06 (1H, d, J=8.6 Hz), 7.16 (1H, dd, J=9.8, 2.2 Hz), 7.23-7.43 (5H, m), 7.58-7.64 (2H, m), 7.81 (1H, dd, J=8.3, 2.6 Hz), 8.18 (1H, s), 8.59 (1H, d, J=2.6 Hz).

Example 103

1-{5-tert-Butyl-2-[3-(2-dimethylamino-ethoxy)-phenyl]-2H-pyrazol-3-yl}-3-[(1S,4R)-4-(3-diisopropylamino-[1,2,4]triazolo[4,3-a]pyridin-6-yloxy)-1,2,3,4-tetrahydro-naphthalen-1-yl]-urea

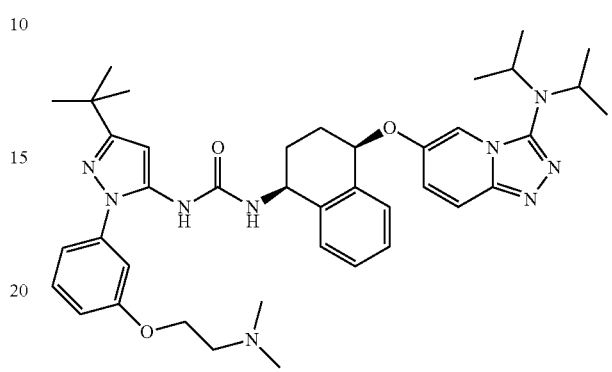

a. 2-(5-Fluoropyridin-2-yl)-N,N-di(propan-2-yl)hydrazinecarboxamide (Intermediate 103a).

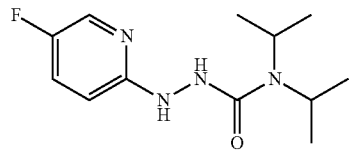 [SMILES: CC(C)N(C(=O)NNc1ccc(F)cn1)C(C)C]

To a solution of (5-fluoro-pyridin-2-yl)-hydrazine (for reference procedure see WO2010022076; 200 mg, 1.57 mmol) in DCM (15 mL) was added triethylamine (328 μL, 2.35 mmol) followed by N,N-diisopropylcarbamoyl chloride (282 mg, 1.73 mmol). The reaction mixture was heated at 45° C. for 4 h then poured into water and extracted with DCM (×3). The combined organic layers were washed with brine, dried (MgSO$_4$) and concentrated in vacuo. The resultant residue was purified by FCC on silica, using a gradient of 0-100% EtOAc in cyclohexane, to afford the title compound (200 mg, 50%). $^1$H NMR (400 MHz, CDCl$_3$): 1.30 (12H, d, J=6.8 Hz), 3.80-4.03 (2H, m), 6.17 (1H, s), 6.53 (1H, s), 6.67-6.81 (1H, m), 7.24-7.36-(1H, m), 8.02 (1H, d, J=3.0 Hz).

b. (6-Fluoro-[1,2,4]triazolo[4,3-a]pyridin-3-yl)-diisopropylamine (Intermediate 103b).

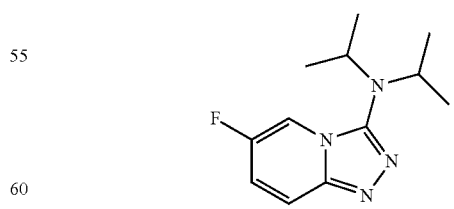

The title compound was prepared starting from Intermediate 103a using analogous procedures to those described in Intermediate 99c. $^1$H NMR (400 MHz, CDCl$_3$): 1.09 (12H, d, J=6.5 Hz), 3.60-3.79 (2H, m), 7.11-7.24 (1H, m), 7.44-7.62 (1H, m), 7.98-8.05 (1H, m).

c. [6-((1R,4S)-4-Amino-1,2,3,4-tetrahydro-naphthalen-1-yloxy)-[1,2,4]triazolo[4,3-a]pyridin-3-yl]-diisopropyl-amine (Intermediate 103c).

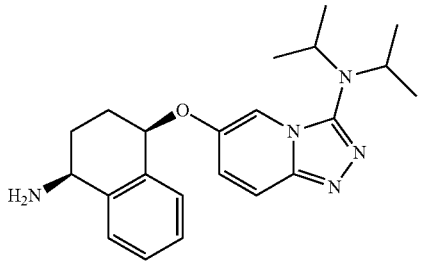 [SMILES: CC(C)N(c1nnc2ccc(O[C@@H]3CC[C@H](N)c4ccccc43)cn12)C(C)C]

To a suspension of sodium hydride (60% in mineral oil, 136 mg, 3.39 mmol) in DMF (5 mL) was added Intermediate A (138 mg, 0.85 mmol) and the reaction mixture was stirred for 15 min at RT. A solution of Intermediate 103b (200 mg, 0.85 mmol) in DMF (3 mL) was added and the reaction mixture was heated at 60° C. for 1 h. The reaction mixture was quenched by careful addition of MeOH and then loaded onto an SCX cartridge. The cartridge was washed with MeOH and the product eluted with 2M NH₃ in MeOH. The product containing fractions were concentrated in vacuo and the resultant residue was purified by FCC on silica, using a gradient of 0-10% [2M NH₃ in MeOH] in DCM, to give the title compound (220 mg, 68%). LCMS (Method 4): Rt 2.07 min, m/z 380 [MH⁺].

d. 1-(5-tert-Butyl-2-{3-[2-(tetrahydro-pyran-2-yloxy)-ethoxy]-phenyl}-2H-pyrazol-3-yl)-3-[(1S,4R)-4-(3-diisopropylamino-[1,2,4]triazolo[4,3-a]pyridin-6-yloxy)-1,2,3,4-tetrahydro-naphthalen-1-yl]-urea (Intermediate 103d).

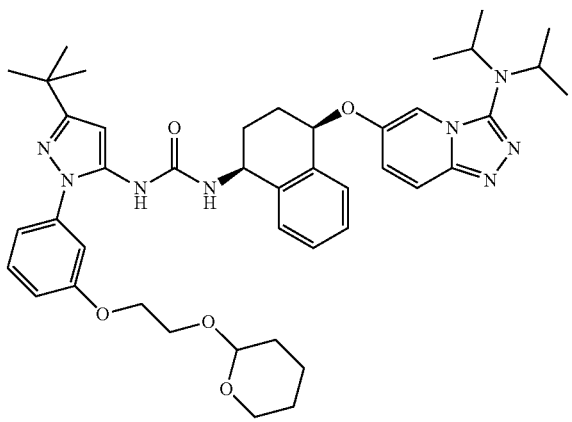 [SMILES: CC(C)N(c1nnc2ccc(O[C@@H]3CC[C@H](NC(=O)Nc4cc(C(C)(C)C)nn4-c4cccc(OCCOC5CCCCO5)c4)c4ccccc43)cn12)C(C)C]

The title compound was prepared starting from Intermediate 103c and Intermediate 95c using analogous procedures to those described in Intermediate 95d. LCMS (Method 4): Rt 3.92 min, m/z 765 [MH⁺].

e. 1-{5-tert-Butyl-2-[3-(2-hydroxy-ethoxy)-phenyl]-2H-pyrazol-3-yl}-3-[(1S,4R)-4-(3-diisopropylamino-[1,2,4]triazolo[4,3-a]pyridin-6-yloxy)-1,2,3,4-tetrahydro-naphthalen-1-yl]-urea (Intermediate 103e).

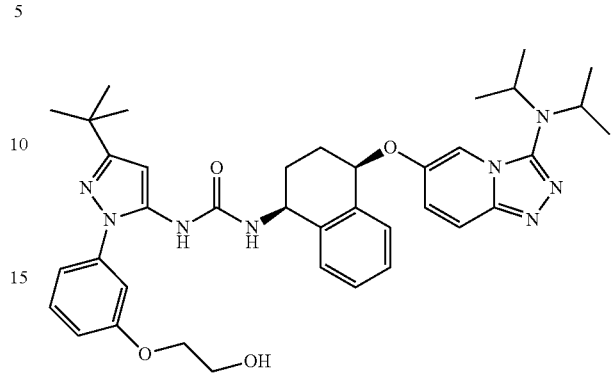

To a solution of Intermediate 103d (100 mg, 0.13 mmol) in MeOH (2 mL) was added pyridinium p-toluenesulfonate (65 mg, 0.26 mmol) and the reaction mixture was heated to reflux temperature for 3 h. The volatiles were concentrated in vacuo and the resultant residue was partitioned between EtOAc and water. The aqueous phase was extracted with EtOAc (×3) and the combined organic layers were washed with brine, dried (MgSO₄) and concentrated in vacuo to afford the title compound (97 mg, 99%). LCMS (Method 2): Rt 3.39 min, m/z 681 [MH⁺].

f. Methanesulfonic acid 2-[3-(3-tert-butyl-5-{3-[(1S,4R)-4-(3-diisopropylamino-[1,2,4]triazolo[4,3-a]pyridin-6-yloxy)-1,2,3,4-tetrahydro-naphthalen-1-yl]-ureido}-pyrazol-1-yl)-phenoxy]-ethyl ester (Intermediate 103f).

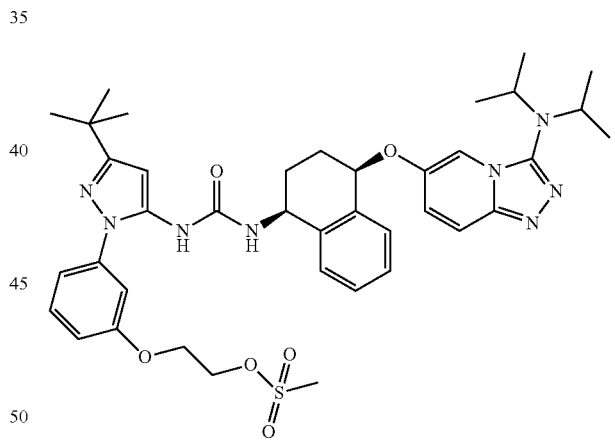

To an ice-bath cooled solution of Intermediate 103e (97 mg, 0.13 mmol) in DCM (2 mL) was added DIPEA (58 μL, 0.32 mmol) followed by methanesulfonyl chloride (22 μL, 0.27 mmol). The reaction mixture was stirred for 2 h then partitioned between DCM and water. The aqueous phase was extracted with DCM (×3) and the combined organic layers were washed with brine, dried (MgSO₄) and concentrated in vacuo to afford the title compound (130 mg, quantitative). LCMS (Method 1): Rt 3.69 min, m/z 759 [MH⁺].

g. 1-{5-tert-Butyl-2-[3-(2-dimethylamino-ethoxy)-phenyl]-2H-pyrazol-3-yl}-3-[(1S,4R)-4-(3-diisopropylamino-[1,2,4]triazolo[4,3-a]pyridin-6-yloxy)-1,2,3,4-tetrahydro-naphthalen-1-yl]-urea (Example 103).

To a solution of Intermediate 103f (130 mg, 0.13 mmol) in THF (1.5 mL) was added dimethylamine (2M in MeOH, 520

μL, 1.04 mmol). The reaction mixture was heated at 50° C. for 18 h, then cooled and partitioned between EtOAc and water. The aqueous phase was extracted with EtOAc (×3) and the combined organic layers were washed with brine, dried (MgSO$_4$) and concentrated in vacuo. The resultant residue was purified by FCC on silica, using a gradient of 0-10% [2M NH$_3$ in MeOH] in DCM followed by HPLC (C18 X-select column, 10-98% gradient MeCN in H$_2$O, 0.1% HCO$_2$H), to give the title compound (37 mg, 40%). LCMS (Method 5): Rt 3.70 min, m/z 708 [MH$^+$]. $^1$H NMR (400 MHz, CD$_3$OD): 1.05 (12H, dd, J=6.4, 1.8 Hz), 1.33 (9H, s), 21.89-2.30 (4H, m), 2.43 (6H, s), 2.91 (2H, t, J=5.2 Hz), 3.62-3.74 (2H, m), 4.19 (2H, t, J=5.3 Hz), 4.88-4.97 (1H, m), 5.42 (1H, t, J=4.1 Hz), 6.37 (1H, s), 7.04-7.13 (3H, m), 7.19-7.34 (5H, m), 7.44 (1H, t, J=8.3 Hz), 7.60 (1H, d, J=9.8 Hz), 7.87 (1H, d, J=2.1 Hz).

Example 104

N-(5-tert-Butyl-2-methoxy-3-{3-[(1S,4R)-4-(3-piperidin-1-yl-[1,2,4]triazolo[4,3-a]pyridin-6-yloxy)-1,2,3,4-tetrahydro-naphthalen-1-yl]-ureido}-phenyl)-methanesulfonamide

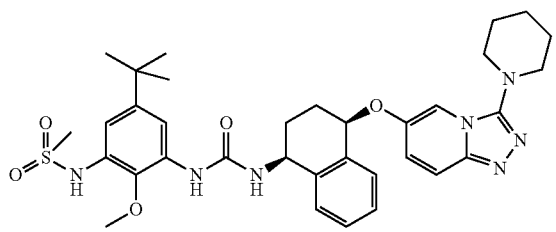 [SMILES: COc1c(NC(=O)N[C@H]2CC[C@@H](Oc3ccc4nnc(N5CCCCC5)n4c3)c3ccccc32)cc(C(C)(C)C)cc1NS(C)(=O)=O]

a. (5-tert-Butyl-3-methanesulfonylamino-2-methoxy-phenyl)-carbamic acid 2,2,2-trichloro-ethyl ester (Intermediate 104a).

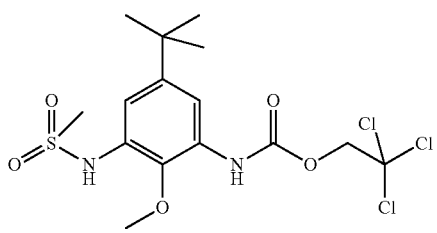 [SMILES: COc1c(NC(=O)OCC(Cl)(Cl)Cl)cc(C(C)(C)C)cc1NS(C)(=O)=O]

NaOH (199 mg, 4.97 mmol) was added to an ice-bath cooled solution of N-[3-amino-5-(1,1-dimethylethyl)-2-methoxyphenyl]-methanesulfonamide (for reference procedure see for example WO2010026096, which is incorporated herein by reference in its entirety; 500 mg, 1.84 mmol). The ice bath was removed and complete dissolution of reagents occurred. 2,2,2-trichloroethyl chloroformate (380 μL, 2.76 mmol) was added and the reaction mixture was warmed to RT and stirred for 90 min. The reaction mixture was partitioned between EtOAc and water. The aqueous phase was extracted with EtOAc (×3) and the combined organic layers were washed with brine, dried (MgSO$_4$) and concentrated in vacuo. The resultant residue was purified by FCC on silica, using a gradient of 0-60% EtOAc in cyclohexane, to afford the title compound (620 mg, 75%) as a white solid. LCMS (Method 1): Rt 3.98 min, m/z 445, 447, 449 [MH$^+$].

b. N-(5-tert-Butyl-2-methoxy-3-{3-[(1S,4R)-4-(3-piperidin-1-yl-[1,2,4]triazolo[4,3-a]pyridin-6-yloxy)-1,2,3,4-tetrahydro-naphthalen-1-yl]-ureido}-phenyl)-methane sulfonamide (Example 104).

A mixture of Intermediate 3c (50 mg, 0.14 mmol), Intermediate 104a (62 mg, 0.14 mmol) and DIPEA (48 μL, 0.27 mmol) in dioxane (1.5 mL) was stirred at 70° C. for 18 h and then at 80° C. for 48 h. The reaction mixture was diluted with EtOAc and then poured into water. The aqueous phase was extracted with EtOAc (×3) and the combined organic layers were washed with brine, dried (MgSO$_4$) and concentrated in vacuo. The resultant residue was purified by FCC on silica, using a gradient of 1-8% MeOH in DCM and then by HPLC (C18 X-select column, 10-98% gradient MeCN in H$_2$O, 0.1% HCO$_2$H), to afford the title compound (19 mg, 21%). LCMS (Method 5): Rt 4.47 min, m/z 662 [MH$^+$]. $^1$H NMR (400 MHz, d$_6$-DMSO): 1.25 (9H, s), 1.57-1.66 (2H, m), 1.69-1.78 (4H, m), 1.83-1.95 (1H, m), 1.98-2.24 (3H, m), 3.05 (3H, s), 3.15 (4H, t, J=5.3 Hz), 3.69 (3H, s), 4.87-4.96 (1H, m), 5.59 (1H, t, J=4.5 Hz), 6.94 (1H, d, J=2.3 Hz), 7.19 (1H, dd, J 9.9, 2.1 Hz), 7.31 (1H, dd, J=8.2, 6.7 Hz), 7.35-7.45 (4H, m), 7.60-7.69 (2H, m), 8.07 (1H, s), 8.19 (1H, d, J=2.4 Hz).

Example 105

1-(5-tert-Butyl-2-p-tolyl-2H-pyrazol-3-yl)-3-{(1S,4R)-4-[8-methyl-3-((S)-1-methyl-pyrrolidin-2-yl)-[1,2,4]triazolo[4,3-a]pyridin-6-yloxy]-1,2,3,4-tetrahydro-naphthalen-1-yl}-urea

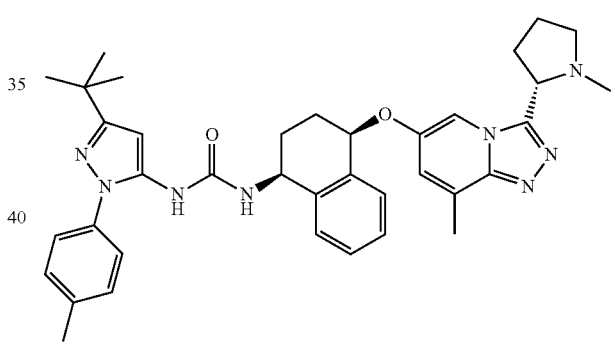

a. N-Benzhydrylidene-N'-(5-fluoro-3-methyl-pyridin-2-yl)-hydrazine (Intermediate 105a).

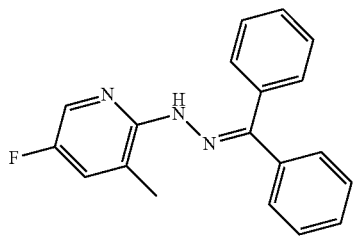 [SMILES: Cc1cc(F)cnc1NN=C(c1ccccc1)c1ccccc1]

A mixture of 2-bromo-5-fluoro-3-methyl-pyridine (190 mg, 1.0 mmol), benzhydrylidene-hydrazine (216 mg, 1.1 mmol), phenylboronic acid (5 mol %, 6 mg) and potassium tert-butoxide (157 mg, 1.4 mmol) in anhydrous toluene (6 mL) was degassed with a stream of argon, treated with Pd(OAc)$_2$ (2 mol %, 5 mg) and racemic (1,1'-binaphthalene-2,2'-diyl)bis(diphenylphosphine) (2 mol %, 12 mg) and stirred at 80° C. for 1 h. After cooling to RT, the reaction mixture was diluted with EtOAc and washed with water followed by a saturated aqueous solution of NaHCO$_3$. The organic layer was dried (MgSO$_4$) and concentrated in vacuo. The resultant residue was purified by FCC on silica, using a gradient of 1-10% MeOH in DCM followed by 100% DCM, to afford the title compound (196 mg, 64%). LCMS (Method 4): Rt 3.44 min, m/z 306 [MH$^+$].

b. (5-Fluoro-3-methyl-pyridin-2-yl)-hydrazine (Intermediate 105b).

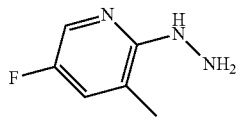

A solution of Intermediate 105a (194 mg, 0.635 mmol) in toluene (13 mL) was treated with HCl (37%, 3.5 mL) and heated at 110° C. for 1.5 h. After cooling to RT, the reaction mixture was diluted with water and extracted with toluene (×3). The aqueous layer was cooled to 0° C., neutralised with 5N NaOH and extracted with DCM (×3). The combined organic layers were dried (MgSO$_4$) and concentrated in vacuo to afford the title compound (78 mg, 86%) as a silver/green solid. LCMS (Method 4): Rt 0.29 min, m/z 142 [MH$^+$].

c. (S)-1-Methyl-pyrrolidine-2-carboxylic acid N'-(5-fluoro-3-methyl-pyridin-2-yl)-hydrazide (Intermediate 105c).

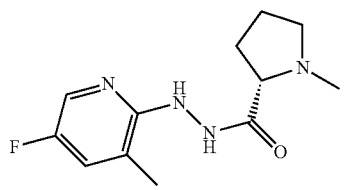 [SMILES: Cc1cc(F)cnc1NNC(=O)[C@@H]1CCCN1C]

A solution of Intermediate 105b (76 mg, 0.537 mmol), (S)-1-methyl-pyrrolidine-2-carboxylic acid (55 mg, 0.72 mmol) and HOBT (8 mg, 0.72 mmol) in anhydrous DCM (5 mL) was treated with EDC (138 mg, 0.717 mmol) and stirred at RT under a nitrogen atmosphere for 18 h. The reaction mixture was diluted with DCM and washed with brine. The organic layer was dried (MgSO$_4$) and concentrated in vacuo. The resultant residue was purified by FCC on silica, using a gradient of 1-10% MeOH in DCM, to afford the title compound (76 mg, 56%). $^1$H NMR (400 MHz, CDCl$_3$): 1.74-2.05 (3H, m), 2.15-2.33 (4H, m), 2.34-2.46 (1H, m), 2.52 (3H, s), 3.02-3.12 (1H, m), 3.15-3.25 (1H, m), 6.70 (1H, s), 7.08-7.18 (1H, m), 7.90 (1H, d, J=2.8 Hz), 9.52 (1H, br s).

d. 6-Fluoro-8-methyl-3-((S)-1-methyl-pyrrolidin-2-yl)-[1,2,4]triazolo[4,3-a]pyridine (Intermediate 105d).

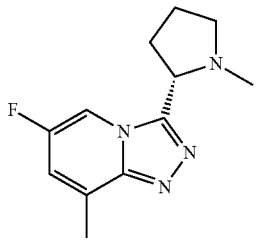 [SMILES: Cc1cc(F)cn2c([C@@H]3CCCN3C)nnc12]

Hexachloroethane (141 mg, 0.587 mmol) was added portionwise at RT to a stirred mixture of Intermediate 105c (74 mg, 0.293 mmol), triethylamine (166 µL, 1.17 mmol) and triphenylphosphine (154 mg, 0.587 mmol) in THF (5 mL). The reaction mixture was stirred at 80° C. for 2 h, then cooled to RT and filtered. The filtrate was concentrated in vacuo and the resultant residue was purified by SCX cartridge. The cartridge was washed with 10% MeOH in DCM and the product eluted with 10% (2M NH$_3$ in MeOH) in DCM. The product containing fractions were concentrated in vacuo and the resultant residue was purified by FCC on silica, using a gradient of 1-10% MeOH in DCM, to afford the title compound (59 mg, 86%) as a colourless oil. $^1$H NMR (400 MHz, CDCl$_3$): 1.88-2.12 (3H, m), 2.15-2.53 (5H, m), 2.69 (3H, s), 3.28 (1H, t, J=7.8 Hz), 4.01-4.15 (1H, m), 6.97 (1H, d, J=8.4 Hz), 8.50 (1H, s).

e. (1S,4R)-4-[8-Methyl-3-((S)-1-methyl-pyrrolidin-2-yl)-[1,2,4]triazolo[4,3-a]pyridin-6-yloxy]-1,2,3,4-tetrahydro-naphthalen-1-ylamine (Intermediate 105e).

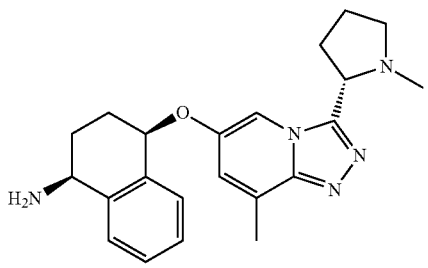 [SMILES: Cc1cc(O[C@@H]2CC[C@H](N)c3ccccc32)cn2c([C@@H]3CCCN3C)nnc12]

A mixture of Intermediate A (44 mg, 0.267 mmol) and sodium hydride (60% in mineral oil, 29 mg, 0.729 mmol) in anhydrous DMF (1 mL) was stirred at RT for 20 min under argon atmosphere. To the reaction mixture was added a solution of Intermediate 105d (57 mg, 0.243 mmol) in anhydrous DMF (2 mL) and stirring at 60° C. was continued for 2.5 h. After cooling to RT, the reaction mixture was diluted with EtOAc and poured into ice-water. The aqueous phase was extracted with EtOAc (×3) and the combined organic layers were dried (MgSO$_4$) and concentrated in vacuo. The resultant residue was purified by SCX cartridge by washing the cartridge with 10% MeOH in DCM and eluting the product with 10% (2M NH$_3$ in MeOH) in DCM and then by FCC on silica, using 10% MeOH in DCM followed by 10% [2M NH$_3$ in MeOH] in DCM, to give the title compound (53 mg, 58%). LCMS (Method 1): Rt 0.38, 1.54 min, m/z 378 [MH$^+$].

f. 1-(5-tert-Butyl-2-p-tolyl-2H-pyrazol-3-yl)-3-{(1S,4R)-4-[8-methyl-3-((S)-1-methyl-pyrrolidin-2-yl)-[1,2,4]triazolo[4,3-a]pyridin-6-yloxy]-1,2,3,4-tetrahydro-naphthalen-1-yl}-urea (Example 105).

A mixture of Intermediate 105e (53 mg, 0.14 mmol), (5-tert-butyl-2-p-tolyl-2H-pyrazol-3-yl)-carbamic acid 2,2,2-trichloro-ethyl ester (for reference procedure see Synthetic Communications, 2009, 39, 3999-4009, which is incorporated herein by reference in its entirety; 67 mg, 0.168 mmol) and DIPEA (49 µL, 0.28 mmol) in DMF (2 mL) was stirred at 100° C. for 1.5 h under argon atmosphere. After cooling to RT, the reaction mixture was diluted with EtOAc and washed with brine. The organic layer was dried (MgSO$_4$) and concentrated in vacuo. The resultant residue was purified by FCC on silica, using a gradient of 0-100% EtOAc in cyclohexane followed by 10% [2M NH$_3$ in MeOH] in EtOAc. The product containing fractions were concentrated in vacuo and the resultant residue was purified by HPLC (C18 Phenomenex Gemini column, 5-98% gradient MeCN in H$_2$O, 0.1% NH$_4$OH), to afford the title compound (52 mg, 74%). LCMS (Method 5): Rt 3.76 min, m/z 633 [MH$^+$]. $^1$H NMR (400 MHz, d$_6$-DMSO): 1.23 (9H, s), 1.75-2.30 (13H, m), 2.32 (3H, s), 2.48 (3H, s), 3.19 (1H, br s), 4.72-4.83 (1H, m), 5.30-5.38 (1H, m), 6.28 (1H, s), 7.03-7.11 (2H, m), 7.20-7.36 (8H, m), 8.00 (1H, s), 8.11 (1H, s).

Example 106

1-{5-tert-Butyl-2-[4-(4-methyl-piperazin-1-ylmethyl)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea

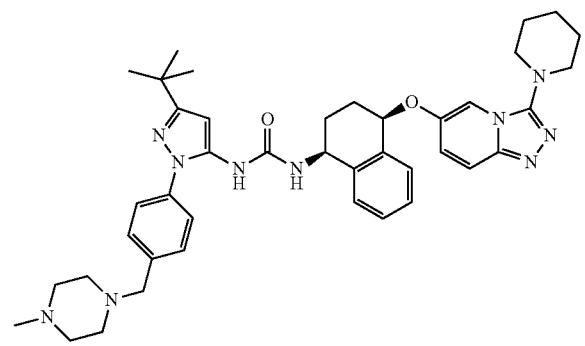 [SMILES: CN1CCN(Cc2ccc(-n3nc(C(C)(C)C)cc3NC(=O)N[C@H]3CC[C@@H](Oc4ccc5nnc(N6CCCCC6)n5c4)c4ccccc43)cc2)CC1]

a. 1-[5-tert-Butyl-2-(4-hydroxymethyl-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea (Intermediate 106a).

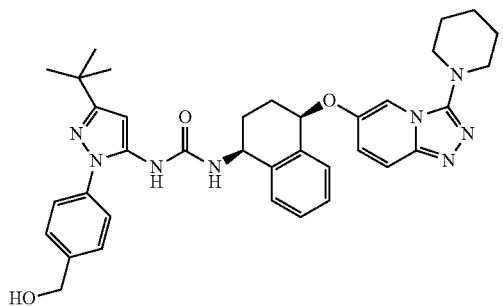 [SMILES: CC(C)(C)c1cc(NC(=O)N[C@H]2CC[C@@H](Oc3ccc4nnc(N5CCCCC5)n4c3)c3ccccc32)n(-c2ccc(CO)cc2)n1]

A mixture of Intermediate 3c (100 mg, 0.28 mmol), Intermediate 33a (116 mg, 0.28 mmol) and DIPEA (96 μL, 0.55 mmol) in dioxane (3 mL) was stirred at 80° C. for 16 h. After cooling, the reaction mixture was partitioned between water and EtOAc. The aqueous phase was extracted with EtOAc (×3) and the combined organic layers were washed with brine, dried (MgSO$_4$) and concentrated in vacuo. The resultant residue was purified by FCC on silica, using a gradient of 1-10% MeOH in DCM, to afford the title compound (156 mg, 88%). LCMS (Method 4): Rt 3.07 min, m/z 635 [MH$^+$].

b. 1-[5-tert-Butyl-2-(4-chloromethyl-phenyl)-2H-pyrazol-3-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea (Intermediate 106b).

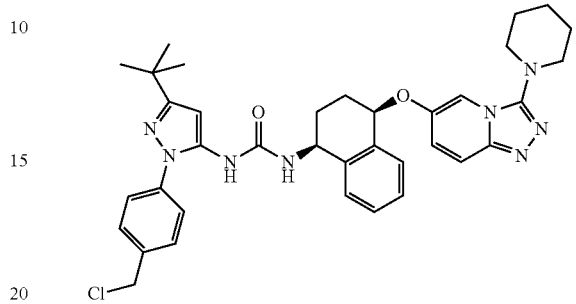

To an ice-bath cooled solution of Intermediate 106a (150 mg, 0.25 mmol) in DCM (3 mL) was added DIPEA (107 μL, 0.61 mmol) followed by methanesulfonyl chloride (29 μL, 0.37 mmol). The reaction mixture was stirred for 2 h. After warming to RT, additional amount of DIPEA (65 μL) and methanesulfonyl chloride (30 μL) were added and stirring was continued for 2 h. The reaction mixture was partitioned between DCM and water. The aqueous phase was extracted with DCM (×3) and the combined organic layers were washed with brine, dried (MgSO$_4$) and concentrated in vacuo to afford the title compound (Quantitative). Product used in the following step without further purification. LCMS (Method 4): Rt 3.59 min, ink 653 [MH$^+$].

c. 1-{5-tert-Butyl-2-[4-(4-methyl-piperazin-1-ylmethyl)-phenyl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea (Example 106).

To a solution of Intermediate 106b (0.25 mmol) in THF (2.5 mL) was added DIPEA (130 μL, 0.75 mmol) followed by N-methylpiperazine (83 μL, 0.75 mmol). The reaction mixture was heated at 50° C. for 18 h in a sealed tube, then cooled and partitioned between EtOAc and water. The aqueous phase was extracted with EtOAc (×3) and the combined organic layers were washed with brine, dried (MgSO$_4$) and concentrated in vacuo. The resultant residue was purified by FCC on silica, using a gradient of 0-10% [2M NH$_3$ in MeOH] in DCM followed by HPLC (C, 18 X-select column, 10-98% gradient MeCN in H$_2$O, 0.1% HCO$_2$H), to give the title compound (13 mg, 7%). LCMS (Method 5): Rt 3.44 min, m/z 717 [MH$^+$]. $^1$H NMR (400 MHz, d$_6$-DMSO): 1.27 (9H, s), 1.57-1.66 (2H, m), 1.68-1.77 (4H, m), 1.79-1.95 (2H, m), 1.98-2.19 (5H, m), 2.22-2.46 (8H, m), 3.14 (4H, t, J=5.3 Hz), 3.49 (2H, s), 4.76-4.85 (1H, m), 5.54 (1H, t, J=4.4 Hz), 6.33 (1H, s), 7.09 (1H, d, J=8.6 Hz), 7.17 (1H, dd, J=9.8, 2.2 Hz), 7.25-7.47 (8H, m), 7.59-7.65 (2H, m), 8.11 (1H, s).

Example 107

1-(3-tert-Butyl-1'-methyl-1'H-[1,4']bipyrazolyl-5-yl)-3-[(1S,4R)-4-(3-piperidin-1-yl-[1,2,4]triazolo[4,3-a]pyridin-6-yloxy)-1,2,3,4-tetrahydro-naphthalen-1-yl]-urea

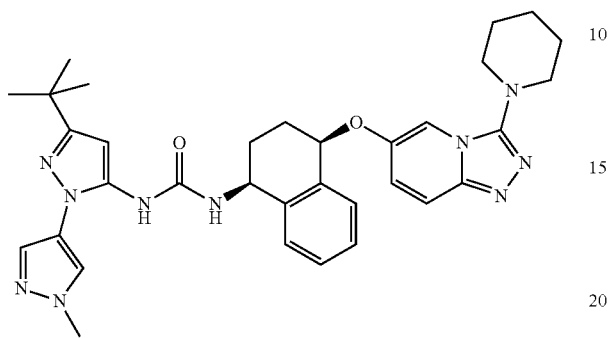

To a solution of Intermediate 3c (100 mg, 0.27 mmol) in dioxane (3 mL) was added DIPEA (90 µL, 0.55 mmol) followed by (3-tert-butyl-1'-methyl-1'H-[1,4']bipyrazolyl-5-yl)-carbamic acid 2,2,2-trichloro-ethyl ester (for reference procedure see for example U.S. Pat. No. 6,492,529, which is incorporated herein by reference; 109 mg, 0.27 mmol). The reaction mixture was heated at 60° C. for 18 h, then cooled and poured into water. The aqueous phase was extracted with EtOAc (×3) and the combined organic layers were washed with brine, dried (MgSO₄) and concentrated in vacuo. The resultant residue was purified by FCC on silica, using a gradient of 0-10% MeOH in DCM followed by MDAP (Method 7) purification, to give the title compound (100 mg, 61%). LCMS (Method 5): Rt 4.05 min, m/z 609 [MH⁺]. ¹H NMR (400 MHz, d₆-DMSO): 1.24 (9H, s), 1.54-1.66 (2H, m), 1.67-1.76 (4H, m), 1.81-2.18 (4H, m), 3.13 (4H, t, J=5.2 Hz), 3.86 (3H, s), 4.78-4.87 (1H, m), 5.55 (1H, t, J=4.1 Hz), 6.26 (1H, s), 7.10-7.18 (2H, m), 7.25-7.41 (4H, m), 7.58-7.64 (3H, m), 7.98-8.02 (2H, m).

Example 108

1-[3-tert-Butyl-1'-(2-dimethylamino-ethyl)-1'H-[1,4']bipyrazolyl-5-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea

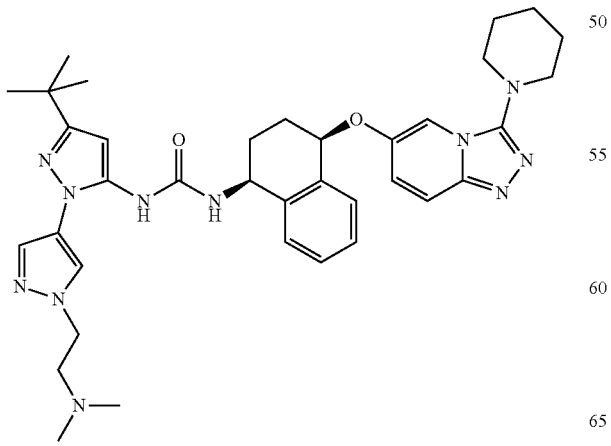

a. 3-tert-Butyl-1'-[2-(tetrahydro-pyran-2-yloxy)-ethyl]-1'H-[1,4']bipyrazolyl-5-ylamine (Intermediate 108a).

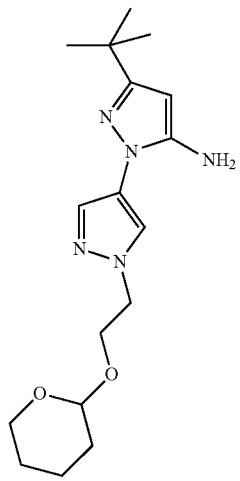 [SMILES: CC(C)(C)c1cc(N)n(-c2cnn(CCOC3CCCCO3)c2)n1]

To a mixture of 4-iodo-1-[2-(tetrahydro-pyran-2-yloxy)-ethyl]-1H-pyrazole (for reference procedure see for example WO 2010/139731, which is incorporated herein by reference; 1.54 g, 4.81 mmol), 5-tert-butyl-2H-pyrazol-3-ylamine (668 mg, 4.81 mmol), copper (I) iodide (45 mg, 0.24 mmol) and K₂CO₃ (1.39 g, 10.1 mmol) was added a solution of toluene (5 mL), previously degassed by using a stream of argon. (R,R)-(−)-N,N'-Dimethyl-1,2-cyclohexanediamine (151 µL, 0.96 mmol) was then added and the reaction mixture was heated at 150° C. for 2.5 h under microwave irradiation. The crude reaction mixture was poured into water and extracted with EtOAc (×3). The combined organic layers were washed with brine, dried (MgSO₄) and concentrated in vacuo. The resultant residue was purified by FCC on silica, using a gradient of 0-100% EtOAc in cyclohexane, to give the title compound (1.29 g, 81%). LCMS (Method 1): Rt 2.31 min, m/z 334 [MH⁺].

b. {3-tert-Butyl-1'-[2-(tetrahydro-pyran-2-yloxy)-ethyl]-1'H-[1,4']bipyrazolyl-5-yl}-carbamic acid 2,2,2-trichloro-ethyl ester (Intermediate 108b).

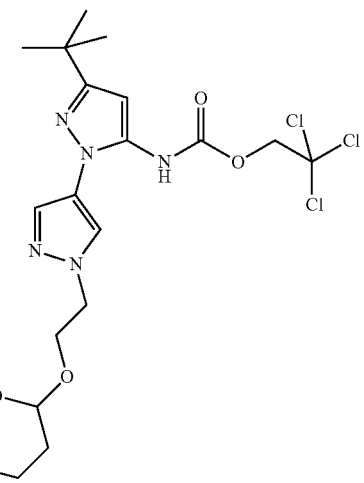

To a mixture of Intermediate 108a (1.29 g, 3.87 mmol) in water (5 mL) and EtOAc (13 mL) was added NaOH (310 mg, 7.74 mmol). After 10 min stirring, 2,2,2-trichloroethyl chloroformate (640 µL, 4.65 mmol) was added and the reaction mixture was stirred at RT for 1 h. The aqueous layer was extracted with EtOAc (×3) and the combined organic layers were washed with brine, dried (MgSO$_4$) and concentrated in vacuo. The resultant residue was purified by FCC on silica, using a gradient of 0-75% EtOAc in cyclohexane, to afford the title compound (1.24 g, 63%). LCMS (Method 4): Rt 3.92 min, m/z 508, 510 [MH$^+$].

c. 1-{3-tert-Butyl-1'-[2-(tetrahydro-pyran-2-yloxy)-ethyl]-1'H-[1,4']bipyrazolyl-5-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea (Intermediate 108c).

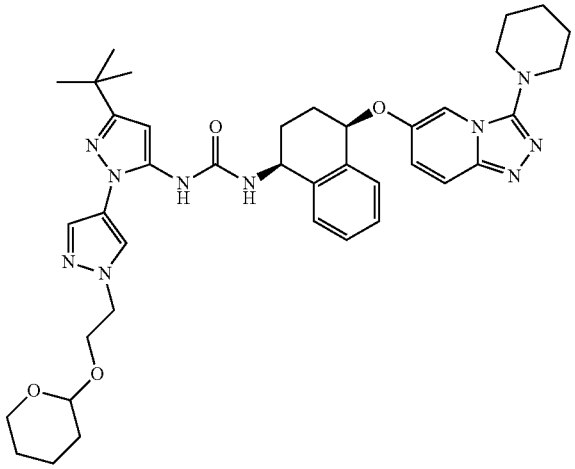 [SMILES: CC(C)(C)c1cc(NC(=O)N[C@H]2CC[C@@H](Oc3ccc4nnc(N5CCCCC5)n4c3)c3ccccc32)n(-c2cnn(CCOC3CCCCO3)c2)n1]

The title compound was prepared starting from Intermediate 3c and Intermediate 108b using analogous procedures to those described in Intermediate 106a. LCMS (Method 4): Rt 3.27 min, m/z 723.5 [MH$^+$].

d. 1-[3-tert-Butyl-1'-(2-hydroxy-ethyl)-1'H-[1,4']bipyrazolyl-5-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea (Intermediate 108d).

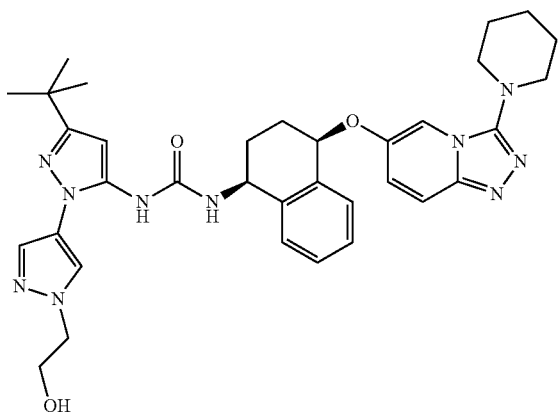 [SMILES: CC(C)(C)c1cc(NC(=O)N[C@H]2CC[C@@H](Oc3ccc4nnc(N5CCCCC5)n4c3)c3ccccc32)n(-c2cnn(CCO)c2)n1]

To a solution of Intermediate 108c (170 mg, 0.23 mmol) in MeOH (2.5 mL) was added pyridinium p-toluenesulfonate (118 mg, 0.47 mmol) and the reaction mixture was heated at 60° C. for 2 h. The resultant mixture was poured into water and a saturated aqueous solution of NaHCO$_3$ was added. The aqueous phase was extracted with EtOAc (×3) and the combined organic layers were washed with brine, dried (MgSO$_4$) and concentrated in vacuo. The resultant residue was purified by FCC on silica, using a gradient of 0-10% MeOH in DCM, to give the title compound (105 mg, 72%). LCMS (Method 1): Rt 2.96 min, m/z 639 [MH$^+$].

e. Methanesulfonic acid 2-(3-tert-butyl-5-{3-[(1S,4R)-4-(3-piperidin-1-yl-[1,2,4]triazolo[4,3-a]pyridin-6-yloxy)-1,2,3,4-tetrahydro-naphthalen-1-yl]-ureido}-[1,4']bipyrazolyl-1'-yl)-ethyl ester (Intermediate 108e).

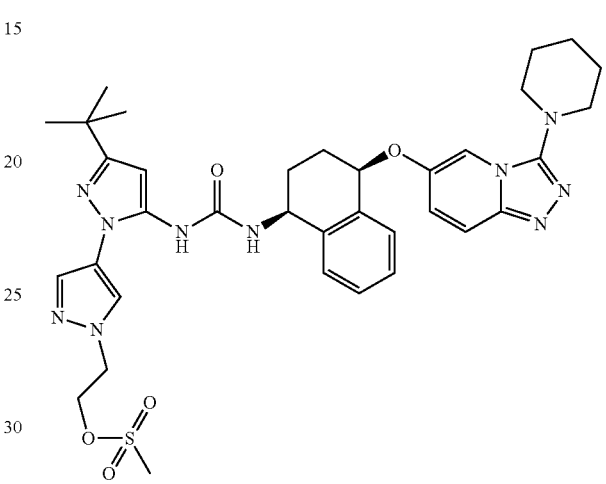

To an ice-bath cooled solution of Intermediate 108d (105 mg, 0.16 mmol) in DCM (2 mL) was added DIPEA (43 µL, 0.25 mmol) followed by methanesulfonyl chloride (15 µL, 0.20 mmol). The reaction mixture was stirred for 2 h and then quenched with water. The aqueous phase was extracted with DCM (×3) and the combined organic layers were washed with brine, dried (MgSO$_4$) and concentrated in vacuo to afford the title compound (Quantitative). Product used in the following step without further purification. LCMS (Method 4): Rt 3.09 min, m/z 717 [MH$^+$].

f. 1-[3-tert-Butyl-1'-(2-dimethylamino-ethyl)-1'H-[1,4']bipyrazolyl-5-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea (Example 108).

To a solution of Intermediate 108e (0.20 mmol) in THF (2 mL) was added dimethylamine (2M in MeOH, 0.8 mL, 1.6 mmol) and stirring at RT was continued for 48 h. The crude reaction mixture was partitioned between EtOAc and water. The aqueous phase was extracted with EtOAc (×3) and the combined organic layers were washed with brine, dried (MgSO$_4$) and concentrated in vacuo. The resultant residue was purified by FCC on silica, using a gradient of 0-10% [2M NH$_3$ in MeOH] in DCM followed by MDAP (Method 7) purification, to give the title compound (20 mg, 15%). LCMS (Method 5): Rt 3.34 min, m/z 666 [MH$^+$]. $^1$H NMR (400 MHz, d$_6$-DMSO): 1.24 (9H, s), 1.54-1.65 (2H, m), 1.67-1.77 (4H, m), 1.81-2.13 (4H, m), 2.16 (6H, s), 2.67 (2H, t, J=6.5 Hz), 3.13 (4H, t, J=5.3 Hz), 4.20 (2H, t, J=6.5 Hz), 4.79-4.87 (1H, m), 5.55 (1H, t, J=4.5 Hz), 6.26 (1H, s), 7.11-7.19 (2H, m), 7.26-7.41 (4H, m), 7.58-7.64 (3H, m), 7.99-8.05 (2H, m).

Example 109

N-[5-tert-Butyl-2-methoxy-3-(3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-ureido)-phenyl]-methanesulfonamide formate salt

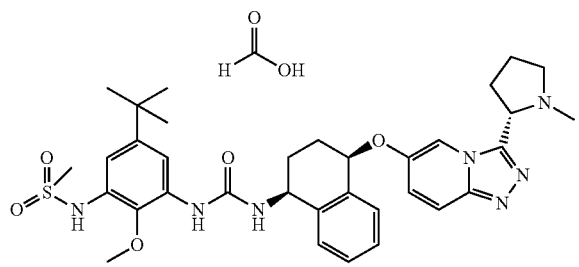 [SMILES: COc1c(NC(=O)N[C@H]2CC[C@@H](Oc3ccc4nnc([C@@H]5CCCN5C)n4c3)c3ccccc32)cc(C(C)(C)C)cc1NS(C)(=O)=O ; O=CO]

A mixture of Intermediate 5c (122 mg, 0.33 mmol), Intermediate 104a (150 mg, 0.33 mmol) and DIPEA (87 µL, 0.50 mmol) in dioxane (2 mL) was stirred at 60° C. for 18 h and then at 85° C. for 48 h. The volatiles were concentrated in vacuo and the resultant residue was purified by MDAP (Method 7) to afford the title compound (88 mg, 40%). LCMS (Method 5): Rt 3.41 min, m/z 662 [MH$^+$]. $^1$H NMR (400 MHz, d$_6$-DMSO): 1.24 (9H, s), 1.81-2.27 (10H, m), 2.28-2.40 (1H, m), 3.04 (3H, s), 3.11-3.18 (2H, m), 3.67 (3H, s), 3.99 (1H, t, J=8.3 Hz), 4.83-4.99 (1H, m), 5.43 (1H, t, J=4.5 Hz), 6.93 (1H, d, J=2.3 Hz), 7.25-7.44 (7H, m), 7.76 (1H, d, J=10.3 Hz), 8.05 (1H, s), 8.15 (1H, s), 8.18 (1H, d, J=2.8 Hz), 8.27 (1H, d, J=2.1 Hz).

Example 110

1-[5-tert-Butyl-2-(2-hydroxy-ethyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea

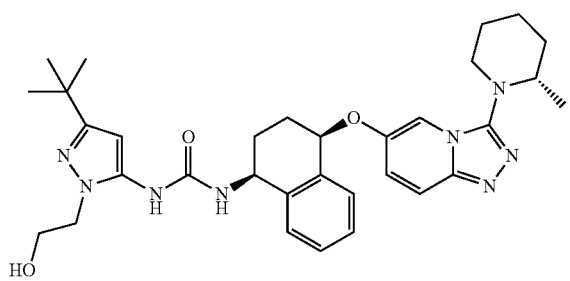 [SMILES: C[C@H]1CCCCN1c1nnc2ccc(O[C@@H]3CC[C@H](NC(=O)Nc4cc(C(C)(C)C)nn4CCO)c4ccccc43)cn12]

a. 2-(5-Amino-3-tert-butyl-pyrazol-1-yl)-ethanol (Intermediate 110a).

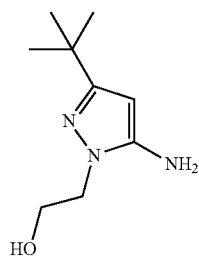

2-Hydrazino-ethanol (2.98 mL, 44.0 mmol) was added to a stirred solution of 4,4-dimethyl-3-oxo-pentanenitrile (5.0 g, 40.0 mmol) in EtOH (IMS grade, 40 mL) at RT followed by concentrated HCl (0.4 mL). The reaction mixture was heated at reflux temperature for 18 h then cooled and concentrated in vacuo. The resultant residue was triturated with pentane to give the title compound (7.4 g, quantitative) as a yellow solid. LCMS (Method 3): Rt 0.81 min, m/z 184 [MH$^+$].

b. [5-tert-Butyl-2-(2-hydroxy-ethyl)-2H-pyrazol-3-yl]-carbamic acid 2,2,2-trichloro-ethyl ester (Intermediate 110b).

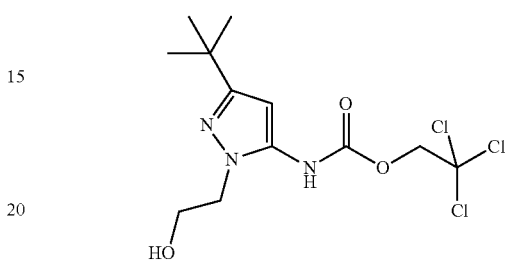

2,2,2-Trichloroethyl chloroformate (3.24 mL, 23.5 mmol) was added dropwise over 5 min to a solution of Intermediate 110a (4.11 g, 22.4 mmol) in NaOH (1M in water, 33.6 mL, 33.6 mmol) and EtOAc (35 mL) cooled at 0° C. under argon atmosphere. The reaction mixture was stirred at RT for 5 h. Additional 2,2,2-trichloroethyl chloroformate (462 µL) was added and stirring at RT was continued for 16 h. Additional NaOH (1M in water, 15 mL) and 2,2,2-trichloroethyl chloroformate (462 µL) were added and stirring at RT was continued for 1 h. The aqueous layer was extracted with EtOAc (×3) and the combined organic layers were washed with brine, dried (Na$_2$SO$_4$) and concentrated in vacuo. The resultant residue was dissolved in cyclohexane (100 mL) and left to stand for 5 days. The resulting suspension was filtered and the solid collected by filtration washing with additional cyclohexane affording the title compound (3.64 g, 45%) as a white solid. The filtrate was concentrated in vacuo and the resultant residue was purified by FCC on silica, using a mixture of 50% EtOAc in cyclohexane, then partitioned between DCM and water. The organic layer was dried through a phase separator and concentrated in vacuo to afford additional title compound (1.43 g, 18%) as an orange gum. LCMS (Method 3): Rt 3.72 min, m/z 358 [MH$^+$].

c. 1-[5-tert-Butyl-2-(2-hydroxy-ethyl)-2H-pyrazol-3-yl]-3-{(1S,4R)-4-[3-((S)-2-methyl-piperidin-1-yl)-[1,2,4]triazolo[4,3-a]pyridin-6-yl oxy]-1,2,3,4-tetrahydro-naphthalen-1-yl}-urea (Example 110).

A mixture of Intermediate 110b (143 mg, 0.40 mmol), Intermediate 81d (1151 mg, 0.40 mmol) and DIPEA (82 µL, 0.50 mmol) in dioxane (5 mL) was stirred at 100° C. for 4 h. After cooling, the reaction mixture was concentrated in vacuo and then partitioned between water and DCM. The aqueous phase was extracted with DCM (×3) and the combined organic layers were washed with brine, dried through a phase separator and concentrated in vacuo. The resultant residue was purified by FCC on silica, using a gradient of 3-15% MeOH in DCM followed by MDAP (Method 7) purification, to afford the title compound (36 mg, 15%) as a glassy white solid. LCMS (Method 5): Rt 4.02 min, m/z 587 [MH$^+$]. $^1$H NMR (400 MHz, d$_6$-DMSO): 0.92 (3H, d, J=6.3 Hz), 1.21 (9H, s), 1.44-1.57 (2H, m), 1.60-1.74 (2H, m), 1.74-1.87 (2H, m), 1.88-2.22 (4H, m), 2.86-2.96 (1H, m), 3.12-3.20 (2H, m), 3.63-3.71 (2H, m), 3.95 (2H, t, J=6.0 Hz), 4.82-4.91 (1H, m), 5.00 (1H, br s), 5.54 (1H, t, J=4.3 Hz), 6.07 (1H, s), 7.10 (1H, d, J=8.6 Hz), 7.22 (1H, dd, J=9.8, 2.2 Hz), 7.26-7.32 (1H, m), 7.35-7.42 (3H, m), 7.65 (1H, d, J=10.8 Hz), 7.71 (1H, d, J=2.1 Hz), 8.19-8.23 (1H, m).

Example 111

1-(5-tert-Butyl-isoxazol-3-yl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea

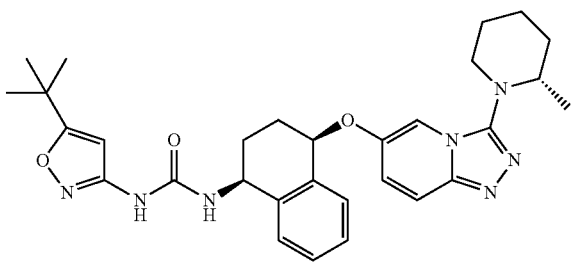 [SMILES: C[C@H]1CCCCN1c1nnc2ccc(O[C@@H]3CC[C@H](NC(=O)Nc4cc(C(C)(C)C)on4)c4ccccc43)cn12]

The title compound was prepared starting from Intermediate 81 d and (5-tert-butyl-isoxazol-3-yl)-carbamic acid 2,2,2-trichloro-ethyl ester (for reference procedure see WO 2006/091671, which is incorporated herein by reference in its entirety) using analogous procedures to those described in Example 110 step c. LCMS (Method 5): Rt 4.67 min, m/z 544 [MH+]. 1H NMR (400 MHz, d$_6$-DMSO): 0.91 (3H, d, J=6.3 Hz), 1.28 (9H, s), 1.44-1.57 (2H, m), 1.60-1.73 (2H, m), 1.74-1.86 (2H, m), 1.88-2.22 (4H, m), 2.86-2.94 (1H, m), 3.12-3.20 (2H, m), 4.86-4.95 (1H, m), 5.54 (1H, t, J=4.2 Hz), 6.40 (1H, s), 7.00 (1H, d, J=8.6 Hz), 7.21-7.26 (1H, m), 7.27-7.33 (1H, m), 7.34-7.42 (3H, m), 7.64 (1H, dd, J=9.8, 0.8 Hz), 7.71 (1H, d, J=2.10 Hz), 9.31 (1H, s).

Example 112

1-[3-tert-Butyl-1'-(2-morpholin-4-yl-ethyl)-1'H-[1,4']bipyrazolyl-5-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea formate salt

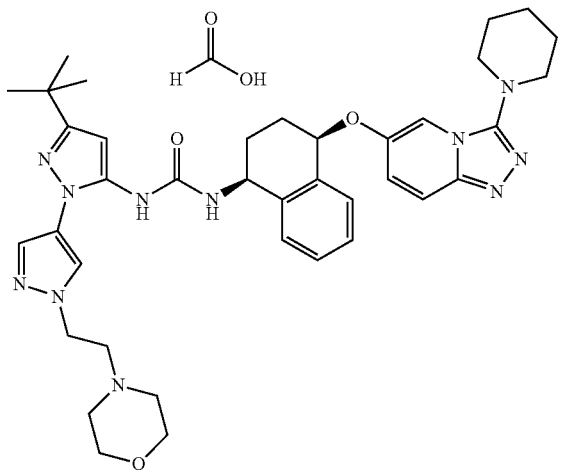

The title compound was prepared starting from Intermediate 108e and morpholine using analogous procedures to those described in Example 108. LCMS (Method 5): Rt 3.37 min, m/z 708 [MH+]. 1H NMR (400 MHz, d$_6$-DMSO): 1.24 (9H, s), 1.55-1.65 (2H, m), 1.67-1.76 (4H, m), 1.79-2.19 (4H, m), 2.41 (4H, d, J=4.7 Hz), 2.72 (2H, t, J=6.7 Hz), 3.13 (4H, t, J=5.3 Hz), 3.53 (4H, t, J=4.6 Hz), 4.23 (2H, t, J=6.6 Hz), 4.78-4.87 (1H, m), 5.55 (1H, t, J=4.4 Hz), 6.25 (1H, s), 7.11-7.18 (2H, m), 7.25-7.41 (4H, m), 7.58-7.64 (3H, m), 8.00 (1H, s), 8.05 (1H, s), 8.16 (1H, s).

Example 113

1-[3-tert-Butyl-1'-(3-dimethylamino-propyl)-1'H-[1,4']bipyrazolyl-5-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea formate salt

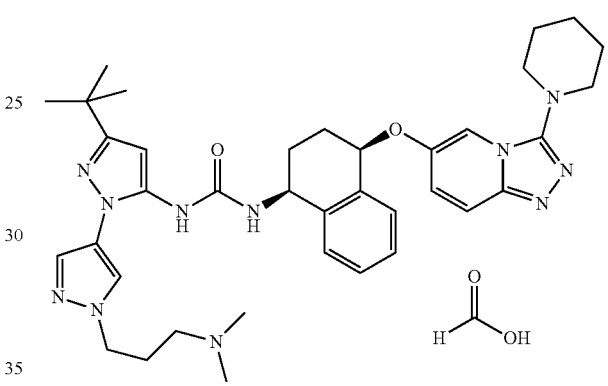

a. 4-Iodo-1-[3-(tetrahydro-pyran-2-yloxy)-propyl]-1H-pyrazole (Intermediate 113a).

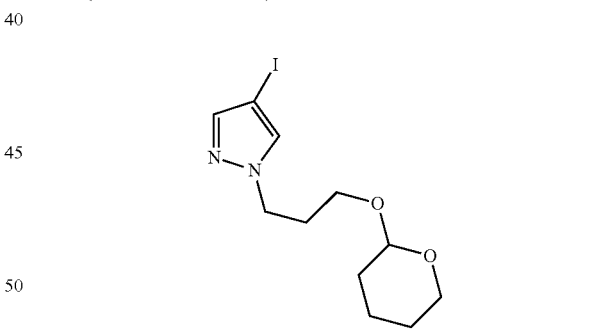

To a mixture of 4-iodo-1H-pyrazole (2.0 g, 10.3 mmol) and Cs$_2$CO$_3$ (5.04 g, 15.5 mmol) in MeCN (28 mL) was added 2-(3-bromopropoxy)tetrahydro-2H-pyran (1.84 mL, 10.8 mmol) and the mixture stirred overnight. The crude reaction mixture was poured into water and extracted with EtOAc (×3). The combined organic layers were washed with brine, dried (MgSO$_4$) and concentrated in vacuo. The resultant residue was purified by FCC on silica, using a gradient of 0-80% EtOAc in cyclohexane, to give the title compound (2.95 g, 81%). 1H NMR (300 MHz, CDCl$_3$): 150-1.58 (4H, m), 1.65-1.90 (2H, m), 2.12 (2H, qn, J=6.4 Hz), 3.35 (1H, dt, J=10.2, 5.9 Hz), 3.46-3.54 (1H, m), 3.73 (1H, dt, J=10.2, 5.9 Hz), 3.80-3.88 (1H, m), 4.26 (2H, td, J=6.9, 1.5 Hz), 4.54 (1H, dd, J=4.5, 3.1 Hz), 7.46 (1H, s), 7.50 (1H, s).

b. 3-tert-Butyl-1'-[3-(tetrahydro-pyran-2-yloxy)-propyl]-1'H-[1,4']bipyrazolyl-5-ylamine (Intermediate 113b).

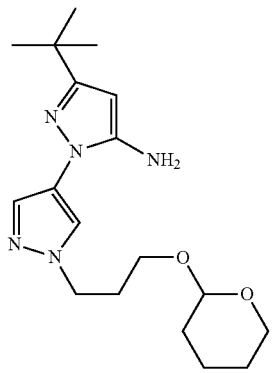 [SMILES: CC(C)(C)c1cc(N)n(-c2cnn(CCCOC3CCCCO3)c2)n1]

To a mixture of intermediate 113a (1.50 g, 4.46 mmol), 5-tert-butyl-2H-pyrazol-3-ylamine (620 mg, 4.46 mmol), copper (I) iodide (42 mg, 0.22 mmol) and K$_2$CO$_3$ (1.29 g, 9.37 mmol) was added a solution of toluene (4.6 mL), previously degassed by using a stream of argon. (R,R)-(−)-N,N'-Dimethyl-1,2-cyclohexanediamine (141 μL, 0.89 mmol) was then added and the reaction mixture was heated at 140° C. for 2.5 h under microwave irradiation. The crude reaction mixture was poured into water and extracted with EtOAc (×3). The combined organic layers were washed with brine, dried (MgSO$_4$) and concentrated in vacuo. The resultant residue was purified by FCC on silica, using a gradient of 0-100% EtOAc in cyclohexane, to give the title compound (1.14 g, 73%). LCMS (Method 4): Rt 2.34 min, m/z 348 [MH$^+$].

c. {3-tert-Butyl-1'-[3-(tetrahydro-pyran-2-yloxy)-propyl]-1'H-[1,4']bipyrazolyl-5-yl}-carbamic acid 2,2,2-trichloroethyl ester (Intermediate 113c).

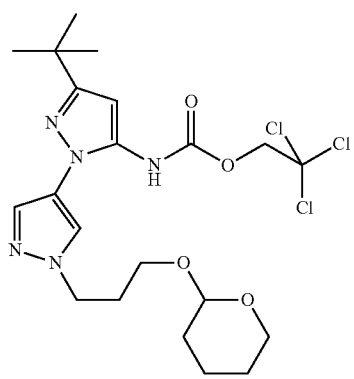 [SMILES: CC(C)(C)c1cc(NC(=O)OCC(Cl)(Cl)Cl)n(-c2cnn(CCCOC3CCCCO3)c2)n1]

To a stirred mixture of Intermediate 113b (1.14 g, 3.28 mmol) in water (6 mL) and EtOAc (12 mL) was added NaOH (263 mg, 6.57 mmol). After 10 min, 2,2,2-trichloroethyl chloroformate (543 μL, 3.94 mmol) was added and the reaction mixture was stirred at RT for 1 h. The aqueous layer was extracted with EtOAc (×3) and the combined organic layers were washed with brine, dried (MgSO$_4$) and concentrated in vacuo. The resultant residue was purified by FCC on silica, using a gradient of 0-100% EtOAc in cyclohexane, to afford the title compound (1.57 g, 91%). LCMS (Method 4): Rt 3.99 min, m/z 522, 524 [MH$^+$].

d. 1-{3-tert-Butyl-1'-[3-(tetrahydro-pyran-2-yloxy)-propyl]-1'H-[1,4']bipyrazolyl-5-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea (Intermediate 113d).

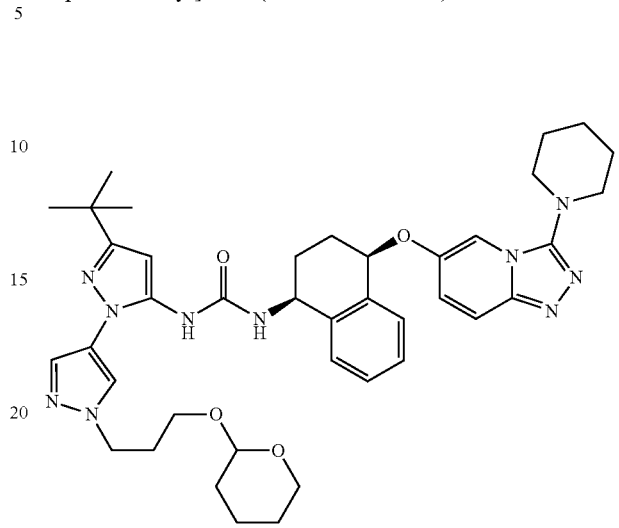

The title compound was prepared starting from Intermediate 3c and Intermediate 113c using analogous procedures to those described in Intermediate 106a. LCMS (Method 4): Rt 3.34 min, m/z 737 [MH$^+$].

e. 1-[3-tert-Butyl-1'-(3-hydroxy-propyl)-1'H-[1,4']bipyrazolyl-5-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea (Intermediate 113e).

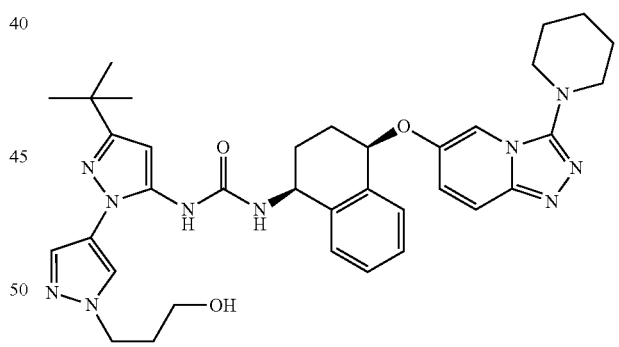

To a solution of Intermediate 113d (263 mg, 0.36 mmol) in MeOH (2.5 mL) was added pyridinium p-toluenesulfonate (179 mg, 0.71 mmol) and the reaction mixture was heated at 60° C. for 3 h. The resultant mixture was poured into water and a saturated aqueous solution of NaHCO$_3$ was added. The aqueous phase was extracted with EtOAc (×3) and the combined organic layers were washed with brine, dried (MgSO$_4$) and concentrated in vacuo. The resultant residue was purified by FCC on silica, using a gradient of 3-10% MeOH in DCM, to give the title compound (163 mg, 70%). LCMS (Method 4): Rt 3.00 min, m/z 653 [MH$^+$].

f. Methanesulfonic acid 3-(3-tert-butyl-5-{3-[(1S,4R)-4-(3-piperidin-1-yl-[1,2,4]triazolo[4,3-a]pyridin-6-yloxy)-1,2,3,4-tetrahydro-naphthalen-1-yl]-ureido}-[1,4']bipyrazolyl-1'-yl)-propyl ester (Intermediate 113f).

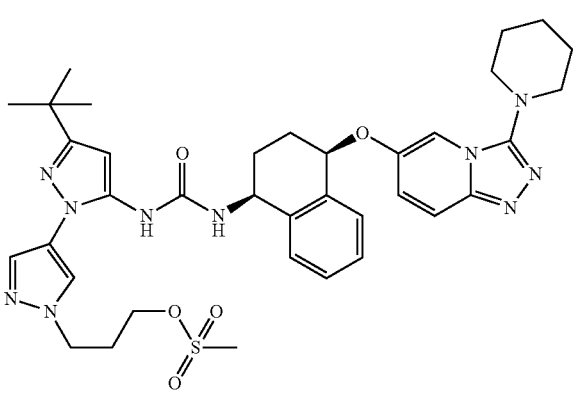 [SMILES: CC(C)(C)c1cc(NC(=O)N[C@H]2CC[C@@H](Oc3ccc4nnc(N5CCCCC5)n4c3)c3ccccc32)n(-c2cnn(CCCOS(C)(=O)=O)c2)n1]

To an ice-bath cooled solution of Intermediate 113e (163 mg, 0.25 mmol) in DCM (3 mL) was added DIPEA (174 µL, 1.0 mmol) followed by methanesulfonyl chloride (39 µL, 0.50 mmol). The reaction mixture was stirred for 1 h and then quenched with water. The aqueous phase was extracted with DCM (×3) and the combined organic layers were washed with brine, dried (MgSO$_4$) and concentrated in vacuo to afford the title compound (Quantitative). Product used in the following step without further purification. LCMS (Method 4): Rt 3.12 min, m/z 731 [MH$^+$].

g. 1-[3-tert-Butyl-1'-(3-dimethylamino-propyl)-1'H-[1,4']bipyrazolyl-5-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea formate salt (Example 113).

To a solution of Intermediate 113f (0.125 mmol) in THF (1.5 mL) was added dimethylamine (2M in MeOH, 0.5 mL, 1.0 mmol) and the reaction stirred at 50° C. for 24 h. The crude reaction mixture was cooled and partitioned between EtOAc and water. The aqueous phase was extracted with EtOAc (×3) and the combined organic layers were washed with brine, dried (MgSO$_4$) and concentrated in vacuo. The resultant residue was purified by FCC on silica, using a gradient of 0-10% [2M NH$_3$ in MeOH] in DCM, followed by MDAP (Method 7) purification, to give the title compound (10 mg, 12%). LCMS (Method 5): Rt 3.36 min, m/z 680 [MH$^+$]. $^1$H NMR (400 MHz, d$_6$-DMSO): 1.21 (9H, s), 1.54-1.65 (2H, m), 1.67-1.77 (4H, m), 1.81-1.95 (4H, m), 1.99-2.07 (4H, m) 2.08 (6H, s), 2.16 (2H, t, J=6.9 Hz), 3.10 (4H, t, J=5.2 Hz), 4.09 (2H, t, J=7.1 Hz), 4.79 (1H, td, J=8.4, 5.5 Hz), 5.51 (1H, t, J=4.5 Hz), 6.21 (1H, s), 7.09-7.14 (2H, m), 7.22-7.37 (4H, m), 7.55-7.62 (3H, m), 7.97-8.01 (2H, m), 8.22 (0.4H, br s).

Example 114

1-[3-tert-Butyl-1'-(3-morpholin-4-yl-propyl)-1'H-[1,4']bipyrazolyl-5-yl]-3-[(1S,4R)-4-(3-piperidin-1-yl-[1,2,4]triazolo[4,3-a]pyridin-6-yloxy)-1,2,3,4-tetrahydro-naphthalen-1-yl]-urea formate salt

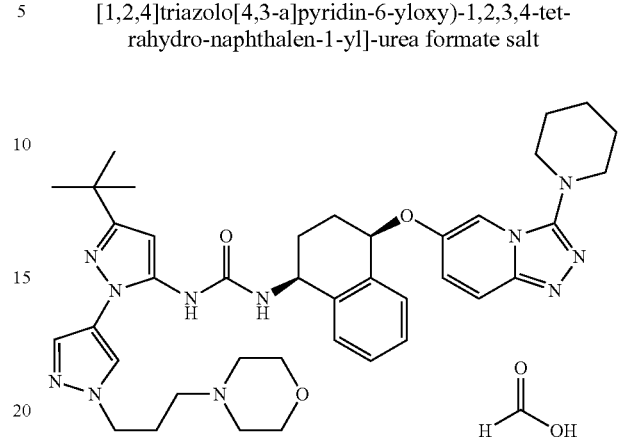

The title compound was prepared starting from Intermediate 113f and morpholine using analogous procedures to those described in Example 113. LCMS (Method 5): Rt 3.36 min, m/z 722 [MH$^+$]. $^1$H NMR (400 MHz, d$_6$-DMSO): 1.20 (9H, s), 1.54-1.60 (2H, m), 1.65-1.72 (4H, m), 1.80-1.96 (4H, m), 1.98-2.10 (4H, m) 2.22 (2H, t, J=7.0 Hz), 2.24-2.30 (4H, m), 3.10 (4H, t, J=5.2 Hz), 3.50 (4H, t, J=4.6 Hz), 4.09 (2H, t, J=7.0 Hz), 4.79 (1H, td, J=8.4, 5.5 Hz), 5.51 (1H, t, J=4.5 Hz), 6.21 (1H, s), 7.10-7.15 (2H, m), 7.22-7.36 (4H, m), 7.55-7.62 (3H, m), 7.97-8.01 (2H, m), 8.22 (0.3H, br s).

Example 115

1-{(1S,4R)-4-[3-((2S,6R)-2,6-Dimethyl-piperidin-1-yl)-[1,2,4]triazolo[4,3-a]pyridin-6-yloxy]-1,2,3,4-tetrahydro-naphthalen-1-yl}-3-(3-fluoro-5-morpholin-4-yl-phenyl)-urea

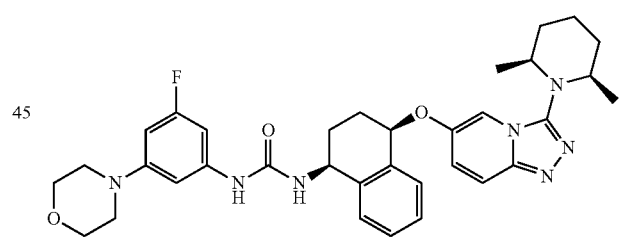

a. (3-Fluoro-5-morpholin-4-yl-phenyl)-carbamic acid 2,2,2-trichloro-ethyl ester (Intermediate 115a).

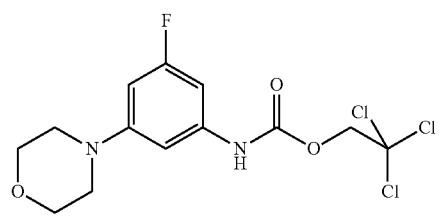 [SMILES: O=C(Nc1cc(F)cc(N2CCOCC2)c1)OCC(Cl)(Cl)Cl]

2,2,2-Trichloroethyl chloroformate (1.05 mL, 7.65 mmol) was added to an ice cold solution of 3-fluoro-5-morpholin-4-ylaniline (reference procedure see EP1102743; 1.0 g, 5.10 mmol) and triethylamine (1.77 mL, 10.2 mmol) in THF (25 mL). The reaction mixture was stirred at RT for 1.5 h, then quenched with water. The aqueous layer was extracted with EtOAc (×3) and the combined organic layers were washed with brine, dried (MgSO$_4$) and concentrated in vacuo to afford the title compound (1.89 g, 99%) as a clear oil. LCMS (Method 3): Rt 3.75 min, m/z 371, 373 [MH$^+$].

b. 1-{(1S,4R)-4-[3-((2S,6R)-2,6-Dimethyl-piperidin-1-yl)-[1,2,4]triazolo[4,3-a]pyridin-6-yloxy]-1,2,3,4-tetrahydro-naphthalen-1-yl}-3-(3-fluoro-5-morpholin-4-yl-phenyl)-urea (Example 115).

The title compound was prepared starting from Intermediate 96c and intermediate 115a using analogous procedures to those described in Example 99. LCMS (Method 5): Rt 4.70 min, m/z 614 [MH$^+$]. $^1$H NMR (400 MHz, d$_6$-DMSO): 0.55 (3H, d, J=6.3 Hz), 0.59 (3H, d, J=6.3 Hz), 1.35-1.53 (3H, m), 1.63-1.69 (2H, m), 1.72-1.78 (1H, m), 1.82-1.99 (2H, m), 2.00-2.13 (2H, m), 3.03 (4H, t, J=4.8 Hz), 3.08-3.20 (2H, m), 3.65-3.69 (2H, t, J=4.8 Hz), 4.80-4.88 (1H, td, J=8.7, 5.5 Hz), 5.50 (1H, t, J=4.0 Hz), 6.31 (1H, dt, J=12.4, 2.0 Hz), 6.68 (1H, br s), 6.71 (1H, d, J=8.9 Hz), 6.81 (1H, dt, J=11.3, 1.9 Hz), 7.18-7.25 (2H, m), 7.29-7.37 (3H, m), 7.62 (1H, dd, J=9.8, 0.6 Hz), 7.86 (1H, d, J=2.0 Hz), 8.51 (1H, s).

Example 116

1-[5-tert-Butyl-2-(2-morpholin-4-yl-ethyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea

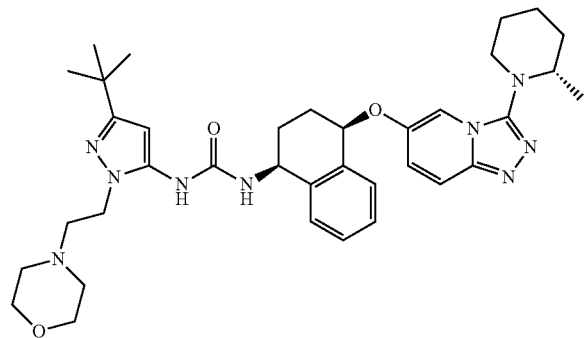 [SMILES: C[C@H]1CCCCN1c1nnc2ccc(O[C@@H]3CC[C@H](NC(=O)Nc4cc(C(C)(C)C)nn4CCN4CCOCC4)c4ccccc43)cn12]

A solution of Example 110 (80 mg, 0.136 mmol), DIPEA (71 μL, 0.409 mmol) and methanesulfonyl chloride (26 μL, 0.34 mmol) in DCM (3 mL) was stirred at RT for 90 min. Additional DIPEA (71 μL) and methanesulfonyl chloride (26 μL) were added and stirring was continued for 1 h. Water (1 mL) and a saturated aqueous solution of NaHCO$_3$ (2 mL) were added and the reaction mixture was vigorously stirred for 30 min. The aqueous phase was extracted with DCM (×3) and the combined organic layers were dried through a phase separator and concentrated in vacuo. The resultant residue was dissolved in DMF (2 mL) and morpholine (36 μL, 0.41 mmol) and heated at 75° C. for 18 h. After cooling, the volatiles were concentrated in vacuo and the resultant residue was loaded onto an SCX cartridge. The cartridge was washed with MeOH and the product eluted with 2M NH$_3$ in MeOH. The product containing fractions were combined and concentrated in vacuo and the resultant residue was purified by MDAP (Method 7) to afford the title compound (23 mg, 26%) as a white solid. LCMS (Method 5): Rt 3.48 min, m/z 656 [MH$^+$]. $^1$H NMR (400 MHz, d$_6$-DMSO): 0.92 (3H, d, J=6.3 Hz), 1.21 (9H, s), 1.46-1.58 (2H, m), 1.63-1.73 (2H, m), 1.74-1.87 (2H, m), 1.89-2.02 (2H, m), 2.02-2.24 (2H, m), 2.35-2.43 (4H, m), 2.63 (2H, t, J=7.1 Hz), 2.87-2.97 (1H, m), 3.14-3.22 (2H, m), 3.55 (4H, t, J=4.5 Hz), 4.01 (2H, t, J=7.1 Hz), 4.82-4.92 (1H, m), 5.51-5.57 (1H, m), 6.04 (1H, s), 7.10 (1H, d, J=8.6 Hz), 7.23 (1H, dd, J=9.8, 2.2 Hz), 7.27-7.42 (4H, m), 7.65 (1H, d, J=9.9 Hz), 7.72 (1H, s), 8.37-8.45 (1H, m).

Example 117

1-Cyclopropyl-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt

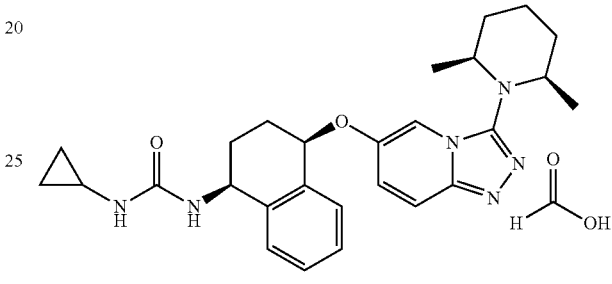

The title compound was prepared starting from Intermediate 96c and 4-nitrophenyl cyclopropylcarbamate (for reference procedure see WO 2007/72158, which is incorporated herein by reference in its entirety) using analogous procedures to those described in Example 99. LCMS (Method 5): Rt 4.70 min, m/z 614 [MH$^+$]. $^1$H NMR (400 MHz, d$_6$-DMSO): 0.31-0.35 (2H, m), 0.52-0.60 (8H, m), 1.33-1.56 (3H, m), 1.63-1.70 (2H, m), 1.73-1.88 (3H, m), 1.94-2.11 (2H, m), 3.08-3.20 (2H, m), 4.78 (1H, td, J=8.6, 6.8 Hz), 5.47 (1H, t, J=3.8 Hz), 6.07 (1H, d, J=2.1 Hz), 6.24 (1H, d, J=8.9 Hz), 7.15-7.22 (2H, m), 7.27-7.32 (3H, m), 7.62 (1H, d, J=9.8 Hz), 7.84 (1H, d, J=1.7 Hz), 8.12 (0.6H, br s).

Example 118

1-[5-tert-Butyl-2-(2-hydroxy-ethyl)-2H-pyrazol-3-yl]-3-{(1S,4R)-4-[3-((2S,6R)-2,6-dimethyl-piperidin-1-yl)-[1,2,4]triazolo[4,3-a]pyridin-6-yl oxy]-1,2,3,4-tetrahydro-naphthalen-1-yl}-urea

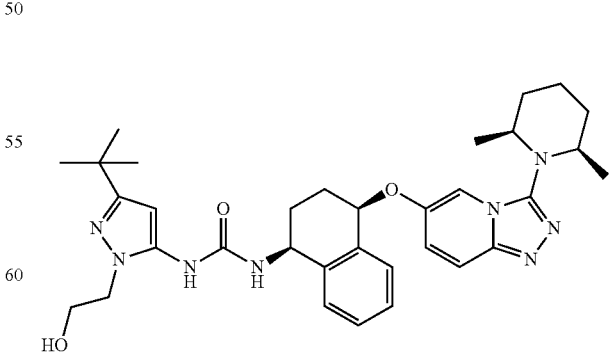

A mixture of Intermediate 96c (160 mg, 0.41 mmol), Intermediate 110b (142 mg, 0.41 mmol) and DIPEA (142 μL, 0.82 mmol) in dioxane (5 mL) was stirred at 80° C. overnight.

After cooling, the reaction mixture was partitioned between water and DCM. The aqueous phase was extracted with EtOAc (×3) and the combined organic layers were washed with brine, dried (MgSO$_4$) and concentrated in vacuo. The resultant residue was purified by FCC on silica, using a gradient of 1-8% MeOH in DCM followed by MDAP (Method 7) purification, to afford the title compound (86 mg, 32%) as a glassy white solid. LCMS (Method 5): Rt 4.32 min, m/z 601 [MH$^+$]. $^1$H NMR (400 MHz, d$_6$-DMSO): 0.55 (3H, d, J=6.2 Hz), 0.58 (3H, d, J=6.2 Hz), 1.17 (9H, s), 1.35-1.55 (3H, m), 1.63-1.69 (2H, m), 1.73-1.79 (1H, m), 1.82-2.00 (2H, m), 2.00-2.13 (2H, m), 3.09-3.19 (2H, m), 3.62 (2H, br s), 3.90 (2H, t, J=5.9 Hz), 4.82 (1H, td, J=8.6, 5.7 Hz), 4.92-4.98 (1H, br s), 5.50 (1H, t, J=4.2 Hz), 6.02 (1H, s), 7.04 (1H, d, J=8.6 Hz), 7.18 (1H, dd, J=9.8, 2.3 Hz), 7.20-7.25 (1H, m), 7.30-7.36 (3H, m), 7.62 (1H, dd, J=9.7, 0.6 Hz), 7.86 (1H, d, J=2.1 Hz), 8.14 (1H, s).

Example 119

1-{5-tert-Butyl-2-[1-(2-dimethylamino-ethyl)-1H-imidazol-4-yl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea

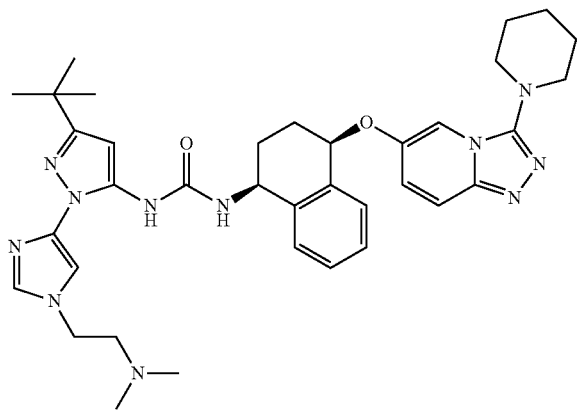 [SMILES: CN(C)CCn1cnc(-n2nc(C(C)(C)C)cc2NC(=O)N[C@H]2CC[C@@H](Oc3ccc4nnc(N5CCCCC5)n4c3)c3ccccc32)c1]

a. 4-Iodo-1-[2-(tetrahydro-pyran-2-yloxy)-ethyl]-1H-imidazole and 5-Iodo-1-[2-(tetrahydro-pyran-2-yloxy)-ethyl]-1H-imidazole (Intermediate 119a).

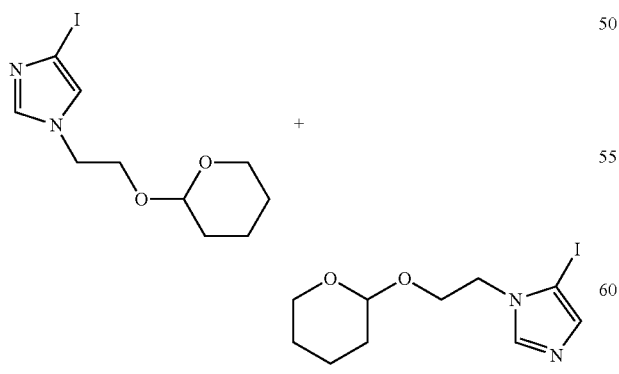

To an ice cold mixture of 4-iodo-1H-imidazole (1.0 g, 5.13 mmol) and sodium hydroxide (226 mg, 5.64 mmol) in DMF (10 mL) was added 2-(2-bromothoxy)tetrahydro-2H-pyran (1.18 mL, 5.64 mmol) and the mixture stirred overnight. The crude reaction mixture was poured into water and extracted with EtOAc (×3). The combined organic layers were washed with brine, dried (MgSO$_4$) and concentrated in vacuo. The resultant residue was purified by FCC on silica, using a gradient of 20-100% EtOAc in cyclohexane, to give the title compound (1.50 g, 91%) as a 2:1 mixture of regioisomers. LCMS (Method 4): Rt 2.03 min, m/z 323 [MH$^+$].

b. 5-tert-Butyl-2-{1-[2-(tetrahydro-pyran-2-yloxy)-ethyl]-1H-imidazol-4-yl}-2H-pyrazol-3-ylamine (Intermediate 119b).

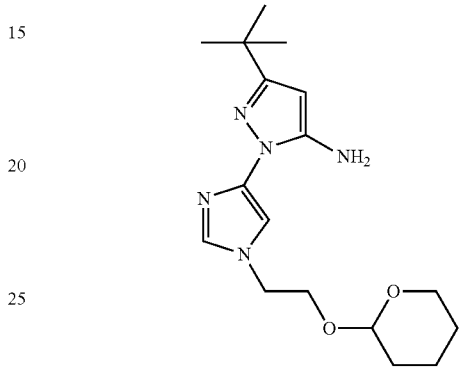

To a mixture of Intermediate 119a (1.50 g, 4.66 mmol), 5-tert-butyl-2H-pyrazol-3-ylamine (648 mg, 4.66 mmol), copper(I)iodide (44 mg, 0.23 mmol) and K$_2$CO$_3$ (1.35 g, 9.78 mmol) was added a solution of toluene (10 mL), previously degassed by using a stream of argon. (R,R)-(−)-N,N'-Dimethyl-1,2-cyclohexanediamine (147 µL, 0.93 mmol) was then added and the reaction mixture was heated at 150° C. for 3 h under microwave irradiation. The crude reaction mixture was poured into water and extracted with EtOAc (×3). The combined organic layers were washed with brine, dried (MgSO$_4$) and concentrated in vacuo. The resultant residue was purified by FCC on silica, using a gradient of 0-100% EtOAc in cyclohexane, to give a product consisting of the title compound (550 mg) in mixture with the un-reacted 5-iodo-1-[2-(tetrahydro-pyran-2-yloxy)-ethyl]-1H-imidazole isomer. LCMS (Method 4): Rt 2.32 min, m/z 334 [MH$^+$].

c. (5-tert-Butyl-2-{1-[2-(tetrahydro-pyran-2-yloxy)-ethyl]-1H-imidazol-4-yl}-2H-pyrazol-3-yl)-carbamic acid 2,2,2-trichloro-ethyl ester (Intermediate 119c).

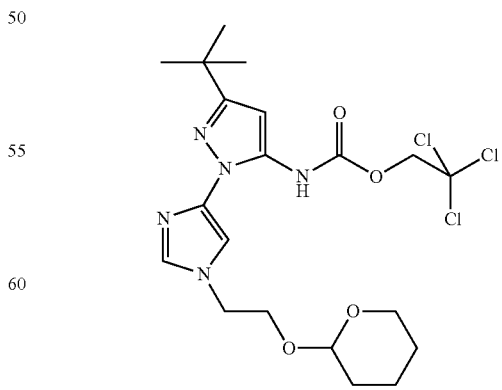

To a mixture of Intermediate 119b (550 mg) in water (3 mL) and EtOAc (6 mL) was added NaOH (132 mg, 3.30 mmol). After 10 min stirring, 2,2,2-trichloroethyl chloroformate (273 μL, 1.98 mmol) was added and the reaction mixture was stirred at RT for 2 h. The aqueous layer was extracted with EtOAc (×3) and the combined organic layers were washed with brine, dried (MgSO₄) and concentrated in vacuo. The resultant residue was purified by FCC on silica, using a gradient of 0-80% EtOAc in cyclohexane, to afford the title compound (175 mg). LCMS (Method 4): Rt 4.54 min, m/z 508, 510 [MH⁺].

d. 1-(5-tert-Butyl-2-{1-[2-(tetrahydro-pyran-2-yloxy)-ethyl]-1H-imidazol-4-yl}-2H-pyrazol-3-yl)-3-[(1S,4R)-4-(3-piperidin-1-yl-[1,2,4]triazolo[4,3-a]pyridin-6-yloxy)-1,2,3,4-tetrahydro-naphthalen-1-yl]-urea (Intermediate 119d).

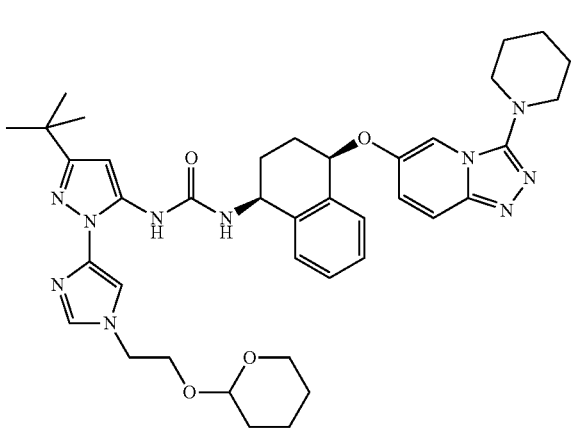 [SMILES: CC(C)(C)c1cc(NC(=O)N[C@H]2CC[C@@H](Oc3ccc4nnc(N5CCCCC5)n4c3)c3ccccc32)n(-c2cn(CCOC3CCCCO3)cn2)n1]

The title compound was prepared starting from Intermediate 3c and Intermediate 119c using analogous procedures to those described in Intermediate 106a. LCMS (Method 4): Rt 5.52 min, m/z 723 [MH⁺].

e. 1-{5-tert-Butyl-2-[1-(2-hydroxy-ethyl)-1H-imidazol-4-yl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea (Intermediate 119e).

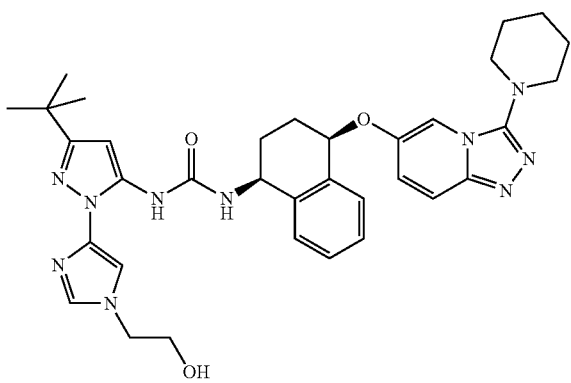 [SMILES: CC(C)(C)c1cc(NC(=O)N[C@H]2CC[C@@H](Oc3ccc4nnc(N5CCCCC5)n4c3)c3ccccc32)n(-c2cn(CCO)cn2)n1]

To a solution of intermediate 119d (135 mg, 0.19 mmol) in MeOH (2 mL) was added pyridinium p-toluenesulfonate (94 mg, 0.37 mmol) and the reaction mixture was heated at 60° C. for 3 h. The resultant mixture was poured into water and a saturated aqueous solution of NaHCO₃ was added. The aqueous phase was extracted with EtOAc (×3) and the combined organic layers were washed with brine, dried (MgSO₄) and concentrated in vacuo. The resultant residue was purified by FCC on silica, using a gradient of 2-10% MeOH in DCM, to give the title compound (65 mg, 53%). LCMS (Method 4): Rt 2.96 min, m/z 639 [MH⁺].

f. Methane sulfonic acid 2-[4-(3-tert-butyl-5-{3-[(1S,4R)-4-(3-piperidin-1-yl-[1,2,4]triazolo[4,3-a]pyridin-6-yloxy)-1,2,3,4-tetrahydro-naphthalen-1-yl]-ureido}-pyrazol-1-yl)-imidazol-1-yl]-ethyl ester (Intermediate 119f).

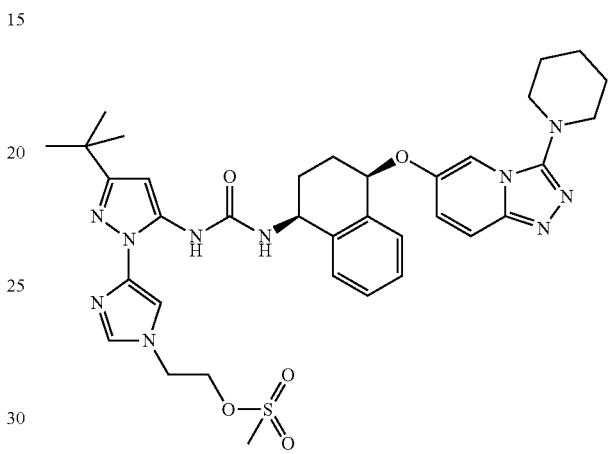

To an ice-bath cooled solution of Intermediate 119e (65 mg, 0.10 mmol) in DCM (1.5 mL) was added DIPEA (71 μL, 0.41 mmol) followed by methanesulfonyl chloride (16 μL, 0.20 mmol). The reaction mixture was stirred for 1 h and then quenched with water. The aqueous phase was extracted with DCM (×3) and the combined organic layers were washed with brine, dried (MgSO₄) and concentrated in vacuo to afford the title compound (Quantitative). Product used in the following step without further purification. LCMS (Method 4): Rt 3.23 min, m/z 717 [MH⁺].

g. 1-{5-tert-Butyl-2-[1-(2-dimethylamino-ethyl)-1H-imidazol-4-yl]-2H-pyrazol-3-yl}-3-[(1S,4R)-4-(3-piperidin-1-yl-[1,2,4]triazolo[4,3-a]pyridin-6-yloxy)-1,2,3,4-tetrahydro-naphthalen-1-yl]-urea (Example 119).

To a solution of Intermediate 119f (0.10 mmol) in THF (2 mL) was added dimethylamine (2M in MeOH, 0.4 mL, 0.8 mmol) and the reaction stirred at 50° C. for 24 h. The crude reaction mixture was cooled and partitioned between EtOAc and water. The aqueous phase was extracted with EtOAc (×3) and the combined organic layers were washed with brine, dried (MgSO₄) and concentrated in vacuo. The resultant residue was purified by FCC on silica, using a gradient of 0-10% [2M NH₃ in MeOH] in DCM followed by HPLC (XBridge C18 column, 30-98% MeCN in H₂O, 0.1% NH₄OH), to give the title compound (12 mg, 18%). LCMS (Method 5): Rt 3.43 min, m/z 666 [MH⁺]. ¹H NMR (400 MHz, d₆-DMSO): 1.21 (9H, s), 1.54-1.60 (2H, m), 1.65-1.71 (4H, m), 1.86-1.94 (2H, m), 1.95-2.05 (1H, m) 2.13 (6H, s), 2.13-2.16 (1H, m), 2.55 (2H, t, J=6.3 Hz), 3.10 (4H, t, J=5.2 Hz), 4.05 (2H, t, J=7.1 Hz), 4.86 (1H, td, J=8.4, 5.5 Hz), 5.51 (1H, t, J=4.5 Hz), 6.32 (1H, s), 7.12 (1H, dd, J=10.0, 1.9 Hz), 7.20-7.25 (2H, m), 7.28-7.36 (3H, m), 7.56-7.59 (2H, m), 7.63 (1H, d, J=1.4 Hz), 7.90 (1H, d, J=8.6 Hz), 9.63 (1H, br s).

Example 120

1-[5-tert-Butyl-2-(2-hydroxy-ethyl)-2H-pyrazol-3-yl]-3-{(1S,4R)-4-[3-((S)-1-methyl-piperidin-2-yl)-[1,2,4]triazolo[4,3-a]pyridin-6-yloxy]-1,2,3,4-tetrahydro-naphthalen-1-yl}-urea

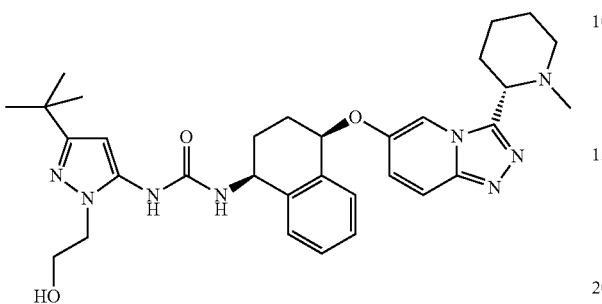

a. (S)-1-Methyl-piperidine-2-carboxylic acid N'-(5-fluoro-pyridin-2-yl)-hydrazide (Intermediate 120a).

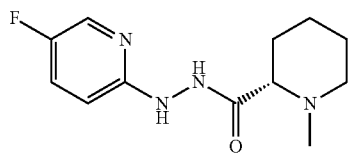 [SMILES: CN1CCCC[C@H]1C(=O)NNc1ccc(F)cn1]

To a solution of (S)-1-methyl-piperidine-2-carboxylic acid (250 mg, 1.74 mmol) and (5-fluoro-pyridin-2-yl)-hydrazine (244 mg, 1.92 mmol) in DCM (20 mL) was added HATU (790 mg, 2.09 mmol) and DIPEA (606 μL, 3.48 mmol) and the reaction stirred for 18 h. The reaction was then heated to 45° C. for 1 h then cooled and partitioned between EtOAc and water. The aqueous phase was extracted with EtOAc (×3) and the combined organic layers were washed with brine, dried (MgSO$_4$) and concentrated in vacuo. The resultant residue was purified by FCC on silica, using a gradient of 0-10% [2M NH$_3$ in MeOH] in DCM to give the title compound (272 mg, 62%). LCMS (Method 4): Rt 0.87 min, ink 253 [MH$^+$].

b. 6-Fluoro-3-((S)-1-methyl-piperidin-2-yl)-[1,2,4]triazolo[4,3-a]pyridine (Intermediate 120b).

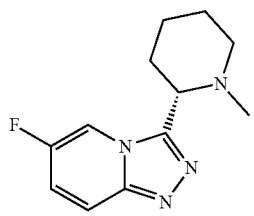

Hexachloroethane (505 mg, 2.14 mmol) was added portionwise over 5 min at RT to a stirred mixture of Intermediate 120a (270 mg, 1.07 mmol), triethylamine (595 μL, 4.28 mmol) and triphenylphosphine (560 mg, 2.14 mmol) in THF (10 mL). The reaction mixture was stirred for 1.5 h and then diluted with methanol and loaded onto an SCX cartridge. The cartridge was washed with MeOH and the product eluted with 2M NH$_3$ in MeOH and concentrated in vacuo. The resultant residue was purified by FCC on silica, using a gradient of 0-8% [2M NH$_3$ in MeOH] in EtOAc to give the title compound (105 mg, 42%). $^1$H NMR (400 MHz, CDCl$_3$): 1.34-1.51 (1H, m), 1.62-1.92 (5H, m), 2.00 (3H, s), 2.20 (1H, td, J=11.4, 3.7 Hz), 3.06 (1H, m), 3.87 (1H, dd, J=10.9, 3.3 Hz), 7.18 (1H, ddd, J=9.8, 7.6, 2.3 Hz), 7.71 (1H, ddd, J=9.9, 5.0, 0.7 Hz), 8.75-7.79 (1H, m).

c. (1S,4R)-4-[3-((S)-1-Methyl-piperidin-2-yl)-[1,2,4]triazolo[4,3-a]pyridin-6-yloxy]-1,2,3,4-tetrahydro-naphthalen-1-ylamine (Intermediate 120c).

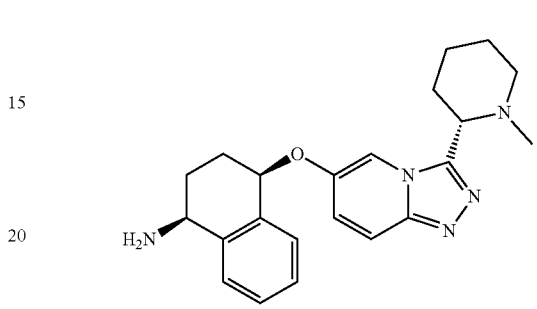

To a suspension of sodium hydride (60% in mineral oil, 54 mg, 1.34 mmol) in DMF (1 mL) was added Intermediate A (88 mg, 0.54 mmol) and the reaction mixture was stirred for 20 min. A solution of Intermediate 120b (105 mg, 0.45 mmol) in DMF (1 mL) was added and the reaction mixture was heated at 60° C. for 90 min. After cooling, the reaction mixture was quenched by careful addition of MeOH and then loaded onto an SCX cartridge. The cartridge was washed with MeOH and the product eluted with 2M NH$_3$ in MeOH. The product containing fractions were concentrated in vacuo and the resultant residue was purified by FCC on silica, using a gradient of 0-10% [2M NH$_3$ in MeOH] in DCM, to give the title compound (77 mg, 45%). $^1$H NMR (400 MHz, CDCl$_3$): 1.38-1.51 (1H, m), 1.52-1.90 (6H, m), 1.90-2.05 (1H, m), 2.03 (3H, s), 2.04-2.15 (1H, m), 2.15-2.22 (1H, m), 2.33-2.44 (1H, m), 2.99-3.06 (1H, m), 3.82 (1H, dd, J=11.3, 3.2 Hz), 3.99 (1H, dd, J=7.9, 5.1 Hz), 5.23 (1H, t, J=4.5 Hz), 7.11 (1H, dd, J=9.9, 2.2 Hz), 7.23-7.30 (1H, m), 7.34-7.41 (2H, m), 7.60 (1H, d, J=7.7 Hz), 7.65 (1H, dd, J=9.9, 0.7 Hz), 8.42 (1H, d, J=2.2 Hz).

d. 1-[5-tert-Butyl-2-(2-hydroxy-ethyl)-2H-pyrazol-3-yl]-3-{(1S,4R)-4-[3-((S)-1-methyl-piperidin-2-yl)-[1,2,4]triazolo[4,3-a]pyridin-6-yloxy]-1,2,3,4-tetrahydro-naphthalen-1-yl}-urea (Example 120).

A mixture of Intermediate 120c (35 mg, 0.10 mmol), Intermediate 110b (54 mg, 0.15 mmol) and DIPEA (53 μL, 0.30 mmol) in dioxane (1 mL) was stirred at 50° C. overnight. After cooling, the reaction mixture was loaded onto an SCX cartridge. The cartridge was washed with MeOH and the product eluted with 2M NH$_3$ in MeOH. The resultant residue was purified by FCC on silica, using a gradient of 1-8% MeOH in DCM followed by MDAP (Method 7) purification, to afford the title compound (4 mg, 7%) as a glassy white solid. LCMS (Method 5): Rt 3.02 min, m/z 586 [MH$^+$]. $^1$H NMR (400 MHz, d$_4$-MeOD): 1.20-1.30 (2H, m), 1.25 (9H, s), 1.40-1.52 (1H, m), 1.63-1.83 (3H, m), 1.85-1.92 (2H, m), 2.01 (3H, s), 2.06-2.20 (3H, m), 2.24 (1H, td, J=11.7, 3.1 Hz), 2.31-2.38 (1H, m), 3.04-3.09 (1H, m), 3.76-3.81 (1H, m), 3.81 (2H, t, J=5.4 Hz), 4.08 (2H, t, J=5.4 Hz), 4.98 (1H, dd, J=8.1, 6.5 Hz), 5.36 (1H, t, J=3.8 Hz), 6.12 (1H, s), 7.24 (1H, t, J=7.4 Hz), 7.28-7.37 (3H, m), 7.44 (1H, d, J=7.8 Hz), 7.66 (1H, dd, J=9.9, 0.6 Hz), 8.46 (1H, d, J=1.9 Hz).

Example 121

1-[5-tert-Butyl-2-(2-morpholin-4-yl-ethyl)-2H-pyrazol-3-yl]-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea

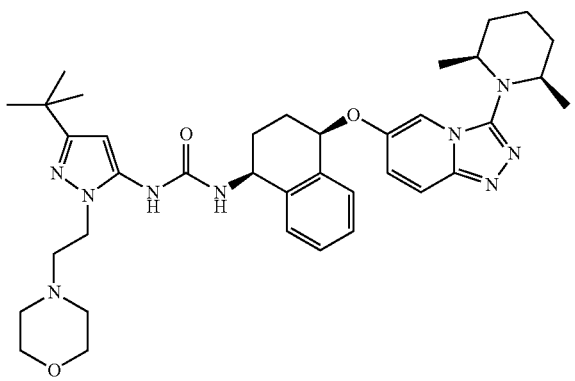 [SMILES: C[C@@H]1CCC[C@H](C)N1c1nnc2ccc(O[C@@H]3CC[C@H](NC(=O)Nc4cc(C(C)(C)C)nn4CCN4CCOCC4)c4ccccc43)cn12]

a. Methanesulfonic acid 2-[3-tert-butyl-5-(3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-ureido)-pyrazol-1-yl]-ethyl ester (Intermediate 121a).

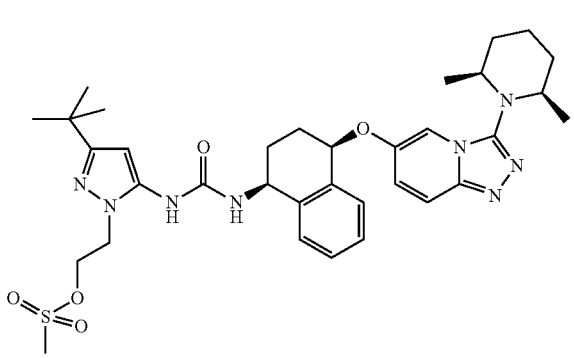 [SMILES: C[C@@H]1CCC[C@H](C)N1c1nnc2ccc(O[C@@H]3CC[C@H](NC(=O)Nc4cc(C(C)(C)C)nn4CCOS(C)(=O)=O)c4ccccc43)cn12]

To an ice-bath cooled solution of Example 118 (43 mg, 0.07 mmol) in DCM (1.5 mL) was added DIPEA (49 μL, 0.18 mmol) followed by methanesulfonyl chloride (11 μL, 0.11 mmol). The reaction mixture was stirred for 1 h and then quenched with water.

The aqueous phase was extracted with DCM (×3) and the combined organic layers were washed with brine, dried (MgSO$_4$) and concentrated in vacuo to afford the title compound (Quantitative). Product used in the following step without further purification. LCMS (Method 4): Rt 3.38 min, m/z 679 [MH$^+$].

b. 1-[5-tert-Butyl-2-(2-morpholin-4-yl-ethyl)-2H-pyrazol-3-yl]-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea (Example 121).

To a solution of Intermediate 121a (0.07 mmol) in THF (2 mL) was added DIPEA (50 μL, 0.29 mmol) and morpholine (25 μL, 0.29 mmol) and the reaction stirred at 50° C. for 24 h. The crude reaction mixture was cooled and partitioned between EtOAc and water. The aqueous phase was extracted with EtOAc (×3) and the combined organic layers were washed with brine, dried (MgSO$_4$) and concentrated in vacuo. The resultant residue was purified by FCC on silica, using a gradient of 0-10% [2M NH$_3$ in MeOH] in DCM followed by MDAP (Method 7) purification, to give the title compound (19 mg, 39%). LCMS (Method 5): Rt 3.65 min, m/z 670 [MH$^+$]. $^1$H NMR (400 MHz, d$_6$-DMSO): 0.56 (3H, d, J=6.2 Hz), 0.59 (3H, d, J=6.2 Hz), 1.16 (9H, s), 1.37-1.55 (3H, m), 1.63-1.69 (2H, m), 1.73-1.79 (1H, m), 1.85-2.00 (2H, m), 2.04-2.10 (2H, m), 2.34 (4H, t, J=4.5 Hz), 2.57 (2H, t, J=7.2 Hz), 3.09-3.19 (2H, m), 3.50 (4H, t, J=4.5 Hz), 3.95 (2H, t, J=7.2 Hz), 4.82 (1H, td, J=8.6, 5.7 Hz), 5.50 (1H, t, J=4.2 Hz), 5.99 (1H, s), 6.92 (1H, d, J=8.6 Hz), 7.18 (1H, dd, J=9.8, 2.3 Hz), 7.20-7.26 (1H, m), 7.30-7.36 (3H, m), 7.62 (1H, dd, J=9.7, 0.6 Hz), 7.86 (1H, d, J=2.1 Hz), 8.19 (1H, s).

Example 122

1-{(1S,4R)-4-[3-(8-Aza-bicyclo[3.2.1]oct-8-yl)-[1,2,4]triazolo[4,3-a]pyridin-6-yloxy]-1,2,3,4-tetrahydro-naphthalen-1-yl}-3-{5-tert-butyl-2-[3-(2-dimethylamino-ethoxy)-phenyl]-2H-pyrazol-3-yl}-urea formate salt

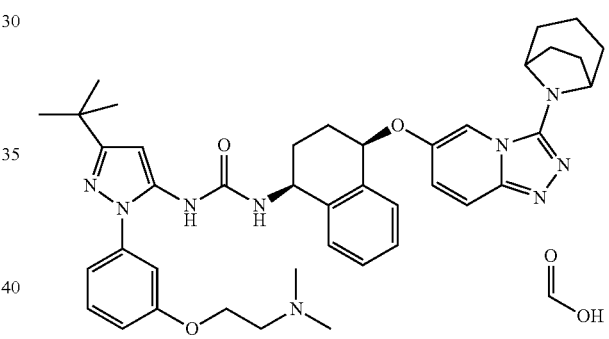

a. 8-Aza-bicyclo[3.2.1]octane-8-carbonyl chloride (Intermediate 122a).

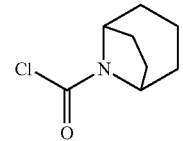 [SMILES: O=C(Cl)N1C2CCCC1CC2]

To a cooled (10° C.) solution 8-aza-bicyclo[3.2.1]octane (295 mg, 2.00 mmol) and pyridine (486 μL, 6.02 mmol) in DCM (10 mL) was added triphosgene (595 mg, 2.00 mmol) portionwise. The reaction was allowed to reach room temperature and stirred overnight. The mixture was quenched with HCl (1M aqueous, 10 mL) and stirred for 30 min. The aqueous phase was extracted with DCM (×3) and the combined organic layers were washed with HCl (1M aqueous), brine, dried (MgSO$_4$) and concentrated in vacuo, to give the title compound (244 mg, 70%). $^1$H NMR (400 MHz, CDCl$_3$): 1.46-1.70 (4H, m), 1.72-1.92 (5H, m), 2.04-2.11 (2H, m), 4.39-4.44 (2H, m).

b. 8-Aza-bicyclo[3.2.1]octane-8-carboxylic acid N'-(5-fluoro-pyridin-2-yl)-hydrazide (Intermediate 122b).

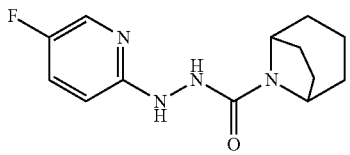 [SMILES: O=C(NNc1ccc(F)cn1)N1C2CCCC1CC2]

To a solution of Intermediate 122a (240 mg, 1.38 mmol) and (5-fluoro-pyridin-2-yl)-hydrazine (176 mg, 1.38 mmol) in DCM (10 mL) was added DIPEA (721 μL, 4.15 mmol) and the reaction stirred for 5 days. The reaction was then partitioned between DCM and water. The aqueous phase was extracted with DCM (×3) and the combined organic layers were washed with brine, dried (MgSO$_4$) and concentrated in vacuo. The resultant residue was purified by FCC on silica, using a gradient of 0-10% MeOH in DCM to give the title compound (170 mg, 47%). LCMS (Method 3): Rt 2.31 min, m/z 265 [MH$^+$].

c. 3-(8-Aza-bicyclo[3.2.1]oct-8-yl)-6-fluoro-[1,2,4]triazolo[4,3-a]pyridine (Intermediate 122c).

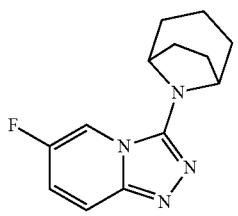 [SMILES: Fc1ccc2nnc(N3C4CCCC3CC4)n2c1]

Hexachloroethane (296 mg, 1.25 mmol) was added portionwise over 5 min at RT to a stirred mixture of Intermediate 122b (165 mg, 0.62 mmol), triethylamine (350 μL, 2.50 mmol) and triphenylphosphine (327 mg, 1.25 mmol) in THF (10 mL). The reaction mixture was stirred for 3.5 h and then heated to 60° C. overnight. The temperature was increased to 70° C. for 5 days, then cooled and concentrated in vacuo. The residue was taken up in dioxane, and re-treated with hexachloroethane (150 mg, 0.63 mmol) and triethylamine (200 μL, 1.43 mmol) at 115° C. overnight. The mixture was cooled and concentrated in vacuo. The residue was taken up in methanol and loaded onto an SCX cartridge. The cartridge was washed with MeOH and the product eluted with 2M NH$_3$ in MeOH and concentrated in vacuo to give the title compound (117 mg, 76%). LCMS (Method 3): Rt 2.88 min, m/z 247 [MH$^+$].

d. (1S,4R)-4-[3-(8-Aza-bicyclo[3.2.1]oct-8-yl)-[1,2,4]triazolo[4,3-a]pyridin-6-yloxy]-1,2,3,4-tetrahydro-naphthalen-1-ylamine (Intermediate 122d).

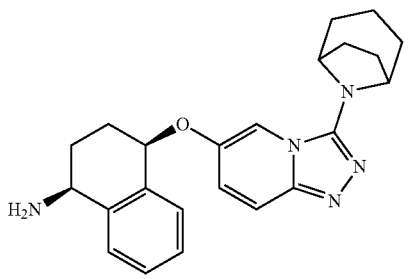 [SMILES: N[C@H]1CC[C@@H](Oc2ccc3nnc(N4C5CCCC4CC5)n3c2)c2ccccc21]

To a suspension of sodium hydride (60% in mineral oil, 51 mg, 1.3 mmol) in DMF (1.5 mL) was added Intermediate A (73 mg, 0.45 mmol) followed by intermediate 122c (110 mg, 0.45 mmol) and the reaction mixture was heated at 60° C. for 1 h. After cooling, the reaction mixture was quenched by careful addition of NH$_4$Cl (saturated aqueous) and the aqueous phase was extracted with EtOAc (×3). The combined organic layers were washed with brine, dried (MgSO$_4$) and concentrated in vacuo. The resultant residue was purified by FCC on silica, using a gradient of 0-10% [2M NH$_3$ in MeOH] in DCM to give the title compound (98 mg, 56%). LCMS (Method 3): Rt 2.26 min, m/z 390 [MH$^+$].

e. 1-{(1S,4R)-4-[3-(8-Aza-bicyclo[3.2.1]oct-8-yl)-[1,2,4]triazolo[4,3-a]pyridin-6-yloxy]-1,2,3,4-tetrahydro-naphthalen-1-yl}-3-{5-tert-butyl-2-[3-(2-dimethylamino-ethoxy)-phenyl]-2H-pyrazol-3-yl}-urea formate salt (Example 122).

The titled compound was prepared using Intermediate 95c and Intermediate 122d following the procedures described in Example 95. LCMS (Method 5): Rt 3.55 min, m/z 318.5 [MH$^+$]. $^1$H NMR (400 MHz, d$_6$-DMSO): 1.27 (9H, s), 1.46-1.58 (3H, m), 1.63-1.79 (3H, m), 1.87-2.16 (8H, m), 2.19 (6H, s), 2.61 (2H, t, J=5.9 Hz), 3.99 (2H, m), 4.08 (2H, t, J=5.9 Hz), 4.81 (1H, m), 5.52 (1H, m), 6.32 (1H, s), 6.96 (1H, m), 7.05-7.17 (4H, m), 7.25-7.42 (5H, m), 7.56-7.61 (2H, m), 8.14 (1H, s), 8.19 (1H, s).

Example 123

1-{5-tert-Butyl-2-[3-(2-dimethylamino-ethoxy)-phenyl]-2H-pyrazol-3-yl}-3-{(1S,4R)-4-[3-((R)-2-methyl-piperidin-1-yl)-[1,2,4]triazolo[4,3-a]pyridin-6-yloxy]-1,2,3,4-tetrahydro-naphthalen-1-yl}-urea partial formate salt

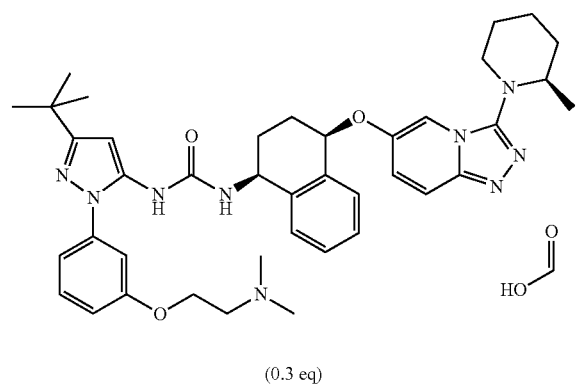 [SMILES: C[C@@H]1CCCCN1c1nnc2ccc(O[C@@H]3CC[C@H](NC(=O)Nc4cc(C(C)(C)C)nn4-c4cccc(OCCN(C)C)c4)c4ccccc43)cn12 ; O=CO]

(0.3 eq)

a. 1-{5-tert-Butyl-2-[3-(2-hydroxy-ethoxy)-phenyl]-2H-pyrazol-3-yl}-3-{(1S,4R)-4-[3-((R)-2-methyl-piperidin-1-yl)-[1,2,4]triazolo[4,3-a]pyridin-6-yloxy]-1,2,3,4-tetrahydro-naphthalen-1-yl}-urea (Intermediate 123a).

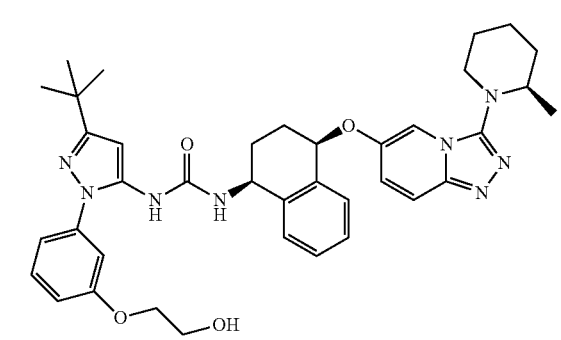 [SMILES: C[C@@H]1CCCCN1c1nnc2ccc(O[C@@H]3CC[C@H](NC(=O)Nc4cc(C(C)(C)C)nn4-c4cccc(OCCO)c4)c4ccccc43)cn12]

The title compound was prepared from (R)-2-methyl piperidine using analogous procedures to those described for the preparation of Intermediate 95e. LCMS (Method 3): Rt 3.63 min, m/z 679 [MH$^+$].

b. 1-{5-tert-Butyl-2-[3-(2-dimethylamino-ethoxy)-phenyl]-2H-pyrazol-3-yl}-3-{(1S,4R)-4-[3-((R)-2-methyl-piperidin-1-yl)-[1,2,4]triazolo[4,3-a]pyridin-6-yloxy]-1,2,3,4-tetrahydro-naphthalen-1-yl}-urea partial formate salt (Example 123).

To a solution of Intermediate 123a (108 mg, 0.159 mmol) and DIPEA (0.083 mL, 0.48 mmol) in DCM (4 mL) was added methanesulfonyl chloride (36.5 mg, 0.318 mmol) and the resulting yellow solution stirred at RT for 20 min. Water (2 mL) and sat. aq. NaHCO₃ solution (2 mL) were added, then the aqueous extracted with DCM (4 mL). The combined organics were passed through a hydrophobic fit and concentrated in vacuo to leave a yellow solid. The solid was dissolved in THF (2 mL), then dimethylamine (2 M in THF, 1.6 mL, 3.2 mmol) added, and the mixture stirred at 60° C. in a sealed vial for 18 h. The cooled solution was concentrated in vacuo, redissolved in MeOH (1 mL), applied to an SCX-2 cartridge (5 g), washed with MeOH (20 mL) and eluted with 2 M NH₃ in MeOH (20 mL); concentration in vacuo gave a glassy yellow solid (98 mg). MDAP (Method 7) gave a pale yellow solid (63 mg). Additional purification by HPLC (Gemini C18, 15-65% MeCN in water, 0.1% HCO₂H, 20 min, ×2) gave the title compound as a white solid (18.6 mg, 17%). LCMS (Method 5): Rt 3.62 min, m/z 706.6 [MH⁺]. ¹H NMR (400 MHz, d₆-DMSO): 0.88 (3H, d, J=6.3 Hz), 1.28 (9H, s), 1.48-1.56 (2H, m), 1.65-1.71 (2H, m), 1.76-1.96 (4H, m), 2.00-2.14 (2H, m), 2.17 (6H, s), 2.59 (2H, t, J=5.8 Hz), 2.95 (1H, ddd, J=12.2, 8.1, 4.8 Hz), 3.18 (1H, dt, J=12.1, 4.3 Hz), 3.26-3.29 (1H, m), 4.07 (2H, t, J=5.8 Hz), 4.81 (1H, td, J=8.6, 5.6 Hz), 5.53 (1H, t, J=4.3 Hz), 6.31 (1H, s), 6.95 (1H, dd, J=8.4, 2.2 Hz), 7.09 (2H, m), 7.18 (1H, dd, J=9.8, 2.2 Hz), 7.25-7.41 (6H, m), 7.64 (1H, d, J=9.9 Hz), 7.70 (1H, d, J=2.1 Hz), 8.34 (1H, s), 8.50 (0.3H, s).

Example 124

1-[3-tert-Butyl-1'-(2-morpholin-4-yl-ethyl)-1'H-[1,4']bipyrazolyl-5-yl]-3-((1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl)-urea formate salt

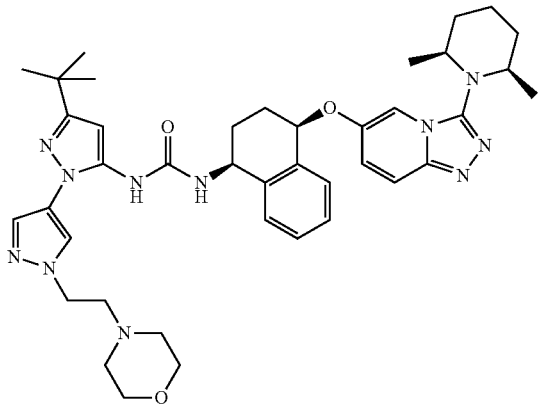 [SMILES: C[C@@H]1CCC[C@H](C)N1c1nnc2ccc(O[C@@H]3CC[C@H](NC(=O)Nc4cc(C(C)(C)C)nn4-c4cnn(CCN5CCOCC5)c4)c4ccccc43)cn12]

a. 1-{3-tert-Butyl-1'-[2-(tetrahydro-pyran-2-yloxy)-ethyl]-1'H-[1,4']bipyrazolyl-5-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea (Intermediate 124a).

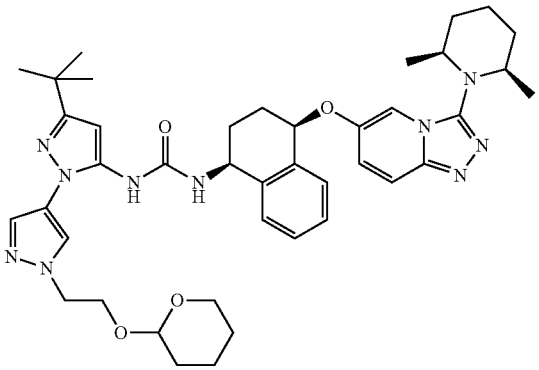 [SMILES: C[C@@H]1CCC[C@H](C)N1c1nnc2ccc(O[C@@H]3CC[C@H](NC(=O)Nc4cc(C(C)(C)C)nn4-c4cnn(CCOC5CCCCO5)c4)c4ccccc43)cn12]

A mixture of Intermediate 96c (200 mg, 0.51 mmol), Intermediate 108b (261 mg, 0.51 mmol) and DIPEA (178 µL, 1.02 mmol) in dioxane (5 mL) was stirred at 80° C. overnight. After cooling, the reaction mixture was partitioned between water and DCM. The aqueous phase was extracted with EtOAc (×3) and the combined organic layers were washed with brine, dried (MgSO₄) and concentrated in vacuo. The resultant residue was purified by FCC on silica, using a gradient of 1-10% MeOH in DCM to afford the title compound (364 mg, 95%) as a glassy white solid %). LCMS (Method 4): Rt 3.69 min, m/z 751 [MH⁺].

b. 1-[3-tert-Butyl-1'-(2-hydroxy-ethyl)-1'H-[1,4']bipyrazolyl-5-yl]-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea (Intermediate 124b).

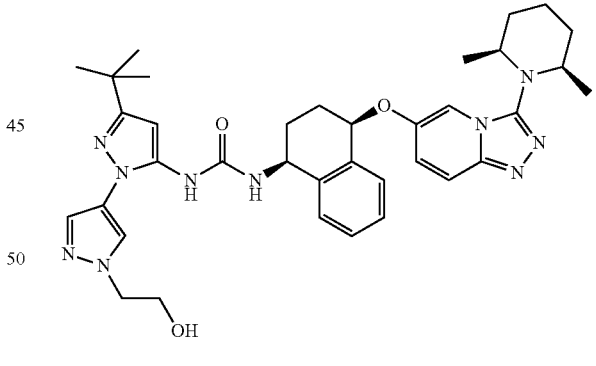

To a solution of Intermediate 124a (239 mg, 0.32 mmol) in MeOH (3.5 mL) was added pyridinium p-toluenesulfonate (160 mg, 0.64 mmol) and the reaction mixture was heated at 60° C. for 3 h. The resultant mixture was poured into water and a saturated aqueous solution of NaHCO₃ was added. The aqueous phase was extracted with EtOAc (×3) and the combined organic layers were washed with brine, dried (MgSO₄) and concentrated in vacuo. The resultant residue was purified by FCC on silica, using a gradient of 3-10% MeOH in DCM, to give the title compound (174 mg, 82%). LCMS (Method 4): Rt 3.22 min, m/z 667 [MH⁺].

c. Methanesulfonic acid 2-[3-tert-butyl-5-(3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-ureido)-[1,4']bipyrazolyl-1'-yl]-ethyl ester (Intermediate 124c).

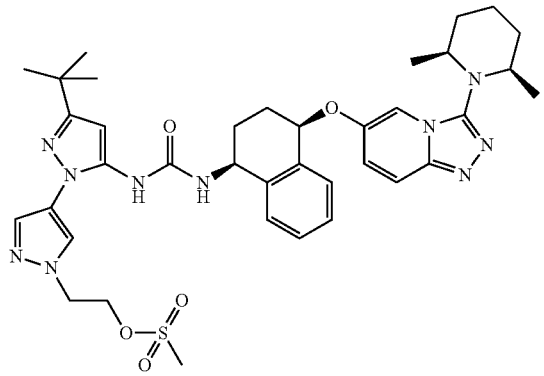 [SMILES: C[C@@H]1CCC[C@H](C)N1c1nnc2ccc(O[C@@H]3CC[C@H](NC(=O)Nc4cc(C(C)(C)C)nn4-c4cnn(CCOS(C)(=O)=O)c4)c4ccccc43)cn12]

To an ice-bath cooled solution of Intermediate 124b (174 mg, 0.26 mmol) in DCM (3 mL) was added DIPEA (182 μL, 1.0 mmol) followed by methanesulfonyl chloride (41 μL, 0.52 mmol). The reaction mixture was stirred for 1 h and then quenched with water. The aqueous phase was extracted with DCM (×3) and the combined organic layers were washed with brine, dried (MgSO$_4$) and concentrated in vacuo to afford the title compound (Quantitative). Product used in the following step without further purification. LCMS (Method 4): Rt 3.47 min, m/z 746 [MH$^+$].

d. 1-[3-tert-Butyl-1'-(2-morpholin-4-yl-ethyl)-1'H-[1,4']bipyrazolyl-5-yl]-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt (Example 124).

To a solution of Intermediate 124c (0.13 mmol) in THF (2.5 mL) was added DIPEA (90 μL, 0.52 mmol) and morpholine (45 μL, 0.52 mmol) and the reaction stirred at 50° C. for 24 h. The crude reaction mixture was cooled and partitioned between EtOAc and water. The aqueous phase was extracted with EtOAc (×3) and the combined organic layers were washed with brine, dried (MgSO$_4$) and concentrated in vacuo. The resultant residue was purified by FCC on silica, using a gradient of 0-10% [2M NH$_3$ in MeOH] in DCM, followed by MDAP (Method 7) purification, to give the title compound (26 mg, 26%). LCMS (Method 5): Rt 3.70 min, m/z 736 [MH$^+$]. $^1$H NMR (400 MHz, d$_6$-DMSO): 0.55 (3H, d, J=6.2 Hz), 0.58 (3H, d, J=6.2 Hz), 1.20 (9H, s), 1.34-1.54 3H, m), 1.63-1.68 (2H, m), 1.72-1.86 (2H, m), 1.89-1.97 (1H, m), 2.01-2.07 (2H, m), 2.37 (4H, t, J=4.4 Hz), 2.69 (2H, t, J=6.7 Hz), 3.08-3.18 (2H, m), 3.49 (4H, t, J=4.6 Hz), 4.19 (2H, t, J=6.7 Hz), 4.80 (1H, dt, J=8.6, 5.6 Hz), 5.49 (1H, t, J=4.3 Hz), 6.22 (1H, s), 7.11 (1H, d, J=8.6 Hz), 7.16 (1H, dd, J=9.8, 2.2 Hz), 7.19-7.25 (1H, m), 7.28-7.33 (3H, m), 7.59 (1H, s), 7.62 (1H, d, J=9.6 Hz), 7.84 (1H, d, J=1.9 Hz), 7.96 (1H, s), 8.02 (1H, s), 8.14 (0.6H, br s).

Example 125

1-[3-tert-Butyl-1'-(2-dimethylamino-ethyl)-1'H-[1,4']bipyrazolyl-5-yl]-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea

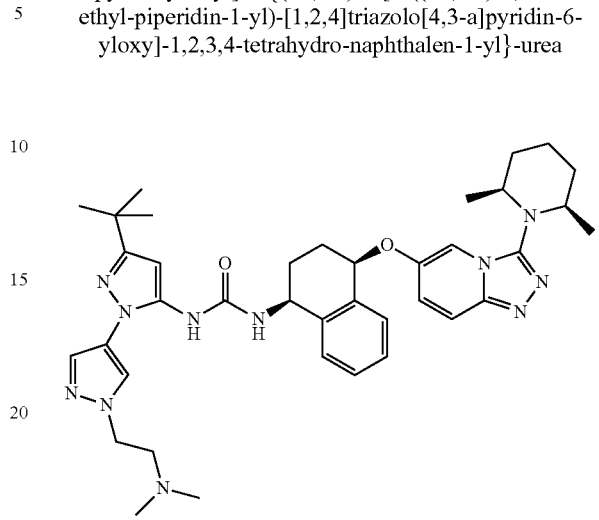

To a solution of Intermediate 124c (0.13 mmol) in THF (2.5 mL) was added dimethylamine (2M in MeOH, 1.3 mL, 2.6 mmol) and the reaction stirred at 50° C. for 24 h. The crude reaction mixture was cooled and partitioned between EtOAc and water. The aqueous phase was extracted with EtOAc (×3) and the combined organic layers were washed with brine, dried (MgSO$_4$) and concentrated in vacuo. The resultant residue was purified by FCC on silica, using a gradient of 2-10% [2M NH$_3$ in MeOH] in DCM, followed by MDAP (Method 7) purification, to give the title compound (26 mg, 29%). LCMS (Method 5): Rt 3.68 min, m/z 694 [MH$^+$]. $^1$H NMR (400 MHz, d$_6$-DMSO): 0.55 (3H, d, J=6.2 Hz), 0.58 (3H, d, J=6.2 Hz), 1.20 (9H, s), 1.34-1.54 3H, m), 1.63-1.68 (2H, m), 1.72-1.86 (2H, m), 1.89-1.97 (1H, m), 2.01-2.07 (2H, m), 2.23 (6H, br s), 2.77 (2H, br s), 3.08-3.18 (2H, m), 4.22 (2H, br s), 4.80 (1H, dt, J=8.6, 5.6 Hz), 5.49 (1H, t, J=4.3 Hz), 6.22 (1H, s), 7.11 (1H, d, J=8.6 Hz), 7.16 (1H, dd, J=9.8, 2.2 Hz), 7.19-7.25 (1H, m), 7.28-7.33 (3H, m), 7.60 (1H, s), 7.62 (1H, d, J=9.6 Hz), 7.84 (1H, d, J=1.9 Hz), 7.98 (1H, s), 8.02 (1H, s).

Example 126

1-(5-tert-Butyl-2-methyl-2H-pyrazol-3-yl)-3-{(1S,4R)-4-[3-((S)-2-methyl-piperidin-1-yl)-[1,2,4]triazolo[4,3-a]pyridin-6-yloxy]-1,2,3,4-tetrahydronaphthalen-1-yl]-urea

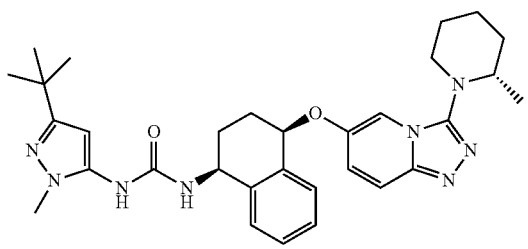 [SMILES: C[C@H]1CCCCN1c1nnc2ccc(O[C@@H]3CC[C@H](NC(=O)Nc4cc(C(C)(C)C)nn4C)c4ccccc43)cn12]

a. (5-tert-Butyl-2-methyl-2H-pyrazol-3-yl)-carbamic acid 2,2,2-trichloro-ethyl ester (Intermediate 126a).

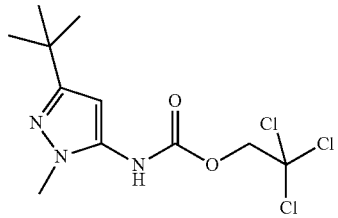 [SMILES: Cn1nc(C(C)(C)C)cc1NC(=O)OCC(Cl)(Cl)Cl]

A solution of 5-tert-butyl-2-methyl-2H-pyrazol-3-ylamine (0.5 g, 3.26 mmol) in EtOAc (10 mL) was treated with aqueous NaOH (1M, 5.87 mmol), followed by 2,2,2-trichloroethyl chloroformate (0.54 mL, 3.92 mmol) and the reaction mixture was stirred at RT for 1 h. The mixture was partitioned between EtOAc (10 mL) and water (2×10 mL). The organic layer was dried (MgSO$_4$), filtered and concentrated in vacuo. The residue was purified by FCC, using 0-100% EtOAc in cyclohexane to afford the title compound as a pale orange gum (0.915 g, 86%). LCMS (Method 3): Rt 3.88 min, m/z 328/330 [MH$^+$].

b. 1-(5-tert-Butyl-2-methyl-2H-pyrazol-3-yl)-3-{(1S,4R)-4-[3-((S)-2-methyl-piperidin-1-yl)-[1,2,4]triazolo[4,3-a]pyridin-6-yloxy]-1,2,3,4-tetrahydronaphthalen-1-yl]-urea (Example 126).

A solution of intermediate 126a (70 mg, 0.21 mmol), intermediate 81d (80 mg, 0.21 mmol) and DIPEA (55 µL, 0.32 mmol) in dioxane (1 mL) was heated at 70° C. for 18 h. The mixture was triturated with diethyl ether (1 mL) and the solid obtained was purified by MDAP (Method 7) to afford the title compound as a glassy solid (25 mg, 21%). LCMS (Method 5): Rt 4.19 min, m/z 557.3 [MH$^+$]. $^1$H NMR (400 MHz, d$_6$-DMSO): 0.91 (3H, d, J=6.1 Hz), 1.20 (9H, s), 1.44-1.57 (2H, m), 1.61-1.73 (2H, m), 1.74-1.87 (2H, m), 1.87-2.03 (2H, m), 2.03-2.22 (2H, m), 2.87-2.95 (1H, m), 3.13-3.20 (1H, m), 3.39 (1H, m, obscured by water), 3.57 (3H, s), 4.83-4.91 (1H, m), 5.54 (1H, t, J=4.0 Hz), 6.02 (1H, s), 6.93 (1H, d, J=8.9 Hz), 7.22 (1H, dd, J=9.8 Hz), 7.26-7.32 (1H, m), 7.35-7.42 (3H, m), 7.65 (1H, dd, J=9.7, 1.0 Hz), 7.70-7.73 (1H, m), 8.28 (1H, s).

Example 127

1-[5-tert-Butyl-2-(2-dimethylamino-ethyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

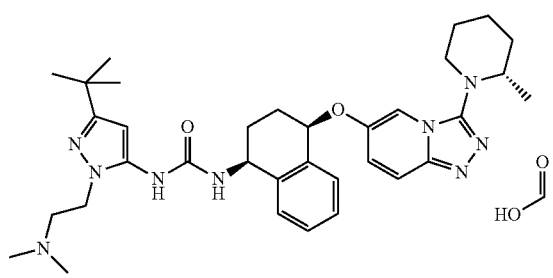

a. Methanesulfonic acid 2-[3-tert-butyl-5-(3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-ureido)-pyrazol-1-yl]-ethyl ester (Intermediate 127a).

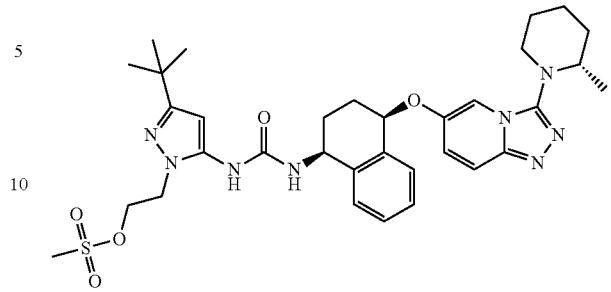

To a solution of Example 110 (176 mg, 0.300 mmol) and DIPEA (0.157 mL, 0.900 mmol) in DCM (5 mL) at 0° C. was added methanesulfonyl chloride (0.047 mL, 0.600 mmol) and the resulting orange solution stirred at 0° C. for 30 min. Water (2 mL) and sat. aq. NaHCO$_3$ solution (2 mL) were added and the mixture shaken. The aqueous was extracted with DCM (5 mL) then the combined organics passed through a hydrophobic frit and concentrated in vacuo to leave the title compound as a yellow gum (199 mg, 100%). LCMS (Method 3): Rt 3.59 min, m/z 665 [MH$^+$].

b. 1-[5-tert-Butyl-2-(2-dimethylamino-ethyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt (Example 127).

A yellow solution of Intermediate 127a (0.100 mmol) and dimethylamine (2M in THF, 1.0 mL, 2.0 mmol) in THF (1 mL) was stirred in a sealed vial at 60° C. for 16 h. The cooled solution was concentrated in vacuo, redissolved in MeOH (2 mL), applied to an SCX-2 cartridge (5 g) and washed with MeOH (15 mL). The product was eluted with 2M NH$_3$ in MeOH (15 mL); concentration in vacuo left a yellow film. MDAP (Method 7) gave the title compound as an off-white solid (42 mg, 62%). LCMS (Method 5): Rt 3.43 min, m/z 614.4 [MH$^+$]. $^1$H NMR (400 MHz, d$_6$-DMSO): 0.91 (3H, d, J=6.3 Hz), 1.21 (9H, s), 1.46-1.56 (2H, m), 1.63-1.72 (2H, m), 1.76-1.85 (2H, m), 1.92-2.01 (2H, m), 2.03-2.11 (1H, m), 2.15-2.19 (1H, m), 2.21 (6H, s), 2.61 (2H, t, J=6.9 Hz), 2.91 (1H, ddd, J=12.2, 9.2, 4.0 Hz), 3.17 (1H, dt, J=12.2, 4.3 Hz), 3.28-3.36 (1H, m), 3.99 (2H, t, J=6.9 Hz), 4.87 (1H, td, J=8.5, 6.2 Hz), 5.53 (1H, t, J=4.1 Hz), 6.03 (1H, s), 6.97 (1H, d, J=8.7 Hz), 7.21 (1H, dd, J=9.8, 2.2 Hz), 7.29 (1H, td, J=7.3, 2.0 Hz), 7.34-7.41 (3H, m), 7.65 (1H, dd, J=9.8, 0.8 Hz), 7.71 (1H, d, J=2.1 Hz), 8.17 (1.4H, s), 8.48 (1H, s).

Example 128

1-[5-tert-Butyl-2-(2-piperidin-1-yl-ethyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

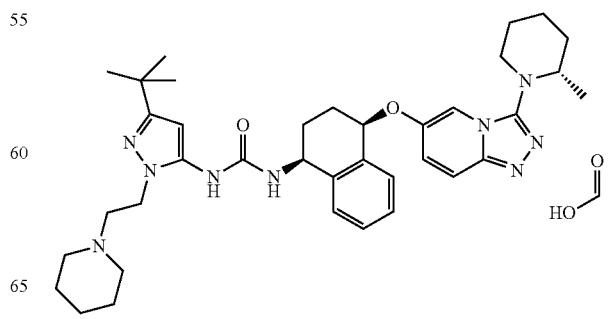

A yellow solution of Intermediate 127a (0.100 mmol) and piperidine (0.049 mL, 0.50 mmol) in dry DMF (2 mL) was stirred at 75° C. for 2.5 h. The cooled solution was concentrated in vacuo, redissolved in MeOH (2 mL), applied to an SCX-2 cartridge (2 g) and washed with MeOH (20 mL). The product was eluted with 2M $NH_3$ in MeOH (15 mL); concentration in vacuo left a yellow solid. MDAP (Method 7) gave the title compound as an off-white solid (37 mg, 52%). LCMS (Method 5): Rt 3.68 min, m/z 654.5 [MH$^+$]. $^1$H NMR (400 MHz, d$_6$-DMSO): 0.91 (3H, d, J=6.3 Hz), 1.20 (9H, s), 1.33-1.38 (2H, m), 1.45-1.55 (6H, m), 1.63-1.72 (2H, m), 1.75-1.86 (2H, m), 1.89-2.02 (2H, m), 2.04-2.12 (1H, m), 2.14-2.21 (1H, m), 2.40 (4H, t, J=4.7 Hz), 2.61 (2H, t, J=7.1 Hz), 2.91 (1H, ddd, J=12.2, 9.2, 4.2 Hz), 3.16 (1H, dt, J=12.0, 4.3 Hz), 3.32 (1H, m), 3.99 (2H, t, J=7.1 Hz), 4.87 (1H, td, J=8.5, 5.7 Hz), 5.54 (1H, t, J=4.3 Hz), 6.04 s), 6.95 (1H, d, J=8.6 Hz), 7.22 (1H, dd, J=9.8, 2.2 Hz), 7.29 (1H, td, J=7.2, 1.8 Hz), 7.34-7.41 (3H, m), 7.65 (1H, dd, J=9.8, 0.8 Hz), 7.71 (1H, d, J=2.1 Hz), 8.16 (1.4H, s), 8.29 (1H, s).

Example 129

1-{5-tert-Butyl-2-[2-(4-methyl-piperazin-1-yl)-ethyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

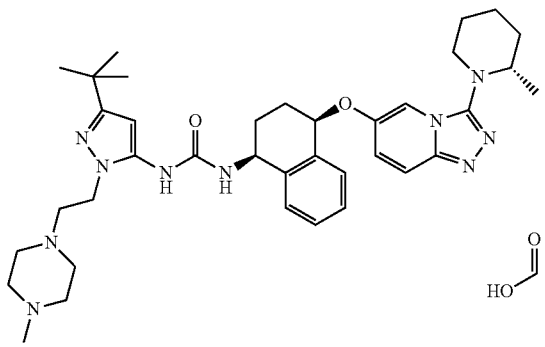 [SMILES: C[C@H]1CCCCN1c1nnc2ccc(O[C@@H]3CC[C@H](NC(=O)Nc4cc(C(C)(C)C)nn4CCN4CCN(C)CC4)c4ccccc43)cn12 ; O=CO]

A yellow solution of Intermediate 127a (0.100 mmol) and N-methyl piperazine (0.056 mL, 0.50 mmol) in dry DMF (2 mL) was stirred at 75° C. for 2.5 h. The cooled solution was concentrated in vacuo, redissolved in MeOH (2 mL), applied to an SCX-2 cartridge (5 g) and washed with MeOH (20 mL). The product was eluted with 2M $NH_3$ in MeOH (15 mL); concentration in vacuo left an orange solid. MDAP (Method 7) gave the title compound as an off-white solid (12 mg, 17%). LCMS (Method 5): Rt 3.36 min, m/z 669.5 [MH$^+$]. $^1$H NMR (400 MHz, d$_6$-DMSO): 0.91 (3H, d, J=6.3 Hz), 1.20 (9H, s), 1.49-1.56 (2H, m), 1.63-1.72 (2H, m), 1.75-1.85 (2H, m), 1.91-2.02 (2H, m), 2.04-2.10 (1H, m), 2.12 (3H, s), 2.14-2.21 (1H, m), 2.29 (4H, br s), 2.40 (4H, br s), 2.60 (2H, t, J=7.1 Hz), 2.91 (1H, ddd, J=12.2, 9.0, 4.0 Hz), 3.17 (1H, dt, J=12.0, 4.3 Hz), 3.28-3.36 (1H, m), 3.97 (2H, t, J=7.1 Hz), 4.87 (1H, td, J=8.5, 5.7 Hz), 5.54 (1H, t, J=4.3 Hz), 6.04 (1H, s), 6.95 (1H, d, J=8.6 Hz), 7.22 (1H, dd, J=9.8, 2.1 Hz), 7.29 (1H, td, J=7.2, 1.7 Hz), 7.34-7.41 (3H, m), 7.65 (1H, dd, J=9.8, 0.8 Hz), 7.71 (1H, d, J=2.1 Hz), 8.20 (1H, s), 8.27 (1H, s).

Example 130

1-[5-tert-Butyl-2-(3-morpholin-4-ylmethyl-phenyl)-2H-pyrazol-3-yl]-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt

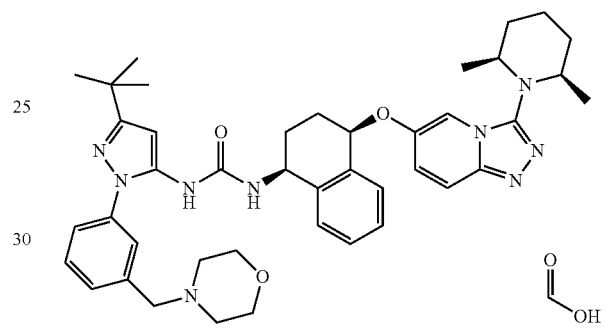

a. 1-[5-tert-Butyl-2-(3-hydroxymethyl-phenyl)-2H-pyrazol-3-yl]-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea (Intermediate 130a).

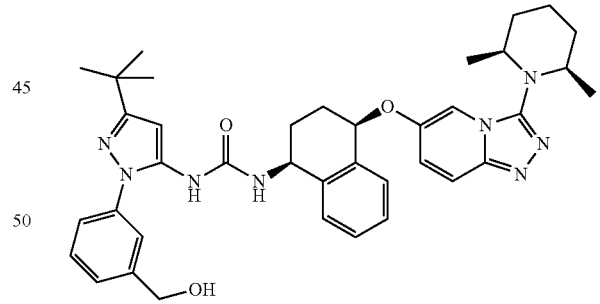

A mixture of Intermediate 96c (150 mg, 0.38 mmol), Intermediate 29c (161 mg, 0.38 mmol) and DIPEA (133 pt, 0.77 mmol) in dioxane (4 mL) was stirred at 80° C. for 7 hours. After cooling, the reaction mixture was partitioned between water and DCM. The aqueous phase was extracted with EtOAc (×3) and the combined organic layers were washed with brine, dried (MgSO$_4$) and concentrated in vacuo. The resultant residue was purified by FCC on silica, using a gradient of 1-10% MeOH in DCM to afford the title compound (364 mg, 95%) as a glassy white solid %). LCMS (Method 4): Rt 3.50 min, m/z 663 [MH$^+$].

b. Methanesulfonic acid 3-[3-tert-butyl-5-(3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-ureido)-pyrazol-1-yl]-benzyl ester (Intermediate 130b).

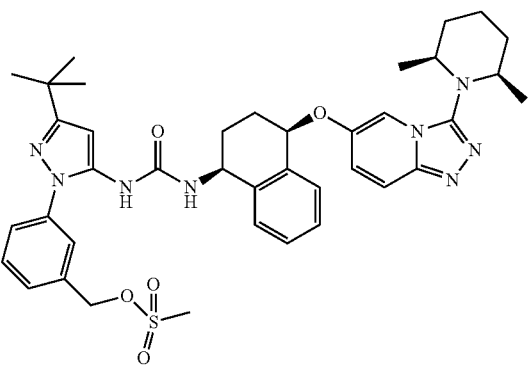 [SMILES: C[C@@H]1CCC[C@H](C)N1c1nnc2ccc(O[C@@H]3CC[C@H](NC(=O)Nc4cc(C(C)(C)C)nn4-c4cccc(COS(C)(=O)=O)c4)c4ccccc43)cn12]

To an ice-bath cooled solution of Intermediate 130a (175 mg, 0.26 mmol) in DCM (2.5 mL) was added DIPEA (184 µl, 1.0 mmol) followed by methanesulfonyl chloride (41 µL, 0.52 mmol). The reaction mixture was stirred for 1 h and then quenched with water. The aqueous phase was extracted with DCM (×3) and the combined organic layers were washed with brine, dried (MgSO$_4$) and concentrated in vacuo to afford the title compound (Quantitative). Product used in the following step without further purification. LCMS (Method 4): Rt 3.72 min, m/z 741 [MH$^+$].

c. 1-[5-tert-Butyl-2-(3-morpholin-4-ylmethyl-phenyl)-2H-pyrazol-3-yl]-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt (Example 130).

To a solution of Intermediate 130b (0.17 mmol) in THF (2 mL) was added DIPEA (122 µL, 0.70 mmol) and morpholine (62 µL, 0.70 mmol) and the reaction stirred at 50° C. for 24 h. The crude reaction mixture was cooled and partitioned between EtOAc and water. The aqueous phase was extracted with EtOAc (×3) and the combined organic layers were washed with brine, dried (MgSO$_4$) and concentrated in vacuo. The resultant residue was purified by FCC on silica, using a gradient of 0-10% (2M NH$_3$ in MeOH) in DCM, followed by MDAP (Method 7) purification, to give the title compound (25 mg, 19%). LCMS (Method 5): Rt 3.75 min, in/z 732 [MH$^+$]. $^1$H NMR (400 MHz, d$_6$-DMSO): 0.55 (3H, d, J=6.2 Hz), 0.58 (3H, d, J=6.2 Hz), 1.23 (9H, s), 1.35-1.53 3H, m), 1.63-1.68 (2H, m), 1.72-1.86 (2H, m), 1.86-1.92 (1H, m), 2.01-2.07 (2H, m), 2.32 (4H, t, J=4.1 Hz), 308-3.20 (2H, m), 3.46 (2H, s), 3.50 (4H, t, J=4.5 Hz), 4.78 (1H, td, J=8.6, 5.9 Hz), 5.47 (1H, t, J=4.2 Hz), 6.28 (1H, s), 6.98 (1H, d, J=8.6 Hz), 7.15 (1H, dd, J=9.8, 2.1 Hz), 7.17-7.23 (2H, m), 7.25-7.31 (3H, m), 7.32-7.44 (3H, m), 7.61 (1H, d, J=9.7 Hz), 7.83 (1H, d, J=1.8 Hz), 8.05 (1H, s), 8.12 (1.6H, s).

Example 131

1-{5-tert-Butyl-2-[3-(2-morpholin-4-yl-ethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

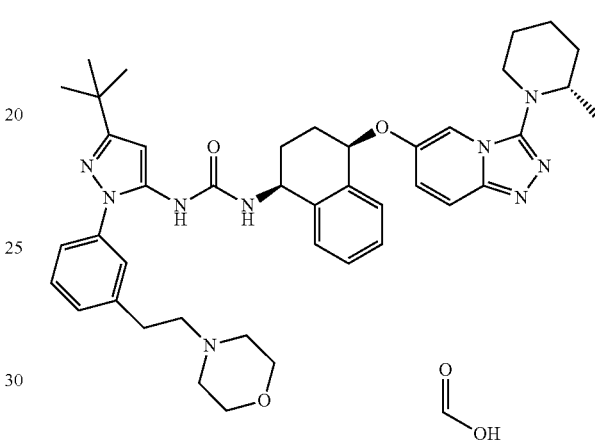

a. 2-[3-(5-Amino-3-tert-butyl-pyrazol-1-yl-phenol]-ethanol (Intermediate 131a).

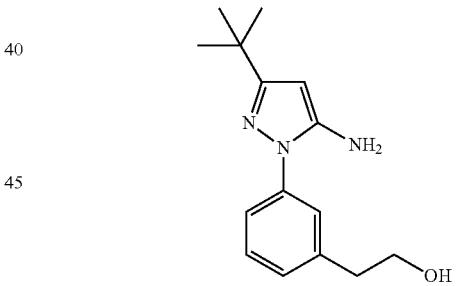

A mixture of 5-tert-butyl-2H-pyrazol-3-ylamine (629 mg, 4.52 mmol), 2-(3-bromophenyl)-ethanol (1 g, 4.52 mmol), copper (I) iodide (43 mg, 0.23 mmol), (1S,2S)—N,N'-dimethyl cyclohexane-1,2-diamine (129 mg, 0.90 mmol) and potassium carbonate (1.31 g, 9.50 mmol) in toluene (8 mL) was de-gassed and flushed with argon (3×). The reaction mixture was then treated with microwave irradiation, at 150° C. for 3 h and then at 160° C. for 16 h. The mixture was diluted with EtOAc (10 mL) and washed with water (10 mL). The aqueous layer was extracted with a further 10 mL of EtOAc and the combined organic layers were washed with brine (10 mL), dried (MgSO$_4$), filtered and concentrated in vacuo. The residue obtained was purified by FCC, using 0-100% EtOAc in cyclohexane to afford the title compound as a brown gum (364 mg, 31%). LCMS (Method 3): Rt 0.43/2.00/2.24 min, m/z 260 [MH$^+$].

b. {5-tert-Butyl-2-[3-[2-(hydroxyethyl)-phenyl]-2H-pyrazol-3-yl}-carbamic acid 2,2,2-trichloro-ethyl ester (Intermediate 131 b).

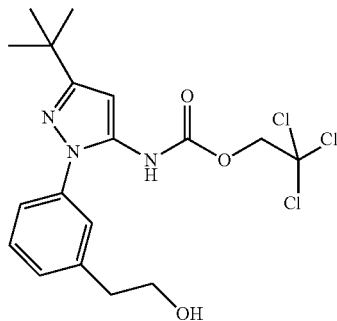 [SMILES: CC(C)(C)c1cc(NC(=O)OCC(Cl)(Cl)Cl)n(-c2cccc(CCO)c2)n1]

A solution of Intermediate 131a (364 mg, 1.40 mmol) in EtOAc (5 mL) was treated with aqueous NaOH (1M, 2.53 mmol), followed by 2,2,2-trichloroethyl chloroformate (231 μL, 1.68 mmol) and the reaction mixture was stirred at RT for 1 h. The mixture was partitioned between EtOAc (5 mL) and water (5 mL). The layers were separated and the aqueous layer was extracted with a further 5 mL EtOAc. The combined organic layers were dried (MgSO4), filtered and concentrated in vacuo. The residue was purified by FCC, using 0-50% EtOAc in cyclohexane to afford the title compound as a red gum (516 mg, 85%). LCMS (Method 3): Rt 4.03 min, m/z 434/436 [MH$^+$].

c. 1-{5-tert-Butyl-2-[3-(2-(hydroxyethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea (Intermediate 131c).

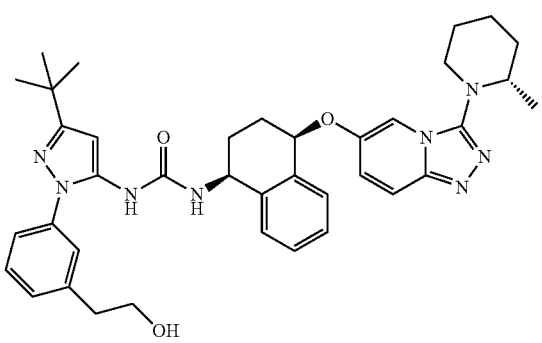 [SMILES: C[C@H]1CCCCN1c1nnc2ccc(O[C@@H]3CC[C@H](NC(=O)Nc4cc(C(C)(C)C)nn4-c4cccc(CCO)c4)c4ccccc43)cn12]

A mixture of Intermediate 131b (328 mg, 0.75 mmol), Intermediate 81d (285 mg, 0.75 mmol) and DIPEA (197 μL, 1.13 mmol) in dioxane (4.5 mL) was heated at 70° C. for 20 h. The reaction mixture was cooled to RT, diluted with DCM (10 mL) and washed with water (2×10 mL). The organic layer was passed through a hydrophobic fit and concentrated in vacuo. The residue was purified by FCC, using 0-10% [2M NH$_3$ in MeOH] in DCM to afford the title compound as a beige solid (358 mg, 72%). LCMS (Method 3): Rt 3.67 min, m/z 663 [MH$^+$].

d. Methanesulfonic acid 2-{3-[3-tert-butyl-5-(3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-ureido)-pyrazol-1-yl]-phenyl}-ethyl ester (Intermediate 131d).

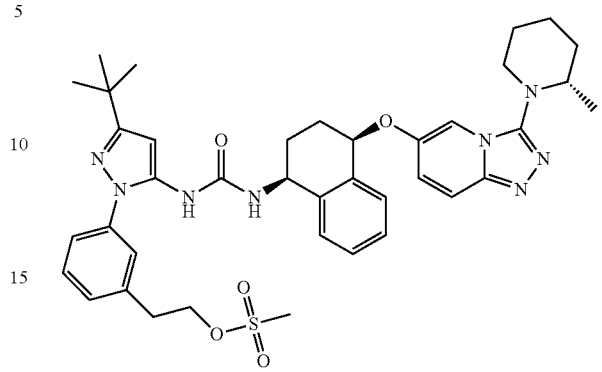

To a yellow solution of Intermediate 131c (358 mg, 0.540 mmol) and DIPEA (0.28 mL, 1.6 mmol) in DCM at 0° C. was added mesyl chloride (0.084 mL, 1.1 mmol) dropwise over 30 seconds, then the solution stirred at 0° C. for 30 min. Water (10 mL) and sat. aq. NaHCO$_3$ (10 mL) were added and the mixture shaken. The aqueous was extracted with DCM (10 mL), then the combined organics passed through a hydrophobic frit and concentrated in vacuo to leave a brown gum. LCMS (Method 3): Rt 3.91 min, m/z 741 [MH$^+$].

e. 1-{5-tert-Butyl-2-[3-(2-morpholin-4-yl-ethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt (Example 131).

A solution of Intermediate 131d (44.5 mg, 0.06 mmol) and morpholine (25.9 μL, 0.30 mmol) in THF (1 mL) was stirred at 60° C. for 20 h in a sealed tube. The mixture was concentrated in vacuo and the residue purified by MDAP (Method 7). The title product was isolated as an off-white solid (12 mg, 27%). LCMS (Method 5): Rt 3.64 min, m/z 732.6 [MH$^+$]. $^1$H NMR (400 MHz, d$_6$-DMSO): 0.91 (3H, d, J=6.2 Hz), 1.28 (9H, s), 1.50 (2H, m), 1.66 (2H, m), 1.76-2.18 (6H, overlapped m), 2.40 (4H, m), 2.53 (m, obscured by solvent), 2.80 (2H, m), 2.90 (1H, m), 3.15 (1H, m, obscured by solvent), 3.31 (m, obscured by solvent), 3.54 (4H, m), 4.82 (1H, m), 5.51 (1H, t, J=4.0 Hz), 6.32 (1H, s), 7.09 (1H, d, J=8.7 Hz), 7.19 (1H, dd, J=9.8, 2.4 Hz), 7.24-7.44 (8H, m), 7.63 (1H, m), 7.69 (1H, m), 8.10 (1H, s), 8.20 (1H, s).

Example 132

1-{5-tert-Butyl-2-[3-(2-pyrrolidin-1-yl-ethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

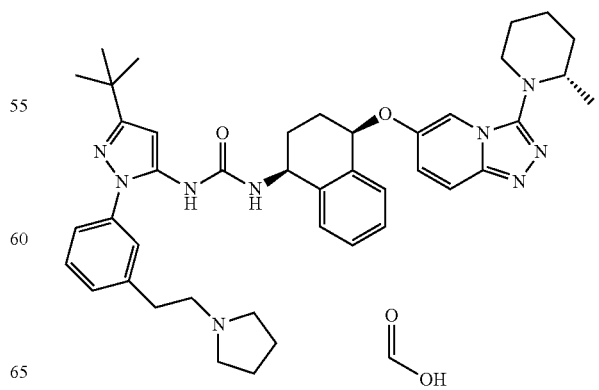

A solution of Intermediate 131d (44.5 mg, 0.06 mmol) and pyrrolidine (24.8 μL, 0.30 mmol) in THF (1 mL) was stirred at 60° C. for 20 h in a sealed tube. The mixture was concentrated in vacuo and the residue purified by MDAP (Method 7). The title product was isolated as an off-white solid (15 mg, 35%). LCMS (Method 5): Rt 3.70 min, ink 716.6 [MH+]. $^1$H NMR (400 MHz, d$_6$-DMSO): 0.91 (3H, d, J=6.6 Hz), 1.28 (9H, s), 1.50 (2H, m), 1.61-1.72 (6H, m), 1.76-2.18 (6H, overlapped m), 2.53 (m, obscured by solvent), 2.72 (2H, m), 2.82 (2H, m), 2.90 (1H, m), 3.16 (1H, m, obscured by solvent), 3.31 (m, obscured by solvent), 4.82 (1H, m), 5.52 (1H, t, J=4.2 Hz), 6.33 (1H, s), 7.10 (1H, d, J=8.4 Hz), 7.19 (1H, dd, J=10.0, 2.0 Hz), 7.24-7.44 (8H, m), 7.64 (1H, m), 7.69 (1H, m), 8.14 (1H, s), 8.19 (1H, s).

Example 133

1-(5-tert-Butyl-2-{3-[2-(ethyl-methyl-amino)-ethyl]-phenyl}-2H-pyrazol-3-yl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

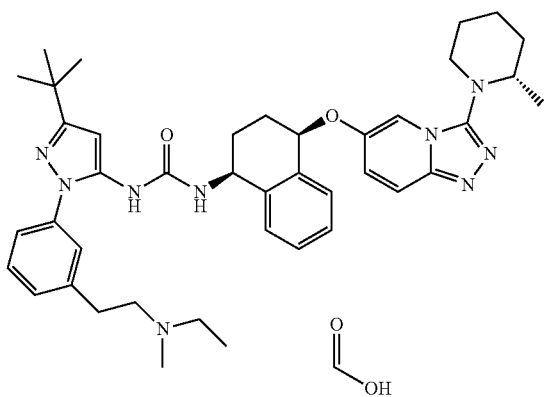 [SMILES: CCN(C)CCc1cccc(-n2nc(C(C)(C)C)cc2NC(=O)N[C@H]2CC[C@@H](Oc3ccc4nnc(N5CCCC[C@@H]5C)n4c3)c3ccccc32)c1 ; O=CO]

A solution of Intermediate 131d (44.5 mg, 0.06 mmol) and N-ethylmethylamine (25.8 μL, 0.30 mmol) in THF (1 mL) was stirred at 60° C. for 20 h in a sealed tube. The mixture was concentrated in vacuo and the residue purified by MDAP (Method 7). The title product was isolated as an off-white solid (10 mg, 24%). LCMS (Method 5): Rt 3.68 min, m/z 704.6 [MH+]. $^1$H NMR (400 MHz, d$_6$-DMSO): 0.91 (3H, d, J=6.2 Hz), 0.96 (3H, t, J=7.5 Hz), 1.28 (9H, s), 1.50 (2H, m), 1.66 (2H, m), 1.76-2.17 (6H, overlapped m), 2.20 (3H, s), 2.42 (2H, q, J=7.5 Hz), 2.60 (2H, m), 2.78 (2H, m), 2.90 (1H, m), 3.16 (1H, m, obscured by solvent), 3.31 (m, obscured by solvent), 4.82 (1H, m), 5.52 (1H, t, J=4.4 Hz), 6.33 (1H, s), 7.10 (1H, d, J=8.5 Hz), 7.19 (1H, dd, J=9.7, 2.2 Hz), 7.24-7.43 (8H, m), 7.64 (1H, d, J=9.6 Hz), 7.69 (1H, m), 8.12 (1H, s), 8.20 (1H, s).

Example 134

1-{5-tert-Butyl-2-[3-(2-dimethylamino-ethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

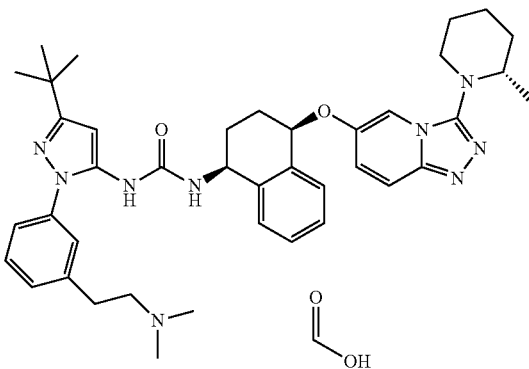 [SMILES: C[C@H]1CCCCN1c1nnc2ccc(O[C@@H]3CC[C@H](NC(=O)Nc4cc(C(C)(C)C)nn4-c4cccc(CCN(C)C)c4)c4ccccc43)cn12 ; O=CO]

A solution of Intermediate 131d (44.5 mg, 0.06 mmol) and dimethylamine solution (2M in THF, 0.6 mL, 1.2 mmol) in THF (1 mL) was stirred at 60° C. for 20 h in a sealed tube. The mixture was concentrated in vacuo and the residue purified by MDAP (Method 7). The title product was isolated as an off-white solid (18 mg, 41%). LCMS (Method 5): Rt 3.63 min, m/z 690.6 [MH+]. $^1$H NMR (400 MHz, d$_6$-DMSO): 0.91 (3H, d, J=6.3 Hz), 1.28 (9H, s), 1.47-1.55 (2H, m), 1.63-1.71 (2H, m), 1.75-1.97 (4H, m), 2.00-2.16 (2H, m), 2.19 (6H, s), 2.53 (2H, t, J=8.1 Hz), 2.78 (2H, t, J=7.6 Hz), 2.90 (1H, ddd, J=12.2, 9.0, 4.0 Hz), 3.16 (1H, dt, J=12.1, 4.2 Hz), 3.31 (1H, m), 4.82 (1H, td, J=8.6, 5.5 Hz), 5.52 (1H, t, J=4.3 Hz), 6.33 (1H, s), 7.09 (1H, d, J=8.6 Hz), 7.19 (1H, dd, J=9.8, 2.2 Hz), 7.24-7.42 (8H, m), 7.64 (1H, dd, J=9.8, 0.8 Hz), 7.69 (1H, d, J=2.1 Hz), 8.12 (1H, s), 8.19 (1H, s).

Example 135

1-{5-tert-Butyl-2-[3-(2-piperidin-1-yl-ethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

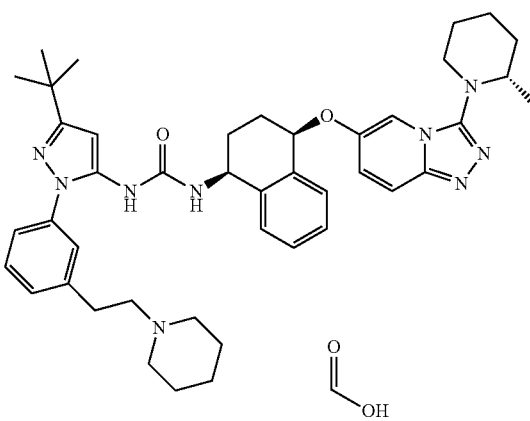

A solution of Intermediate 131d (44.5 mg, 0.06 mmol) and piperidine (30 μL, 0.30 mmol) in THF (1 mL) was stirred at 60° C. for 20 h in a sealed tube. The mixture was concentrated in vacuo and the residue purified by MDAP (Method 7). The title product was isolated as an off-white solid (26 mg, 55%). LCMS (Method 5): Rt 3.75 min, m/z 730.7 [MH$^+$]. $^1$H NMR (400 MHz, d$_6$-DMSO): 0.91 (3H, d, J=6.3 Hz), 1.28 (9H, s), 1.31-1.37 (2H, m), 1.43-1.55 (6H, m), 1.62-1.71 (2H, m), 1.75-1.97 (4H, m), 2.00-2.17 (2H, m), 2.41 (4H, t, J=4.4 Hz), 2.52-2.56 (2H, m), 2.79 (2H, t, J=7.9 Hz), 2.90 (1H, ddd, J=12.1, 9.1, 4.0 Hz), 3.16 (1H, dt, J=11.8, 4.1 Hz), 3.28-3.35 (1H, m), 4.82 (1H, td, J=8.6, 5.5 Hz), 5.52 (1H, t, J=4.3 Hz), 6.32 (1H, s), 7.09 (1H, d, J=8.6 Hz), 7.19 (1H, dd, J=9.9, 2.1 Hz), 7.24-7.42 (8H, m), 7.64 (1H, dd, J=9.8, 0.8 Hz), 7.69 (1H, d, J=2.1 Hz), 8.11 (1H, s), 8.19 (1.4H, s).

Example 136

1-(5-tert-Butyl-2-{3-[2-(4-methyl-piperazin-1-yl)-ethyl]-phenyl}-2H-pyrazol-3-yl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

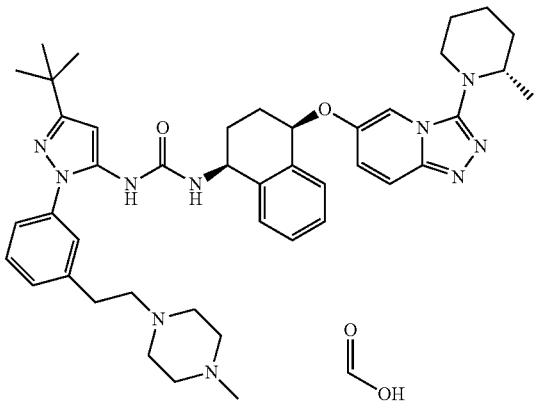 [SMILES: C[C@H]1CCCCN1c1nnc2ccc(O[C@@H]3CC[C@H](NC(=O)Nc4cc(C(C)(C)C)nn4-c4cccc(CCN5CCN(C)CC5)c4)c4ccccc43)cn12 ; O=CO]

A solution of Intermediate 131 d (44.5 mg, 0.06 mmol) and N-methylpiperazine (33 μL, 0.30 mmol) in THF (1 mL) was stirred at 60° C. for 20 h in a sealed tube. The mixture was concentrated in vacuo and the residue purified by MDAP (Method 7). The title product was isolated as an off-white solid (16 mg, 33%). LCMS (Method 5): Rt 3.54 min, adz 745.6 [MH$^+$]. $^1$H NMR (400 MHz, d$_6$-DMSO): 0.91 (3H, d, J=6.3 Hz), 1.28 (9H, s), 1.47-1.55 (2H, m), 1.63-1.71 (2H, m), 1.75-1.97 (4H, m), 2.00-2.08 (1H, m), 2.11 (3H, s), 2.12-2.17 (1H, m), 2.29 (4H, br s), 2.42 (4H, br s), 2.51-2.55 (2H, m), 2.76-2.80 (2H), 2.90 (1H, ddd, J=12.1, 9.1, 4.1 Hz), 3.16 (1H, dt, J=11.9, 4.2 Hz), 3.28-3.34 (1H, m), 4.82 (1H, td, J=8.6, 5.6 Hz), 5.52 (1H, t, J=4.3 Hz), 6.32 (1H, s), 7.08 (1H, d, J=8.6 Hz), 7.19 (1H, dd, J=9.8, 2.2 Hz), 7.24-7.42 (8H, m), 7.64 (1H, dd, J=9.8, 0.8 Hz), 7.69 (1H, d, J=2.1 Hz), 8.10 (1H, s), 8.19 (1.4H, s).

Example 137

1-{5-tert-Butyl-2-[3-(2-[1,4]oxazepan-4-yl-ethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

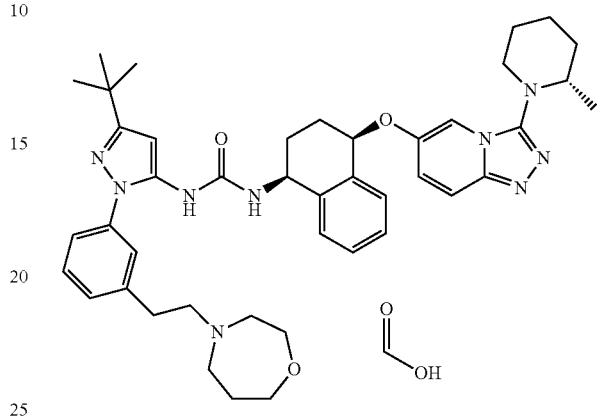

A solution of Intermediate 131d (44.5 mg, 0.06 mmol) and homomorpholine (30.4 mg, 0.30 mmol) in THF (1 mL) was stirred at 60° C. for 20 h in a sealed tube. The mixture was concentrated in vacuo and the residue purified by MDAP (Method 7). The title product was isolated as an off-white solid (15 mg, 31%). LCMS (Method 5): Rt 3.66 min, m/z 746.6 [MH$^+$]. $^1$H NMR (400 MHz, d$_6$-DMSO): 0.91 (3H, d, J=6.3 Hz), 1.28 (9H, s), 1.47-1.55 (2H, m), 1.63-1.71 (2H, m), 1.73-1.97 (6H, m), 2.00-2.17 (2H, m), 2.66-2.81 (8H, m), 2.90 (1H, ddd, J=12.2, 9.0, 4.0 Hz), 3.16 (1H, dt, J=12.2, 4.4 Hz), 3.28-3.34 (1H, m), 3.56-3.59 (2H, m), 3.63 (2H, t, J=6.0 Hz), 4.82 (1H, td, J=8.6, 5.5 Hz), 5.52 (1H, t, J=4.3 Hz), 6.33 (1H, s), 7.08 (1H, d, J=8.6 Hz), 7.19 (1H, dd, J=9.8, 2.2 Hz), 7.24-7.42 (8H, m), 7.64 (1H, dd, J=9.8, 0.8 Hz), 7.69 (1H, dd, J=2.1, 0.9 Hz), 8.09 (1H, s), 8.18 (1.3H, s).

Example 138

1-(5-tert-Butyl-2-{3-[2-(4-methyl-[1,4]diazepan-1-yl)-ethyl]-phenyl}-2H-pyrazol-3-yl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

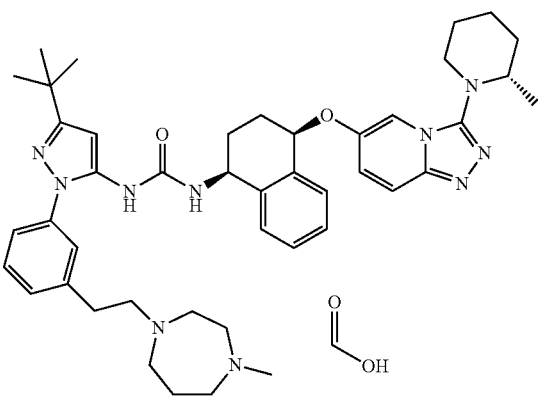 [SMILES: C[C@H]1CCCCN1c1nnc2ccc(O[C@@H]3CC[C@H](NC(=O)Nc4cc(C(C)(C)C)nn4-c4cccc(CCN5CCCN(C)CC5)c4)c4ccccc43)cn12 ; O=CO]

A solution of Intermediate 131 d (44.5 mg, 0.06 mmol) and N-methylhomopiperazine (34.3 mg, 0.300 mmol) in THF (1 mL) was stirred at 60° C. for 20 h in a sealed tube. The mixture was concentrated in vacuo and the residue purified by MDAP (Method 7) to give an off-white solid (22 mg). Prep HPLC (Gemini C, 18, 20-60% MeCN in water, 0.1% HCO$_2$H, 20 min) and concentration of the desired fractions removed the MeCN. The aqueous was washed with DCM (30 mL), then basified with aq. NaOH solution (1M, 0.5 mL) and extracted with DCM (2×10 mL). The combined organics were passed through a hydrophobic fit, then HCO$_2$H (0.01 mL) added and the mixture concentrated in vacuo to leave the title compound as a clear film that became a solid on standing (10.6 mg, 23%). LCMS (Method 5): Rt 3.19 min, m/z 759.7 [MH$^+$]. $^1$H NMR (400 MHz, d$_6$-DMSO): 0.91 (3H, d, J=6.3 Hz), 1.28 (9H, s), 1.48-1.55 (2H, m), 1.64-1.74 (4H, m), 1.77-1.96 (4H, m), 2.00-2.16 (2H, m), 2.29 (3H, s), 2.58-2.62 (4H, m), 2.69-2.80 (8H, m), 2.91 (1H, ddd, J=12.4, 9.3, 4.3 Hz), 3.16 (1H, dt, J=11.9, 4.3 Hz), 3.28-3.34 (1H, m), 4.82 (1H, td, J=9.0, 5.7 Hz), 5.52 (1H, t, J=4.3 Hz), 6.33 (1H, s), 7.09 (1H, d, J=8.6 Hz), 7.19 (1H, dd, J=9.8, 2.2 Hz), 7.24-7.42 (8H, m), 7.64 (1H, dd, J=9.8, 0.8 Hz), 7.69 (1H, dd, J=2.2, 0.9 Hz), 8.10 (1H, s), 8.19 (1.4H, s).

Example 139

1-[5-tert-Butyl-2-(2-hydroxy-ethyl)-2H-pyrazol-3-yl]-3-{(1S,4R)-4-[3-((S)-3-methyl-morpholin-4-yl)-[1,2,4]triazolo[4,3-a]pyridin-6-yloxy]-1,2,3,4-tetrahydro-naphthalen-1-yl}-urea

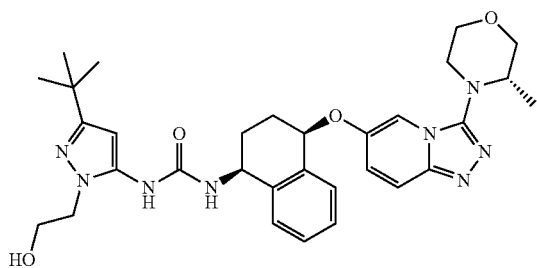 [SMILES: C[C@H]1COCCN1c1nnc2ccc(O[C@@H]3CC[C@H](NC(=O)Nc4cc(C(C)(C)C)nn4CCO)c4ccccc43)cn12]

a. (S)-3-Methyl-morpholine-4-carboxylic acid N-(5-fluoro-pyridin-2-yl)-hydrazide (Intermediate 139a).

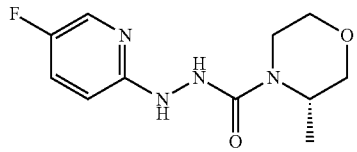 [SMILES: C[C@H]1COCCN1C(=O)NNc1ccc(F)cn1]

Pyridine (1.60 mL, 19.8 mmol) was added dropwise to an ice cold suspension of triphosgene (2.94 g, 9.90 mmol) in DCM (20.0 mL). (S)-3-Methylmorpholine (1.00 mL, 9.90 mmol) was added and the reaction stirred for 3 hours, then quenched by dropwise addition of HCl (1M aqueous, 20 mL). The mixture was extracted into DCM (3×). The combined organic layers were washed with brine, dried (MgSO$_4$), filtered and evaporated in vacuo to give (S)-3-methylmorpholine-carbamoylchloride (1.25 g, 77%). The product was used in the next reaction without purification. (S)-3-Methylmorpholine-carbamoylchloride (766 mg, 4.33 mmol) was dissolved in DCM (35.0 mL) and DIPEA (1.03 mL, 5390 mmol) was added followed by (5-fluoro-pyridin-2-yl)-hydrazine (WO2010022076, 500 mg, 3.94 mmol) and the reaction heated to 45° C. overnight. The reaction was cooled and quenched into water. The mixture was extracted into DCM (3×). The combined organic layers were washed with brine, dried (MgSO$_4$), filtered and evaporated in vacuo. The residue was purified by FCC using 0-10% [2M NH$_3$ in MeOH] in DCM to give the title compound (574 mg, 57%). $^1$H NMR (300 MHz, CDCl$_3$): 1.36 (3H, d, J=6.9 Hz), 3.30 (1H, td, J=12.5, 3.9 Hz), 3.47-3.74 (4H, m), 3.89-4.03 (2H, m), 6.41 (1H, br s), 6.45 (1H, br s), 6.73 (1H, dd, J=9.0, 3.5 Hz), 7.29 (1H, ddd, J=9.0, 7.9, 2.9 Hz), 8.04 (1H, d, J=2.9 Hz).

b. 6-Fluoro-3-((S)-3-methyl-morpholin-4-yl)-[1,2,4]triazolo[4,3-a]pyridine (Intermediate 139b).

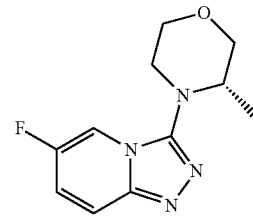

To an ice cold solution of Intermediate 139a (574 mg, 2.26 mmol) in THF (23.0 mL) was added sequentially triphenylphosphine (1.18 g, 4.52 mmol), triethylamine (1.26 mL, 9.04 mmol) and hexachloroethane (1.07 g, 4.52 mmol). The cooling bath was removed and the reaction was heated to 55° C. overnight. The reaction was cooled and partitioned between EtOAc and water. The aqueous layer was then extracted with EtOAc (3×). The combined organic layers were washed with brine, dried (MgSO$_4$), filtered and evaporated in vacuo. The residue was taken up in MeOH and loaded onto an SCX-2 cartridge, which was washed with MeOH and eluted with 2M NH$_3$ in MeOH. The residue was concentrated in vacuo and then re-submitted to the above reaction conditions overnight. The reaction was cooled and partitioned between EtOAc and water. The aqueous layer was then extracted with EtOAc (3×). The combined organic layers were washed with brine, dried (MgSO$_4$), filtered and evaporated in vacuo. The residue was purified by FCC using 0-10% [2M NH$_3$ in MeOH] in DCM to give the title compound (154 mg, 29%). $^1$H NMR (300 MHz, CDCl$_3$): 0.94 (3H, d, J=6.3 Hz), 3.13 (1H, dt, J=12.2, 3.1 Hz), 3.32 (1H, ddd, J=12.4, 9.5, 3.2 Hz), 3.49 (1H, dd, J=11.1, 8.6 Hz), 3.56-3.68 (1H, m), 3.84 (1H, ddd, J=12.1, 9.4, 2.7 Hz), 3.92-4.01 (2H, m), 7.16 (1H, ddd, J=9.9, 7.5, 2.3 Hz), 7.68 (1H, ddd, J=10.0, 4.8, 0.8 Hz), 7.85 (1H, m).

c. (1S,4R)-4-[3-((S)-3-Methyl-morpholin-4-yl)-[1,2,4]triazolo[4,3-a]pyridin-6-yloxy]-1,2,3,4-tetrahydro-naphthalen-1-ylamine (Intermediate 139c).

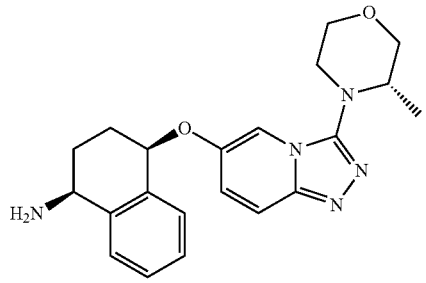 [SMILES: C[C@H]1COCCN1c1nnc2ccc(O[C@@H]3CC[C@H](N)c4ccccc43)cn12]

To a suspension of sodium hydride (60% in mineral oil, 187 mg, 4.68 mmol) in DMF (6.0 mL) was added Intermediate A (191 mg, 1.17 mmol) and the reaction stirred for 20 min. Intermediate 139b (276 mg, 1.17 mmol) was added in DMF (2.00 mL) and the reaction heated to 60° C. for 1 h. The reaction was cooled and quenched by dropwise addition of methanol, before being diluted with methanol and loaded onto an SCX-2 cartridge, which was washed with MeOH. The product was eluted with 2M NH₃ in MeOH. The residue was purified by FCC, using 0-10% [2M NH₃ in MeOH] in DCM, to give the title compound (250 mg, 56%). LCMS (Method 4): Rt 1.83, m/z 380 [MH⁺].

d. 1-[5-tert-Butyl-2-(2-hydroxy-ethyl)-2H-pyrazol-3-yl]-3-{(1S,4R)-4-[3-((S)-3-methyl-morpholin-4-yl)-[1,2,4]triazolo[4,3-a]pyridin-6-yloxy]-1,2,3,4-tetrahydro-naphthalen-1-yl}-urea (Example 139).

A mixture of Intermediate 139c (125 mg, 0.33 mmol), Intermediate 110b (115 mg, 0.33 mmol) and DIPEA (115 µL, 0.66 mmol) in dioxane (3 mL) was stirred at 80° C. overnight. After cooling, the reaction mixture was partitioned between water and DCM. The aqueous phase was extracted with EtOAc (×3) and the combined organic layers were washed with brine, dried (MgSO₄) and concentrated in vacuo. The resultant residue was purified by FCC, using a gradient of 0-10% MeOH in DCM, to afford the title compound (94 mg, 48%). A sample of this (40.0 mg) was further purified by MDAP (Method 7) purification to afford the title compound (20 mg) as a white solid. LCMS (Method 5): Rt 3.64 min, m/z 589 [MH⁺]. ¹H NMR (400 MHz, d₆-DMSO): 0.83 (3H, d, J=5.6 Hz), 1.16 (9H, s), 1.83-1.96 (2H, m), 1.97-2.07 (1H, m), 2.08-2.17 (1H, m), 2.95 (1H, ddd, J=12.0, 7.2, 4.9 Hz), 3.17 (1H, dt, J=12.2, 3.3 Hz), 3.36-3.44 (2H, m), 3.62 (2H, q, J=5.5 Hz), 3.72-3.80 (2H, m), 3.81-3.88 (1H, m), 3.88-3.92 (2H, t, J=6.0 Hz), 4.81 (1H, td, J=8.5, 6.1 Hz), 4.96 (1H, t, J=5.0 Hz), 5.52 (1H, t, J=4.2 Hz), 6.02 (1H, s), 7.05 (1H, d, J=8.6 Hz), 7.18 (1H, dd, J=9.9, 2.1 Hz), 7.22-7.27 (1H, m), 7.30-7.37 (3H, m), 7.62 (1H, d, J 9.9 Hz), 7.79 (1H, d, J=1.9 Hz), 8.16 (1H, s).

Example 140

1-(5-tert-Butyl-2-{2-[(2-dimethylamino-ethyl)-methyl-amino]-pyrimidin-4-yl}-2H-pyrazol-3-yl)-3-{((1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea

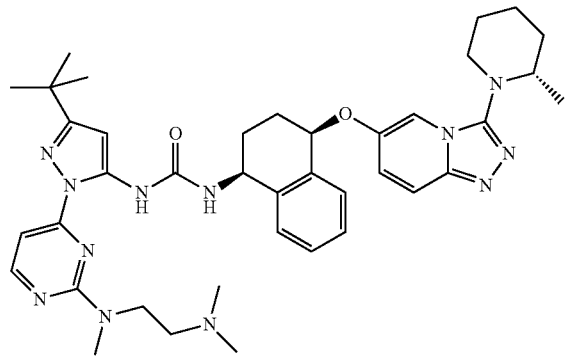 [SMILES: C[C@H]1CCCCN1c1nnc2ccc(O[C@@H]3CC[C@H](NC(=O)Nc4cc(C(C)(C)C)nn4-c4ccnc(N(C)CCN(C)C)n4)c4ccccc43)cn12]

a. 5-tert-Butyl-2-(2-chloro-pyrimidin-4-yl)-2H-pyrazol-3-ylamine (Intermediate 140a).

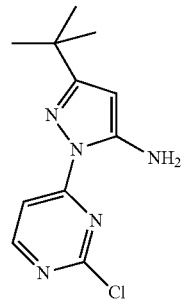 [SMILES: CC(C)(C)c1cc(N)n(-c2ccnc(Cl)n2)n1]

A mixture of 2,4-dichloropyrimidine (1.0 g, 6.7 mmol), 3-(tert-butyl)-1H-pyrazol-5-amine (1.03 g, 7.4 mmol) and sodium carbonate (1.42 g, 13.4 mmol) in 1,4-dioxane was treated with 4,5-bis(diphenylphosphino)-9,9-dimethylxanthene (xantphos) (58 mg, 0.10 mmol) followed by tris(dibenzylideneacetone)dipalladium (31 mg, 0.03 mmol). The mixture was degassed then heated to 70° C. under N₂ for 5 h. After cooling to room temperature the mixture was filtered and the filtrate was concentrated in vacuo. The residue was partitioned between EtOAc and water and the phases were separated. The aqueous layer was extracted with EtOAc (×2) and the combined organic phase was washed with brine, dried (Na₂SO₄) and concentrated in vacuo. The residue was purified by FCC, using 0-15% EtOAc in cyclohexane, to give the title compound (0.59 g, 35%). LCMS (Method 3): Rt 3.97 min, m/z 252.2 [MH⁺].

b. N-[4-(5-Amino-3-tert-butyl-pyrazol-1-yl)-pyrimidin-2-yl]-N,N',N'-trimethyl-ethane-1,2-diamine (Intermediate 140b).

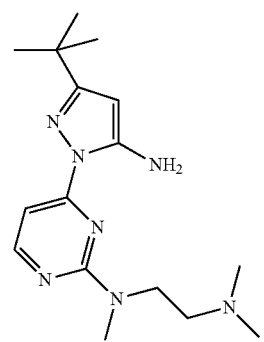 [SMILES: CN(C)CCN(C)c1nccc(-n2nc(C(C)(C)C)cc2N)n1]

A solution of Intermediate 140a (250 mg, 0.99 mmol) and N,N,N'-trimethylethylenediamine (0.32 mL, 2.48 mmol) in IPA (2.5 mL) was heated to 120° C. for 10 mins under microwave irradiation. The cooled reaction mixture was concentrated in vacuo and the residue was partitioned between EtOAc and water. The phases were separated and the aqueous layer was extracted with EtOAc (×2). The combined organic phase was washed with brine, dried (Na₂SO₄) and concentrated in vacuo to give the title compound (0.31 g, quant.) as a golden oil that was used in the next step without purification. LCMS (Method 3): Rt 2.51 min, m/z 318.3 [MH⁺].

c. (5-tert-Butyl-2-{2-[(2-dimethyl amino-ethyl)-methyl-amino]-pyrimidin-4-yl}-2H-pyrazol-3-yl)-carbamic acid phenyl ester (Intermediate 140c).

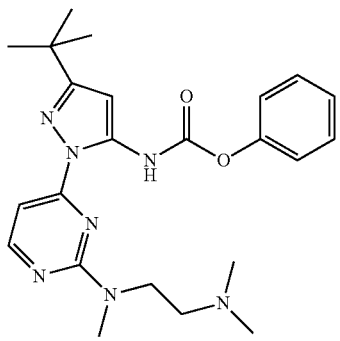 [SMILES: CN(C)CCN(C)c1nccc(-n2nc(C(C)(C)C)cc2NC(=O)Oc2ccccc2)n1]

A solution of Intermediate 140b (129 mg, 0.41 mmol) in DCM (4.1 mL) was treated with pyridine (0.046 mL, 0.57 mmol) and the mixture was cooled 0° C. Phenyl chloroformate (0.066 mL, 0.53 mmol) was added and the resulting mixture was stirred at RT for 16 h. The mixture was cooled to 0° C. and treated with pyridine (0.013 mL, 0.16 mmol) then phenyl chloroformate (0.015 mL, 0.12 mmol) and stirred at RT for a further 1.75 h. Once again the mixture was cooled to 0° C. and treated with pyridine (0.013 mL, 0.16 mmol) then phenyl chloroformate (0.015 mL, 0.12 mmol) and stirred at RT for 1.75 h. The mixture was diluted with water and the phases were separated. The aqueous layer was extracted with DCM (×2) and the combined organic phase was washed with brine, dried (Na$_2$SO$_4$), and concentrated in vacuo to give a yellow gum (236 mg). Trituration with ether and filtration of the resulting solid gave the title compound as a white solid (75 mg, 39%). LCMS (Method 3): Rt 3.21 min, m/z 438.4 [MH$^+$].

d. 1-(5-tert-Butyl-2-{2-[(2-dimethylamino-ethyl)-methyl-amino]-pyrimidin-4-yl}-2H-pyrazol-3-yl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea (Example 140).

A solution of Intermediate 81d (25 mg, 0.066 mmol) in 1,4-dioxane (0.7 mL) was treated with Intermediate 140c (32 mg, 0.073 mmol) and DIPEA (0.014 mL, 0.083 mmol) and the mixture was stirred at 70° C. for 18 h. The cooled solution was concentrated in vacuo, and the residue was partitioned between DCM and water. The phases were separated and the aqueous layer was extracted with DCM (×2). The combined organic phase was washed with brine, dried (Na$_2$SO$_4$) and concentrated in vacuo to a brown gum. FCC, using 0-8% MeOH in DCM, gave a colourless glass (27 mg). The glass was purified further by HPLC (Phenomenex Gemini C18 column, 5-95% MeCN in H$_2$O, 0.1% HCO$_2$H) over 30 mins. Concentration of the fractions in vacuo gave a colourless glass that was dissolved in ether. A solid was precipitated out of solution by addition of cyclohexane. The solid was filtered off to give the title compound as a white solid (8 mg, 17%). LCMS (Method 5): Rt 4.07 min, m/z 721.6 [MH$^+$]. $^1$H NMR (400 MHz, d$_6$-DMSO, 353K): 0.92 (3H, d, J=6.4 Hz), 1.29 (9H, s), 1.49-1.58 (2H, m), 1.65-1.72 (2H, m), 1.77-1.86 (2H, m), 1.99 (6H, s), 2.00-2.14 (4H, m), 2.20-2.29 (1H, m), 3.12-3.19 (5H, m), 3.30-3.39 (1H, m), 3.58-3.72 (2H, m), 4.94-5.02 (1H, m), 5.42 (1H, t, J=3.9 Hz), 6.55 (1H, s), 7.03 (1H, d, J=5.5 Hz), 7.15 (1H, dd, J=9.8, 2.3 Hz), 7.22-7.27 (1H, m), 7.31-7.37 (2H, m), 7.41-7.45 (1H, m), 7.56-7.61 (2H, m), 7.70 (1H, br s), 8.35 (1H, d, J=5.5 Hz), 10.18 (1H, br s).

Example 141

1-{5-tert-Butyl-2-[3-(2-dimethylamino-ethoxy)-phenyl]-2H-pyrazol-3-yl}-3-{(1S,4R)-4-[3-((S)-3-methyl-morpholin-4-yl)-[1,2,4]triazolo[4,3-a]pyridin-6-yloxy]-1,2,3,4-tetrahydro-naphthalen-1-yl}-urea formate salt

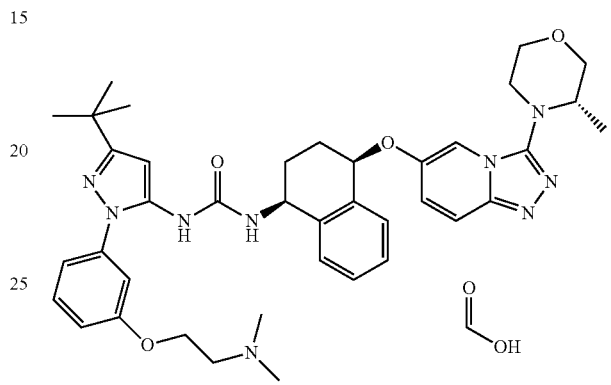

a. 1-(5-tert-Butyl-2-{3-[2-(tetrahydro-pyran-2-yloxy)-ethoxy]-phenyl}-2H-pyrazol-3-yl)-3-{(1S,4R)-4-[3-((S)-3-methyl-morpholin-4-yl)-[1,2,4]triazolo[4,3-a]pyridin-6-yloxy]-1,2,3,4-tetrahydro-naphthalen-1-yl}-urea (Intermediate 141a).

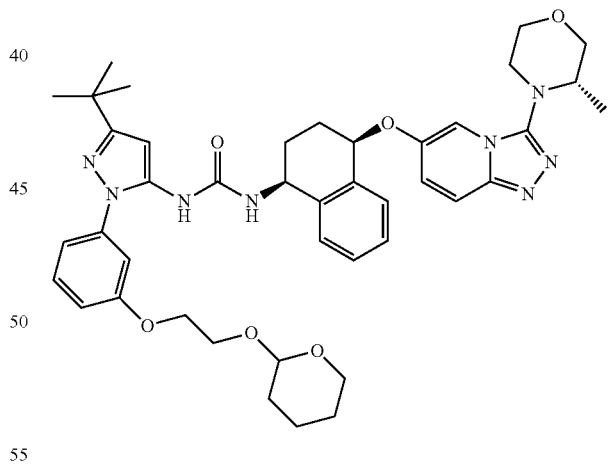

A mixture of Intermediate 139c (125 mg, 0.33 mmol), Intermediate 39b (177 mg, 0.33 mmol) and DIPEA (115 μL, 0.66 mmol) in dioxane (3 mL) was stirred at 80° C. overnight. After cooling, the reaction mixture was partitioned between water and DCM. The aqueous phase was extracted with EtOAc (×3) and the combined organic layers were washed with brine, dried (MgSO$_4$) and concentrated in vacuo. The resultant residue was purified by FCC on silica, using a gradient of 0-10% MeOH in DCM, to afford the title compound (214 mg, 85%). LCMS (Method 4): Rt 3.65 min, m/z 765 [MH$^+$].

b. 1-{5-tert-Butyl-2-[3-(2-hydroxy-ethoxy)-phenyl]-2H-pyrazol-3-yl}-3-{(1S,4R)-4-[3-((S)-3-methyl-morpholin-4-yl)-[1,2,4]triazolo[4,3-a]pyridin-6-yloxy]-1,2,3,4-tetrahydro-naphthalen-1-yl}-urea (Intermediate 141 b).

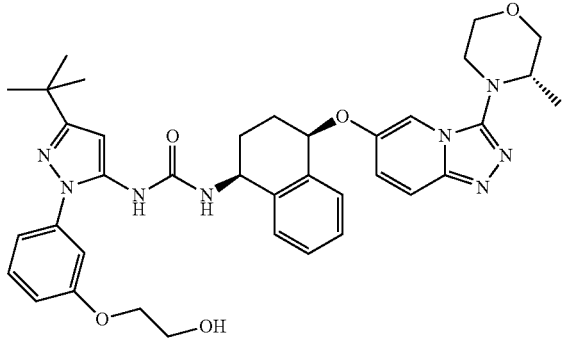 [SMILES: C[C@H]1COCCN1c1nnc2ccc(O[C@@H]3CC[C@H](NC(=O)Nc4cc(C(C)(C)C)nn4-c4cccc(OCCO)c4)c4ccccc43)cn12]

To a solution of Intermediate 141a (214 mg, 0.28 mmol) in MeOH (3.0 mL) was added pyridinium p-toluenesulfonate (141 mg, 0.56 mmol) and the reaction mixture was heated at 60° C. for 3 h. The resultant mixture was poured into water and a saturated aqueous solution of NaHCO$_3$ was added. The aqueous phase was extracted with EtOAc (×3) and the combined organic layers were washed with brine, dried (MgSO$_4$) and concentrated in vacuo. The resultant residue was purified by FCC on silica, using a gradient of 0-10% MeOH in DCM, to give the title compound (132 mg, 69%). LCMS (Method 4): Rt 3.04 min, m/z 681 [MH$^+$].

c. Methanesulfonic acid 2-{3-[3-tert-butyl-5-(3-{(1S,4R)-4-[3-((S)-3-methyl-morpholin-4-yl)-[1,2,4]triazolo[4,3-a]pyridin-6-yloxy]-1,2,3,4-tetrahydro-naphthalen-1-yl}-ureido)-pyrazol-1-yl]-phenoxy}-ethyl ester (Intermediate 141c).

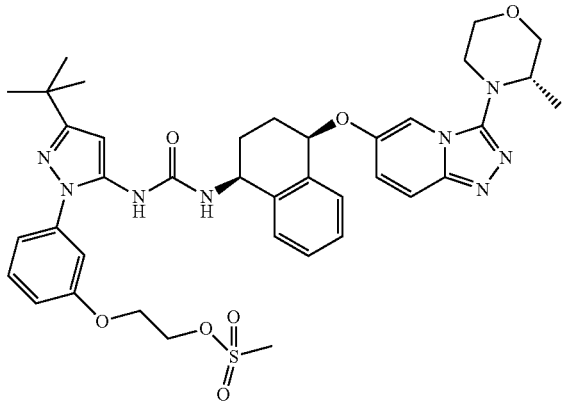 [SMILES: C[C@H]1COCCN1c1nnc2ccc(O[C@@H]3CC[C@H](NC(=O)Nc4cc(C(C)(C)C)nn4-c4cccc(OCCOS(C)(=O)=O)c4)c4ccccc43)cn12]

To an ice-bath cooled solution of Intermediate 141b (132 mg, 0.19 mmol) in DCM (2.0 mL) was added DIPEA (135 µL, 0.78 mmol) followed by methanesulfonyl chloride (30 µL, 0.39 mmol). The reaction mixture was stirred for 2 h and then quenched with water. The aqueous phase was extracted with DCM (×3) and the combined organic layers were washed with brine, dried (MgSO$_4$) and concentrated in vacuo to afford the title compound (Quantitative). Product used in the subsequent step without further purification. LCMS (Method 4): Rt 3.30 min, m/z 759 [MH$^+$].

d. 1-{5-tert-Butyl-2-[3-(2-dimethylamino-ethoxy)-phenyl]-2H-pyrazol-3-yl}-3-{(1S,4R)-4-[3-((S)-3-methyl-morpholin-4-yl)-[1,2,4]triazolo[4,3-a]pyridin-6-yloxy]-1,2,3,4-tetrahydro-naphthalen-1-yl}-urea formate salt (Example 141).

To a solution of Intermediate 141c (0.19 mmol) in THF (2.0 mL) was added dimethylamine (2M in MeOH, 1.9 mL, 3.8 mmol) and the reaction was heated to 50° C. in a sealed tube overnight. The crude reaction mixture was partitioned between EtOAc and water. The aqueous phase was extracted with EtOAc (×3) and the combined organic layers were washed with brine, dried (MgSO$_4$) and concentrated in vacuo. The resulting residue was purified by FCC on silica, using a gradient of 0-10% [2M NH$_3$ in MeOH] in DCM, followed by MDAP (Method 7) purification, to give the title compound (50 mg, 34%). LCMS (Method 5): Rt 3.33 min, m/z 708 [MH$^+$]. $^1$H NMR (400 MHz, d$_6$-DMSO): 0.83 (3H, d, J=5.7 Hz), 1.23 (9H, s), 1.78-1.92 (2H, m), 1.94-2.04 (1H, m), 2.04-2.12 (1H, m), 2.16 (6H, s), 2.59 (2H, t, J=5.7 Hz), 2.94 (1H, ddd, J=12.2, 7.3, 4.7 Hz), 3.16 (1H, dt, J=12.2, 3.3), 3.35-3.43 (2H, m), 3.72-3.80 (2H, m), 3.81-3.87 (1H, m), 4.04 (2H, t, J=5.7 Hz), 4.77 (1H, td, J=8.5, 5.9 Hz), 5.50 (1H, t, J=4.1 Hz), 6.28 (1H, s), 6.90-6.94 (1H, m), 7.01-7.09 (3H, m), 7.14-7.18 (1H, dd, J=9.8, 2.1 Hz), 7.20-7.26 (2H, m), 7.26-7.30 (1H, m), 7.30-7.38 (2H, m), 7.62 (1H, d, J=9.8 Hz), 7.78 (1H, d, J=1.8 Hz), 8.09 (1H, s), 8.12 (1.4H, s).

Example 142

1-[5-tert-Butyl-2-(2-morpholin-4-yl-ethyl)-2H-pyrazol-3-yl]-3-{(1S,4R)-4-[3-((S)-3-methyl-morpholin-4-yl)-[1,2,4]triazolo[4,3-a]pyridin-6-yloxy]-1,2,3,4-tetrahydro-naphthalen-1-yl}-urea formate salt

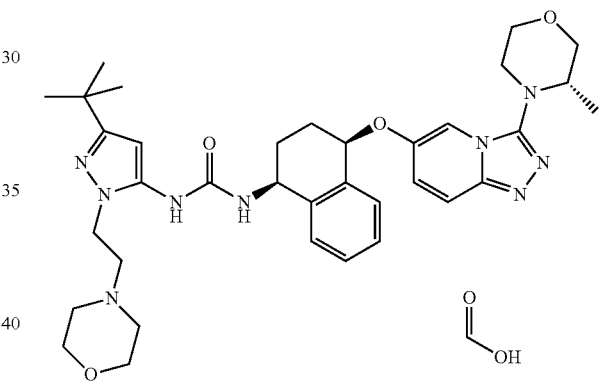

a. Methanesulfonic acid 2-[3-tert-butyl-5-(3-{(1S,4R)-4-[3-((S)-3-methyl-morpholin-4-yl)-[1,2,4]triazolo[4,3-c]pyridin-6-yloxy]-1,2,3,4-tetrahydro-naphthalen-1-yl}-ureido)-pyrazol-1-yl]-ethyl ester (Intermediate 142a).

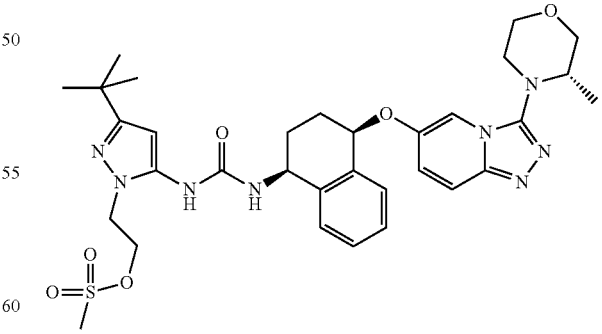

To an ice-bath cooled solution of Example 139 (54 mg, 0.092 mmol) in DCM (2.0 mL) was added DIPEA (65 µL, 0.37 mmol) followed by methanesulfonyl chloride (14 µL, 0.18 mmol). The reaction mixture was stirred for 1 h and then quenched with water. The aqueous phase was extracted with DCM (×3) and the combined organic layers were washed with brine, dried (MgSO$_4$) and concentrated in vacuo to afford the title compound (Quantitative). Product used in the following step without further purification. LCMS (Method 4): Rt 3.04 min, m/z 667 [MH$^+$].

b. 1-[5-tert-Butyl-2-(2-morpholin-4-yl-ethyl)-2H-pyrazol-3-yl]-3-{(1S,4R)-4-[3-((S)-3-methyl-morpholin-4-yl)-[1,2,4]triazolo[4,3-a]pyridin-6-yloxy]-1,2,3,4-tetrahydro-naphthalen-1-yl}-urea formate salt (Example 142).

To a solution of Intermediate 142a (0.092 mmol) in THF (2 mL) was added DIPEA (64 µL, 0.37 mmol) and morpholine (21 µL, 0.37 mmol) and the reaction stirred at 50° C. for 24 h. The crude reaction mixture was cooled and partitioned between EtOAc and water. The aqueous phase was extracted with EtOAc (×3) and the combined organic layers were washed with brine, dried (MgSO$_4$) and concentrated in vacuo. The resultant residue was purified by FCC on silica, using a gradient of 0-10% [2M NH$_3$ in MeOH] in DCM, followed by MDAP (Method 7) purification, to give the title compound (21 mg, 34%). LCMS (Method 5): Rt 3.16 min, m/z 658 [MH$^+$]. $^1$H NMR (400 MHz, d$_6$-DMSO): 0.83 (3H, d, J=5.6 Hz), 1.16 (9H, s), 1.83-1.96 (2H, m), 1.97-2.07 (1H, m), 2.08-2.17 (1H, m), 3.34 (4H, t, J=4.5 Hz), 2.57 (2H, t, J=7.1 Hz), 2.95 (1H, ddd, J=12.0, 7.2, 4.9 Hz), 3.17 (1H, dt, J=12.2, 3.3 Hz), 3.36-3.43 (2H, m), 3.50 (4H, t, J=4.5 Hz), 3.72-3.80 (2H, m), 3.81-3.88 (1H, m), 3.92-3.98 (2H, t, J=7.1 Hz), 4.82 (1H, td, J=8.5, 6.1 Hz), 5.52 (1H, t, J=4.2 Hz), 5.99 (1H, s), 6.89 (1H, d, J=8.6 Hz), 7.18 (1H, dd, J=9.9, 2.1 Hz), 7.22-7.27 (1H, m), 7.30-7.38 (3H, m), 7.62 (1H, d, J=9.9 Hz), 7.79 (1H, d, J=1.9 Hz), 8.16 (1H, s), 8.16 (0.2H, s).

Example 143

1-{5-tert-Butyl-2-[3-(4-methyl-piperazin-1-ylmethyl)-phenyl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt

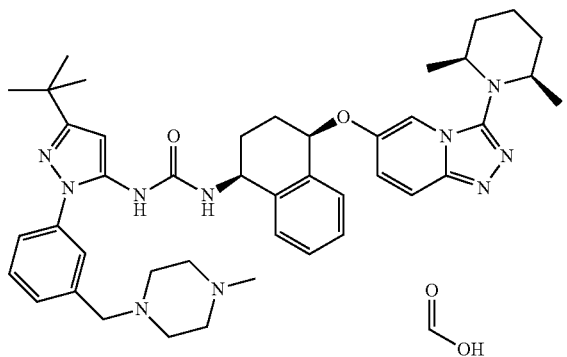 [SMILES: C[C@@H]1CCC[C@H](C)N1c1nnc2ccc(O[C@@H]3CC[C@H](NC(=O)Nc4cc(C(C)(C)C)nn4-c4cccc(CN5CCN(C)CC5)c4)c4ccccc43)cn12 ; O=CO]

To a solution of Intermediate 130b (0.25 mmol) in THF (2.5 mL) was added N-methylpiperazine (277 µL, 2.50 mmol) and the reaction stirred at 50° C. for 24 h. After cooling, the mixture was partitioned between EtOAc and water. The aqueous phase was extracted with EtOAc (×3) and the combined organic layers were washed with brine, dried (MgSO$_4$) and concentrated in vacuo. The resulting residue was purified by FCC on silica, using a gradient of 0-10% [2M NH$_3$ in MeOH] in DCM, followed by MDAP (Method 7) purification, to give the title compound (37 mg, 19%). LCMS (Method 5): Rt 3.77 min, m/z 745 [MH$^+$]. $^1$H NMR (400 MHz, d$_6$-DMSO): 0.55 (3H, d, J=6.2 Hz), 0.58 (3H, d, J=6.2 Hz), 1.23 (9H, s), 1.35-1.54 (3H, m), 1.63-1.68 (2H, m), 1.72-1.86 (2H, m), 1.86-1.92 (1H, m), 2.01-2.06 (2H, m), 2.07 (3H, s), 2.26 (4H, br s), 2.34 (4H, br s), 3.08-3.20 (2H, m), 3.46 (2H, s), 4.78 (1H, td, J=8.6, 5.9 Hz), 5.47 (1H, t, J=4.2 Hz), 6.28 (1H, s), 7.00 (1H, d, J=8.6 Hz), 7.15 (1H, dd, J=9.8, 2.1 Hz), 7.18-7.25 (2H, m), 7.25-7.31 (3H, m), 7.32-7.37 (2H, m), 7.41 (1H, t, J=7.6 Hz), 7.61 (1H, d, J=9.7 Hz), 7.83 (1H, d, J=1.8 Hz), 8.05 (1H, s), 8.12 (1.1H, s).

Example 144

1-[5-tert-Butyl-2-(3-pyrrolidin-1-ylmethyl-phenyl)-2H-pyrazol-3-yl]-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt

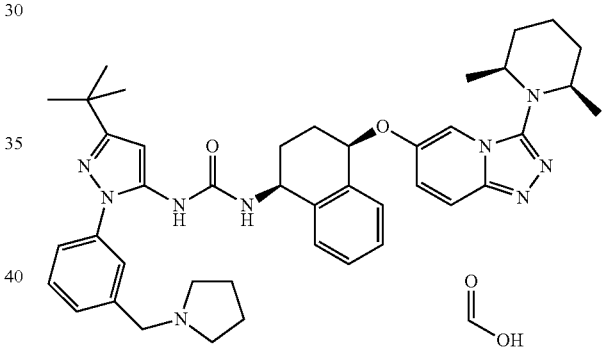

To a solution of Intermediate 130b (0.32 mmol) in THF (3.0 mL) was added pyrrolidine (530 µL, 6.4 mmol) and the reaction stirred at 50° C. for 24 h. After cooling, the mixture was partitioned between EtOAc and water. The aqueous phase was extracted with EtOAc (×3) and the combined organic layers were washed with brine, dried (MgSO4) and concentrated in vacuo. The resulting residue was purified by FCC on silica, using a gradient of 0-10% [2M NH$_3$ in MeOH] in DCM, followed by MDAP (Method 7) purification, to give the title compound (60 mg, 24%). LCMS (Method 5): Rt 3.79 min, ink 716 [MH$^+$]. $^1$H NMR (400 MHz, d$_6$-DMSO): 0.55 (3H, d, J=6.2 Hz), 0.58 (3H, d, J=6.2 Hz), 1.23 (9H, s), 1.35-1.54 (3H, m), 1.60-1.68 (6H, m), 1.72-1.85 (2H, m), 1.86-1.92 (1H, m), 2.01-2.06 (2H, m), 2.38-2.44 (4H, m), 3.08-3.20 (2H, m), 3.58 (2H, s), 4.77 (1H, td, J=8.6, 5.9 Hz), 5.48 (1H, t, J=4.2 Hz), 6.28 (1H, s), 7.00 (1H, d, J=8.6 Hz), 7.15 (1H, dd, J=9.8, 2.1 Hz), 7.18-7.25 (2H, m), 7.26-7.35 (4H, m), 7.37 (1H, s), 7.41 (1H, t, J=7.6 Hz), 7.61 (1H, d, J=9.7 Hz), 7.83 (1H, d, J=1.8 Hz), 8.05 (1H, s), 8.13 (1.2H, s).

Example 145

1-{5-tert-Butyl-2-[3-(2-pyrrolidin-1-yl-ethoxy)-phenyl]-2H-pyrazol-3-yl}-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea

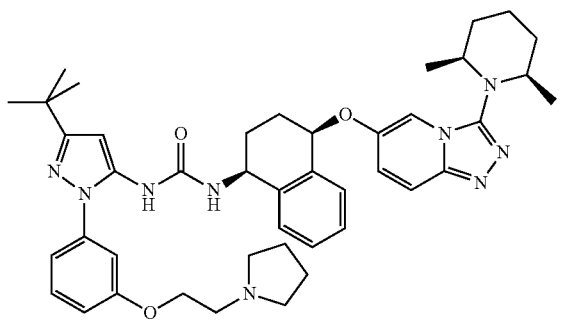 [SMILES: C[C@@H]1CCC[C@H](C)N1c1nnc2ccc(O[C@@H]3CC[C@H](NC(=O)Nc4cc(C(C)(C)C)nn4-c4cccc(OCCN5CCCC5)c4)c4ccccc43)cn12]

Pyrrolidine (36 µL, 0.43 mmol) was added to a solution of Intermediate 96f (111 mg, 0.14 mmol) in THF (2 mL). The reaction was heated to 60° C. in a sealed vial overnight. The mixture was cooled, evaporated in vacuo and the residue was purified by FCC, using 0-15% MeOH in DCM, then triturated with Et$_2$O to give the title compound (27 mg, 25%) as an off-white solid. LCMS (Method 5): Rt 3.87 min, m/z 746.6 [MH$^+$]. $^1$H NMR (400 MHz, d$_6$-DMSO): 0.55 (3H, d, J=6.0 Hz), 0.58 (3H, d, J 6.0 Hz), 1.23 (9H, s), 1.32-1.54 (3H, m), 1.53-1.78 (7H, m), 1.79-1.95 (2H, m), 1.96-2.10 (2H, m), 2.49-2.60 (2H, m), 2.68-2.94 (2H, m), 3.06-3.20 (3H, m), 3.27 (1H, m, obscured by water), 4.03-4.14 (2H, m), 4.74-4.83 (1H, m), 5.49 (1H, t, J=4.0 Hz), 6.29 (1H, s), 6.90-6.96 (1H, m), 7.01-7.09 (3H, m), 7.16 (1H, dd, J=9.7, 2.0 Hz), 7.19-7.25 (2H, m), 7.26-7.32 (2H, m), 7.33-7.39 (1H, m), 7.62 (1H, d, J=9.7 Hz), 7.84 (1H, m), 8.06 (1H, s).

Example 146

1-(5-tert-Butyl-2-{3-[2-(4-methyl-piperazin-1-yl)-ethoxy]-phenyl}-2H-pyrazol-3-yl)-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea

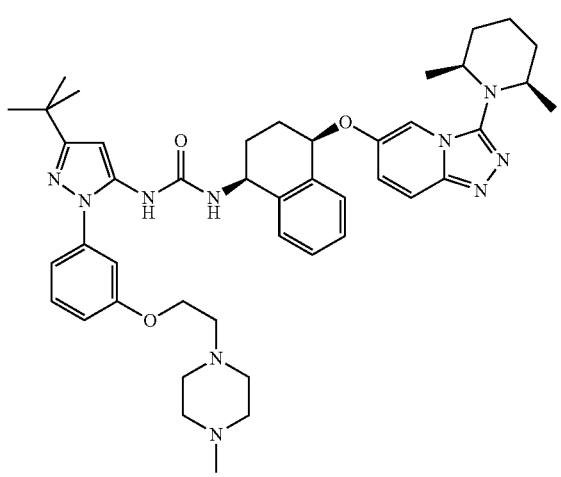 [SMILES: C[C@@H]1CCC[C@H](C)N1c1nnc2ccc(O[C@@H]3CC[C@H](NC(=O)Nc4cc(C(C)(C)C)nn4-c4cccc(OCCN5CCN(C)CC5)c4)c4ccccc43)cn12]

1-Methylpiperazine (48 µL, 0.43 mmol) was added to a solution of Intermediate 96f (111 mg, 0.14 mmol) in THF (2 mL). The reaction was heated to 60° C. in a sealed vial overnight. 1-Methylpiperazine (48 µL, 0.43 mmol) was added and the reaction continued for a further 24 h. The mixture was cooled, evaporated in vacuo and the residue was purified by FCC, using 0-15% MeOH in DCM, then triturated with Et$_2$O to give the title compound (42 mg, 38%) as an off-white solid. LCMS (Method 5): Rt 3.76 min, m/z 775.6 [MH$^+$]. $^1$H NMR (400 MHz, d$_6$-DMSO): 0.60 (3H, d, J=6.0 Hz), 0.63 (3H, d, J=6.0 Hz), 1.28 (9H, s), 1.36-1.62 (3H, m), 1.65-1.75 (2H, m), 1.76-1.99 (3H, m), 2.03-2.12 (2H, m), 2.14-2.26 (3H, m), 2.34-2.61 (5H, m, obscured by solvent), 2.63-2.74 (3H, m), 3.11-3.24 (2H, m), 3.28-3.38 (2H, m), 4.1 (2H, t, J=5.8 Hz), 4.78-4.87 (1H, m), 5.50-5.56 (1H, m), 6.33 (1H, s), 6.93-7.00 (1H, m), 7.05-7.13 (3H, m), 7.20 (1H, dd, J=9.9, 2.4 Hz), 7.23-7.31 (2H, m), 7.34 (2H, t, J=8.0 Hz), 7.40 (1H, t, J=8.0 Hz), 7.67 (1H, d, J=9.9 Hz), 7.87-7.91 (1H, m), 8.11 (1H, s).

Example 147

1-(5-tert-Butyl-2-{3-[2-(ethyl-methyl-amino)-ethoxy]-phenyl}-2H-pyrazol-3-yl)-3-{(1S,4R)-4-[3-((2S,6R)-2,6-dimethyl-piperidin-1-yl)-[1,2,4]triazolo[4,3-a]pyridin-6-yloxy]-1,2,3,4-tetrahydro-naphthalen-1-yl}-urea formate salt

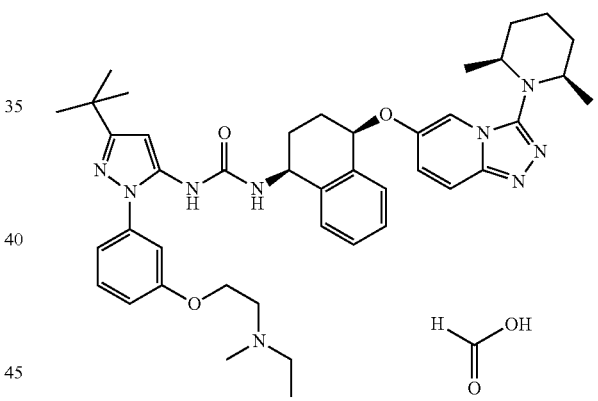

N-Ethylmethylamine (37 µL, 0.43 mmol) was added to a solution of Intermediate 96f (111 mg, 0.14 mmol) in THF (2 mL). The reaction was heated to 60° C. in a sealed vial overnight. N-Ethylmethylamine (37 µL, 0.43 mmol) was added and the reaction continued for a further 24 h. The mixture was cooled, evaporated in vacuo and the residue was purified by FCC, using 0-15% MeOH in DCM, then triturated with Et$_2$O. Further purification by HPLC (Gemini C, 18 column, 10-98% MeCN in H$_2$O, 0.1% formic acid) followed by evaporation of the fractions and trituration with Et$_2$O gave the title compound (12 mg, 11%) as an off-white solid. LCMS (Method 5): Rt 3.85 min, m/z 734.6 [MH$^+$]. $^1$H NMR (400 MHz, d$_6$-DMSO): 0.55 (3H, d, J=6 Hz), 0.58 (3H, d, J=6 Hz), 0.89 (3H, t, J=7.0 Hz), 1.23 (9H, m), 1.33-1.57 (3H, m), 1.62-1.70 (2H, m), 1.71-1.95 (3H, m), 1.96-2.09 (2H, m), 2.13 (3H, s), 2.35 (2H, q, J=7.2 Hz), 2.63 (2H, t, J=5.7 Hz), 3.06-3.20 (3H, m), 3.21-3.36 (2H, m, obscured by solvent), 4.03 (2H, t, J=5.7 Hz), 4.74-4.83 (1H, m), 5.48 (1H, t, J=5.5 Hz), 6.28 (1H, s), 6.88-6.94 (1H, m), 7.00-7.10 (3H, m), 7.16 (1H, dd, J=9.8, 2.0 Hz), 7.18-7.26 (2H, m), 7.26-7.32 (2H, m), 7.35 (1H, t, J=8.0 Hz), 7.62 (1H, d, J=9.8 Hz), 7.81-7.86 (1H, m), 8.09 (1H, s), 8.37 (0.2H, s).

Example 148

1-{(1S,4R)-4-[3-(4-Aza-spiro[2.5]oct-4-yl)-[1,2,4]triazolo[4,3-a]pyridin-6-yloxy]-1,2,3,4-tetrahydro-naphthalen-1-yl}-3-{5-tert-butyl-2-[3-(2-dimethylamino-ethoxy)-phenyl]-2H-pyrazol-3-yl}-urea formate salt

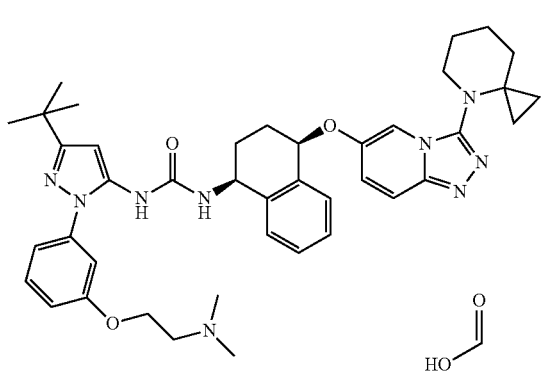 [SMILES: CN(C)CCOc1cccc(-n2nc(C(C)(C)C)cc2NC(=O)N[C@H]2CC[C@@H](Oc3ccc4nnc(N5CCCCC56CC6)n4c3)c3ccccc32)c1 ; O=CO]

a. 4-Aza-spiro[2.5]octane-4-carbonyl chloride (Intermediate 148a).

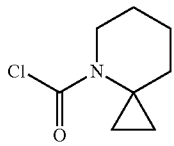

To a vigorously stirred pale yellow solution of 4-azaspiro[2.5]octane hydrochloride (ABCR, 443 mg, 3.00 mmol), pyridine (0.36 mL, 4.5 mmol) and DIPEA (0.52 mL, 3.0 mmol) in DCM (10 mL) at 0° C. was added a solution of triphosgene (594 mg, 2.00 mmol) in DCM (5 mL) dropwise over 5 min. The resulting orange solution was stirred at 0° C. for 30 min, and at RT for 66 h. Aq. HCl solution (1M, 15 mL) was added and the mixture stirred for 30 min. The aqueous was extracted with DCM (4×15 mL), then the combined organics passed through a hydrophobic fit and concentrated in vacuo to leave the title compound as a red-brown oil (100% yield). $^{1}$H NMR (300 MHz, CDCl$_{3}$): ~2:1 ratio of rotamers, 0.71-0.76 (1.33H, m), 0.82 (0.67H, br s), 1.00-1.04 (1.33H, m), 1.09 (0.67H, br s), 1.53-1.59 (2H, m), 1.64-1.72 (2H, m), 1.75-1.83 (2H, m), 3.61-3.74 (2H, m).

b. 4-Aza-spiro[2.5]octane-4-carboxylic acid N'-(5-fluoro-pyridin-2-yl)-hydrazide (Intermediate 148b).

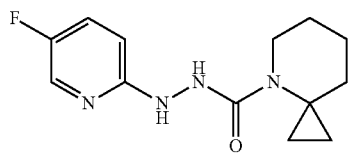 [SMILES: O=C(NNc1ccc(F)cn1)N1CCCCC12CC2]

A red solution of (5-fluoro-pyridin-2-yl)-hydrazine (477 mg, 3.75 mmol), Intermediate 148a (3.00 mmol) and DIPEA (0.78 mL, 4.5 mmol) in DCM (20 mL) was stirred at reflux for 40 h. To the cooled solution was added water (20 mL) and the mixture shaken. The aqueous was extracted with DCM (2×10 mL), then the combined organics passed through a hydrophobic frit and concentrated in vacuo. Flash chromatography (silica 40 g, 1-5% [2M NH$_{3}$ in MeOH] in DCM) gave the title compound as a yellow solid (587 mg, 74%). LCMS (Method 3): Rt 2.66 min, m/z 265 [MH$^{+}$].

c. 3-(4-Aza-spiro[2.5]oct-4-yl)-6-fluoro-[1,2,4]triazolo[4,3-a]pyridine (Intermediate 148c).

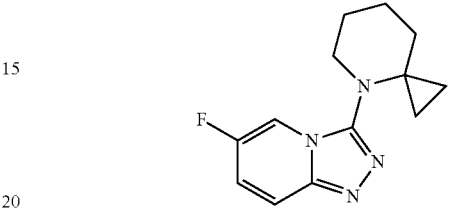

To a solution of Intermediate 148b (587 mg, 2.22 mmol), triphenyl phosphine (1.17 g, 4.44 mmol) and triethylamine (1.24 mL, 8.88 mmol) in dioxane (25 mL) at RT was added hexachloroethane (1.05 g, 4.44 mmol). The resulting opaque solution was stirred at RT for 30 min, and at reflux for 16 h. The cooled solution was filtered, and the filter-cake washed with THF (5 mL). The combined organics were applied to an SCX-2 cartridge, which was washed with MeOH (100 mL). The product was eluted with 2M NH$_{3}$ in MeOH (75 mL); concentration in vacuo left a brown oil. Flash chromatography (silica 40 g, 1.5-4.5% MeOH in DCM) gave the title compound as a brown gum (82%). LCMS (Method 3): Rt 2.92 min, m/z 247 [MH$^{+}$].

d. (1S,4R)-4-[3-(4-Aza-spiro[2.5]oct-4-yl)-[1,2,4]triazolo[4,3-a]pyridin-6-yloxy]-1,2,3,4-tetrahydro-naphthalen-1-ylamine (Intermediate 148d).

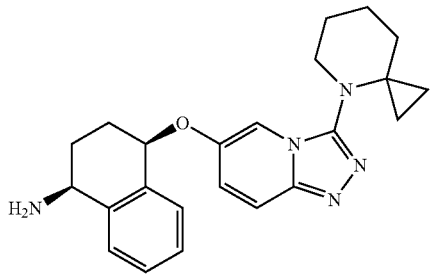 [SMILES: N[C@H]1CC[C@@H](Oc2ccc3nnc(N4CCCCC45CC5)n3c2)c2ccccc21]

To an opaque brown solution of Intermediate A (371 mg, 2.28 mmol) in dry DMF (5 mL) under N$_{2}$ was added sodium hydride (60% dispersion in mineral oil, 273 mg, 6.83 mmol) and the resulting mixture stirred at RT for 30 min. (CARE: gas evolution) A solution of Intermediate 148c (448 mg, 1.82 mmol) in dry DMF (5 mL) was added and the resulting dark brown solution stirred at 60° C. for 1 h. The solution was cooled to RT, then water (0.2 mL) added (CARE: gas evolution) and the mixture concentrated in vacuo. The residue was redissolved in MeOH (10 mL), applied to an SCX-2 cartridge (25 g) and washed with MeOH (100 mL). The product was eluted with 2M NH$_{3}$ in MeOH (75 mL); concentration in vacuo left a dark brown gum. Flash chromatography (silica 40 g, 4-7% [2M NH$_{3}$ in MeOH] in DCM) gave the title compound as a pale brown foam (446 mg, 63%). LCMS (Method 3): Rt 2.31 min, m/z 390 [MH$^{+}$].

e. {5-tert-Butyl-2-[3-(2-hydroxy-ethoxy)-phenyl]-2H-pyrazol-3-yl}-carbamic acid 2,2,2-trichloro-ethyl ester (Intermediate 148e).

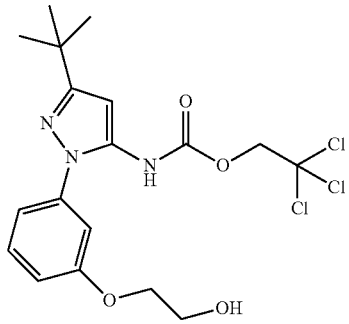 [SMILES: CC(C)(C)c1cc(NC(=O)OCC(Cl)(Cl)Cl)n(-c2cccc(OCCO)c2)n1]

A colourless solution of Intermediate 39b (120 mg, 0.224 mmol) and pyridinium p-toluenesulfonate (169 mg, 0.673 mmol) in MeOH (5 mL) was stirred at 40° C. for 90 min. The solution was concentrated in vacuo, suspended in water (3 mL) and sat. aq. NaHCO₃ solution (3 mL), then extracted with DCM (2×5 mL). The combined organics were passed through a hydrophobic frit, concentrated in vacuo and azeotroped with toluene (2×5 mL) to leave the title compound as a white solid (100 mg, 99%). LCMS (Method 3): Rt 4.01 min, m/z 450, 452 [MH⁺].

f. 1-{(1S,4R)-4-[3-(4-Aza-spiro[2.5]oct-4-yl)-[1,2,4]triazolo[4,3-a]pyridin-6-yloxy]-1,2,3,4-tetrahydro-naphthalen-1-yl}-3-{5-tert-butyl-2-[3-(2-hydroxy-ethoxy)-phenyl]-2H-pyrazol-3-yl}-urea (Intermediate 148f).

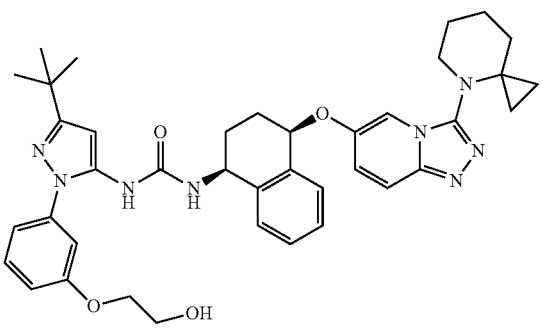 [SMILES: CC(C)(C)c1cc(NC(=O)N[C@H]2CC[C@@H](Oc3ccc4nnc(N5CCCCC56CC6)n4c3)c3ccccc32)n(-c2cccc(OCCO)c2)n1]

An orange-brown solution of Intermediate 148d (87.2 mg, 0.224 mmol), Intermediate 148e (100 mg, 0.224 mmol) and DIPEA (0.049 mL, 0.28 mmol) in dry dioxane (3 mL) was stirred at 75° C. for 16 h. The cooled solution was concentrated in vacuo, suspended in water (5 mL) and extracted with DCM (2×5 mL). The combined organics were passed through a hydrophobic frit and concentrated in vacuo to leave a brown gum. Flash chromatography (silica 12 g, 4-8% MeOH in DCM) gave the title compound as a pale yellow solid (138 mg, 89%). LCMS (Method 3): Rt 3.57 min, m/z 691 [MH⁺].

g. Methanesulfonic acid 2-{3-[5-(3-{(1S,4R)-4-[3-(4-aza-spiro[2.5]oct-4-yl)-[1,2,4]triazolo[4,3-a]pyridin-6-yloxy]-1,2,3,4-tetrahydro-naphthalen-1-yl}-ureido)-3-tert-butyl-pyrazol-1-yl]-phenoxy}-ethyl ester (Intermediate 148g).

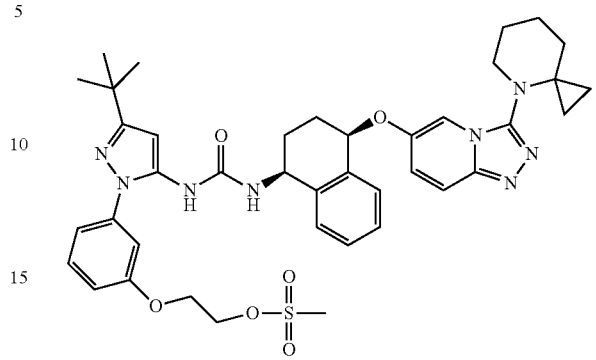

A yellow-orange solution of Intermediate 148f (137 mg, 0.198 mmol), DIPEA (0.10 mL, 0.60 mmol) and methanesulfonyl chloride (45 mg, 0.40 mmol) in DCM (5 mL) was stirred at 0° C. for 30 min, and at RT for 30 min. DIPEA (0.052 mL, 0.30 mmol) and MsCl (23 mg, 0.20 mmol) were added and the solution stirred at RT for 30 min. Water (2 mL) and sat. aq. NaHCO₃ solution (2 mL) were added and the mixture shaken. The aqueous was extracted with DCM (5 mL), then the combined organics passed through a hydrophobic frit and concentrated in vacuo to leave the title compound as a yellow solid (100%). LCMS (Method 3): Rt 3.80 min, m/z 769 [MH⁺].

h. 1-{(1S,4R)-4-[3-(4-Aza-spiro[2.5]oct-4-yl)-[1,2,4]triazolo[4,3-a]pyridin-6-yloxy]-1,2,3,4-tetrahydro-naphthalen-1-yl}-3-{(5-tert-butyl-2-[3-(2-dimethylamino-ethoxy)-phenyl]-2H-pyrazol-3-yl}-urea formate salt (Example 148).

A brown solution of Intermediate 148g (0.099 mmol) and dimethylamine (2M in THF, 0.99 mL, 1.98 mmol) in THF (1 mL) was stirred in a sealed vial at 60° C. for 16 h. The solution was decanted and concentrated. MDAP (Method 7) gave the title compound as a pale yellow solid (50 mg, 65%). LCMS (Method 5): Rt 3.62 min, m/z 718.6 [MH⁺]. ¹H NMR (400 MHz, d₆-DMSO): 0.42-0.53 (4H, m), 1.27 (9H, s), 1.53-1.61 (2H, m), 1.74-1.96 (6H, m), 1.99-2.15 (2H, m), 2.20 (6H, s), 2.63 (2H, t, J=5.8 Hz), 3.22-3.29 (2H, m), 4.09 (2H, t, J=5.8 Hz), 4.81 (1H, td, J=8.6, 5.5 Hz), 5.48 (1H, t, J=4.3 Hz), 6.33 (1H, s), 6.95-6.98 (1H, m), 7.06-7.12 (3H, m), 7.14 (1H, dd, J=9.9, 2.2 Hz), 7.25-7.42 (5H, m), 7.56 (1H, d, J=2.1 Hz), 7.61 (1H, dd, J=9.8, 0.8 Hz), 8.12 (1H, s), 8.17 (1.4H, s).

Example 149

1-[5-tert-Butyl-2-(3-morpholin-4-yl-methyl-phenyl)-2H-pyrazol-3-yl]-3-{(1S,4R)-4-[3-((S)-1-methyl-pyrrolidin-2-yl)-[1,2,4]triazolo[4,3-a]pyridin-6-yloxy]-1,2,3,4-tetrahydronaphthalen-1-yl}-urea formate salt

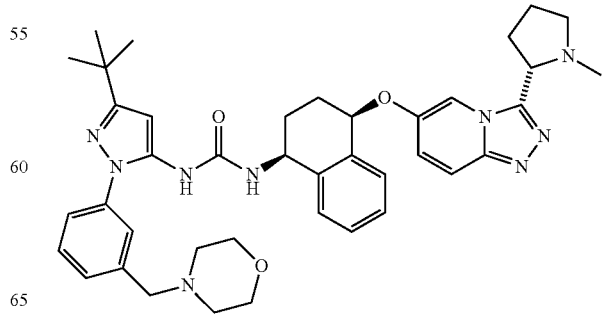

a. 1-[5-tert-butyl-2-[3-hydroxymethyl-phenyl)-2H-pyrazol-3-yl]-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea (Intermediate 149a).

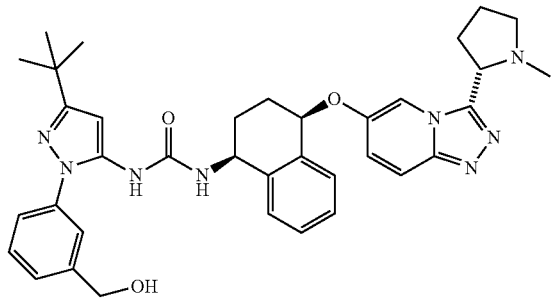 [SMILES: CN1CCC[C@H]1c1nnc2ccc(O[C@@H]3CC[C@H](NC(=O)Nc4cc(C(C)(C)C)nn4-c4cccc(CO)c4)c4ccccc43)cn12]

A solution of Intermediate 5c (1.60 g, 4.40 mmol) and Intermediate 29c (1.85 g, 4.40 mmol) in dioxane (20 mL) was treated with DIPEA (1.15 mL, 6.60 mmol) and the reaction mixture was heated at 70° C. for 36 h. The mixture was concentrated in vacuo and the residue was dissolved in DCM (150 mL) and washed with water (2×75 mL) and brine (75 mL). The organic layer was dried (MgSO$_4$), filtered and concentrated in vacuo and the foam obtained purified by FCC, using 0-5% MeOH in DCM then 0-5% [2M NH$_3$ in MeOH] in DCM to afford the title compound as a yellow foamy solid (0.94 g, 85%). LCMS (Method 3): Rt 2.76 min, m/z 635 [MH$^+$].
b. Methanesulfonic acid 3-[3-tert-butyl-5-(3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-ureido)-pyrazol-1-yl]-benzyl ester (Intermediate 149b).

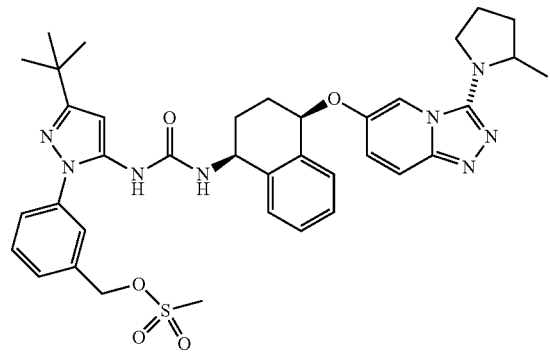

A solution of Intermediate 149a (200 mg, 0.32 mmol) and DIPEA (164 µL, 0.95 mmol) in DCM (4 mL) was treated with methanesulfonyl chloride (32 µL, 0.41 mmol) and the reaction mixture was stirred at RT for 0.5 h. The mixture was diluted with DCM (5 mL) and washed with water (10 mL) and brine (10 mL). The layers were separated and the organic layer was passed through a phase separator and concentrated in vacuo to afford the title compound as a pale yellow solid (208 mg, 92%). LCMS (Method 3): Rt 3.02 min, in/z 713 [MH$^+$].
c. 1-[5-tert-Butyl-2-(3-morpholin-4-yl-methyl-phenyl)-2H-pyrazol-3-yl]-3-{(1S,4R)-4-[3-((S)-1-methyl-pyrrolidin-2-yl)-[1,2,4]triazolo[4,3-a]pyridin-6-yloxy]-1,2,3,4-tetrahydronaphthalen-1-yl}-urea formate salt (Example 149).

A mixture of Intermediate 149b (104 mg, 0.15 mmol) and morpholine (64 µL, 0.73 mmol) in THF (2 mL) was stirred at 60° C. for 18 h. The reaction mixture was cooled to RT, diluted with DCM (5 mL) and washed with water (5 mL) and brine (5 mL). The organic layer was passed through a phase separator and concentrated in vacuo and the resultant residue was purified by prep. HPLC, using 5-50% CH$_3$CN in water, buffered with formic acid, on a Gemini C$_{18}$ column, over 20 mins to afford the title compound as an off white solid (22 mg, 21%). LCMS (Method 5): Rt 2.66 min, m/z 704.6 [MH$^+$]. $^1$H NMR (400 MHz, d$_6$-DMSO): 1.28 (9H, s), 1.84-2.11 (6H, m), 2.13 (3H, s), 2.15-2.26 (2H, m), 2.31-2.40 (5H, m), 3.10-3.17 (1H, m, obscured by water), 3.51 (2H, s, obscured by water), 3.55 (4H, t, J=4.6 Hz), 3.99 (1H, t, J=8.0 Hz), 4.78-4.86 (1H, m), 5.39 (1H, t, J=4.2 Hz), 6.33 (1H, s), 7.06 (1H, d, J=8.6 Hz), 7.24-7.49 (9H, m), 7.75 (1H, d, J=9.7 Hz), 8.10 (1H, s), 8.19 (0.6H, br s), 8.24 (1H, d, J=1.8 Hz).

Example 150

1-(5-tert-Butyl-2-{3-[(2-dimethylamino-ethyl)-methyl-amino]-phenyl}-2H-pyrazol-3-yl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formic acid salt

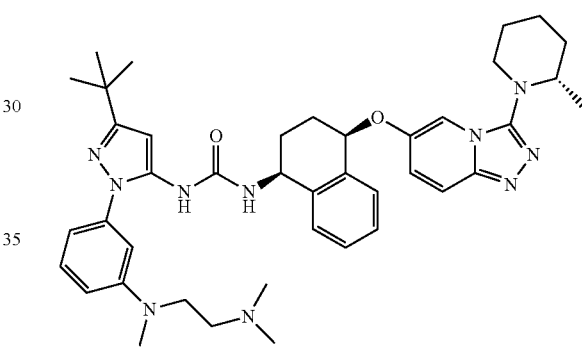

a. N-(3-Bromo-phenyl)-N,N',N'-trimethyl-ethane-1,2-diamine (Intermediate 150a).

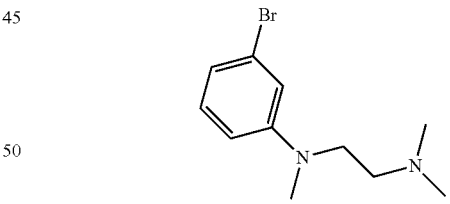

A solution of N'-(3-bromo-phenyl)-N,N-dimethyl-ethane-1,2-diamine (400 mg, 1.6 mmol) was formed in 1,2-dichloroethane (10 mL). Formaldehyde (250 µL, 37% in water, 3.3 mmol) was added and the mixture stirred for 10 minutes at RT. Sodium triacetoxyborohydride (700 mg, 3.3 mmol) was added and the mixture stirred for 2 h at RT. Further formaldehyde (250 µL, 37% in water, 3.3 mmol) and sodium triacetoxyborohydride (700 mg, 3.3 mmol) were added and the mixture stirred at RT for 16 h. Mixture quenched with sat. NaHCO$_3$ (aq) and extracted with DCM. The combined organic phases were dried (Na$_2$SO$_4$) and concentrated in vacuo. The residue was purified by FCC, using 0-20% MeOH in DCM, to give the title compound (200 mg, 47%). LCMS (Method 3): Rt 2.35 min, m/z 257, 259 [MH$^+$].

b. N-[3-(5-Amino-3-tert-butyl-pyrazol-1-yl)-phenyl]-N,N',N'-trimethyl-ethane-1,2-diamine (Intermediate 150b).

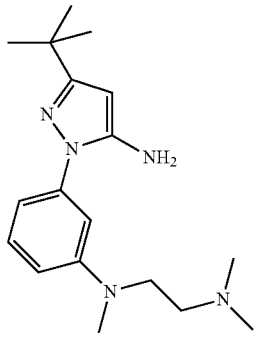 [SMILES: CN(C)CCN(C)c1cccc(-n2nc(C(C)(C)C)cc2N)c1]

A solution of Intermediate 150a (200 mg, 0.78 mmol), 3-(tert-butyl)-1H-pyrazol-5-amine (130 mg, 0.93 mmol) and trans-N,N'-dimethylcyclohexane diamine (22 mg, 0.16 mmol) was formed in toluene (2 mL). Potassium carbonate (226 mg, 1.6 mmol) was added and the mixture degassed by bubbling nitrogen through it. Copper (I) iodide (15 mg, 0.08 mmol) was added and the mixture was heated to 150° C. for 24 h under microwave irradiation. The cooled reaction mixture was concentrated in vacuo and the residue was partitioned between EtOAc and water. The phases were separated and the aqueous layer was extracted with EtOAc. The combined organic phase was washed with brine, dried ($Na_2SO_4$) and concentrated in vacuo. The residue was purified by FCC, using 0-20% MeOH in DCM, to give the title compound (50 mg, 20%). LCMS (Method 3): Rt 1.84 min, m/z 316 [MH$^+$].

c. (5-tert-Butyl-2-{3-[(2-dimethylamino-ethyl)-methyl-amino]-phenyl}-2H-pyrazol-3-yl)-carbamic acid phenyl ester (Intermediate 150c).

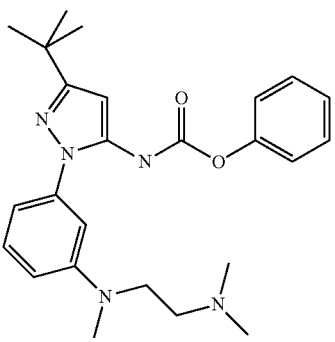 [SMILES: CN(C)CCN(C)c1cccc(-n2nc(C(C)(C)C)cc2NC(=O)Oc2ccccc2)c1]

A solution of Intermediate 150b (50 mg, 0.16 mmol) in DCM (2 mL) was treated with pyridine (26 µL, 0.32 mmol) and phenyl chloroformate (32 µL, 0.25 mmol). The resulting mixture was stirred at RT for 2 h. Further pyridine (26 µL, 0.32 mmol) and phenyl chloroformate (32 µL, 0.25 mmol) were added and the mixture stirred at RT for 16 h. The mixture was diluted with water and the phases separated. The aqueous layer was extracted with DCM and the combined organic phase was washed with brine, dried ($Na_2SO_4$), and concentrated in vacuo. The residue was purified by FCC, using 0-20% MeOH in DCM, to give the title compound (30 mg, 43%). LCMS (Method 3): Rt 2.97 min, m/z 436 [MH$^+$].

d. 1-(5-tert-Butyl-2-{3-[(2-dimethylamino-ethyl)-methyl-amino]-phenyl}-2H-pyrazol-3-yl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formic acid salt (Example 150).

A solution of Intermediate 81d (26 mg, 0.07 mmol) in 1,4-dioxane (2 mL) was treated with Intermediate 150c (30 mg, 0.07 mmol) and DIPEA (24 µL, 0.13 mmol) and the mixture was stirred at 70° C. for 18 h. After cooling to RT the mixture was concentrated in vacuo. The residue was purified by FCC, using 0-20% MeOH in DCM, then by prep HPLC (C18 column, 10-98% MeCN in $H_2O$, 0.1% $HCO_2H$) over 20 mins. Concentration of the fractions in vacuo gave pale yellow glass. Trituration with $Et_2O$ gave the title compound as an off white solid (20 mg, 40%). LCMS (Method 5): Rt 3.70 min, m/z 719.6 [MH$^+$]. $^1$H NMR (400 MHz, $d_6$-DMSO): 0.91 (3H, d, J=6.4 Hz), 1.27 (9H, s), 1.47-1.53 (2H, m), 1.64-1.71 (2H, m), 1.77-1.97 (4H, m), 2.00-2.15 (2H, m), 2.16 (3H, s), 2.39 (2H, t, J=7.2 Hz), 2.87-2.92 (1H, m), 2.93 (3H, s), 3.13-3.21 (4H, m), 3.35-3.46 (4H, m), 4.80-4.87 (1H, m), 5.52 (1H, t, J=4.3 Hz), 6.32 (1H, s), 6.68-6.72 (3H, m), 7.13 (1H, d, J=8.6 Hz), 7.19 (1H, dd, J=9.7, 2.2 Hz), 7.24-7.38 (5H, m), 7.64 (1H, d, J=9.7 Hz), 7.69 (1H, m), 8.11 (1H, s).

Example 151

1-{5-tert-Butyl-2-[3-((R)-2-dimethylamino-1-methyl-ethoxy)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

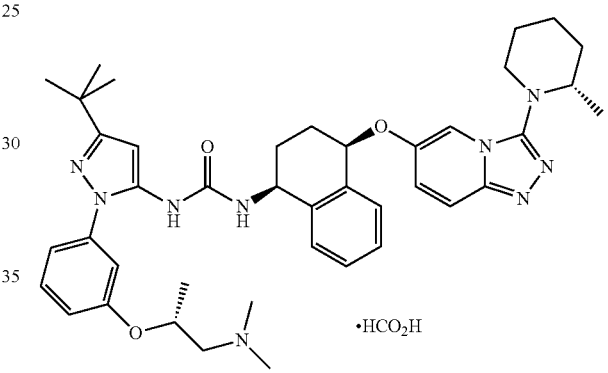

a. 2-[3-((R)-2-Benzyloxy-1-methyl-ethoxy)-phenyl]-5-tert-butyl-2H-pyrazol-3-ylamine (Intermediate 151a).

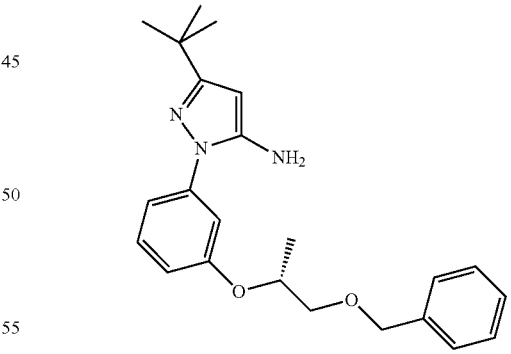

A mixture of Intermediate 95a (0.50 g, 2.2 mmol) in dry THF (17 mL) was treated with triphenylphosphine (1.13 g, 4.32 mmol) and (S)-(+)-1-Benzyloxy-2-propanol (0.52 mL, 3.24 mmol). The mixture was cooled to 0° C. then diisopropylazodicarboxylate (0.85 mL, 4.32 mmol) was added dropwise. After stirring at ambient temperature for 1.75 h the mixture was treated with water (0.2 mL) then applied to a pre-conditioned (with MeOH) SCX-2 cartridge. The cartridge was eluted with MeOH then 2N $NH_3$ in MeOH. The product containing fractions were combined and concentrated in vacuo to a viscous brown oil. The oil was purified by FCC, using 0-30% EtOAc in cyclohexane, to give the title compound as a golden oil (0.37 g, 45%). LCMS (Method 3): Rt 3.71 min, m/z 380.3 [MH$^+$].

b. (R)-2-[3-(5-Amino-3-tert-butyl-pyrazol-1-yl)-phenoxy]-propan-1-ol (Intermediate 151b).

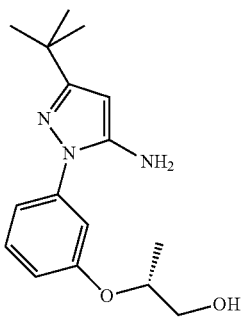 [SMILES: C[C@H](CO)Oc1cccc(-n2nc(C(C)(C)C)cc2N)c1]

A solution of Intermediate 151a (0.37 g, 0.97 mmol) in ethanol (IMS grade, 8 mL) was treated with water (1 mL) and ammonium formate (0.61 g, 9.7 mmol). The mixture was purged with N$_2$ then 10% Pd/C (0.31 g, 0.29 mmol Pd) was added. The mixture was heated to reflux for 16 h then filtered through celite and the filtrate was concentrated in vacuo. The residue was partitioned between EtOAc and water. The phases were separated and the aqueous layer was extracted with EtOAc (×2). The combined organic phase was washed with saturated aqueous sodium bicarbonate solution and brine, dried (Na$_2$SO$_4$) and concentrated in vacuo. The residue was purified by FCC, using 0-75% EtOAc in cyclohexane to give the title compound (0.22 g, 79%) as a pink gum. LCMS (Method 3): Rt 2.44 min, m/z 290.3 [MH$^+$].

c. {5-tert-Butyl-2-[3-((R)-2-hydroxy-1-methyl-ethoxy)-phenyl]-2H-pyrazol-3-yl}-carbamic acid 2,2,2-trichloro-ethyl ester (Intermediate 151c).

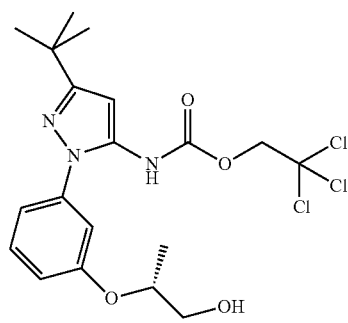 [SMILES: C[C@H](CO)Oc1cccc(-n2nc(C(C)(C)C)cc2NC(=O)OCC(Cl)(Cl)Cl)c1]

A solution of Intermediate 151b (112 mg, 0.39 mmol) in EtOAc (2.1 mL) was treated with aqueous 1N NaOH (0.7 mL, 0.70 mmol) then 2,2,2-trichloroethyl chloroformate (0.056 mL, 0.41 mmol) and the mixture was stirred at RT for 2.5 h. The mixture was treated with another portion of 2,2,2-trichloroethyl chloroformate (0.015 mL, 0.11 mmol) and stirred at RT for a further 1 h. The mixture was diluted with EtOAc and water and the phases were separated. The aqueous layer was extracted with EtOAc (×2) and the combined organic phase was washed with brine, dried (Na$_2$SO$_4$), and concentrated in vacuo to give a pale red gum (195 mg). The gum was purified by FCC, using 0-40% EtOAc in cyclohexane, to give the title compound as a pale golden gum (134 mg, 74%). LCMS (Method 3): Rt 4.15 min, m/z 464.2, 466.2 [MH$^+$].

d. 1-{5-tert-Butyl-2-[3-((R)-2-hydroxy-1-methyl-ethoxy)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea (Intermediate 151 d).

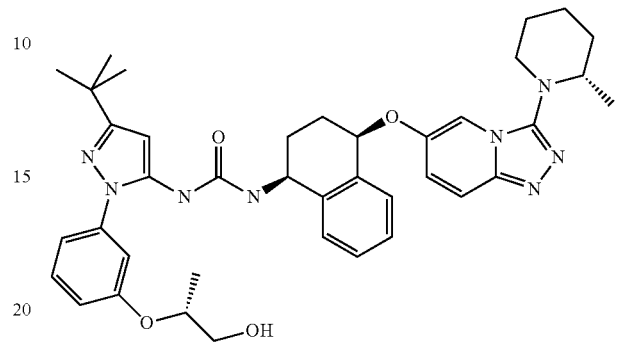

A solution of Intermediate 151c (102 mg, 0.22 mmol) in 1,4-dioxane (2.0 mL) was treated with Intermediate 81d (75 mg, 0.20 mmol) and DIPEA (0.043 mL, 0.25 mmol) and the mixture was stirred at 70° C. for 7.5 h then at 50° C. for 64 h. The cooled solution was concentrated in vacuo, and the residue was partitioned between DCM and water. The phases were separated and the aqueous layer was extracted with DCM (×2). The combined organic phase was washed with brine, dried (Na$_2$SO$_4$) and concentrated in vacuo to a brown gum. The gum was purified by FCC, using 0-10% MeOH in DCM to give the title compound as a yellow glass (84 mg, 61%). LCMS (Method 3): Rt 3.75 min, m/z 693.5 [MH$^+$].

e. Methanesulfonic acid (R)-2-{3-[3-tert-butyl-5-(3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-ureido)-pyrazol-1-yl]-phenoxy)-propyl urea (Intermediate 151e).

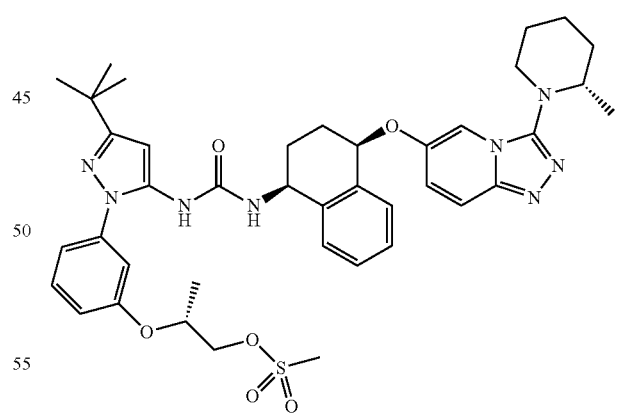

A solution of Intermediate 151d (81 mg, 0.12 mmol) in DCM (2.7 mL) was treated with DIPEA (0.061 mL, 0.35 mmol) then methanesulfonyl chloride (0.012 mL, 0.15 mmol). After 30 mins the mixture was treated with methanesulfonyl chloride (0.012 mL, 0.15 mmol) and then, after another 30 mins, with DIPEA (0.030 mL, 0.18 mmol). The mixture was stirred at RT for 16 h. Another portion of methanesulfonyl chloride (0.012 mL, 0.15 mmol) was added and then after 30 mins another portion of methanesulfonyl chloride (0.012 mL, 0.15 mmol) and DIPEA (0.030 mL, 0.18 mmol) were added. After 30 mins the mixture was diluted with DCM and saturated aqueous sodium bicarbonate solution. The phases were separated and the aqueous layer was extracted with DCM (×2). The combined organic phase was washed with water, saturated aqueous sodium bicarbonate solution and brine, dried (Na₂SO₄) and concentrated in vacuo to give the title compound as a brown glass (92 mg, quant.). LCMS (Method 3): Rt 3.97 min, m/z 771.5 [MH⁺].

f. 1-{5-tert-Butyl-2-[3-((R)-2-dimethylamino-1-methyl-ethoxy)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt (Example 151).

A solution of Intermediate 151e (89 mg, 0.12 mmol) in THF (0.8 mL) was treated with a 2M solution of dimethylamine in THF (1.2 mL, 2.3 mmol) and the mixture was stirred at 60° C. for 42 h. The cooled solution was concentrated in vacuo, and the residue was partitioned between DCM and water. The phases were separated and the aqueous layer was extracted with DCM (×2). The combined organic phase was washed with brine, dried (Na₂SO₄) and concentrated in vacuo to a brown glass. The glass was purified by HPLC (Phenomenex Gemini C18 column, 5-95% MeCN in H₂O, 0.1% HCO₂H) over 25 mins. Concentration of the fractions in vacuo gave a pale yellow glass. The glass was triturated with ether to give a solid that was filtered off to give the title compound as a fawn coloured solid (16 mg, 19%). LCMS (Method 5): Rt 3.68 min, m/z 720.5 [MH⁺]. $^1$H NMR (400 MHz, d₆-DMSO): 0.91 (3H, d, J=6.5 Hz), 1.24 (3H, d, J=6.1 Hz), 1.27 (9H, s), 1.46-1.56 (2H, m), 1.61-1.72 (2H, m), 1.74-1.98 (4H, m), 1.99-2.16 (2H, m), 2.17 (6H, s), 2.32-2.39 (1H, m), 2.86-2.95 (1H, m), 3.13-3.19 (1H, m), 3.29-3.34 (1H, m), 4.56-4.65 (1H, m), 4.79-4.86 (1H, m), 5.52 (1H, t, J=4.4 Hz), 6.32 (1H, s), 6.94-6.99 (1H, m), 7.03-7.12 (3H, m), 7.19 (1H, dd, J=9.9, 2.0 Hz), 7.24-7.41 (5H, m), 7.64 (1H, d, J=10.2 Hz), 7.68-7.70 (1H, m), 8.15 (1H, s), 8.20 (1H, s).

Example 152

1-{5-tert-Butyl-2-[3-((S)-2-dimethylamino-1-methyl-ethoxy)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

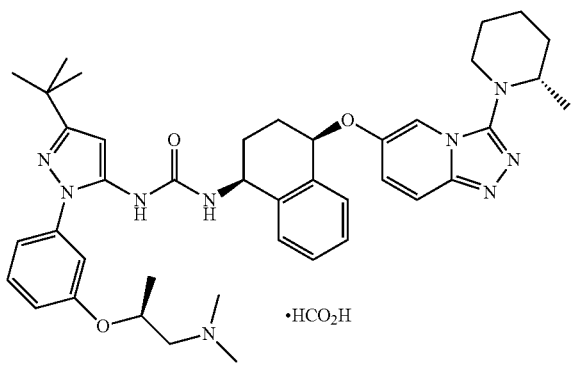 [SMILES: C[C@@H](CN(C)C)Oc1cccc(-n2nc(C(C)(C)C)cc2NC(=O)N[C@H]2CC[C@@H](Oc3ccc4nnc(N5CCCC[C@@H]5C)n4c3)c3ccccc32)c1 ; "·HCO2H"]

a. 2-[3-((S)-2-Benzyloxy-1-methyl-ethoxy)-phenyl]-5-tert-butyl-2H-pyrazol-3-ylamine (Intermediate 152a).

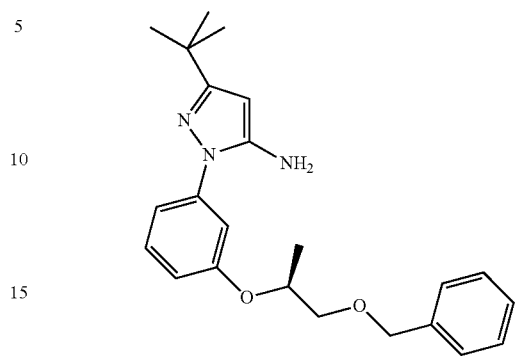

A mixture of Intermediate 95a (0.50 g, 2.2 mmol) in dry THF (17 mL) was treated with triphenylphosphine (1.13 g, 4.32 mmol) and (R)-(−)-1-benzyloxy-2-propanol (0.52 mL, 3.24 mmol) then diisopropylazodicarboxylate (0.85 mL, 4.32 mmol) was added dropwise (the reaction mixture became very warm). After stirring at ambient temperature for 1.75 h the mixture was treated with water (0.2 mL) then concentrated in vacuo to a viscous orange oil. The oil was purified by FCC, using 0-7% EtOAc in DCM. The resulting oil was purified further by FCC, using 0-30% EtOAc in cyclohexane. The product was applied to a pre-conditioned (with MeOH) SCX-2 cartridge and eluted with MeOH then 2N NH₃ in MeOH. The product containing fractions were combined and concentrated in vacuo to give the title compound as a viscous golden oil (0.39 g, 48%). LCMS (Method 3): Rt 3.77 min, m/z 380.4 [MH⁺].

b. (S)-2-[3-(5-Amino-3-tert-butyl-pyrazol-1-yl)-phenoxy]-propan-1-ol (Intermediate 152b).

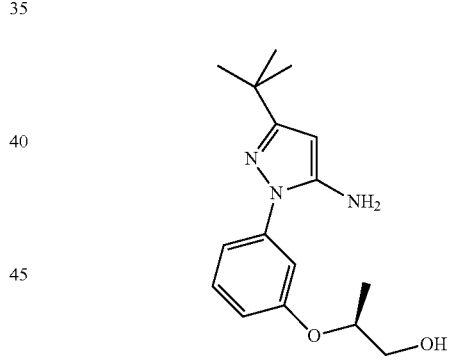

A solution of Intermediate 152a (0.39 g, 1.0 mmol) in ethanol (IMS grade, 10 mL) was purged with N₂ then 10% Pd/C (0.11 g, 0.1 mmol Pd) was added. The mixture was purged with H₂ then stirred under an atmosphere of H₂ (balloon) at ambient temperature for 2 h, then at 50° C. for 1.5 h and 45° C. for 30 mins. Another portion of Pd/C (0.11 g, 0.1 mmol Pd) was added and the mixture was stirred at 45° C. for 16 h. The cooled reaction mixture was purged with N₂ and treated with water (2 mL) then ammonium formate (0.65 g, 10.3 mmol) and heated to reflux for 5. Another portion of ammonium formate (0.65 g, 10.3 mmol) and Pd/C (0.11 g, 0.1 mmol) were added and the mixture was stirred at reflux for 16 h. The mixture was filtered through celite and the filtrate was concentrated in vacuo. The residue was partitioned between EtOAc and water. The phases were separated and the aqueous layer was extracted with EtOAc (×2). The combined organic phase was washed with saturated aqueous sodium bicarbonate solution and brine, dried (Na₂SO₄) and concentrated in vacuo. The residue was purified by FCC, using 0-75% EtOAc in cyclohexane to give the title compound (0.25 g, 83%) as a pink gum. LCMS (Method 3): Rt 2.44 min, m/z 290.3 [MH⁺].
c. {5-tert-Butyl-2-[3-((S)-2-hydroxy-1-methyl-ethoxy)-phenyl]-2H-pyrazol-3-yl}-carbamic acid 2,2,2-trichloro-ethyl ester (Intermediate 152c).

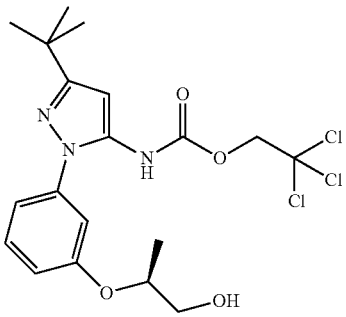 [SMILES: C[C@@H](CO)Oc1cccc(-n2nc(C(C)(C)C)cc2NC(=O)OCC(Cl)(Cl)Cl)c1]

A solution of Intermediate 152b (69 mg, 0.24 mmol) in EtOAc (1.2 mL) was treated with aqueous 1N NaOH (0.4 mL, 0.43 mmol) then 2,2,2-trichloroethyl chloroformate (0.034 mL, 0.25 mmol) and the mixture was stirred at RT for 2.5 h. The mixture was treated with another portion of 2,2,2-trichloroethyl chloroformate (0.010 mL, 0.07 mmol) and stirred at RT for a further 0.75 h. The mixture was diluted with EtOAc and water and the phases were separated. The aqueous layer was extracted with EtOAc (×2) and the combined organic phase was washed with brine, dried (Na₂SO₄), and concentrated in vacuo to give a pale red gum (121 mg). The gum was purified by FCC, using 0-40% EtOAc in cyclohexane, to give the title compound as a pale golden gum (62 mg, 56%). LCMS (Method 3): Rt 4.15 min, m/z 464.2, 466.2 [MH⁺].
d. 1-{5-tert-Butyl-2-[3-((S)-2-hydroxy-1-methyl-ethoxy)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea (Intermediate 152d).

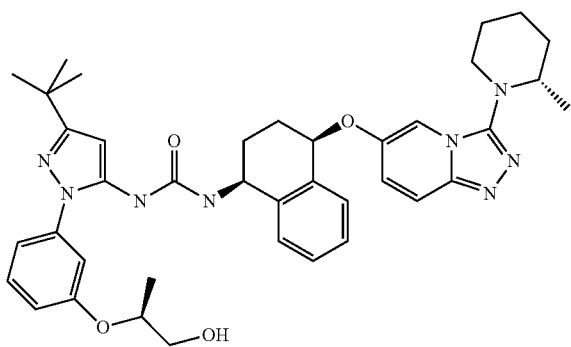 [SMILES: C[C@@H](CO)Oc1cccc(-n2nc(C(C)(C)C)cc2NC(=O)N[C@H]2CC[C@@H](Oc3ccc4nnc(N5CCCC[C@@H]5C)n4c3)c3ccccc32)c1]

A solution of Intermediate 152c (59 mg, 0.13 mmol) in 1,4-dioxane (1.3 mL) was treated with Intermediate 81d (44 mg, 0.12 mmol) and DIPEA (0.025 mL, 0.14 mmol) and the mixture was stirred at 70° C. for 6.75 h then at 50° C. for 64 h. The cooled solution was concentrated in vacuo, and the residue was partitioned between DCM and water. The phases were separated and the aqueous layer was extracted with DCM (×2). The combined organic phase was washed with brine, dried (Na₂SO₄) and concentrated in vacuo to a brown gum. The gum was purified by FCC, using 0-10% MeOH in DCM to give the title compound as a pale yellow glass (49 mg, 61%). LCMS (Method 3): Rt 3.74 min, m/z 693.5 [MH⁺].

e. Methanesulfonic acid (S)-2-{3-[3-tert-butyl-5-(3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-ureido)-pyrazol-1-yl]-phenoxy}-propyl urea (Intermediate 152e).

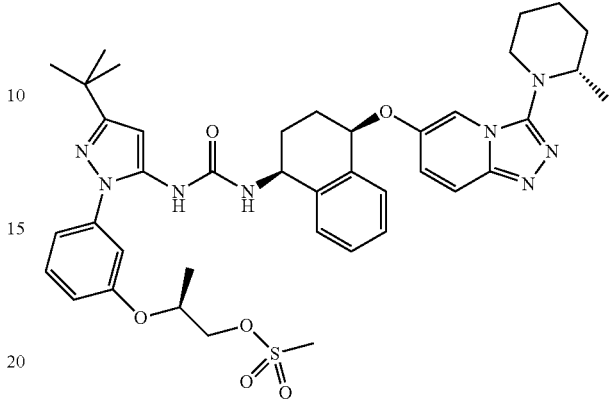

A solution of Intermediate 152d (46 mg, 0.066 mmol) in DCM (1.5 mL) was treated with DIPEA (0.035 mL, 0.20 mmol) then methanesulfonyl chloride (0.0067 mL, 0.086 mmol). After 30 mins the mixture was treated with methanesulfonyl chloride (0.0067 mL, 0.086 mmol) and then, after another 30 mins, with DIPEA (0.018 mL, 0.10 mmol). The mixture was stirred at RT for 16 h. Another portion of methanesulfonyl chloride (0.0067 mL, 0.086 mmol) was added and then after 30 mins another portion of methanesulfonyl chloride (0.0067 mL, 0.086 mmol) and DIPEA (0.018 mL, 0.10 mmol) were added. After 30 mins the mixture was diluted with DCM and saturated aqueous sodium bicarbonate solution. The phases were separated and the aqueous layer was extracted with DCM (×2). The combined organic phase was washed with water, saturated aqueous sodium bicarbonate solution and brine, dried (Na₂SO₄) and concentrated in vacuo to give the title compound as a brown glass (54 mg, quant.). LCMS (Method 3): Rt 3.99 min, m/z 771.5 [MH⁺].
f. 1-{5-tert-Butyl-2-[3-((S)-2-dimethylamino-1-methyl-ethoxy)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt (Example 152).

A solution of Intermediate 152e (51 mg, 0.066 mmol) in THF (0.4 mL) was treated with a 2M solution of dimethylamine in THF (0.66 mL, 1.32 mmol) and the mixture was stirred at 60° C. for 42 h. The cooled solution was concentrated in vacuo, and the residue was partitioned between DCM and water. The phases were separated and the aqueous layer was extracted with DCM (×2). The combined organic phase was washed with brine, dried (Na₂SO₄) and concentrated in vacuo to a brown glass. The glass was purified by HPLC (Phenomenex Gemini C18 column, 5-95% MeCN in H₂O, 0.1% HCO₂H) over 25 mins. Concentration of the fractions in vacuo gave a pale yellow glass. The glass was triturated with diethyl ether to give title compound as a fawn coloured solid (2.5 mg, 5%). LCMS (Method 5): Rt 3.68 min, m/z 720.5 [MH⁺]. ¹H NMR (400 MHz, d₆-DMSO): 0.91 (3H, d, J=6.5 Hz), 1.24 (3H, d, J=6.5 Hz), 1.27 (9H, s), 1.46-1.56 (2H, m), 1.61-1.72 (2H, m), 1.74-1.98 (4H, m), 1.99-2.16 (2H, m), 2.18 (6H, s), 2.32-2.38 (1H, m), 2.86-2.95 (1H, m), 3.12-3.19 (1H, m), 4.56-4.65 (1H, m), 4.78-4.86 (1H, m), 5.52 (1H, t, J=4.1 Hz), 6.32 (1H, s), 6.94-6.99 (1H, m), 7.03-7.11 (3H, m), 7.19 (1H, dd, J=9.6, 2.4 Hz), 7.24-7.41 (5H, m), 7.64 (1H, d, J=10.0 Hz), 7.68-7.70 (1H, m), 8.15 (1H, s), 8.21 (1H, s).

Example 153

1-[2-[3-(2-Dimethylamino-ethoxy)-phenyl]-5-(2-hydroxy-1,1-dimethyl-ethyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

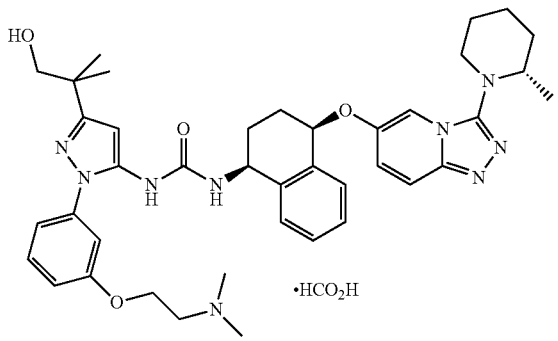 [SMILES: C[C@H]1CCCCN1c1nnc2ccc(O[C@@H]3CC[C@H](NC(=O)Nc4cc(C(C)(C)CO)nn4-c4cccc(OCCN(C)C)c4)c4ccccc43)cn12 ; "·HCO2H"]

a. 3-(tert-Butyl-diphenyl-silanyloxy)-2,2-dimethyl-propionic acid methyl ester (Intermediate 153a).

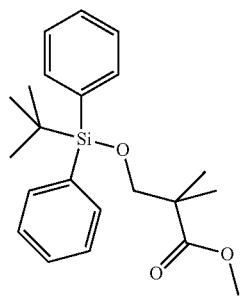 [SMILES: COC(=O)C(C)(C)CO[Si](c1ccccc1)(c1ccccc1)C(C)(C)C]

A solution of methyl 2,2-dimethyl-3-hydroxypropionate (5.0 g, 37.8 mmol) in DMF (75 mL) was cooled to 0° C. and treated with imidazole (3.86 g, 56.7 mmol) then tert-butyl diphenylchlorosilane (11.8 mL, 45.4 mmol). The mixture was stirred at RT for 22 h then concentrated in vacuo. The residue was partitioned between EtOAc and water. The phases were separated and the aqueous layer was extracted with EtOAc (×2). The combined organic phase was washed with 10% aqueous citric acid solution, saturated aqueous sodium bicarbonate solution and brine, dried ($Na_2SO_4$) and concentrated in vacuo to give the title compound as a golden oil (15.93 g, quant.). LCMS (Method 3): Rt 5.32 min, m/z 393.3 [M+Na$^+$].

b. 5-(tert-Butyl-diphenyl-silanyloxy)-4,4-dimethyl-3-oxo-pentanenitrile (Intermediate 153b).

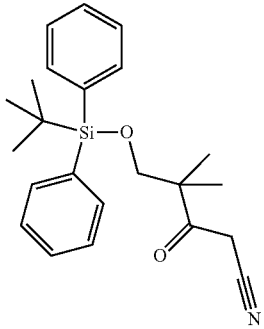 [SMILES: CC(C)(CO[Si](c1ccccc1)(c1ccccc1)C(C)(C)C)C(=O)CC#N]

A suspension of sodium hydride (60% dispersion in oil) (2.12 g, 52.9 mmol) in toluene (65 mL) at reflux under $N_2$ was added over 55 mins a solution of Intermediate 153a (15.93 g, assumed 37.8 mmol) and acetonitrile (2.87 mL, 54.9 mmol) in toluene (31 mL). The mixture was heated at reflux for 67 h. The cooled reaction mixture was slowly acidified to pH 5 with aqueous 1N HCl and extracted with EtOAc. The aqueous layer was extracted with EtOAc (×2) and the combined organic phase was washed with brine, dried ($Na_2SO_4$) and concentrated in vacuo. The residue was purified by FCC, using 0-50% ether in pentane, to give the title compound (3.52 g, 25%) as a yellow oil. LCMS (Method 3): Rt 4.94 min, m/z 402.3 [M+Na$^+$].

c. 2-(3-Benzyloxy-phenyl)-5-[2-(tert-butyl-diphenyl-silanyloxy)-1,1-dimethyl-ethyl]-2H-pyrazol-3-ylamine (Intermediate 153c).

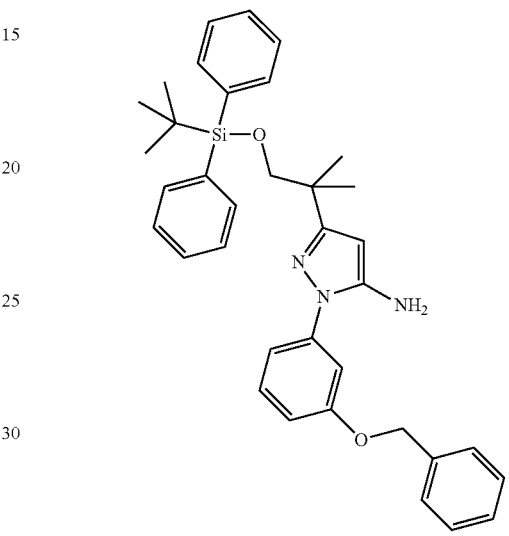

A solution of Intermediate 153b (1.00 g, 2.63 mmol) in ethanol (IMS grade, 20 mL) was treated with 3-benzyloxyphenylhydrazine hydrochloride (0.66 mL, 2.63 mmol) then DIPEA (0.46 mL, 2.63 mmol) and the mixture was heated to reflux for 114 h. The cooled reaction mixture was diluted with EtOAc and a saturated aqueous sodium bicarbonate solution and the mixture was filtered and the phases separated. The aqueous layer was extracted with EtOAc (×2) and the combined organic phase was washed with brine, dried ($Na_2SO_4$), and concentrated in vacuo to give an orange oil (1.62 g). The gum was purified by FCC, using 0-20% EtOAc in cyclohexane, to give the title compound as a yellow oil (1.21 g, 80%). LCMS (Method 3): Rt 5.40 min, m/z 576.5 [MH$^+$].

d. 3-{5-Amino-3-[2-(tert-butyl-diphenyl-silanyloxy)-1,1-dimethyl-ethyl]-pyrazol-1-yl}-phenol (Intermediate 153d).

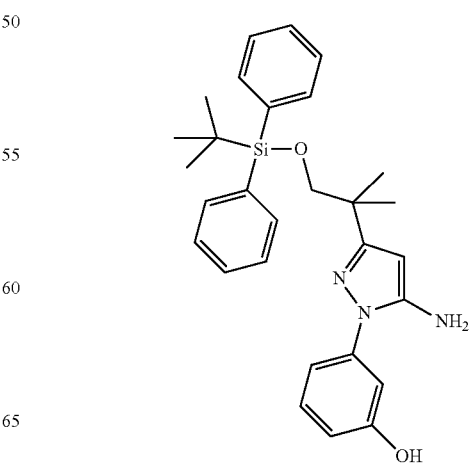

A solution of Intermediate 153c (1.21 g, 2.1 mmol) in ethanol (IMS grade, 20 mL) was treated with water (1 mL) and ammonium formate (1.33 g, 21 mmol). The mixture was purged with N₂ then 10% Pd/C (0.67 g, 0.63 mmol Pd) was added. The mixture was heated to reflux for 1 h then filtered through celite and the filtrate was concentrated in vacuo. The residue was partitioned between EtOAc and water. The phases were separated and the aqueous layer was extracted with EtOAc (×2). The combined organic phase was washed with brine, dried (Na₂SO₄) and concentrated in vacuo. The residue was purified by FCC, using 0-40% EtOAc in cyclohexane, to give the title compound (0.53 g, 41% over 2 steps) as a golden gum. LCMS (Method 3): Rt 4.55 min, m/z 486.5 [MH⁺].

e.  5-[2-(tert-Butyl-diphenyl-silanyloxy)-1,1-dimethyl-ethyl]-2-{3-[2-(tetrahydro-pyran-2-yloxy)-ethoxy]-phenyl}-2H-pyrazol-3-ylamine (Intermediate 153e).

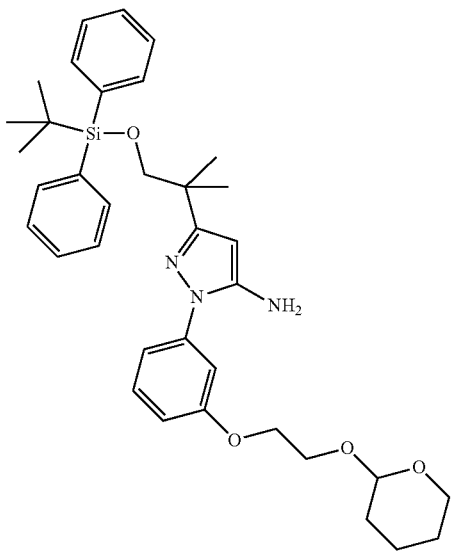 [SMILES: CC(C)(CO[Si](c1ccccc1)(c1ccccc1)C(C)(C)C)c1cc(N)n(-c2cccc(OCCOC3CCCCO3)c2)n1]

A mixture of Intermediate 153d (0.53 g, 1.09 mmol) in dry TI-IF (8 mL) was treated with triphenylphosphine (0.57 g, 2.18 mmol) and 2-(tetrahydro-2H-pyran-2-yloxy)ethanol (0.22 mL, 1.64 mmol). The mixture was cooled to 0° C. then diisopropylazodicarboxylate (0.43 mL, 2.18 mmol) was added dropwise. After stirring at ambient temperature for 20 h the mixture was treated with water (0.1 mL) and concentrated in vacuo to a yellow oil. The oil was purified by FCC, using 0-30% EtOAc in cyclohexane, to give the title compound as an orange oil (0.41 g, 61%). LCMS (Method 3): Rt 5.25 min, ink 614.6 [MH⁺].

f.  (5-[2-(tert-Butyl-diphenyl-silanyloxy)-1,1-dimethyl-ethyl]-2-{3-[2-(tetrahydro-pyran-2-yloxy)-ethoxy]-phenyl}-2H-pyrazol-3-yl)-carbamic acid 2,2,2-trichloro-ethyl ester (Intermediate 153f).

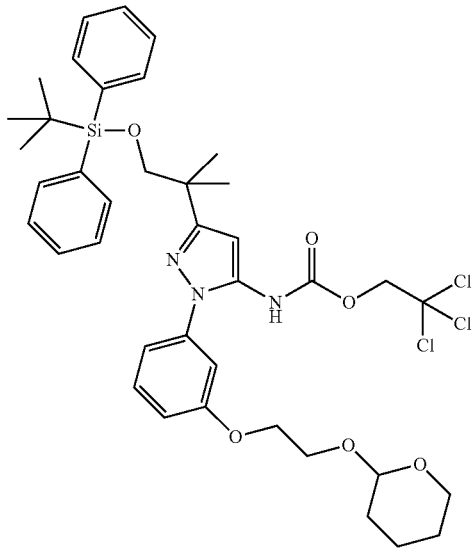 [SMILES: CC(C)(CO[Si](c1ccccc1)(c1ccccc1)C(C)(C)C)c1cc(NC(=O)OCC(Cl)(Cl)Cl)n(-c2cccc(OCCOC3CCCCO3)c2)n1]

A solution of Intermediate 153e (0.41 g, 0.67 mmol) in EtOAc (3.6 mL) was treated with aqueous 1N NaOH (1.2 mL, 1.2 mmol) then 2,2,2-trichloroethyl chloroformate (0.10 mL, 0.74 mmol) and the mixture was stirred at RT for 4 h. The mixture was diluted with EtOAc and water and the phases were separated. The aqueous layer was extracted with EtOAc (×2) and the combined organic phase was washed with brine, dried (Na₂SO₄), and concentrated in vacuo to give a pale red oil (0.67 g). The oil was purified by FCC, using 0-25% EtOAc in cyclohexane to give the title compound as a pale golden gum (0.38 g, 72%). LCMS (Method 3): Rt 5.86 min, m/z 788.3, 790.3 [MH⁺].

g. 1-[3-(1-{[tert-Butyl(diphenyl)silyl]oxy}-2-methylpropan-2-yl)-1-{3-[2-(tetrahydro-2H-pyran-2-yloxy)ethoxy]phenyl}-1H-pyrazol-5-yl]-3-[(1S,4R)-4-({3-[(2S)-2-methylpiperidin-1-yl][1,2,4]triazolo[4,3-a]pyridin-6-yl}oxy)-1,2,3,4-tetrahydronaphthalen-1-yl]urea (Intermediate 153g).

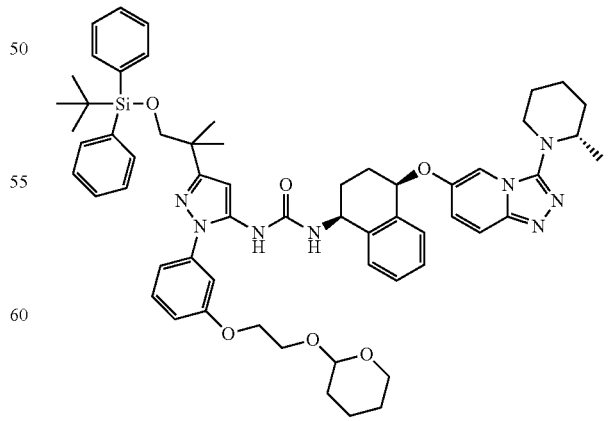

A solution of Intermediate 153f (377 mg, 0.48 mmol) in 1,4-dioxane (4.8 mL) was treated with Intermediate 81d (164 mg, 0.43 mmol) and DIPEA (0.095 mL, 0.54 mmol) and the mixture was stirred at 70° C. for 30 mins then at 50° C. for 64 h then at 70° C. for 22 h. The cooled solution was concentrated in vacuo, and the residue was partitioned between DCM and water. The phases were separated and the aqueous layer was extracted with DCM (×2). The combined organic phase was washed with brine, dried (Na$_2$SO$_4$) and concentrated in vacuo to a brown gum. The gum was purified by FCC, using 0-7% MeOH in DCM to give the title compound as a brown glass (320 mg, 72%). LCMS (Method 3): Rt 5.66 min, m/z 1017.7 [MH$^+$].

h. 1-{3-(1-[tert-Butyl(diphenyl)silyl]oxy}-2-methylpropan-2-yl)-1-[3-(2-hydroxyethoxy)phenyl]-1H-pyrazol-5-yl)-3-[(1S,4R)-4-({3-[(2S)-2-methylpiperidin-1-yl][1,2,4]triazolo[4,3-a]pyridin-6-yl}oxy)-1,2,3,4-tetrahydronaphthalen-1-yl]urea (Intermediate 153h).

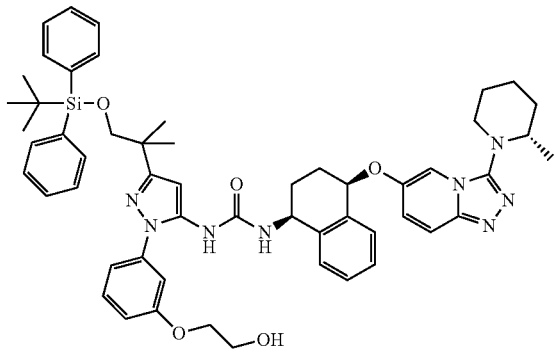 [SMILES: C[C@H]1CCCCN1c1nnc2ccc(O[C@@H]3CC[C@H](NC(=O)Nc4cc(C(C)(C)CO[Si](c5ccccc5)(c5ccccc5)C(C)(C)C)nn4-c4cccc(OCCO)c4)c4ccccc43)cn12]

A solution of Intermediate 153g (317 mg, 0.31 mmol) in MeOH (3.1 mL) was treated with pyridinium para-toluenesulfonate (235 mg, 0.93 mmol) and the mixture was stirred at 45° C. for 19 h. The cooled solution was concentrated in vacuo, and the residue was partitioned between DCM and a saturated aqueous sodium bicarbonate solution. The phases were separated and the aqueous layer was extracted with DCM (×2). The combined organic phase was washed with water, a saturated aqueous sodium bicarbonate solution, and brine, dried (Na$_2$SO$_4$) and concentrated in vacuo to a cream coloured foam. The foam was purified by FCC, using 0-10% MeOH in DCM, to give the title compound as a colourless glass (217 mg, 75%). LCMS (Method 3): Rt 5.06 min, ink 933.7 [MH$^+$].

i. 2-{3-[3-(1-{[tert-Butyl(diphenyl)silyl]oxy}-2-methylpropan-2-yl)-5-({[(1S,4R)-4-({3-[(2S)-2-methylpiperidin-1-yl][1,2,4]triazolo[4,3-a]pyridin-6-yl}oxy)-1,2,3,4-tetrahydronaphthalen-1-yl]carbamoyl}amino)-1H-pyrazol-1-yl]phenoxy}ethyl methanesulfonate (Intermediate 153i).

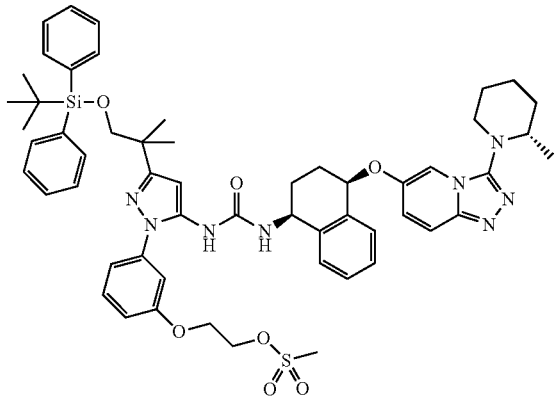 [SMILES: C[C@H]1CCCCN1c1nnc2ccc(O[C@@H]3CC[C@H](NC(=O)Nc4cc(C(C)(C)CO[Si](c5ccccc5)(c5ccccc5)C(C)(C)C)nn4-c4cccc(OCCOS(C)(=O)=O)c4)c4ccccc43)cn12]

A solution of Intermediate 153h (214 mg, 0.23 mmol) in DCM (2.3 mL) was treated with DIPEA (0.12 mL, 0.69 mmol) then methanesulfonyl chloride (0.037 mL, 0.48 mmol). After 30 mins the mixture was diluted with DCM and saturated aqueous sodium bicarbonate solution. The phases were separated and the aqueous layer was extracted with DCM (×2). The combined organic phase was washed with water, saturated aqueous sodium bicarbonate solution and brine, dried (Na$_2$SO$_4$) and concentrated in vacuo to an orange gum. The gum was purified by FCC, using 0-8% MeOH in DCM, to give the title compound as a pale brown glass (134 mg, 58%). LCMS (Method 3): Rt 5.18 min, m/z 1011.7 [MH$^+$].

j. 1-[3-(1-{[tert-Butyl(diphenyl)silyl]oxy}-2-methylpropan-2-yl)-1-{3-[2-(dimethylamino)ethoxy]phenyl}-1H-pyrazol-5-yl]-3-[(1S,4R)-4-({3-[(2S)-2-methylpiperidin-1-yl][1,2,4]triazolo[4,3-a]pyridin-6-yl}oxy)-1,2,3,4-tetrahydronaphthalen-1-yl]urea (Example 153j).

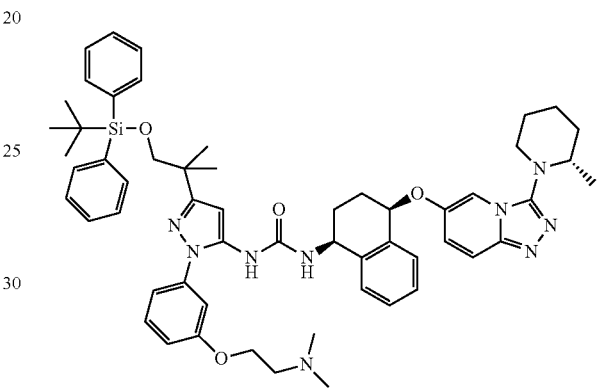

A solution of Intermediate 153i (131 mg, 0.13 mmol) in THF (0.8 mL) was treated with a 2M solution of dimethylamine in THF (1.3 mL, 2.6 mmol) and the mixture was stirred at 60° C. for 18 h. The cooled solution was concentrated in vacuo, and the residue was partitioned between DCM and water. The phases were separated and the aqueous layer was extracted with DCM (×2). The combined organic phase was washed with brine, dried (Na$_2$SO$_4$) and concentrated in vacuo to a brown gum. The gum was purified by FCC, using 0-8% (2N NH$_3$/MeOH) in DCM, to give the title compound as a white foam (93 mg, 75%). LCMS (Method 3): Rt 3.91 min, m/z 960.6 [MH$^+$].

1-[2-[3-(2-Dimethylamino-ethoxy)-phenyl]-5-(2-hydroxy-1,1-dimethyl-ethyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt (Example 153).

A solution of Intermediate 153j (90 mg, 0.09 mmol) in THF (0.5 mL) was treated with a 1M solution of tetrabutylammonium fluoride in THF (0.5 mL, 0.5 mmol) and the reaction mixture was stirred at RT for 1 h then at 50° C. for 16 h. The cooled solution was concentrated in vacuo, and the residue was partitioned between DCM and a saturated aqueous sodium bicarbonate solution. The phases were separated and the aqueous layer was extracted with DCM (×2). The combined organic phase was washed with brine, dried (Na$_2$SO$_4$) and concentrated in vacuo to a brown gum. The gum was purified by FCC, using 0-8% [2M NH$_3$ in MeOH] in DCM, and then purified further by HPLC (Phenomenex Gemini C18 column, 5-95% MeCN in H$_2$O, 0.1% HCO$_2$H) over 25 mins to give a colourless glass. The glass was triturated with diethyl ether to give the title compound as a white solid (11 mg, 16%). LCMS (Method 5): Rt 3.17 min, m/z 722.6 [MH+]. ¹H NMR (400 MHz, d₆-DMSO): 0.91 (3H, d, J=6.3 Hz), 1.21 (6H, s), 1.44-1.57 (2H, m), 1.62-1.73 (2H, m), 1.74-1.98 (4H, m), 1.99-2.17 (2H, m), 2.18 (6H, s), 2.61 (2H, t, J=6.0 Hz), 2.86-2.95 (1H, m), 3.12-3.20 (1H, m), 3.27-3.36 (1H, m), 3.44 (2H, s), 4.08 (2H, t, J=6.0 Hz), 4.78-4.86 (1H, m), 5.52 (1H, t, J=4.0 Hz), 6.32 (1H, s), 6.94-6.99 (1H, m), 7.06-7.14 (3H, m), 7.19 (1H, dd, J=10.1, 2.0 Hz), 7.24-7.43 (5H, m), 7.64 (1H, d, J=9.7 Hz), 7.68-7.71 (1H, m), 8.15 (1H, s), 8.20 (1H, s).

Example 154

1-{5-tert-Butyl-2-[3-(2-pyrrolidin-1-yl-ethoxy)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

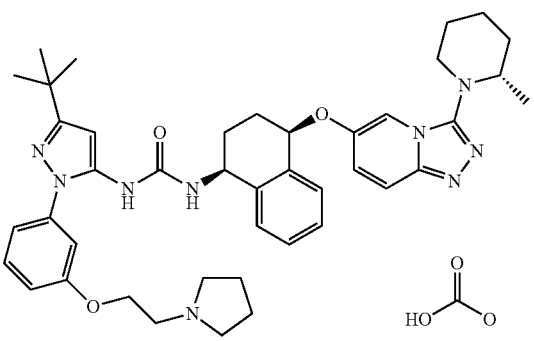

a. Methanesulfonic acid 2-{3-[3-tert-butyl-5-(3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-ureido)-pyrazol-1-yl]-phenoxy}-ethyl ester (Intermediate 154a).

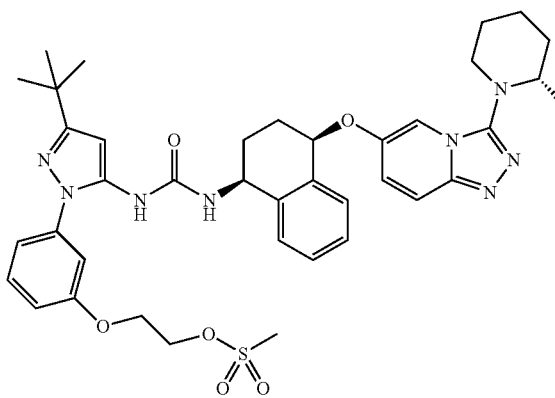

Methanesulfonyl chloride (81 µL, 1.05 mmol) was added to a stirred solution of Intermediate 95e (545 mg, 803 mmol) and DIPEA (420 µL, 2.41 mmol) in DCM (20 mL), under argon and the reaction mixture was stirred at RT for 1.5 h. A further 25 µl, 0.32 mmol of methanesulfonyl chloride was added and the reaction mixture continued to stir at RT for 2 h. Water (20 mL) was added and the two layers were shaken thoroughly before being separated. The aqueous layer was extracted with DCM (2×20 mL) and the combined organics were passed through a phase separator and concentrated in vacuo to afford the title compound as an orange glass (690 mg, >100%). LCMS (Method 3): Rt 3.89 min, m/z 757 [MH+].

b. 1-{5-tert-Butyl-2-[3-(2-pyrrolidin-1-yl-ethoxy)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt (Example 154).

A solution of Intermediate 154a (50.5 mg, 0.067 mmol) and pyrrolidine (27 µL, 0.33 mmol) in THF (1 mL) was stirred at 60° C. for 20 h in a sealed tube. The mixture was concentrated in vacuo and the residue purified by MDAP (Method 7). The title product was isolated as an off-white solid (29 mg, 59%). LCMS (Method 5): Rt 3.72 min, m/z 732.6 [MH+]. ¹H NMR (400 MHz, d₆-DMSO): 0.91 (3H, d, J=8.0 Hz), 1.28 (9H, s), 1.46-1.56 (2H, m), 1.61-1.72 (6H, m), 1.75-1.98 (4H, m), 1.99-2.18 (2H, m), 2.52 (4H, m, obscured by solvent), 2.80 (2H, t, J=8.0 Hz), 2.86-2.95 (1H, m), 3.12-3.19 (1H, m, obscured by water), 3.27-3.35 (1H, m, obscured by water), 4.11 (2H, t, J=8.0 Hz), 4.78-4.86 (1H, m), 5.52 (1H, t, J=4.0 Hz), 6.33 (1H, s), 6.97 (1H, dd, J=8.0 Hz, 4.0 Hz), 7.05-7.14 (3H, m), 7.19 (1H, dd, J=8.0 Hz, 4.0 Hz), 7.24-7.42 (5H, m), 7.64 (1H, d, J=8.0 Hz), 7.69 (1H, d, J=4.0 Hz), 8.14 (1H, s), 8.18 (1.3H, s).

Example 155

1-{5-tert-Butyl-2-[3-(2-diethylamino-ethoxy)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

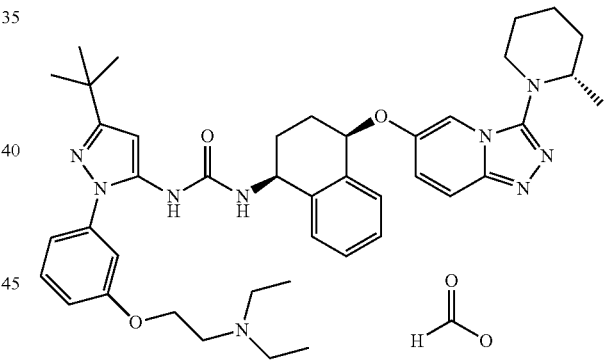

A solution of Intermediate 154a (50.5 mg, 0.067 mmol) and diethylamine (34 µL, 0.33 mmol) in THF (1 mL) was stirred at 60° C. for 20 h in a sealed tube. Additional diethylamine (102 µL, 0.99 mmol) was added and the mixture subsequently stirred at 60° C. in a sealed tube for 24 h. The mixture was concentrated in vacuo and the residue purified by MDAP (Method 7). The title product was isolated as an off-white solid (22 mg, 45%). LCMS (Method 5): Rt 3.74 min, m/z 734.6 [MH+]. ¹H NMR (400 MHz, d₆-DMSO): 0.89-0.96 (9H, m), 1.28 (9H, s), 1.46-1.56 (2H, m), 1.62-1.73 (2H, m), 1.74-1.98 (4H, m), 1.99-2.18 (2H, m), 2.52 (4H, m, obscured by solvent), 2.76 (2H, t, J=8.0 Hz), 2.87-2.94 (1H, m), 3.12-3.19 (1H, m, obscured by water), 3.30 (1H, m, obscured by water), 4.05 (2H, t, J=8.0 Hz), 4.77-4.86 (1H, m), 5.52 (1H, t, J=4.0 Hz), 6.33 (1H, s), 6.95 (1H, dd, J=8.0 Hz, 4.0 Hz), 7.05-7.13 (3H, m), 7.19 (1H, dd, J=8.0 Hz, 4.0 Hz), 7.24-7.42 (5H, m), 7.64 (1H, d, J=8.0 Hz), 7.69 (1H, d, J=4.0 Hz), 8.13 (1H, s), 8.19 (1H, s).

Example 156

1-{5-tert-Butyl-2-[3-(2-morpholin-4-yl-ethoxy)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea partial formate salt

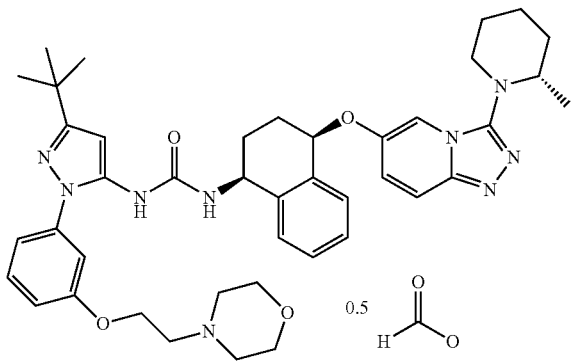 [SMILES: C[C@H]1CCCCN1c1nnc2ccc(O[C@@H]3CC[C@H](NC(=O)Nc4cc(C(C)(C)C)nn4-c4cccc(OCCN5CCOCC5)c4)c4ccccc43)cn12 ; O=CO]

A solution of Intermediate 154a (50.5 mg, 0.067 mmol) and morpholine (29 µL, 0.33 mmol) in THF (1 mL) was stirred at 60° C. for 20 h in a sealed tube. Additional morpholine (29 µL, 0.33 mmol) was added and the mixture subsequently stirred at 60° C. in a sealed tube for 24 h. The mixture was concentrated in vacuo and the residue purified by MDAP (Method 7). The title product was isolated as an off-white solid (25 mg, 50%). LCMS (Method 5): Rt 3.66 min, m/z 748.6 [MH$^+$]. $^1$H NMR (400 MHz, d$_6$-DMSO): 0.91 (3H, d, J=6.0 Hz), 1.27 (9H, s), 1.46-1.56 (2H, m), 1.61-1.73 (2H, m), 1.75-1.98 (4H, m), 1.99-2.19 (2H, m), 2.42 (4H, t, J=4.0 Hz), 2.67 (2H, t, J=8.0 Hz), 2.86-2.95 (1H, m), 3.12-3.20 (1H, m, obscured by water), ~3.30 (1H, m, obscured by water), 3.53 (4H, t, J=8.0 Hz), 4.12 (2H, t, J=8.0 Hz), 4.77-4.86 (1H, m), 5.52 (1H, t, J=4.0 Hz), 6.33 (1H, s), 6.95-6.99 (1H, m), 7.07-7.13 (3H, m), 7.19 (1H, dd, J=8.0 Hz, 4.0 Hz), 7.25-7.43 (5H, m), 7.64 (1H, d, J=8.0 Hz), 7.69 (1H, d, J=4.0 Hz), 8.13 (1H, s), 8.21 (0.5H, s).

Example 157

1-{5-tert-Butyl-2-[3-(2-piperidin-1-yl-ethoxy)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

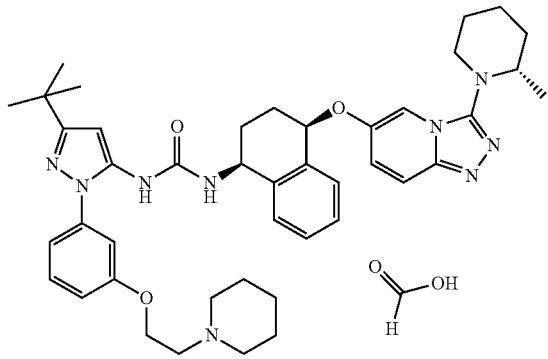 [SMILES: C[C@H]1CCCCN1c1nnc2ccc(O[C@@H]3CC[C@H](NC(=O)Nc4cc(C(C)(C)C)nn4-c4cccc(OCCN5CCCCC5)c4)c4ccccc43)cn12 ; O=CO]

A solution of Intermediate 154a (66 mg, 88 µmol) and piperidine (44 µL, 0.45 mmol) in THF (2 mL) was heated at 60° C. overnight in a sealed vessel. The reaction mixture was concentrated in vacuo and the residue purified by MDAP (Method 7) to give the title compound as a white solid (31 mg, 46%). LCMS (Method 5): Rt 3.77 min, m/z 746 [MH$^+$]. $^1$H NMR (400 MHz, d$_6$-DMSO): 0.91 (3H, d, J=6.2 Hz), 1.24-1.34 (11H, m), 1.39-1.55 (6H, m), 1.61-2.18 (8H, m), 2.34-2.43 (4H, m), 2.63 (2H, t, J 6.1 Hz), 2.86-2.94 (1H, m), 3.11-3.19 (1H, m), 3.27-3.36 (1H, m), 4.09 (2H, t, J=5.9 Hz), 4.77 (1H, m), 5.52 (1H, t, J=4.0 Hz), 6.32 (1H, s), 6.93-6.98 (1H, m), 7.04-7.13 (3H, m), 7.19 (1H, dd, J=9.5 Hz, 2.6 Hz), 7.24-7.42 (5H, m), 7.64 (1H, d, J=9.9 Hz), 7.69 (1H, d, J=1.8 Hz), 8.12 (1H, s), 8.17 (1.5H, s).

Example 158

1-(5-tert-Butyl-2-{3-[2-(4-methyl-piperazin-1-yl)-ethoxy]-phenyl}-2H-pyrazol-3-yl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

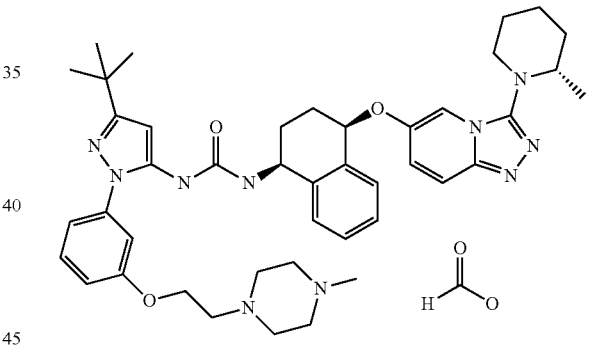

A solution of Intermediate 154a (50.5 mg, 0.067 mmol) and 1-methylpiperazine (37 µL, 0.33 mmol) in THF (1 mL) was stirred at 60° C. for 20 h in a sealed tube. The mixture was concentrated in vacuo and the residue purified by MDAP (Method 7). The title product was isolated as an off-white solid (28 mg, 55%). LCMS (Method 5): Rt 3.62 min, m/z 761.6 [MH$^+$]. $^1$H NMR (400 MHz, d$_6$-DMSO): 0.91 (3H, d, J=8.0 Hz), 1.28 (9H, s), 1.47-1.56 (2H, m), 1.61-1.73 (2H, m), 1.74-1.97 (4H, m), 2.00-2.19 (5H, m), 2.21-2.35 (4H, m), 2.36-2.49 (4H, m), 2.66 (2H, t, J=8.0 Hz), 2.86-2.95 (1H, m), 3.12-3.19 (1H, m, obscured by water), 3.27-3.35 (1H, m, obscured by water), 4.10 (2H, t, J=8.0 Hz), 4.78-4.86 (1H, m), 5.52 (1H, t, J=4.0 Hz), 6.33 (1H, s), 6.94-6.98 (1H, m), 7.05-7.13 (3H, m), 7.19 (1H, dd, J=8.0 Hz, 4.0 Hz), 7.24-7.42 (5H, m), 7.64 (1H, d, J=8.0 Hz), 7.69 (1H, d, J=4.0 Hz), 8.13 (1H, s), 8.17 (1.4H, s).

Example 159

1-{5-tert-Butyl-2-{3-[2-(4-fluoropiperidin-1-yl)-ethoxy]-phenyl}-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

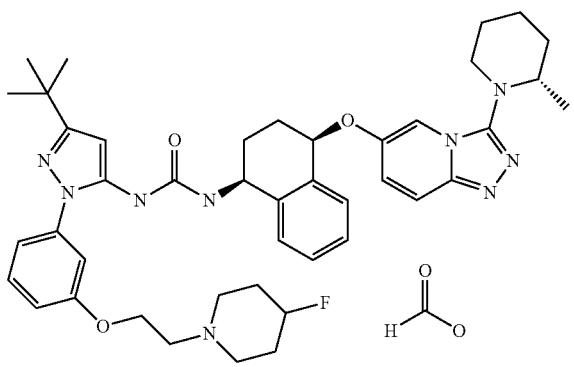 [SMILES: C[C@H]1CCCCN1c1nnc2ccc(O[C@@H]3CC[C@H](NC(=O)Nc4cc(C(C)(C)C)nn4-c4cccc(OCCN5CCC(F)CC5)c4)c4ccccc43)cn12 ; O=CO]

A solution of Intermediate 154a (50.5 mg, 0.067 mmol) and 4-fluoropiperdine (34 mg, 0.33 mmol) in THF (1 mL) was stirred at 60° C. for 20 h in a sealed tube. Additional 4-fluoropiperidine (34 mg, 0.33 mmol) was added and the mixture subsequently stirred at 60° C. in a sealed tube for 24 h. The mixture was concentrated in vacuo and the residue purified by MDAP (Method 7). The title product was isolated as an off-white solid (24 mg, 47%). LCMS (Method 5): Rt 3.75 min, m/z 764.6 [MH$^+$]. $^1$H NMR (400 MHz, d$_6$-DMSO): 0.91 (3H, d, J=8.0 Hz), 1.27 (9H, s), 1.44-1.64 (2H, m), 1.59-1.72 (4H, m), 1.72-1.98 (6H, m), 1.99-2.19 (2H, m), 2.31-2.40 (2H, m), 2.55-2.64 (2H, m), 2.68 (2H, t, J=8.0 Hz), 2.87-2.95 (1H, m), 3.12-3.19 (1H, m, obscured by water), 3.30 (1H, m, completely obscured by water), 4.10 (2H, t, J=8.0 Hz), 4.51-4.59 (0.5H, m), 4.64-4.71 (0.5H, m), 4.78-4.86 (1H, m), 5.52 (1H, t, J=4.0 Hz), 6.33 (1H, s), 6.95-6.99 (1H, m), 7.06-7.13 (3H, m), 7.19 (1H, dd, J=8.0 Hz, 4.0 Hz), 7.25-7.42 (5H, m), 7.64 (1H, d, J=8.0 Hz), 7.69 (1H, d, J=4.0 Hz), 8.12 (1H, s), 8.18 (1H, s).

Example 160

1-(5-tert-Butyl-2-{3-[2-(4-methyl-[1,4]-diazepan-1-yl)-ethoxy]-phenyl}-2H-pyrazol-3-yl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

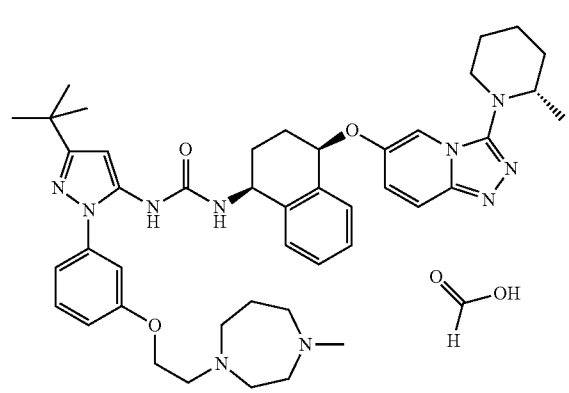 [SMILES: C[C@H]1CCCCN1c1nnc2ccc(O[C@@H]3CC[C@H](NC(=O)Nc4cc(C(C)(C)C)nn4-c4cccc(OCCN5CCCN(C)CC5)c4)c4ccccc43)cn12 ; O=CO]

A solution of Intermediate 154a (50.5 mg, 0.066 mmol) and N-methyl homopiperazine (39 mg, 0.34 mmol) in THF (1 mL) was heated at 60° C. overnight in a sealed vessel. The reaction mixture was concentrated in vacuo and the residue purified by MDAP (Method 7) to give a white solid of the title compound (28 mg, 54%). LCMS (Method 5): Rt 3.28 min, m/z 775 [MH$^+$]. $^1$H NMR (400 MHz, d$_6$-DMSO): 0.91 (3H, d, J=6.0 Hz), 1.27 (9H, s), 1.47-1.56 (2H, m), 1.62-1.73 (4H, m), 1.75-2.18 (6H, m), 2.28 (3H, s), 2.56-2.63 (4H, m), 2.70-2.77 (4H, m), 2.85 (2H, t, J=6.0 Hz), 2.87-2.95 (1H, m), 3.12-3.20 (1H, m), 3.27-3.35 (1H, m), 4.07 (2H, t, J=5.6 Hz), 4.77-4.86 (1H, m), 5.52 (1H, t, J=3.8 Hz), 6.32 (1H, s), 6.93-6.98 (1H, m), 7.04-7.10 (2H, m), 7.14 (1H, d, J=8.9 Hz), 7.19 (1H, dd, J=9.8 Hz, 2.2 Hz), 7.24-7.42 (5H, m), 7.64 (1H, d, J=4.9 Hz), 7.69 (1H, d, J=1.8 Hz), 8.18 (1H, s), 8.20 (2H, s).

Example 161

1-{5-tert-Butyl-2-[3-(2-[1,4]oxazepan-4-yl-ethoxy)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

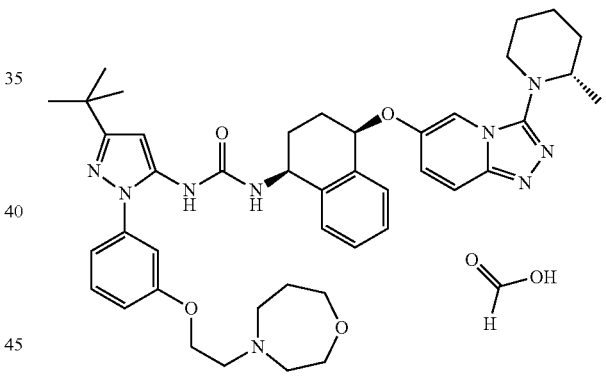

A solution of Intermediate 154a (50.5 mg, 66 μmol) and [1,4]oxazepine (70 mg, 0.68 mmol) in THF (1 mL) was heated at 60° C. for 48 h in a sealed vessel. The reaction mixture was concentrated in vacuo and the residue purified by MDAP (Method 7) to give the title compound as a white solid (27 mg, 53%). LCMS (Method 5): Rt 3.68 min, m/z 762 [MH$^+$]. $^1$H NMR (400 MHz, d$_6$-DMSO): 0.91 (3H, d, J=6.2 Hz), 1.27 (9H, s), 1.46-1.54 (2H, m), 1.62-2.17 (12H, m), 2.67-2.72 (3H, m), 2.86 (2H, t, J=6.0 Hz), 2.88-2.94 (1H, m), 3.12-3.19 (1H, m), 3.28-3.34 (1H, m, obscured by water peak), 3.53-3.58 (2H, m), 3.61 (2H, t, J=6.0 Hz), 4.09 (2H, t, J=6.1 Hz), 4.77-4.86 (1H, m), 5.52 (1H, t, J=4.3 Hz), 6.33 (1H, s), 6.94-6.99 (1H, m), 7.05-7.12 (2H, m), 7.19 (1H, dd, J=8.6 Hz, 2.0 Hz), 7.24-7.42 (5H, m), 7.64 (1H, d, J=9.8 Hz), 7.69 (1H, d, J=2.0 Hz), 8.17 (1H, s), 8.18 (1H, s).

Example 162

1-(2-{3-[2-(8-Aza-bicyclo[3.2.1]oct-8-yl)-ethoxy]-phenyl}-5-tert-butyl-2H-pyrazol-3-yl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

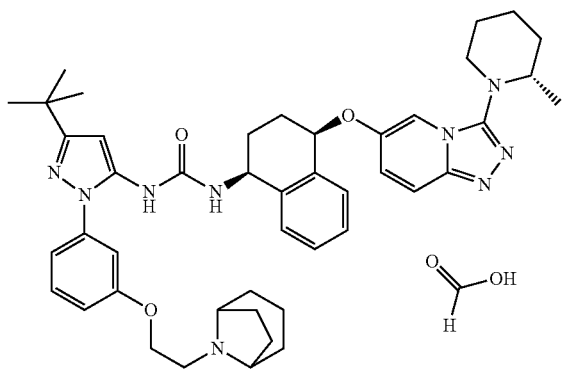 [SMILES: C[C@H]1CCCCN1c1nnc2ccc(O[C@@H]3CC[C@H](NC(=O)Nc4cc(C(C)(C)C)nn4-c4cccc(OCCN5C6CCCC5CC6)c4)c4ccccc43)cn12 ; O=CO]

A solution of Intermediate 154a (50.5 mg, 66 μmol) and 8-aza-bicyclo[3.2.1]octane (38 mg, 0.34 mmol) in THF (1 mL) was heated at 60° C. overnight in a sealed vessel. The reaction mixture was concentrated in vacuo and the residue purified by MDAP (Method 7) to give the title compound as a white solid (32 mg, 62%). LCMS (Method 5): Rt 3.84 min, m/z 772 [MH$^+$]. $^1$H NMR (400 MHz, d$_6$-DMSO): 0.91 (3H, d, J=6.4 Hz), 1.21-1.36 (11H, m), 1.37-1.54 (4H, m), 1.58-1.72 (4H, m), 1.74-2.18 (8H, m), 2.72 (2H, d, J=6.4 Hz), 2.86-2.95 (1H, m), 3.11-3.20 (1H, m), 3.22-3.36 (5H, m), 4.09 (2H, t, J=6.1 Hz), 4.77-4.86 (1H, m), 5.52 (1H, t, J=4.1 Hz), 6.33 (1H, s), 6.94-6.99 (1H, m), 7.04-7.11 (2H, m), 7.14 (1H, d, J=8.6 Hz), 7.18 (1H, dd, J=10.2 Hz, 2.1 Hz), 7.24-7.42 (5H, m), 7.64 (1H, d, J=10.2 Hz), 7.69 (1H, d, J=2.0 Hz), 8.17 (1H, s), 8.19 (1.6H, s).

Example 163

1-(5-tert-Butyl-2-{3-[2-(ethyl-methyl-amino)-ethoxy]-phenyl}-2H-pyrazol-3-yl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

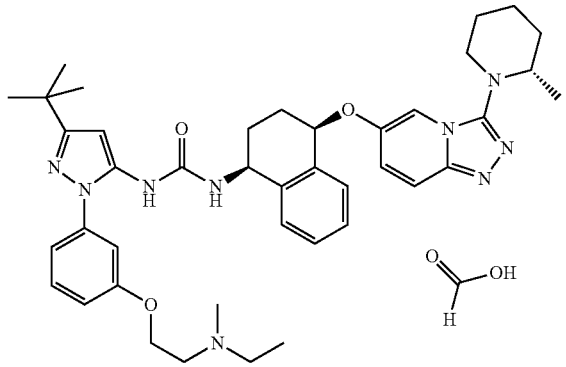 [SMILES: CCN(C)CCOc1cccc(-n2nc(C(C)(C)C)cc2NC(=O)N[C@H]2CC[C@@H](Oc3ccc4nnc(N5CCCC[C@@H]5C)n4c3)c3ccccc32)c1 ; O=CO]

A solution of Intermediate 154a (50.5 mg, 66 μmol) and N-ethylmethylamine (40 mg, 0.68 mmol) in THF (1 mL) was heated at 60° C. for 48 h in a sealed vessel. The reaction mixture was concentrated in vacuo and the residue purified by MDAP (Method 7) to give the title compound as a white solid (24 mg, 50%). LCMS (Method 5): Rt 3.69 min, m/z 720 [MH$^+$]. $^1$H NMR (400 MHz, d$_6$-DMSO): 0.91 (3H, d, J=6.3 Hz), 0.94 (3H, t, J=7.2 Hz), 1.27 (9H, s), 1.46-1.55 (2H, m), 1.64-1.72 (2H, m), 1.76-2.09 (6H, m), 2.19 (3H, s), 2.41 (2H, quart, J=7.0 Hz), 2.68 (2H, t, J=4.7 Hz), 2.86-2.94 (1H, m), 3.12-3.19 (1H, m), 3.29-3.34 (1H, m, obscured by water peak), 4.08 (2H, t, J=6.1 Hz), 4.77-4.86 (1H, m), 5.52 (1H, t, J=4.4 Hz), 6.33 (1H, s), 6.94-6.98 (1H, m), 7.05-7.13 (3H, m), 7.19 (1H, dd, J=9.6 Hz, 2.2 Hz), 7.23-7.42 (5H, m), 7.64 (1H, d, J=10.2 Hz), 7.69 (1H, d, J=2.2 Hz), 8.13 (1H, s), 8.18 (1H, s).

Example 164

1-{5-tert-Butyl-2-(3-{2-[(2-methoxy-ethyl)-methyl-amino]-ethoxy}-phenyl)-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

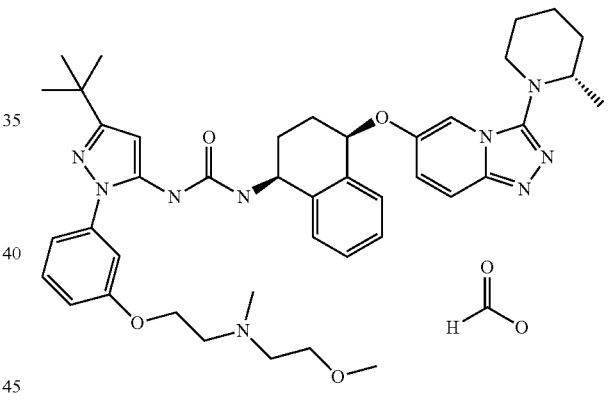

A solution of Intermediate 154a (50.5 mg, 0.067 mmol) and N-(2-methoxyethyl)methylamine (35 μL, 0.33 mmol) in THF (1 mL) was stirred at 60° C. for 20 h in a sealed tube. Additional N-(2-methoxyethyl)methylamine (35 μL, 0.33 mmol) was added and the mixture subsequently stirred at 60° C. in a sealed tube for 24 h. The mixture was concentrated in vacuo and the residue purified by MDAP (Method 7). The title product was isolated as an off-white solid (24 mg, 48%). LCMS (Method 5): Rt 3.72 min, m/z 750.6 [MH$^+$]. $^1$H NMR (400 MHz, d$_6$-DMSO): 0.91 (3H, d, J=8.0 Hz), 1.27 (9H, s), 1.44-1.56 (2H, m), 1.61-1.73 (2H, m), 1.73-1.98 (4H, m), 1.98-2.22 (2H, m), 2.24 (3H, s), 2.55 (2H, t, J=8.0 Hz), 2.74 (2H, t, J=8.0 Hz), 2.86-2.95 (1H, m), 3.12-3.18 (1H, m, obscured by water), 3.19 (3H, s, obscured by water), 3.30 (1H, m, obscured by water), 3.38 (2H, t, J=8.0 Hz, obscured by water), 4.07 (2H, t, J=8.0 Hz), 4.78-4.86 (1H, m), 5.52 (1H, t, J=4.0 Hz), 6.33 (1H, s), 6.94-6.99 (1H, m), 7.05-7.14 (3H, m), 7.19 (1H, dd, J=8.0 Hz, 4.0 Hz), 7.24-7.42 (5H, m), 7.64 (1H, d, J=8.0 Hz), 7.69 (1H, d, J=4.0 Hz), 8.13 (1H, s), 8.19 (1H, s).

Example 165

1-(5-tert-Butyl-2-{3-[2-(4-methoxy-piperidin-1-yl-ethoxy]-phenyl}-2H-pyrazol-3-yl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

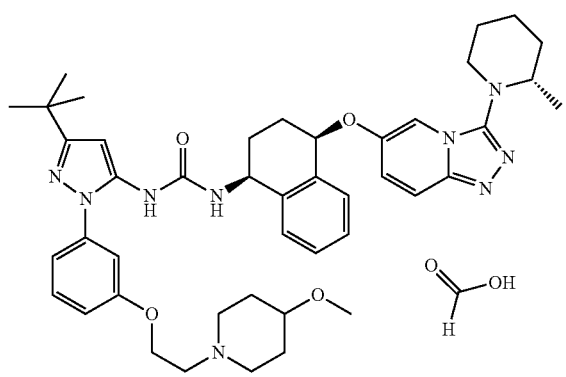 [SMILES: COC1CCN(CCOc2cccc(-n3nc(C(C)(C)C)cc3NC(=O)N[C@H]3CC[C@@H](Oc4ccc5nnc(N6CCCC[C@@H]6C)n5c4)c4ccccc43)c2)CC1 ; O=CO]

A solution of Intermediate 154a (50.5 mg, 0.066 mmol) and 4-methoxypiperidine (39 □L, 0.34 mmol) in THF (1 mL) was heated at 60° C. overnight in a sealed vessel. The reaction mixture was concentrated in vacuo and the residue purified by MDAP (Method 7) to give a white solid of the title compound (31 mg, 60%). LCMS (Method 5): Rt 3.75 min, m/z 776 [MH$^+$]. $^1$H NMR (400 MHz, d$_6$-DMSO): 0.91 (3H, d, J=6.2 Hz), 1.27 (9H, s), 1.30-1.42 (2H, m), 1.45-1.57 (2H, m), 1.61-2.18 (13H, m), 2.66 (2H, t, J=5.7 Hz), 2.68-2.76 (1H, m), 2.86-2.95 (1H, m), 3.04-3.19 (2H, m), 3.16 (3H, s), 3.28-3.34 (1H, m), 4.09 (2H, t, J=5.9 Hz), 4.77-4.85 (1H, m), 5.52 (1H, t, J=4.3 Hz), 6.33 (1H, s), 6.93-6.98 (1H, m), 7.04-7.13 (3H, m), 7.18 (1H, dd, J=10.3 Hz, 2.3 Hz), 7.24-7.42 (5H, m), 7.64 (1H, d, J=9.5 Hz), 7.69 (1H, d, J=2.3 Hz), 8.12 (1H, s), 8.16 (1.7H, s).

Example 166

1-(5-tert-Butyl-2-{3-[2-(3-oxa-8-aza-bicyclo[3.2.1]oct-8-yl)-ethoxy]-phenyl}-2H-pyrazol-3-yl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

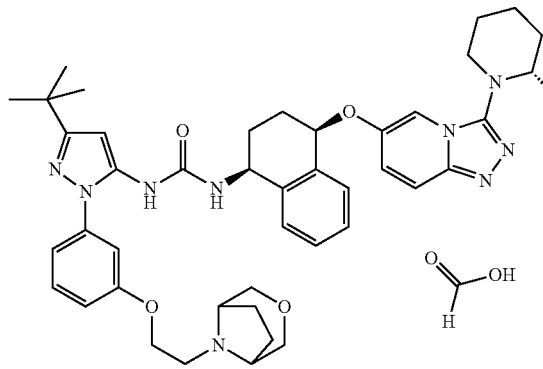

A solution of Intermediate 154a (50.5 mg, 66 μmol) and 3-oxa-8-aza-bicyclo[3.2.1]octane (76 mg, 0.68 mmol) in THF (1 mL) was heated at 60° C. for 48 h in a sealed vessel. The reaction mixture was concentrated in vacuo and the residue purified by MDAP (Method 7) to give the title compound as a white solid (24 mg, 46%). LCMS (Method 5): Rt 3.72 min, m/z 774 [MH$^+$]. $^1$H NMR (400 MHz, d$_6$-DMSO): 0.91 (3H, d, J=6.3 Hz), 1.28 (9H, s), 1.46-1.54 (2H, m), 1.64-1.71 (4H, m), 1.75-2.17 (8H, m), 2.59 (2H, t, J=5.9 Hz), 2.86-2.95 (1H, m), 3.07-3.11 (2H, m), 3.12-3.19 (1H, m), 3.28-3.34 (3H, m, obscured by water peak), 3.49 (2H, d, J=9.6 Hz), 4.09 (2H, t, J=6.3 Hz), 4.78-4.85 (1H, m), 5.52 (1H, t, J=4.3 Hz), 6.33 (1H, s), 6.94-6.99 (1H, m), 7.05-7.14 (3H, m), 7.19 (1H, dd, J=9.6 Hz, 2.4 Hz), 7.24-7.42 (5H, m), 7.64 (1H, d, J=10.0 Hz), 7.69 (1H, d, J=2.2 Hz), 8.15 (1H, s), 8.20 (1H, s).

Example 167

1-{5-tert-Butyl-2-[3-(4-methoxy-piperidin-1-ylmethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

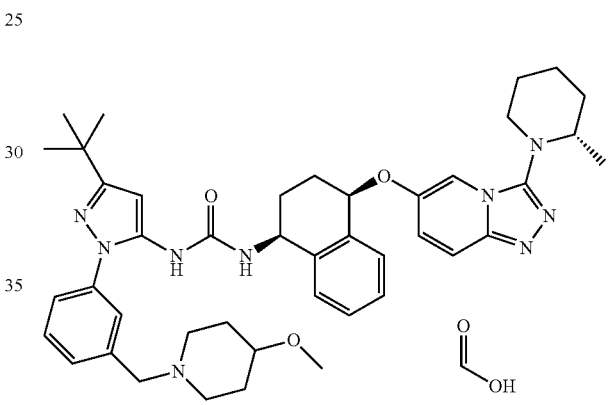

a. 1-[5-tert-Butyl-2-(3-hydroxymethyl-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea (Intermediate 167a).

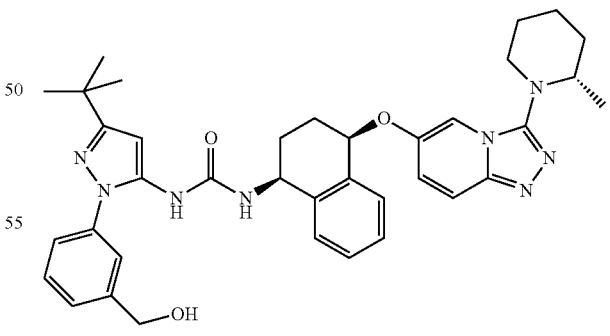

A mixture of Intermediate 81d (319 mg, 0.85 mmol), Intermediate 29c (335 mg, 0.85 mmol) and DIPEA (294 μL, 1.69 mmol) in dioxane (10 mL) was stirred at 80° C. for 18 hours. After cooling, the reaction mixture was partitioned between water and DCM. The aqueous phase was extracted with EtOAc (×3) and the combined organic layers were washed with brine, dried (MgSO$_4$) and concentrated in vacuo. The resulting residue was purified by FCC on silica, using a gradient of 0-10% MeOH in DCM, to afford the title compound (362 mg, 66%). LCMS (Method 4): Rt 3.29 min, m/z 649 [MH$^+$].

b. Methanesulfonic acid 3-[3-tert-butyl-5-(3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-ureido)-pyrazol-1-yl]benzyl ester (Intermediate 167b).

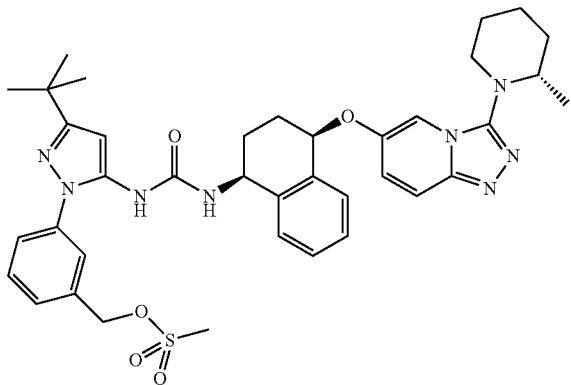 [SMILES: C[C@H]1CCCCN1c1nnc2ccc(O[C@@H]3CC[C@H](NC(=O)Nc4cc(C(C)(C)C)nn4-c4cccc(COS(C)(=O)=O)c4)c4ccccc43)cn12]

To an ice-bath cooled solution of Intermediate 167a (316 mg, 0.49 mmol) in DCM (5.0 mL) was added DIPEA (339 µL, 1.95 mmol) followed by methanesulfonyl chloride (76 µL, 0.97 mmol). The reaction mixture was stirred for 3 h and then quenched with water. The aqueous phase was extracted with DCM (×3) and the combined organic layers were washed with brine, dried (MgSO$_4$) and concentrated in vacuo to afford the title compound (Quantitative, assumed 0.49 mmol). The isolated product was used in the following step without further purification. LCMS (Method 4): Rt 3.61 min, m/z 727 [MH$^+$].

c. 1-{5-tert-Butyl-2-[3-(4-methoxy-piperidin-1-ylmethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt (Example 167).

To a solution of Intermediate 167b (0.19 mmol) in THF (2 mL) was added DIPEA (130 µL, 0.75 mmol) and 4-methoxypiperidine (86 mg, 0.75 mmol) and the reaction stirred at 50° C. for 24 h. The crude reaction mixture was cooled and partitioned between EtOAc and water. The aqueous phase was extracted with EtOAc (×3) and the combined organic layers were washed with brine, dried (MgSO$_4$) and concentrated in vacuo. The resulting residue was purified by FCC on silica, using a gradient of 0-10% (2M NH$_3$ in MeOH) in DCM, followed by MDAP (Method 7) purification, to give the title compound (20 mg, 14%). LCMS (Method 5): Rt 3.66 min, m/z 746 [MH$^+$]. $^1$H NMR (400 MHz, d$_6$-DMSO): 0.86 (3H, d, J=6.2 Hz), 1.23 (9H, s), 1.30-1.40 (2H, m), 1.42-1.50 (2H, m), 1.58-1.67 (2H, m), 1.70-1.83 (5H, m), 1.83-1.93 (1H, m), 1.96-2.12 (4H, m), 2.56-2.64 (2H, m), 2.86 (1H, ddd, J=12.7, 9.0, 3.9 Hz), 3.05-3.12 (3H, m), 3.13 (3H, s), 3.45 (2H, s), 4.77 (1H, td, J=8.4, 5.7 Hz), 5.47 (1H, t, J=4.2 Hz), 6.28 (1H, s), 7.00 (1H, d, J=8.6 Hz), 7.14 (1H, dd, J=9.8, 2.1 Hz), 7.20-7.30 (4H, m), 7.30-7.37 (3H, m), 7.40 (1H, t, J=7.7 Hz), 7.59 (1H, d, J=10.0 Hz), 7.64 (1H, d, J=1.8 Hz), 8.07 (1H, s), 8.23 (0.3H, s).

Example 168

1-[5-tert-Butyl-2-(3-{[(2-methoxy-ethyl)-methyl-amino]-methyl}-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

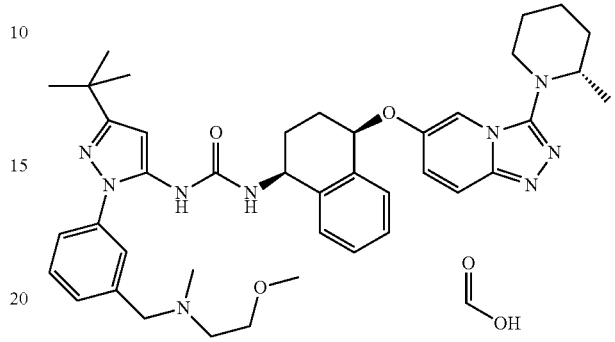

To a solution of Intermediate 167b (0.19 mmol) in THF (2 mL) was added DIPEA (130 µL, 0.75 mmol) and N-(methoxyethyl)methylamine (81 µL, 0.75 mmol) and the reaction stirred at 50° C. for 24 h. The crude reaction mixture was cooled and partitioned between EtOAc and water. The aqueous phase was extracted with EtOAc (×3) and the combined organic layers were washed with brine, dried (MgSO$_4$) and concentrated in vacuo. The resultant residue was purified by FCC on silica, using a gradient of 0-10% (2M NH$_3$ in MeOH) in DCM, followed by MDAP (Method 7) purification, to give the title compound (20 mg, 14%). LCMS (Method 5): Rt 3.65 min, m/z 720 [MH$^+$]. $^1$H NMR (400 MHz, d$_6$-DMSO): 0.86 (3H, d, J=6.2 Hz), 1.23 (9H, s), 1.42-1.48 (2H, m), 1.58-1.67 (2H, m), 1.72-1.92 (4H, m), 1.96-2.12 (2H, m), 2.12 (3H, s), 2.49 (2H, t, J=6.0 Hz), 2.86 (1H, ddd, J=12.7, 9.0, 3.9 Hz), 3.12 (1H, dt, J=12.1, 4.3 Hz), 3.16 (3H, s), 3.39 (2H, t, J=6.0 Hz), 3.50 (2H, s), 4.77 (1H, td, J=8.4, 5.7 Hz), 5.47 (1H, t, J=4.2 Hz), 6.28 (1H, s), 7.02 (1H, d, J=8.6 Hz), 7.14 (1H, dd, J=9.8, 2.1 Hz), 7.20-7.25 (2H, m), 7.25-7.30 (2H, m), 7.30-7.35 (2H, m), 7.38 (1H, s), 7.40 (1H, t, J=7.7 Hz), 7.59 (1H, d, J=10.0 Hz), 7.64 (1H, d, J=1.8 Hz), 8.07 (1H, s), 8.28 (0.2H, s).

Example 169

1-{5-tert-Butyl-2-[3-(4-fluoro-piperidin-1-ylmethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

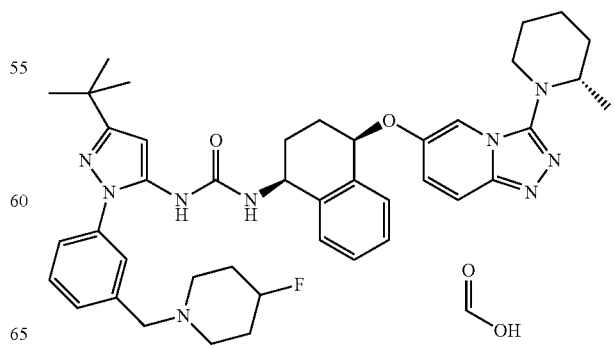

To a solution of Intermediate 167b (0.19 mmol) in THF (2 mL) was added DIPEA (260 µL, 1.5 mmol) and 4-fluoropiperidine hydrochloride (104 mg, 0.75 mmol) and the reaction stirred at 50° C. for 24 h. The crude reaction mixture was cooled and partitioned between EtOAc and water. The aqueous phase was extracted with EtOAc (×3) and the combined organic layers were washed with brine, dried (MgSO$_4$) and concentrated in vacuo. The resulting residue was purified by FCC on silica, using a gradient of 0-10% (2M NH$_3$ in MeOH) in DCM, followed by MDAP (Method 7) purification, to give the title compound (25 mg, 16%). LCMS (Method 5): Rt 3.68 min, m/z 734 [MH$^+$]. $^1$H NMR (400 MHz, d$_6$-DMSO): 0.86 (3H, d, J=6.2 Hz), 1.23 (9H, s), 1.42-1.50 (2H, m), 1.58-1.70 (4H, m), 1.70-1.92 (6H, m), 1.95-2.12 (2H, m), 2.23-2.31 (2H, m), 2.86 (1H, ddd, J=12.7, 9.0, 3.9 Hz), 3.11 (1H, dt, J=12.2, 4.3 Hz), 3.24-3.30 (2H, m), 3.48 (2H, s), 4.60 (1H, dsp, J=48.9, 3.5 Hz), 4.77 (1H, td, J=8.4, 5.7 Hz), 5.47 (1H, t, J=4.2 Hz), 6.28 (1H, s), 6.98 (1H, d, J=8.6 Hz), 7.14 (1H, dd, J=9.8, 2.1 Hz), 7.20-7.25 (2H, m), 7.25-7.34 (3H, m), 7.35-7.38 (2H, m), 7.40 (1H, t, J=7.7 Hz), 7.59 (1H, d, J=10.0 Hz), 7.62 (1H, d, J=1.8 Hz), 8.05 (1H, s), 8.10 (1.8H, s).

Example 170

1-[5-tert-Butyl-2-(3-dimethylaminomethyl-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

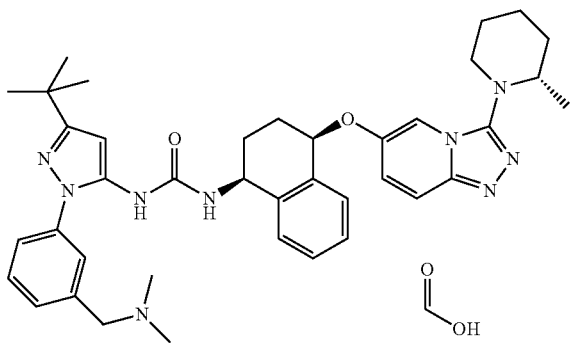 [SMILES: C[C@H]1CCCCN1c1nnc2ccc(O[C@@H]3CC[C@H](NC(=O)Nc4cc(C(C)(C)C)nn4-c4cccc(CN(C)C)c4)c4ccccc43)cn12 ; O=CO]

To a solution of Intermediate 167b (0.16 mmol) in THF (2.5 mL) was added dimethylamine solution (2M THF, 1.6 mL, 3.27 mmol) and the reaction stirred at 50° C. for 24 h in a sealed vessel. The crude reaction mixture was cooled and partitioned between EtOAc and water. The aqueous phase was extracted with EtOAc (×3) and the combined organic layers were washed with brine, dried (MgSO$_4$) and concentrated in vacuo. The resulting residue was purified by FCC on silica, using a gradient of 0-10% (2M NH$_3$ in MeOH) in DCM, followed by MDAP (Method 7) purification, to give the title compound (20 mg, 16%). LCMS (Method 5): Rt 3.58 min, m/z 676 [MH$^+$]. $^1$H NMR (400 MHz, d$_6$-DMSO): 0.86 (3H, d, J=6.2 Hz), 1.23 (9H, s), 1.42-1.50 (2H, m), 1.58-1.67 (2H, m), 1.70-1.90 (4H, m), 1.94-2.03 (1H, m), 2.04-2.12 (2H, m), 2.11 (6H, s), 2.86 (1H, ddd, J=12.7, 9.0, 3.9 Hz), 3.12 (1H, dt, J=11.9, 4.1 Hz), 3.39 (2H, s), 4.77 (1H, td, J=8.4, 5.7 Hz), 5.46 (1H, t, J=4.2 Hz), 6.27 (1H, s), 7.02 (1H, d, J=8.6 Hz), 7.15 (1H, dd, J=9.8, 2.1 Hz), 7.20-7.29 (4H, m), 7.29-7.34 (1H, m), 7.35-7.41 (3H, m), 7.59 (1H, d, J=10.0 Hz), 7.64 (1H, d, J=1.8 Hz), 8.07 (1H, s), 8.25 (0.3H, s).

Example 171

1-[5-tert-Butyl-2-(3-pyrrolidin-1-ylmethyl-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

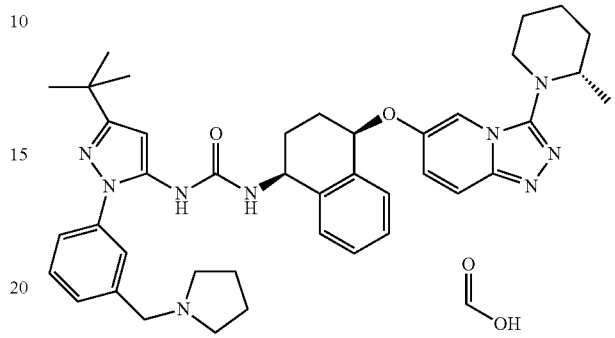

To a solution of Intermediate 167b (0.16 mmol) in THF (2 mL) was added pyrrolidine (273 µl, 3.27 mmol) and the reaction stirred at 50° C. for 24 h. The crude reaction mixture was cooled and partitioned between EtOAc and water. The aqueous phase was extracted with EtOAc (×3) and the combined organic layers were washed with brine, dried (MgSO$_4$) and concentrated in vacuo. The resultant residue was purified by FCC on silica, using a gradient of 0-10% (2M NH$_3$ in MeOH) in DCM, followed by MDAP (Method 7) purification, to give the title compound (26 mg, 22%). LCMS (Method 5): Rt 3.64 min, m/z 702 [MH$^+$]. $^1$H NMR (400 MHz, d$_6$-DMSO): 0.86 (3H, d, J=6.2 Hz), 1.23 (9H, s), 1.42-1.50 (2H, m), 1.58-1.66 (6H, m), 1.70-1.84 (3H, m), 1.84-1.92 (1H, m), 1.95-2.12 (2H, m), 2.36-2.42 (4H, m), 2.86 (1H, ddd, J=12.7, 9.0, 3.9 Hz), 3.12 (1H, dt, J=11.9, 4.1 Hz), 3.58 (2H, s), 4.77 (1H, td, J=8.4, 5.7 Hz), 5.46 (1H, t, J 4.2 Hz), 6.28 (1H, s), 7.01 (1H, d, J=8.6 Hz), 7.15 (1H, dd, J=9.8, 2.1 Hz), 7.20-7.25 (2H, m), 7.26-7.34 (4H, m), 7.35 (1H, s), 7.39 (1H, t, J=7.8 Hz), 7.59 (1H, d, J=10.0 Hz), 7.64 (1H, d, J=1.8 Hz), 8.07 (1H, s), 8.19 (0.7H, s).

Example 172

1-{(1S,4R)-4-[3-(4-Aza-spiro[2.5]oct-4-yl)-[1,2,4]triazolo[4,3-a]pyridin-6-yloxy]-1,2,3,4-tetrahydro-naphthalen-1-yl}-3-{5-tert-butyl-2-[3-(2-morpholin-4-yl-ethoxy)-phenyl]-2H-pyrazol-3-yl}-urea formate salt

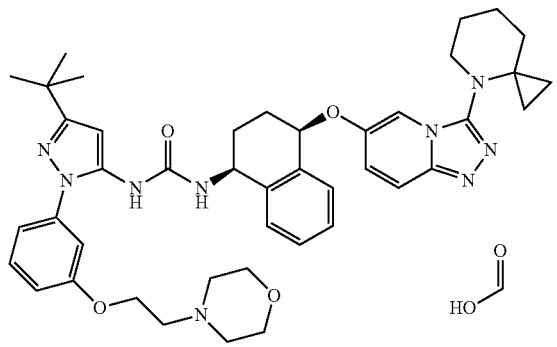 [SMILES: CC(C)(C)c1cc(NC(=O)N[C@H]2CC[C@@H](Oc3ccc4nnc(N5CCCCC56CC6)n4c3)c3ccccc32)n(-c2cccc(OCCN3CCOCC3)c2)n1 ; O=CO]

A brown solution of Intermediate 148g (0.099 mmol) and morpholine (43 mg, 0.50 mmol) in THF (1 mL) was stirred in a sealed vial at 60° C. for 18 h. The solution was decanted and concentrated. MDAP (Method 7) gave the title compound as an off-white solid (44 mg, 54%). LCMS (Method 5): Rt 3.64 min, m/z 760.6 [MH$^+$]. $^1$H NMR (400 MHz, d$_6$-DMSO): 0.41-0.54 (4H, m), 1.27 (9H, s), 1.52-1.62 (2H, m), 1.72-1.81 (3H, m), 1.83-1.96 (3H, m), 1.99-2.15 (2H, m), 2.42 (4H, t, J=4.4 Hz), 2.66 (2H, t, J=5.7 Hz), 3.22-3.29 (2H, m), 3.52 (4H, t, J=4.58 Hz), 4.11 (2H, t, J=5.7 Hz), 4.81 (1H, td, J=8.6, 5.5 Hz), 5.48 (1H, t, J=4.3 Hz), 6.33 (1H, s), 6.95-6.98 (1H, m), 7.06-7.12 (3H, m), 7.14 (1H, dd, J=9.9, 2.2 Hz), 7.25-7.42 (5H, m), 7.57 (1H, dd, J=2.1, 0.9 Hz), 7.61 (1H, dd, J=9.8, 0.8 Hz), 8.11 (1H, s), 8.16 (1.3H, s).

Example 173

1-[5-tert-Butyl-2-(3-piperidin-1-ylmethyl-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

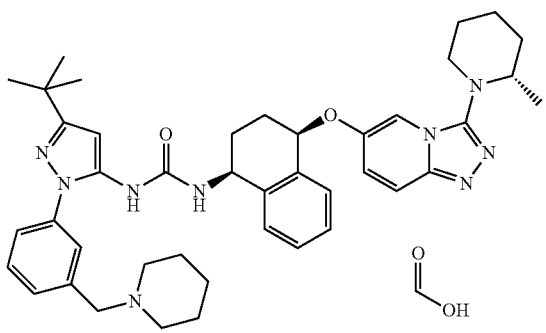 [SMILES: C[C@H]1CCCCN1c1nnc2ccc(O[C@@H]3CC[C@H](NC(=O)Nc4cc(C(C)(C)C)nn4-c4cccc(CN5CCCCC5)c4)c4ccccc43)cn12 ; O=CO]

To a solution of Intermediate 167b (0.22 mmol) in THF (2.5 mL) was added piperidine (424 μL, 4.3 mmol) and the reaction stirred at 50° C. for 24 h. The crude reaction mixture was cooled and partitioned between EtOAc and water. The aqueous phase was extracted with EtOAc (×3) and the combined organic layers were washed with brine, dried (MgSO$_4$) and concentrated in vacuo. The resultant residue was purified by FCC on silica, using a gradient of 0-10% (2M NH$_3$ in MeOH) in DCM, followed by MDAP (Method 7) purification, to give the title compound (44 mg, 25%). LCMS (Method 5): Rt 3.69 min, m/z 716 [MH$^+$]. $^1$H NMR (400 MHz, d$_6$-DMSO): 0.86 (3H, d, J=6.2 Hz), 1.23 (9H, s), 1.28-1.33 (2H, m), 1.38-1.48 (6H, m), 1.58-1.66 (2H, m), 1.70-1.92 (4H, m), 1.95-2.12 (2H, m), 2.26-2.34 (4H, m), 2.86 (1H, ddd, J=12.7, 9.0, 3.9 Hz), 3.11 (1H, dt, J=11.9, 4.1 Hz), 3.23-3.29 (1H, m), 3.44 (2H, s), 4.77 (1H, td, J=8.4, 5.7 Hz), 5.46 (1H, t, J=4.2 Hz), 6.28 (1H, s), 6.99 (1H, d, J=8.6 Hz), 7.15 (1H, dd, J=9.8, 2.1 Hz), 7.20-7.25 (2H, m), 7.25-7.29 (2H, m), 7.29-7.36 (3H, m), 7.39 (1H, t, J=7.8 Hz), 7.59 (1H, d, J=10.0 Hz), 7.64 (1H, d, J=1.8 Hz), 8.06 (1H, s), 8.12 (1.8H, s).

Example 174

1-{5-tert-Butyl-2-[3-(4-methyl-[1,4]diazepan-1-ylmethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

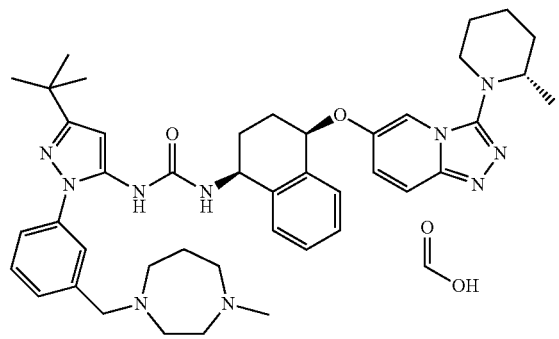

To a solution of Intermediate 167b (0.22 mmol) in THF (2.5 mL) was added 1-methylhomopiperazine (534 μL, 4.3 mmol) and the reaction stirred at 50° C. for 24 h. The crude reaction mixture was cooled and partitioned between EtOAc and water. The aqueous phase was extracted with EtOAc (×3) and the combined organic layers were washed with brine, dried (MgSO$_4$) and concentrated in vacuo. The resultant residue was purified by FCC on silica, using a gradient of 0-10% (2M NH$_3$ in MeOH) in DCM, followed by MDAP (Method 7) purification, to give the title compound (28 mg, 15%). LCMS (Method 5): Rt 3.27 min, m/z 745 [MH$^+$]. $^1$H NMR (400 MHz, d$_6$-DMSO): 0.86 (3H, d, J=6.2 Hz), 1.23 (9H, s), 1.42-1.50 (2H, m), 1.58-1.66 (2H, m), 1.68-1.84 (5H, m), 1.84-1.92 (1H, m), 1.95-2.05 (1H, m), 2.05-2.12 (1H, m), 2.32 (3H, s), 2.58-2.66 (6H, m), 2.69 (2H, t, J=5.7 Hz), 2.86 (1H, ddd, J=12.7, 9.0, 3.9 Hz), 3.11 (1H, dt, J=11.9, 4.1 Hz), 3.23-3.29 (1H, m), 3.62 (2H, s), 4.77 (1H, td, J=8.4, 5.7 Hz), 5.47 (1H, t, J=4.2 Hz), 6.28 (1H, s), 7.04 (1H, d, J=8.6 Hz), 7.14 (1H, dd, J=9.8, 2.1 Hz), 7.20-7.25 (2H, m), 7.26-7.36 (4H, m), 7.38-7.43 (2H, m), 7.59 (1H, d, J=10.0 Hz), 7.64 (1H, d, J=1.8 Hz), 8.12 (1H, s), 8.16 (2.4H, s).

Example 175

1-{5-tert-Butyl-2-[3-((1S,4S)-5-methyl-2,5-diaza-bicyclo[2.2.1]hept-2-ylmethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-aphthalen-1-yl}-urea formate salt

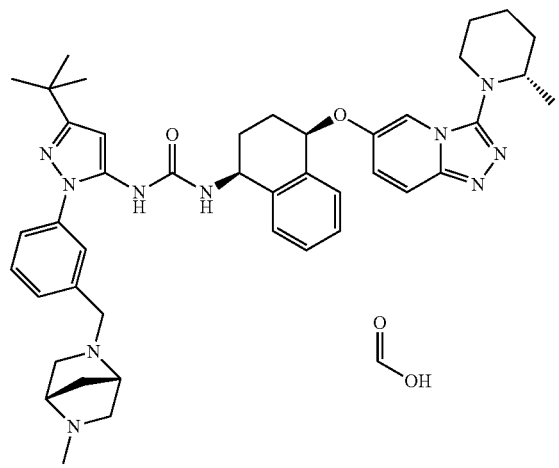 [SMILES: C[C@H]1CCCCN1c1nnc2ccc(O[C@@H]3CC[C@H](NC(=O)Nc4cc(C(C)(C)C)nn4-c4cccc(CN5C[C@@H]6C[C@H]5CN6C)c4)c4ccccc43)cn12 ; O=CO]

To a solution of Intermediate 167b (0.15 mmol) in THF (20 mL) was added (1S,4S)-2-methyl-2,5-diaza-bicyclo[2.2.1]heptane (366 mg, 3.3 mmol) and the reaction stirred at 50° C. for 24 h. The crude reaction mixture was cooled and partitioned between EtOAc and water. The aqueous phase was extracted with EtOAc (×3) and the combined organic layers were washed with brine, dried (MgSO$_4$) and concentrated in vacuo. The resultant residue was purified by FCC on silica, using a gradient of 0-10% (2M NH$_3$ in MeOH) in DCM, then further purified by HPLC (C18 X-select column, 10-75% MeCN in H$_2$O, 0.1% formic acid) to give the title compound (11 mg, 9%). LCMS (Method 5): Rt 3.45 min, m/z 743 [MH$^+$]. $^1$H NMR (400 MHz, d$_6$-DMSO): 0.86 (3H, d, J=6.2 Hz), 1.23 (9H, s), 1.42-1.50 (2H, m), 1.54-1.66 (4H, m), 1.72-1.84 (3H, m), 1.84-1.92 (1H, m), 1.95-2.15 (2H, m), 2.22 (3H, s), 2.46-2.48 (1H, m), 2.52 (1H, dd, J=9.6, 2.4 Hz), 2.59 (1H, d, J=9.7 Hz), 2.71 (1H, d, J=9.6 Hz), 2.86 (1H, ddd, J=12.7, 9.0, 3.9 Hz), 3.09-3.13 (2H, m), 3.22 (1H, s), 3.28-3.32 (1H, m), 3.63 (1H, d, J=13.9 Hz), 3.70 (1H, d, J=13.9 Hz), 4.77 (1H, td, J=8.4, 5.7 Hz), 5.47 (1H, t, J=4.2 Hz), 6.28 (1H, s), 7.04 (1H, d, J=8.6 Hz), 7.14 (1H, dd, J=9.8, 2.1 Hz), 7.20-7.25 (2H, m), 7.26-7.36 (4H, m), 7.36-7.41 (2H, m), 7.59 (1H, d, J=10.0 Hz), 7.64 (1H, d, J=1.8 Hz), 8.11 (1H, s), 8.25 (0.7H, s).

Example 176

1-[5-tert-Butyl-2-(4-morpholin-4-ylmethyl-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea

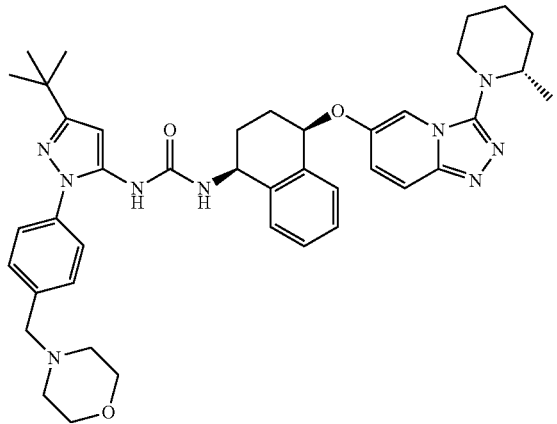 [SMILES: C[C@H]1CCCCN1c1nnc2ccc(O[C@@H]3CC[C@H](NC(=O)Nc4cc(C(C)(C)C)nn4-c4ccc(CN5CCOCC5)cc4)c4ccccc43)cn12]

a. 1-[5-tert-Butyl-2-(4-hydroxymethyl-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea dichloromethane solvate (Intermediate 176a).

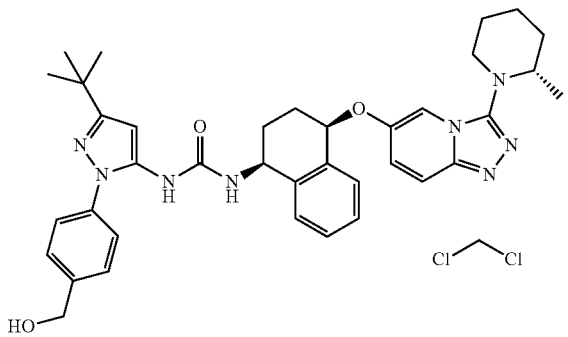

A red-brown solution of Intermediate 33a (883 mg, 2.10 mmol), Intermediate 81d (755 mg, 2.00 mmol) and DIPEA (0.44 mL, 2.5 mmol) in dry dioxane (20 mL) was stirred at 70° C. for 16 h, and at 80° C. for 5 h. The cooled solution was concentrated in vacuo, suspended in water (15 mL) and extracted with DCM (2×15 mL). The combined organics were passed through a hydrophobic frit and concentrated in vacuo to leave a brown oil. Flash chromatography (silica 80 g, 4-8% MeOH in DCM) gave the title compound as a pale yellow foam (1.27 g, 87%). LCMS (Method 3): Rt 3.61 min, m/z 649 [MH$^+$].

b. 1-[5-tert-Butyl-2-(4-formyl-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea (Intermediate 176b).

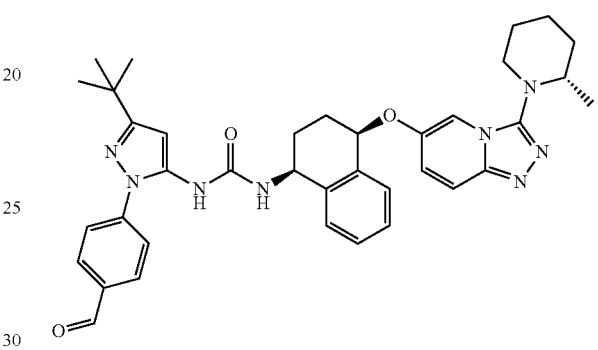

To a solution of Intermediate 176a (1.10 g, 1.70 mmol) in DCM (25 mL) at 0° C. was added Dess-Martin periodinane (791 mg, 1.86 mmol) and the resulting red-brown solution stirred at 0° C. for 45 min. Sodium metabisulfite (920 mg), water (10 mL) and sat. aq. NaHCO$_3$ solution (10 mL) were added and the mixture stirred at RT until gas evolution ceased (15 min). The mixture was diluted with water (25 mL) and extracted with DCM (2×25 mL). The combined organics were passed through a hydrophobic fit and concentrated in vacuo to leave the title compound as a glassy orange solid (1.10 g, 100%). LCMS (Method 3): Rt 3.91 min, m/z 647 [MH$^+$].

c. 1-[5-tert-Butyl-2-(4-morpholin-4-ylmethyl-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea (Example 176).

To a solution of Intermediate 176b (0.10 mmol) and morpholine (17.4 mg, 0.200 mmol) in DCM (3 mL) was added sodium triacetoxyborohydride (31.8 mg, 0.15 mmol) and the resulting yellow solution stirred at RT for 1 h. Water (3 mL) was added and the mixture shaken. The aqueous was extracted with DCM (3 mL), then the combined organics passed through a hydrophobic frit and concentrated in vacuo to leave a vivid yellow gum. Flash chromatography (silica 12 g, 3.5-4.5% (2M NH3 in MeOH) in DCM) gave a vivid yellow gum (70 mg). Prep HPLC (Gemini C18, 25-75% MeCN in water, 0.1% HCO$_2$H, 20 min) and concentration of the desired fractions removed the MeCN. The aqueous was extracted with DCM (3×15 mL), then the combined organics passed through a hydrophobic frit and concentrated in vacuo to leave a glassy orange solid (43.7 mg). Prep HPLC (Gemini C18, 25-50% MeCN in water, 20 min) and concentration of the desired fractions removed the MeCN. The aqueous was extracted with DCM (3×5 mL), then the combined organics passed through a hydrophobic fit and concentrated in vacuo to leave the title compound as a white solid (25.4 mg, 35%).

LCMS (Method 5): Rt 3.61 min, m/z 718.6 [MH⁺]. ¹H NMR (400 MHz, d₆-DMSO): 0.91 (3H, d, J=6.3 Hz), 1.27 (9H, s), 1.47-1.55 (2H, m), 1.63-1.71 (2H, m), 1.76-1.95 (4H, m), 2.00-2.16 (2H, m), 2.37 (4H, t, J=4.3 Hz), 2.90 (1H, ddd, J=12.1, 9.0, 3.9 Hz), 3.16 (1H, dt, J=12.2, 4.3 Hz), 3.29-3.34 (1H, m, obscured by water signal), 3.50 (2H, s), 3.56 (4H, t, J=4.5 Hz), 4.81 (1H, td, J=8.6, 5.6 Hz), 5.51 (1H, t, J=4.3 Hz), 6.34 (1H, s), 7.09 (1H, d, J=8.6 Hz), 7.19 (1H, dd, J=9.9, 2.2 Hz), 7.25-7.37 (4H, m), 7.43 (2H, d, J=8.7 Hz), 7.45 (2H, d, J=8.7 Hz), 7.64 (1H, dd, J=9.8, 0.8 Hz), 7.69 (1H, dd, J=2.2, 0.9 Hz), 8.08 (1H, s).

Example 177

1-[5-tert-Butyl-2-(4-dimethylaminomethyl-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea partial formate salt

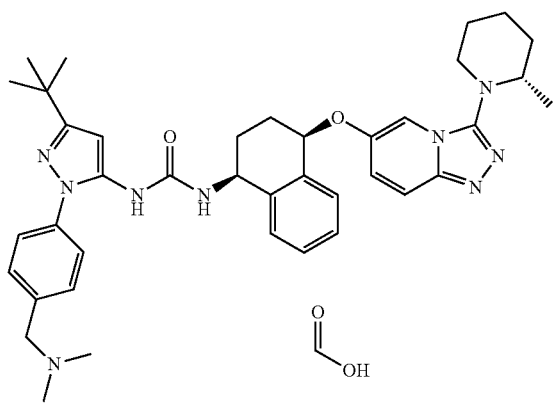 [SMILES: C[C@H]1CCCCN1c1nnc2ccc(O[C@@H]3CC[C@H](NC(=O)Nc4cc(C(C)(C)C)nn4-c4ccc(CN(C)C)cc4)c4ccccc43)cn12 ; O=CO]

To an orange solution of Intermediate 176b (0.188 mmol) and dimethylamine solution (2M in THF, 0.19 mL, 0.38 mmol) in DCM (3 mL) was added sodium triacetoxyborohydride (60 mg, 0.28 mmol) and the mixture stirred at RT for 1 h. Water (3 mL) was added and the mixture shaken. The aqueous was extracted with DCM (3 mL) then the combined organics passed through a hydrophobic frit and concentrated in vacuo to leave a brown gum. Flash chromatography (silica 12 g, 4-6.5% [2M NH₃ in MeOH] in DCM) gave a yellow solid (88 mg). Prep HPLC (Gemini C18, 25-50% MeCN in water, 0.1% HCO₂H, 20 min) and concentration in vacuo of the relevant fractions gave a pale yellow film. Trituration with diethyl ether gave the title compound as on off-white solid (48.4 mg, 36%). LCMS (Method 3): Rt 2.99 min, m/z 676 [MH⁺]. ¹H NMR (400 MHz, d₆-DMSO): 0.91 (3H, d, J=6.3 Hz), 1.27 (9H, s), 1.45-1.56 (2H, m), 1.62-1.71 (2H, m), 1.75-1.96 (4H, m), 2.00-2.15 (2H, m), 2.17 (6H, s), 2.90 (1H, dd, J=12.3, 9.1, 3.9), 3.16 (1H, dt, J=12.3, 4.3 Hz), 3.28-3.34 (1H, m obscured by water peak), 3.44 (2H, s), 4.82 (1H, td, J=8.6, 5.7 Hz), 5.51 (1H, t, J=4.3 Hz), 6.34 (1H, s), 7.10 (1H, d, J=8.6 Hz), 7.19 (1H, dd, J=9.8, 2.2 Hz), 7.25-7.47 (8H, m), 7.64 (1H, dd, J=9.8, 0.8 Hz), 7.69 (1H, dd, J=2.2, 0.9 Hz), 8.10 (1H, s), 8.16 (0.7H, s).

Example 178

1-{5-tert-Butyl-2-[4-(4-methyl-piperazin-1-ylmethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea partial formate salt

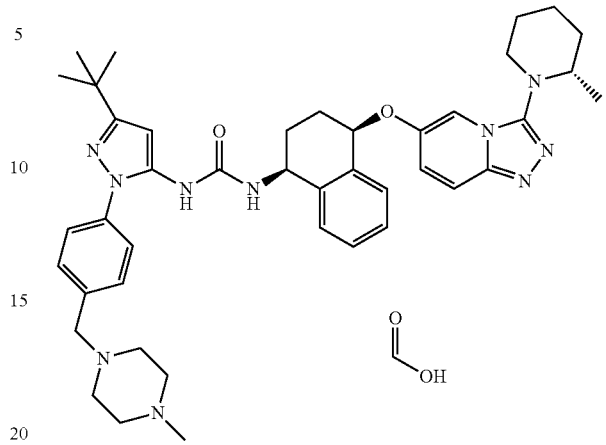

To an orange solution of Intermediate 176b (0.188 mmol) and N-methyl piperazine (38 mg, 0.38 mmol) in DCM (3 mL) was added sodium triacetoxyborohydride (60 mg, 0.28 mmol) and the mixture stirred at RT for 1 h. Water (3 mL) was added and the mixture shaken. The aqueous was extracted with DCM (3 mL) then the combined organics passed through a hydrophobic frit and concentrated in vacuo to leave a brown gum. Flash chromatography (silica 12 g, 5-8% (2M NH₃ in MeOH) in DCM) gave a yellow solid (47 mg). Prep HPLC (Gemini C18, 25-50% MeCN in water, 0.1% HCO₂H, 20 min) and concentration in vacuo of the relevant fractions gave a pale yellow film. Trituration with diethyl ether gave the title compound as on off-white solid (20.6 mg, 14%). LCMS (Method 3): Rt 2.98 min, m/z 731 [MH⁺]. ¹H NMR (400 MHz, d₆-DMSO): 0.91 (3H, d, J=6.3 Hz), 1.27 (9H, s), 1.45-1.56 (2H, m), 1.62-1.71 (2H, m), 1.75-1.95 (4H, m), 1.99-2.16 (2H, m), 2.14 (3H, s), 2.26-2.45 (8H, m), 2.90 (1H, ddd, J=12.2, 9.0, 4.0 Hz), 3.16 (1H, dt, J=12.2, 4.2 Hz), 3.28-3.34 (1H, m, obscured by water signal), 3.49 (2H, s), 4.81 (1H, td, J=8.6, 5.6 Hz), 5.51 (1H, t, J=4.3 Hz), 6.33 (1H, s), 7.10 (1H, d, J=8.6 Hz), 7.20 (1H, dd, J=9.9, 2.1 Hz), 7.25-7.47 (8H, m), 7.64 (1H, dd, J=9.8, 0.8 Hz), 7.69 (1H, dd, J=2.2, 0.9 Hz), 8.10 (1H, s), 8.17 (0.6H, s).

Example 179

1-{5-tert-Butyl-2-[4-(4-methyl-[1,4]diazepan-1-ylmethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea

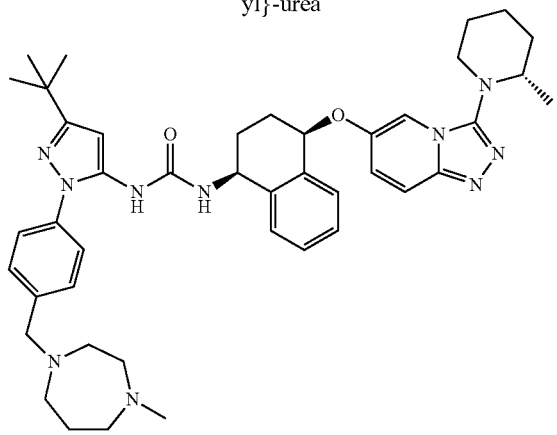

To an orange solution of Intermediate 176b (0.188 mmol) and N-methyl homopiperazine (43 mg, 0.38 mmol) in DCM (3 mL) was added sodium triacetoxyborohydride (60 mg, 0.28 mmol) and the mixture stirred at RT for 1 h. Water (3 mL) was added and the mixture shaken. The aqueous was extracted with DCM (3 mL) then the combined organics passed through a hydrophobic frit and concentrated in vacuo to leave a brown gum. Flash chromatography (silica 12 g, 7-11% [2M NH$_3$ in MeOH] in DCM) gave the title compound as a yellow solid (102 mg, 73%). LCMS (Method 3): Rt 2.84 min, m/z 745 [MH$^+$]. $^1$H NMR (300 MHz, CDCl$_3$): 0.91 (3H, d, J=6.2 Hz), 1.34 (9H, s), 1.40-1.55 (2H, m), 1.62-1.99 (7H, m), 2.15-2.02-2.14 (2H, m), 2.21-2.30 (1H, m), 2.33 (3H, s), 2.55-2.69 (8H, m), 2.90 (1H, ddd, J=12.1, 9.3, 4.1), 3.04 (1H, dt, J=12.1, 4.2 Hz), 3.23-3.32 (1H, m), 3.58 (2H, s), 5.09 (1H, td, J=8.9, 5.2 Hz), 5.19 (1H, t, J=3.9 Hz), 6.04 (1H, br d, J=8.6 Hz), 6.33 (1H, s), 6.94 (1H, dd, J=9.9, 2.1 Hz), 7.22 (1H, br s), 7.25-7.39 (7H, m), 7.43 (1H, d, J=2.2 Hz), 7.47 (2H, m).

Example 180

1-{5-tert-Butyl-2-[4-(4-methoxy-piperidin-1-ylmethyl)-phenyl]-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea partial formate salt

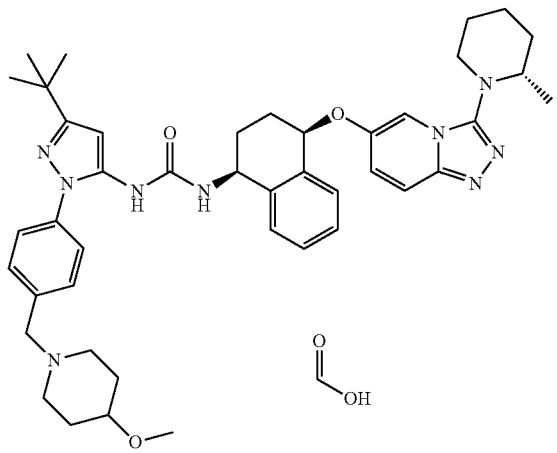 [SMILES: COC1CCN(Cc2ccc(-n3nc(C(C)(C)C)cc3NC(=O)N[C@H]3CC[C@@H](Oc4ccc5nnc(N6CCCC[C@@H]6C)n5c4)c4ccccc43)cc2)CC1 ; O=CO]

To an orange solution of Intermediate 176b (0.188 mmol) and 4-methoxypiperidine (43 mg, 0.38 mmol) in DCM (3 mL) was added sodium triacetoxyborohydride (60 mg, 0.28 mmol) and the mixture stirred at RT for 1 h. Water (3 mL) was added and the mixture shaken. The aqueous was extracted with DCM (3 mL) then the combined organics passed through a hydrophobic fit and concentrated in vacuo to leave a brown gum. Flash chromatography (silica 12 g, 3.5-6% [2M NH$_3$ in MeOH] in DCM) gave a yellow solid (140 mg). Prep HPLC (Gemini C18, 25-50% MeCN in water, 0.1% HCO$_2$H, 20 min, ×2) and concentration in vacuo of the relevant fractions gave a pale yellow film. Trituration with diethyl ether gave the title compound as on off-white solid (70.5 mg, 48%). LCMS (Method 5): Rt 3.69 min, in/z 746.6 [MH$^+$]. $^1$H NMR (400 MHz, d$_6$-DMSO): 0.91 (3H, d, J=6.3 Hz), 1.27 (9H, s), 1.37-1.56 (4H, m), 1.62-1.71 (2H, m), 1.75-1.95 (6H, m), 2.00-2.16 (4H, m), 2.62-2.69 (2H, m), 2.90 (1H, ddd, J=12.2, 9.1, 4.1 Hz), 3.12-3.18 (2H, m), 3.20 (3H, s), 3.29-3.34 (1H, m), 3.49 (2H, s), 4.82 (1H, td, J=8.6, 5.6 Hz), 5.51 (1H, t, J=4.3 Hz), 6.33 (1H, s), 7.10 (1H, d, J=8.6 Hz), 7.19 (1H, dd, J=9.8, 2.2 Hz), 7.25-7.46 (8H, m), 7.64 (1H, dd, J=9.8, 0.8 Hz), 7.69 (1H, dd, J=2.2, 0.9 Hz), 8.10 (1H, s), 8.16 (0.75H, s).

Example 181

1-[5-tert-Butyl-2-(4-pyrrolidin-1-ylmethyl-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

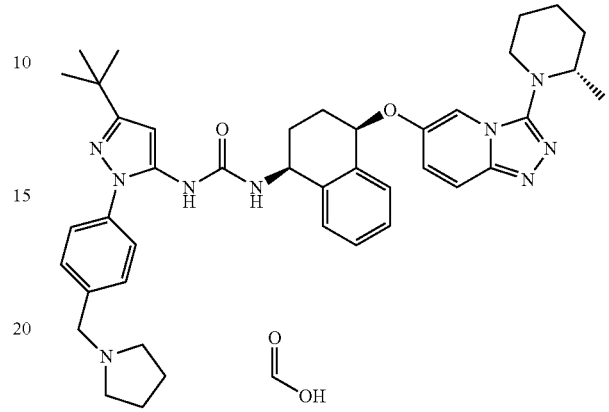

To a solution of Intermediate 176b (0.188 mmol) and pyrrolidine (31.1 μL, 0.38 mmol) in DCM (3 mL), sodium triacetoxyborohydride (59.8 mg, 0.28 mmol) was added. The mixture was stirred at RT for 1 h. Water was added and the mixture extracted with DCM. The combined organics were passed through a phase separator and concentrated to dryness. The resulting residue was purified by RP-HPLC (C18, 18 mL/min, 20-85% MeCN in H$_2$O+0.1% HCO$_2$H) and the relevant fractions combined and concentrated to dryness. The title product was isolated as a light orange solid (49.5 mg). LCMS (Method 5): Rt 3.66 min, m/z 702.6 [MH+]. $^1$H NMR (400 MHz, d$_6$-DMSO): 0.91 (3H, d, J=6.3 Hz), 1.27 (9H, s), 1.50 (2H, m), 1.69 (6H, m), 1.75-1.95 (4H, m), 1.98-2.17 (2H, m), 2.47 (4H, m, obscured by solvent), 2.90 (1H, m), 3.15 (1H, m, obscured by solvent), 3.63 (2H, s, obscured by solvent), 4.81 (1H, m), 5.51 (1H, t, J=4.3 Hz), 6.33 (1H, s), 7.09 (1H, d, J=8.9 Hz), 7.19 (1H, dd, J=9.6, 2.2 Hz), 7.24-7.38 (4H, m), 7.43 (4H, m), 7.64 (1H, d, J=9.6 Hz), 7.69 (1H, d, J=1.3 Hz), 8.09 (1H, s), 8.16 (1.4H, s).

Example 182

1-[5-tert-Butyl-2-(4-piperidin-1-ylmethyl-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

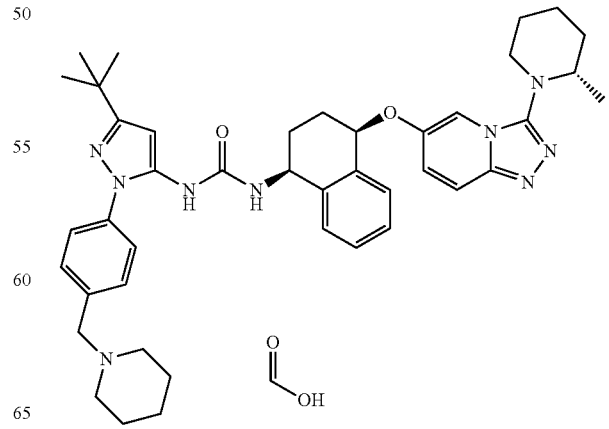

To a solution of Intermediate 176b (0.188 mmol) and piperidine (37.2 μL, 0.38 mmol) in DCM (3 mL), sodium triacetoxyborohydride (59.8 mg, 0.28 mmol) was added. The mixture was stirred at RT for 1 h. Water was added and the mixture extracted with DCM. The combined organics were passed through a phase separator and concentrated to dryness. The resulting residue was purified by RP-HPLC (C18, 18 mL/min, 20-85% MeCN in $H_2O$+0.1% $HCO_2H$) and the relevant fractions combined and concentrated to dryness. The title product was isolated as an off white solid (14 mg). LCMS (Method 5): Rt 3.71 min, m/z 716.6 [MH+]. $^1H$ NMR (400 MHz, $d_6$-DMSO): 0.91 (3H, d, J=6.4 Hz), 1.27 (9H, s), 1.36 (2H, m), 1.47 (6H, m), 1.67 (2H, m), 1.76-1.96 (4H, m), 1.98-2.16 (2H, m), 2.33 (4H, m), 2.90 (1H, m), 3.15 (1H, m, obscured by solvent), 3.46 (2H, s, obscured by solvent), 4.81 (1H, m), 5.51 (1H, t, J=4.1 Hz), 6.33 (1H, s), 7.09 (1H, d, J=8.6 Hz), 7.19 (1H, dd, J=10.0, 2.2 Hz), 7.24-7.46 (8H, m), 7.64 (1H, d, J=10.0 Hz), 7.69 (1H, d, J=1.5 Hz), 8.09 (1H, s), 8.17 (1H, s).

Example 183

1-{5-tert-Butyl-2-[4-(4-fluoro-piperidin-1-ylmethyl)-phenyl]-2H-pyrazol-3-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

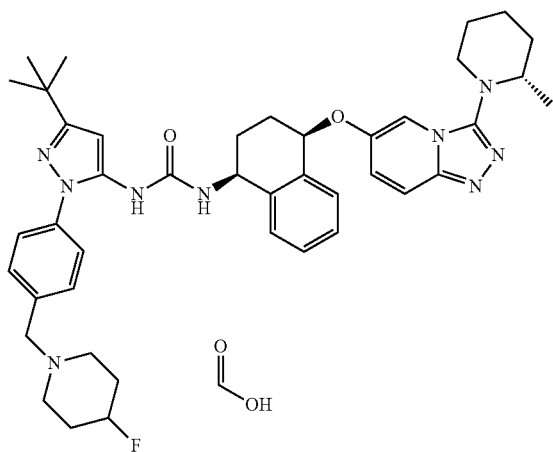 [SMILES: C[C@H]1CCCCN1c1nnc2ccc(O[C@@H]3CC[C@H](NC(=O)Nc4cc(C(C)(C)C)nn4-c4ccc(CN5CCC(F)CC5)cc4)c4ccccc43)cn12 ; O=CO]

To a solution of Intermediate 176b (0.188 mmol) and 4-fluoropiperidine (38.8 mg, 0.38 mmol) in DCM (3 mL), sodium triacetoxyborohydride (59.8 mg, 0.28 mmol) was added. The mixture was stirred at RT for 1 h. Water was added and the mixture extracted with DCM. The combined organics were passed through a phase separator and concentrated to dryness. The resulting residue was purified by RP-HPLC (C, 18, 18 mL/min, 20-85% MeCN in $H_2O$+0.1% $HCO_2H$) and the relevant fractions combined and concentrated to dryness. The title product was isolated as an off white solid (31 mg). LCMS (Method 5): Rt 3.71 min, m/z 734.6 [MH+]. $^1H$ NMR (400 MHz, $d_6$-DMSO): 0.91 (3H, d, J=6.1 Hz), 1.27 (9H, s), 1.50 (2H, m), 1.67 (4H, m), 1.76-1.96 (6H, m), 1.98-2.17 (2H, m), 2.31 (2H, m), 2.54 (m, obscured by solvent), 2.90 (1H, m), 3.16 (1H, m, obscured by solvent), 3.51 (2H, s, obscured by solvent), 4.66 (1H, dm, J=48 Hz), 4.82 (1H, m), 5.51 (1H, t, J=4.2 Hz), 6.33 (1H, s), 7.09 (1H, d, J=8.7 Hz), 7.19 (1H, dd, J=9.8, 2.3 Hz), 7.24-7.50 (8H, m), 7.63 (1H, d, J=10.2 Hz), 7.69 (1H, d, J=1.4 Hz), 8.10 (1H, s), 8.16 (1H, s).

Example 184

1-(5-tert-Butyl-2-{4-[(ethyl-methyl-amino)-methyl]-phenyl}-2H-pyrazol-3-yl)-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

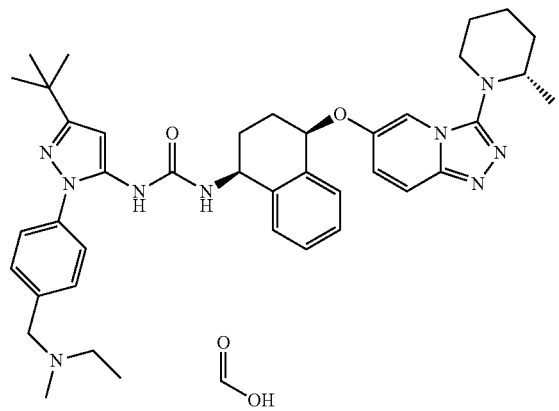 [SMILES: CCN(C)Cc1ccc(-n2nc(C(C)(C)C)cc2NC(=O)N[C@H]2CC[C@@H](Oc3ccc4nnc(N5CCCC[C@@H]5C)n4c3)c3ccccc32)cc1 ; O=CO]

To a solution of Intermediate 176b (0.188 mmol) and N-ethylmethylamine (32.3 μL, 0.38 mmol) in DCM (3 mL), sodium triacetoxyborohydride (59.8 mg, 0.28 mmol) was added. The mixture was stirred at RT for 1 h. Water was added and the mixture extracted with DCM. The combined organics were passed through a phase separator and concentrated to dryness. The resulting residue was purified by RP-HPLC (C, 18, 18 mL/min, 20-85% MeCN in $H_2O$+0.1% $HCO_2H$) and the relevant fractions combined and concentrated to dryness. The title product was isolated as an off white solid (26.1 mg). LCMS (Method 5): Rt 3.65 min, m/z 690.6 [MH+]. $^1H$ NMR (400 MHz, $d_6$-DMSO): 0.91 (3H, d, J=6.4 Hz), 1.02 (3H, t, J=7.1 Hz), 1.27 (9H, s), 1.50 (2H, m), 1.66 (2H, m), 1.74-1.97 (4H, m), 1.98-2.11 (2H, m), 2.12 (3H, s), 2.40 (2H, q, J=7.1 Hz), 2.90 (1H, m), 3.16 (1H, m, obscured by solvent), 3.49 (2H, s, obscured by solvent), 4.81 (1H, m), 5.51 (1H, t, J=4.6 Hz), 6.33 (1H, s), 7.09 (1H, d, J=8.6 Hz), 7.19 (1H, dd, J=9.6, 2.1 Hz), 7.24-7.47 (8H, m), 7.64 (1H, d, J=10.2 Hz), 7.69 (1H, d, J=1.6 Hz), 8.09 (1H, s), 8.17 (1H, s).

Example 185

1-[5-tert-Butyl-2-(4-{[(2-methoxy-ethyl)-methyl-amino]-methyl}-phenyl)-2H-pyrazol-3-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

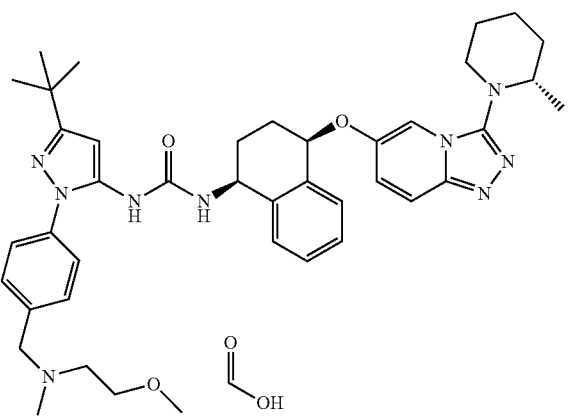

To a solution of Intermediate 176b (0.188 mmol) and N-(2-methoxyethyl)methyl amine (32.7 mg, 0.38 mmol) in DCM (3 mL), sodium triacetoxyborohydride (59.8 mg, 0.28 mmol) was added. The mixture was stirred at RT for 1 h. Water was added and the mixture extracted with DCM. The combined organics were passed through a phase separator and concentrated to dryness. The resulting residue was purified by RP-HPLC (C18, 18 mL/min, 20-85% MeCN in H$_2$O+0.1% HCO$_2$H) and the relevant fractions combined and concentrated to dryness. The title product was isolated as an off white solid (23.9 mg). LCMS (Method 5): Rt 3.68 min, m/z 720.5 [MH+]. $^1$H NMR (400 MHz, d$_6$-DMSO): 0.91 (3H, d, J=6.3 Hz), 1.27 (9H, s), 1.50 (2H, m), 1.66 (2H, m), 1.74-1.96 (4H, m), 1.98-2.16 (2H, m), 2.17 (3H, s), 2.54 (2H, t, J=6.0 Hz, obscured by solvent), 2.90 (1H, m), 3.16 (1H, m, obscured by solvent), 3.23 (3H, s, obscured by solvent), 3.45 (2H, t, J=6.0 Hz, obscured by solvent), 3.54 (2H, s, obscured by solvent), 4.82 (1H, m), 5.51 (1H, t, J=4.3 Hz), 6.33 (1H, s), 7.09 (1H, d, J=8.8 Hz), 7.19 (1H, dd, J=9.7, 2.2 Hz), 7.24-7.50 (8H, m), 7.64 (1H, d, J=10.0 Hz), 7.69 (1H, d, J=1.5 Hz), 8.09 (1H, s), 8.17 (1H, s).

Example 186

1-{5-tert-Butyl-2-[3-(2-dimethylamino-ethoxy)-phenyl]-2H-pyrazol-3-yl-3-{(1S,4S)-4-[3-((S)-2-methyl-piperidin-1-yl)-[1,2,4]triazolo[4,3-a]pyridin-6-yloxy]-1,2,3,4-tetrahydronaphthalen-1-yl]-urea

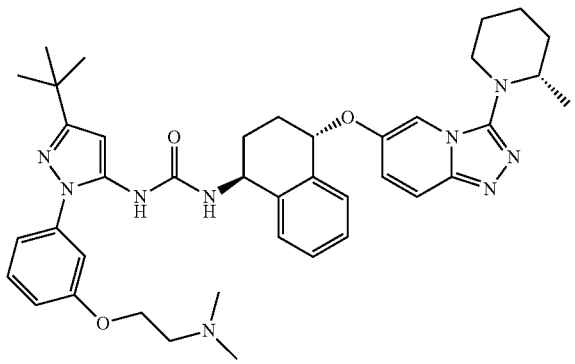 [SMILES: C[C@H]1CCCCN1c1nnc2ccc(O[C@H]3CC[C@H](NC(=O)Nc4cc(C(C)(C)C)nn4-c4cccc(OCCN(C)C)c4)c4ccccc43)cn12]

a. 2-[3-(5-Amino-3-tert-butyl-pyrazol-1-yl)-phenoxy]-ethanol (Intermediate 186a).

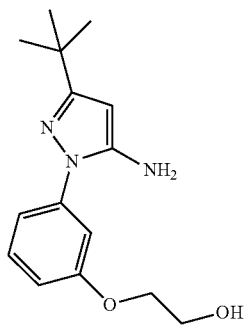 [SMILES: CC(C)(C)c1cc(N)n(-c2cccc(OCCO)c2)n1]

A solution of Intermediate 95a (1.2 g, 5.2 mmol) and triphenyl phosphine (2.72 g, 10.4 mmol) in THF (30 mL), under an atmosphere of argon was treated with 2-(tetrahydro-pyran-2-yloxy)-ethanol (1.05 mL, 7.78 mmol), followed by the dropwise addition of diisopropylazodicarboxylate (1.64 mL, 10.4 mmol). The reaction mixture was then stirred at RT for 1 h. The reaction mixture was eluted on a SCX-2 cartridge using MeOH and 2M NH$_3$ in MeOH. The basic fractions were evaporated under reduced pressure and the product was purified by FCC, using EtOAc/DCM 0-60% to afford the title compound as a brown gum (1.0 g, 80%). LCMS (Method 3): Rt 2.27 min, m/z 276 [MH+].

b. {5-tert-Butyl-2-[3-(2-hydroxy-ethoxy)-phenyl]-2H-pyrazol-3-yl}-carbamic acid 2,2,2-trichloro-ethyl ester (Intermediate 148e).

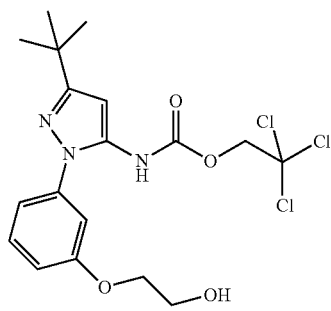 [SMILES: CC(C)(C)c1cc(NC(=O)OCC(Cl)(Cl)Cl)n(-c2cccc(OCCO)c2)n1]

A solution of Intermediate 186a (1.0 g, 3.63 mmol) in EtOAc (20 mL) was treated with aqueous NaOH (1M, 6.53 mmol), followed by 2,2,2-trichloroethyl chloroformate (0.529 mL, 3.85 mmol) and the reaction mixture was stirred at RT for 1 h. The mixture was partitioned between EtOAc (20 mL) and water (20 mL). The layers were separated and the aqueous layer was extracted with a further 20 mL EtOAc. The combined organic layers were dried (Na$_2$SO4), filtered and concentrated in vacuo. The residue was purified by FCC, using 0-40% EtOAc in DCM. The combined fractions were evaporated under reduced pressure and the product was triturated with DCM. The solid was filtered and washed with Diethyl ether to afford the title compound as a white solid (0.930 g, 58%). LCMS (Method 3): Rt 4.01 min, m/z 450 [M].

c. (1S,4S)-4-[3-((S)-2-Methyl-piperidin-1-yl)-[1,2,4]triazolo[4,3-a]pyridin-6-yloxy]-1,2,3,4-tetrahydro-naphthalen-1-ylamine (Intermediate 186b).

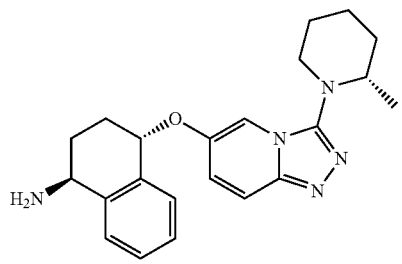 [SMILES: C[C@H]1CCCCN1c1nnc2ccc(O[C@H]3CC[C@H](N)c4ccccc43)cn12]

To a solution of Intermediate B (232 mg, 1.6 mmol) in dry DMF (10 mL) under N$_2$ was added sodium (60% dispersion in oil, 320 mg, 8.0 mmol) and the resulting opaque brown solution was stirred at RT for 45 min (CARE: gas evolution). A solution of Intermediate 81c (342 mg, 1.46 mmol) in dry DMF (7 mL) was added and the dark brown solution stirred at 60° C. under N$_2$ for 90 min. The cooled solution was concentrated in vacuo, redissolved in MeOH (3 mL) and then applied to an SCX-2 cartridge (20 g), washing with MeOH (50 mL). The product was eluted with 2M NH$_3$ in MeOH (50 mL);

concentration in vacuo gave a dark brown solid. FCC, using 0-10% [2M NH$_3$ in MeOH] in DCM, gave the title compound as a pale brown foam (262 mg, 45%). LCMS (Method 3): Rt 2.30 min, m/z 378 [MH$^+$].

d. 1-{5-tert-Butyl-2-[3-(2-hydroxy-ethoxy)-phenyl]-2H-pyrazol-3-yl}-3-{(1S,4S)-4-[3-((S)-2-methyl-piperidin-1-yl)-[1,2,4]triazolo[4,3-a]pyridin-6-yloxy]-1,2,3,4-tetrahydro-naphthalen-1-yl}-urea (Intermediate 186c).

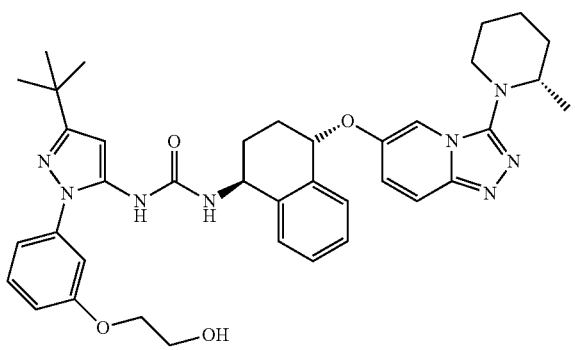

A mixture of Intermediate 148e (313 mg, 0.7 mmol), Intermediate 186b (262 mg, 0.7 mmol) and DIPEA (182 µL, 1.05 mmol) in dioxane (4 mL) was heated at 70° C. for 20 h. The reaction mixture was cooled to RT and eluted directly on SCX-2 using MeOH and 2M NH$_3$ in MeOH. The basic fractions were evaporated under reduced pressure. The residue was purified by FCC, using 0-10% [2M NH$_3$ in MeOH] in DCM, to afford the title compound as a yellow glass (293 mg). LCMS (Method 3): Rt 3.63 min, m/z 679 [MH$^+$].

e. 1-{5-tert-Butyl-2-[3-(2-dimethylamino-ethoxy)-phenyl]-2H-pyrazol-3-yl-3-{(1S,4S)-4-[3-((S)-2-methyl-piperidin-1-yl)-[1,2,4]triazolo[4,3-a]pyridin-6-yloxy]-1,2,3,4-tetrahydronaphthalen-1-yl]urea (Example 186).

To a solution of Intermediate 186c (293 mg, 0.44 mmol) and DIPEA (304 pit, 1.76 mmol) in DCM (10 mL) was added methanesulfonyl chloride (103 µL, 1.33 mmol). The reaction mixture was stirred at RT for 1 hour. The mixture was concentrated in vacuo. The residue was taken up in THF (2 mL) and dimethylamine solution in THF (2M, 3.3 mL) was added. The reaction mixture was heated at 60° C. in a sealed tube for 72 h. The reaction mixture was cooled to RT and concentrated in vacuo. The product was purified by HPLC using a gemini C18 column and using a gradient of 20-35%+0.1% Formic acid over 10 minutes. The combined fractions were evaporated under reduced pressure and crystallised by MeCN/Et2O to afford the title compound as a white solid (90 mg, 30%). LCMS (Method 3): Rt 3.01 min, m/z 706 [MH$^+$]. $^1$H NMR (300 MHz, d$_6$-DMSO): 0.91 (3H, d, J=6.7 Hz), 1.23 (9H, s), 1.46-1.54 (2H, m), 1.63-1.72 (2H, m), 1.75-1.76 (2H, m), 2.00-2.18 (2H, m), 2.43 (6H, s), 2.66 (2H, t, J 5.8 Hz), 2.85-2.95 (2H, m), 3.12-3.20 (4H, m), 4.10 (2H, t, J=5.4 Hz), 4.78-4.86 (1H, m), 5.52 (1H, t, J=4.0 Hz), 6.33 (1H, s), 6.95-6.99 (2H, m), 7.06-7.14 (2H, m), 7.19 (1H, dd, J=10.0 Hz), 7.25-7.32 (3H, m), 7.33-7.42 (2H, m), 7.58 (1H, d, J=10.6 Hz), 7.63 (1H, d, J=1.8 Hz), 8.17 (1H, s).

Example 187

1-[3-tert-Butyl-1'-(2-dimethylamino-ethyl)-1'H-[1,4']bipyrazolyl-5-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt

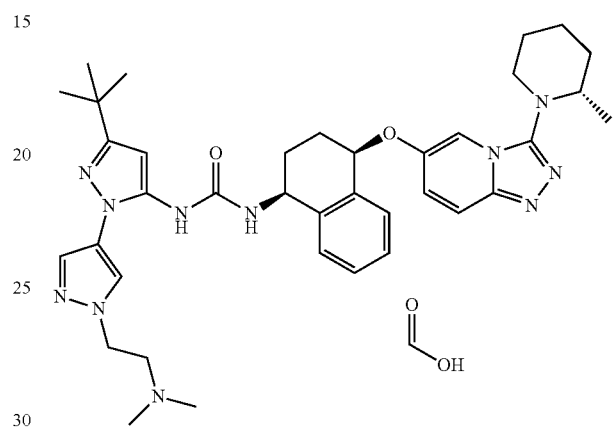

a. 1-{3-tert-Butyl-1'-[2-(tetrahydro-pyran-2-yloxy)-ethyl]-1'H-[1,4']bipyrazolyl-5-yl}-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea (Intermediate 187a).

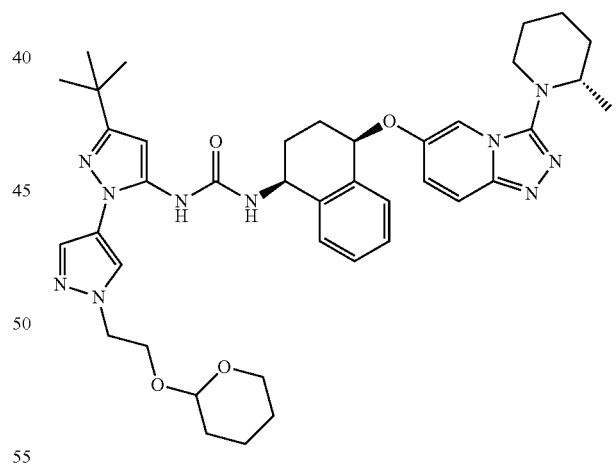

A mixture of Intermediate 81d (240 mg, 0.64 mmol), Intermediate 108b (325 mg, 0.64 mmol) and DIPEA (221 µL, 1.27 mmol) in dioxane (6 mL) was stirred at 80° C. overnight. After cooling, the reaction mixture was partitioned between water and EtOAc. The aqueous phase was extracted with EtOAc (×3) and the combined organic layers were washed with brine, dried (MgSO$_4$) and concentrated in vacuo. The resultant residue was purified by FCC on silica, using a gradient of 0-10% MeOH in DCM to afford the title compound (377 mg, 80%). LCMS (Method 4): Rt 3.48 min, m/z 737 [MH$^+$].

b. 1-[3-tert-Butyl-1'-(2-hydroxy-ethyl)-1'H-[1,4']bipyrazolyl-5-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea (Intermediate 187b).

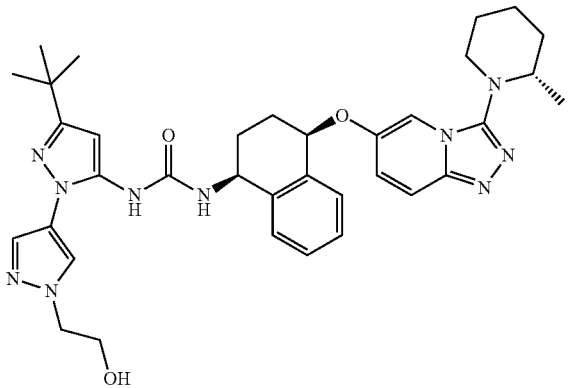 [SMILES: C[C@H]1CCCCN1c1nnc2ccc(O[C@@H]3CC[C@H](NC(=O)Nc4cc(C(C)(C)C)nn4-c4cnn(CCO)c4)c4ccccc43)cn12]

To a solution of Intermediate 187a (377 mg, 0.51 mmol) in MeOH (5 mL) was added pyridinium p-toluenesulfonate (257 mg, 1.02 mmol) and the reaction mixture was heated at 55° C. for 3 h. The resultant mixture was poured into water and a saturated aqueous solution of NaHCO$_3$ was added. The aqueous phase was extracted with EtOAc (×3) and the combined organic layers were washed with brine, dried (MgSO$_4$) and concentrated in vacuo. The resultant residue was purified by FCC on silica, using a gradient of 3-10% MeOH in DCM, to give the title compound (250 mg, 75%). LCMS (Method 1): Rt 3.09 min, m/z 653 [MH$^+$].

c. Methanesulfonic acid 2-[3-tert-butyl-5-(3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-ureido)-[1,4']bipyrazolyl-1'-yl]-ethyl ester (Intermediate 187c).

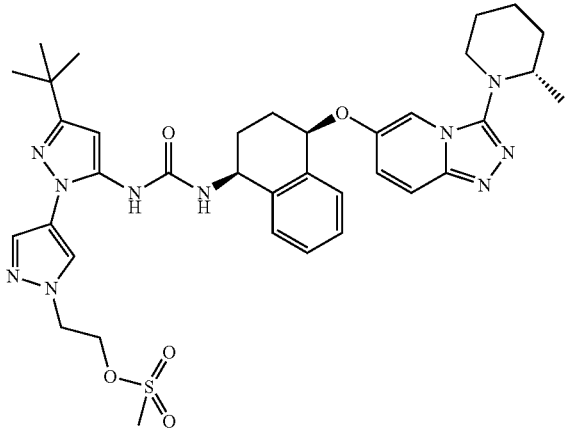 [SMILES: C[C@H]1CCCCN1c1nnc2ccc(O[C@@H]3CC[C@H](NC(=O)Nc4cc(C(C)(C)C)nn4-c4cnn(CCOS(C)(=O)=O)c4)c4ccccc43)cn12]

To an ice-bath cooled solution of Intermediate 187b (250 mg, 0.38 mmol) in DCM (4 mL) was added DIPEA (267 μL, 1.53 mmol) followed by methanesulfonyl chloride (60 μL, 0.77 mmol). The reaction mixture was stirred for 2 h and then quenched with water. The aqueous phase was extracted with DCM (×3) and the combined organic layers were washed with brine, dried (MgSO$_4$) and concentrated in vacuo to afford the title compound (Quantitative). Product used in the following step without further purification. LCMS (Method 4): Rt 3.25 min, m/z 732 [MH$^+$].

d. 1-[3-tert-Butyl-1'-(2-dimethylamino-ethyl)-1'H-[1,4']bipyrazolyl-5-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea formate salt (Example 187).

To a solution of Intermediate 187c (0.19 mmol) in THF (3 mL) was added dimethylamine (2M in MeOH, 1.9 mL, 3.8 mmol) and the reaction stirred at 50° C. in a sealed vial overnight. The crude reaction mixture was partitioned between EtOAc and water. The aqueous phase was extracted with EtOAc (×3) and the combined organic layers were washed with brine, dried (MgSO$_4$) and concentrated in vacuo. The resultant residue was purified by FCC on silica, using a gradient of 0-10% [2M NH$_3$ in MeOH] in DCM followed by MDAP (Method 7) purification, to give the title compound (46 mg, 33%). LCMS (Method 5): Rt 3.50 min, m/z 680 [MH$^+$]. $^1$H NMR (400 MHz, d$_6$-DMSO): 0.87 (3H, d, J=6.4 Hz), 1.20 (9H, s), 1.43-1.51 (2H, m), 1.58-1.69 (2H, m), 1.70-1.88 (3H, m), 1.88-1.96 (1H, m), 1.96-2.12 (2H, m), 2.13 (6H, s), 2.63 (2H, t, J=6.5 Hz), 2.87 (1H, ddd, J=12.6, 9.1, 3.9 Hz), 3.12 (1H, dt, J=12.1, 4.2 Hz), 4.16 (2H, t, J=6.5 Hz), 4.80 (1H, td, J=8.5, 5.8 Hz), 5.48 (1H, t, J=4.3 Hz), 6.22 (1H, s), 7.12 (1H, d, J=8.5 Hz), 7.15 (1H, dd, J=9.9, 2.2 Hz), 7.21-7.26 (1H, m), 7.28-7.36 (3H, m), 7.58 (1H, s), 7.60 (1H, d, J=9.5 Hz), 7.66 (1H, d, J=2.1 Hz), 7.96 (1H, s), 8.00 (1H, s), 8.13 (1H, s).

Example 188

1-[3-tert-Butyl-1'-(2-morpholin-4-yl-ethyl)-1'H-[1,4'] bipyrazolyl-5-yl]-3-{(1S,4R)-4-[3-((S)-2-methyl-piperidin-1-yl)-[1,2,4]triazolo[4,3-a]pyridin-6-yloxy]-1,2,3,4-tetrahydro-naphthalen-1-yl}-urea partial formate salt

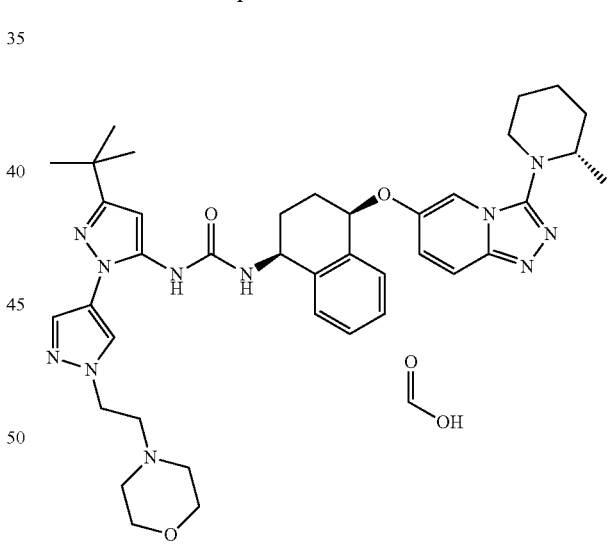

To a solution of Intermediate 187c (0.19 mmol) in THF (3 mL) was added morpholine (166 μL, 1.9 mmol) and the reaction stirred at 50° C. overnight. The crude reaction mixture was partitioned between EtOAc and water. The aqueous phase was extracted with EtOAc (×3) and the combined organic layers were washed with brine, dried (MgSO$_4$) and concentrated in vacuo. The resultant residue was purified by FCC on silica, using a gradient of 2.5-10% (2M NH$_3$ in MeOH) in DCM followed by MDAP (Method 7) purification, to give the title compound (49 mg, 35%). LCMS (Method 5): Rt 3.53 min, m/z 722 [MH$^+$]. $^1$H NMR (400 MHz, d$_6$-DMSO): 0.87 (3H, d, J=6.4 Hz), 1.20 (9H, s), 1.43-1.51

(2H, m), 1.58-1.69 (2H, m), 1.70-1.88 (3H, m), 1.88-1.96 (1H, m), 1.96-2.12 (2H, m), 2.37 (4H, t, J=4.5 Hz), 2.69 (2H, t, J=6.5 Hz), 2.87 (1H, ddd, J=12.6, 9.1, 3.9 Hz), 3.12 (1H, dt, J=12.1, 4.2 Hz), 1H UNDER SOLVENT, 3.50 (4H, t, J=4.6 Hz), 4.20 (2H, t, J=6.5 Hz), 4.80 (1H, td, J=8.5, 5.8 Hz), 5.48 (1H, t, J=4.3 Hz), 6.22 (1H, s), 7.11 (1H, d, J=8.5 Hz), 7.15 (1H, dd, J=9.9, 2.2 Hz), 7.21-7.26 (1H, m), 7.28-7.35 (3H, m), 7.60 (1H, d, J=9.8 Hz), 7.60 (1H, s), 7.66 (1H, d, J=2.1 Hz), 7.96 (1H, s), 8.02 (1H, s), 8.12 (0.5H, s).

Example 189

1-{5-tert-Butyl-2-[3-(4-methyl-piperazin-1-ylmethyl)-phenyl]-2H-pyrazol-3-yl}-3-{(1S,4R)-4-[3-((S)-1-methyl-pyrrolidin-2-yl)-[1,2,4]triazolo[4,3-a]pyridin-6-yloxy]-1,2,3,4-tetrahydro-naphthalen-1-yl}-urea formate salt

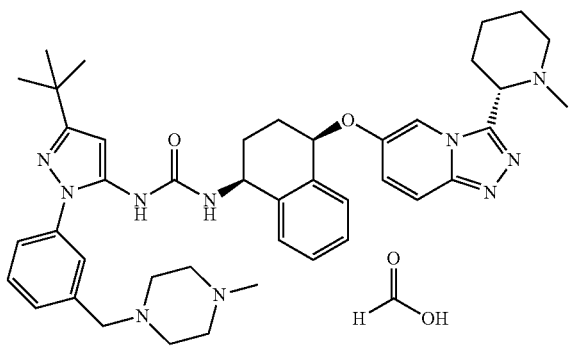

A mixture of Intermediate 149b (87 mg, 0.12 mmol) and 1-methylpiperazine (68 μL, 0.61 mmol) in THF (2 mL) was stirred at 60° C. for 18 h. The reaction mixture was cooled to RT, diluted with DCM (5 mL) and washed with water (5 mL). The aqueous layer was extracted with DCM (5 mL). The combined organic extracts were washed with water (2×5 mL) and passed through a phase separator. The filtrate was concentrated in vacuo and the resultant residue was purified by MDAP (Method 7) to afford the title compound (23 mg, 27%). LCMS (Method 5): Rt 2.69 min, m/z 717.6 [MH$^+$]. $^1$H NMR (400 MHz, d$_6$-DMSO): 1.28 (9H, s), 1.84-2.11 (6H, m), 2.13 (6H, br s), 2.15-2.26 (2H, m), 2.26-2.46 (8H, m), 3.13 (1H, m, obscured by water), 3.50 (2H, s, obscured by water), 3.99 (1H, t, J=8.4 Hz), 4.82 (1H, m), 5.39 (1H, t, J=4.3 Hz), 6.33 (1H, s), 7.06 (1H, d, J=8.8 Hz), 7.24-7.48 (9H, m), 7.75 (1H, d, J=9.7 Hz), 8.10 (1H, s), 8.19 (1.9H, br s), 8.24 (1H, d, J=1.7 Hz).

Biological Assays.
P38Alpha Enzyme Inhibition Assay.

The inhibitory activity of compounds was determined using an Alphascreen® (Perkin Elmer) based kinase activity assay. Kinase reactions consisted of 25 mM HEPES pH 7.5, 10 mM MgCl$_2$, 100 μM Na$_3$VO$_4$, 2 mM DTT, 0.05 mg/ml Tween 20, 100 pM p38alpha (Invitrogen, PV3304), 1% DMSO and 0.3 μg/ml ATF-2 fusion protein (New England Biolabs, 9224). Compounds were incubated under these conditions for 2 hours, at 25° C., prior to the initiation of the kinase activity by the addition of the 250 μM ATP. Reaction volumes were 20 uL. After 1 hr at 25° C. reactions were stopped by the adding 10 uL of 25 mM HEPES pH 7.5 containing 62.5 mM EDTA, 0.05% Triton X-100, 10% BSA and 0.83 ng/uL anti-phospho-ATF2 antibody (Abeam, ab28812). Detection was performed by measuring luminescence following the addition of Alphascreen Donor beads (Perkin Elmer 6765300) and Protein A Alphascreen Acceptor beads (Perkin Elmer 6760137), both at a final concentration of 20 ug/ml. IC$_{50}$ values were determined from concentration-response curves. Results are shown in the following Table:

| Example | p38α inhibition |
|---|---|
| 1, 2, 3, 4, 5, 6, 7, 8, 9, 10, 11, 12, 13, 18, 19, 20, 22, 23, 24, 25, 26, 27, 28, 29, 30, 31, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 118, 119, 120, 121, 122, 123, 124, 125, 126, 127, 128, 129, 130, 131, 132, 133, 134, 135, 136, 137, 138, 139, 140, 141, 142, 143, 144, 148, 154, 155, 156, 157, 158, 159, 160, 162, 163, 165, 166, 167, 168, 169, 170, 171, 176, 178, 181, 182, 183, 184, 185 | ++++ |
| 21 | +++ |
| 32 | ++ |

In the table above, p38α binding potencies (IC$_{50}$ values) are indicated as follows: 7000 to 500 nM '+'; 500 to 100 nM, '++'; 100 to 10 nM, '+++'; <10 nM, '++++'.

LPS-Stimulated PBMC TNFα Release Assay.

Peripheral Blood Mononuclear Cells (PBMCs) were isolated from healthy human volunteer blood using a standard density gradient centrifugation technique. Citrated blood was placed onto Histopaque™ and centrifuged. The PBMCs were removed from the density gradient interface and washed in phosphate buffered saline (PBS). The PBMCs were suspended in RPMI 1640 medium (without serum), dispensed into a 96-well plate and incubated at 37° C. for 3 h in a humidified incubator. After incubation, the medium was replaced (with medium containing 1% foetal bovine serum) and the plate incubated at 37° C., for 1 h, in the presence of test compound or the appropriate vehicle. LPS (10 ng/ml), or an appropriate vehicle control, was then added to the cells and the plate returned to the incubator for 18 h. Cell-free supernatants were removed and assayed for TNFα levels using an ELISA kit from R&D Systems.

A dose response curve to each test compound was performed and the effect of compound in each experiment was expressed as a percentage inhibition of the control TNFα release. Dose response curves were plotted and compound potency (IC$_{50}$) was determined. Compounds were tested in at least three separate experiments. Results are shown in the following Table:

| Example numbers | p38α inhibition |
|---|---|
| 3, 5, 8, 10, 12, 13, 15, 16, 18, 19, 20, 23, 24, 25, 26, 27, 28, 29, 30, 31, 33, 34, 35, 36, 37, 38, 39, 40, 41, 42, 43, 44, 46, 47, 48, 49, 50, 52, 53, 54, 55, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 92, 93, 95, 96, 97, 98, 99, 100, 101, 102, 103, 104, 105, 106, 107, 108, 109, 110, 111, 112, 113, 114, 115, 116, 117, 118, 120, 121, 122, 123, 124, 125, 126, 127, 128, 130 | ++++ |
| 1, 2, 11, 14, 21, 57, 94, 119, 129 | +++ |
| 4, 7, 9, 22 | ++ |

In the table above, p38α potencies (IC$_{50}$ values) are indicated as follows: >1000 nM, '+'; 1000 to 100 nM, '++'; 100 to 10 nM, '+++'; <10 nM, '++++'. All compounds tested exhibited IC$_{50}$ values <1000 nM.

Pre-Clinical Mouse Model of COPD Tobacco Smoke Induced Pulmonary Inflammation.

Previous studies have established that the number of inflammatory cells recovered by bronchoalveolar lavage (BAL) is significantly elevated 24 h following the final of four consecutive daily tobacco smoke (TS) exposures. This timepoint was used in the studies reported here.

Protocols for the exposure of mice to TS, obtaining bronchoalveolar lavage fluid (BALF) and preparation of cytospin slides for differential cell counts are as outlined below.

Daily Exposure of Mice to TS for 4 Consecutive Days.

In this exposure protocol, mice were exposed in groups of 5 in individual clear polycarbonate chambers (27 cm×16 cm×12 cm). The TS from the cigarettes was allowed to enter the exposure chambers at a flow rate of 100 ml/min. In order to minimise any potential problems caused by repeated exposure to a high level of TS, the exposure of the mice to TS was increased gradually over the exposure period to a maximum of 6 cigarettes. The exposure schedule used over the four days was as follows:

| | |
|---|---|
| Day 1: 5 cigarettes | (approximately 25 min exposure) |
| Day 2: 7 cigarettes | (approximately 35 min exposure) |
| Day 3: 9 cigarettes | (approximately 45 min exposure) |
| Day 4: 9 cigarettes | (approximately 45 min exposure) |

A further group of mice were exposed to air on a daily basis for equivalent lengths of time as controls (no TS-exposure).

Bronchoalveolar Lavage (BAL) Analysis.

Bronchoalveolar lavage was performed as follows: the trachea was cannulated using a 10 mm long Luer-fitting stainless steel cannula. Phosphate buffered saline (PBS) was used as the lavage fluid. A volume of 0.4 ml was gently instilled and withdrawn 3 times, using a 1 ml syringe and then placed in an Eppendorf tube and kept on ice prior to subsequent determinations.

Cell Counts:

Lavage fluid was separated from cells by centrifugation and the supernatant decanted and frozen for subsequent analyses. The cell pellet was re-suspended in a known volume of PBS and total cell numbers calculated by counting a stained (Turks stain) aliquot under a microscope using a haemocytometer.

Differential Cell Counts were Performed as Follows:

The residual cell pellet was diluted to approximately $10^5$ cells per ml. A volume of 500 µl was placed in the funnel of a cytospin slide and centrifuged for 6 min at 800 rpm, RCF=72.26×g (Shandon Cytospin 3). The slide was air-dried and stained using Wrights/Giemsa stain as per the proprietary instructions. When dried and cover-slipped, differential cell counts were performed using light microscopy. Approximately four hundred cells were counted by an unbiased operator using light microscopy. Cells were differentiated using standard morphometric techniques.

Drug Treatment

Rodents such as mice and rats are obligate nose breathers, thus oral delivery of test materials (such as therapeutic agents) for inhalation will not produce good lung exposure. As a consequence, delivery of therapeutic agents to the lungs in rodents is generally achieved by intranasal, intratracheal or inhalation by either nose-only or whole body aerosol exposure.

Nose-only or whole body aerosol exposure methods utilise large amounts of test material and are generally reserved for inhalation toxicology studies rather than more routine pharmacological efficacy studies. Intratracheal administration is a very efficient delivery method as almost all of the test material is delivered to the lungs but is an invasive technique. For studies in the mouse particularly, it is also technically demanding as the diameter of the trachea is small. The intranasal route is less invasive than the intratracheal route and so is particularly suitable for repeat dosing studies such as the four day mouse model described. Following intranasal administration, ~50% of the dose administered is delivered to the lungs (Eyles J E, Williamson E D and Alpar H O. 1999, Int J Pharm, 189(1):75-9, which is incorporated herein by reference in its entirety).

As a surrogate route for oral inhalation, mice were dosed intra-nasally with vehicle (0.2% tween 80 in saline) containing test compound. The control groups of mice received vehicle 1 hr prior to being exposed to air or TS.

Data Management and Statistical Analysis:

All results are presented as individual data points for each animal and the mean value was calculated for each group. Since tests for normality were positive, the data were subjected to a one-way analysis of variance test (ANOVA), followed by a Bonferroni correction for multiple comparisons in order to test for statistically significant differences between treatment groups. A "p" value of <0.05 was considered to be statistically significant. Percentage inhibitions were automatically calculated within Excel spreadsheets for the cell data using the formula below:

$$\% \text{ Inhibition} = \left(1 - \left(\frac{\text{Treatment group result} - \text{air group result}}{\text{TS vehicle group result} - \text{air group result}}\right)\right) \times 100$$

Inhibition data for other parameters were calculated manually using the above formula.

Example 5 of the invention was tested in the above reported model and results are herebelow reported.

Figure 2:
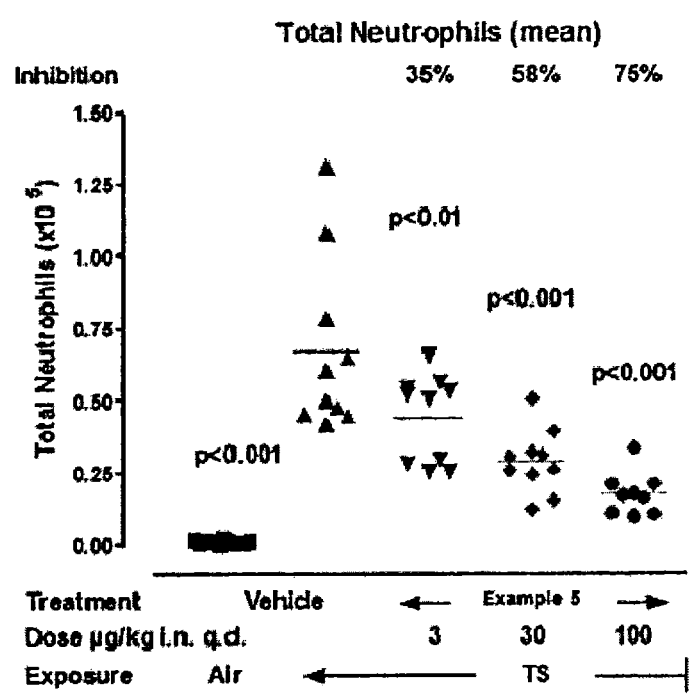
FIG. 2 is a graph that illustrates the effect of intranasal administration to laboratory mice with vehicle (0.2% tween 80 in saline), Example 5 (3 μg/kg), Example 5 (30 μg/kg) or Example 5 (100 μg/kg) on the number of BAL neutrophils induced by tobacco smoke 24 hours post the final exposure.

As illustrated in FIG. 1, Example 5 significantly inhibited the BAL cell influx induced by TS at 3, 30 or 100 µg/kg when administered by the intranasal route. Similar findings were observed with BAL neutrophils (FIG. 2). The results demonstrate a clear anti-inflammatory effect in the lungs of mice exposed to TS.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method of treating a disease or condition in a human subject which benefits from inhibition of p38 MAP kinase activity, comprising administering, to a subject in need thereof, a compound represented by formula (I) or a pharmaceutically acceptable salt thereof:

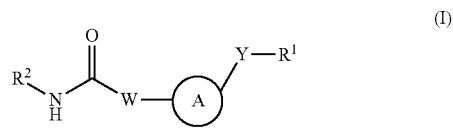

wherein;
W is N substituted with hydrogen;
Y is O;
$R^1$ is a group represented by formula (IIc):

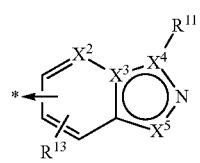
(IIc)

$X^2$ is a —CH— group, $X^3$ is a nitrogen atom, $X^4$ is a carbon atom, and $X^5$ is a nitrogen atom;

$R^{11}$ is linked to $X^4$ and is $C_1$-$C_6$ alkyl which is substituted by —$OR^C$ or —$SR^C$; —$NR^AR^B$; —($C_1$-C6) alkylene-$NR^AR^B$; or —($C_3$-$C_7$)heterocycloalkyl, wherein any of said $NR^AR^B$, —($C_1$-$C_6$)alkylene-$NR^AR^B$, or —($C_3$-$C_7$)heterocycloalkyl may be optionally substituted by one or two $C_1$-$C_6$ alkyl;

$R^A$ and $R^B$ form, together with the nitrogen atom to which they are attached, a 5-11-membered saturated heterocyclic monocyclic ring system which is optionally substituted by one or more $C_1$-$C_6$ alkyl and which 5-11-membered saturated heterocyclic monocyclic ring optionally contains a further heteroatom which is oxygen or nitrogen;

$R^C$ is at each occurrence independently hydrogen or $C_1$-$C_6$ alkyl, said $C_1$-$C_6$ alkyl being optionally substituted —$OR^D$;

$R^D$ is at each occurrence independently hydrogen, —$CH_3$, or —$C_2H_5$;

$R^{13}$ is independently hydrogen, $C_1$-$C_6$ alkyl, or halogen;

A is a group represented by one of the following formulae:

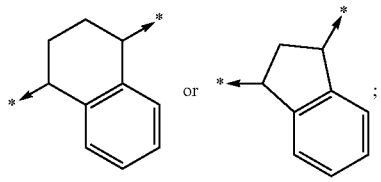

and
$R^2$ is a group of formula (IIIa):

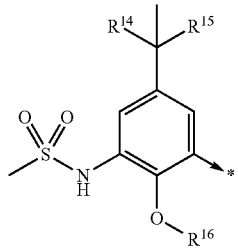
(IIIa)

wherein
$R^{14}$, $R^{15}$, and $R^{16}$ are —$CH_3$,
wherein said disease or condition is chronic obstructive pulmonary disease, chronic bronchitis, lung fibrosis, pneumonia, acute respiratory distress syndrome, adult respiratory distress syndrome, emphysema, asthma, cystic fibrosis, pulmonary fibrosis, bronchiectasis, exacerbation of airways hyper-reactivity consequent to other drug therapy, or airways disease that is associated with pulmonary hypertension.

2. A method according to claim 1, wherein said compound or pharmaceutically acceptable salt thereof is a compound of formula (Ia) or pharmaceutically acceptable salt thereof wherein the carbon stereogenic center on the cycloalkylene portion of ring A which is linked to group W and identified with number (1) herebelow, possess the absolute configuration herebelow represented:

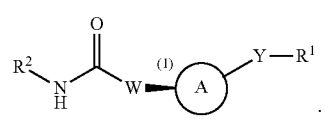
(Ia)

3. A method according to claim 1, wherein said compound or pharmaceutically acceptable salt thereof is a compound of formula (Ib) or pharmaceutically acceptable salt thereof wherein the carbon stereogenic centers on the cycloalkylene portion of ring A which are linked to group W and Y and identified, respectively, with numbers (1) and (2) herebelow, possess the absolute configuration herebelow represented:

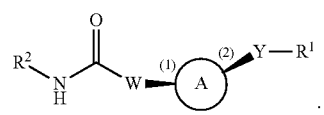
(Ib)

4. A method according to claim 1, wherein $R^{11}$ is a group:

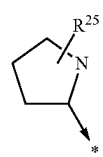

wherein $R^{25}$ is optionally present and represents one, two, or three substituents independently selected from the group consisting of $C_1$-$C_6$ alkyl, ($C_1$-$C_3$) haloalkyl, ($C_1$-$C_4$)hydroxyalkyl, $C_3$-$C_7$ cycloalkyl, hydroxyl, and halo; and wherein the asterisk represents the point of attachment for group $R^{11}$ to the rest of the molecule via $X^4$.

5. method according to claim 1, wherein $R^{11}$ is a group:

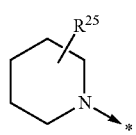

wherein $R^{25}$ is optionally present and represents one, two, or three substituents independently selected from the group consisting of $C_1$-$C_6$ alkyl, ($C_1$-$C_3$) haloalkyl, ($C_1$-$C_4$)hydroxyalkyl, $C_3$-$C_7$ cycloalkyl, hydroxyl, and halo;

and wherein the asterisk represents the point of attachment for group $R^{11}$ to the rest of the molecule via $X^4$.

6. A method according to claim 1, wherein A is a group represented by the following formula:

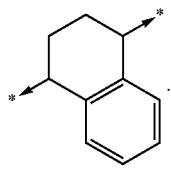

7. A method according to claim 1, wherein $R^{11}$ is linked to $X^4$ and is $NR^A R^B$ and $R^A$ and $R^B$ form, together with the nitrogen atom to which they are attached, a 5-11-membered saturated heterocyclic monocyclic ring system which is optionally substituted by one or more $C_1$-$C_6$ alkyl and which 5-11-membered saturated heterocyclic monocyclic ring optionally contains a further heteroatom which is oxygen or nitrogen.

8. A method according to claim 1, wherein said disease or condition is chronic eosinophilic pneumonia, asthma, chronic obstructive pulmonary disease, adult respiratory distress syndrome, exacerbation of airways hyper-reactivity consequent to other drug therapy or airways disease that is associated with pulmonary hypertension.

9. A method according to claim 8, wherein said compound or pharmaceutically acceptable salt thereof is a compound of formula (Ia) or pharmaceutically acceptable salt thereof wherein the carbon stereogenic center on the cycloalkylene portion of ring A which is linked to group W and identified with number (1) herebelow, possess the absolute configuration herebelow represented:

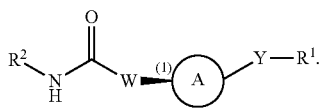
(Ia)

10. A method according to claim 8, wherein said compound or pharmaceutically acceptable salt thereof is a compound of formula (Ib) or pharmaceutically acceptable salt thereof wherein the carbon stereogenic centers on the cycloalkylene portion of ring A which are linked to group W and Y and identified, respectively, with numbers (1) and (2) herebelow, possess the absolute configuration herebelow represented:

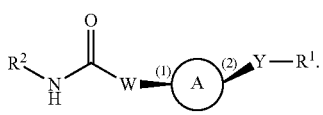
(Ib)

11. A method according to claim 8, wherein $R^{11}$ is a group:

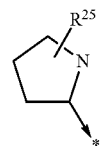

wherein $R^{25}$ is optionally present and represents one, two, or three substituents independently selected from the group consisting of $C_1$-$C_6$ alkyl, ($C_1$-$C_3$) haloalkyl, ($C_1$-$C_4$)hydroxyalkyl, $C_3$-$C_7$ cycloalkyl, hydroxyl, and halo; and wherein the asterisk represents the point of attachment for group $R^{11}$ to the rest of the molecule via $X^4$.

12. A method according to claim 8, wherein $R^{11}$ is a group:

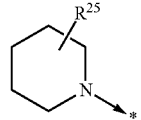

wherein $R^{25}$ is optionally present and represents one, two, or three substituents independently selected from the group consisting of $C_1$-$C_6$ alkyl, ($C_1$-$C_3$) haloalkyl, ($C_1$-$C_4$)hydroxyalkyl, $C_3$-$C_7$ cycloalkyl, hydroxyl, and halo; and wherein the asterisk represents the point of attachment for group $R^{11}$ to the rest of the molecule via $X^4$.

13. A method according to claim 8, wherein A is a group represented by the following formula:

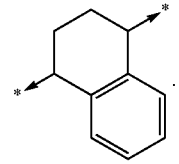

14. A method according to claim 8, wherein $R^{11}$ is linked to $X^4$ and is $NR^A R^B$ and $R^A$ and $R^B$ form, together with the nitrogen atom to which they are attached, a 5-11-membered saturated heterocyclic monocyclic ring system which is optionally substituted by one or more $C_1$-$C_6$ alkyl and which 5-11-membered saturated heterocyclic monocyclic ring optionally contains a further heteroatom which is oxygen or nitrogen.

15. A method according to claim 8, wherein said disease or condition is chronic eosinophilic pneumonia.

16. A method according to claim 8, wherein said disease or condition is asthma.

17. A method according to claim 8, wherein said disease or condition is chronic obstructive pulmonary disease.

18. A method according to claim 8, wherein said disease or condition is adult respiratory distress syndrome.

19. A method according to claim 8, wherein said disease or condition is exacerbation of airways hyper-reactivity consequent to other drug therapy.

20. A method according to claim 8, wherein said disease or condition is airways disease that is associated with pulmonary hypertension.

\* \* \* \* \*